United States Patent
Rutz et al.

(10) Patent No.: US 12,239,664 B2
(45) Date of Patent: Mar. 4, 2025

(54) EFFICIENT TCR GENE EDITING IN T LYMPHOCYTES

(71) Applicant: Genentech, Inc., South San Francisco, CA (US)

(72) Inventors: Sascha Rutz, San Francisco, CA (US); Benjamin Joseph Haley, San Francisco, CA (US); Shravan Madireddi, Fremont, CA (US); Soyoung Oh, San Bruno, CA (US); David Shaw, Burlingame, CA (US); Kate Halliwell Senger, Oakland, CA (US)

(73) Assignee: GENENTECH, INC., South San Francisco, CA (US)

( * ) Notice: Subject to any disclaimer, the term of this patent is extended or adjusted under 35 U.S.C. 154(b) by 8 days.

(21) Appl. No.: 17/703,927

(22) Filed: Mar. 24, 2022

(65) Prior Publication Data

US 2023/0041268 A1   Feb. 9, 2023

Related U.S. Application Data

(60) Provisional application No. 63/323,065, filed on Mar. 24, 2022, provisional application No. 63/165,509, filed on Mar. 24, 2021.

(51) Int. Cl.
| | |
|---|---|
| *A61K 35/17* | (2015.01) |
| *A61K 38/00* | (2006.01) |
| *C07K 14/725* | (2006.01) |
| *C12N 5/0783* | (2010.01) |
| *C12N 9/22* | (2006.01) |
| *C12N 15/11* | (2006.01) |
| *C12N 15/62* | (2006.01) |
| *C12N 15/90* | (2006.01) |

(52) U.S. Cl.
CPC .......... *A61K 35/17* (2013.01); *C07K 14/7051* (2013.01); *C12N 5/0636* (2013.01); *C12N 9/22* (2013.01); *C12N 15/11* (2013.01); *C12N 15/625* (2013.01); *C12N 15/907* (2013.01); *A61K 38/00* (2013.01); *C07K 2319/00* (2013.01); *C12N 2310/20* (2017.05); *C12N 2501/2302* (2013.01); *C12N 2501/2307* (2013.01); *C12N 2501/2315* (2013.01); *C12N 2800/80* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton et al. |
| 5,235,033 A | 8/1993 | Summerton et al. |
| 2013/0065768 A1 | 3/2013 | Zheng et al. |
| 2013/0150252 A1 | 6/2013 | Faham et al. |
| 2013/0196328 A1 | 8/2013 | Pepin et al. |
| 2013/0236895 A1 | 9/2013 | Faham et al. |
| 2015/0275296 A1 | 10/2015 | Klinger et al. |
| 2016/0138011 A1 | 5/2016 | Dewitt et al. |
| 2016/0348073 A1* | 12/2016 | Meissner ........... C12N 15/1138 |
| 2018/0087109 A1 | 3/2018 | Klinger et al. |
| 2018/0282808 A1 | 10/2018 | Milla et al. |
| 2018/0355429 A1 | 12/2018 | Klinger et al. |
| 2022/0017882 A1* | 1/2022 | Marson ................. C12N 15/88 |

FOREIGN PATENT DOCUMENTS

| | | |
|---|---|---|
| WO | 2010053587 A2 | 5/2010 |
| WO | 2011139371 A1 | 11/2011 |
| WO | 2011139372 A1 | 11/2011 |
| WO | 2013059725 A1 | 4/2013 |
| WO | 2013134162 A2 | 9/2013 |
| WO | 2013169957 A1 | 11/2013 |
| WO | 2013188471 A2 | 12/2013 |
| WO | 2013188831 A1 | 12/2013 |
| WO | 2014055561 A1 | 4/2014 |
| WO | 2014130685 A1 | 8/2014 |
| WO | 2014145992 A1 | 9/2014 |
| WO | 2015002908 A1 | 1/2015 |
| WO | 2015058159 A1 | 4/2015 |
| WO | 2015106161 A1 | 7/2015 |
| WO | 2015160439 A2 | 10/2015 |
| WO | 2016069886 A1 | 5/2016 |
| WO | 2016086029 A1 | 6/2016 |
| WO | 2016161273 A1 | 10/2016 |
| WO | 2017112944 A1 | 6/2017 |
| WO | 2019089610 A1 | 5/2019 |
| WO | 2022204443 A1 | 9/2022 |

OTHER PUBLICATIONS

Schober, K., Müller, T.R., Gökmen, F. et al. Orthotopic replacement of T-cell receptor α- and β-chains with preservation of near-physiological T-cell function. Nat Biomed Eng 3, 974-984 (2019). https://doi.org/10.1038/s41551-019-0409-0 (Year: 2019).*
International Search Report and Written Opinion for PCT/US2022/21820, mailed Sep. 12, 2022, 19 pages.
Albers et al. (2019) "Gene Editing Enables T-cell Engineering to Redirect Antigen Specificity for Potent Tumor Rejection", Life Science Alliance, 2(2):e201900367, 10 pages.
Oh et al. (2022) "High-efficiency Nonviral CRISPR/Cas9-mediated Gene Editing of Human T Cells Using Plasmid Donor DNA", Journal of Experimental Medicine, 219(5):e20211530, 24 pages.
Anders et al. (Oct. 27, 2010) "Differential Expression Analysis for Sequence Count Data", Genome Biology, Article No. R106, 11(10):12 pages.

(Continued)

*Primary Examiner* — Allison M Fox
*Assistant Examiner* — Alyssa G Weston
(74) *Attorney, Agent, or Firm* — MINTZ, LEVIN, COHN, FERRIS, GLOVSKY AND POPEO, P.C.

(57) ABSTRACT

The present disclosure relates to engineered T cells and methods of making and using the same, as well as reagents for making the engineered T cells.

26 Claims, 234 Drawing Sheets

Specification includes a Sequence Listing.

(56) References Cited

OTHER PUBLICATIONS

Bak et al. (Feb. 2018) "CRISPR/Cas9 Genome Editing in Human Hematopoietic Stem Cells", Nature Protocols, 13(2):358-376.
Bloemberg et al. (Jan. 1, 2020) "A High-Throughput Method for Characterizing Novel Chimeric Antigen Receptors in Jurkat Cells", Molecular Therapy—Methods & Clinical Development, 16:238-254.
Choi et al. (Nov. 14, 2019) "CRISPR-Cas9 Disruption of PD-1 Enhances Activity of Universal EGFRvIII CAR T Cells in a Preclinical Model of Human Glioblastoma", Journal for ImmunoTherapy of Cancer, Article No. 304, 7:8 pages.
Chu et al. (Mar. 24, 2015) "Increasing the Efficiency of Homology-Directed Repair for CRISPR-Cas9-Induced Precise Gene Editing in Mammalian Cells", Nature Biotechnology, 33(5):543-548.
Dai et al. (Feb. 25, 2019) "One-step Generation of Modular CAR-T Cells with AAV-Cpf1", Nature Methods, 16(3):247-254.
Dash et al. (Jan. 2011) "Paired analysis of TCRα and TCRβ chains at the single-cell level in mice", Journal of Clinical Investigation, 121(1):288-295.
Davidsson et al. (Dec. 9, 2020) "A Comparison of AAV-vector Production Methods for Gene Therapy and Preclinical Assessment", Scientific Reports, 21532, 10(1):11 pages.
Doench et al. (Jan. 18, 2016) "Optimized sgRNA Design to Maximize Activity and Minimize Off-target Effects of CRISPR-Cas9", Nature Biotechnology, 34:184-191.
Eyquem et al. (Feb. 22, 2017) "Targeting a CAR to the TRAC Locus with CRISPR/Cas9 Enhances Tumour Rejection", Nature, 543(7643):113-117.
Fu et al. (Nov. 13, 2013) "Themis Sets the Signal Threshold for Positive and Negative Selection in T-cell Development", Nature, 504(7480):441-445.
Gray et al. (Sep. 2011) "Optimizing Promoters for Recombinant Adeno-Associated Virus-Mediated Gene Expression in the Peripheral and Central Nervous System Using Self-Complementary Vectors", Human Gene Therapy, 22(9):1143-1153.
Grist et al. (Feb. 1, 2018) "Extracellular Lactate: A Novel Measure of T Cell Proliferation", Journal of Immunology, 200(3):1220-1226.
Hacein-Bey-Abina et al. (Sep. 2, 2008) "Insertional Oncogenesis in 4 Patients after Retrovirus-mediated Gene Therapy of SCID-X1", Journal of Clinical Investigation, 118(9):3132-3142.
Hacein-Bey-Abina et al. (Oct. 17, 2007) "LMO2-Associated Clonal T Cell Proliferation in Two Patients after Gene Therapy for SCID-X1", Science, 302(5644):415-419.
Halbert et al. (2018) "AAV6 Vector Production and Purification for Muscle Gene Therapy", Methods in Molecular Biology, 1687:257-266.
Hardee et al. (Feb. 2017) "Advances in Non-Viral DNA Vectors for Gene Therapy", Genes, 8(2):65(22 pages).
Hendel et al. (Jun. 29, 2015) "Chemically Modified Guide RNAs Enhance CRISPR-Cas Genome Editing in Human Primary Cells", Nature Biotechnology, 33(9):985-989.
Hockemeyer et al. (Aug. 13, 2009) "Efficient Targeting of Expressed and Silent Genes in Human ESCs and iPSCs using Zinc-finger Nucleas", Nature Biotechnology, 27(9):851-857.
Hudecek et al. (Oct. 2018) "Non-viral Therapeutic Cell Engineering with the Sleeping Beauty Transposon System", Current Opinion in Genetics & Development, 52:100-108.
Kebriaei et al. (Sep. 1, 2016) "Phase I Trials using Sleeping Beauty to Generate CD19-specific Car T cells", Journal of Clinical Investigation, 126(9):3363-3376.
Li et al. (Jan. 3, 2020) "Applications of Genome Editing Technology in the Targeted Therapy of Human Diseases: Mechanisms, Advances and Prospects", Signal Transduction and Targeted Therapy, 5(1):23 pages.
Li et al. (Feb. 20, 2005) "Directed Evolution of Human T-cell Receptors with Picomolar Affinities by Phage Display", Nature Biotechnology, 23(3):349-354.
Liberzon et al. (Dec. 23, 2015) "The Molecular Signatures Database (MSigDB) Hallmark Gene Set Collection", Cell Systems, 1(6):417-425 (18 pages).
Loo et al. (Apr. 15, 2016) "Progress and Challenges in Viral Vector Manufacturing", Human Molecular Genetics, 25(R1):R42-R52.
Luke et al. (Oct. 30, 2009) "Improved Antibiotic-free DNA Vaccine Vectors Utilizing a Novel RNA based Plasmid Selection System", Vaccine, 27(46):6454-6459.
Mandal et al. (Nov. 6, 2014) "Efficient Ablation of Genes in Human Hematopoietic Stem and Effector Cells using CRISPR/Cas9", Cell Stem Cell, 15(5):643-652.
Mansilla-Soto et al. (Feb. 2022) "HLA-independent T Cell Receptors for Targeting Tumors with Low Antigen Density", Nature Medicine, 28(2):345-352.
Miller et al. (Mar. 2019) "Subsets of Exhausted CD8 + T Cells Differentially Mediate Tumor Control and Respond to Checkpoint Blockade", Nature Immunology, 20(3):326-336.
Modlich et al. (Nov. 2009) "Insertional Transformation of Hematopoietic Cells by Self-inactivating Lentiviral and Gammaretroviral Vectors", Molecular Therapy, 17(11):1919-1928.
Monjezi et al. (Jan. 2017) "Enhanced CAR T-cell Engineering using Non-viral Sleeping Beauty Transposition from Minicircle Vectors", Leukemia, 31(1):186-194.
Nguyen et al. (Jan. 2020) "A Cas9 Nanoparticle System with Truncated Cas9 Target Sequences on DNA Repair Templates Enhances Genome Targeting in Diverse Human Immune Cell Types", BioRxiv, 38(1):44-49.
Nguyen et al. (Jan. 2020) "Polymer-stabilized Cas9 Nanoparticles and Modified Repair Templates Increase Genome Editing Efficiency", Nature Biotechnology, 38(1):44-49.
Oh et al. (Feb. 2019) "Ribonucleoprotein Transfection for CRISPR/Cas9-Mediated Gene Knockout in Primary T Cells", Current Protocols in Immunology, e69, 124(1):18 pages.
Redmond et al. (Jul. 27, 2016) "Single-cell TCRseq: Paired Recovery of Entire T-cell Alpha and Beta Chain Transcripts in T-cell Receptors from Single-cell RNAseq", Genome Medicine, Article No. 80, 8(1):12 pages.
Roth et al. (Jul. 11, 2018) "Reprogramming Human T Cell Function and Specificity with Non-viral Genome Targeting", Nature, 559(7714):405-409.
Sade-Feldman et al. (Nov. 1, 2018) "Defining T Cell States Associated with Response to Checkpoint Immunotherapy in Melanoma", Cell, e20, 175(4):998-1013.
Salganik et al. (Jul. 2, 2015) "Adeno-associated Virus as a Mammalian DNA Vector", Microbiology Spectrum, 3(4):21 pages.
Sather et al. (Sep. 30, 2015) "Efficient Modification of CCR5 in Primary Human Hematopoietic Cells Using a megaTAL Nuclease and AAV Donor Template", Science Translational Medicine, 7(307):307ra156 (29 pages).
Schober et al. (Jun. 1, 2020) "Orthotopic Replacement of T-cell Receptor α- and β- chains with Preservation of Near-physiological T-cell Function", Cells, 9(6):20 pages.
Schuldt et al. (Feb. 1, 2019) "Dual TCR T Cells: Identity Crisis or Multitaskers?", The Journal of Immunology, 202(3):637-644.
Schumann et al. (Aug. 18, 2015) "Generation of Knock-in Primary Human T Cells using Cas9 Ribonucleoproteins", Proceedings of the National Academy of Sciences, 112(33):10437-10442.
Seki et al. (Feb. 7, 2018) "Optimized RNP Transfection for Highly Efficient CRISPR/Cas9-mediated Gene Knockout in Primary T cells", Journal of Experimental Medicine, 215(3):985-997.
Shaner et al. (May 2013) "A Bright Monomeric Green Fluorescent Protein Derived from Branchiostoma Lanceolatum", Nature Methods, 10(5):407-409.
Siddiqui et al. (Jan. 15, 2019) "Intratumoral Tcf1 + PD-1 + CD8 + T Cells with Stem-like Properties Promote Tumor Control in Response to Vaccination and Checkpoint Blockade Immunotherapy", Immunity, e10, 50(1):195-211.
Simeonov et al. (Apr. 26, 2019) "CRISPR-Based Tools in Immunity", Annual Review of Immunology, 37:571-597.
Singh et al. (Dec. 2017) "Genome-Editing Technologies in Adoptive T Cell Immunotherapy for Cancer", Current Hematologic Malignancy Reports, 12(6):522-529.

(56) References Cited

OTHER PUBLICATIONS

Smith et al. (Feb. 2008) "Robust, Persistent Transgene Expression in Human Embryonic Stem Cells Is Achieved with AAVS1-Targeted Integration", Stem Cells. 26(2):496-504.

Stadtmauer et al. (Feb. 28, 2020) "CRISPR-engineered T Cells in Patients with Refractor Cancer", Science, eaba7365, 367(6481):20 pages.

Su et al. (Jan. 28, 2016) "CRISPR-Cas9 Mediated Efficient PD-1 Disruption on Human Primary T Cells from Cancer Patients", Scientific Reports, 20070, 6:13 pages.

Subramanian et al. (Oct. 25, 2005) "Gene Set Enrichment Analysis: A Knowledge-based Approach for Interpreting Genome-wide Expression Profiles", Proceedings of the National Academy of Sciences of the United States of America, 102(43):15545-15550.

Vakulskas et al. (Aug. 2018) "A High-fidelity Cas9 Mutant Delivered as a Ribonucleoprotein Complex Enables Efficient Gene Editing in Human Hematopoietic Stem and Progenitor Cells", Nature Medicine, 24(8):1216-1224.

Wang et al. (Jun. 15, 2018) "Clinical Manufacturing of CAR T Cells: foundation of a Promising Therapy", Molecular Therapy—Oncolytics, 16015, 3:7 pages.

Wang et al. (Feb. 18, 2016) "Highly Efficient Homology-driven Genome Editing in Human T Cells by Combining Zinc-finger Nuclease mRNA and AAV6 Donor Delivery", Nucleic Acids Research, e30, 44(3):9 pages.

Wang et al. (Sep. 19, 2019) "Optimized CRISPR Guide RNA Design for Two High-fidelity Cas9 Variants by Deep Learning", Nature Communications, 10(1):14 pages.

Ward-Kavanagh et al. (May 17, 2016) "The TNF Receptor Superfamily in Co-activating and Co-inhibitory Responses", Immunity, 44(5):1005-1019.

Williams et al. (May 22, 2006) "pDNAVACCultra Vector Family: High Throughput Intracellular Targeting DNA Vaccine Plasmids", Vaccine, 24(21):4671-4676.

Zhang et al. (Jun. 23, 2021) "AsCas12a Ultra Nuclease Facilitates the Rapid Generation of Therapeutic Cell Medicines", Nature Communications, Article No. 3908, 12:15 pages.

Zhang et al. (2017) "Engineering CAR-T Cells", Biomarker Research, 5:22 (6 pages).

\* cited by examiner

Day 4 post-electroporation

Day 5 post-electroporation

Cytokines:
- 10 ng/ml IL-2
- 25 ng/ml IL-7
- 50 ng/ml IL-15

FIG. 33B

Donor #2

Frequency of Neon+ cells on day 3 post-electroporation

Recovery of Neon+ cells on day 3 post-electroporation

Frequency of Neon+ cells on day 5 post-electroporation

Recovery of Neon+ cells on day 5 post-electroporation

FIG. 70

- Nv = naïve
- SCM = stem cell memory
- TE = terminal effector
- CM = central memory
- EM = effector memory $T_N \Rightarrow T_{SCM} \Rightarrow T_{CM} \Rightarrow T_{EM} \Rightarrow T_{TE}$

| | $T_N$ | $T_{SCM}$ | $T_{CM}$ | $T_{EM}$ | $T_{TE}$ |
|---|---|---|---|---|---|
| CD45RA | + | + | − | − | + |
| CD45RO | − | − | + | + | − |
| CCR7 | + | + | + | − | − |
| CD62L | + | + | + | − | − |
| CD28 | + | + | + | +/− | − |
| CD27 | + | + | + | +/− | − |
| IL-7Rα | + | + | + | +/− | − |
| CXCR3 | − | + | + | − | − |
| CD95 | − | + | + | + | + |
| CD11a | − | + | + | + | + |
| IL-2Rβ | − | + | + | + | + |
| CD58 | − | + | + | + | + |
| CD57 | − | − | − | +/− | + |

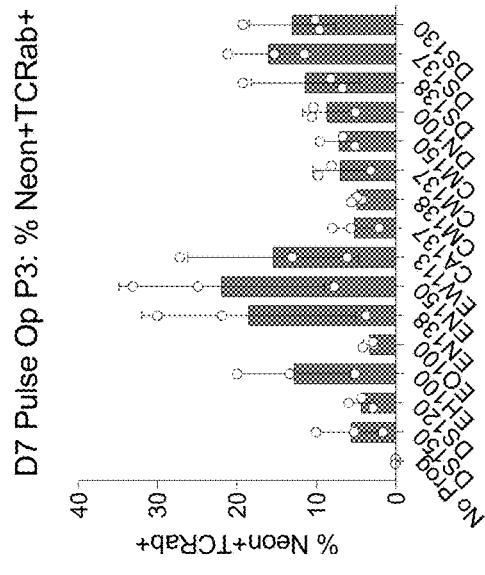
FIG. 79C
FIG. 79A
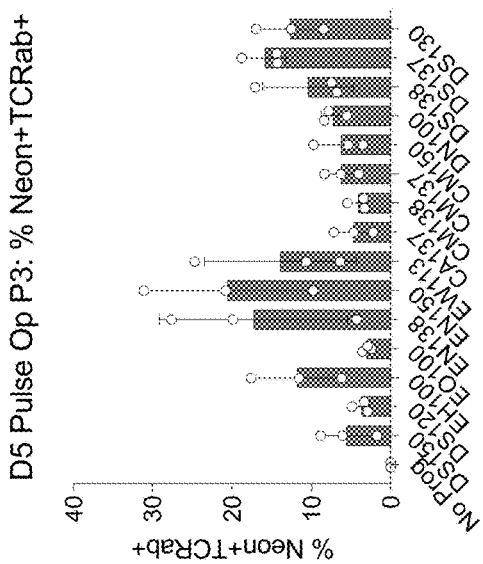
FIG. 79B
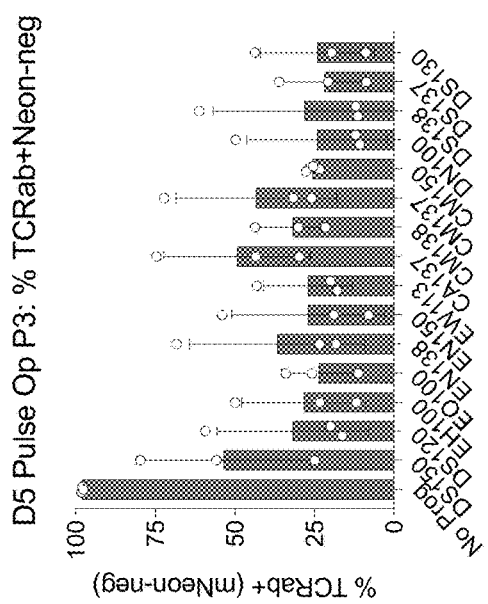
FIG. 79D

FIG. 85D

DNA quantities used in this experiment:

| Construct | Size (bp) | Micrograms | # Molecules |
|---|---|---|---|
| pUC57 TRACg3 mNeon | 5254 | 0.5 | 0.88e11 |
| | | 1 | 1.76e11 |
| | | 2 | 3.52e11 |
| | | 4 | 7.04e11 |
| Nanoplasmid TRACg3 mNeon | 2983 | 0.29 | 0.88e11 |
| | | 0.57 | 1.76e11 |
| | | 1.14 | 3.52e11 |
| | | 2.28 | 7.04e11 |
| Minicircle TRACg3 mNeon | 2611 | 0.25 | 0.88e11 |
| | | 0.5 | 1.76e11 |
| | | 1 | 3.52e11 |
| | | 2 | 7.04e11 |
| PCR product (SEC purified) | 2211 | 0.42 | 1.76e11 |

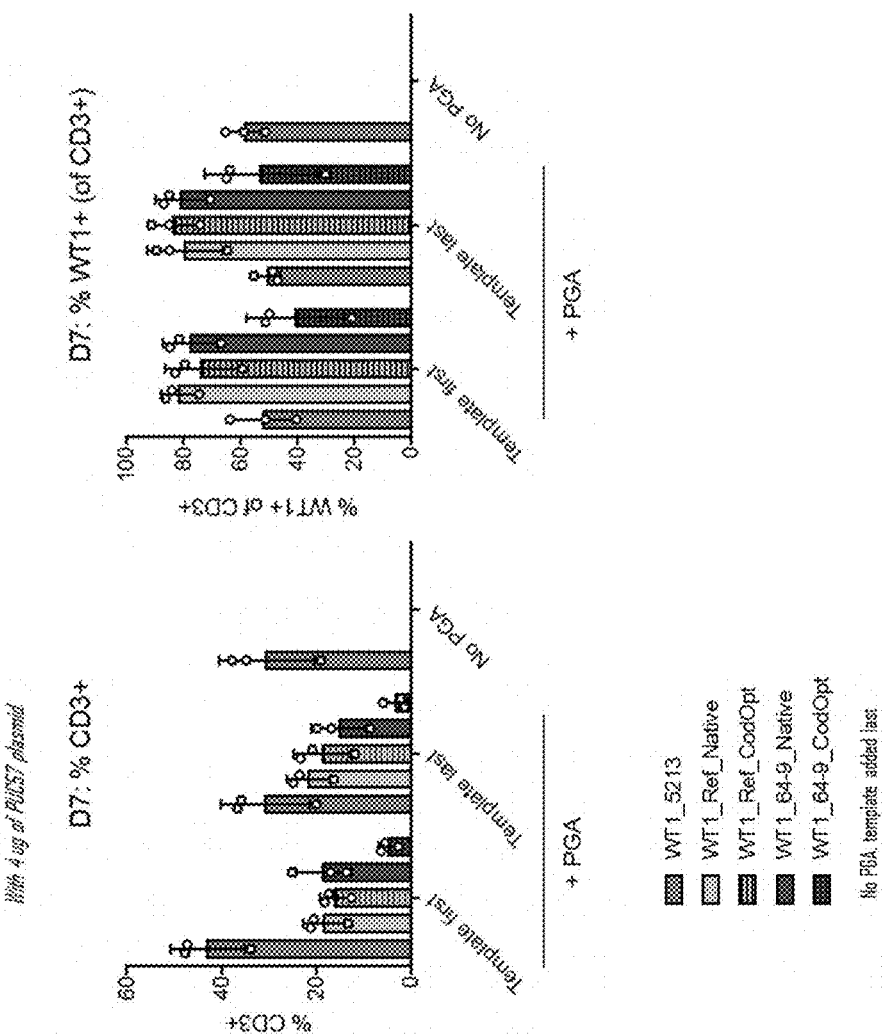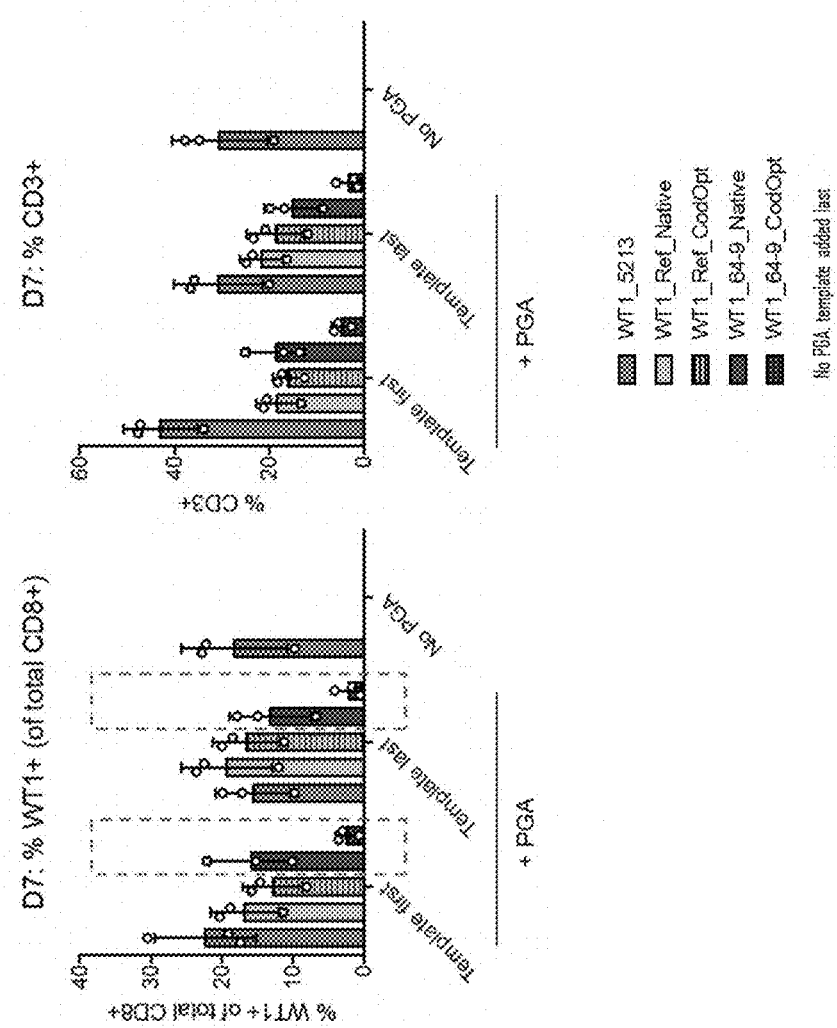
FIG. 132A  FIG. 132B  FIG. 132C

FIG. 140A    linear dsDNA
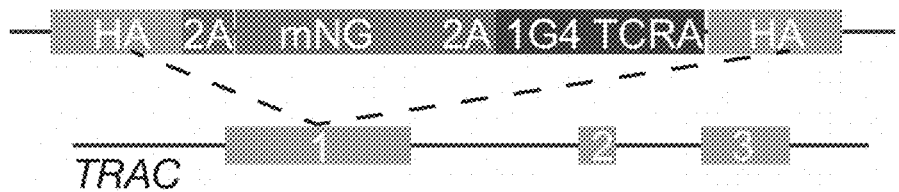
FIG. 140B
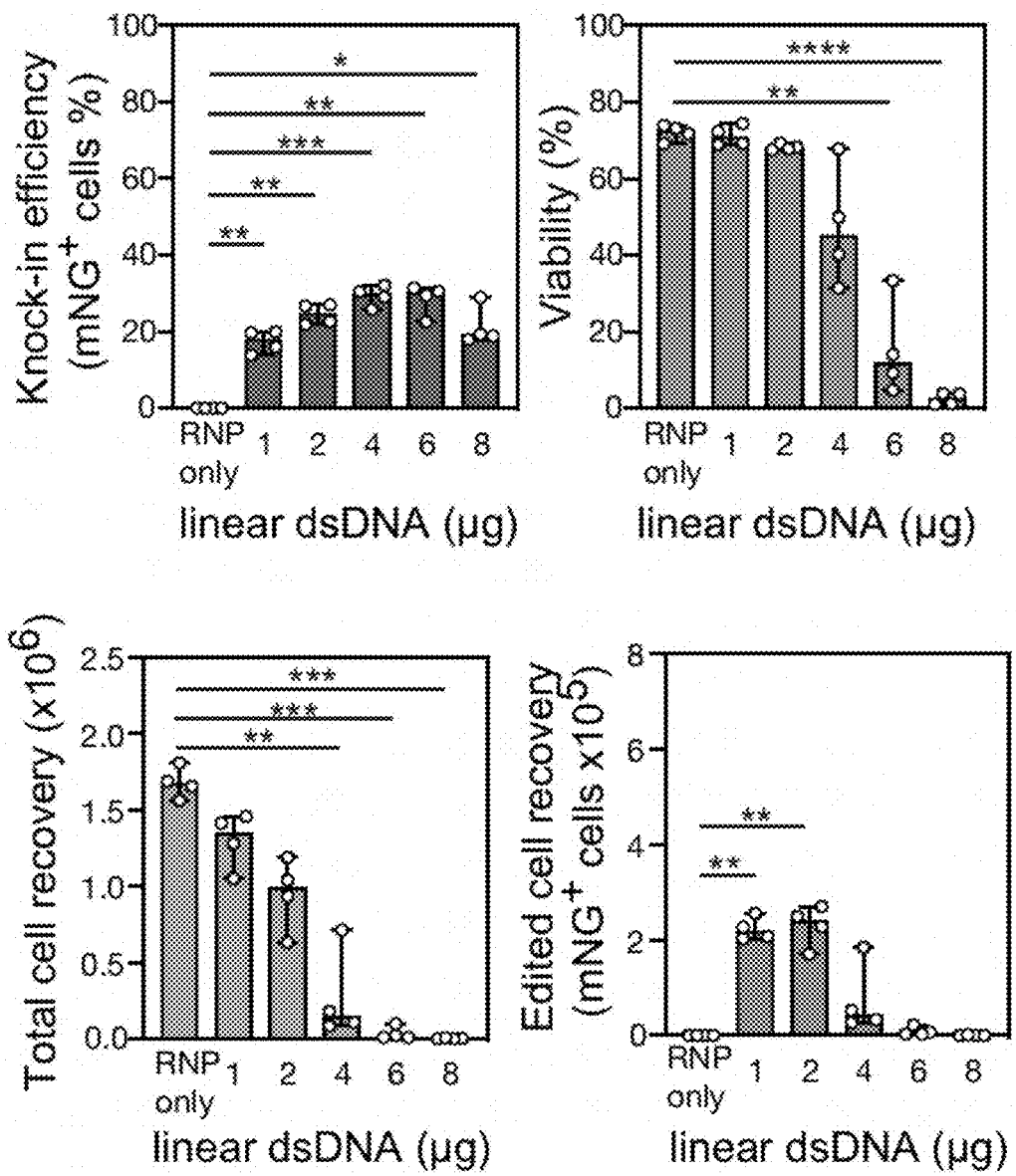

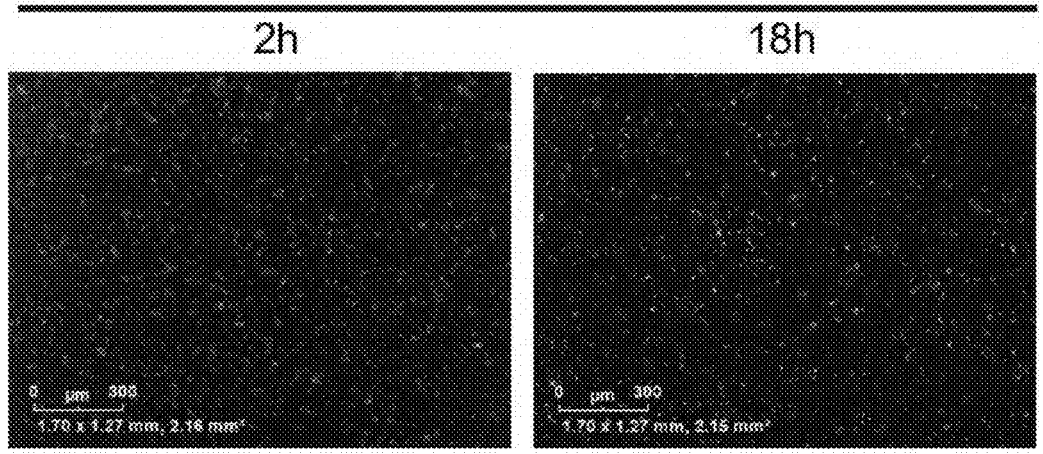
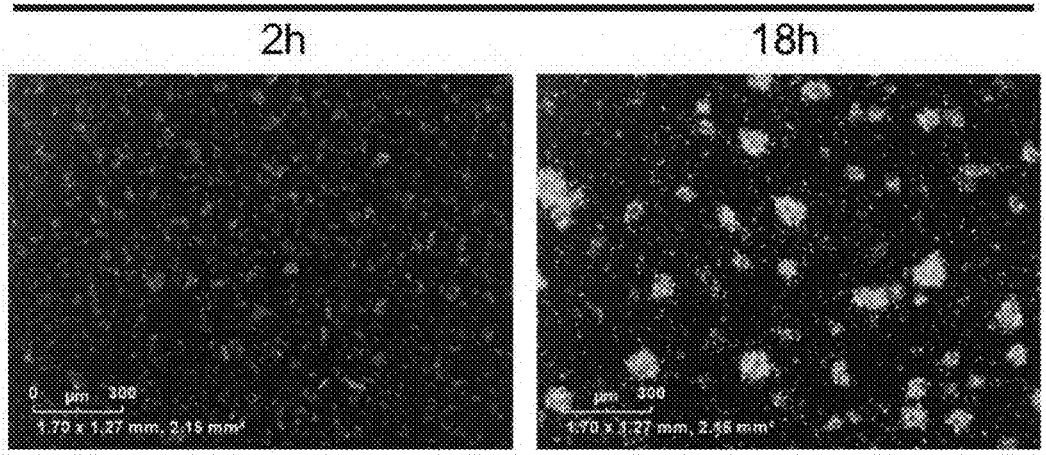
FIG. 143H
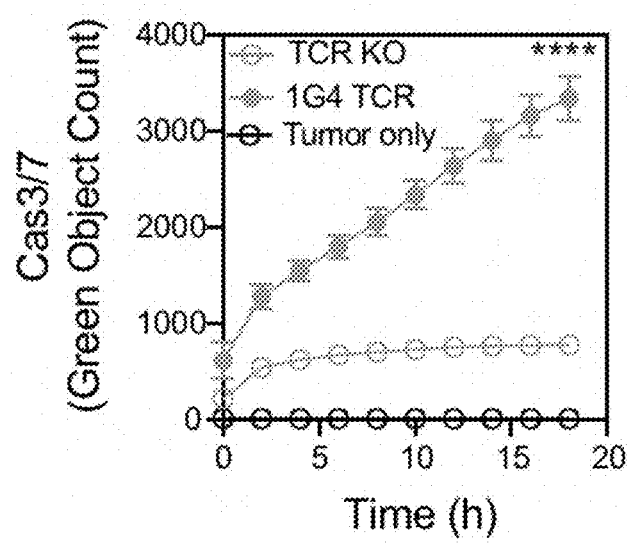
FIG. 143I

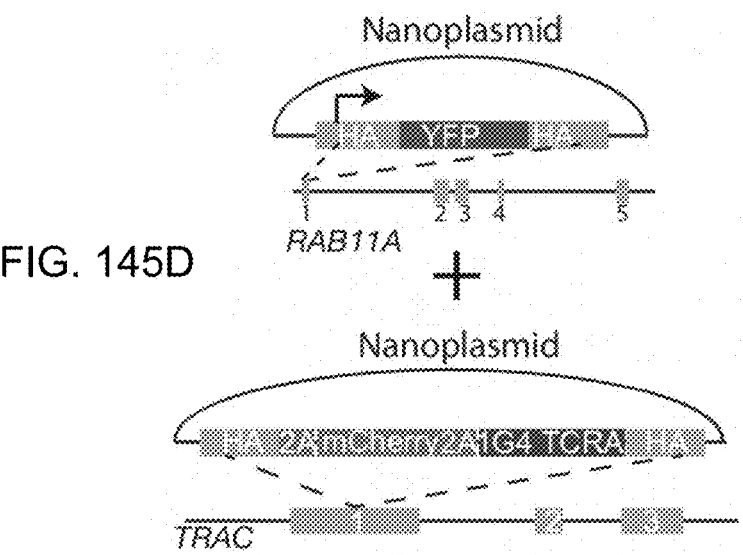
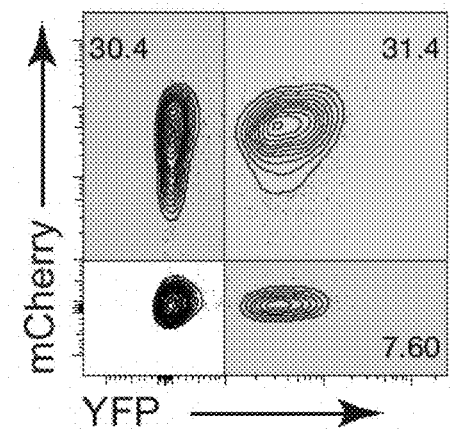
FIG. 145D
FIG. 145E
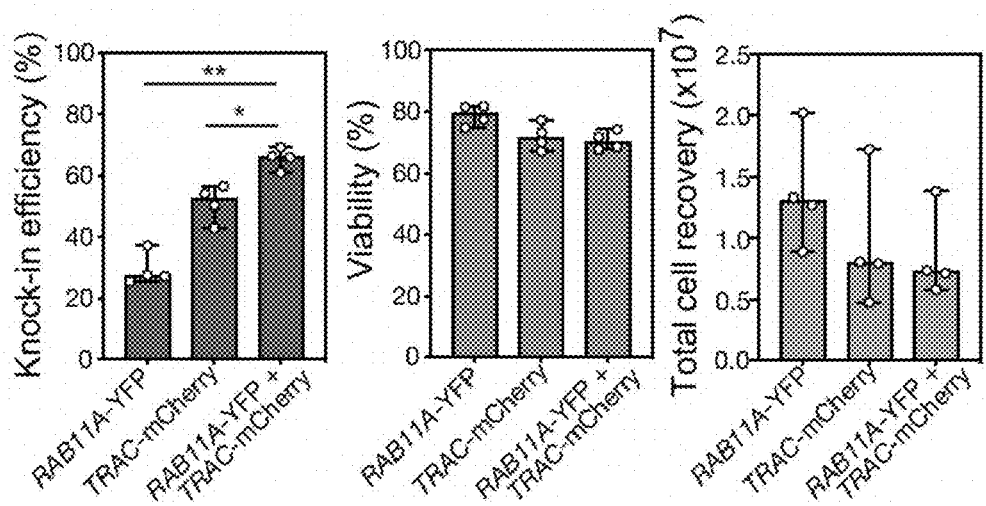
FIG. 145F
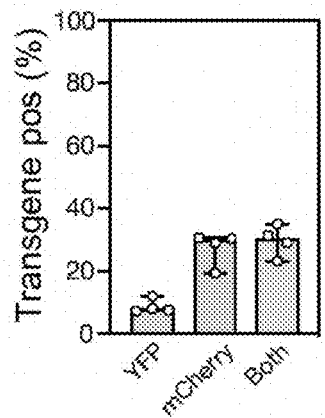
FIG. 145G FIG. 145H
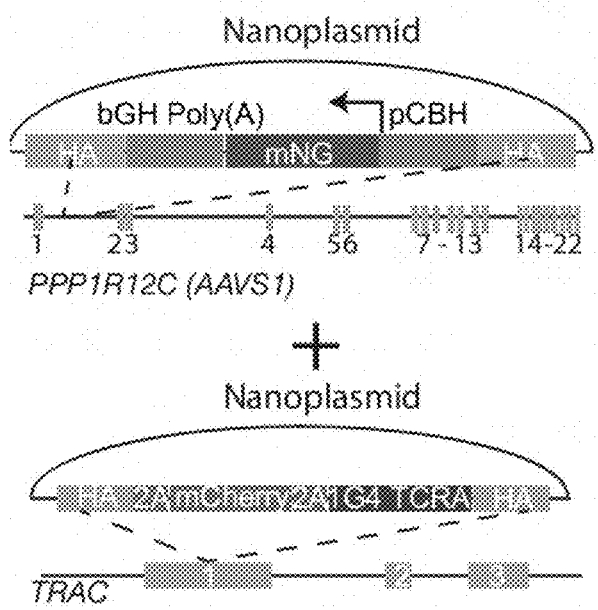
FIG. 145I
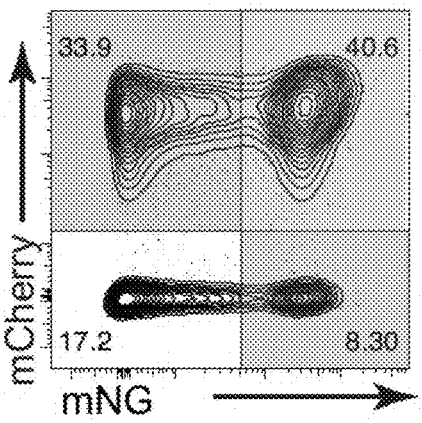
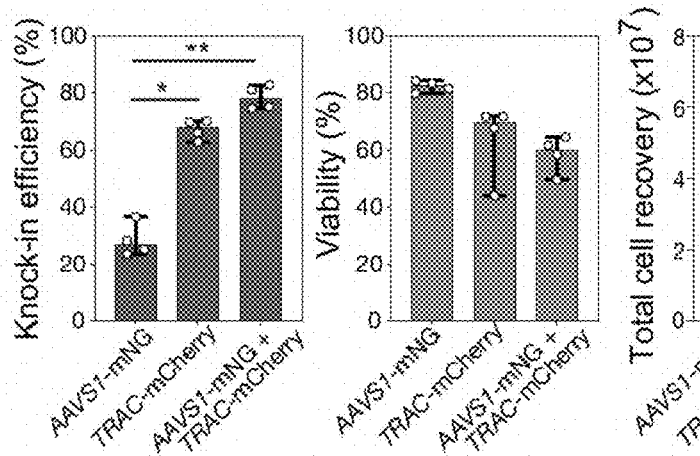
FIG. 145J
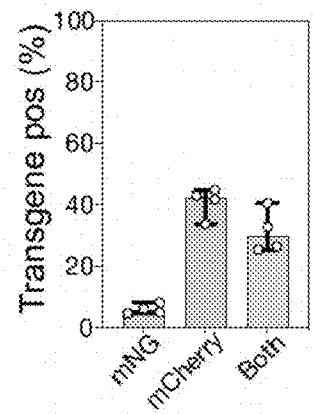
FIG. 145K

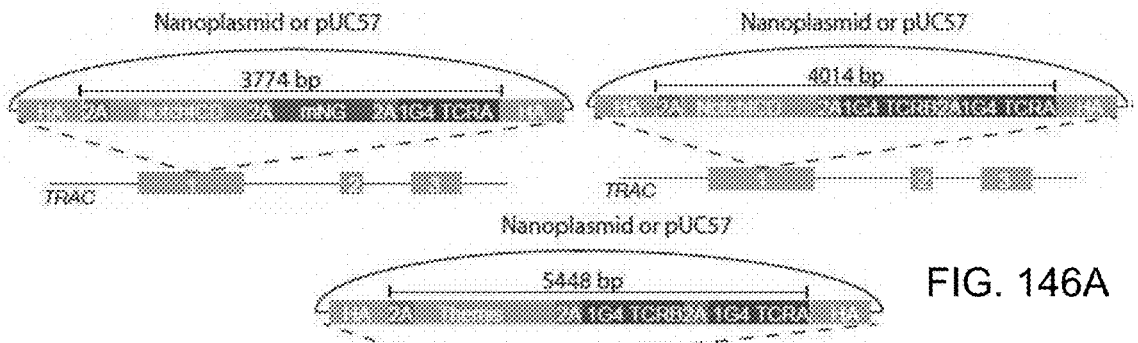
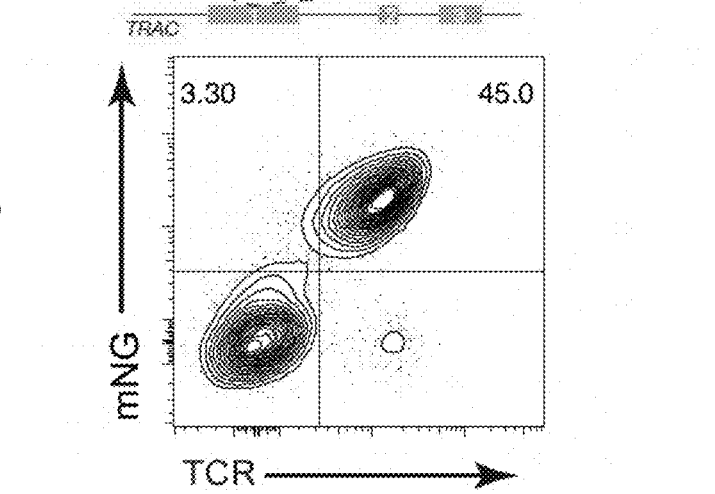
FIG. 146A
FIG. 146B
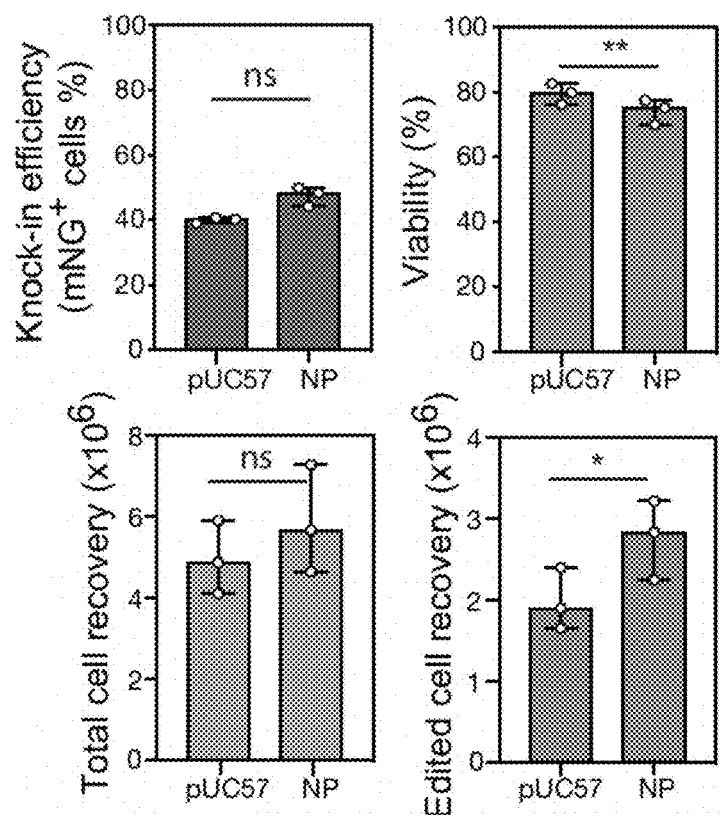
FIG. 146C

FIG. 146D
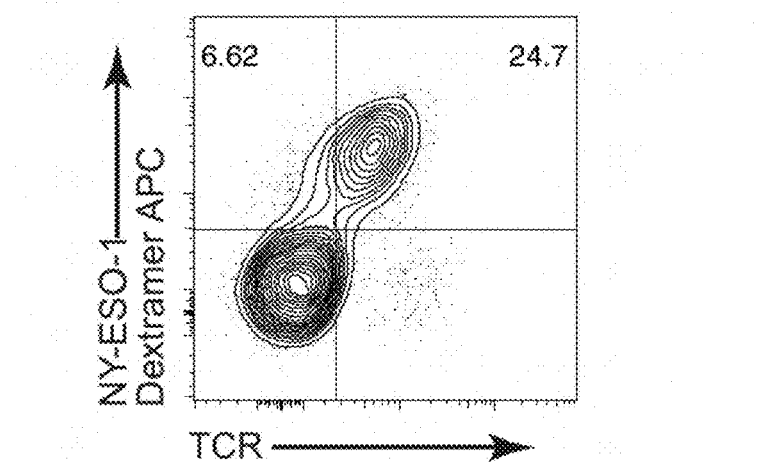
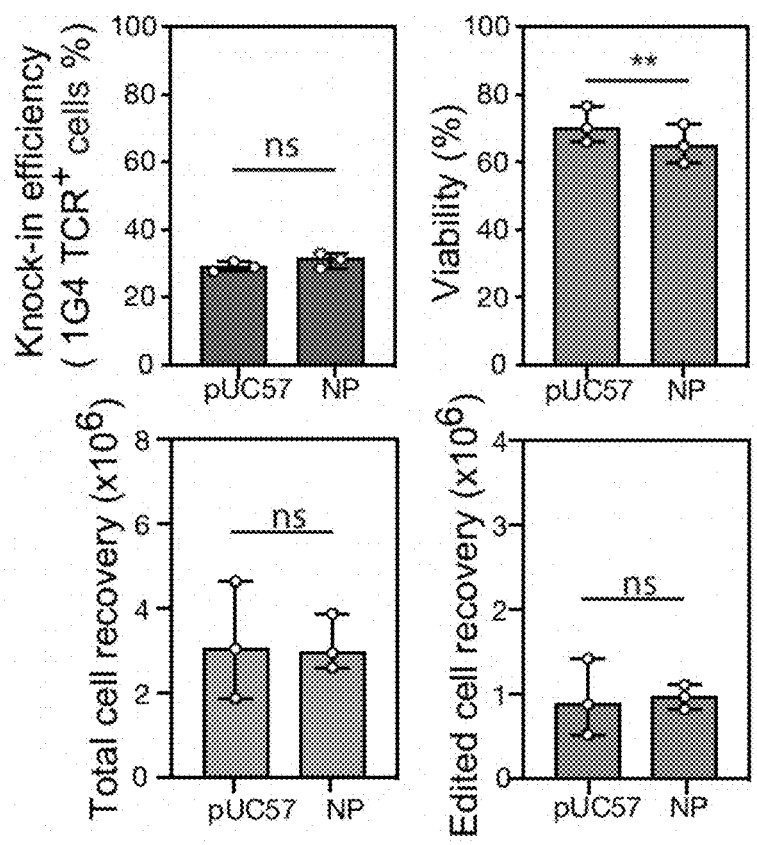
FIG. 146E

FIG. 149O
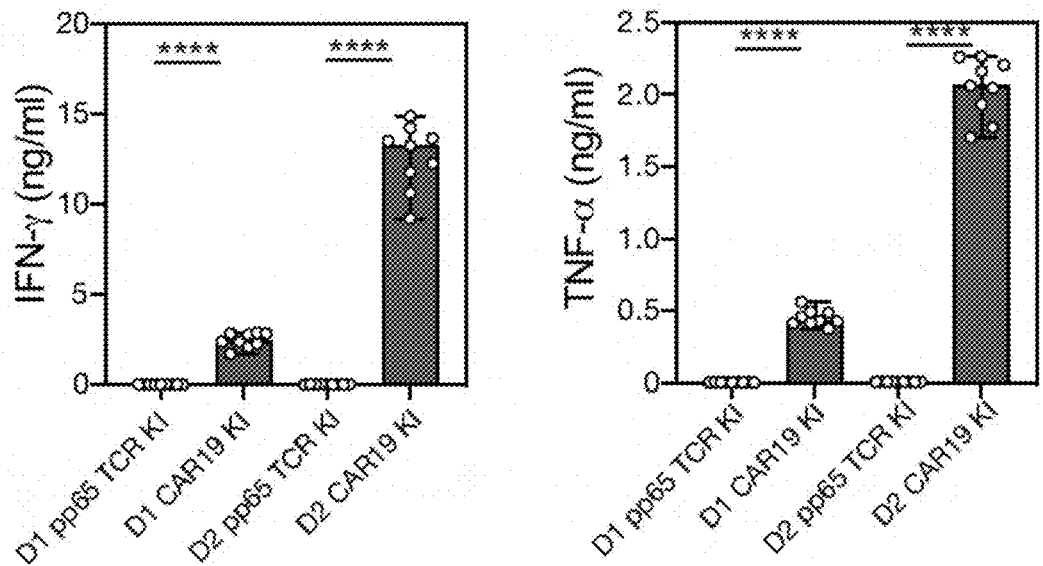
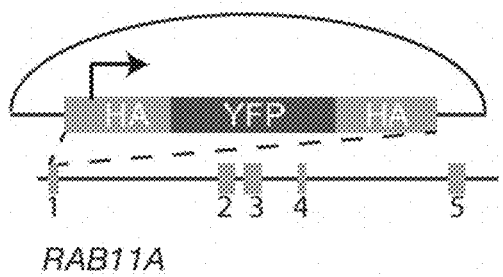
FIG. 150A
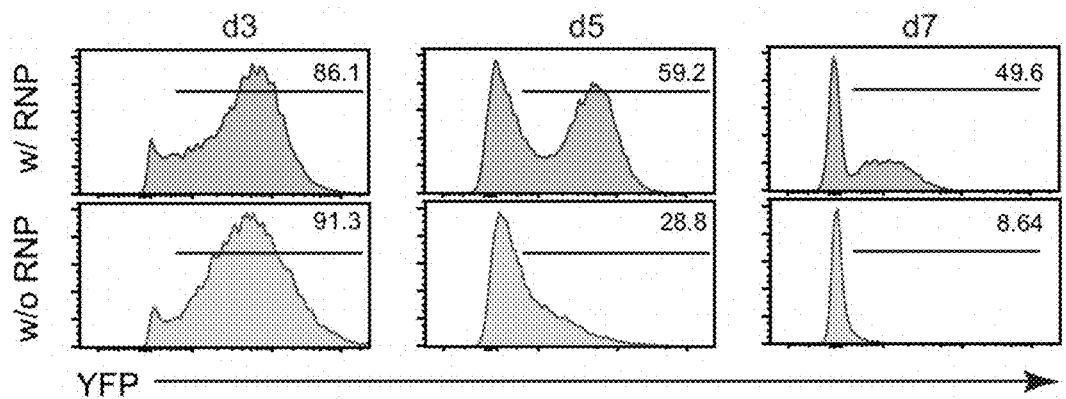
FIG. 150B

SEQUENCE LISTING

```
<160> NUMBER OF SEQ ID NOS: 108

<210> SEQ ID NO 1
<211> LENGTH: 3298
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3298)

<400> SEQUENCE: 1
gagcaatctc ctggtaatgt gatagatttc ccaacttaat gccaacatac cataaacctc      60
ccattctgct aatgcccagc ctaagttggg gagaccactc cagattccaa gatgtacagt     120
ttgctttgct gggcctttt cccatgcctg cctttactct gccagagtta tattgctggg     180
gttttgaaga agatcctatt aaataaaaga ataagcagta ttattaagta gccctgcatt     240
tcaggtttcc ttgagtggca ggccaggcct ggccgtgaac gttcactgaa atcatggcct     300
cttggccaag attgatagct tgtgcctgtc cctgagtccc agtccatcac gagcagctgg     360
tttctaagat gctattccc gtataaagca tgagaccgtg acttgccagc ccacagagc      420 cccgcccttg tccatcactg gcatctggac tccagcctgg gttggggcaa agagggaaat     480
gagatcatgt cctaaccctg atcctcttgt cccacagata tccagaaccc tgaccctgcc     540
gtgtaccagc tgagagactc taaatccagt gacaagtctg tctgcctatt caccgatttt     600
gattctcaaa caaatgtgtc acaaagtaag gattctgatg tgtatatcac agacaaaact     660
gtgctagacg gcagcggcgc caccaacttc agcctgctga gcaggccgg cgacgtggaa      720 gagaaccccg ggcccatgga cagctggacc ttctgctgcg tgagcctgtg catcctggtg     780
gccaagcaca cagacgcagg cgtgatccag agcccaaggc acgaggtgac agagatgggc     840
caggaggtga ccctgaggtg taagcccatc agcggccaca actccctgtt ctggtatagg     900
cagaccatga tgcggggact ggagctgctg atctacttca caacaacgt gcccatcgat      960 gacagcggca tgcccgagga cagattcagc gccaagatgc caacgccag cttcagcacc    1020 ctgaagatcc agcccagcga gcccagagac tccgccgtgt atttctgcgc cagcagcagc    1080
ctgcagtatg agcagtactt cggcccaggc acacgcctga ccgtgacaga ggatctgaag    1140
aacgtgttcc ccctgaggt ggccgtgttt gagccttctg aggccgagat cagccacacc    1200
```

```
cagaaggcca ccctggtgtg cctggcaacc ggcttctacc cagaccacgt ggagctgagc   1260
tggtgggtga acggcaagga ggtgcacagc ggcgtgtcca cagacccaca gcccctgaag   1320
gagcagcccg ccctgaatga ttctagatat tgcctgtcta gccggctgag agtgagcgcc   1380 acctttggc agaaccctag gaatcacttc cgctgtcagg tgcagtttta cggcctgagc   1440
gagaatgacg agtggaccca ggatagggcc aagcctgtga cacagatcgt gtccgccgag   1500
gcatggggaa gggcagattg cggcttcaca agcgagtcct accagcaggg cgtgctgtcc   1560
gccaccatcc tgtatgagat cctgctgggc aaggccacac tgtacgccgt gctggtgagc   1620
gccctggtgc tgatggccat ggtgaagagg aaggactcca ggggccgcgc aaagagaggc   1680
tccggtgcta ccaatttctc actgttgaaa caagcgggcg atgttgaaga aaatcccggt   1740
ccaatgaccc gggtgagcct gctgtgggcc gtggtggtga gcacctgcct ggagagcggc   1800
atggcccaga ccgtgaccca gtctcagccc gagatgagcg tgcaggaggc cgagaccgtg   1860
accctgagct gtacctacga caccagcgag aacaactact acctgttctg gtacaagcag   1920 cccccagcc ggcagatgat cctggtgatc cggcaggagg cctacaagca gcagaacgcc   1980
accgagaaca gattctctgt gaacttccag aaggccgcca agagcttcag cctgaagatc   2040
agcgactccc agctgggcga taccgccatg tatttctgcg ccttcatggg ctactacggc   2100
ggcagccagg gcaatctgat cttttggcaag ggcacaaagc tgagcgtgaa gcccaacatc   2160
cagaaccccg accctgccgt gtaccagctg agggactcca gtctagcga taagagcgtg   2220 tgcctgttca ccgactttga ttcccagaca acgtgagcc agagcaagga ctctgacgtg   2280
tacatcaccg acaagacagt gctggatatg aggtctatgg acttcaagag caacagtgct   2340
gtggcctgga gcaacaaatc tgactttgca tgtgcaaacg ccttcaacaa cagcattatt   2400
ccagaagaca ccttcttccc cagcccagaa agttcctgtg atgtcaagct ggtcgagaaa   2460
agctttgaaa cagatacgaa cctaaacttt caaaacctgt cagtgattgg gttccgaatc   2520
ctcctcctga aagtggccgg gtttaatctg ctcatgacgc tgcggctgtg gtccagctga   2580
ctagagctcg ctgatcagcc tcgactgtgc cttctagttg ccagccatct gttgtttgcc   2640
cctcccccgt gccttccttg acctggaag gtgccactcc cactgtcctt tcctaataaa   2700
atgaggaaat tgcatcgcat tgtctgagta ggtgtcattc tattctgggg ggtggggtgg   2760
ggcaggacag caaggggag gattgggaag agaatagcag gcatgctggg gaatgaggtc   2820
tatggacttc aagagcaaca gtgctgtggc ctggagcaac aaatctgact ttgcatgtgc   2880
aaacgccttc aacaacagca ttattccaga agacaccttc ttccccagcc caggtaaggg   2940
cagctttggt gccttcgcag ctgtttcct tgcttcagga atggcaggt tctgcccaga   3000 gctctggtca atgatgtcta aaactcctct gattggtggt ctcggcctta tccattgcca   3060
ccaaaaccct cttttttacta agaaacagtg agccttgttc tggcagtcca gagaatgaca   3120
cgggaaaaaa gcagatgaag agaaggtggc aggagagggc acgtggccca gcctcagtct   3180
ctccaactga gttcctgcct gcctgccttt gctcagactg tttgcccctt actgctcttc   3240
taggcctcat tctaagcccc ttctccaagt tgcctctcct tatttctccc tgtctgcc    3298
```

<210> SEQ ID NO 2
<211> LENGTH: 2781
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature

<222> LOCATION: (1)..(2781)

<400> SEQUENCE: 2

| | | | | | |
|---|---|---|---|---|---|
| gagcaatctc | ctggtaatgt | gatagatttc | ccaacttaat | gccaacatac | cataaacctc | 60 |
| ccattctgct | aatgcccagc | ctaagttggg | gagaccactc | cagattccaa | gatgtacagt | 120 |
| ttgctttgct | gggcctttt | cccatgcctg | cctttactct | gccagagtta | tattgctggg | 180 |
| gttttgaaga | agatcctatt | aaataaaaga | ataagcagta | ttattaagta | gcccctgcatt | 240 |
| tcaggtttcc | ttgagtggca | ggccaggcct | ggccgtgaac | gttcactgaa | atcatggcct | 300 |
| cttggccaag | attgatagct | tgtgcctgtc | cctgagtccc | agtccatcac | gagcagctgg | 360 |
| tttctaagat | gctatttccc | gtataaagca | tgagaccgtg | acttgccagc | cccacagagc | 420 |
| cccgcccttg | tccatcactg | gcatctggac | tccagcctgg | gttggggcaa | agagggaaat | 480 |
| gagatcatgt | cctaaccctg | atcctcttgt | cccacagata | tccagaaccc | tgaccctgcc | 540 |
| gtgtaccagc | tgagagactc | taaatccagt | gacaagtctg | tctgcctatt | caccgatttt | 600 |
| gattctcaaa | caaatgtgtc | acaaagtaag | gattctgatg | tgtatatcac | agacaaaact | 660 |
| gtgctagacg | gaagcggaga | aggtagaggt | tctctcctca | cttgtggtga | tgttgaagaa | 720 |
| aaccctggtc | caatgagcat | aggattgctg | tgctgtgcag | ccctgtccct | tttgtgggca | 780 |
| gggccagtca | acgcgggcgt | tacgcagacc | ccaaaattcc | aagtcctcaa | gacgggccaa | 840 |
| tccatgacat | tgcaatgtgc | gcaggatatg | aatcacgaat | acatgagttg | gtaccgccaa | 900 |
| gaccccggaa | tgggactccg | gcttatacat | tatagtgttg | gcgctggaat | cactgaccag | 960 |
| ggagaagtgc | cgaatggata | caacgtctcc | aggagcacca | cagaggactt | tccgctgcgc | 1020 |
| ctcctgagcg | cggctccgtc | acaaaccagt | gtttacttt | gtgcatcaag | ttatgtaggc | 1080 |
| aacacggag | aactcttttt | tggcgaaggt | tccaggttga | ctgttctcga | ggacctcaaa | 1140 |
| aatgtttttc | caccagaggt | cgcagtattt | gagcctagtg | aggctgaaat | ttctcacact | 1200 |
| cagaaggcga | ccctcgtctg | tctggcgaca | ggatttacc | ccgatcatgt | tgaacttcc | 1260 |
| tggtgggtca | acgggaagga | ggttcacagt | ggggtatcaa | ctgatcccca | accactgaag | 1320 |
| gaacagccag | cactcaatga | ctcacggtat | tgcctttctt | ccaggctgag | agtttctgct | 1380 |
| acgttctggc | agaatcctag | aaatcatttc | cgatgccagg | tccaattcta | cggtcttagc | 1440 |
| gaaaatgacg | agtggactca | ggacagggca | aagcccgtga | cgcaaattgt | gtcagccgag | 1500 |
| gcttggggca | gagcggactg | cggcttcacg | tcagagagtt | accagcaggg | tgttctcagt | 1560 |
| gcgactatcc | tgtacgaaat | attgcttggc | aaggcaacgt | tgtatgcagt | tctggtctct | 1620 |
| gctctcgtac | tcatggcaat | ggtaaagcgg | aaagattcca | gaggccgcgc | caagcgcggc | 1680 |
| tccggtgcta | ccaatttctc | actgttgaaa | caagcgggcg | atgttgaaga | aaatcccggt | 1740 |
| ccaatggaga | cattgctcgg | cttgttgatc | ttgtggctcc | agctgcaatg | ggtatcatct | 1800 |
| aagcaagagg | ttacgcaaat | tcctgcagct | cttagcgtac | cggagggcga | gaatttggtc | 1860 |
| cttaattgtt | ctttcaccga | ctcagcgatc | tataatctcc | aatggtttcg | acaagacccc | 1920 |
| ggtaaaggcc | tgacctcttt | gttgctgata | cagagttccc | agcgcgagca | gacgtccggt | 1980 |
| aggcttaatg | caagtctgga | taagagctct | ggacgctcaa | cactctacat | agctgcttca | 2040 |
| caaccggggg | atagtgcaac | ttatctgtgt | gctgtgcggc | cactttatgg | cggatcctac | 2100 |
| attcctactt | tcgggagggg | aactagtctc | atcgtgcacc | catacattca | gaatccagac | 2160 |
| cctgcggtgt | accagctgag | ggactcaaaa | agttctgata | agtccgtctg | cctgttcact | 2220 |
| gactttgact | ctcaaacaaa | tgtatcccag | tctaaagatt | ccgatgttta | catcaccgac | 2280 |

```
aagaccgtgc tcgatatgag gtctatggac ttcaagagca acagtgctgt ggcctggagc    2340
aacaaatctg actttgcatg tgcaaacgcc ttcaacaaca gcattattcc agaagacacc    2400
ttcttcccca gcccaggtaa gggcagcttt ggtgccttcg caggctgttt ccttgcttca    2460
ggaatggcca ggttctgccc agagctctgg tcaatgatgt ctaaaactcc tctgattggt    2520
ggtctcggcc ttatccattg ccaccaaaac cctcttttta ctaagaaaca gtgagccttg    2580
ttctggcagt ccagagaatg acacgggaaa aagcagatg aagagaaggt ggcaggagag     2640
ggcacgtggc ccagcctcag tctctccaac tgagttcctg cctgcctgcc tttgctcaga    2700
ctgtttgccc cttactgctc ttctaggcct cattctaagc cccttctcca agttgcctct    2760
ccttatttct ccctgtctgc c                                              2781
```

```
<210> SEQ ID NO 3
<211> LENGTH: 2615
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2615)

<400> SEQUENCE: 3
```

```
atattgctgg ggttttgaag aagatcctat taaataaaag aataagcagt attattaagt      60
agccctgcat ttcaggtttc cttgagtggc aggccaggcc tggccgtgaa cgttcactga     120
aatcatggcc tcttggccaa gattgatagc ttgtgcctgt ccctgagtcc cagtccatca     180
cgagcagctg gtttctaaga tgctatttcc cgtataaagc atgagaccgt gacttgccag     240
ccccacagag ccccgccctt gtccatcact ggcatctgga ctccagcctg gttggggca     300 aagagggaaa tgagatcatg tcctaaccct gatcctcttg tcccacagat atccagaacc     360
ctgaccctgc cgtgtaccag ctgagagact ctaaatccag tgacaagtct gtctgcctat     420
tcaccgattt tgattctcaa acaaatgtgt cacaaagtaa ggattctgat gtgtatatca     480
cagacaaaac tgtgctagac ggaagcggag aaggtagagg ttctctcctc acttgtggtg     540
atgttgaaga aaaccctggt ccaatgagca accaggtgct gtgctgcgtg gtgctgtgct     600
ttctgggagc caacaccgtg gacggcggca tcacccagag cccaaagtac ctgttccgga     660
aggagggcca gaacgtgacc ctgagctgtg agcagaacct gaaccacgac gccatgtact     720
ggtataggca ggaccccgga cagggactgc ggctgatcta ctacagccag atcgtgaacg     780
acttccagaa gggcgacatc gccgagggct acagcgtgag ccgggagaag aaggagagct     840
tccccctgac agtgaccagc gcccagaaga acccccaccgc cttctatctg tgcgccagct     900
ccgtgaccgg cggcttctct tatgagcagt acttcggccc aggcacacgc ctgaccgtga     960
cagaggatct gaagaacgtg ttcccccctg aggtggccgt gtttgagcct tctgaggccg    1020
agatcagcca cacccagaag gccaccctgg tgtgcctggc aaccggcttc tacccagacc    1080
acgtggagct gagctggtgg gtgaacggca aggaggtgca cagcggcgtg tccacagacc    1140
cacagcccct gaaggagcag cccgccctga atgattctag atattgcctg tctagccggc    1200
tgagagtgag cgccaccttt tggcagaacc ctaggaatca cttccgctgt caggtgcagt    1260
tttacggcct gagcgagaat gacgagtgga cccaggatag gccaagcct gtgacacaga     1320 tcgtgtccgc cgaggcatgg ggaagggcag attgcggctt cacaagcgag tcctaccagc    1380
agggcgtgct gtccgccacc atcctgtatg agatcctgct gggcaaggcc acactgtacg    1440
```

```
ccgtgctggt gagcgccctg gtgctgatgg ccatggtgaa gaggaaggac tccaggggcc    1500
gcgcaaagag aggctccggt gctaccaatt tctcactgtt gaaacaagcg ggcgatgttg    1560
aagaaaatcc cggtccaatg gccggcatcc gggccctgtt catgtacctg tggctgcagc    1620
tggactgggt gtcccggggc gagagcgtgg gcctgcacct gcccaccctg agcgtgcagg    1680
agggcgataa cagcatcatc aactgtgcct acagcaacag cgccagcgac tacttcatct    1740
ggtacaagca ggagagcggc aagggccccc agttcatcat cgacatccgg agcaacatgg    1800
acaagcggca gggccagaga gtgaccgtgc tgctgaataa gaccgtgaag cacctgagcc    1860
tgcagatcgc cgccacccag ccaggcgatt ctgccgtgta tttctgcgcc gagaacatcg    1920
cctacagcgg cagccggctg acctttggcg agggcacaca gctgaccgtg aaccccgaca    1980
tccagaaccc cgaccctgcc gtgtaccagc tgagggactc caagtctagc gataagagcg    2040
tgtgcctgtt caccgacttt gattcccaga caaacgtgag ccagagcaag gactctgacg    2100
tgtacatcac cgacaagaca gtgctggata tgaggtctat ggacttcaag agcaacagtg    2160
ctgtggcctg gagcaacaaa tctgactttg catgtgcaaa cgccttcaac aacagcatta    2220
ttccagaaga caccttcttc cccagcccag gtaagggcag cttttggtgcc ttcgcaggct    2280 gtttccttgc ttcaggaatg ccaggttct gcccagagct ctggtcaatg atgtctaaaa     2340
ctcctctgat tggtggtctc ggccttatcc attgccacca aaaccctctt tttactaaga    2400
aacagtgagc cttgttctgg cagtccagag aatgacacgg gaaaaaagca gatgaagaga    2460
aggtggcagg agagggcacg tggcccagcc tcagtctctc caactgagtt cctgcctgcc    2520
tgcctttgct cagactgttt gcccttact gctcttctag gcctcattct aagccccttc     2580
tccaagttgc ctctccttat ttctccctgt ctgcc                               2615
```

<210> SEQ ID NO 4
<211> LENGTH: 2597
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2597)

<400> SEQUENCE: 4

```
atattgctgg ggttttgaag aagatcctat taaataaaag aataagcagt attattaagt      60
agccctgcat ttcaggtttc cttgagtggc aggccaggcc tggccgtgaa cgttcactga    120
aatcatggcc tcttggccaa gattgatagc ttgtgcctgt ccctgagtcc cagtccatca    180
cgagcagctg gtttctaaga tgctatttcc cgtataaagc atgagaccgt gacttgccag    240
ccccacagag ccccgcccctt gtccatcact ggcatctgga ctccagcctg ggttggggca   300
aagagggaaa tgagatcatg tcctaaccct gatcctcttg tcccacagat atccagaacc    360
ctgaccctgc cgtgtaccag ctgagagact ctaaatccag tgacaagtct gtctgcctat    420
tcaccgattt tgattctcaa acaaatgtgt cacaaagtaa ggattctgat gtgtatatca    480
cagacaaaac tgtgctagac ggaagcggag aaggtagagg ttctctcctc acttgtggtg    540
atgttgaaga aaaccctggt ccaatgagcc tgggcctgct gtgctgcggc gccttcagcc    600
tgctgtgggc cggccccgtg aacgcaggcg tgacccagac cccaaagttc cgggtgctga    660
agaccggcca gagcatgacc ctgctgtgtg cccaggacat gaaccacgag tacatgtact    720
ggtataggca ggaccccgga atgggactgc ggctgatcca ctacagcgtg ggcgagggca    780
```

```
ccaccgccaa gggcgaggtg cccgacggct acaacgtgag ccggctgaag aagcagaact    840
tcctgctggg cctggagagc gccgccccca gccagaccag cgtgtatttc tgcgccagct    900
cctacggctt caaccagccc cagcacttcg gcgacggcac acgcctgagc atcctggagg    960
atctgaacaa ggtgttcccc cctgaggtgg ccgtgtttga gccttctgag gccgagatca   1020
gccacaccca gaaggccacc ctggtgtgcc tggcaaccgg cttcttccca gaccacgtgg   1080
agctgagctg tgggtgaac ggcaaggagt gcacagcgg cgtgtccaca gacccacagc    1140
ccctgaagga gcagcccgcc ctgaatgatt ctagatattg cctgtctagc cggctgagag   1200
tgagcgccac cttttggcag aaccctagga atcacttccg ctgtcaggtg cagttttacg   1260
gcctgagcga gaatgacgag tggacccagg atagggccaa gcctgtgaca cagatcgtgt   1320
ccgccgaggc atggggaagg gcagattgcg gcttcacaag cgtgtcctac cagcagggcg   1380
tgctgtccgc caccatcctg tatgagatcc tgctgggcaa ggccacactg tacgccgtgc   1440
tggtgagcgc cctggtgctg atggccatgg tgaagaggaa ggacttccgc gcaaagagag   1500
gctccggtgc taccaatttc tcactgttga acaagcggg cgatgttgaa gaaaatcccg    1560
gtccaatgaa gagcctgcgg gtgctgctgg tgatcctgtg gctgcagctg agctgggtgt   1620
ggtcccagca gaaggaggtg gagcagaaca gcggcccccct gagcgtgccc gagggcgcca   1680
tcgccagcct gaactgtacc tacagcgacc ggggcagcca gagcttcttc tggtacagac   1740
agtacagcgg caagagcccc gagctgatca tgttcatcta cagcaacggc gacaaggagg   1800
acggcagatt caccgcccag ctgaataagg ccagccagta cgtgagcctg ctgatccggg   1860
actcccagcc aagcgattct gccacctatc tgtgcgccgt gccctacaac aacaacgaca   1920
tgcggtttgg cgccggcaca agactgaccg tgaagcccaa catccagaac cccgaccctg   1980
ccgtgtacca gctgagggac tccaagtcta gcgataagag cgtgtgcctg ttcaccgact   2040
ttgattccca gacaaacgtg agccagagca aggactctga cgtgtacatc accgacaaga   2100
cagtgctgga tatgaggtct atggacttca agagcaacag tgctgtggcc tggagcaaca   2160
aatctgactt tgcatgtgca aacgccttca caacagcat tattccagaa gacaccttct    2220
tccccagccc aggtaagggc agctttggtg ccttcgcagg ctgtttcctt gcttcaggaa   2280
tggccaggtt ctgcccagag ctctggtcaa tgatgtctaa aactcctctg attggtggtc   2340
tcggccttat ccattgccac caaaaccctc tttttactaa gaaacagtga gccttgttct   2400
ggcagtccag agaatgacac gggaaaaaag cagatgaaga gaaggtggca ggagagggca   2460
cgtggcccag cctcagtctc tccaactgag ttcctgcctg cctgcctttg ctcagactgt   2520
ttgcccctta ctgctcttct aggcctcatt ctaagcccct tctccaagtt gcctctcctt   2580
atttctccct gtctgcc                                                  2597
```

<210> SEQ ID NO 5
<211> LENGTH: 2790
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2790)

<400> SEQUENCE: 5

```
gagcaatctc ctggtaatgt gatagatttc ccaacttaat gccaacatac cataaacctc     60
ccattctgct aatgcccagc ctaagttggg gagaccactc cagattccaa gatgtacagt    120
```

```
ttgctttgct gggccttttt cccatgcctg cctttactct gccagagtta tattgctggg    180
gttttgaaga agatcctatt aaataaaaga ataagcagta ttattaagta gccctgcatt    240
tcaggtttcc ttgagtggca ggccaggcct ggccgtgaac gttcactgaa atcatggcct    300
cttggccaag attgatagct tgtgcctgtc cctgagtccc agtccatcac gagcagctgg    360
tttctaagat gctatttccc gtataaagca tgagaccgtg acttgccagc cccacagagc    420
cccgcccttg tccatcactg gcatctggac tccagcctgg gttggggcaa agagggaaat    480
gagatcatgt cctaaccctg atcctcttgt cccacagata tccagaaccc tgaccctgcc    540
gtgtaccagc tgagagactc taaatccagt gacaagtctg tctgcctatt caccgatttt    600
gattctcaaa caaatgtgtc acaaagtaag gattctgatg tgtatatcac agacaaaact    660
gtgctagacg gaagcggaga aggtagaggt tctctcctca cttgtggtga tgttgaagaa    720
aaccctggtc aatggacagc tggaccttc tgctgcgtga gcctgtgcat cctggtggcc    780
aagcacacag acgcaggcgt gatccagagc ccaaggcacg aggtgacaga gatgggccag    840
gaggtgaccc tgaggtgtaa gcccatcagc ggccacaact ccctgttctg gtataggcag    900
accatgatgc ggggactgga gctgctgatc tacttcaaca caacgtgcc catcgatgac    960
agcggcatgc ccgaggacag attcagcgcc aagatgccca cgccagctt cagcaccctg   1020
aagatccagc ccagcgagcc cagagactcc gccgtgtatt tctgcgccag cagcagcctg   1080
cagtatgagc agtacttcgg cccaggcaca cgcctgaccg tgacagagga tctgaagaac   1140
gtgttccccc ctgaggtggc cgtgtttgag ccttctgagg ccgagatcag ccacacccag   1200
aaggccaccc tggtgtgcct ggcaaccggc ttctacccag accacgtgga gctgagctgg   1260
tgggtgaacg gcaaggaggt gcacagcggc gtgtccacag acccacagcc cctgaaggag   1320
cagcccgccc tgaatgattc tagatattgc ctgtctagcc ggctgagagt gagcgccacc   1380
ttttggcaga accctaggaa tcacttccgc tgtcaggtgc agttttacgg cctgagcgag   1440
aatgacgagt ggacccagga tagggccaag cctgtgacac agatcgtgtc cgccgaggca   1500
tggggaaggg cagattgcgg cttcacaagc gagtcctacc agcagggcgt gctgtccgcc   1560
accatcctgt atgagatcct gctgggcaag gccacactgt acgccgtgct ggtgagcgcc   1620
ctggtgctga tggccatggt gaagaggaag gactccaggg gccgcgcaaa gagaggctcc   1680
ggtgctacca atttctcact gttgaaacaa gcgggcgatg ttgaagaaaa tcccggtcca   1740
atgacccggg tgagcctgct gtgggccgtg gtggtgagca cctgcctgga gagcggcatg   1800
gcccagaccg tgacccagtc tcagcccgag atgagcgtgc aggaggccga gaccgtgacc   1860
ctgagctgta cctacgacac cagcgagaac aactactacc tgttctggta caagcagccc   1920
cccagccggc agatgatcct ggtgatccgg caggaggcct acaagcagca gaacgccacc   1980
gagaacagat tctctgtgaa cttccagaag gccgccaaga gcttcagcct gaagatcagc   2040
gactcccagc tgggcgatac cgccatgtat ttctgcgcct tcatgggcta ctacggcggc   2100
agccagggca atctgatctt tggcaagggc acaaagctga cgtgaagcc caacatccag   2160
aaccccgacc ctgccgtgta ccagctgagg gactccaagt ctagcgataa gagcgtgtgc   2220
ctgttcaccg actttgattc ccagacaaac gtgagccaga cgaggactc tgacgtgtac   2280
atcaccgaca agacagtgct ggatatgagg tctatggact tcaagagcaa cagtgctgtg   2340
gcctggagca caaatctga ctttgcatgt gcaaacgcct tcaacaacag cattattcca   2400
gaagacacct tcttccccag cccaggtaag ggcagctttg gtgccttcgc aggctgtttc   2460
```

| | |
|---|---|
| cttgcttcag gaatggccag gttctgccca gagctctggt caatgatgtc taaaactcct | 2520 |
| ctgattggtg gtctcggcct tatccattgc caccaaaacc ctcttttttac taagaaacag | 2580 |
| tgagccttgt tctggcagtc cagagaatga cacgggaaaa aagcagatga agagaaggtg | 2640 |
| gcaggagagg gcacgtggcc cagcctcagt ctctccaact gagttcctgc ctgcctgcct | 2700 |
| ttgctcagac tgtttgcccc ttactgctct tctaggcctc attctaagcc ccttctccaa | 2760 |
| gttgcctctc cttatttctc cctgtctgcc | 2790 |

```
<210> SEQ ID NO 6
<211> LENGTH: 2612
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2612)

<400> SEQUENCE: 6
```

| | |
|---|---|
| atattgctgg ggttttgaag aagatcctat taaataaaag aataagcagt attattaagt | 60 |
| agccctgcat ttcaggtttc cttgagtggc aggccaggcc tggccgtgaa cgttcactga | 120 |
| aatcatggcc tcttggccaa gattgatagc ttgtgcctgt ccctgagtcc cagtccatca | 180 |
| cgagcagctg gtttctaaga tgctatttcc cgtataaagc atgagaccgt gacttgccag | 240 |
| ccccacagag ccccgccctt gtccatcact ggcatctgga ctccagcctg ggttggggca | 300 |
| aagagggaaa tgagatcatg tcctaaccct gatcctcttg tcccacagat atccagaacc | 360 |
| ctgaccctgc cgtgtaccag ctgagagact ctaaatccag tgacaagtct gtctgcctat | 420 |
| tcaccgattt tgattctcaa acaaatgtgt cacaaagtaa ggattctgat gtgtatatca | 480 |
| cagacaaaac tgtgctagac ggaagcggag aaggtagagg ttctctcctc acttgtggtg | 540 |
| atgttgaaga aaaccctggt ccaatgggca cccggctgtt cttctacgtg gccctgtgcc | 600 |
| tgctgtgggc cggccaccgg gacgcaggca tcacccagag cccaaggtac aagatcacag | 660 |
| agaccggccg gcaggtgacc ctgatgtgtc accagcctg gagccacagc tacatgttct | 720 |
| ggtataggca ggacctggga cacggactgc ggctgatcta ctacagcgcc gccgccgaca | 780 |
| tcaccgataa gggcgaggtg cccgacggct acgtggtgag ccggagcaag accgagaact | 840 |
| ccccctgac actggagagc gccacccgga gccagaccag cgtgtatttc tgcgccagct | 900 |
| ccgagggcgg cctgaacacc gaggccttct tcggccaggg cacacgcctg accgtggtgg | 960 |
| aggatctgaa caaggtgttc ccccctgagg tggccgtgtt tgagccttct gaggccgaga | 1020 |
| tcagccacac ccagaaggcc accctggtgt gcctggcaac cggcttcttc ccagaccacg | 1080 |
| tggagctgag ctggtgggtg aacggcaagg aggtgcacag cggcgtgtcc acagacccac | 1140 |
| agccctgaa ggagcagccc gccctgaatg attctagata ttgcctgtct agccggctga | 1200 |
| gagtgagcgc cacctttgg cagaacccta ggaatcactt ccgctgtcag gtgcagttt | 1260 |
| acggcctgag cgagaatgac gagtggaccc aggataggc caagcctgtg acacagatcg | 1320 |
| tgtccgccga ggcatgggga agggcagatt gcggcttcac aagcgtgtcc taccagcagg | 1380 |
| gcgtgctgtc cgccaccatc ctgtatgaga tcctgctggg caaggccaca ctgtacgccg | 1440 |
| tgctggtgag cgccctggtg ctgatggcca tggtgaagag gaaggacttc gcgcaaaga | 1500 |
| gaggctccgg tgctaccaat ttctcactgt tgaaacaagc gggcgatgtt gaagaaaatc | 1560 |
| ccggtccaat gagcctgagc agcctgctga aggtggtgac cgccagcctg tggctgggcc | 1620 |

| | |
|---|---|
| ccggcatcgc ccagaagatc acccagaccc agcccggcat gttcgtgcag gagaaggagg | 1680 |
| ccgtgaccct ggactgtacc tacgacacca gcgaccagag ctacggcctg ttctggtaca | 1740 |
| agcagcccag cagcggcgag atgatcttcc tgatctacca gggcagctac gacgagcaga | 1800 |
| acgccaccga gggcagatac tctctgaact tccagaaggc ccggaagagc gccaacctgg | 1860 |
| tgatcagcgc ctcccagctg ggcgattctg ccatgtattt ctgcgccatc gccgagggca | 1920 |
| caggcttcca gaagctggtg tttggcaccg gcacaagact gctggtgagc cccaacatcc | 1980 |
| agaaccccga ccctgccgtg taccagctga gggactccaa gtctagcgat aagagcgtgt | 2040 |
| gcctgttcac cgactttgat cccagacaa acgtgagcca gagcaaggac tctgacgtgt | 2100 |
| acatcaccga caagacagtg ctggatatga ggtctatgga cttcaagagc aacagtgctg | 2160 |
| tggcctggag caacaaatct gactttgcat gtgcaaacgc cttcaacaac agcattattc | 2220 |
| cagaagacac cttcttcccc agcccaggta agggcagctt tggtgccttc gcaggctgtt | 2280 |
| tccttgcttc aggaatggcc aggttctgcc cagagctctg gtcaatgatg tctaaaactc | 2340 |
| ctctgattgg tggtctcggc cttatccatt gccaccaaaa ccctcttttt actaagaaac | 2400 |
| agtgagcctt gttctggcag tccagagaat gacacgggaa aaaagcagat gaagagaagg | 2460 |
| tggcaggaga gggcacgtgg cccagcctca gtctctccaa ctgagttcct gcctgcctgc | 2520 |
| ctttgctcag actgtttgcc ccttactgct cttctaggcc tcattctaag ccccttctcc | 2580 |
| aagttgcctc tccttatttc tccctgtctg cc | 2612 |

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 7
agagtctctc agctggtaca                                           20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 8
tggatttaga gtctctcagc                                           20

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 9
acaaaactgt gctagacatg                                           20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 10
cttcaagagc aacagtgctg                                          20

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 11
taaacccggc cactttcagg                                          20

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 12
ttaatctgct catgacgctg                                          20

<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 13
gctggtacac ggcagggtca                                          20

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 14
ctctcagctg gtacacggca                                          20

<210> SEQ ID NO 15
<211> LENGTH: 20
<212> TYPE: DNA

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 15
taggcagaca gacttgtcac                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 16
aagttcctgt gatgtcaagc                                                    20

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 17
gtcgagaaaa gctttgaaac                                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 18
ttcggaaccc aatcactgac                                                    20

<210> SEQ ID NO 19
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 19
ccgaatcctc ctcctgaaag                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
```

```
<221> NAME/KEY: misc_feature
<222> LOCATION: (1)..(20)

<400> SEQUENCE: 20
tcctcctcct gaaagtggcc                                                   20

<210> SEQ ID NO 21
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 21
cgtcatgagc agattaaacc                                                   20

<210> SEQ ID NO 22
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 22
ctgcggctgt ggtccagctg                                                   20

<210> SEQ ID NO 23
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 23
gaaaaacgtg ttcccaccca                                                   20

<210> SEQ ID NO 24
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 24
caaacacagc gaccttgggt                                                   20

<210> SEQ ID NO 25
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 25
```

```
ccacacccaa aaggccacac                                          20

<210> SEQ ID NO 26
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 26
tgtggccagg cacaccagtg                                          20

<210> SEQ ID NO 27
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 27
gtggtcgggg tagaagcctg                                          20

<210> SEQ ID NO 28
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 28
aggcttctac cccgaccacg                                          20

<210> SEQ ID NO 29
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 29
cccaccagct cagctccacg                                          20

<210> SEQ ID NO 30
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 30
ccacgtggag ctgagctggt                                          20
```

```
<210> SEQ ID NO 31
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 31
gagctggtgg gtgaatggga                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 32
ctggtgggtg aatgggaagg                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 33
aatgggaagg aggtgcacag                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 34
tgggaaggag gtgcacagtg                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 35
tatctggagt cattgagggc                                               20

<210> SEQ ID NO 36
<211> LENGTH: 20
<212> TYPE: DNA
<213> ORGANISM: Artificial Sequence
```

```
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 36
gtatctggag tcattgaggg                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 37
ggcagtatct ggagtcattg                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 38
aggtggccga gaccctcagg                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 39
gacagcggaa gtggttgcgg                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 40
cgtagaactg gacttgacag                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
```

```
<222> LOCATION: (1)..(20)

<400> SEQUENCE: 41
ggctctcgga gaatgacgag                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 42
ggagaatgac gagtggaccc                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 43
cacccagatc gtcagcgccg                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 44
tggctcaaac acagcgacct                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 45
agagatctcc cacacccaaa                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 46
```
accacgtgga gctgagctgg                                               20

<210> SEQ ID NO 47
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 47
tgacagcgga agtggttgcg                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 48
atcgtcagcg ccgaggcctg                                               20

<210> SEQ ID NO 49
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(18)

<400> SEQUENCE: 49

Glu Gly Arg Gly Ser Leu Leu Thr Cys Gly Asp Val Glu Glu Asn Pro
1               5                   10                  15

Gly Pro

<210> SEQ ID NO 50
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(19)

<400> SEQUENCE: 50

Ala Thr Asn Phe Ser Leu Leu Lys Gln Ala Gly Asp Val Glu Glu Asn
1               5                   10                  15

Pro Gly Pro

<210> SEQ ID NO 51
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(20)

```
<400> SEQUENCE: 51

Gln Cys Thr Asn Tyr Ala Leu Leu Lys Leu Ala Gly Asp Val Glu Ser
1               5                   10                  15

Asn Pro Gly Pro
            20

<210> SEQ ID NO 52
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(22)

<400> SEQUENCE: 52

Val Lys Gln Thr Leu Asn Phe Asp Leu Leu Lys Leu Ala Gly Asp Glu
1               5                   10                  15

Val Ser Asn Pro Gly Pro
            20

<210> SEQ ID NO 53
<211> LENGTH: 278
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(278)

<400> SEQUENCE: 53

Met Thr Arg Val Ser Leu Leu Trp Ala Val Val Ser Thr Cys Leu
1               5                   10                  15

Glu Ser Gly Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Asn Asn Tyr Tyr Leu Phe Trp Tyr Lys Gln Pro Pro Ser Arg Gln
        50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110

Ala Phe Met Gly Tyr Tyr Gly Gly Ser Gln Gly Asn Leu Ile Phe Gly
        115                 120                 125

Lys Gly Thr Lys Leu Ser Val Lys Pro Asn Ile Gln Asn Pro Asp Pro
130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
        195                 200                 205
```

```
Ala Cys Ala Asn Ala Phe Asn Asn Ser Ile Ile Pro Glu Asp Thr Phe
    210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
                245                 250                 255

Phe Arg Ile Leu Leu Leu Lys Val Ala Gly Phe Asn Leu Leu Met Thr
            260                 265                 270

Leu Arg Leu Trp Ser Ser
            275

<210> SEQ ID NO 54
<211> LENGTH: 310
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(310)

<400> SEQUENCE: 54

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
            35                  40                  45

Asn Ser Leu Phe Trp Tyr Arg Gln Thr Met Met Arg Gly Leu Glu Leu
        50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Ser Leu Gln Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270
```

Val Leu Ser Ala Thr Ile Leu Tyr Glu Ile Leu Gly Lys Ala Thr
    275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 55
<211> LENGTH: 837
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(837)

<400> SEQUENCE: 55
atgacccggg tgagcctgct gtgggccgtg gtggtgagca cctgcctgga gagcggcatg      60
gcccagaccg tgacccagtc tcagcccgag atgagcgtgc aggaggccga gaccgtgacc     120
ctgagctgta cctacgacac cagcgagaac aactactacc tgttctggta caagcagccc     180
cccagccggc agatgatcct ggtgatccgg caggaggcct acaagcagca gaacgccacc     240
gagaacagat tctctgtgaa cttccagaag gccgccaaga gcttcagcct gaagatcagc     300
gactcccagc tgggcgatac cgccatgtat ttctgcgcct tcatgggcta ctacggcggc     360
agccagggca atctgatctt tggcaagggc acaaagctga gcgtgaagcc caacatccag     420
aaccccgacc tgccgtgta ccagctgagg gactccaagt ctagcgataa gagcgtgtgc     480
ctgttcaccg actttgattc ccagacaaac gtgagccaga gcaaggactc tgacgtgtac     540
atcaccgaca gacagtgct ggatatgagg tctatggact tcaagagcaa cagtgctgtg     600
gcctggagca acaaatctga ctttgcatgt gcaaacgcct caacaacag cattattcca     660 gaagacacct tcttccccag cccagaaagt tcctgtgatg tcaagctggt cgagaaaagc     720
tttgaaacag atacgaacct aaactttcaa aacctgtcag tgattgggtt ccgaatcctc     780
ctcctgaaag tggccgggt taatctgctc atgacgctgc ggctgtggtc cagctga        837

<210> SEQ ID NO 56
<211> LENGTH: 930
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(930)

<400> SEQUENCE: 56
atggacagct ggaccttctg ctgcgtgagc ctgtgcatcc tggtggccaa gcacacagac      60
gcaggcgtga tccagagccc aaggcacgag gtgacagaga tgggccagga ggtgaccctg     120
aggtgtaagc ccatcagcgg ccacaactcc ctgttctggt ataggcagac catgatgcgg     180
ggactggagc tgctgatcta cttcaacaac aacgtgccca tcgatgacag cggcatgccc     240
gaggacagat tcagcgccaa gatgcccaac gccagcttca gcaccctgaa gatccagccc     300
agcgagccca gagactccgc cgtgtatttc tgcgccagca gcagcctgca gtatgagcag     360
tacttcggcc caggcacacg cctgaccgtg acagaggatc tgaagaacgt gttccccct      420 gaggtggccg tgtttgagcc ttctgaggcc gagatcagcc acacccagaa ggccacccctg     480

```
gtgtgcctgg caaccggctt ctacccagac cacgtggagc tgagctggtg ggtgaacggc    540
aaggaggtgc acagcggcgt gtccacagac ccacagcccc tgaaggagca gcccgccctg    600
aatgattcta gatattgcct gtctagccgg ctgagagtga gcgccacctt ttggcagaac    660
cctaggaatc acttccgctg tcaggtgcag ttttacggcc tgagcgagaa tgacgagtgg    720
acccaggata gggccaagcc tgtgacacag atcgtgtccg ccgaggcatg gggaagggca    780
gattgcggct tcacaagcga gtcctaccag cagggcgtgc tgtccgccac catcctgtat    840
gagatcctgc tgggcaaggc cacactgtac gccgtgctgg tgagcgccct ggtgctgatg    900
gccatggtga agaggaagga ctccaggggc                                     930

<210> SEQ ID NO 57
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(25)

<400> SEQUENCE: 57
aacataccat aaacctccca ttctg                                           25

<210> SEQ ID NO 58
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(25)

<400> SEQUENCE: 58
ttggagagac tgaggctggg ccacg                                           25

<210> SEQ ID NO 59
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(21)

<400> SEQUENCE: 59
tggggcaaag agggaaatga g                                               21

<210> SEQ ID NO 60
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(21)

<400> SEQUENCE: 60
agaacctggc cattcctgaa g                                               21

<210> SEQ ID NO 61
<211> LENGTH: 25
```

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(25)

<400> SEQUENCE: 61
catgtgcaaa cgccttcaac aacag                                              25

<210> SEQ ID NO 62
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 62
ctgggatggt gaccccaaaa                                                    20

<210> SEQ ID NO 63
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 63
ggccacatag aaagggggacc                                                   20

<210> SEQ ID NO 64
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(24)

<400> SEQUENCE: 64
accatgaagg agaattgggc acct                                               24

<210> SEQ ID NO 65
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 65
gggggatgga cagacaatgg                                                    20

<210> SEQ ID NO 66
<211> LENGTH: 20
<212> TYPE: DNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<222> LOCATION: (1)..(20)

<400> SEQUENCE: 66
gctgaccctg tgaaccttga                                               20

<210> SEQ ID NO 67
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(25)

<400> SEQUENCE: 67
atccaggtag cggacaagac tagat                                         25

<210> SEQ ID NO 68
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)

<400> SEQUENCE: 68
tcagccatat tgtccctaa act                                            23

<210> SEQ ID NO 69
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 69
tggtctgtcc atggcatctt                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

<400> SEQUENCE: 70
ctgtatggac acagtgccta                                               20

<210> SEQ ID NO 71
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(9)
```

<400> SEQUENCE: 71

Val Leu Asp Phe Ala Pro Pro Gly Ala
1               5

<210> SEQ ID NO 72
<211> LENGTH: 2503
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2503)

<400> SEQUENCE: 72

```
aacataccat aaacctccca ttctgctaat gcccagccta agttggggag accactccag     60
attccaagat gtacagtttg ctttgctggg cctttttccc atgcctgcct ttactctgcc    120
agagttatat tgctggggtt ttgaagaaga tcctattaaa taaaagaata agcagtatta    180
ttaagtagcc ctgcatttca ggtttccttg agtggcaggc caggcctggc cgtgaacgtt    240
cactgaaatc atggcctctt ggccaagatt gatagcttgt gcctgtccct gagtcccagt    300
ccatcacgag cagctggttt ctaagatgct atttcccgta taaagcatga accgtgact    360 tgccagcccc acagagcccc gcccttgtcc atcactggca tctggactcc agcctgggtt    420
ggggcaaaga gggaaatgag atcatgtcct aaccctgatc ctcttgtccc acagatatcc    480
agaaccctga ccctgccgtg ggaagcggag aaggtagagg ttctctcctc acttgtggtg    540
atgttgaaga aaaccctggt ccaatgagca tcggcctcct gtgctgtgca gccttgtctc    600
tcctgtgggc aggtccagtg aatgctggtg tcactcagac cccaaaattc caggtcctga    660
agacaggaca gagcatgaca ctgcagtgtg cccaggatat gaaccatgaa tacatgtcct    720
ggtatcgaca agacccaggc atgggctga ggctgattca ttactcagtt ggtgctggta    780
tcactgacca aggagaagtc cccaatggct acaatgtctc cagatcaacc acagaggatt    840
tcccgctcag gctgctgtcg gctgctccct ccagacatc tgtgtacttc tgtgccagca    900
gttacgtcgg gaacaccggg gagctgtttt tggagaagg ctctaggctg accgtactgg    960
aggacctgaa aaacgtgttc ccacccgagg tcgctgtgtt tgagccatca gaagcagaga   1020
tctcccacac ccaaaaggcc acactggtat gcctggccac aggcttctac cccgaccacg   1080
tggagctgag ctggtgggtg aatgggaagg aggtgcacag tgggggtcagc acagacccgc   1140 agcccctcaa ggagcagccc gccctcaatg actccagata ctgcctgagc agccgcctga   1200
gggtctcggc caccttctgg cagaaccccc gcaaccactt ccgctgtcaa gtccagttct   1260
acgggctctc agaaaacgat gaatggacac aagatagggc caaacccgtc acccagatcg   1320
tcagcgccga ggcctggggt agagcagact gtggcttcac ctccgagtct taccagcaag   1380
gggtcctgtc tgccaccatc ctctatgaga tcttgctagg gaaggccacc ttgtatgccg   1440
tgctggtcag tgccctcgtg ctgatggcta tggtcaagag aaaggattcc agaggccgcg   1500
ccaagcgctc cggctccggt gctaccaatt tctcactgtt gaaacaagcg ggcgatgttg   1560
aagaaaatcc cggtccaatg gagaccctct gggcctgct tatcctttgg ctgcagctgc   1620
aatgggtgag cagcaaacag gaggtgacgc agattcctgc agctctgagt gtcccagaag   1680
gagaaaactt ggttctcaac tgcagtttca ctgatagcgc tatttacaac ctccagtggt   1740
ttaggcagga ccctgggaaa ggtctcacat ctctgttgct tattcagtca agtcagagag   1800
agcaaacaag tggaagactt aatgcctcgc tggataaatc atcaggacgt agtactttat   1860
```

-continued

| | |
|---|---|
| acattgcagc ttctcagcct ggtgactcag ccacctacct ctgtgctgtg aggcccctgt | 1920 |
| acggaggaag ctacatacct acatttggaa gaggaaccag ccttattgtt catccgtata | 1980 |
| tccagaaccc tgaccctgcg gtataccagc tgagagactc taaatccagt gacaagtctg | 2040 |
| tctgcctatt caccgatttt gattctcaaa caaatgtgtc acaaagtaag gattctgatg | 2100 |
| tgtatatcac agacaaaact gtgctagaca tgaggtctat ggacttcaag agcaacagtg | 2160 |
| ctgtggcctg gagcaacaaa tctgactttg catgtgcaaa cgccttcaac aacagcatta | 2220 |
| ttccagaaga caccttcttc cccagcccag gtaagggcag ctttggtgcc ttcgcaggct | 2280 |
| gtttccttgc ttcaggaatg gccaggttct gcccagagct ctggtcaatg atgtctaaaa | 2340 |
| ctcctctgat tggtggtctc ggccttatcc attgccacca aaaccctctt tttactaaga | 2400 |
| aacagtgagc cttgttctgg cagtccagag aatgacacgg gaaaaaagca gatgaagaga | 2460 |
| aggtggcagg agagggcacg tggcccagcc tcagtctctc caa | 2503 |

<210> SEQ ID NO 73
<211> LENGTH: 2503
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2503)

<400> SEQUENCE: 73

| | |
|---|---|
| aacataccat aaacctccca ttctgctaat gcccagccta agttggggag accactccag | 60 |
| attccaagat gtacagtttg ctttgctggg ccttttttccc atgcctgcct ttactctgcc | 120 |
| agagttatat tgctggggtt ttgaagaaga tcctattaaa taaagaata agcagtatta | 180 |
| ttaagtagcc ctgcatttca ggtttccttg agtggcaggc caggcctggc cgtgaacgtt | 240 |
| cactgaaatc atggcctctt ggccaagatt gatagcttgt gcctgtccct gagtcccagt | 300 |
| ccatcacgag cagctggttt ctaagatgct atttcccgta taaagcatga gaccgtgact | 360 |
| tgccagcccc acagagcccc gcccttgtcc atcactggca tctggactcc agcctgggtt | 420 |
| ggggcaaaga gggaaatgag atcatgtcct aaccctgatc ctcttgtccc acagatatcc | 480 |
| agaaccctga ccctgccgtg ggaagcggag aaggtagagg ttctctcctc acttgtggtg | 540 |
| atgttgaaga aaaccctggt ccaatgagca tcggcctcct gtgctgtgca gccttgtctc | 600 |
| tcctgtgggc aggtccagtg aatgctggtg tcactcagac cccaaaattc caggtcctga | 660 |
| agacaggaca gagcatgaca ctgcagtgtg cccaggatat gaaccatgaa tacatgtcct | 720 |
| ggtatcgaca gacccaggc atggggctga ggctgattca ttactcagtt ggtgctggta | 780 |
| tcactgacca aggagaagtc cccaatggct acaatgtctc cagatcaacc acagaggatt | 840 |
| tcccgctcag gctgctgtcg gctgctccct cccagacatc tgtgtacttc tgtgccagca | 900 |
| gttacgtcgg gaacaccggg gagctgtttt ttggagaagg ctctaggctg accgtactgg | 960 |
| aggacctgaa aaacgtgttc ccacccgagg tcgctgtgtt tgagccatca gaagcagaga | 1020 |
| tctcccacac ccaaaaggcc acactggtat gcctggccac aggcttctac ccgaccacg | 1080 |
| tggagctgag ctggtgggtg aatgggaagg aggtgcacag tggggtcagc acagacccgc | 1140 |
| agccccctcaa ggagcagccc gccctcaatg actccagata ctgcctgagc agccgcctga | 1200 |
| gggtctcggc cacctctctgg cagaaccccc gcaaccactt ccgctgtcaa gtccagttct | 1260 |
| acgggctctc agaaaacgat gaatggacac aagatagggc caaacccgtc acccagatcg | 1320 |

```
tcagcgccga ggcctggggt agagcagact gtggcttcac ctccgagtct taccagcaag   1380
gggtcctgtc tgccaccatc ctctatgaga tcttgctagg gaaggccacc ttgtatgccg   1440
tgctggtcag tgccctcgtg ctgatggcta tggtcaagag aaaggattcc agaggccgcg   1500
ccaagcgctc cggctccggt gctaccaatt tctcactgtt gaaacaagcg ggcgatgttg   1560
aagaaaatcc cggtccaatg gagaccctct gggcctgct  tatcctttgg ctgcagctgc   1620
aatgggtgag cagcaaacag gaggtgacgc agattcctgc agctctgagt gtcccagaag   1680
gagaaaactt ggttctcaac tgcagtttca ctgatagcgc tatttacaac ctccagtggt   1740
ttaggcagga ccctgggaaa ggtctcacat ctctgttgct tattcagtca agtcagagag   1800
agcaaacaag tggaagactt aatgcctcgc tggataaatc atcaggacgt agtactttat   1860
acattgcagc ttctcagcct ggtgactcag ccacctacct ctgtgctgtg aggcccctgt   1920
acggaggaag ctacatacct acatttggaa gaggaaccag ccttattgtt catccgtata   1980
tccagaaccc tgaccctgcg gtataccagc tgagagactc taaatccagt gacaagtctg   2040
tctgcctatt caccgatttt gattctcaaa caaatgtgtc acaaagtaag gattctgatg   2100
tgtatatcac agacaaaact gtgctagaca tgaggtctat ggacttcaag agcaacagtg   2160
ctgtggcctg agcaacaaa  tctgactttg catgtgcaaa cgccttcaac aacagcatta   2220
ttccagaaga caccttcttc cccagcccag gtaaggcag  cttggtgcc  ttcgcaggct   2280 gtttccttgc ttcaggaatg ccaggttct  gcccagagct ctggtcaatg atgtctaaaa   2340
ctcctctgat tggtggtctc ggccttatcc attgccacca aaaccctctt tttactaaga   2400
aacagtgagc cttgttctgg cagtccagag aatgacacgg aaaaaagca  gatgaagaga   2460 aggtggcagg agagggcacg tggcccagcc tcagtctctc caa                     2503

<210> SEQ ID NO 74
<211> LENGTH: 2503
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2503)

<400> SEQUENCE: 74
aacataccat aaacctccca ttctgctaat gcccagccta agttggggag accactccag     60
attccaagat gtacagtttg ctttgctggg ccttttccc  atgcctgcct ttactctgcc    120
agagttatat tgctggggtt ttgaagaaga tcctattaaa taaaagaata agcagtatta    180
ttaagtagcc ctgcatttca ggtttccttg agtggcaggc caggcctggc cgtgaacgtt    240
cactgaaatc atggcctctt ggccaagatt gatagcttgt gcctgtccct gagtcccagt    300
ccatcacgag cagctggttt ctaagatgct atttcccgta taaagcatga gaccgtgact    360
tgccagcccc acagagcccc gcccttgtcc atcactggca tctggactcc agcctgggtt    420
ggggcaaaga gggaaatgag atcatgtcct aaccctgatc ctcttgtccc acagatatcc    480
agaaccctga ccctgccgtg ggaagcgag  aaggtagagg ttctctcctc acttgtggtg    540
atgttgaaga aaaccctggt ccaatgagca tcggcctcct gtgctgtgca gccttgtctc    600
tcctgtgggc aggtccagtg aatgctggtg tcactcagac cccaaaattc caggtcctga    660
agacaggaca gagcatgaca ctgcagtgtg cccaggatat gaaccatgaa tacatgtcct    720
ggtatcgaca agacccaggc atggggctga ggctgattca ttactcagtt ggtgctggta    780
```

```
tcactgacca aggagaagtc cccaatggct acaatgtctc cagatcaacc acagaggatt      840
tcccgctcag gctgctgtcg gctgctccct cccagacatc tgtgtacttc tgtgccagca      900
gttacgtcgg gaacaccggg gagctgtttt ttggagaagg ctctaggctg accgtactgg      960
aggacctgaa aaacgtgttc ccacccgagg tcgctgtgtt tgagccatca gaagcagaga     1020
tctcccacac ccaaaaggcc acactggtat gcctggccac aggcttctac cccgaccacg     1080
tggagctgag ctggtgggtg aatgggaagg aggtgcacag tggggtcagc acagacccgc     1140
agcccctcaa ggagcagccc gccctcaatg actccagata ctgcctgagc agccgcctga     1200
gggtctcggc caccttctgg cagaaccccc gcaaccactt ccgctgtcaa gtccagttct     1260
acgggctctc agaaaacgat gaatggacac aagatagggc caaacccgtc acccagatcg     1320
tcagcgccga ggcctggggt agagcagact gtggcttcac ctccgagtct taccagcaag     1380
gggtcctgtc tgccaccatc ctctatgaga tcttgctagg gaaggccacc ttgtatgccg     1440
tgctggtcag tgccctcgtg ctgatggcta tggtcaagag aaaggattcc agaggccgcg     1500
ccaagcgctc cggctccggt gctaccaatt tctcactgtt gaaacaagcg ggcgatgttg     1560
aagaaaatcc cggtccaatg gagaccctct tgggcctgct tatcctttgg ctgcagctgc     1620
aatgggtgag cagcaaacag gaggtgacgc agattcctgc agctctgagt gtcccagaag     1680
gagaaaactt ggttctcaac tgcagtttca ctgatagcgc tatttacaac ctccagtggt     1740
ttaggcagga ccctgggaaa ggtctcacat ctctgttgct tattcagtca agtcagagag     1800
agcaaacaag tggaagactt aatgcctcgc tggataaatc atcaggacgt agtactttat     1860
acattgcagc ttctcagcct ggtgactcag ccacctacct ctgtgctgtg aggcccctgt     1920
acggaggaag ctacatacct acatttggaa gaggaaccag ccttattgtt catccgtata     1980
tccagaaccc tgaccctgcg gtataccagc tgagagactc taaatccagt gacaagtctg     2040
tctgcctatt caccgatttt gattctcaaa caaatgtgtc acaaagtaag gattctgatg     2100
tgtatatcac agacaaaact gtgctagaca tgaggtctat ggacttcaag agcaacagtg     2160
ctgtggcctg gagcaacaaa tctgactttg catgtgcaaa cgccttcaac aacagcatta     2220
ttccagaaga caccttcttc cccagcccag gtaagggcag ctttggtgcc ttcgcaggct     2280
gtttccttgc ttcaggaatg ccaggttct gcccagagct ctggtcaatg atgtctaaaa     2340
ctcctctgat tggtggtctc ggccttatcc attgccacca aaaccctctt tttactaaga     2400
aacagtgagc cttgttctgg cagtccagag aatgacacgg gaaaaaagca gatgaagaga     2460
aggtggcagg agagggcacg tggcccagcc tcagtctctc caa                       2503
```

<210> SEQ ID NO 75
<211> LENGTH: 2263
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2263)

<400> SEQUENCE: 75

```
aacataccat aaacctccca ttctgctaat gcccagccta agttggggag accactccag       60
attccaagat gtacagtttg ctttgctggg ccttttttccc atgcctgcct ttactctgcc      120
agagttatat tgctggggtt ttgaagaaga tcctattaaa taaagaata agcagtatta      180 ttaagtagcc ctgcatttca ggtttccttg agtggcaggc caggcctggc cgtgaacgtt      240
```

```
cactgaaatc atggcctctt ggccaagatt gatagcttgt gcctgtccct gagtcccagt    300
ccatcacgag cagctggttt ctaagatgct atttcccgta taaagcatga gaccgtgact    360
tgccagcccc acagagcccc gcccttgtcc atcactggca tctggactcc agcctgggtt    420
ggggcaaaga gggaaatgag atcatgtcct aaccctgatc ctcttgtccc acagatatcc    480
agaaccctga ccctgccgtg ggaagcggag aaggtagagg ttctctcctc acttgtggtg    540
atgttgaaga aaaccctggt ccaatggtga gcaagggcga ggaggataac atggcctctc    600
tcccagcgac acatgagtta cacatctttg ctccatcaa cggtgtggac tttgacatgg    660
tgggtcaggg caccggcaat ccaaatgatg ttatgagga gttaaacctg aagtccacca    720
agggtgacct ccagttctcc ccctggattc tggtccctca tatcgggtat ggcttccatc    780
agtacctgcc ctaccctgac gggatgtcgc ctttccaggc cgccatggta gatggctccg    840
gataccaagt ccatcgcaca atgcagtttg aagatggtgc ctcccttact gttaactacc    900 gctcaccta cgagggaagc cacatcaaag gagaggccca ggtgaagggg actggtttcc    960
ctgctgacgg tcctgtgatg accaactcgc tgaccgctgc ggactggtgc aggtcgaaga    1020
agacttaccc caacgacaaa accatcatca gtacctttaa gtggagttac accactggaa    1080
atggcaagcg ctaccggagc actgcgcgga ccacctacac ctttgccaag ccaatggcgg    1140
ctaactatct gaagaaccag ccgatgtacg tgttccgtaa gacggagctc aagcactcca    1200
agaccgagct caacttcaag gagtggcaaa aggcctttac cgatgtgatg ggcatggacg    1260
agctgtacaa gggctccggt gctaccaatt tctcactgtt gaaacaagcg ggcgatgttg    1320
aagaaaatcc cggtccaatg gagaccctct gggcctgct tatcctttgg ctgcagctgc    1380
aatgggtgag cagcaaacag gaggtgacgc agattcctgc agctctgagt gtcccagaag    1440
gagaaaactt ggttctcaac tgcagtttca ctgatagcgc tatttacaac ctccagtggt    1500
ttaggcagga ccctgggaaa ggtctcacat ctctgttgct tattcagtca agtcagagag    1560
agcaaacaag tggaagactt aatgcctcgc tggataaatc atcaggacgt agtactttat    1620
acattgcagc ttctcagcct ggtgactcag ccacctacct ctgtgctgtg aggcccctgt    1680
acggaggaag ctacatacct acatttggaa gaggaaccag ccttattgtt catccgtata    1740
tccagaaccc tgaccctgcg gtataccagc tgagagactc taaatccagt gacaagtctg    1800
tctgcctatt caccgatttt gattctcaaa caaatgtgtc acaaagtaag gattctgatg    1860
tgtatatcac agacaaaact gtgctagaca tgaggtctat ggacttcaag agcaacagtg    1920
ctgtggcctg gagcaacaaa tctgactttg catgtgcaaa cgccttcaac aacagcatta    1980
ttccagaaga caccttcttc cccagcccag gtaagggcag ctttggtgcc ttcgcaggct    2040
gtttccttgc ttcaggaatg gccaggttct gcccagagct ctggtcaatg atgtctaaaa    2100
ctcctctgat tggtggtctc ggccttatcc attgccacca aaaccctctt tttactaaga    2160
aacagtgagc cttgttctgg cagtccagag aatgacacgg aaaaaagca gatgaagaga    2220 aggtggcagg agagggcacg tggcccagcc tcagtctctc caa                     2263
```

<210> SEQ ID NO 76
<211> LENGTH: 2263
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2263)

```
<400> SEQUENCE: 76
aacataccat aaacctccca ttctgctaat gcccagccta agttggggag accactccag      60
attccaagat gtacagtttg ctttgctggg ccttttccc  atgcctgcct ttactctgcc     120
agagttatat tgctggggtt ttgaagaaga tcctattaaa taaaagaata agcagtatta     180
ttaagtagcc ctgcatttca ggtttccttg agtggcaggc caggcctggc cgtgaacgtt     240
cactgaaatc atggcctctt ggccaagatt gatagcttgt gcctgtccct gagtcccagt     300
ccatcacgag cagctggttt ctaagatgct atttcccgta taaagcatga gaccgtgact     360
tgccagcccc acagagcccc gcccttgtcc atcactggca tctggactcc agcctgggtt     420
ggggcaaaga gggaaatgag atcatgtcct aaccctgatc ctcttgtccc acagatatcc     480
agaaccctga ccctgccgtg ggaagcgag  aaggtagagg ttctctcctc acttgtggtg     540
atgttgaaga aaaccctggt ccaatggtga gcaagggcga ggaggataac atggcctctc     600
tcccagcgac acatgagtta cacatctttg gctccatcaa cggtgtggac tttgacatgg     660
tgggtcaggg caccggcaat ccaaatgatg ttatgagga  gttaaacctg aagtccacca     720
agggtgacct ccagttctcc ccctggattc tggtccctca tatcgggtat ggcttccatc     780
agtacctgcc ctaccctgac gggatgtcgc cttttccaggc cgccatggta gatggctccg    840
gataccaagt ccatcgcaca atgcagtttg aagatggtgc ctcccttact gttaactacc     900
gctacaccta cgagggaagc cacatcaaag agagggccca ggtgaagggg actggttttcc    960
ctgctgacgg tcctgtgatg accaactcgc tgaccgctgc ggactggtgc aggtcgaaga    1020
agacttaccc caacgacaaa accatcatca gtaccttaa  gtggagttac accactggaa    1080
atggcaagcg ctaccggagc actgcgcgga ccacctacac ctttgccaag ccaatggcgg    1140
ctaactatct gaagaaccag ccgatgtacg tgttccgtaa gacggagctc aagcactcca    1200
agaccgagct caacttcaag gagtggcaaa aggcctttac cgatgtgatg ggcatggacg    1260
agctgtacaa gggctccggt gctaccaatt tctcactgtt gaaacaagcg ggcgatgttg    1320
aagaaaatcc cggtccaatg gagaccctct tgggcctgct tatcctttgg ctgcagctgc    1380
aatgggtgag cagcaaacag gaggtgacgc agattcctgc agctctgagt gtcccagaag    1440
gagaaaactt ggttctcaac tgcagtttca ctgatagcgc tatttacaac ctccagtggt    1500
ttaggcagga ccctgggaaa ggtctcacat ctctgttgct tattcagtca agtcagagag    1560
agcaaacaag tggaagactt aatgcctcgc tggataaatc atcaggacgt agtactttat    1620
acattgcagc ttctcagcct ggtgactcag ccacctacct ctgtgctgtg aggccctgt    1680
acggaggaag ctacatacct acatttggaa gaggaaccag ccttattgtt catccgtata    1740
tccagaaccc tgaccctgcg gtataccagc tgagagactc taaatccagt gacagtctg    1800
tctgcctatt caccgatttt gattctcaaa caaatgtgtc acaaagtaag gattctgatg    1860
tgtatatcac agacaaaact gtgctagaca tgaggtctat ggacttcaag agcaacagtg    1920
ctgtggcctg gagcaacaaa tctgactttg catgtgcaaa cgccttcaac aacagcatta    1980
ttccagaaga caccttcttc cccagcccag gtaaggcag  cttggtgcc  ttcgcaggct    2040
gtttccttgc ttcaggaatg gccaggttct gcccagagct ctggtcaatg atgtctaaaa    2100
ctcctctgat tggtggtctc ggccttatcc attgccacca aaaccctctt tttactaaga    2160
aacagtgagc cttgttctgg cagtccagag aatgacacgg gaaaaaagca gatgaagaga    2220
aggtggcagg agagggcacg tggcccagcc tcagtctctc caa                       2263
```

<210> SEQ ID NO 77
<211> LENGTH: 2263
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2263)

<400> SEQUENCE: 77

```
aacataccat aaacctccca ttctgctaat gcccagccta agttggggag accactccag      60
attccaagat gtacagtttg ctttgctggg ccttttttccc atgcctgcct ttactctgcc    120
agagttatat tgctggggtt ttgaagaaga tcctattaaa taaaagaata agcagtatta    180
ttaagtagcc ctgcatttca ggtttccttg agtggcaggc caggcctggc cgtgaacgtt    240
cactgaaatc atggcctctt ggccaagatt gatagcttgt gcctgtccct gagtcccagt    300
ccatcacgag cagctggttt ctaagatgct atttcccgta taaagcatga gaccgtgact    360
tgccagcccc acagagcccc gcccttgtcc atcactggca tctggactcc agcctgggtt    420
ggggcaaaga gggaaatgag atcatgtcct aaccctgatc ctcttgtccc acagatatcc    480
agaaccctga ccctgccgtg ggaagcggag aaggtagagg ttctctcctc acttgtggtg    540
atgttgaaga aaaccctggt ccaatggtga gcaaggggcga ggaggataac atggcctctc    600
tcccagcgac acatgagtta cacatctttg gctccatcaa cggtgtggac tttgacatgg    660
tgggtcaggg caccggcaat ccaaatgatg gttatgagga gttaaacctg aagtccacca    720
agggtgacct ccagttctcc ccctggattc tggtccctca tatcgggtat ggcttccatc    780
agtacctgcc ctaccctgac gggatgtcgc ctttccaggc cgccatggta gatggctccg    840
gataccaagt ccatcgcaca atgcagtttg aagatggtgc ctcccttact gttaactacc    900
gctacaccta cgagggaagc cacatcaaag gagaggccca ggtgaagggg actggtttcc    960
ctgctgacgg tcctgtgatg accaactcgc tgaccgctgc ggactggtgc aggtcgaaga   1020
agacttaccc caacgacaaa accatcatca gtaccttaa gtggagttac accactggaa   1080
atggcaagcg ctaccggagc actgcgcgga ccacctacac ctttgccaag ccaatggcgg   1140
ctaactatct gaagaaccag ccgatgtacg tgttccgtaa gacggagctc aagcactcca   1200
agaccgagct caacttcaag gagtggcaaa aggcctttac cgatgtgatg ggcatggacg   1260
agctgtacaa gggctccggt gctaccaatt tctcactgtt gaaacaagcg ggcgatgttg   1320
aagaaaatcc cggtccaatg gagaccctct gggcctgct tatcctttgg ctgcagctgc   1380
aatgggtgag cagcaaacag gaggtgacgc agattcctgc agctctgagt gtcccagaag   1440
gagaaaactt ggttctcaac tgcagtttca ctgatagcgc tatttacaac ctccagtggt   1500
ttaggcagga ccctgggaaa ggtctcacat ctctgttgct tattcagtca agtcagagag   1560
agcaaacaag tggaagactt aatgcctcgc tggataaatc atcaggacgt agtactttat   1620
acattgcagc ttctcagcct ggtgactcag ccacctacct ctgtgctgtg aggcccctgt   1680
acggaggaag ctacatacct acatttggaa gaggaaccag ccttattgtt catccgtata   1740
tccagaaccc tgaccctgcg gtataccagc tgagagactc taaatccagt gacagtctg   1800
tctgcctatt caccgatttt gattctcaaa caaatgtgtc acaaagtaag gattctgatg   1860
tgtatatcac agacaaaact gtgctagaca tgaggtctat ggacttcaag agcaacagtg   1920
ctgtggcctg gagcaacaaa tctgactttg catgtgcaaa cgccttcaac aacagcatta   1980
```

| ttccagaaga caccttcttc cccagcccag gtaagggcag ctttggtgcc ttcgcaggct | 2040 |
| gtttccttgc ttcaggaatg gccaggttct gcccagagct ctggtcaatg atgtctaaaa | 2100 |
| ctcctctgat tggtggtctc ggccttatcc attgccacca aaaccctctt tttactaaga | 2160 |
| aacagtgagc cttgttctgg cagtccagag aatgacacgg gaaaaaagca gatgaagaga | 2220 |
| aggtggcagg agagggcacg tggcccagcc tcagtctctc caa | 2263 |

```
<210> SEQ ID NO 78
<211> LENGTH: 1463
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1463)

<400> SEQUENCE: 78
```

| tctggactcc agcctgggtt ggggcaaaga gggaaatgag atcatgtcct aaccctgatc | 60 |
| ctcttgtccc acagatatcc agaaccctga ccctgccgtg ggaagcggag aaggtagagg | 120 |
| ttctctcctc acttgtggtg atgttgaaga aaaccctggt ccaatggtga gcaagggcga | 180 |
| ggaggataac atggcctctc tcccagcgac acatgagtta cacatctttg gctccatcaa | 240 |
| cggtgtggac tttgacatgg tgggtcaggg caccggcaat ccaaatgatg gttatgagga | 300 |
| gttaaacctg aagtccacca agggtgacct ccagttctcc cctggattc tggtccctca | 360 |
| tatcgggtat ggcttccatc agtacctgcc ctaccctgac gggatgtcgc ctttccaggc | 420 |
| cgccatggta gatggctccg gataccaagt ccatcgcaca atgcagtttg aagatggtgc | 480 |
| ctcccttact gttaactacc gctacaccta cgagggaagc cacatcaaag agaggcccca | 540 |
| ggtgaagggg actggtttcc ctgctgacgg tcctgtgatg accaactcgc tgaccgctgc | 600 |
| ggactggtgc aggtcgaaga agacttaccc caacgacaaa accatcatca gtaccttaa | 660 |
| gtggagttac accactggaa atggcaagcg ctaccggagc actgcgcgga ccacctacac | 720 |
| ctttgccaag ccaatggcgg ctaactatct gaagaaccag ccgatgtacg tgttccgtaa | 780 |
| gacggagctc aagcactcca agaccgagct caacttcaag gagtggcaaa aggcctttac | 840 |
| cgatgtgatg ggcatggacg agctgtacaa gggctccggt gctaccaatt tctcactgtt | 900 |
| gaaacaagcg ggcgatgttg aagaaaatcc cggtccaatg gagaccctct gggcctgct | 960 |
| tatcctttgg ctgcagctgc aatgggtgag cagcaaacag gaggtgacgc agattcctgc | 1020 |
| agctctgagt gtcccagaag gagaaaactt ggttctcaac tgcagtttca ctgatagcgc | 1080 |
| tatttacaac ctccagtggt ttaggcagga ccctgggaaa ggtctcacat ctctgttgct | 1140 |
| tattcagtca gtcagagag agcaaacaag tggaagactt aatgcctcgc tggataaatc | 1200 |
| atcaggacgt agtactttat acattgcagc ttctcagcct ggtgactcag ccacctacct | 1260 |
| ctgtgctgtg aggcccctgt acggaggaag ctacatacct acatttggaa gaggaaccag | 1320 |
| ccttattgtt catccgtata tccagaaccc tgaccctgcg gtataccagc tgagagactc | 1380 |
| taaatccagt gacaagtctg tctgcctatt caccgatttt gattctcaaa caaatgtgtc | 1440 |
| acaaagtaag gattctgatg tgt | 1463 |

```
<210> SEQ ID NO 79
<211> LENGTH: 1463
<212> TYPE: DNA
<213> ORGANISM: Artificial Sequence
<220> FEATURE:
```

<223> OTHER INFORMATION: Synthetic Polynucleotide
<220> FEATURE:
<221> NAME/KEY: misc_feature
<222> LOCATION: (1)..(1463)

<400> SEQUENCE: 79

```
tctggactcc agcctgggtt ggggcaaaga gggaaatgag atcatgtcct aaccctgatc        60
ctcttgtccc acagatatcc agaaccctga ccctgccgtg ggaagcggag aaggtagagg       120
ttctctcctc acttgtggtg atgttgaaga aaaccctggt ccaatggtga gcaagggcga       180
ggaggataac atggcctctc tcccagcgac acatgagtta cacatctttg gctccatcaa       240
cggtgtggac tttgacatgg tgggtcaggg caccggcaat ccaaatgatg gttatgagga       300
gttaaacctg aagtccacca agggtgacct ccagttctcc ccctggattc tggtccctca       360
tatcgggtat ggcttccatc agtacctgcc ctacccctgac gggatgtcgc ctttccaggc      420
cgccatggta gatggctccg ataccaagt ccatcgcaca atgcagtttg aagatggtgc        480
ctcccttact gttaactacc gctacaccta cgagggaagc cacatcaaag agaggcca         540
ggtgaagggg actggtttcc ctgctgacgg tcctgtgatg accaactcgc tgaccgctgc       600
ggactggtgc aggtcgaaga agacttaccc caacgacaaa accatcatca gtacctttaa       660
gtggagttac accactggaa atggcaagcg ctaccggagc actgcgcgga ccacctacac       720
ctttgccaag ccaatggcgg ctaactatct gaagaaccag ccgatgtacg tgttccgtaa       780
gacggagctc aagcactcca agaccgagct caacttcaag gagtggcaaa aggcctttac       840
cgatgtgatg ggcatggacg agctgtacaa gggctccggt gctaccaatt tctcactgtt       900
gaaacaagcg ggcgatgttg aagaaaatcc cggtccaatg gagaccctct gggcctgct        960
tatcctttgg ctgcagctgc aatgggtgag cagcaaacag gaggtgacgc agattcctgc      1020
agctctgagt gtcccagaag gagaaaactt ggttctcaac tgcagtttca ctgatagcgc      1080
tatttacaac ctccagtggt ttaggcagga ccctgggaaa ggtctcacat ctctgttgct      1140
tattcagtca agtcagagag agcaaacaag tggaagactt aatgcctcgc tggataaatc      1200
atcaggacgt agtactttat acattgcagc ttctcagcct ggtgactcag ccacctacct      1260
ctgtgctgtg aggccctgt acggaggaag ctacatacct acatttggaa gaggaaccag       1320
ccttattgtt catccgtata tccagaaccc tgaccctgcg gtataccagc tgagagactc      1380
taaatccagt gacaagtctg tctgccattt caccgatttt gattctcaaa caaatgtgtc      1440
acaaagtaag gattctgatg tgt                                              1463
```

<210> SEQ ID NO 80
<211> LENGTH: 1663
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1663)

<400> SEQUENCE: 80

```
ccatcacgag cagctggttt ctaagatgct atttcccgta taaagcatga gaccgtgact        60
tgccagcccc acagagcccc gcccttgtcc atcactggca tctggactcc agcctgggtt       120
ggggcaaaga gggaaatgag atcatgtcct aaccctgatc ctcttgtccc acagatatcc       180
agaaccctga ccctgccgtg ggaagcggag aaggtagagg ttctctcctc acttgtggtg       240
atgttgaaga aaaccctggt ccaatggtga gcaagggcga ggaggataac atggcctctc       300
```

```
tcccagcgac acatgagtta cacatctttg gctccatcaa cggtgtggac tttgacatgg      360
tgggtcaggg caccggcaat ccaaatgatg gttatgagga gttaaacctg aagtccacca      420
agggtgacct ccagttctcc ccctggattc tggtccctca tatcgggtat ggcttccatc      480
agtacctgcc ctaccctgac gggatgtcgc ctttccaggc cgccatggta gatggctccg      540
gataccaagt ccatcgcaca atgcagtttg aagatggtgc ctcccttact gttaactacc      600
gctacaccta cgagggaagc cacatcaaag agaggccca ggtgaagggg actggtttcc       660
ctgctgacgg tcctgtgatg accaactcgc tgaccgctgc ggactggtgc aggtcgaaga      720
agacttaccc caacgacaaa accatcatca gtacctttaa gtggagttac accactggaa      780
atggcaagcg ctaccggagc actgcgcgga ccacctacac ctttgccaag ccaatggcgg      840
ctaactatct gaagaaccag ccgatgtacg tgttccgtaa cggagctc aagcactcca        900 agaccgagct caacttcaag gagtggcaaa aggcctttac cgatgtgatg ggcatggacg      960
agctgtacaa gggctccggt gctaccaatt tctcactgtt gaaacaagcg ggcgatgttg     1020
aagaaaatcc cggtccaatg gagaccctct tgggcctgct tatcctttgg ctgcagctgc     1080
aatgggtgag cagcaaacag gaggtgacgc agattcctgc agctctgagt gtcccagaag     1140
gagaaaactt ggttctcaac tgcagtttca ctgatagcgc tatttacaac ctccagtggt     1200
ttaggcagga ccctgggaaa ggtctcacat ctctgttgct tattcagtca agtcagagag     1260
agcaaacaag tggaagactt aatgcctcgc tggataaatc atcaggacgt agtactttat     1320
acattgcagc ttctcagcct ggtgactcag ccacctacct ctgtgctgtg aggcccctgt     1380
acggaggaag ctacatacct acatttggaa gaggaaccag ccttattgtt catccgtata     1440
tccagaaccc tgaccctgcg gtataccagc tgagagactc taaatccagt gacaagtctg     1500
tctgcctatt caccgatttt gattctcaaa caaatgtgtc acaaagtaag gattctgatg     1560
tgtatatcac agacaaaact gtgctagaca tgaggtctat ggacttcaag agcaacagtg     1620
ctgtggcctg gagcaacaaa tctgactttg catgtgcaaa cgc                       1663
```

<210> SEQ ID NO 81  
<211> LENGTH: 1663  
<212> TYPE: DNA  
<213> ORGANISM: Artificial Sequence  
<220> FEATURE:  
<223> OTHER INFORMATION: Synthetic Polynucleotide  
<220> FEATURE:  
<221> NAME/KEY: misc_feature  
<222> LOCATION: (1)..(1663)

<400> SEQUENCE: 81

```
ccatcacgag cagctggttt ctaagatgct atttcccgta taaagcatga gaccgtgact       60
tgccagcccc acagagcccc gcccttgtcc atcactggca tctggactcc agcctgggtt      120
ggggcaaaga gggaaatgag atcatgtcct aaccctgatc ctcttgtccc acagatatcc      180
agaaccctga ccctgccgtg ggaagcggag aaggtagagg ttctctcctc acttgtggtg      240
atgttgaaga aaaccctggt ccaatggtga gcaagggcga ggaggataac atggcctctc      300
tcccagcgac acatgagtta cacatctttg gctccatcaa cggtgtggac tttgacatgg      360
tgggtcaggg caccggcaat ccaaatgatg gttatgagga gttaaacctg aagtccacca      420
agggtgacct ccagttctcc ccctggattc tggtccctca tatcgggtat ggcttccatc      480
agtacctgcc ctaccctgac gggatgtcgc ctttccaggc cgccatggta gatggctccg      540
gataccaagt ccatcgcaca atgcagtttg aagatggtgc ctcccttact gttaactacc      600
```

```
gctacaccta cgagggaagc cacatcaaag gagaggccca ggtgaagggg actggtttcc      660
ctgctgacgg tcctgtgatg accaactcgc tgaccgctgc ggactggtgc aggtcgaaga      720
agacttaccc caacgacaaa accatcatca gtacctttaa gtggagttac accactggaa      780
atggcaagcg ctaccggagc actgcgcgga ccacctacac ctttgccaag ccaatggcgg      840
ctaactatct gaagaaccag ccgatgtacg tgttccgtaa dacggagctc aagcactcca      900
agaccgagct caacttcaag gagtggcaaa aggcctttac cgatgtgatg ggcatggacg      960
agctgtacaa gggctccggt gctaccaatt tctcactgtt gaaacaagcg ggcgatgttg     1020
aagaaaatcc cggtccaatg gagaccctct gggcctgct atcctttgg ctgcagctgc       1080 aatgggtgag cagcaaacag gaggtgacgc agattcctgc agctctgagt gtcccagaag     1140
gagaaaactt ggttctcaac tgcagtttca ctgatagcgc tatttacaac ctccagtggt     1200
ttaggcagga ccctgggaaa ggtctcacat ctctgttgct tattcagtca agtcagagag     1260
agcaaacaag tggaagactt aatgcctcgc tggataaatc atcaggacgt agtactttat     1320
acattgcagc ttctcagcct ggtgactcag ccacctacct ctgtgctgtg aggcccctgt     1380
acggaggaag ctacatacct acatttggaa gaggaaccag ccttattgtt catccgtata     1440
tccagaaccc tgaccctgcg gtataccagc tgagagactc taaatccagt gacaagtctg     1500
tctgcctatt caccgatttt gattctcaaa caaatgtgtc acaaagtaag gattctgatg     1560
tgtatatcac agacaaaact gtgctagaca tgaggtctat ggacttcaag agcaacagtg     1620
ctgtggcctg gagcaacaaa tctgactttg catgtgcaaa cgc                       1663

<210> SEQ ID NO 82
<211> LENGTH: 1863
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1863)

<400> SEQUENCE: 82
ggtttccttg agtggcaggc caggcctggc cgtgaacgtt cactgaaatc atggcctctt       60
ggccaagatt gatagcttgt gcctgtccct gagtcccagt ccatcacgag cagctggttt      120
ctaagatgct atttcccgta taaagcatga gaccgtgact tgccagcccc acagagcccc      180
gcccttgtcc atcactggca tctggactcc agcctgggtt ggggcaaaga gggaaatgag      240
atcatgtcct aaccctgatc ctcttgtccc acagatatcc agaaccctga ccctgccgtg      300
ggaagcggag aaggtagagg ttctctcctc acttgtggtg atgttgaaga aaaccctggt      360
ccaatggtga gcaagggcga ggaggataac atggcctctc tcccagcgac acatgagtta      420
cacatctttg ctccatcaa cggtgtggac tttgacatgg tgggtcaggg caccggcaat      480
ccaaatgatg gttatgagga gttaaacctg aagtccacca agggtgacct ccagttctcc      540
ccctggattc tggtccctca tatcgggtat ggcttccatc agtacctgcc ctaccctgac      600
gggatgtcgc ctttccaggc cgccatggta gatggctccg gataccaagt ccatcgcaca      660
atgcagtttg aagatggtgc ctcccttact gttaactacc gctacaccta cgagggaagc      720
cacatcaaag gagaggccca ggtgaagggg actggtttcc ctgctgacgg tcctgtgatg      780
accaactcgc tgaccgctgc ggactggtgc aggtcgaaga agacttaccc caacgacaaa      840
accatcatca gtacctttaa gtggagttac accactggaa atggcaagcg ctaccggagc      900
```

```
actgcgcgga ccacctacac ctttgccaag ccaatggcgg ctaactatct gaagaaccag    960
ccgatgtacg tgttccgtaa gacggagctc aagcactcca agaccgagct caacttcaag   1020
gagtggcaaa aggcctttac cgatgtgatg ggcatggacg agctgtacaa gggctccggt   1080
gctaccaatt tctcactgtt gaaacaagcg ggcgatgttg aagaaaatcc cggtccaatg   1140
gagaccctct tgggcctgct tatcctttgg ctgcagctgc aatgggtgag cagcaaacag   1200
gaggtgacgc agattcctgc agctctgagt gtcccagaag gagaaaactt ggttctcaac   1260
tgcagtttca ctgatagcgc tatttacaac ctccagtggt ttaggcagga ccctgggaaa   1320
ggtctcacat ctctgttgct tattcagtca agtcagagag agcaaacaag tggaagactt   1380
aatgcctcgc tggataaatc atcaggacgt agtactttat acattgcagc ttctcagcct   1440
ggtgactcag ccacctacct ctgtgctgtg aggcccctgt acggaggaag ctacatacct   1500
acatttggaa gaggaaccag ccttattgtt catccgtata ccagaaccc tgaccctgcg   1560 gtataccagc tgagagactc taaatccagt gacaagtctg tctgcctatt caccgatttt   1620
gattctcaaa caaatgtgtc acaaagtaag gattctgatg tgtatatcac agacaaaact   1680
gtgctagaca tgaggtctat ggacttcaag agcaacagtg ctgtggcctg gagcaacaaa   1740
tctgactttg catgtgcaaa cgccttcaac aacagcatta ttccagaaga caccttcttc   1800
cccagcccag gtaagggcag cttttggtgcc ttcgcaggct gtttccttgc ttcaggaatg   1860
gcc                                                                1863

<210> SEQ ID NO 83
<211> LENGTH: 1863
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1863)

<400> SEQUENCE: 83
ggtttccttg agtggcaggc caggcctggc cgtgaacgtt cactgaaatc atggcctctt     60
ggccaagatt gatagcttgt gcctgtccct gagtcccagt ccatcacgag cagctggttt    120
ctaagatgct atttcccgta taaagcatga ccgtgact tgccagcccc acagagcccc      180
gcccttgtcc atcactggca tctggactcc agcctgggtt ggggcaaaga gggaaatgag    240
atcatgtcct aaccctgatc ctcttgtccc acagatatcc agaaccctga ccctgccgtg    300
ggaagcggag aaggtagagg ttctctcctc acttgtggtg atgttgaaga aaaccctggt    360
ccaatggtga gcaagggcga ggaggataac atggcctctc tcccagcgac acatgagtta    420
cacatctttg gctccatcaa cggtgtggac tttgacatgg tgggtcaggg caccggcaat    480
ccaaatgatg gttatgagga gttaaacctg aagtccacca agggtgacct ccagttctcc    540
ccctggattc tggtccctca tatcgggtat ggcttccatc agtacctgcc ctaccctgac    600
gggatgtcgc ctttccaggc cgccatggta gatggctccg gataccaagt ccatcgcaca    660
atgcagtttg aagatggtgc ctcccttact gttaactacc gctacaccta cgagggaagc    720
cacatcaaag agaggcccca ggtgaagggg actggtttcc ctgctgacgg tcctgtgatg    780
accaactcgc tgaccgctgc ggactggtgc aggtcgaaga agacttaccc caacgacaaa    840
accatcatca gtacctttaa gtggagttac accactggaa atggcaagcg ctaccggagc    900
actgcgcgga ccacctacac ctttgccaag ccaatggcgg ctaactatct gaagaaccag    960
```

```
ccgatgtacg tgttccgtaa gacggagctc aagcactcca agaccgagct caacttcaag    1020
gagtggcaaa aggcctttac cgatgtgatg ggcatggacg agctgtacaa gggctccggt    1080
gctaccaatt tctcactgtt gaaacaagcg ggcgatgttg aagaaaatcc cggtccaatg    1140
gagaccctct tgggcctgct tatcctttgg ctgcagctgc aatgggtgag cagcaaacag    1200
gaggtgacgc agattcctgc agctctgagt gtcccagaag gagaaaactt ggttctcaac    1260
tgcagtttca ctgatagcgc tatttacaac ctccagtggt ttaggcagga ccctgggaaa    1320
ggtctcacat ctctgttgct tattcagtca agtcagagag agcaaacaag tggaagactt    1380
aatgcctcgc tggataaatc atcaggacgt agtactttat acattgcagc ttctcagcct    1440
ggtgactcag ccacctacct ctgtgctgtg aggcccctgt acggaggaag ctacatacct    1500
acatttggaa gaggaaccag ccttattgtt catccgtata tccagaaccc tgaccctgcg    1560
gtataccagc tgagagactc taaatccagt gacaagtctg tctgcctatt caccgatttt    1620
gattctcaaa caaatgtgtc acaaagtaag gattctgatg tgtatatcac agacaaaact    1680
gtgctagaca tgaggtctat ggacttcaag agcaacagtg ctgtggcctg gagcaacaaa    1740
tctgactttg catgtgcaaa cgccttcaac aacagcatta ttccagaaga caccttcttc    1800
cccagcccag gtaagggcag ctttggtgcc ttcgcaggct gtttccttgc ttcaggaatg    1860
gcc                                                                  1863
```

<210> SEQ ID NO 84
<211> LENGTH: 2663
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2663)

<400> SEQUENCE: 84

```
ggaaggtgga tgaggcacca tattcatttt gcaggtgaaa ttcctgagat gtaaggagct      60
gctgtgactt gctcaaggcc ttatatcgag taaacggtag tgctggggct tagacgcagg     120
tgttctgatt tatagttcaa aacctctatc aatgagagag caatctcctg gtaatgtgat     180
agatttccca acttaatgcc aacataccat aaacctccca ttctgctaat gcccagccta     240
agttggggag accactccag attccaagat gtacagtttg ctttgctggg ccttttttccc    300 atgcctgcct ttactctgcc agagttatat tgctggggtt ttgaagaaga tcctattaaa     360
taaaagaata agcagtatta ttaagtagcc ctgcatttca ggtttccttg agtggcaggc     420
caggcctggc cgtgaacgtt cactgaaatc atggcctctt ggccaagatt gatagcttgt     480
gcctgtccct gagtcccagt ccatcacgag cagctggttt ctaagatgct atttcccgta     540
taaagcatga gaccgtgact tgccagcccc acagagcccc gcccttgtcc atcactggca     600
tctggactcc agcctgggtt ggggcaaaga gggaaatgag atcatgtcct aaccctgatc     660
ctcttgtccc acagatatcc agaaccctga ccctgccgtg ggaagcggag aaggtagagg     720
ttctctcctc acttgtggtg atgttgaaga aaaccctggt ccaatggtga gcaagggcga     780
ggaggataac atggcctctc tcccagcgac acatgagtta cacatctttg ctccatcaa     840 cggtgtggac tttgacatgg tgggtcaggg caccggcaat ccaaatgatg gttatgagga     900
gttaaacctg aagtccacca agggtgacct ccagttctcc cctggattc tggtccctca     960 tatcgggtat ggcttccatc agtacctgcc ctaccctgac gggatgtcgc ctttccaggc    1020
```

```
cgccatggta gatggctccg gataccaagt ccatcgcaca atgcagtttg aagatggtgc    1080
ctcccttact gttaactacc gctacaccta cgagggaagc cacatcaaag gagaggccca    1140
ggtgaagggg actggtttcc ctgctgacgg tcctgtgatg accaactcgc tgaccgctgc    1200
ggactggtgc aggtcgaaga agacttaccc caacgacaaa accatcatca gtacctttaa    1260
gtggagttac accactggaa atggcaagcg ctaccggagc actgcgcgga ccacctacac    1320
ctttgccaag ccaatggcgg ctaactatct gaagaaccag ccgatgtacg tgttccgtaa    1380
gacggagctc aagcactcca agaccgagct caacttcaag gagtggcaaa aggcctttac    1440
cgatgtgatg ggcatggacg agctgtacaa gggctccggt gctaccaatt tctcactgtt    1500
gaaacaagcg gcgatgttg aagaaaatcc cggtccaatg gagaccctct gggcctgct     1560 tatcctttgg ctgcagctgc aatgggtgag cagcaaacag gaggtgacgc agattcctgc    1620
agctctgagt gtcccagaag agaaaacttt ggttctcaac tgcagtttca ctgatagcgc    1680
tatttacaac ctccagtggt ttaggcagga ccctgggaaa ggtctcacat ctctgttgct    1740
tattcagtca agtcagagag agcaaacaag tggaagactt aatgcctcgc tggataaatc    1800
atcaggacgt agtactttat acattgcagc ttctcagcct ggtgactcag ccacctacct    1860
ctgtgctgtg aggcccctgt acggaggaag ctacatacct acatttggaa gaggaaccag    1920
ccttattgtt catccgtata tccagaaccc tgaccctgcg gtataccagc tgagagactc    1980
taaatccagt gacaagtctg tctgcctatt caccgatttt gattctcaaa caaatgtgtc    2040
acaaagtaag gattctgatg tgtatatcac agacaaaact gtgctagaca tgaggtctat    2100
ggacttcaag agcaacagtg ctgtggcctg gagcaacaaa tctgactttg catgtgcaaa    2160
cgccttcaac aacagcatta ttccagaaga caccttcttc cccagcccag gtaagggcag    2220 cttttggtgcc ttcgcaggct gtttccttgc ttcaggaatg gccaggttct gcccagagct    2280
ctggtcaatg atgtctaaaa ctcctctgat tggtggtctc ggccttatcc attgccacca    2340
aaaccctctt tttactaaga aacagtgagc cttgttctgg cagtccagag aatgacacgg    2400 gaaaaagca gatgaagaga aggtggcagg agagggcacg tggcccagcc tcagtctctc    2460
caactgagtt cctgcctgcc tgcctttgct cagactgttg gccccttact gctcttctag    2520
gcctcattct aagcccttc tccaagttgc ctctccttat ttctccctgt ctgccaaaaa     2580
atctttccca gctcactaag tcagtctcac gcagtcactc attaacccac caatcactga    2640
ttgtgccggc acatgaatgc acc                                            2663

<210> SEQ ID NO 85
<211> LENGTH: 2663
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2663)

<400> SEQUENCE: 85
ggaaggtgga tgaggcacca tattcatttt gcaggtgaaa ttcctgagat gtaaggagct      60
gctgtgactt gctcaaggcc ttatatcgag taaacggtag tgctggggct tagacgcagg     120
tgttctgatt tatagttcaa aacctctatc aatgagagag caatctcctg gtaatgtgat     180
agatttccca acttaatgcc aacataccat aaacctccca ttctgctaat gcccagccta     240
agttggggag accactccag attccaagat gtacagtttg cttttgctggg ccttttttccc    300
```

```
atgcctgcct ttactctgcc agagttatat tgctggggtt ttgaagaaga tcctattaaa      360
taaaagaata agcagtatta ttaagtagcc ctgcatttca ggtttccttg agtggcaggc      420
caggcctggc cgtgaacgtt cactgaaatc atggcctctt ggccaagatt gatagcttgt      480
gcctgtccct gagtcccagt ccatcacgag cagctggttt ctaagatgct atttcccgta      540
taaagcatga gaccgtgact tgccagcccc acagagcccc gcccttgtcc atcactggca      600
tctggactcc agcctgggtt ggggcaaaga gggaaatgag atcatgtcct aaccctgatc      660
ctcttgtccc acagatatcc agaaccctga ccctgccgtg ggaagcggag aaggtagagg      720
ttctctcctc acttgtggtg atgttgaaga aaaccctggt ccaatggtga gcaagggcga      780
ggaggataac atggcctctc tcccagcgac acatgagtta cacatctttg gctccatcaa      840
cggtgtggac tttgacatgg tgggtcaggg caccggcaat ccaaatgatg gttatgagga      900
gttaaacctg aagtccacca agggtgacct ccagttctcc ccctggattc tggtccctca      960
tatcgggtat ggcttccatc agtacctgcc ctaccctgac gggatgtcgc ctttccaggc     1020
cgccatggta gatggctccg gataccaagt ccatcgcaca atgcagtttg aagatggtgc     1080
ctcccttact gttaactacc gctacaccta cgagggaagc cacatcaaag gagaggccca     1140
ggtgaagggg actggtttcc ctgctgacgg tcctgtgatg accaactcgc tgaccgctgc     1200
ggactggtgc aggtcgaaga agacttaccc caacgacaaa accatcatca gtacctttaa     1260
gtggagttac accactggaa atggcaagcg ctaccggagc actgcgcgga ccacctacac     1320
ctttgccaag ccaatggcgg ctaactatct gaagaaccag ccgatgtacg tgttccgtaa     1380
gacggagctc aagcactcca agaccgagct caacttcaag gagtggcaaa aggcctttac     1440
cgatgtgatg ggcatggacg agctgtacaa gggctccggt gctaccaatt tctcactgtt     1500
gaaacaagcg ggcgatgttg aagaaaatcc cggtccaatg gagaccctct gggcctgct      1560 tatcctttgg ctgcagctgc aatgggtgag cagcaaacag gaggtgacgc agattcctgc     1620
agctctgagt gtcccagaag gagaaaactt ggttctcaac tgcagtttca ctgatagcgc     1680
tatttacaac ctccagtggt ttaggcagga ccctgggaaa ggtctcacat ctctgttgct     1740
tattcagtca agtcagagag agcaaacaag tggaagactt aatgcctcgc tggataaatc     1800
atcaggacgt agtactttat acattgcagc ttctcagcct ggtgactcag ccacctacct     1860
ctgtgctgtg aggcccctgt acggaggaag ctacatacct acatttggaa gaggaaccag     1920
ccttattgtt catccgtata tccagaaccc tgaccctgcg gtataccagc tgagagactc     1980
taaatccagt gacaagtctg tctgcctatt caccgatttt gattctcaaa caatgtgtc      2040 acaaagtaag gattctgatg tgtatatcac agacaaaact gtgctagaca tgaggtctat     2100
ggacttcaag agcaacagtg ctgtggcctg agcaacaaaa tctgactttg catgtgcaaa     2160
cgccttcaac aacagcatta ttccagaaga caccttcttc cccagccagg taagggcag      2220 ctttggtgcc ttcgcaggct gtttccttgc ttcaggaatg ccaggttct gcccagagct      2280 ctggtcaatg atgtctaaaa ctcctctgat tggtggtctc ggccttatcc attgccacca     2340
aaaccctctt tttactaaga aacagtgagc cttgttctgg cagtccagag aatgacacgg     2400
gaaaaaagca gatgaagaga aggtggcagg agagggcacg tggcccagcc tcagtctctc     2460
caactgagtt cctgcctgcc tgcctttgct cagactgttt gccccttact gctcttctag     2520
gcctcattct aagcccttc tccaagttgc ctctccttat ttctccctgt ctgccaaaaa       2580
atctttccca gctcactaag tcagtctcac gcagtcactc attaacccac caatcactga     2640
```

```
ttgtgccggc acatgaatgc acc                                            2663
```

<210> SEQ ID NO 86
<211> LENGTH: 3263
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3263)

<400> SEQUENCE: 86

```
tttcctcctc aaaaggcagg aggtcggaaa gaataaacaa tgagagtcac attaaaaaca     60
caaaatccta cggaaatact gaagaatgag tctcagcact aaggaaaagc ctccagcagc    120
tcctgctttc tgagggtgaa ggatagacgc tgtggctctg catgactcac tagcactcta    180
tcacggccat attctggcag ggtcagtggc tccaactaac atttgtttgg tactttacag    240
tttattaaat agatgtttat atggagaagc tctcatttct ttctcagaag agcctggcta    300
ggaaggtgga tgaggcacca tattcatttt gcaggtgaaa ttcctgagat gtaaggagct    360
gctgtgactt gctcaaggcc ttatatcgag taaacggtag tgctggggct tagacgcagg    420
tgttctgatt tatagttcaa aacctctatc aatgagagag caatctcctg gtaatgtgat    480
agatttccca acttaatgcc aacataccat aaacctccca ttctgctaat gcccagccta    540
agttggggag accactccag attccaagat gtacagtttg ctttgctggg ccttttttccc    600
atgcctgcct ttactctgcc agagtttatat tgctggggtt ttgaagaaga tcctattaaa    660
taaaagaata agcagtatta ttaagtagcc ctgcatttca ggtttccttg agtggcaggc    720
caggcctggc cgtgaacgtt cactgaaatc atggcctctt ggccaagatt gatagcttgt    780
gcctgtccct gagtcccagt ccatcacgag cagctggttt ctaagatgct atttcccgta    840
taaagcatga gaccgtgact tgccagcccc acagagcccc gcccttgtcc atcactggca    900
tctggactcc agcctgggtt ggggcaaaga gggaaatgag atcatgtcct aaccctgatc    960
ctcttgtccc acagatatcc agaacccctga ccctgccgtg ggaagcggag aaggtagagg   1020
ttctctcctc acttgtggtg atgttgaaga aaaccctggt ccaatggtga gcaagggcga   1080
ggaggataac atggcctctc tcccagcgac acatgagtta cacatctttg gctccatcaa   1140
cggtgtggac tttgacatgg tgggtcaggg caccggcaat ccaaatgatg gttatgagga   1200
gttaaacctg aagtccacca agggtgacct ccagttctcc ccctggattc tggtccctca   1260
tatcgggtat ggcttccatc agtacctgcc ctacccctgac gggatgtcgc ctttccaggc   1320
cgccatggta gatggctccg gataccaagt ccatcgcaca atgcagtttg aagatggtgc   1380
ctcccttact gttaactacc gctacaccta cgagggaagc cacatcaaag gagaggccca   1440
ggtgaagggg actggtttcc ctgctgacgg tcctgtgatg accaactcgc tgaccgctgc   1500
ggactggtgc aggtcgaaga agacttaccc caacgacaaa accatcatca gtacctttaa   1560
gtggagttac accactggaa atggcaagcg ctaccggagc actgcgcgga ccacctacac   1620
ctttgccaag ccaatggcgg ctaactatct gaagaaccag ccgatgtacg tgttccgtaa   1680
gacggagctc aagcactcca agaccgagct caacttcaag gagtggcaaa aggcctttac   1740
cgatgtgatg ggcatggacg agctgtacaa gggctccggt gctaccaatt tctcactgtt   1800
gaaacaagcg ggcgatgttg aagaaaatcc cggtccaatg gagaccctct ggggcctgct   1860
tatcctttgg ctgcagctgc aatgggtgag cagcaaacag gaggtgacgc agattcctgc   1920
```

```
agctctgagt gtcccagaag gagaaaactt ggttctcaac tgcagtttca ctgatagcgc    1980
tatttacaac ctccagtggt ttaggcagga ccctgggaaa ggtctcacat ctctgttgct    2040
tattcagtca agtcagagag agcaaacaag tggaagactt aatgcctcgc tggataaatc    2100
atcaggacgt agtactttat acattgcagc ttctcagcct ggtgactcag ccacctacct    2160
ctgtgctgtg aggcccctgt acggaggaag ctacatacct acatttggaa gaggaaccag    2220
ccttattgtt catccgtata tccagaaccc tgaccctgcg gtataccagc tgagagactc    2280
taaatccagt gacaagtctg tctgcctatt caccgatttt gattctcaaa caaatgtgtc    2340
acaaagtaag gattctgatg tgtatatcac agacaaaact gtgctagaca tgaggtctat    2400
ggacttcaag agcaacagtg ctgtggcctg gagcaacaaa tctgactttg catgtgcaaa    2460
cgccttcaac aacagcatta ttccagaaga caccttcttc cccagcccag gtaagggcag    2520
ctttggtgcc ttcgcaggct gtttccttgc ttcaggaatg ccaggttct  gcccagagct    2580 ctggtcaatg atgtctaaaa ctcctctgat tggtggtctc ggccttatcc attgccacca    2640
aaaccctctt tttactaaga aacagtgagc cttgttctgg cagtccagag aatgacacgg    2700 gaaaaagca gatgaagaga aggtggcagg agagggcacg tggcccagcc tcagtctctc     2760
caactgagtt cctgcctgcc tgcctttgct cagactgttt gccccttact gctcttctag    2820
gcctcattct aagccccttc tccaagttgc ctctccttat ttctccctgt ctgccaaaaa    2880
atctttccca gctcactaag tcagtctcac gcagtcactc attaacccac caatcactga    2940
ttgtgccggc acatgaatgc accaggtgtt gaagtggagg aattaaaaag tcagatgagg    3000
ggtgtgccca gaggaagcac cattctagtt gggggagccc atctgtcagc tgggaaaagt    3060
ccaaataact tcagattgga atgtgtttta actcagggtt gagaaaacag ctaccttcag    3120
gacaaaagtc agggaagggc tctctgaaga aatgctactt gaagatacca gccctaccaa    3180
gggcagggag aggaccctat agaggcctgg gacaggagct caatgagaaa ggagaagagc    3240
agcaggcatg agttgaatga agg                                            3263
```

<210> SEQ ID NO 87
<211> LENGTH: 3263
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3263)

<400> SEQUENCE: 87

```
tttcctcctc aaaaggcagg aggtcggaaa gaataaacaa tgagagtcac attaaaaaca      60
caaaatccta cggaaatact gaagaatgag tctcagcact aaggaaaagc ctccagcagc     120
tcctgctttc tgagggtgaa ggatagacgc tgtggctctg catgactcac tagcactcta     180
tcacggccat attctggcag ggtcagtggc tccaactaac atttgtttgg tactttacag     240
tttattaaat agatgtttat atggagaagc tctcatttct ttctcagaag agcctggcta     300
ggaaggtgga tgaggcacca tattcatttt gcaggtgaaa ttcctgagat gtaaggagct     360
gctgtgactt gctcaaggcc ttatatcgag taaacggtag tgctgggact tagacgcagg     420
tgttctgatt tatagttcaa aacctctatc aatgagagag caatctcctg gtaatgtgat     480
agatttccca acttaatgcc aacataccat aaacctccca ttctgctaat gcccagccta     540
agttggggag accactccag attccaagat gtacagtttg ctttgctggg ccttttttccc    600
```

```
atgcctgcct ttactctgcc agagttatat tgctggggtt ttgaagaaga tcctattaaa    660
taaaagaata agcagtatta ttaagtagcc ctgcatttca ggtttccttg agtggcaggc    720
caggcctggc cgtgaacgtt cactgaaatc atggcctctt ggccaagatt gatagcttgt    780
gcctgtccct gagtcccagt ccatcacgag cagctggttt ctaagatgct atttcccgta    840
taaagcatga gaccgtgact tgccagcccc acagagcccc gcccttgtcc atcactggca    900
tctggactcc agcctgggtt ggggcaaaga gggaaatgag atcatgtcct aaccctgatc    960
ctcttgtccc acagatatcc agaaccctga ccctgccgtg ggaagcggag aaggtagagg   1020
ttctctcctc acttgtggtg atgttgaaga aaaccctggt ccaatggtga gcaagggcga   1080
ggaggataac atggcctctc tcccagcgac acatgagtta cacatctttg gctccatcaa   1140
cggtgtggac tttgacatgg tgggtcaggg caccggcaat ccaaatgatg ttatgaggag   1200
gttaaacctg aagtccacca agggtgacct ccagttctcc ccctggattc tggtccctca   1260
tatcgggtat ggcttccatc agtacctgcc ctaccctgac gggatgtcgc ctttccaggc   1320
cgccatggta gatggctccg ataccaagt ccatcgcaca atgcagtttg aagatggtgc   1380
ctcccttact gttaactacc gctacaccta cgagggaagc cacatcaaag gagaggccca   1440
ggtgaagggg actggtttcc ctgctgacgg tcctgtgatg accaactcgc tgaccgctgc   1500
ggactggtgc aggtcgaaga agacttaccc caacgacaaa accatcatca gtacctttaa   1560
gtggagttac accactggaa atggcaagcg ctaccgagc actgcgcgga ccacctacac   1620
ctttgccaag ccaatggcgg ctaactatct gaagaaccag ccgatgtacg tgttccgtaa   1680
gacgagctc aagcactcca agaccgagct caacttcaag gagtggcaaa aggcctttac   1740
cgatgtgatg ggcatggacg agctgtacaa gggctccggt gctaccaatt tctcactgtt   1800
gaaacaagcg ggcgatgttg aagaaaatcc cggtccaatg gagaccctct gggcctgct   1860
tatcctttgg ctgcagctgc aatgggtgag cagcaaacag gaggtgacgc agattcctgc   1920
agctctgagt gtcccagaag gagaaaactt ggttctcaac tgcagtttca ctgatagcgc   1980
tatttacaac ctccagtggt ttaggcagga ccctgggaaa ggtctcacat ctctgttgct   2040
tattcagtca agtcagagag agcaaacaag tggaagactt aatgcctcgc tggataaatc   2100
atcaggacgt agtactttat acattgcagc ttctcagcct ggtgactcag ccacctacct   2160
ctgtgctgtg aggcccctgt acggaggaag ctacatacct acatttggaa gaggaaccag   2220
ccttattgtt catccgtata tccagaaccc tgaccctgcg gtataccagc tgagagactc   2280
taaatccagt gacaagtctg tctgcctatt caccgatttt gattctcaaa caatgtgtc   2340
acaaagtaag gattctgatg tgtatatcac agacaaaact gtgctagaca tgaggtctat   2400
ggacttcaag agcaacagtg ctgtggcctg gagcaacaaa tctgactttg catgtgcaaa   2460
cgccttcaac aacagcatta ttccagaaga caccttcttc cccagcccag gtaagggcag   2520
ctttggtgcc ttcgcaggct gtttccttgc ttcaggaatg gccaggttct gcccagagct   2580
ctggtcaatg atgtctaaaa ctcctctgat tggtggtctc ggccttatcc attgccacca   2640
aaaccctctt tttactaaga aacagtgagc cttgttctgg cagtccagag aatgacacgg   2700
gaaaaaagca gatgaagaga aggtggcagg agagggcacg tggcccagcc tcagtctctc   2760
caactgagtt cctgcctgcc tgcctttgct cagactgttt gccccttact gctcttctag   2820
gcctcattct aagccccttc tccaagttgc ctctccttat ttctccctgt ctgccaaaaa   2880
atctttccca gctcactaag tcagtctcac gcagtcactc attaacccac caatcactga   2940
ttgtgccggc acatgaatgc accaggtgtt gaagtggagg aattaaaaag tcagatgagg   3000
```

| | |
|---|---:|
| ggtgtgccca gaggaagcac cattctagtt gggggagccc atctgtcagc tgggaaaagt | 3060 |
| ccaaataact tcagattgga atgtgtttta actcagggtt gagaaaacag ctaccttcag | 3120 |
| gacaaaagtc agggaagggc tctctgaaga aatgctactt gaagatacca gccctaccaa | 3180 |
| gggcagggag aggaccctat agaggcctgg gacaggagct caatgagaaa ggagaagagc | 3240 |
| agcaggcatg agttgaatga agg | 3263 |

<210> SEQ ID NO 88
<211> LENGTH: 5263
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5263)

<400> SEQUENCE: 88

| | |
|---|---:|
| aaaaggtaca tgggaatgaa aggataaaaa ggctaaaaaa attaagtacc tctaactcag | 60 |
| cccctgttgc catttctcag agtcttgtgt tctgtggcat tgcgctttct agaccaacag | 120 |
| tgtccaatag aactttctgt ggcaatgaaa atgtcctgtc aatctgcact gtcccataca | 180 |
| atagccacca gctacatgtg gctattgagc tcttgaaatg aagtttccat ttttaattga | 240 |
| aaacatttta tttcacattg actaattttt atttcaacag ccacatgtag ctagagacta | 300 |
| ttataccaga cagagcagcc tagatcttct ccagtctgac acccaccagc cccaggactt | 360 |
| gagtgagtgt ttaaccagga ctcaaagttg ggtttctgcc ccacaaggcc acccccttc | 420 |
| ctctttaaag ccaacctgca tctggtggcc cctgatcccc tgccttgagg atcggcactt | 480 |
| ccagactcct ctcccctct gcagtgctgt ccagtacccc cactgatgac taacaatcag | 540 |
| ggggatgtgt tggtagagct aatggctttc tgtctgtccc ttcccagcaa aggaactatg | 600 |
| ccttagggcc ttcacccaga gtgatgtcag gctgcccaag catgaggagg gaagtaggca | 660 |
| gaatcctctg gagccaaagc tctggatgtc tctcccctct gaccatggag cccaccctg | 720 |
| ctccactgct ccaggacag ccctatgctg caggcagctc tgcccccact cagcatccca | 780 |
| ggggctgatt tctttggttt tggatccagc tggatgtctg cattgccgag gccaccaggg | 840 |
| ctggctcagc aactgtcggg gaatcaccag ggtctgagaa atcttgtgcg catgtgaggg | 900 |
| gctgtgggag cagagaacca ctgggtggga aattctaatc cccaccctgc tggaaactct | 960 |
| ctgggtggcc ccaacatgct aatcctccgg caaacctctg tttcctcctc aaaaggcagg | 1020 |
| aggtcggaaa gaataaacaa tgagagtcac attaaaaaca caaaatccta cggaaatact | 1080 |
| gaagaatgag tctcagcact aaggaaaagc ctccagcagc cctgctttc tgagggtgaa | 1140 |
| ggatagacgc tgtggctctg catgactcac tagcactcta tcacggccat attctggcag | 1200 |
| ggtcagtggc tccaactaac atttgtttgg tactttacag tttattaaat agatgtttat | 1260 |
| atggagaagc tctcatttct ttctcagaag agcctggcta ggaaggtgga tgaggcacca | 1320 |
| tattcatttt gcaggtgaaa ttcctgagat gtaaggagct gctgtgactt gctcaaggcc | 1380 |
| ttatatcgag taaacggtag tgctgggggct tagacgcagg tgttctgatt tatagttcaa | 1440 |
| aacctctatc aatgagagag caatctcctg gtaatgtgat agatttccca acttaatgcc | 1500 |
| aacataccat aaacctccca ttctgctaat gcccagccta agttggggag accactccag | 1560 |
| attccaagat gtacagtttg ctttgctggg cctttttccc atgcctgcct ttactctgcc | 1620 |
| agagttatat tgctggggtt ttgaagaaga tcctattaaa taaaagaata agcagtatta | 1680 |

```
ttaagtagcc ctgcatttca ggtttccttg agtggcaggc caggcctggc cgtgaacgtt    1740
cactgaaatc atggcctctt ggccaagatt gatagcttgt gcctgtccct gagtcccagt    1800
ccatcacgag cagctggttt ctaagatgct atttcccgta taaagcatga gaccgtgact    1860
tgccagcccc acagagcccc gcccttgtcc atcactggca tctggactcc agcctgggtt    1920
ggggcaaaga gggaaatgag atcatgtcct aaccctgatc ctcttgtccc acagatatcc    1980
agaaccctga ccctgccgtg ggaagcggag aaggtagagg ttctctcctc acttgtggtg    2040
atgttgaaga aaaccctggt ccaatggtga gcaagggcga ggaggataac atggcctctc    2100
tcccagcgac acatgagtta cacatctttg gctccatcaa cggtgtggac tttgacatgg    2160
tgggtcaggg caccggcaat ccaaatgatg gttatgagga gttaaacctg aagtccacca    2220
agggtgacct ccagttctcc ccctggattc tggtccctca tatcgggtat ggcttccatc    2280
agtacctgcc ctaccctgac gggatgtcgc cttttcaggc cgccatggta gatggctccg    2340
gataccaagt ccatcgcaca atgcagtttg aagatggtgc ctcccttact gttaactacc    2400
gctacaccta cgagggaagc cacatcaaag agaggcccca ggtgaagggg actggtttcc    2460
ctgctgacgg tcctgtgatg accaactcgc tgaccgctgc ggactggtgc aggtcgaaga    2520
agacttaccc caacgacaaa accatcatca gtaccttaa gtggagttac accactggaa    2580
atggcaagcg ctaccggagc actgcgcgga ccacctacac cttgccaag ccaatggcgg    2640
ctaactatct gaagaaccag ccgatgtacg tgttccgtaa gacggagctc aagcactcca    2700
agaccgagct caacttcaag gagtggcaaa aggcctttac cgatgtgatg ggcatggacg    2760
agctgtacaa gggctccggt gctaccaatt tctcactgtt gaaacaagcg ggcgatgttg    2820
aagaaaatcc cggtccaatg gagaccctct gggcctgct tatcctttgg ctgcagctgc    2880
aatgggtgag cagcaaacag gaggtgacgc agattcctgc agctctgagt gtcccagaag    2940
gagaaaactt ggttctcaac tgcagtttca ctgatagcgc tatttacaac ctccagtggt    3000
ttaggcagga ccctgggaaa ggtctcacat ctctgttgct tattcagtca agtcagagag    3060
agcaaacaag tggaagactt aatgcctcgc tggataaatc atcaggacgt agtactttat    3120
acattgcagc ttctcagcct ggtgactcag ccacctacct ctgtgctgtg aggcccctgt    3180
acggaggaag ctacatacct acatttggaa gaggaaccag ccttattgtt catccgtata    3240
tccagaaccc tgaccctgcg gtataccagc tgagagactc taaatccagt gacagtctg    3300
tctgcctatt caccgatttt gattctcaaa caaatgtgtc acaaagtaag gattctgatg    3360
tgtatatcac agacaaaact gtgctagaca tgaggtctat ggacttcaag agcaacagtg    3420
ctgtggcctg gagcaacaaa tctgactttg catgtgcaaa cgccttcaac aacagcatta    3480
ttccagaaga caccttcttc cccagcccag gtaagggcag ctttggtgcc ttcgcaggct    3540
gtttccttgc ttcaggaatg ccaggttct gcccagagct ctggtcaatg atgtctaaaa    3600
ctcctctgat tggtggtctc ggccttatcc attgccacca aaaccctctt tttactaaga    3660
aacagtgagc cttgttctgg cagtccagag aatgacacgg aaaaaagca gatgaagaga    3720
aggtggcagg agagggcacg tggcccagcc tcagtctctc caactgagtt cctgcctgcc    3780
tgcctttgct cagactgttt gccccttact gctcttctag gcctcattct aagccccttc    3840
tccaagttgc ctctccttat ttctccctgt ctgccaaaaa atctttccca gctcactaag    3900
tcagtctcac gcagtcactc attaacccac caatactga ttgtgccggc acatgaatgc    3960
accaggtgtt gaagtggagg aattaaaaag tcagatgagg ggtgtgccca gaggaagcac    4020
```

```
cattctagtt gggggagccc atctgtcagc tgggaaaagt ccaaataact tcagattgga    4080
atgtgtttta actcagggtt gagaaaacag ctaccttcag gacaaaagtc agggaagggc    4140
tctctgaaga aatgctactt gaagatacca gccctaccaa gggcagggag aggaccctat    4200
agaggcctgg gacaggagct caatgagaaa ggagaagagc agcaggcatg agttgaatga    4260
aggaggcagg gccgggtcac agggccttct aggccatgag agggtagaca gtattctaag    4320
gacgccagaa agctgttgat cggcttcaag caggggaggg acacctaatt tgcttttctt    4380
tttttttttt tttttttttt tttttttga gatggagttt tgctcttgtt gcccaggctg    4440
gagtgcaatg gtgcatcttg gctcactgca acctccgcct cccaggttca agtgattctc    4500
ctgcctcagc ctcccgagta gctgagatta caggcacccg ccaccatgcc tggctaattt    4560
tttgtatttt tagtagagac agggtttcac tatgttggcc aggctggtct cgaactcctg    4620
acctcaggtg atccacccgc ttcagcctcc caaagtgctg ggattacagg cgtgagccac    4680
cacacccggc ctgctttttct taaagatcaa tctgagtgct gtacggagag tgggttgtaa    4740
gccaagagta gaagcagaaa gggagcagtt gcagcagaga gatgatggag cctgggcag    4800 ggtggtggca gggaggtaac caacaccatt caggtttcaa aggtagaacc atgcagggat    4860
gagaaagcaa agagggatc aaggaaggca gctggatttt ggcctgagca gctgagtcaa    4920
tgatagtgcc gtttactaag aagaaaccaa ggaaaaaatt tggggtgcag ggatcaaaac    4980
tttttggaac atatgaaagt acgtgtttat actcttatg gcccttgtca ctatgtatgc    5040
ctcgctgcct ccattggact ctagaatgaa gccaggcaag agcagggtct atgtgtgatg    5100
gcacatgtgg ccagggtcat gcaacatgta ctttgtacaa acagtgtata ttgagtaaat    5160
agaaatggtg tccaggagcc gaggtatcgg tcctgccagg gccaggggct ctccctagca    5220
ggtgctcata tgctgtaagt tccctccaga tctctccaca agg                      5263

<210> SEQ ID NO 89
<211> LENGTH: 5263
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5263)

<400> SEQUENCE: 89
aaaaggtaca tgggaatgaa aggataaaaa ggctaaaaaa attaagtacc tctaactcag     60
cccctgttgc catttctcag agtcttgtgt tctgtggcat tgcgctttct agaccaacag    120
tgtccaatag aactttctgt ggcaatggaa atgtcctgtc aatctgcact gtcccataca    180
atagccacca gctacatgtg gctattgagc tcttgaaatg aagtttccat ttttaattga    240
aaacatttta tttcacattg actaattttt atttcaacag ccacatgtag ctagagacta    300
ttataccaga cagagcagcc tagatcttct ccagtctgac acccaccagc cccaggactt    360
gagtgagtgt ttaaccagga ctcaaagttg ggtttctgcc ccacaaggcc accccctttc    420
ctctttaaag ccaacctgca tctggtggcc cctgatcccc tgccttgagg atcggcactt    480
ccagactcct ctcccctct gcagtgctgt ccagtacccc cactgatgac taacaatcag    540
ggggatgtgt tggtagagct aatggctttc tgtctgtccc ttcccagcaa aggaactatg    600
ccttagggcc ttcacccaga gtgatgtcag gctgccaag catgaggagg gaagtaggca    660
gaatcctctg gagccaaagc tctggatgtc tctccctct gaccatggag cccacccctg    720
```

-continued

```
ctccactgct ccagggacag ccctatgctg caggcagctc tgcccccact cagcatccca    780
ggggctgatt tctttggttt tggatccagc tggatgtctg cattgccgag gccaccaggg    840
ctggctcagc aactgtcggg gaatcaccag ggtctgagaa atcttgtgcg catgtgaggg    900
gctgtgggag cagagaacca ctgggtggga aattctaatc cccaccctgc tggaaactct    960
ctgggtggcc ccaacatgct aatcctccgg caaacctctg tttcctcctc aaaaggcagg   1020
aggtcggaaa gaataaacaa tgagagtcac attaaaaaca caaatcccta cggaaatact   1080
gaagaatgag tctcagcact aaggaaaagc ctccagcagc tcctgctttc tgagggtgaa   1140
ggatagacgc tgtggctctg catgactcac tagcactcta tcacggccat attctggcag   1200
ggtcagtggc tccaactaac atttgtttgg tactttacag tttattaaat agatgtttat   1260
atggagaagc tctcatttct ttctcagaag agcctggcta ggaaggtgga tgaggcacca   1320
tattcatttt gcaggtgaaa ttcctgagat gtaaggagct gctgtgactt gctcaaggcc   1380
ttatatcgag taaacggtag tgctggggct tagacgcagg tgttctgatt tatagttcaa   1440
aacctctatc aatgagagag caatctcctg gtaatgtgat agatttccca acttaatgcc   1500
aacataccat aaacctccca ttctgctaat gcccagccta agttggggag accactccag   1560
attccaagat gtacagtttg ctttgctggg ccttttttccc atgcctgcct ttactctgcc   1620
agagttatat tgctggggtt ttgaagaaga tcctattaaa taaaagaata agcagtatta   1680
ttaagtagcc ctgcatttca ggtttccttg agtggcaggc caggcctggc cgtgaacgtt   1740
cactgaaatc atggcctctt ggccaagatt gatagcttgt gcctgtccct gagtcccagt   1800
ccatcacgag cagctggttt ctaagatgct atttcccgta taaagcatga daccgtgact   1860
tgccagcccc acagagcccc gcccttgtcc atcactggca tctggactcc agcctgggtt   1920
ggggcaaaga gggaaatgag atcatgtcct aaccctgatc ctcttgtccc acagatatcc   1980
agaaccctga ccctgccgtg ggaagcggag aaggtagagg ttctctcctc acttgtggtg   2040
atgttgaaga aaaccctggt ccaatggtga gcaagggcga ggaggataac atggcctctc   2100
tcccagcgac acatgagtta cacatctttg gctccatcaa cggtgtggac tttgacatgg   2160
tgggtcaggg caccggcaat ccaaatgatg gttatgagga gttaaacctg aagtccacca   2220
agggtgacct ccagttctcc ccctggattc tggtccctca tatcgggtat ggcttccatc   2280
agtacctgcc ctaccctgac gggatgtcgc ctttccaggc cgccatggta gatgcctccg   2340
gataccaagt ccatcgcaca atgcagtttg aagatggtgc ctcccttact gttaactacc   2400
gctacaccta cgagggaagc cacatcaaag gagaggccca ggtgaagggg actggtttcc   2460
ctgctgacgg tcctgtgatg accaactcgc tgaccgctgc ggactggtgc aggtcgaaga   2520
agacttaccc caacgacaaa accatcatca gtaccttta agtggagttac accactggaa   2580
atggcaagcg ctaccggagc actgcgcgga ccacctacac ctttgccaag ccaatggcgg   2640
ctaactatct gaagaaccag ccgatgtacg tgttccgtaa gacggagctc aagcactcca   2700
agaccgagct caacttcaag gagtggcaaa aggcctttac cgatgtgatg ggcatggacg   2760
agctgtacaa gggctccggt gctaccaatt ctctcactgtt gaaacaagcg ggcgatgttg   2820
aagaaaatcc cggtccaatg gagaccctct gggcctgct tatcctttgg ctgcagctgc   2880
aatgggtgag cagcaaacag gaggtgacgc agattcctgc agctctgagt gtcccagaag   2940
gagaaaactt ggttctcaac tgcagtttca ctgatagcgc tatttacaac ctccagtggt   3000
ttaggcagga ccctgggaaa ggtctcacat ctctgttgct tattcagtca agtcagagag   3060
agcaaacaag tggaagactt aatgcctcgc tggataaatc atcaggacgt agtactttat   3120
```

```
acattgcagc ttctcagcct ggtgactcag ccacctacct ctgtgctgtg aggcccctgt   3180
acggaggaag ctacatacct acatttggaa gaggaaccag ccttattgtt catccgtata   3240
tccagaaccc tgaccctgcg gtataccagc tgagagactc taaatccagt gacaagtctg   3300
tctgcctatt caccgatttt gattctcaaa caaatgtgtc acaaagtaag gattctgatg   3360
tgtatatcac agacaaaact gtgctagaca tgaggtctat ggacttcaag agcaacagtg   3420
ctgtggcctg agcaacaaa tctgactttg catgtgcaaa cgccttcaac aacagcatta    3480
ttccagaaga caccttcttc cccagcccag gtaagggcag cttt ggtgcc ttcgcaggct   3540
gtttccttgc ttcaggaatg ccaggttct gcccagagct ctggtcaatg atgtctaaaa    3600
ctcctctgat tggtggtctc ggccttatcc attgccacca aaaccctctt tttactaaga   3660
aacagtgagc cttgttctgg cagtccagag aatgacacgg gaaaaaagca gatgaagaga   3720
aggtggcagg agagggcacg tggcccagcc tcagtctctc caactgagtt cctgcctgcc   3780
tgcctttgct cagactgttt gccccttact gctcttctag gctcattct aagcccccttc    3840
tccaagttgc ctctccttat ttctccctgt ctgccaaaaa atctttccca gctcactaag   3900
tcagtctcac gcagtcactc attaacccac caatcactga ttgtgccggc acatgaatgc   3960
accaggtgtt gaagtggagg aattaaaaag tcagatgagg ggtgtgccca gaggaagcac   4020
cattctagtt gggggagccc atctgtcagc tgggaaaagt ccaaataact tcagattgga   4080
atgtgtttta actcagggtt gagaaaacag ctaccttcag gacaaaagtc agggaagggc   4140
tctctgaaga aatgctactt gaagatacca gccctaccaa gggcagggag aggaccctat   4200
agaggcctgg gacaggagct caatgagaaa ggagaagagc agcaggcatg agttgaatga   4260
aggaggcagg gccgggtcac agggccttct aggccatgag agggtagaca gtattctaag   4320
gacgccagaa agctgttgat cggcttcaag caggggaggg acacctaatt tgcttttctt   4380
tttttttttt tttttttttt tttttttgga gatggagttt tgctcttgtt gcccaggctg   4440
gagtgcaatg gtgcatcttg gctcactgca acctccgcct cccaggttca agtgattctc   4500
ctgcctcagc ctcccgagta gctgagatta caggcacccg ccaccatgcc tggctaattt   4560
tttgtatttt tagtagagac agggtttcac tatgttggcc aggctggtct cgaactcctg   4620
acctcaggtg atccaccgc ttcagcctcc caaagtgctg ggattacagg cgtgagccac    4680
cacacccggc ctgcttttct taaagatcaa tctgagtgct gtacgagag tgggttgtaa    4740
gccaagagta gaagcagaaa gggagcagtt gcagcagaga gatgatggag gcctgggcag   4800
ggtggtggca gggaggtaac caacaccatt caggtttcaa aggtagaacc atgcagggat   4860
gagaaagcaa agaggggatc aaggaaggca gctggatttt ggcctgagca gctgagtcaa   4920
tgatagtgcc gtttactaag aagaaaccaa ggaaaaaatt tggggtgcag ggatcaaaac   4980
ttttt ggaac atatgaaagt acgtgtttat actctttatg gcccttgtca ctatgtatgc    5040
ctcgctgcct ccattggact ctagaatgaa gccaggcaag agcagggtct atgtgtgatg   5100
gcacatgtgg ccagggtcat gcaacatgta ctttgtacaa acagtgtata ttgagtaaat   5160
agaaatggtg tccaggagcc gaggtatcgg tcctgccagg ccaggggct ctccctagca    5220
ggtgctcata tgctgtaagt tccctccaga tctctccaca agg              5263
```

<210> SEQ ID NO 90
<211> LENGTH: 2491
<212> TYPE: DNA
<213> ORGANISM: Artificial Sequence
<220> FEATURE:

<223> OTHER INFORMATION: Synthetic Polynucleotide
<220> FEATURE:
<221> NAME/KEY: misc_feature
<222> LOCATION: (1)..(2491)

<400> SEQUENCE: 90

| | | | | | |
|---|---|---|---|---|---|
| aacataccat | aaacctccca | ttctgctaat | gcccagccta | agttggggag | accactccag | 60 |
| attccaagat | gtacagtttg | ctttgctggg | ccttttccc | atgcctgcct | ttactctgcc | 120 |
| agagttatat | tgctggggtt | ttgaagaaga | tcctattaaa | taaaagaata | agcagtatta | 180 |
| ttaagtagcc | ctgcatttca | ggtttccttg | agtggcaggc | caggcctggc | cgtgaacgtt | 240 |
| cactgaaatc | atggcctctt | ggccaagatt | gatagcttgt | gcctgtccct | gagtcccagt | 300 |
| ccatcacgag | cagctggttt | ctaagatgct | atttcccgta | taaagcatga | gaccgtgact | 360 |
| tgccagcccc | acagagcccc | gcccttgtcc | atcactggca | tctggactcc | agcctgggtt | 420 |
| ggggcaaaga | gggaaatgag | atcatgtcct | aaccctgatc | ctcttgtccc | acagatatcc | 480 |
| agaaccctga | ccctgccgtg | ggaagcgag  | aaggtagagg | ttctctcctc | acttgtggtg | 540 |
| atgttgaaga | aaaccctggt | ccaatgggct | cctggaccct | ctgctgtgtg | tcctttgca  | 600 |
| tcctggtagc | aaagcacaca | gatgctggag | ttatccagtc | accccggcac | gaggtgacag | 660 |
| agatgggaca | agaagtgact | ctgagatgta | aaccaatttc | aggacacgac | tacctttct  | 720 |
| ggtacagaca | gaccatgatg | cggggactgg | agttgctcat | ttactttaac | aacaacgttc | 780 |
| cgatagatga | ttcagggatg | cccgaggatc | gattctcagc | taagatgcct | aatgcatcat | 840 |
| tctccactct | gaagatccag | ccctcagaac | ccagggactc | agctgtgtac | ttctgtgcca | 900 |
| gcagttccgc | taactatggc | tacaccttcg | gttcgggggac | caggttaacc | gttgtagagg | 960 |
| acctgaaaaa | cgtgttccca | cccgaggtcg | ctgtgtttga | gccatcagaa | gcagagatct | 1020 |
| cccacacca | aaaggccaca | ctggtgtgcc | tggccacagg | cttctaccc  | gaccacgtgg | 1080 |
| agctgagctg | gtgggtgaat | gggaaggag  | tgcacagtgg | ggtcagcaca | gacccgcagc | 1140 |
| ccctcaagga | gcagcccgcc | ctcaatgact | ccagatactg | cctgagcagc | cgcctgaggg | 1200 |
| tctcggccac | cttctggcag | aaccccgca  | accacttccg | ctgtcaagtc | cagttctacg | 1260 |
| ggctctcaga | aaacgatgaa | tggacacaag | ataggggcaa | acctgtcacc | cagatcgtca | 1320 |
| gcgccgaggc | ctgggtaga  | gcagactgtg | gcttcacctc | cgagtcttac | cagcaagggg | 1380 |
| tcctgtctgc | caccatcctc | tatgagatct | tgctaggaa  | ggccaccttg | tatgccgtgc | 1440 |
| tggtcagtgc | cctcgtgctg | atggccatgg | tcaagagaaa | ggattccaga | ggccgcgcca | 1500 |
| agcgctccga | ctccggtgct | accaatttct | cactgttgaa | acaagcgggc | gatgttgaag | 1560 |
| aaaatcccgg | tccaatgctc | cttgaacatt | tattaataat | cttgtggatg | cagctgacat | 1620 |
| gggtcagtgg | tcaacagctg | aatcagagtc | ctcaatctat | gtttatccag | gaaggagaag | 1680 |
| atgtctccat | gaactgcact | tcttcaagca | tatttaacac | ctggctatgg | tacaagcagg | 1740 |
| accctgggga | aggtcctgtc | ctcttgatag | ccttatataa | ggctggtgaa | ttgacctcaa | 1800 |
| atggaagact | gactgctcag | tttggtataa | ccagaaagga | cagcttcctg | aatatctcag | 1860 |
| catccatacc | tagtgatgta | ggcatctact | tctgtgctgg | gccgatgaaa | acctcctacg | 1920 |
| acaaggtgat | atttgggcca | gggacaagct | tatcagtcat | tccaaatatc | cagaaccctg | 1980 |
| accctgcggt | ataccagctg | agagactcta | aatccagtga | caagtctgtc | tgcctattca | 2040 |
| ccgattttga | ttctcaaaca | aatgtgtcac | aaagtaagga | ttctgatgtg | tatatcacag | 2100 |
| acaaaactgt | gctagacatg | aggtctatgg | acttcaagag | caacagtgct | gtggcctgga | 2160 |

```
gcaacaaatc tgactttgca tgtgcaaacg ccttcaacaa cagcattatt ccagaagaca    2220
ccttcttccc cagcccaggt aagggcagct ttggtgcctt cgcaggctgt ttccttgctt    2280
caggaatggc caggttctgc ccagagctct ggtcaatgat gtctaaaact cctctgattg    2340
gtggtctcgg ccttatccat tgccaccaaa accctctttt tactaagaaa cagtgagcct    2400
tgttctggca gtccagagaa tgacacggga aaaaagcaga tgaagagaag gtggcaggag    2460
agggcacgtg gcccagcctc agtctctcca a                                  2491

<210> SEQ ID NO 91
<211> LENGTH: 2789
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2789)

<400> SEQUENCE: 91
aacataccat aaacctccca ttctgctaat gcccagccta agttggggag accactccag      60
attccaagat gtacagtttg ctttgctggg ccttttttccc atgcctgcct ttactctgcc    120
agagttatat tgctggggtt ttgaagaaga tcctattaaa taaaagaata agcagtatta    180
ttaagtagcc ctgcatttca ggtttccttg agtggcaggc caggcctggc cgtgaacgtt    240
cactgaaatc atggcctctt ggccaagatt gatagcttgt gcctgtccct gagtcccagt    300
ccatcacgag cagctggttt ctaagatgct atttcccgta taaagcatga gaccgtgact    360
tgccagcccc acagagcccc gcccttgtcc atcactggca tctggactcc agcctgggtt    420
ggggcaaaga gggaaatgag atcatgtcct aaccctgatc ctcttgtccc acagatatcc    480
agaaccctga ccctgccgtg ggaagcggag aaggtagagg ttctctcctc acttgtggtg    540
atgttgaaga aaaccctggt ccaatgctcc ttttggtgac ttccttgctc ctgtgcgagc    600
tcccgcaccc cgcgttcctg ctcattcccg acgattataa agatgacgat gacaagatcc    660
agatgaccca gacgaccagc agcctgtctg cttcgctggg tgaccgcgtc accatctcat    720
gccgcgccag ccaggacatt tccaagtacc tcaactggta ccaacagaag ccagacggca    780
ccgtcaagct gctgatctac catacctctc gccttcatag tggtgtgcca tccaggtttt    840
cagggtctgg ctcaggcacc gactactccc tcactatctc taatctggaa caggaggaca    900
tcgctaccta tttctgtcaa cagggcaaca cgttacccta taccttcggc ggaggcacca    960
agttggagat caccggctcc acaagtggga gcggtaaacc gggctccggg gagggctcta    1020
caaaaggtga agtgaagttg caggagagcg ggcccggtct cgtagcacca tcccagagcc    1080
tgtcggtaac ctgcaccgtg tccggggtgt ccctgcccga ctacgcgtg agttggatcc    1140 gccagccacc caggaaagga ctggaatggc taggcgtgat ctgggctcc gagactacct    1200 actacaactc cgcccctgaaa tctcgcctga ccataatcaa ggacaactct aagtcccagg    1260
tgttcctgaa gatgaattcc ctacagactg atgacaccgc catctactac tgtgccaagc    1320
actactacta cggtgggagc tacgccatgg attattgggg ccagggcacg tccgtgaccg    1380
tgtcgtctgc ggccgctatt gaggtgatgt atccccgcc gtacctggac aacgagaagt    1440
ctaatggcac cattatccac gttaagggga agcacctgtg cccaagcccc ctgttccccg    1500
gccccttcca agcccttctgg gtcctggtgg tggtcggggg tgtcctggcc tgttactctc    1560
tgttagtcac cgtggcattc atcatcttct gggtcagatc caagcgcagt cggctgctgc    1620
```

| | |
|---|---|
| actccgacta catgaacatg acccccgcc ggcctggtcc tacccgcaag cattaccagc | 1680 |
| cgtacgcgcc gccccgggat tttgctgcct accgtagccg tgttaaattt tcacgctcgg | 1740 |
| cggacgcacc tgcgtatcag cagggacaga accagctgta caacgagctg aacctgggca | 1800 |
| ggcgtgagga gtacgacgtg ctggacaagc cgcgcggccg cgaccccgag atgggcggca | 1860 |
| aacctcgtcg caagaaccct caggagggcc tttacaacga gctgcagaag gacaaaatgg | 1920 |
| ccgaggctta ttcggagatc ggaatgaagg gggagcgccg acgcggcaag ggccacgatg | 1980 |
| gcctgtacca gggtttgtcc actgccacta aggatacata tgatgcgctg cacatgcagg | 2040 |
| cccttcctcc tcgatagcta gagctcgctg atcagcctcg actgtgcctt ctagttgcca | 2100 |
| gccatctgtt gtttgcccct ccccgtgcc ttccttgacc ctggaaggtg ccactcccac | 2160 |
| tgtcctttcc taataaaatg aggaaattgc atcgcattgt ctgagtaggt gtcattctat | 2220 |
| tctgggggt ggggtggggc aggacagcaa ggggaggat tgggaagaga atagcaggca | 2280 |
| tgctggggat accagctgag agactctaaa tccagtgaca agtctgtctg cctattcacc | 2340 |
| gattttgatt ctcaaacaaa tgtgtcacaa agtaaggatt ctgatgtgta tatcacagac | 2400 |
| aaaactgtgc tagacatgag gtctatggac ttcaagagca acagtgctgt ggcctggagc | 2460 |
| aacaaatctg actttgcatg tgcaaacgcc ttcaacaaca gcattattcc agaagacacc | 2520 |
| ttcttcccca gcccaggtaa gggcagcttt ggtgccttcg caggctgttt ccttgcttca | 2580 |
| ggaatggcca ggttctgccc agagctctgg tcaatgatgt ctaaaactcc tctgattggt | 2640 |
| ggtctcggcc ttatccattg ccaccaaaac cctctttta ctaagaaaca gtgagccttg | 2700 |
| ttctggcagt ccagagaatg acacgggaaa aaagcagatg aagagaaggt ggcaggagag | 2760 |
| ggcacgtggc ccagcctcag tctctccaa | 2789 |

<210> SEQ ID NO 92
<211> LENGTH: 1350
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1350)

<400> SEQUENCE: 92

| | |
|---|---|
| ggtagctagg agttccagga ctcagtttcc cctttgagcc tcctttagcg actaaagctt | 60 |
| gaagccccac gcatctcgac tctcgcgcac accgcccttg ttgggctcag ggcggggcg | 120 |
| ccgcccccgg aagtacttcc ccttaaaggc tggggcctgc cggaaatggc gcagcggcag | 180 |
| ggagggctc ttcacccagt ccggcagttg aagctcggcg ctcgggttac ccctgcagcg | 240 |
| acgcccctg gtcccacaga taccactgct gctcccgccc tttcgctcct cggccgcgca | 300 |
| atgggcggat cgggtgggac tagtggcagc aagggcgagg agctgttcac cggggtggtg | 360 |
| cccatcctgg tcgagctgga cggcgacgta aacggccaca agttcagcgt gcgcggcgag | 420 |
| ggcgagggcg atgccaccaa cggcaagctg accctgaagt tcatctgcac caccggcaag | 480 |
| ctgcccgtgc cctggcccac cctcgtgacc accctgacct acggcgtgca gtgcttcagc | 540 |
| cgctaccccg accacatgaa gcgccacgac ttcttcaagt ccgccatgcc cgaaggctac | 600 |
| gtccaggagc gcaccatcag cttcaaggac gacggcacct acaagacccg cgccgaggtg | 660 |
| aagttcgagg gcgacaccct ggtgaaccgc atcgagctga agggcatcga cttcaaggag | 720 |
| gacggcaaca tcctggggca caagctggag tacaacttca acagccacaa cgtctatatc | 780 |

```
accgccgaca agcagaagaa cggcatcaag gccaacttca agatccgcca caacgtggag      840
gacggcagcg tgcagctcgc cgaccactac cagcagaaca cccccatcgg cgacggcccc      900
gtgctgctgc ccgacaacca ctacctgagc acccagtccg tgctgagcaa agaccccaac      960
gagaagcgcg atcacatggt cctgctggag ttcgtgaccg ccgccgggat cactggaacc     1020
ggtgctggaa gtggtacacg cgacgacgag tacgactacc tctttaaagg tgaggccatg     1080
ggctctcgca ctctacacag tcctcgttcg gggacccggg ccactcccgg tggaccctcg     1140
tgccggccac ccctgcactg atataggcct ccctcagccc ttccttttttg tgcggttccg    1200 tctcctaccc agctcagcct cttctccccc gctcagacag gggtcccat cacatgccgc      1260 tctctgagcg acctctccat aggccttcgc tggcctcaga gcccctccct gcgtgtcctt     1320
cccctggcgg actgccttct cccacatcgt                                      1350
```

<210> SEQ ID NO 93
<211> LENGTH: 1350
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1350)

<400> SEQUENCE: 93

```
ggtagctagg agttccagga ctcagtttcc cctttgagcc tcctttagcg actaaagctt       60
gaagccccac gcatctcgac tctcgcgcac accgcccttg ttgggctcag ggcggggcg       120 ccgcccccgg aagtacttcc ccttaaaggc tggggcctgc cggaaatggc gcagcggcag      180 ggagggctc ttcacccagt ccggcagttg aagctcggcg ctcgggttac ccctgcagcg       240 acgcccctg gtcccacaga taccactgct gctcccgccc tttcgctcct cggccgcgca      300
atgggcggat cgggtgggac tagtggcagc aagggcgagg agctgttcac cggggtggtg     360
cccatcctgg tcgagctgga cggcgacgta acggccacaa agttcagcgt gcgcggcgag     420
ggcgagggcg atgccaccaa cggcaagctg accctgaagt tcatctgcac caccggcaag     480
ctgcccgtgc cctggcccac cctcgtgacc accctgacct acggcgtgca gtgcttcagc     540
cgctaccccg accacatgaa gcgccacgac ttcttcaagt ccgccatgcc cgaaggctac     600
gtccaggagc gcaccatcag cttcaaggac gacggcacct acaagacccg cgccgaggtg     660
aagttcgagg gcgacaccct ggtgaaccgc atcgagctga agggcatcga cttcaaggag     720
gacggcaaca tcctggggca caagctggag tacaacttca acagccacaa cgtctatatc     780
accgccgaca agcagaagaa cggcatcaag gccaacttca agatccgcca caacgtggag     840
gacggcagcg tgcagctcgc cgaccactac cagcagaaca cccccatcgg cgacggcccc     900
gtgctgctgc ccgacaacca ctacctgagc acccagtccg tgctgagcaa agaccccaac     960
gagaagcgcg atcacatggt cctgctggag ttcgtgaccg ccgccgggat cactggaacc    1020
ggtgctggaa gtggtacacg cgacgacgag tacgactacc tctttaaagg tgaggccatg    1080
ggctctcgca ctctacacag tcctcgttcg gggacccggg ccactcccgg tggaccctcg    1140
tgccggccac ccctgcactg atataggcct ccctcagccc ttccttttttg tgcggttccg   1200 tctcctaccc agctcagcct cttctccccc gctcagacag gggtcccat cacatgccgc     1260 tctctgagcg acctctccat aggccttcgc tggcctcaga gcccctccct gcgtgtcctt    1320
cccctggcgg actgccttct cccacatcgt                                     1350
```

<210> SEQ ID NO 94
<211> LENGTH: 2754
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2754)

<400> SEQUENCE: 94

```
agaaaggtga agagccaaag ttagaactca ggaccaactt attctgattt tgttttccca      60
aactgcttct cctcttggga agtgtaagga agctgcagca ccaggatcag tgaaacgcac     120
cagacggccg cgtcagagca gctcaggttc tgggagaggg tagcgcaggg tggccactga     180
gaaccgggca ggtcacgcat cccccccttc cctcccaccc cctgccaagc tctccctccc     240
aggatcctct ctggctccat cgtaagcaaa ccttagaggt tctggcaagg agagagatgg     300
ctccaggaaa tggggtgtg tcaccagata aggaatctgc ctaacaggag gtgggggtta     360
gacccaatat caggagacta ggaaggagga ggcctaagga tggggctttt ctgtcaccaa     420
tcctgtccct agtggcccca ctgtggggtg gaggggacaa taaaagtac ccagaaccag     480
agccacatta accggccctg cgttacataa cttacggtaa atggcccgcc tggctgaccg     540
cccaacgacc cccgcccatt gacgtcaata gtaacgccaa tagggacttt ccattgacgt     600
caatgggtgg agtatttacg gtaaactgcc cacttggcag tacatcaagt gtatcatatg     660
ccaagtacgc ccctattga cgtcaatgac ggtaaatggc ccgcctggca ttgtgcccag     720
tacatgacct tatgggactt tcctacttgg cagtacatct acgtattagt catcgctatt     780
accatggtcg aggtgagccc cacgttctgc ttcactctcc ccatctcccc ccctccccca     840
cccccaattt tgtatttatt tattttttaa ttattttgtg cagcgatggg ggcggggggg     900
gggggggggc gcgcgccagg cggggcgggg cgggcgagg ggcggggcgg ggcgaggcgg     960
agaggtgcgg cggcagccaa tcagagcggc gcgctccgaa agtttccttt tatggcgagg    1020
cggcggcggc ggcggcccta taaaagcga agcgcgcggc gggcgggagt cgctgcgacg    1080
ctgccttcgc cccgtgcccc gctccgccgc cgcctcgcgc cgcccgcccc ggctctgact    1140
gaccgcgtta ctcccacagg tgagcgggcg ggacggccct tctcctccgg gctgtaatta    1200
gctgagcaag aggtaagggt ttaagggatg gttggttggt ggggtattaa tgtttaatta    1260
cctggagcac ctgcctgaaa tcactttttt tcaggttggt ctagagccac catggtgagc    1320
aagggcgagg aggataacat ggcctctctc ccagcgacac atgagttaca catctttggc    1380
tccatcaacg gtgtggactt tgacatggtg ggtcagggca ccggcaatcc aaatgatggt    1440
tatgaggagt taaacctgaa gtccaccaag ggtgacctcc agttctcccc ctggattctg    1500
gtccctcata tcgggtatgg cttccatcag tacctgccct accctgacgg gatgtcgcct    1560
ttccaggccg ccatggtaga tggctccgga taccaagtcc atcgcacaat gcagtttgaa    1620
gatggtgcct cccttactgt taactaccgc tacacctacg agggaagcca catcaaagga    1680
gaggcccagg tgaaggggac tggtttccct gctgacggtc ctgtgatgac caactcgctg    1740
accgctgcga ctggtgcag tcgaagaag acttacccca cgacaaaac catcatcagt    1800
acctttaagt ggagttacac cactggaaat ggcaagcgct accggagcac tgcgcggacc    1860
acctacacct ttgccaagcc aatgcgcgct aactatctga agaaccagcc gatgtacgtg    1920
ttccgtaaga cggagctcaa gcactccaag accgagctca acttcaagga gtggcaaaag    1980
```

```
gcctttaccg atgtgatggg catggacgag ctgtacaagt agctagagct cgctgatcag   2040
cctcgactgt gccttctagt tgccagccat ctgttgtttg cccctccccc gtgccttcct   2100
tgaccctgga aggtgccact cccactgtcc tttcctaata aaatgaggaa attgcatcgc   2160
attgtctgag taggtgtcat tctattctgg ggggtgggt ggggcaggac agcaagggggg   2220 aggattggga agagaatagc aggcatgctg gggaggaata taaggtggtc ccagctcggg   2280
gacacaggat ccctggaggc agcaaacatg ctgtcctgaa gtggacatag ggcccgggt   2340 tggaggaaga agactagctg agctctcgga cccctggaag atgccatgac aggggctgg   2400 aagagctagc acagactaga gaggtaaggg gggtagggga gctgcccaaa tgaaaggagt   2460
gagaggtgac ccgaatccac aggagaacgg ggtgtccagg caaagaaagc aagaggatgg   2520
agaggtggct aaagccaggg agacggggta ctttggggtt gtccagaaaa acggtgatga   2580
tgcaggccta caagaagggg aggcgggacg caagggagac atccgtcgga gaaggccatc   2640
ctaagaaacg agagatggca caggccccag aaggagaagg aaaagggaac ccagcgagtg   2700
aagacggcat ggggttgggt gagggaggag agatgcccgg agaggaccca gaca          2754
```

<210> SEQ ID NO 95
<211> LENGTH: 2754
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2754)

<400> SEQUENCE: 95

```
agaaaggtga agagccaaag ttagaactca ggaccaactt attctgattt tgttttcca    60 aactgcttct cctcttggga agtgtaagga agctgcagca ccaggatcag tgaaacgcac   120
cagacggccg cgtcagagca gctcaggttc tgggagaggg tagcgcaggg tggccactga   180
gaaccgggca ggtcacgcat ccccccttc cctcccaccc cctgccaagc tctccctccc   240
aggatcctct ctggctccat cgtaagcaaa ccttagaggt tctggcaagg agagagatgg   300
ctccaggaaa tgggggtgtg tcaccagata aggaatctgc ctaacaggag gtgggggtta   360
gacccaatat caggagacta ggaaggagga ggcctaagga tggggctttt ctgtcaccaa   420
tcctgtccct agtggcccca ctgtggggtg gaggggacag ataaaagtac ccagaaccag   480
agccacatta accggccctg cgttacataa cttacggtaa atggcccgcc tggctgaccg   540
cccaacgacc cccgcccatt gacgtcaata gtaacgccaa tagggacttt ccattgacgt   600
caatgggtgg agtatttacg gtaaactgcc cacttggcag tacatcaagt gtatcatatg   660
ccaagtacgc cccctattga cgtcaatgac ggtaaatggc ccgcctggca ttgtgcccag   720
tacatgacct tatgggactt tcctacttgg cagtacatct acgtattagt catcgctatt   780
accatggtcg aggtgagccc cacgttctgc ttcactctcc ccatctcccc ccctccccca   840
ccccaatttt gtatttatt tattttttaa ttattttgtg cagcgatggg ggcggggggg   900
gggggggggc gcgcgccagg cggggcgggg cgggcgagg ggcggggcgg ggcgaggcgg   960
agaggtgcgg cggcagccaa tcagagcggc gcgctccgaa agtttccttt tatggcgagg  1020
cggcggcggc ggcggcccta taaaagcga agcgcgcggc gggcgggagt cgctgcgacg  1080
ctgccttcgc cccgtgcccc gctccgccgc cgcctcgcgc cgcccgcccc ggctctgact  1140
gaccgcgtta ctcccacagg tgagcgggcg ggacggccct tctcctccgg gctgtaatta  1200
```

```
gctgagcaag aggtaagggt ttaagggatg gttggttggt ggggtattaa tgtttaatta    1260
cctggagcac ctgcctgaaa tcactttttt tcaggttggt ctagagccac catggtgagc    1320
aagggcgagg aggataacat ggcctctctc ccagcgacac atgagttaca catctttggc    1380
tccatcaacg gtgtggactt tgacatggtg ggtcagggca ccggcaatcc aaatgatggt    1440
tatgaggagt taaacctgaa gtccaccaag ggtgacctcc agttctcccc ctggattctg    1500
gtccctcata tcgggtatgg cttccatcag tacctgccct accctgacgg gatgtcgcct    1560
ttccaggccg ccatggtaga tggctccgga taccaagtcc atcgcacaat gcagtttgaa    1620
gatggtgcct cccttactgt taactaccgc tacacctacg agggaagcca catcaaagga    1680
gaggcccagg tgaaggggac tggtttccct gctgacggtc ctgtgatgac caactcgctg    1740
accgctgcgg actggtgcag gtcgaagaag acttacccca cgacaaaac catcatcagt    1800 acctttaagt ggagttacac cactggaaat ggcaagcgct accggagcac tgcgcggacc    1860
acctacacct tgccaagcc aatggcggct aactatctga agaaccagcc gatgtacgtg    1920
ttccgtaaga cggagctcaa gcactccaag accgagctca acttcaagga gtggcaaaag    1980
gcctttaccg atgtgatggg catggacgag ctgtacaagt agctagagct cgctgatcag    2040
cctcgactgt gccttctagt tgccagccat ctgttgtttg ccctccccc gtgccttcct    2100 tgaccctgga agtgccact cccactgtcc tttcctaata aaatgaggaa attgcatcgc    2160
attgtctgag taggtgtcat tctattctgg ggggtgggt ggggcaggac agcaaggggg    2220
aggattggga agagaatagc aggcatgctg gggaggaata taaggtggtc ccagctcggg    2280
gacacaggat ccctggaggc agcaaacatg ctgtcctgaa gtggacatag ggcccgggt    2340 tggaggaaga agactagctg agctctcgga ccctggaag atgccatgac aggggctgg    2400 aagagctagc acagactaga gaggtaaggg gggtagggga gctgcccaaa tgaaaggagt    2460
gagaggtgac ccgaatccac aggagaacgg ggtgtccagg caaagaaagc aagaggatgg    2520
agaggtggct aaagccaggg agacggggta ctttggggtt gtccagaaaa acggtgatga    2580
tgcaggccta caagaagggg aggcgggacg caagggagac atccgtcgga gaaggccatc    2640
ctaagaaacg agagatggca caggccccag aaggagaagg aaaagggaac ccagcgagtg    2700
aagacggcat gggggttggt gagggaggag agatgcccgg agaggaccca gaca          2754
```

<210> SEQ ID NO 96
<211> LENGTH: 1841
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1841)

<400> SEQUENCE: 96

```
gcggtgcatt gagcacattt ctctcccttg cagttctgcc cacatggtcc accccggtgc      60
agccaatggc cctgattgtg ctgggggcg tcgccggcct cctgcttttc attgggctag     120
gcatcttctt ctgtgtcagg tgccggcacc gaagggtgag taaccccaca cctggtcccc     180 acaaggcccct caaaccccctg agtcctctac caggagatcc tgtatatggg aactgatttt     240
ggcccagctc cctctgccca ctcgtaagtt cccttgctgc cctgtcccag atcccactca     300
agggagagac aggaaggagc agagagttaa ttccaggata gatggcctgg gccatgtaac     360
tgcttctcct gtcgcagctt ccccactcc ccccaccaag gggcacctcc cttctggagg     420
```

| | |
|---|---|
| cctgggaccc tcgtgactcc ctttcttgtc cctggacagc gccaagcaga gcggatgtct | 480 |
| cagatcaaga gactcctcag cgaaaaaaaa acatgtcagt gtcctcaccg gtttcagaag | 540 |
| acatgtagcc ccattcgcgc aaagagagga agcggagaag gtagaggttc tctcctcact | 600 |
| tgtggtgatg ttgaagaaaa ccctggtcca atggtgagca agggcgagga ggataacatg | 660 |
| gcctctctcc cagcgacaca tgagttacac atctttggct ccatcaacgg tgtggacttt | 720 |
| gacatggtgg gtcagggcac cggcaatcca aatgatggtt atgaggagtt aaacctgaag | 780 |
| tccaccaagg gtgacctcca gttctccccc tggattctgg tccctcatat cgggtatggc | 840 |
| ttccatcagt acctgcccta ccctgacggg atgtcgcctt ccaggccgc catggtagat | 900 |
| ggctccggat accaagtcca tcgcacaatg cagtttgaag atggtgcctc ccttactgtt | 960 |
| aactaccgct acacctacga gggaagccac atcaaaggag aggcccaggt gaagggggact | 1020 |
| ggtttccctg ctgacggtcc tgtgatgacc aactcgctga ccgctgcgga ctggtgcagg | 1080 |
| tcgaagaaga cttaccccaa cgacaaaacc atcatcagta cctttaagtg gagttacacc | 1140 |
| actggaaatg gcaagcgcta ccggagcact gcgcggacca cctacacctt tgccaagcca | 1200 |
| atggcggcta actatctgaa gaaccagccg atgtacgtgt tccgtaagac ggagctcaag | 1260 |
| cactccaaga ccgagctcaa cttcaaggag tggcaaaagg cctttaccga tgtgatgggc | 1320 |
| atggacgagc tgtacaagtg agaagaagac ctgccagtgt cctcagtaag gatctgggag | 1380 |
| gaggggttga gagagggaa aggggagggg ggagggagtt agagaggagg gggaggaagg | 1440 |
| ggagcaaagg ggggcaggaa gggaggatgg agaggaggaa ggagttgagg aggaagagct | 1500 |
| gggagggggtg gaggtgagga gatgggggct aaaggggtgt ggtggagagg atagagggggt | 1560 |
| gggaaaagat ggccaggagc tagaaggagg cagaagtggg aggatggagc tgaaggagca | 1620 |
| gcaggccagg aaaggccctg ctggaaagcc actggagctg tgctgcgctg gaaaggccat | 1680 |
| tggaggtgct agaacgcaaa ggggttgcag tggggacaga cctgctcccc ttcttctttg | 1740 |
| ttcctgcagc cggtttcaga agacatgtag ccccatttga ggcacgaggc caggcagatc | 1800 |
| ccacttgcag cctccccagg tgtctgcccc gcgtttcctg c | 1841 |

<210> SEQ ID NO 97
<211> LENGTH: 1882
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1882)

<400> SEQUENCE: 97

| | |
|---|---|
| ttgtctgatg cccctgacag attctctttg taaggagttt atttcagggg caataagtaa | 60 |
| ttggcattat tgctggttgg tactgcaaag tacctatgaa agtccccaaa agttcttgct | 120 |
| attgttattt ctgcattttg gcagaacatg atggaaaatg caccctcaaa ctttggcaaa | 180 |
| ccggcacaaa gctgtgtgtt taatcacgcc tgccttgtcc tagtggtttc tatgaatctg | 240 |
| ctacttttcc gtaatattgc atcattaatt gttcctgaaa aaccctgagt tatcctctta | 300 |
| tagaattgta taagtaatga ttgcaatata gataattttg aaaggagaaa ccacctttcc | 360 |
| ttggaaatgt ttatcttttg cagagtgaca tttgtgagac cagctaattt gattaaaatt | 420 |
| ctcttggaat cagctttgct agtatcatac ctgtgccaga tttcatcatg ggaaacagct | 480 |
| gttacaacat agtagccact ggaagcggag aaggtagagg ttctctcctc acttgtggtg | 540 |

```
atgttgaaga aaaccctggt ccaatggtga gcaagggcga ggaggataac atggcctctc    600
tcccagcgac acatgagtta cacatctttg gctccatcaa cggtgtggac tttgacatgg    660
tgggtcaggg caccggcaat ccaaatgatg gttatgagga gttaaacctg aagtccacca    720
agggtgacct ccagttctcc ccctggattc tggtccctca tatcgggtat ggcttccatc    780
agtacctgcc ctaccctgac gggatgtcgc ctttccaggc cgccatggta gatggctccg    840
gataccaagt ccatcgcaca atgcagtttg aagatggtgc ctcccttact gttaactacc    900
gctacaccta cgagggaagc cacatcaaag agaggcccca ggtgaagggg actggtttcc    960
ctgctgacgg tcctgtgatg accaactcgc tgaccgctgc ggactggtgc aggtcgaaga    1020
agacttaccc caacgacaaa accatcatca gtaccttaa gtggagttac accactggaa     1080
atggcaagcg ctaccggagc actgcgcgga ccacctacac cttgccaag ccaatggcgg     1140 ctaactatct gaagaaccag ccgatgtacg tgttccgtaa gacggagctc aagcactcca    1200
agaccgagct caacttcaag gagtggcaaa aggcctttac cgatgtgatg ggcatggacg    1260
agctgtacaa gcgcgcaaag agaggctccg gtgctaccaa tttctcactg ttgaaacaag    1320
cgggcgatgt tgaagaaaat cccggtccaa tgggaaacag ctgttacaac atagtagcaa    1380
cactgttgct ggtcctcaac tttgagagga caagatcatt gcaggatcct tgtagtaact    1440
gcccagctgg tgagtaccca gttatcatgt gcatttgatc tgctctgttg gaagtatggt    1500
tcagttagtc tagtagtcag ggctaacgag ctccctttta aggaaaggaa atgaaaatt     1560 cattcattta caaatgttta ttggatgcta caacctagct gtgtgaacac agcaaagtca    1620
ttcaacctct tgtgccttga ctttctcatc tggggataat aagagaacct gttttatagg    1680
atggctggga ggatcaaatg aagggcttag aacagtgcat ggcacaaggc aagacttcaa    1740
taaatgttag ttttgtgtgt agggctttgt gctccgactg ggggcatagc agcgagtaag    1800
cgcgtagtaa agggcttaac agagtgggga cggtcagtcg catttaaatt ttagtgtagg    1860
acattgatgt cctcctggat cc                                             1882
```

<210> SEQ ID NO 98
<211> LENGTH: 2263
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2263)

<400> SEQUENCE: 98

```
aacataccat aaacctccca ttctgctaat gcccagccta agttggggag accactccag     60
attccaagat gtacagtttg ctttgctggg ccttttttccc atgcctgcct ttactctgcc    120
agagttatat tgctggggtt ttgaagaaga tcctattaaa taaaagaata agcagtatta    180
ttaagtagcc ctgcatttca ggtttccttg agtggcaggc caggcctggc cgtgaacgtt    240
cactgaaatc atggcctctt ggccaagatt gatagcttgt gcctgtccct gagtcccagt    300
ccatcacgag cagctggttt ctaagatgct atttcccgta taaagcatga gaccgtgact    360
tgccagcccc acagagcccc gcccttgtcc atcactggca tctggactcc agcctgggtt    420
ggggcaaaga gggaaatgag atcatgtcct aaccctgatc ctcttgtccc acagatatcc    480
agaaccctga ccctgccgtg ggaagcggag aaggtagagg ttctctcctc acttgtggtg    540
atgttgaaga aaaccctggt ccaatggtga gcaagggcga ggaggataac atggcctctc    600
```

```
tcaaggagtt catgcgcttc aaggtgcaca tggagggctc cgtgaacggc cacgagttcg    660
agatcgaggg cgagggcgag ggccgcccct acgagggcac ccagaccgcc aagctgaagg    720
tgaccaaggg tggccccctg cccttcgcct gggacatcct gtcccctcag ttcatgtacg    780
gctccaaggc ctacgtgaag caccccgccg acatccccga ctacttgaag ctgtccttcc    840
ccgagggctt caagtgggag cgcgtgatga acttcgagga cggcggcgtg gtgaccgtga    900
cccaggactc ctccctgcag gacggcgagt tcatctacaa ggtgaagctg cgcggcacca    960
acttcccctc cgacggcccc gtaatgcaga agaagaccat gggctgggag gcctcctccg   1020
agcggatgta ccccgaggac ggcgccctga agggcgagat caagcagagg ctgaagctga   1080
aggacggcgg ccactacgac gctgaggtca agaccaccta caaggccaag aagcccgtgc   1140
agctgcccgg cgcctacaac gtcaacatca gttggacat cacctcccac aacgaggact   1200
acaccatcgt ggaacagtac gaacgcgccg agggccgcca ctccaccggc ggcatggacg   1260
agctgtacaa gggctccggt gctaccaatt tctcactgtt gaaacaagcg ggcgatgttg   1320
aagaaaatcc cggtccaatg gagaccctct gggcctgct tatcctttgg ctgcagctgc   1380
aatgggtgag cagcaaacag gaggtgacgc agattcctgc agctctgagt gtcccagaag   1440
gagaaaactt ggttctcaac tgcagtttca ctgatagcgc tatttacaac ctccagtggt   1500
ttaggcagga ccctgggaaa ggtctcacat ctctgttgct tattcagtca agtcagagag   1560
agcaaacaag tggaagactt aatgcctcgc tggataaatc atcaggacgt agtacttat   1620 acattgcagc ttctcagcct ggtgactcag ccacctacct ctgtgctgtg aggcccctgt   1680
acggaggaag ctacatacct acatttggaa gaggaaccag ccttattgtt catccgtata   1740
tccagaaccc tgaccctgcg gtataccagc tgagagactc taaatccagt gacaagtctg   1800
tctgcctatt caccgatttt gattctcaaa caaatgtgtc acaaagtaag gattctgatg   1860
tgtatatcac agacaaaact gtgctagaca tgaggtctat ggacttcaag agcaacagtg   1920
ctgtggcctg gagcaacaaa tctgactttg catgtgcaaa cgccttcaac aacagcatta   1980
ttccagaaga caccttcttc cccagcccag gtaagggcag cttgtgtcc ttcgcaggct   2040 gtttccttgc ttcaggaatg gccaggttct gcccagagct ctggtcaatg atgtctaaaa   2100
ctcctctgat tggtggtctc ggccttatcc attgccacca aaaccctctt tttactaaga   2160
aacagtgagc cttgttctgg cagtccagag aatgacacgg gaaaaaagca gatgaagaga   2220
aggtggcagg agagggcacg tggcccagcc tcagtctctc caa                    2263

<210> SEQ ID NO 99
<211> LENGTH: 2263
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2263)

<400> SEQUENCE: 99
aacataccat aaacctccca ttctgctaat gcccagccta agttggggag accactccag     60
attccaagat gtacagtttg ctttgctggg ccttttccc atgcctgcct ttactctgcc    120
agagttatat tgctggggtt ttgaagaaga tcctattaaa taaagaata agcagtatta    180 ttaagtagcc ctgcatttca ggtttccttg agtggcaggc caggcctggc cgtgaacgtt    240
cactgaaatc atggcctctt ggccaagatt gatagcttgt gcctgtccct gagtcccagt    300
```

| | | | | |
|---|---|---|---|---|
| ccatcacgag | cagctggttt | ctaagatgct | atttcccgta | taaagcatga gaccgtgact | 360 |
| tgccagcccc | acagagcccc | gcccttgtcc | atcactggca | tctggactcc agcctgggtt | 420 |
| ggggcaaaga | gggaaatgag | atcatgtcct | aaccctgatc | ctcttgtccc acagatatcc | 480 |
| agaaccctga | ccctgccgtg | ggaagcggag | aaggtagagg | ttctctcctc acttgtggtg | 540 |
| atgttgaaga | aaaccctggt | ccaatggtga | gcaagggcga | ggaggataac atggccatca | 600 |
| tcaaggagtt | catgcgcttc | aaggtgcaca | tggagggctc | cgtgaacggc acgagttcg | 660 |
| agatcgaggg | cgagggcgag | ggccgcccct | acgagggcac | ccagaccgcc aagctgaagg | 720 |
| tgaccaaggg | tggccccctg | cccttcgcct | gggacatcct | gtcccctcag ttcatgtacg | 780 |
| gctccaaggc | ctacgtgaag | caccccgccg | acatccccga | ctacttgaag ctgtccttcc | 840 |
| ccgagggctt | caagtgggag | cgcgtgatga | acttcgagga | cggcggcgtg gtgaccgtga | 900 |
| cccaggactc | ctccctgcag | gacggcgagt | tcatctacaa | ggtgaagctg cgcggcacca | 960 |
| acttcccctc | cgacggcccc | gtaatgcaga | agaagaccat | gggctgggag gcctcctccg | 1020 |
| agcggatgta | ccccgaggac | ggcgccctga | agggcgagat | caagcagagg ctgaagctga | 1080 |
| aggacggcgg | ccactacgac | gctgaggtca | agaccaccta | caaggccaag aagcccgtgc | 1140 |
| agctgcccgg | cgcctacaac | gtcaacatca | gttggacat | cacctccac aacgaggact | 1200 |
| acaccatcgt | ggaacagtac | gaacgcgccg | agggccgcca | ctccaccggc ggcatggacg | 1260 |
| agctgtacaa | gggctccggt | gctaccaatt | tctcactgtt | gaaacaagcg ggcgatgttg | 1320 |
| aagaaaatcc | cggtccaatg | gagaccctct | gggcctgct | tatcctttgg ctgcagctgc | 1380 |
| aatgggtgag | cagcaaacag | gaggtgacgc | agattcctgc | agctctgagt gtcccagaag | 1440 |
| gagaaaactt | ggttctcaac | tgcagtttca | ctgatagcgc | tatttacaac ctccagtggt | 1500 |
| ttaggcagga | ccctgggaaa | gtctcacat | ctctgttgct | tattcagtca agtcagagag | 1560 |
| agcaaacaag | tggaagactt | aatgcctcgc | tggataaatc | atcaggacgt agtactttat | 1620 |
| acattgcagc | ttctcagcct | ggtgactcag | ccacctacct | ctgtgctgtg aggcccctgt | 1680 |
| acggaggaag | ctacatacct | acatttggaa | gaggaaccag | ccttattgtt catccgtata | 1740 |
| tccagaaccc | tgaccctgcg | gtataccagc | tgagagactc | taaatccagt gacaagtctg | 1800 |
| tctgcctatt | caccgatttt | gattctcaaa | caaatgtgtc | acaaagtaag gattctgatg | 1860 |
| tgtatatcac | agacaaaact | gtgctagaca | tgaggtctat | ggacttcaag agcaacagtg | 1920 |
| ctgtggcctg | gagcaacaaa | tctgactttg | catgtgcaaa | cgccttcaac aacagcatta | 1980 |
| ttccagaaga | caccttcttc | cccagcccag | gtaaggcag | ctttggtgcc ttcgcaggct | 2040 |
| gtttccttgc | ttcaggaatg | gccaggttct | gcccagagct | ctggtcaatg atgtctaaaa | 2100 |
| ctcctctgat | tggtggtctc | ggccttatcc | attgccacca | aaaccctctt tttactaaga | 2160 |
| aacagtgagc | cttgttctgg | cagtccagag | aatgacacgg | gaaaaagca gatgaagaga | 2220 |
| aggtggcagg | agagggcacg | tggcccagcc | tcagtctctc | caa | 2263 |

<210> SEQ ID NO 100
<211> LENGTH: 4774
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4774)

<400> SEQUENCE: 100

-continued

| | | | | | |
|---|---|---|---|---|---|
| aacataccat | aaacctccca | ttctgctaat | gcccagccta | agttggggag | accactccag | 60 |
| attccaagat | gtacagtttg | ctttgctggg | ccttttctcc | atgcctgcct | ttactctgcc | 120 |
| agagttatat | tgctggggtt | ttgaagaaga | tcctattaaa | taaaagaata | agcagtatta | 180 |
| ttaagtagcc | ctgcatttca | ggtttccttg | agtggcaggc | caggcctggc | cgtgaacgtt | 240 |
| cactgaaatc | atggcctctt | ggccaagatt | gatagcttgt | gcctgtccct | gagtcccagt | 300 |
| ccatcacgag | cagctggttt | ctaagatgct | atttcccgta | taaagcatga | gaccgtgact | 360 |
| tgccagcccc | acagagcccc | gcccttgtcc | atcactggca | tctggactcc | agcctgggtt | 420 |
| ggggcaaaga | gggaaatgag | atcatgtcct | aaccctgatc | ctcttgtccc | acagatatcc | 480 |
| agaaccctga | ccctgccgtg | ggaagcggag | aaggtagagg | ttctctcctc | acttgtggtg | 540 |
| atgttgaaga | aaaccctggt | ccaatggtcc | tgctgagccg | caagcgccgc | cggcagcacg | 600 |
| gccagctttg | gttcccggag | ggcttcaagg | tgtctgaggc | tagcaagaag | aaacgcaggg | 660 |
| agcccctggg | cgaagattct | gttggactta | agcctctcaa | gaacgcatcc | gatggcgccc | 720 |
| tgatggatga | caaccagaat | gagtggggcg | acgaggatct | ggagaccaag | aagttccgct | 780 |
| tcgaggaacc | ggtcgtgctg | cccgacctgg | acgaccagac | cgaccatcgc | cagtggacgc | 840 |
| agcagcacct | ggacgcagcc | gacctgcgga | tgagtgccat | ggcgccaacc | cccctcaag | 900 |
| gcgaggttga | tgccgactgc | atggatgtga | acgtgcgggg | ccccgacggg | ttcaccctc | 960 |
| tgatgatcgc | gtcgtgtagc | ggcggggcc | tggagaccgg | caactccgag | gaagaggagg | 1020 |
| acgcccccgc | cgtcatctct | gatttcatct | accaggtgc | ttcccttcat | aaccagactg | 1080 |
| accgcactgg | ggagacggcc | ctccacctgg | cagcccgcta | tagccgcagc | gatgctcga | 1140 |
| agcggttgtt | ggaagccagc | gccgacgcca | acatacagga | caatatgggc | cgcactcctt | 1200 |
| tgcacgccgc | ggtgtcggcc | gacgctcagg | gcgtgttcca | gatcctaatt | cgcaatcgcg | 1260 |
| ccaccgacct | cgacgcccgc | atgcacgacg | gcaccacacc | cctgatcctg | cggcgcgcc | 1320 |
| tcgccgtgga | gggaatgttg | gaggaccta | ttaacagcca | cgccgacgta | aatgctgttg | 1380 |
| atgacctcgg | gaaatcggcc | ctccattggg | ctgctgcagt | caacaacgtg | gacgctgccg | 1440 |
| tcgtcctgtt | gaaaaatggg | gcaaacaagg | acatgcaaaa | taaccgcgag | gagactcccc | 1500 |
| tcttcctggc | ggctagagag | ggctcgtacg | agactgccaa | ggtgctcctc | gatcacttcg | 1560 |
| ccaaccggga | catcacggat | catatggata | ggctccctcg | ggacatcgcg | caggagcgaa | 1620 |
| tgcaccacga | cattgtccgt | ctgctggacg | agtacaacct | ggtgcgctcc | ccacagctgc | 1680 |
| acggcgcccc | gctgggggt | actcccaccc | tttcccgcc | cctgtgcagc | ccaacggct | 1740 |
| atctgggctc | cctgaagccc | ggcgtccagg | gcaagaaagt | ccgtaaacct | agttccaagg | 1800 |
| gcttagcttg | cgggtcgaag | gaggctaagg | atctgaaagc | taggcggaag | aagtcccaag | 1860 |
| acggcaaagg | gtgcctgtta | gattccagtg | gcatgctgtc | cctgtcgac | tctctggagt | 1920 |
| cgcctcacgg | gtacctgtct | gacgtggcct | cccccccct | gcttccctcc | ccgtttcagc | 1980 |
| agagcccctc | cgtgcccctg | aatcacctcc | ctggtatgcc | cgacacccac | ctaggcatcg | 2040 |
| gccatttgaa | cgtggctgca | aagccagaga | tggccgcttt | ggggggcggg | ggccgtctgg | 2100 |
| catttgagac | aggcccgccc | cgcctgagcc | acctgcccgt | ggcatctggg | acctctaccg | 2160 |
| tgctgggttc | ttcctccggc | ggggccctta | acttcaccgt | gggcggctcc | accagtctga | 2220 |
| acgggcagtg | tgaatggcta | tcacgactgc | agagcggtat | ggtgcctaac | caatacaacc | 2280 |
| ccctgcgggg | atccgtggcc | ccgggcccc | tctccactca | ggctcctagc | ttgcagcatg | 2340 |
| gtatggtggg | ccctctacat | tccagcctgg | cggcgtccgc | cctgtcccag | atgatgtctt | 2400 |

-continued

```
atcagggget accgtctacc cgcctggcca cgcagccgca cctggtgcag acgcagcagg    2460
tgcagcctca gaacctgcag atgcagcagc agaacctgca gcccgccaac atccagcagc    2520
agcagtctct ccagccccca ccgccccccc ctcagccgca tctgggggtc agttccgcag    2580
cgtctggcca cctaggacgc tccttcctgt ctggagaacc atcgcaagct gatgtgcagc    2640
cccttggccc gtcctctctg gccgtgcaca ccatcttgcc tcaggagtcc cccgctctcc    2700
cgaccagcct gccatcaagc ttggtgccac cgtgaccgc tgctcagttt ctgactcctc    2760
caagccagca ctcctattcc agcccgtgg ataacacccc cagccaccag ctgcaggtcc    2820
cggagcaccc ttttctcact cctagcccag agtcgcccga ccagtggtct tcgtcctccc    2880
cacacagcaa cgtgtccgat tggtccgagg gggtgagctc acctcccacg tccatgcagt    2940
cccagattgc ccggatcccg gaggcattta aggattataa agatgacgat gacaagcgcg    3000
ccaagcgctc cggaagcgga gaaggtagag gttctctcct cacttgtggt gatgttgaag    3060
aaaaccctgg tccaatggtg agcaaggggcg aggaggataa catggcctct ctcccagcga    3120
cacatgagtt acacatcttt ggctccatca acggtgtgga ctttgacatg gtgggtcagg    3180
gcaccggcaa tccaaatgat ggttatgagg agttaaacct gaagtccacc aagggtgacc    3240
tccagttctc cccctggatt ctggtccctc atatcgggta tggcttccat cagtacctgc    3300
cctaccctga cgggatgtcg cctttccagg ccgccatggt agatggctcc ggataccaag    3360
tccatcgcac aatgcagttt gaagatggtg cctcccttac tgttaactac cgctacacct    3420
acgagggaag ccacatcaaa ggagaggccc aggtgaaggg gactggtttc cctgctgacg    3480
gtcctgtgat gaccaactcg ctgaccgctg cggactggtg caggtcgaag aagacttacc    3540
ccaacgacaa aaccatcatc agtacccttta agtggagtta caccactgga aatggcaagc    3600
gctaccggag cactgcgcgg accacctaca cctttgccaa gccaatggcg gctaactatc    3660
tgaagaacca gccgatgtac gtgttccgta agacggagct caagcactcc aagaccgagc    3720
tcaacttcaa ggagtggcaa aaggccttta ccgatgtgat gggcatggac gagctgtaca    3780
agggctccgg tgctaccaat ttctcactgt tgaaacaagc gggcgatgtt gaagaaaatc    3840
ccggtccaat ggagaccctc ttgggcctgc ttatcctttg gctgcagctg caatgggtga    3900
gcagcaaaca ggaggtgacg cagattcctg cagctctgag tgtcccagaa ggagaaaact    3960
tggttctcaa ctgcagtttc actgatagcg ctatttacaa cctccagtgg tttaggcagg    4020
accctgggaa aggtctcaca tctctgttgc ttattcagtc aagtcagaga gagcaaacaa    4080
gtggaagact taatgcctcg ctggataaat catcaggacg tagtacttta tacattgcag    4140
cttctcagcc tggtgactca gccacctacc tctgtgctgt gaggcccctg tacggaggaa    4200
gctacatacc tacatttgga agaggaacca gccttattgt tcatccgtat atccagaacc    4260
ctgaccctgc ggtataccag ctgagagact ctaaatccag tgacaagtct gtctgcctat    4320
tcaccgattt tgattctcaa acaaatgtgt cacaaagtaa ggattctgat gtgtatatca    4380
cagacaaaac tgtgctagac atgaggtcta tggacttcaa gagcaacagt gctgtggcct    4440
ggagcaacaa atctgacttt gcatgtgcaa acgccttcaa caacagcatt attccagaag    4500
acaccttctt ccccagccca ggtaagggca gctttggtgc cttcgcaggc tgtttccttg    4560
cttcaggaat ggccaggttc tgcccagagc tctggtcaat gatgtctaaa actcctctga    4620
ttggtggtct cggccttatc cattgccacc aaaaccctct ttttactaag aaacagtgag    4680
ccttgttctg gcagtccaga gaatgacacg ggaaaaaagc agatgaagag aaggtggcag    4740
```

```
gagagggcac gtggcccagc ctcagtctct ccaa                              4774

<210> SEQ ID NO 101
<211> LENGTH: 5014
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5014)

<400> SEQUENCE: 101
aacataccat aaacctccca ttctgctaat gcccagccta agttggggag accactccag    60
attccaagat gtacagtttg ctttgctggg cctttttccc atgcctgcct ttactctgcc   120
agagttatat tgctggggtt ttgaagaaga tcctattaaa taaaagaata agcagtatta   180
ttaagtagcc ctgcatttca ggtttccttg agtggcaggc caggcctggc cgtgaacgtt   240
cactgaaatc atggcctctt ggccaagatt gatagcttgt gcctgtccct gagtcccagt   300
ccatcacgag cagctggttt ctaagatgct atttcccgta taaagcatga gaccgtgact   360
tgccagcccc acagagcccc gcccttgtcc atcactggca tctggactcc agcctgggtt   420
ggggcaaaga gggaaatgag atcatgtcct aaccctgatc ctcttgtccc acagatatcc   480
agaaccctga ccctgccgtg ggaagcggag aaggtagagg ttctctcctc acttgtggtg   540
atgttgaaga aaaccctggt ccaatggtcc tgctgagccg caagcgccgc cggcagcacg   600
gccagctttg gttcccggag ggcttcaagg tgtctgaggc tagcaagaag aaacgcaggg   660
agcccctggg cgaagattct gttggactta agcctctcaa gaacgcatcc gatggcgccc   720
tgatggatga caaccagaat gagtggggcg acgaggatct ggagaccaag aagttccgct   780
tcgaggaacc ggtcgtgctg cccgacctgg acgaccagac cgaccatcgc cagtggacgc   840
agcagcacct ggacgcagcc gacctgcgga tgagtgccat ggcgccaacc cccctcaag    900 gcgaggttga tgccgactgc atggatgtga acgtgcgggg ccccgacggg ttcacccctc   960
tgatgatcgc gtcgtgtagc ggcgggggcc tggagaccgg caactccgag gaagaggagg  1020
acgcccccgc cgtcatctct gatttcatct accagggtgc ttcccttcat aaccagactg  1080
accgcactgg ggagacggcc ctccacctgg cagcccgcta tagccgcagc gatgctgcga  1140
agcggttgtt ggaagccagc gccgacgcca acatacagga caatatgggc cgcactcctt  1200
tgcacgccgc ggtgtcggcc gacgctcagg gcgtgttcca gatcctaatt cgcaatcgcg  1260
ccaccgacct cgacgcccgc atgcacgacg gcaccacacc cctgatcctg gcggcgcgcc  1320
tcgccgtgga gggaatgttg gaggaccta ttaacagcca cgccgacgta aatgctgttg  1380
atgacctcgg gaaatcggcc ctccattggg ctgctgcagt caacaacgtg gacgctgccg  1440
tcgtcctgtt gaaaaatggg gcaaacaagg acatgcaaaa taaccgcgag gagactcccc  1500
tcttcctggc ggctagagag ggctcgtacg agactgccaa ggtgctcctc gatcacttcg  1560
ccaaccggga catcacggat catatggata ggctccctcg ggacatcgcg caggagcgaa  1620
tgcaccacga cattgtccgt ctgctggacg agtacaacct ggtgcgctcc ccacagctgc  1680
acggcgcccc gctggggggt actcccaccc tttccccgcc cctgtgcagc cccaacggct  1740
atctgggctc cctgaagccc ggcgtccagg gcaagaaagt ccgtaaacct agttccaagg  1800
gcttagcttg cgggtcgaag gaggctaagg atctgaaagc taggcggaag aagtcccaag  1860
acggcaaagg gtgcctgtta gattccagtg gcatgctgtc cctgtcgac tctctggagt   1920
```

```
cgcctcacgg gtacctgtct gacgtggcct cccccccct gcttccctcc ccgtttcagc   1980
agagccctc cgtgcccctg aatcacctcc ctggtatgcc cgacacccac ctaggcatcg   2040
gccatttgaa cgtggctgca aagccagaga tggccgcttt gggggcggg ggccgtctgg   2100
catttgagac aggcccgccc cgcctgagcc acctgcccgt ggcatctggg acctctaccg   2160
tgctgggttc ttcctccggc ggggccctta acttcaccgt gggcggctcc accagtctga   2220
acgggcagtg tgaatggcta tcacgactgc agagcggtat ggtgcctaac caatacaacc   2280
ccctgcgggg atccgtggcc ccgggccccc tctccactca ggctcctagc ttgcagcatg   2340
gtatggtggg ccctctacat ccagcctggg cggcgtccgc cctgtcccag atgatgtctt   2400
atcagggct accgtctacc cgcctggcca cgcagccgca cctggtgcag acgcagcagg   2460
tgcagcctca gaacctgcag atgcagcagc agaacctgca gcccgccaac atccagcagc   2520
agcagtctct ccagccccca ccgccccccc ctcagccgca tctgggggtc agttccgcag   2580
cgtctggcca cctaggacgc tccttcctgt ctggagaacc atcgcaagct gatgtgcagc   2640
cccttggccc gtcctctctg gccgtgcaca ccatcttgcc tcaggagtcc cccgctctcc   2700
cgaccagcct gccatcaagc ttggtgccac ccgtgaccgc tgctcagttt ctgactcctc   2760
caagccagca ctcctattcc agcccgtgg ataacacccc cagccaccag ctgcaggtcc   2820
cggagcaccc ttttctcact cctagcccag agtcgcccga ccagtggtct tcgtcctccc   2880
cacacagcaa cgtgtccgat tggtccgagg gggtgagctc acctcccacg tccatgcagt   2940
cccagattgc ccggatcccg gaggcattta aggattataa agatgacgat gacaagcgcg   3000
ccaagcgctc cggaagcgga gaaggtagag gttctctcct cacttgtggt gatgttgaag   3060
aaaaccctgg tccaatgagc atcggcctcc tgtgctgtgc agccttgtct ctcctgtggg   3120
caggtccagt gaatgctggt gtcactcaga ccccaaaatt ccaggtcctg aagacaggac   3180
agagcatgac actgcagtgt gcccaggata tgaaccatga atacatgtcc tggtatcgac   3240
aagacccagg catggggctg aggctgattc attactcagt tggtgctggt atcactgacc   3300
aaggagaagt ccccaatggc tacaatgtct ccagatcaac cacagaggat ttcccgctca   3360
ggctgctgtc ggctgctccc tcccagacat ctgtgtactt ctgtgccagc agttacgtcg   3420
ggaacaccgg ggagctgttt tttggagaag gctctaggct gaccgtactg gaggacctga   3480
aaaacgtgtt cccaccccgag gtcgctgtgt ttgagccatc agaagcagag atctcccaca   3540
cccaaaaggc cacactggta tgcctggcca caggcttcta ccccgaccac gtggagctga   3600
gctggtgggt gaatgggaag gaggtgcaca gtggggtcag cacagacccg cagcccctca   3660
aggagcagcc cgccctcaat gactccagat actgcctgag cagccgcctg agggtctcgg   3720
ccaccttctg gcagaacccc cgcaaccact tccgctgtca agtccagttc tacgggctct   3780
cagaaaacga tgaatggaca caagataggg ccaaacccgt cacccagatc gtcagcgccg   3840
aggcctgggg tagagcagac tgtggcttca cctccgagtc ttaccagcaa ggggtcctgt   3900
ctgccaccat cctctatgag atcttgctag gaaggccac cttgtatgcc gtgctggtca   3960
gtgccctcgt gctgatggct atggtcaaga gaaaggattc cagaggccgc gccaagcgct   4020
ccggctccgg tgctaccaat ttctcactgt tgaaacaagc gggcgatgtt gaagaaaatc   4080
ccggtccaat ggagaccctc ttgggcctgc ttatcctttg gctgcagctg caatgggtga   4140
gcagcaaaca ggaggtgacg cagattcctg cagctctgag tgtcccagaa ggagaaaact   4200
tggttctcaa ctgcagtttc actgatagcg ctatttacaa cctccagtgg tttaggcagg   4260
accctgggaa aggtctcaca tctctgttgc ttattcagtc aagtcagaga gagcaaacaa   4320
```

```
gtggaagact taatgcctcg ctggataaat catcaggacg tagtacttta tacattgcag    4380
cttctcagcc tggtgactca gccacctacc tctgtgctgt gaggcccctg tacggaggaa    4440
gctacatacc tacatttgga agaggaacca gccttattgt tcatccgtat atccagaacc    4500
ctgaccctgc ggtataccag ctgagagact ctaaatccag tgacaagtct gtctgcctat    4560
tcaccgattt tgattctcaa acaaatgtgt cacaaagtaa ggattctgat gtgtatatca    4620
cagacaaaac tgtgctagac atgaggtcta tggacttcaa gagcaacagt gctgtggcct    4680
ggagcaacaa atctgacttt gcatgtgcaa acgccttcaa caacagcatt attccagaag    4740
acaccttctt ccccagccca ggtaagggca gctttggtgc cttcgcaggc tgtttccttg    4800
cttcaggaat ggccaggttc tgcccagagc tctggtcaat gatgtctaaa actcctctga    4860
ttggtggtct cggccttatc cattgccacc aaaaccctct ttttactaag aaacagtgag    4920
ccttgttctg gcagtccaga gaatgacacg ggaaaaaagc agatgaagag aaggtggcag    4980
gagagggcac gtggcccagc ctcagtctct ccaa                                5014

<210> SEQ ID NO 102
<211> LENGTH: 6448
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6448)

<400> SEQUENCE: 102
aacataccat aaacctccca ttctgctaat gcccagccta agttggggag accactccag      60
attccaagat gtacagtttg ctttgctggg cctttttccc atgcctgcct ttactctgcc     120
agagttatat tgctggggtt ttgaagaaga tcctattaaa taaagaata agcagtatta     180 ttaagtagcc ctgcatttca ggtttccttg agtggcaggc caggcctggc cgtgaacgtt    240
cactgaaatc atggcctctt ggccaagatt gatagcttgt gcctgtccct gagtcccagt    300
ccatcacgag cagctggttt ctaagatgct atttcccgta taaagcatga gaccgtgact    360
tgccagcccc acagagcccc gcccttgtcc atcactggca tctggactcc agcctgggtt    420 gggcaaaga gggaaatgag atcatgtcct aaccctgatc ctcttgtccc acagatatcc    480
agaaccctga ccctgccgtg ggaagcggag aaggtagagg ttctctcctc acttgtggtg    540
atgttgaaga aaaccctggt ccaatggatt ataaagatga cgatgacaag gcattatcac    600
tggaagaatt cgtccactcc cttgacctca ggaccctacc cagggttatg gcattatcac    660
tggaagaatt cgtccactcc cttgacctca ggaccctacc cagggttcta gaaatccagg    720
caggcatcta tcttgaaggc tctatttatg aaatgtttgg aaatgaacta gaaatccagg    780
caggcatcta tcttgaaggc tctatttatg aaatgtttgg aaatgaatgc tgtttttcaa    840
caggagaagt gattaaaatt actggtctca agttaagaa gatcatatgc tgtttttcaa    900
caggagaagt gattaaaatt actggtctca agttaagaa gatcatagct gaaatttgtg    960
agcagattga aggttgtgag tctctacagc catttgaact gcctatggct gaaatttgtg   1020
agcagattga aggttgtgag tctctacagc catttgaact gcctatgaat tttccaggtc   1080
tttttaagat tgtggctgat aaaactccat accttactat ggaagaaaat tttccaggtc   1140
tttttaagat tgtggctgat aaaactccat accttactat ggaagaaatc acaaggacca   1200
ttcatattgg accaagtaga ctagggcatc cttgcttcta tcatcagatc acaaggacca   1260
```

```
ttcatattgg accaagtaga ctagggcatc cttgcttcta tcatcagaag gatataaaac    1320
tagagaacct catcataaag cagggtgagc aaatcatgct caactcaaag gatataaaac    1380
tagagaacct catcataaag cagggtgagc aaatcatgct caactcagtt gaagagattg    1440
atggagaaat aatggtgagc tgtgcagtag caaggaatca tcaaactgtt gaagagattg    1500
atggagaaat aatggtgagc tgtgcagtag caaggaatca tcaaactcac tcatttaatt    1560
tgcctttgtc acaagaagga gaattctacg agtgtgaaga tgaacgtcac tcatttaatt    1620
tgcctttgtc acaagaagga gaattctacg agtgtgaaga tgaacgtatt tacactctaa    1680
aggagattgt tgaatggaag attcctaaga acagaacaag aactgtaatt tacactctaa    1740
aggagattgt tgaatggaag attcctaaga acagaacaag aactgtaaac cttacagatt    1800
tttcaaataa gtgggactca acgaatccat ttcctaaaga cttttataac cttacagatt    1860
tttcaaataa gtgggactca acgaatccat ttcctaaaga cttttatggt accctgattc    1920
tcaagcctgt ttatgaaatt caaggtgtga tgaaatttcg aaaagatggt accctgattc    1980
tcaagcctgt ttatgaaatt caaggtgtga tgaaatttcg aaaagatata atccgcatcc    2040
tccccagtct agatgtcgaa gtcaaagaca tcactgattc ttacgatata atccgcatcc    2100
tccccagtct agatgtcgaa gtcaaagaca tcactgattc ttacgatgct aactggtttc    2160
ttcagctgtt atcaacagaa gatctttttg aaatgactag taaagaggct aactggtttc    2220
ttcagctgtt atcaacagaa gatctttttg aaatgactag taaagagttc cccatagtga    2280
ctgaagtcat agaagcacct gaaggaaacc acctgcccca aagcattttc cccatagtga    2340
ctgaagtcat agaagcacct gaaggaaacc acctgcccca aagcatttta cagcctggga    2400
aaaccattgt gatccacaaa aagtaccagg catcaagaat cttagcttta cagcctggga    2460
aaaccattgt gatccacaaa aagtaccagg catcaagaat cttagcttca gaaattagaa    2520
gcaattttcc taaaagacac ttcttgatcc ccactagcta taaaggctca gaaattagaa    2580
gcaattttcc taaaagacac ttcttgatcc ccactagcta taaaggcaag ttcaagcggc    2640
gaccgaggga gttcccaacg gcctatgacc tagagatcgc taagagtaag ttcaagcggc    2700
gaccgaggga gttcccaacg gcctatgacc tagagatcgc taagagtgaa aaggagcctc    2760
ttcacgtggt ggccaccaaa gcgtttcatt cccctcatga caagctggaa aaggagcctc    2820
ttcacgtggt ggccaccaaa gcgtttcatt cccctcatga caagctgtca tccgtatctg    2880
ttggggacca gtttctggtg catcagtcag agacgactga agtcctctca tccgtatctg    2940
ttggggacca gtttctggtg catcagtcag agacgactga agtcctctgt gagggaataa    3000
aaaaagtggt gaatgttctg gcctgtgaaa aaatcctcaa aaagtcctgt gagggaataa    3060
aaaaagtggt gaatgttctg gcctgtgaaa aaatcctcaa aaagtcctat gaggctgcgc    3120
tgctcccttt gtacatggaa ggaggttttg tagaggtgat tcatgattat gaggctgcgc    3180
tgctcccttt gtacatggaa ggaggttttg tagaggtgat tcatgataag aaacagtacc    3240
cgatttctga gctctgtaaa cagttccgtt tgcccttcaa tgtgaagaag aaacagtacc    3300
cgatttctga gctctgtaaa cagttccgtt tgcccttcaa tgtgaaggtg tctgtcaggg    3360
atctttccat tgaagaggac gtgttggctg ccacaccagg actgcaggtg tctgtcaggg    3420
atctttccat tgaagaggac gtgttggctg ccacaccagg actgcagttg gaggaggaca    3480
ttacagactc ttacctactc ataagtgact ttgccaaccc cacggagttg gaggaggaca    3540
ttacagactc ttacctactc ataagtgact ttgccaaccc cacggagtgc tgggaaattc    3600
```

```
ctgtgggccg cttgaatatg actgttcagt tagttagtaa tttctcttgc tgggaaattc    3660
ctgtgggccg cttgaatatg actgttcagt tagttagtaa tttctctagg gatgcagaac    3720
catttctagt caggactctg gtagaagaga tcactgaaga gcaatatagg gatgcagaac    3780
catttctagt caggactctg gtagaagaga tcactgaaga gcaatattac atgatgcgga    3840
gatatgaaag ctcagcctca catcccccac ctcgccctcc gaaacactac atgatgcgga    3900
gatatgaaag ctcagcctca catcccccac ctcgccctcc gaaacacccc tcagtagagg    3960
aaacaaagtt aaccctgcta accttagcag aagaaaggac ggtagacccc tcagtagagg    4020
aaacaaagtt aaccctgcta accttagcag aagaaaggac ggtagacctg cccaagtctc    4080
ccaagcgtca tcacgtagac ataaccaaga aacttcaccc aaatcaactg cccaagtctc    4140
ccaagcgtca tcacgtagac ataaccaaga aacttcaccc aaatcaagct ggcctggatt    4200
caaaagtact gattggtagt cagaatgatt tggtggatga agagaaagct ggcctggatt    4260
caaaagtact gattggtagt cagaatgatt tggtggatga agagaaagaa aggagcaacc    4320
gtggggccac agcaatagca gaaacattca aaaatgaaaa acatcaagaa aggagcaacc    4380
gtggggccac agcaatagca gaaacattca aaaatgaaaa acatcaaaaa cgcgccaagc    4440
gctccggaag cggagaaggt agaggttctc tcctcacttg tggtgatgtt gaagaaaacc    4500
ctggtccaat gagcatcggc ctcctgtgct gtgcagcctt gtctctcctg tgggcaggtc    4560
cagtgaatgc tggtgtcact cagaccccaa aattccaggt cctgaagaca ggacagagca    4620
tgacactgca gtgtgcccag gatatgaacc atgaatacat gtcctggtat cgacaagacc    4680
caggcatggg gctgaggctg attcattact cagttggtgc tggtatcact gaccaaggag    4740
aagtccccaa tggctacaat gtctccagat caaccacaga ggatttcccg ctcaggctgc    4800
tgtcggctgc tccctcccag acatctgtgt acttctgtgc cagcagttac gtcgggaaca    4860
ccggggagct gttttttgga gaaggctcta ggctgaccgt actggaggac ctgaaaaacg    4920 tgttccacc cgaggtcgct gtgtttgagc catcagaagc agagatctcc cacacccaaa    4980
aggccacact ggtatgcctg gccacaggct ctacccccga ccacgtggag ctgagctggt    5040
gggtgaatgg gaaggaggtg cacagtgggg tcagcacaga cccgcagccc ctcaaggagc    5100
agcccgccct caatgactcc agatactgcc tgagcagccg cctgagggtc tcggccacct    5160
tctggcagaa cccccgcaac cacttccgct gtcaagtcca gttctacggg ctctcagaaa    5220
acgatgaatg gacacaagat agggccaaac ccgtcaccca gatcgtcagc gccgaggcct    5280
ggggtagagc agactgtggc ttcacctccg agtcttacca gcaaggggtc ctgtctgcca    5340
ccatcctcta tgagatcttg ctagggaagg ccaccttgta tgccgtgctg gtcagtgccc    5400
tcgtgctgat ggctatggtc aagagaaagg attccagagg ccgcgccaag cgctccggct    5460
ccggtgctac caatttctca ctgttgaaac aagcgggcga tgttgaagaa atcccggtc    5520 caatggagac cctcttgggc ctgcttatcc tttggctgca gctgcaatgg gtgagcagca    5580
aacaggaggt gacgcagatt cctgcagctc tgagtgtccc agaaggagaa aacttggttc    5640
tcaactgcag tttcactgat agcgctattt acaacctcca gtggtttagg caggaccctg    5700
ggaaaggtct cacatctctg ttgcttattc agtcaagtca gagagagcaa acaagtggaa    5760
gacttaatgc ctcgctggat aaatcatcag gacgtagtac tttatacatt gcagcttctc    5820
agcctggtga ctcagccacc tacctctgtg ctgtgaggcc cctgtacgga ggaagctaca    5880
tacctacatt tggaagagga accagcctta ttgttcatcc gtatatccag aaccctgacc    5940
ctgcggtata ccagctgaga gactctaaat ccagtgacaa gtctgtctgc ctattcaccg    6000
```

| | | | | |
|---|---|---|---|---|
| attttgattc | tcaaacaaat | gtgtcacaaa | gtaaggattc tgatgtgtat | atcacagaca | 6060 |
| aaactgtgct | agacatgagg | tctatggact | tcaagagcaa cagtgctgtg | gcctggagca | 6120 |
| acaaatctga | ctttgcatgt | gcaaacgcct | tcaacaacag cattattcca | gaagacacct | 6180 |
| tcttccccag | cccaggtaag | ggcagctttg | gtgccttcgc aggctgtttc | cttgcttcag | 6240 |
| gaatggccag | gttctgccca | gagctctggt | caatgatgtc taaaactcct | ctgattggtg | 6300 |
| gtctcggcct | tatccattgc | caccaaaacc | ctcttttttac taagaaacag | tgagccttgt | 6360 |
| tctggcagtc | cagagaatga | cacgggaaaa | aagcagatga agagaaggtg | gcaggagagg | 6420 |
| gcacgtggcc | cagcctcagt | ctctccaa | | 6448 |

<210> SEQ ID NO 103
<211> LENGTH: 2341
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2341)

<400> SEQUENCE: 103

| | | | | |
|---|---|---|---|---|
| tggcgggact | agtggccaca | tctctcagct | ggtacacgga acataccata | aacctcccat | 60 |
| tctgctaatg | cccagcctaa | gttggggaga | ccactccaga ttccaagatg | tacagtttgc | 120 |
| tttgctgggc | cttttttccca | tgcctgcctt | tactctgcca gagttatatt | gctggggttt | 180 |
| tgaagaagat | cctattaaat | aaaagaataa | gcagtattat taagtagccc | tgcatttcag | 240 |
| gtttccttga | gtggcaggcc | aggcctggcc | gtgaacgttc actgaaatca | tggcctcttg | 300 |
| gccaagattg | atagcttgtg | cctgtccctg | agtcccagtc catcacgagc | agctggtttc | 360 |
| taagatgcta | tttcccgtat | aaagcatgag | accgtgactt gccagcccca | cagagccccg | 420 |
| cccttgtcca | tcactggcat | ctggactcca | gcctgggttg gggcaaagag | ggaaatgaga | 480 |
| tcatgtccta | accctgatcc | tcttgtccca | cagatatcca gaaccctgac | cctgccgtgg | 540 |
| gaagcggaga | aggtagaggt | tctctcctca | cttgtggtga tgttgaagaa | aaccctggtc | 600 |
| caatggtgag | caagggcgag | gaggataaca | tggcctctct cccagcgaca | catgagttac | 660 |
| acatctttgg | ctccatcaac | ggtgtggact | ttgacatggt gggtcagggc | accggcaatc | 720 |
| caaatgatgg | ttatgaggag | ttaaacctga | agtccaccaa gggtgacctc | cagttctccc | 780 |
| cctggattct | ggtccctcat | atcgggtatg | gcttccatca gtacctgccc | tacccctgacg | 840 |
| ggatgtcgcc | tttccaggcc | gccatggtag | atggctccgg ataccaagtc | catcgcacaa | 900 |
| tgcagtttga | agatggtgcc | tcccttactg | ttaactaccg ctacacctac | gagggaagcc | 960 |
| acatcaaagg | agaggcccag | gtgaagggga | ctggtttccc tgctgacggt | cctgtgatga | 1020 |
| ccaactcgct | gaccgctgcg | gactggtgca | ggtcgaagaa gacttacccc | aacgacaaaa | 1080 |
| ccatcatcag | tacctttaag | tggagttaca | ccactgaaaa tggcaagcgc | taccggagca | 1140 |
| ctgcgcggac | cacctacacc | tttgccaagc | caatggcggc taactatctg | aagaaccagc | 1200 |
| cgatgtacgt | gttccgtaag | acggagctca | agcactccaa gaccgagctc | aacttcaagg | 1260 |
| agtggcaaaa | ggcctttacc | gatgtgatgg | gcatggacga gctgtacaag | ggctccggtg | 1320 |
| ctaccaattt | ctcactgttg | aaacaagcgg | gcgatgttga agaaaatccc | ggtccaatgg | 1380 |
| agaccctctt | gggcctgctt | atcctttggc | tgcagctgca atgggtgagc | agcaaacagg | 1440 |
| aggtgacgca | gattcctgca | gctctgagtg | tcccagaagg agaaaacttg | gttctcaact | 1500 |

```
gcagtttcac tgatagcgct atttacaacc tccagtggtt taggcaggac cctgggaaag    1560
gtctcacatc tctgttgctt attcagtcaa gtcagagaga gcaaacaagt ggaagactta    1620
atgcctcgct ggataaatca tcaggacgta gtactttata cattgcagct tctcagcctg    1680
gtgactcagc cacctacctc tgtgctgtga ggcccctgta cggaggaagc tacataccta    1740
catttggaag aggaaccagc cttattgttc atccgtatat ccagaaccct gaccctgcgg    1800
tataccagct gagagactct aaatccagtg acaagtctgt ctgcctattc accgattttg    1860
attctcaaac aaatgtgtca caaagtaagg attctgatgt gtatatcaca gacaaaactg    1920
tgctagacat gaggtctatg gacttcaaga gcaacagtgc tgtggcctgg agcaacaaat    1980
ctgactttgc atgtgcaaac gccttcaaca acagcattat tccagaagac accttcttcc    2040
ccagcccagg taagggcagc tttggtgcct cgcaggctg tttccttgct tcaggaatgg     2100
ccaggttctg cccagagctc tggtcaatga tgtctaaaac tcctctgatt ggtggtctcg    2160
gccttatcca ttgccaccaa aaccctcttt ttactaagaa acagtgagcc ttgttctggc    2220
agtccagaga atgacacggg aaaaaagcag atgaagagaa ggtggcagga gagggcacgt    2280
ggcccagcct cagtctctcc aaccgtgtac cagctgagag atgtggccac tagtcccgcc    2340
a                                                                   2341

<210> SEQ ID NO 104
<211> LENGTH: 2341
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2341)

<400> SEQUENCE: 104
tggcgggact agtggccaca tctctcagct ggtacacgga acataccata aacctcccat      60
tctgctaatg cccagcctaa gttggggaga ccactccaga ttccaagatg tacagtttgc     120
tttgctgggc ctttttccca tgcctgcctt tactctgcca gagttatatt gctgggtttt    180
tgaagaagat cctattaaat aaaagaataa gcagtattat taagtagccc tgcatttcag    240
gtttccttga gtggcaggcc aggcctggcc gtgaacgttc actgaaatca tggcctcttg    300
gccaagattg atagcttgtg cctgtccctg agtcccagtc catcacgagc agctggtttc    360
taagatgcta tttcccgtat aaagcatgag accgtgactt gccagcccca cagagccccg    420
cccttgtcca tcactggcat ctggactcca gcctgggttg gggcaaagag ggaaatgaga    480
tcatgtccta accctgatcc tcttgtccca cagatatcca gaaccctgac cctgccgtgg    540
gaagcggaga aggtagaggt tctctcctca cttgtggtga tgttgaagaa aaccctggtc    600
caatggtgag caagggcgag gaggataaca tggcctctct cccagcgaca catgagttac    660
acatctttgg ctccatcaac ggtgtggact ttgcatggtt gggtcagggc accggcaatc    720
caaatgatgg ttatgaggag ttaaacctga agtccaccaa gggtgacctc cagttctccc    780
cctggattct ggtccctcat atcgggtatg gcttccatca gtacctgccc taccctgacg    840
ggatgtcgcc tttccaggcc gccatggtag atggctccgg ataccaagtc catcgcacaa    900
tgcagtttga agatggtgcc tcccttactg ttaactaccg ctacacctac gagggaagcc    960
acatcaaagg agaggcccag gtgaagggga ctggtttccc tgctgacggt cctgtgatga   1020
ccaactcgct gaccgctgcg gactggtgca ggtcgaagaa gacttacccc aacgacaaaa   1080
```

```
ccatcatcag taccctttaag tggagttaca ccactggaaa tggcaagcgc taccggagca    1140
ctgcgcggac cacctacacc tttgccaagc caatggcggc taactatctg aagaaccagc    1200
cgatgtacgt gttccgtaag acggagctca agcactccaa gaccgagctc aacttcaagg    1260
agtggcaaaa ggccttacc gatgtgatgg gcatggacga gctgtacaag ggctccggtg      1320
ctaccaattt ctcactgttg aaacaagcgg gcgatgttga agaaaatccc ggtccaatgg    1380
agaccctctt gggcctgctt atcctttggc tgcagctgca atgggtgagc agcaaacagg    1440
aggtgacgca gattcctgca gctctgagtg tcccagaagg agaaaacttg gttctcaact    1500
gcagtttcac tgatagcgct atttacaacc tccagtggtt taggcaggac cctgggaaag    1560
gtctcacatc tctgttgctt attcagtcaa gtcagagaga gcaaacaagt ggaagactta    1620
atgcctcgct ggataaatca tcaggacgta gtactttata cattgcagct tctcagcctg    1680
gtgactcagc cacctacctc tgtgctgtga ggcccctgta cggaggaagc tacataccta    1740
catttggaag aggaaccagc cttattgttc atccgtatat ccagaaccct gaccctgcgg    1800
tataccagct gagagactct aaatccagtg acaagtctgt ctgcctattc accgattttg    1860
attctcaaac aaatgtgtca caaagtaagg attctgatgt gtatatcaca gacaaaactg    1920
tgctagacat gaggtctatg gacttcaaga gcaacagtgc tgtggcctgg agcaacaaat    1980
ctgactttgc atgtgcaaac gccttcaaca acagcattat tccagaagac accttcttcc    2040
ccagcccagg taagggcagc tttggtgcct tcgcaggctg tttccttgct tcaggaatgg    2100
ccaggttctg cccagagctc tggtcaatga tgtctaaaac tcctctgatt ggtggtctcg    2160
gccttatcca ttgccaccaa aaccctcttt ttactaagaa acagtgagcc ttgttctggc    2220
agtccagaga atgacacggg aaaaaagcag atgaagagaa ggtggcagga gagggcacgt    2280
ggcccagcct cagtctctcc aaccgtgtac cagctgagag atgtggccac tagtcccgcc    2340
a                                                                     2341
```

<210> SEQ ID NO 105
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(25)

<400> SEQUENCE: 105
aacataccat aaacctccca ttctg                                            25

<210> SEQ ID NO 106
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(25)

<400> SEQUENCE: 106
ttggagagac tgaggctggg ccacg                                            25

<210> SEQ ID NO 107
<211> LENGTH: 25
<212> TYPE: DNA

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(25)

<400> SEQUENCE: 107
tggcgggact agtggccaca tctct                                             25

<210> SEQ ID NO 108
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(25)

<400> SEQUENCE: 108
tggcgggact agtggccaca tctct                                             25
```

EFFICIENT TCR GENE EDITING IN T LYMPHOCYTES

CROSS-REFERENCE TO RELATED APPLICATION

This application claims the benefit of U.S. Provisional Application Nos. 63/165,509, filed Mar. 24, 2021, and 63/323,065, filed Mar. 24, 2022, each of which is incorporated herein by reference in its entirety and for all purposes.

SEQUENCE LISTING

The instant application contains a Sequence Listing which has been submitted electronically in ASCII format and is hereby incorporated by reference in its entirety. Said ASCII copy is written in the file named 048893-532001US_ST25.txt, which was created on Mar. 24, 2022, and is 170,857 bytes in size.

BACKGROUND

T cell therapies are of increasing interest for treatment of many different diseases, including cancer, infectious disease, and inflammatory diseases. However, preparation of therapeutic T cells using current viral-based engineering approaches is time-consuming costly, and poses certain safety concerns. Further, methods of producing engineered T cells using non-viral methods to date have low editing efficiency and can limit cell yield.

SUMMARY

The instant technology generally relates to engineered T cells and related systems, methods, and kits. This technology addresses the low efficiency and low numbers of engineered T cells that are generally produced using known non-viral methods.

In an aspect, an engineered T cell is provided. The engineered T cell includes a nucleic acid sequence encoding a polypeptide comprising an exogenous T cell receptor (TCR) or portion thereof. In embodiments, the exogenous TCR or portion thereof is an exogenous T cell Receptor beta (TCR-beta) and/or an exogenous T cell Receptor alpha (TCR-alpha), or a portion thereof. In embodiments, the nucleic acid sequence is inserted into a TCR locus. In embodiments, the TCR locus is a TCR-alpha locus of the engineered T cell. In embodiments, the TCR locus is a TCR-beta locus of the engineered T cell.

In embodiments, the exogenous TCR-alpha comprises at least of portion of the endogenous TCR-alpha. In embodiments, the exogenous TCR-alpha comprises an exogenous TCR-alpha (VJ) domain and endogenous TCR-alpha constant domain.

In embodiments, the nucleic acid sequence further comprises a polyadenylation (polyA) sequence. In embodiments, the nucleic acid sequence further comprises a stop codon. In embodiments, the stop codon is 3' to the exogenous TCR and 5' to the polyA sequence. In embodiments, a TCR knock-in (KI) construct further comprises a polyA sequence. In embodiments, SEQ ID NO: 1 comprises a polyA sequence.

In another interrelated aspect, a composition comprising isolated T cells is provided, wherein at least 5% of the cells are engineered T cells. In embodiments, each engineered T cell includes a nucleic acid sequence encoding a polypeptide comprising an exogenous TCR-beta and an exogenous TCR-alpha. In embodiments, each engineered T cell includes a nucleic acid sequence encoding a polypeptide comprising an exogenous TCR-beta and an exogenous TCR-alpha. In embodiments, each engineered T cell includes a nucleic acid sequence encoding a polypeptide comprising at least a portion of an exogenous TCR-beta and at least a portion of an exogenous TCR-alpha. In embodiments, the portion of the exogenous TCR-alpha is a TCR-alpha VJ region. In embodiments, the nucleic acid sequence is inserted into a TCR-alpha locus of the engineered T cell.

In embodiments, the engineered T cell does not express a functional endogenous TCR-beta protein. In embodiments, the engineered T cell does not express a functional endogenous TCR-alpha protein. In embodiments, the exogenous TCR-alpha (VJ) domain forms part of a heterologous TCR-alpha comprising at least a portion of the endogenous TCR-alpha of the T cell. In embodiments, the TCR-alpha locus is a TCR-alpha constant region. In embodiments, the exogenous TCR-beta and the heterologous TCR-alpha are expressed from the nucleic acid and form a functional TCR. In embodiments, the engineered T cell is bound to an antigen. In embodiments, the engineered T cell is bound to a cancer cell. In embodiments, the TCR binds to the antigen presented on a major histocompatibility complex class I (MHCI) molecule.

In embodiments, the antigen is a neoantigen or a tumor-associated antigen (TAA). In embodiments, the antigen is a neoantigen. In embodiments, the antigen is a TAA. In embodiments, the neoantigen or TAA is selected from WT1, JAK2, NY-ESO1, PRAME, KRAS, or an antigen from Table 1 or Table 2. In embodiments, the antigen is WT1. The MHCI allele may be any allele known or discovered. In embodiments, the MHCI is selected from the MHCI is selected from HLA-A02:01, A*02:03, A*02:06, A*02:07, A*023:01, A*26:01, A*29:02, A*30:01, A*30:02, A*31:01, A*32:01, A*68:01, A*68:02, B*18:01, B*35:03, B*40:01, B*40:02, B*40:06, B*46:01, B*51:01, B*53:01, B*57:01, B*58:01, C*01:02, C*02:02, C*03:02, C*03:03, C*05:01, C*06:02, C*07:01, C*08:01, C*08:02, C*12:03, C*14:02, or C*15:02. In embodiments, the antigen is specific to a cancer of a subject to be administered the engineered T cell.

Relevant methods, compositions, and reagents are found in the following patent applications: US20180355429A1 "DETERMINING ANTIGEN-SPECIFIC T-CELLS", US20180087109A1 "DETERMINING ANTIGEN-SPECIFIC T-CELLS", WO2017112944A1 "HIGH AFFINITY T CELL RECEPTORS AND USES THEREOF", WO2016161273A1 "METHOD OF IDENTIFYING HUMAN COMPATIBLE T CELL RECEPTORS SPECIFIC FOR AN ANTIGENIC TARGET", US20160138011A1 "MULTIPLEXED DIGITAL QUANTITATION OF REARRANGED LYMPHOID RECEPTORS IN A COMPLEX MIXTURE", WO2016069886A1 "HIGHLY-MULTIPLEXED SIMULTANEOUS DETECTION OF NUCLEIC ACIDS ENCODING PAIRED ADAPTIVE IMMUNE RECEPTOR HETERODIMERS FROM MANY SAMPLES", US20150275296A1 "DETERMINING ANTIGEN-SPECIFIC T-CELLS", WO2010053587A2 "METHODS OF MONITORING CONDITIONS BY SEQUENCE ANALYSIS", WO2011139371A1 "MONITORING HEALTH AND DISEASE STATUS USING CLONOTYPE PROFILES", WO2011139372A1 "SEQUENCE ANALYSIS OF COMPLEX AMPLICONS", WO2013059725A1 "QUANTIFICATION OF ADAPTIVE IMMUNE CELL GENOMES IN A COMPLEX MIXTURE OF CELLS", US20130196328A1 "RARE CLONOTYPES AND USES THEREOF", US20130236895A1 "METHOD OF SEQUENCE DETERMINATION USING SEQUENCE TAGS", US20130065768A1 "RANDOM ARRAY SEQUENCING OF LOW-COMPLEXITY LIBRARIES", US20130150252 "DETECTION AND MEASUREMENT OF TISSUE-INFILTRATING LYMPHOCYTES", WO2013134162A2 "DETERMINING PAIRED IMMUNE RECEPTOR CHAINS FROM FREQUENCY MATCHED SUBUNITS", WO2013169957A1 "COMPOSITIONS AND METHOD FOR MEASURING AND CALIBRATING AMPLIFICATION BIAS IN MULTIPLEXED PCR REACTIONS", WO2013188471A2 "METHOD OF SEQUENCE DETERMINATION USING SEQUENCE TAGS", WO2013188831A1 "UNIQUELY TAGGED REARRANGED ADAPTIVE IMMUNE RECEPTOR GENES IN A COMPLEX GENE SET", WO2014055561A1 "IMMUNOCOMPETENCE ASSESSMENT BY ADAPTIVE IMMUNE RECEPTOR DIVERSITY AND CLONALITY CHARACTERIZATION", WO2014130685A1 "RARE CLONOTYPES AND USES THEREOF", WO2014145992A1 "UNIQUELY TAGGED REARRANGED ADAPTIVE IMMUNE RECEPTOR GENES IN A COMPLEX GENE SET", WO2015002908A1 "LARGE-SCALE BIOMOLECULAR ANALYSIS WITH SEQUENCE TAGS", WO2015058159A1 "PREDICTING PATIENT RESPONSIVENESS TO IMMUNE CHECKPOINT INHIBITORS", WO2015106161A1 "METHODS FOR DEFINING AND PREDICTING IMMUNE RESPONSE TO ALLOGRAFT", WO2015160439A2 "QUANTIFICATION OF ADAPTIVE IMMUNE CELL GENOMES IN A COMPLEX MIXTURE OF CELLS", WO2016086029A1 "CHARACTERIZATION OF ADAPTIVE IMMUNE RESPONSE TO VACCINATION OR INFECTION USING IMMUNE REPERTOIRE SEQUENCING", US20180282808A1 "DETERMINING WT-1 SPECIFIC T CELLS AND WT-1 SPECIFIC T CELL RECEPTORS (TCRS)", each of which is incorporated by reference herein in its entirety for everything taught therein, including, without limitation, all methods of making, methods of using, reagents, cells, proteins, nucleic acids, compositions, etc.

In embodiments, expression of an endogenous TCR-beta gene was disrupted by gene editing. In embodiments, in greater than about 80% of the cells the endogenous TCR-beta gene is disrupted. In embodiments, in greater than about 90% of the cells the endogenous TCR-beta gene is disrupted. In embodiments, in greater than about 95% of the cells the endogenous TCR-beta gene is disrupted.

In embodiments, expression of an endogenous TCR-alpha gene was disrupted by gene editing. In embodiments, in greater than about 80% of the cells the endogenous TCR-alpha gene is disrupted. In embodiments, in greater than about 90% of the cells the endogenous TCR-alpha gene is disrupted. In embodiments, in greater than about 95% of the cells the endogenous TCR-alpha gene is disrupted.

In embodiments, the nucleic acid sequence further encodes a self-cleaving peptide. In embodiments, the self-cleaving peptide is a self-cleaving viral peptide. In embodiments, the self-cleaving viral peptide is T2A (SEQ ID NO: 49), P2A (SEQ ID NO: 50), E2A (SEQ ID NO: 51), F2A (SEQ ID NO: 52). In embodiments, the unique self-cleaving viral peptide sequences are labeled.

In embodiments, the engineered T cell expresses CD45RO, C—C chemokine receptor type 7 (CCR7), and L-selectin (CD62L). In embodiments, the engineered T cell has a central memory (CM) T cell phenotype. In embodiments, the engineered T cell has a naïve T cell phenotype. In embodiments, the engineered T cell having a naïve T cell phenotype is CD45RA+CD45RO−CD27+CD95−. In embodiments, the engineered T cell has a stem cell memory T cell phenotype. In embodiments, the engineered T cell having a stem cell memory T cell phenotype is CD45RA+CD45RO−CD27+CD95+CD58+CCR7−Hi TCF1+. In embodiments, the engineered T cell has a central memory T cell phenotype. In embodiments, the engineered T cell having a central memory T cell phenotype is CD45RO+CD45RA−CD27+CD95+CD58+. In embodiments, the engineered T cell has a progenitor exhausted T cell phenotype. In embodiments, the engineered T cell having a progenitor exhausted T cell phenotype is PD-1+SLAMF6+TCF1+TIM3-CD39−. In embodiments, the engineered T cell having a progenitor exhausted T cell phenotype expresses PD-1 at a low or intermediate level compared to PD-1 high exhausted T cells. In embodiments, the engineered T cell having a progenitor exhausted T cell phenotype expresses PD-1 at a low or intermediate level compared to recently activated T cells. In embodiments, the T cell is autologous to a subject in need thereof.

In another interrelated aspect, a pharmaceutical composition is provided. The pharmaceutical composition includes a population of engineered T cells as described herein, including embodiments, and a pharmaceutically acceptable excipient.

In embodiments, at least 10% of the cells in the composition comprising isolated T cells are engineered T cells. In embodiments, at least 20% of the cells are engineered T cells. In embodiments, at least 30% of the cells are engineered T cells. In embodiments, at least 40% of the cells are engineered T cells. In embodiments, at least 50% of the cells are engineered T cells. In embodiments, at least 60% of the cells are engineered T cells. In embodiments, at least 70% of the cells are engineered T cells. In embodiments, at least 80% of the cells are engineered T cells.

In embodiments, the composition includes between about $0.1 \times 10^5$ and about $1 \times 10^{11}$ engineered T cells. In embodiments, the composition includes at least $1 \times 10^8$ engineered T cells. In embodiments, the composition includes between about $1 \times 10^8$ and about $1 \times 10^{11}$ engineered T cells. In embodiments, the composition includes at least $1 \times 10^9$ engineered T cells. In embodiments, the composition includes at least $1 \times 10^{10}$ engineered T cells. In embodiments, the composition includes at least $1 \times 10^{11}$ engineered T cells. In embodiments, the composition further includes a pharmaceutically acceptable excipient.

In another interrelated aspect, a T cell comprising an RNA transcript, having the mRNA transcript transcribed from a TCR transgene inserted into the TCR-alpha or TCR-beta locus is provided.

In another, interrelated aspect, a non-viral method for making an engineered T cell is provided. In embodiments, the method uses clustered regularly interspaced short palindromic repeats (CRISPR)-based gene editing. In embodiments, the method uses Cas9. In embodiments, the method uses high fidelity Cas9. In embodiments, the method uses SpyFi Cas9. In embodiments, the gene editing reagents are provided as Cas9 ribonucleoprotein particle (RNP). The method includes: a) contacting a T cell with a first CRISPR/Cas9 RNP and a donor DNA, wherein the first Cas9/RNP comprises a first guide RNA that targets an endogenous TCR locus, and wherein the donor DNA comprises a nucleic acid sequence encoding a TCR in the formats specified herein, under conditions to allow the RNP and the donor DNA to enter the cell; b) incubating the T cell for a period of time; and c) culturing the cell in a medium for a period of time to allow the donor DNA to be recombined into an endogenous TCR locus, thereby forming an engineered T cell. In embodiments, the TCR locus targeted by the first guide RNA is a TCR-alpha locus. In embodiments, the TCR locus targeted by the second guide RNA is a TCR-beta locus. In embodiments, the first RNP comprises a first gene editing protein, and the first guide RNA in a molar excess of the guide RNA. In embodiments, the first RNP comprises a first gene editing protein, and the ratio of the first guide RNA to the first gene editing protein is between 1:1 and 100:1.

In embodiments, the TCR locus targeted by the first guide RNA is a TCR-alpha locus, and the T cell is further contacted with a second RNP comprising a second guide RNA that targets an endogenous TCR-beta loci. In embodiments, the T cell is also contacted with a second donor DNA, wherein the second donor DNA comprises a nucleic acid sequence encoding a TCR in the formats specified herein. Contacting the cell may be done in any order. In embodiments, the T cell is contacted with the second RNP and optionally second donor DNA in step a). In embodiments, the T cell is contacted with the second RNP and second donor DNA between step a) and b). In embodiments, the T cell is contacted with the second RNP and second donor DNA prior to step a). In embodiments, the T cell is contacted with the second RNP and second donor DNA after step c). In embodiments, the second RNP comprises a second gene editing protein, and the second guide RNA in a molar excess of the guide RNA. In embodiments, the second RNP comprises a second gene editing protein, and the ratio of the second guide RNA to the second gene editing protein is between 1:1 and 100:1. In embodiments, less than 10% of the engineered T cells express a functional endogenous TCR-beta, compared to a control. In embodiments, less than 1% of the engineered T cells express a functional endogenous TCR-beta, compared to a control. In embodiments, the engineered T cell does not express a functional endogenous TCR-beta.

In embodiments, the first guide RNA is discovered through methods known to one skilled in the art such that it targets the exon 1, exon 2, or exon 3 region of the TCR constant alpha region locus (TRAC). In embodiments, the first guide RNA includes one or more of: TRAC1 (SEQ ID NO: 7), TRAC2 (SEQ ID NO: 8), TRAC3 (SEQ ID NO: 9), TRAC4 (SEQ ID NO: 10), TRAC5 (SEQ ID NO: 11), TRAC6 (SEQ ID NO: 12), TRAC7 (SEQ ID NO: 13), TRAC8 (SEQ ID NO: 14), TRAC9 (SEQ ID NO: 15), TRAC10 (SEQ ID NO: 16), TRAC11 (SEQ ID NO: 17), TRAC12 (SEQ ID NO: 18), TRAC13 (SEQ ID NO: 19), TRAC14 (SEQ ID NO: 20), TRAC15 (SEQ ID NO: 21), or TRAC16 (SEQ ID NO: 22). In embodiments, the first guide RNA includes one or more of: TRAC1, TRAC3, TRAC4, TRAC5, TRAC7, TRAC12, or TRAC15. In embodiments, the first guide RNA targets TRAC1. In embodiments, the first guide RNA includes TRAC3. In embodiments, the first guide RNA comprises a nucleic acid sequence in Table 10.

In embodiments, the second guide RNA is discovered through methods known to one skilled in the art such that it targets the exon 1 regions of both TCR constant beta region loci (TRBC) in a T cell. In embodiments, the second guide RNA includes one or more of: TRBC1 (SEQ ID NO: 23), TRBC2 (SEQ ID NO: 24), TRBC3 (SEQ ID NO: 25), TRBC4 (SEQ ID NO: 26), TRBC5 (SEQ ID NO: 27), TRBC6 (SEQ ID NO: 28), TRBC7 (SEQ ID NO: 29), TRBC8 (SEQ ID NO: 30), TRBC9 (SEQ ID NO: 31), TRBC10 (SEQ ID NO: 32), TRBC11 (SEQ ID NO: 33), TRBC12 (SEQ ID NO: 34), TRBC13 (SEQ ID NO: 35), TRBC14 (SEQ ID NO: 36), TRBC15 (SEQ ID NO: 37), TRBC16 (SEQ ID NO: 38), TRBC17 (SEQ ID NO: 39), TRBC18 (SEQ ID NO: 40), TRBC19 (SEQ ID NO: 41), TRBC20 (SEQ ID NO: 42), TRBC21 (SEQ ID NO: 43), TRBC22 (SEQ ID NO: 44), TRBC23 (SEQ ID NO: 45), TRBC24 (SEQ ID NO: 46), TRBC25 (SEQ ID NO: 47), or TRBC26 (SEQ ID NO: 48). In embodiments, the second guide RNA includes one or more of: TRBC4, TRBC8, TRBC13, TRBC19, TRBC20, TRBC21, TRBC22, TRBC23, or TRBC26. In embodiments, the second guide RNA comprises the nucleic acid sequence in Table 11.

In embodiments, the conditions to allow the RNP and the donor DNA to enter the cell comprise electroporation. In embodiments, the electroporation method comprises a commercial electroporation kit (e.g. NUCLEOFECTION (Lonza). In embodiments, in method step b), the T cell is incubated for at least 10 minutes. In embodiments, the T cell is incubated at about 37° C. In embodiments, the T cell is incubated at less than about 37° C. In embodiments, the medium comprises cytokines. In embodiments, the cytokines comprise interleukin-2 (IL-2), interleukin-7 (IL-7), and/or interleukin-15 (IL-15). In embodiments, the cytokines comprise IL-2. In embodiments, the cytokines comprise IL-7. In embodiments, the cytokines comprise IL-15. In embodiments, the cytokines comprise IL-7 and IL-15.

In embodiments, method step a) is performed in the presence of a negatively charged polymer. In embodiments, the polymer is poly(glutamic acid) (PGA) or variant thereof, poly(aspartic acid), heparin, or poly(acrylic acid). In embodiments, the PGA is poly(L-glutamic acid) or variant thereof. In embodiments, the PGA is poly(D-glutamic acid) or variant thereof. In embodiments, the PGA or variant thereof has an average molecular weight between 15 kiloDaltons (kDa) and 50 kDa. In embodiments, about 2 µg/µL to about 15 µg/µL of the polymer is added.

In embodiments, the amount of the first and/or second RNP is about 0.2 pmol/µL to about 10 pmol/µL. In embodiments, the amount of donor DNA is about 0.5 fmol/µL to about 0.5 pmol/µL. In embodiments, the amount of RNP is about 5 pmol to about 200 pmol. In embodiments, the amount of donor DNA is about 0.01 pmol to about 10 pmol. In embodiments, part of the donor DNA recombines into an endogenous TCR-alpha locus. In embodiments, the TCR-alpha locus is a TCR-alpha constant region locus. In embodiments, the exogenous TCR-alpha (VJ) domain forms part of a heterologous TCR-alpha comprising at least a portion of the endogenous TCR-alpha of the engineered T cell. In embodiments, the donor DNA comprises a left homology arm and a right homology arm.

In embodiments, the left homology arm and right homology arm are homologous to an endogenous TCR-alpha locus. In embodiments, the left homology arm is about 50 bases to about 2000 bases long. In embodiments, the left homology arm is about 100 bases to about 1000 bases long. In embodiments, the left homology arm is about 200 bases to about 800 bases long. In embodiments, the right homology arm is about 200 bases to about 2000 bases long. In embodiments, the right homology arm is about 100 bases to about 1000 bases. In embodiments, the left homology arm and right homology arm are homologous to an endogenous TCR-beta locus. In embodiments, the left homology arm is about 200 bases to about 800 bases long. In embodiments, the left homology arm is about 250 bases to about 700 bases long. In embodiments, the right homology arm is about 200 bases to about 800 bases long. In embodiments, the right homology arm is about 250 bases to about 700 bases long.

In embodiments, the donor DNA comprises double stranded DNA (dsDNA). In embodiments, the donor DNA is on a plasmid, nanoplasmid, or minicircle. In embodiments, the donor DNA is contained within a plasmid. In embodiments, the donor DNA is on a nanoplasmid. In embodiments, the donor DNA is on a minicircle. In embodiments, the donor DNA is linear. In embodiments, the donor DNA is a PCR product. In embodiments, the donor DNA comprises single stranded DNA (ssDNA). In embodiments, the donor DNA is not chemically modified. In embodiments, the donor DNA comprises a chemical modification. In embodiments, the modification comprises a 5' phosphate or a 5' phosphorothioate.

In embodiments, the donor DNA and RNP are incubated together prior to method step a). In embodiments, the gene editing protein comprises at least one nuclear localization signal (NLS).

In embodiments, the T cell is activated prior to method step a). In embodiments, the T cell is activated for between 24 hours and 96 hours. In embodiments, the T cell is activated in the presence of cytokines. In embodiments, the cytokines comprise IL-2, IL-7, and/or IL-15. In embodiments, the T cell is activated in the presence of between about 1 ng/ml and about 200 ng/mL IL-2. In embodiments, the T cell is activated in the presence of between about 0 ng/ml and about 50 ng/ml IL-2. In embodiments, the T cell is activated in the presence of about 10 ng/mL IL-2. In embodiments, the T cell is activated in the presence of between about 1 ng/ml and about 100 ng/ml IL-7. In embodiments, the T cell is activated in the presence of between about 5 ng/mL and about 500 ng/mL IL-15. In embodiments, the T cell is activated in the presence of anti-CD3 antibody and/or anti-CD28 antibody. In embodiments, the T cell is activated in the presence of CD3 agonist and/or CD28 agonist. In embodiments, the anti-CD3 antibody and/or anti-CD28 antibody is conjugated to a substrate. In embodiments, the CD3 agonist and/or CD28 agonist is conjugated to a substrate. In embodiments, method step a) is performed no more than about 24 hours after activation. In embodiments, method step a) is performed between about 24 hours and about 72 hours after activation. In embodiments, method step a) is performed between about 36 hours and about 60 hours after activation.

In another interrelated aspect, a method for making a population of engineered T cells is provided, comprising performing the method described herein, including embodiments, on a population of T cells. In embodiments, at least about 5% of the population of T cells are engineered T cells. In embodiments, about 5% to about 100% of the population of T cells are engineered T cells. In embodiments, at least about 50% of the population of T cells are engineered T cells. In embodiments, at least about 60% of the population of T cells are engineered T cells. In embodiments, at least about 25% of the population of T cells are viable after method step c). In embodiments, at least about 50% of the population of T cells are viable after method step c). In embodiments, at least about 75% of the population of T cells are viable after method step c). Amounts may be any value or subrange within the recited ranges, including endpoints.

In embodiments, the method further includes contacting the T cells with a second RNP comprising a guide RNA that targets an endogenous TCR-beta locus. In embodiments, at least about 5% of the population of T cells are engineered T cells, wherein less than about 20% of the engineered T cells express endogenous TCR-beta. In embodiments, about 10% to about 100% of the population of T cells are engineered T cells. Contacting of the T cells with the second RNP may be performed before, during, or after contacting with the first RNP. In embodiments, the first RNP comprises a guide RNA that targets an endogenous TCR-alpha locus.

In embodiments, method step a) comprises the following steps in any order: (i) adding the donor DNA to a chamber; (ii) adding the RNP to the chamber; and (iii) adding the T cell to the chamber. In embodiments, method step a) comprises the following steps in order: (i) adding the RNP to a chamber; (ii) adding the donor DNA to the chamber; and (iii) adding the T cell to the chamber. In embodiments, method step a) comprises the following steps in order: (i) adding the RNP to a chamber; (ii) adding the T cell to the chamber, and (iii) adding the donor DNA to the chamber. In embodiments, method step a) comprises the following steps in any order: (i) adding the donor DNA to a chamber; (ii) adding the RNP to the chamber; (iii) adding a negatively charged polymer to the chamber; and (iv) adding the T cell to the chamber. In embodiments, method step a) comprises the following steps in order: (i) adding the donor DNA to a chamber; (ii) adding the RNP to the chamber; (iii) adding a negatively charged polymer to the chamber; and (iv) adding the T cell to the chamber. In embodiments, method step a) comprises the following steps in order: (i) combining the RNP and negatively charged polymer to form a RNP-polymer mixture; (ii) adding the donor DNA to a chamber; (iii) adding the RNP-polymer mixture to the chamber; and (iv) adding the T cell to the chamber. In embodiments, method step a) comprises the following steps in order: (i) adding the RNP to a chamber; (ii) adding the donor DNA to the chamber; (iii) adding negatively charged polymer to the chamber; and (iv) adding the T cell to the chamber. In embodiments, the T cell is not pipetted during method steps a) and b). In embodiments, the negatively-charged polymer includes PGA. Where two or more RNP and/or two or more donor DNAs are used, they may be added at the same time, or in any order. In embodiments, no negatively charged polymer is added to the chamber.

In another interrelated aspect, an engineered T cell is provided. The engineered T cell is made by the methods described herein including embodiments. In another interrelated aspect, a population of engineered T cells is provided. The population of engineered T cells are made by the methods described herein including embodiments.

In another, interrelated aspect, a method for treating a subject having cancer is provided. The method includes: a) providing a population of T cells; b) engineering at least a subset of the population of T cells to express an exogenous T cell receptor (TCR) and to knock out an endogenous TCR-beta, thereby forming a population of engineered T cells, wherein the exogenous TCR binds to an antigen expressed by the cancer; c) expanding the population of engineered T cells; and d) administering the expanded population of engineered T cells to the subject.

In embodiments, the antigen is a neoantigen or a tumor-associated antigen (TAA). In embodiments, at least a portion of the genome and/or transcriptome of the cancer was sequenced to determine the presence of the antigen. In embodiments, the engineered T cells are made using the methods described herein including embodiments. In embodiments, the antigen is Wilms tumor gene 1 (WT1), Janus kinase 2 (JAK2), New York esophageal squamous cell carcinoma-1 (NY-ESO1), PRAME nuclear receptor transcriptional regulator (PRAME), or mutant Kirsten rat sarcoma virus (KRAS). In embodiments, the antigen is specific for the cancer. In embodiments, the TCR binds to the antigen presented on a major histocompatibility complex class I (MHCI) molecule. In embodiments, the MHCI comprises an MHCI allele expressed by the subject. In embodiments, the expanded population of engineered T cells comprises between $1 \times 10^5$ and $1 \times 10^9$ engineered T cells. In embodiments, the expanded population of engineered T cells comprises at least $1 \times 10^8$ engineered T cells. In embodiments, the expanded population of engineered T cells comprises between about $1 \times 10^8$ and about $1 \times 10^{11}$ engineered T cells. In embodiments, the expanded population of engineered T cells comprises at least $1 \times 10^9$ engineered T cells. In embodiments, the expanded population of engineered T cells comprises at least $1 \times 10^{10}$ engineered T cells. In embodiments, the expanded population of engineered T cells comprises at least $1 \times 10^{11}$ engineered T cells. In embodiments, the T cells are autologous to the subject.

In another interrelated aspect, a method for treating a subject having cancer is provided. The method includes: a) providing a first population of T cells isolated from the subject; b) engineering at least a subset of the first population of T cells to express a first exogenous T cell receptor (TCR) and to knock out an endogenous TCR-beta, thereby forming a first population of engineered T cells, wherein the exogenous TCR binds to a first antigen expressed by the cancer; c) expanding the first population of engineered T cells; d) administering the expanded first population of engineered T cells to the subject; e) providing a second population of T cells isolated from the subject; f) engineering at least a subset of the second population of T cells to express a second exogenous TCR and to knock out the endogenous TCR-beta, thereby forming a second population of engineered T cells, wherein the exogenous TCR binds to a second antigen expressed by the cancer; g) expanding the second population of engineered T cells; and h) administering the expanded second population of engineered T cells to the subject.

In embodiments, at least a portion of the genome or transcriptome of the cancer was sequenced to determine the presence of the first antigen and the second antigen. In embodiments, the first antigen is WT1, JAK2, NY-ESO1, PRAME, mutant KRAS, or HPV. In embodiments, the first TCR and/or second TCR binds to the antigen presented on a MHCI molecule. In embodiments, the antigen is a neoantigen or a TAA. In embodiments, the MHCI comprises an MHCI allele expressed by the subject.

In embodiments, the first expanded population of engineered T cells comprises between $1 \times 10^5$ and $1 \times 10^9$ engineered T cells. In embodiments, the first expanded population of engineered T cells comprises at least $1 \times 10^8$ engineered T cells. In embodiments, the first expanded population of engineered T cells comprises at least $1 \times 10^9$ engineered T cells. In embodiments, the first expanded population of engineered T cells comprises between about $1 \times 10^8$ and about $1 \times 10^{11}$ engineered T cells. In embodiments, the second expanded population of engineered T cells comprises between $1 \times 10^5$ and $1 \times 10^9$ engineered T cells. In embodiments, the second expanded population of engineered T cells comprises at least $1 \times 10^8$ engineered T cells. In embodiments, the second expanded population of engineered T cells comprises at least $1 \times 10^9$ engineered T cells. In embodiments, the second expanded population of engineered T cells comprises between about $1 \times 10^8$ and about $1 \times 10^{11}$ engineered T cells.

In embodiments, the T cells are autologous to the subject. In embodiments, an additional population of engineered T cells is administered to the patient, and the T cells in the additional population of engineered T cells express a third exogenous TCR that binds to a third antigen expressed by the cancer, and do not express an endogenous TCR-beta. In embodiments, an additional population of engineered T cells is administered to the patient, and the T cells in the additional population of engineered T cells express up to five exogenous TCRs that bind an antigen (one at a time) expressed by the cancer, and do not express an endogenous TCR-beta. In embodiments, an additional population of engineered T cells is administered to the patient, and the T cells in the additional population of engineered T cells express up to ten exogenous TCRs that bind an antigen (one at a time) expressed by the cancer, and do not express an endogenous TCR-beta. In embodiments, further additional pluralities of engineered T cells are administered to the patient, and the T cells in the these additional pluralities of engineered T cells express additional exogenous TCRs (one at a time) that bind to an additional antigens expressed by the cancer, and do not express an endogenous TCR-beta.

In another interrelated aspect, a method of treating cancer is provided. The method includes administering a T cell, composition, or pharmaceutical composition as described herein including embodiments, to a patient having a cancer. In embodiments, the method further comprises administering an anti-cancer therapy to the subject. In embodiments, the anti-cancer therapy comprises immunotherapy, chemotherapy, and/or radiation.

In another interrelated aspect, a guide RNA is provided. The guide RNA is discovered through methods known to one skilled in the art such that it targets the exon 1, exon 2 or exon 3 region of the TCR constant alpha region locus (TRAC). In embodiments, the guide RNA targets an endogenous TCR-alpha locus. In embodiments, the guide RNA targets one of the following sequences from the TCR-alpha locus: TRAC1 (SEQ ID NO: 7), TRAC2 (SEQ ID NO: 8), TRAC3 (SEQ ID NO: 9), TRAC4 (SEQ ID NO: 10), TRAC5 (SEQ ID NO: 11), TRAC6 (SEQ ID NO: 12), TRAC7 (SEQ ID NO: 13), TRAC8 (SEQ ID NO: 14), TRAC9 (SEQ ID NO: 15), TRAC10 (SEQ ID NO: 16), TRAC11 (SEQ ID NO: 17), TRAC12 (SEQ ID NO: 18), TRAC13 (SEQ ID NO: 19), TRAC14 (SEQ ID NO: 20), TRAC15 (SEQ ID NO: 21), or TRAC16 (SEQ ID NO: 22). In embodiments, the guide RNA that targets an endogenous TCR-alpha locus comprises a nucleic acid sequence of Table 10. In embodiments, the endogenous TCR-alpha locus is an endogenous TCR-alpha constant region.

In another interrelated aspect, a guide RNA is provided. The guide RNA is discovered through methods known to one skilled in the art such that it targets the exon I regions of both TCR constant beta region loci (TRBC). In embodiments, the guide RNA targets an endogenous TCR-beta locus. In embodiments, the guide RNA targets one of the following sequences from the TCR-beta locus: TRBC1 (SEQ ID NO: 23), TRBC2 (SEQ ID NO: 24), TRBC3 (SEQ ID NO: 25), TRBC4 (SEQ ID NO: 26), TRBC5 (SEQ ID NO: 27), TRBC6 (SEQ ID NO: 28), TRBC7 (SEQ ID NO: 29), TRBC8 (SEQ ID NO: 30), TRBC9 (SEQ ID NO: 31), TRBC10 (SEQ ID NO: 32), TRBC11 (SEQ ID NO: 33), TRBC12 (SEQ ID NO: 34), TRBC13 (SEQ ID NO: 35), TRBC14 (SEQ ID NO: 36), TRBC15 (SEQ ID NO: 37), TRBC16 (SEQ ID NO: 38), TRBC17 (SEQ ID NO: 39), TRBC18 (SEQ ID NO: 40), TRBC19 (SEQ ID NO: 41), TRBC20 (SEQ ID NO: 42), TRBC21 (SEQ ID NO: 43), TRBC22 (SEQ ID NO: 44), TRBC23 (SEQ ID NO: 45), TRBC24 (SEQ ID NO: 46), TRBC25 (SEQ ID NO: 47), or TRBC26 (SEQ ID NO: 48). In embodiments, the guide RNA that targets an endogenous TCR-beta locus comprises the nucleic acid sequence in Table 11.

In another interrelated aspect, a nucleic acid is provided. The nucleic acid includes a nucleic acid sequence comprising an exogenous TCR-beta encoding sequence and an exogenous TCR-alpha encoding sequence, wherein the nucleic acid sequence further comprises a first self-cleaving peptide encoding sequence. In embodiments, the nucleic acid further includes a first homology arm and a second homology arm. In embodiments, the nucleic acid further includes a second self-cleaving peptide encoding sequence. In embodiments, the nucleic acid includes, in order from 5' to 3': (i) the first homology arm; (ii) the first self-cleaving viral peptide encoding sequence; (iii) the exogenous TCR-beta encoding sequence; (iv) the second self-cleaving viral peptide encoding sequence; (v) the exogenous TCR-alpha encoding sequence; and (vi) the second homology arm. In embodiments, the nucleic acid further includes an enzymatic cleavage site. In embodiments, the enzymatic cleavage site is located between the TCR-beta encoding sequence and the second self-cleaving viral peptide encoding sequence. In embodiments, the enzymatic cleavage site is a furin enzymatic cleavage site. In embodiments, the nucleic acid further includes a GSG amino acid sequence. In embodiments, the GSG precedes one or both of the first self-cleaving viral peptide encoding sequence and the second self-cleaving viral peptide encoding sequence.

In embodiments, the nucleic acid further contains a polyadenylation (polyA) sequence. In embodiments, the polyadenylation sequence can be located immediately 3'-adjacent from the TCR-encoding sequence. In embodiments, the polyadenylation sequence can be located immediately 5'adjacent to the second homology arm. In embodiments, the polyadenylation sequence is a bovine growth hormone polyadenylation sequence (bgh-polyA).

In embodiments, the first homology arm is homologous to an endogenous TCR-alpha locus in a human T cell. In embodiments, the second homology arm is homologous to an endogenous TCR-alpha locus in a human T cell. In embodiments, the endogenous TCR-alpha locus is a TCR-alpha constant region. In embodiments, the first self-cleaving viral peptide is T2A, P2A, E2A, or F2A. In embodiments, the second self-cleaving viral peptide is T2A, P2A, E2A, or F2A. In embodiments, the first self-cleaving viral peptide and the second self-cleaving viral peptide are different. In embodiments, the first self-cleaving peptide encoding sequence is 5' of the exogenous TCR-beta encoding sequence. In embodiments, the second self-cleaving peptide encoding sequence is 5' of the exogenous TCR-alpha encoding sequence. In embodiments, the second self-cleaving peptide encoding sequence is 5' of the exogenous TCR-alpha encoding sequence. In embodiments, the nucleic acid is a plasmid, nanoplasmid, or minicircle.

In another, interrelated aspect, a kit for producing engineered T cells is provided. The kit includes a TCR-alpha-targeting guide RNA as described herein including embodiments. In embodiments, the kit further includes a TCR-beta-targeting guide RNA as described herein including embodiments. In embodiments, the kit further includes a gene editing reagent or nucleic acid sequence encoding a gene editing reagent. In embodiments, the gene editing reagent is a CRISPR system. In embodiments, the kit further includes a donor DNA. In embodiments, the donor DNA comprises a nucleic acid sequence encoding a polypeptide comprising an exogenous TCR-beta and an exogenous TCR-alpha. In embodiments, the donor DNA comprises a nucleic acid sequence encoding a polypeptide comprising an exogenous TCR-beta and an exogenous TCR-alpha (VJ) domain. In embodiments, the exogenous TCR-beta and the heterologous TCR-alpha form a TCR capable of binding to an antigen. In embodiments, the TCR binds to the antigen presented on a major histocompatibility complex class I (MHCI) molecule. In embodiments, the antigen is WT1, JAK2, NY-ESO1, PRAME, mutant KRAS, or an antigen from Table 1 or Table 2. In embodiments, the kit further includes poly(glutamic acid) (PGA) or variant thereof. In embodiments, the kit further includes a nucleic acid as described herein including embodiments.

BRIEF DESCRIPTION OF THE DRAWINGS

FIG. 1A illustrates frequency of knock-in positive mNeon+TCRab+ cells and FIG. 1B shows frequency of residual TCRab expressing cells. Cells were electroporated with TRAC1 RNP only (RNP), NTC (non-targeting guide control with no TCR knockout) RNP+4 μg TRAC1-mNeon (4 μg), or 6 μg/4 μg/2 μg/1 μg TRAC1-mNeon+TRAC1 RNP (6 μg, 4 μg, 2 μg and 1 μg, respectively). All cells were electroporated in P2 buffer with the EH100 pulse code, except for the rightmost group of two bars, which represent groups of cells electroporated in P3 buffer with the EH115 pulse code. Post-electroporation, cells were incubated at either 37° C. or 32° C.

FIG. 9A shows frequency of knock-in positive mNeon+TCRab+ cells generated with the TRAC1-mNeon template and FIG. 9B shows frequency of knock-in positive mNeon+TCRab+ cells generated with the TRAC3-mNeon template.

FIGS. 11A and 11B illustrate recovery of mNeon+TCRab+ cells from T cells electroporated with various amounts of the TRAC1-mNeon and TRAC3-mNeon templates, respectively. FIGS. 11C and 11D illustrate recovery of total CD8+ cells from cells electroporated with various amounts of the TRAC1-mNeon and TRAC3-mNeon templates, respectively.

FIG. 23A are flow-cytometry dot-plots illustrating TRAC3-mNeon knock-in in T cells. Cells were subject to electroporation with TRAC3 NRP or control NT RNP and various amounts of TRAC3-mNEON template. Either dsDNA, forward ssDNA strand (ssDNA FW) or reverse ssDNA strand (ssDNA RV) template was used. FIG. 23B is a graph showing cell viability and FIG. 23C is a graph illustrating percent knock-in under the indicated conditions.

FIG. 25A shows recovery of CD8+ cells following electroporation of cells activated with varying TRANSACT™ titrations. Media and cytokine conditions tested are as indicated for FIG. 24. FIG. 25B shows expansion of mNeon+TCRab+ cells from Day 4 to Day 5 post-electroporation with groups of cells activated in varying media and TRANSACT™ titration conditions. TA 20, TA 50, TA 100 and TA 200 indicate 1:20, 1:50, 1:100 and 1:200 TRANSACT™ titrations, respectively. RPMI and XV indicate RPMI media and X-VIVO media, respectively.

FIG. 26A shows recovery of CD8+ cells from cells activated with varying TRANSACT™ titrations. Media and cytokine conditions tested are as indicated for FIG. 24. FIG. 26B shows expansion of CD8+ cells from Day 4 to Day 5 post electroporation with groups of cells activated in varying media and TRANSACT™ titration conditions. TA 20, TA 50, TA 100 and TA 200 indicate 1:20, 1:50, 1:100 and 1:200 TRANSACT™ titrations, respectively. Cells were expanded in RPMI media or X-VIVO™ (XV) media.

Figure 24A:
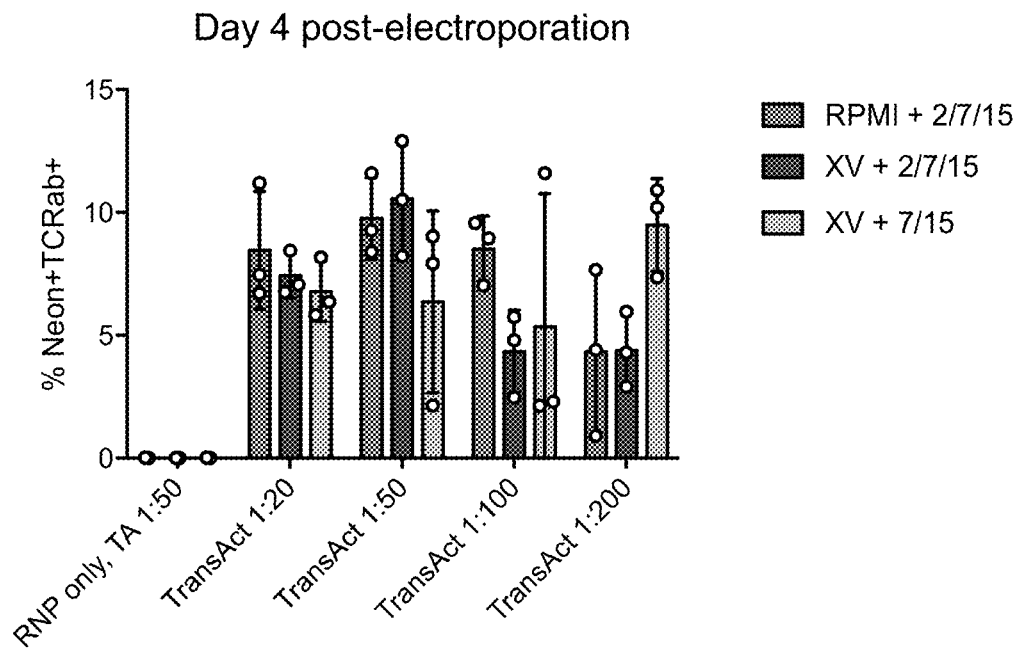
FIGS. 24A and 24B illustrate knock-in efficiency depending on varying TRANSACT™ titrations and media conditions used for T cell activation. Bar graphs show frequency of knock-in positive T cells 4 days (FIG. 24A) or 5 days (FIG. 24B) post-electroporation with the TRAC3-mNeon template. Media and cytokine conditions tested were RPMI and X-VIVO (XV) media with either IL-2 (10 ng/ml), IL-7 (25 ng/ml) and IL-15 (50 ng/ml) (2/7/15); or IL-7 (25 ng/mL) and IL-15 (50 ng/ml) (7/15).
Figure 24B:
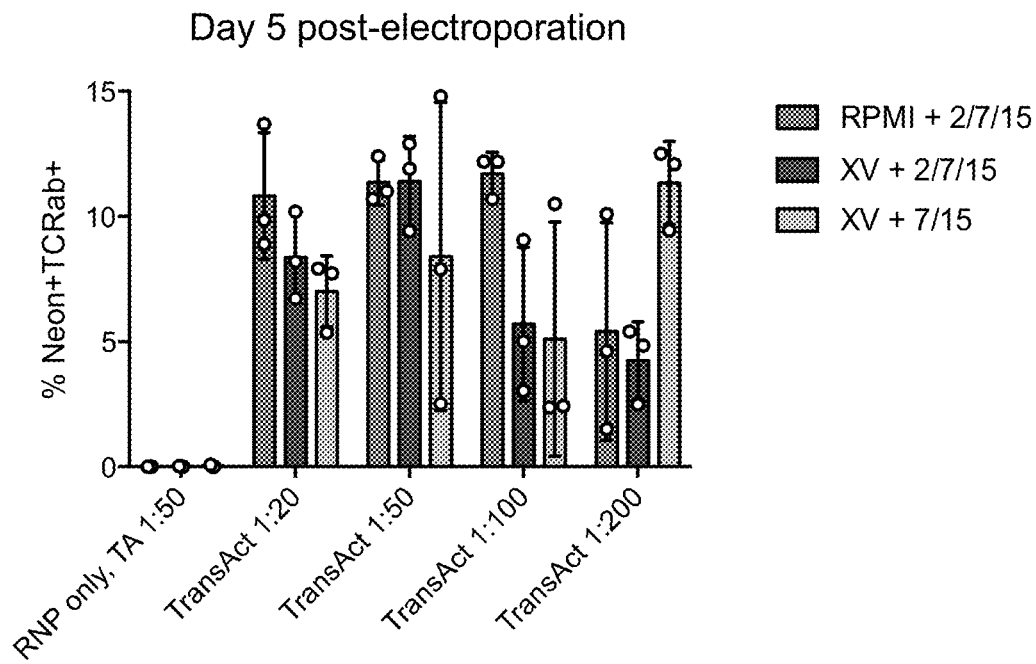
Figure 25A:
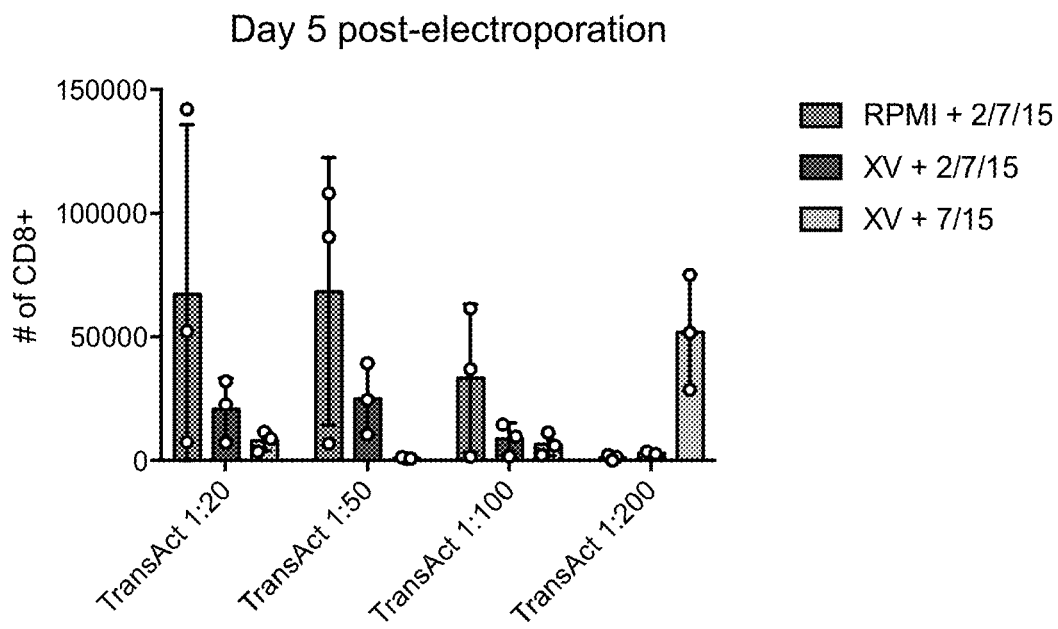
FIGS. 25A and 25B are graphs illustrating recovery and expansion of knock-in positive mNeon+TCRab+ cells following electroporation with TRAC3-mNeon.
Figure 25B:
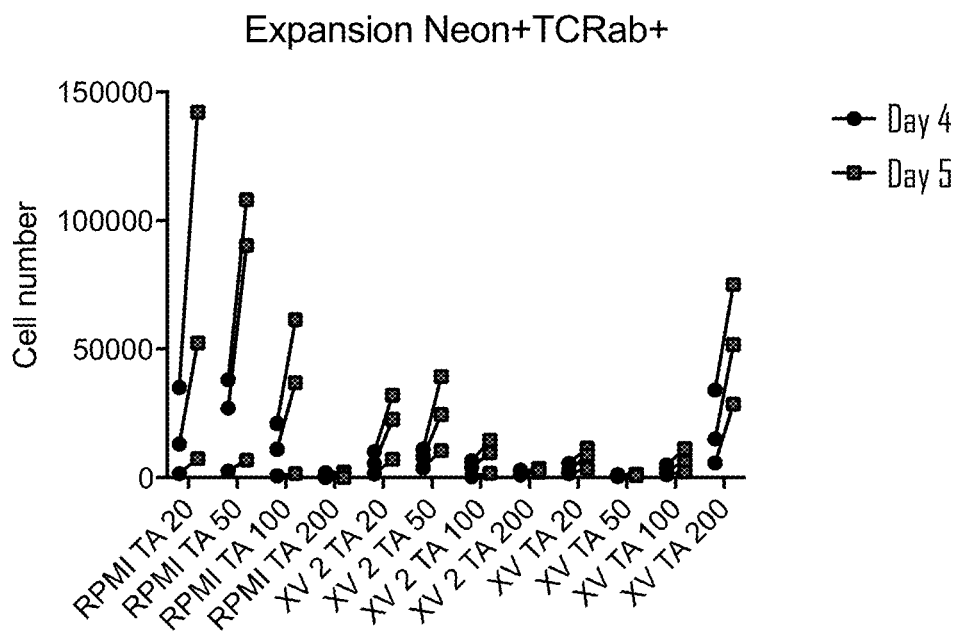
Figure 26A:
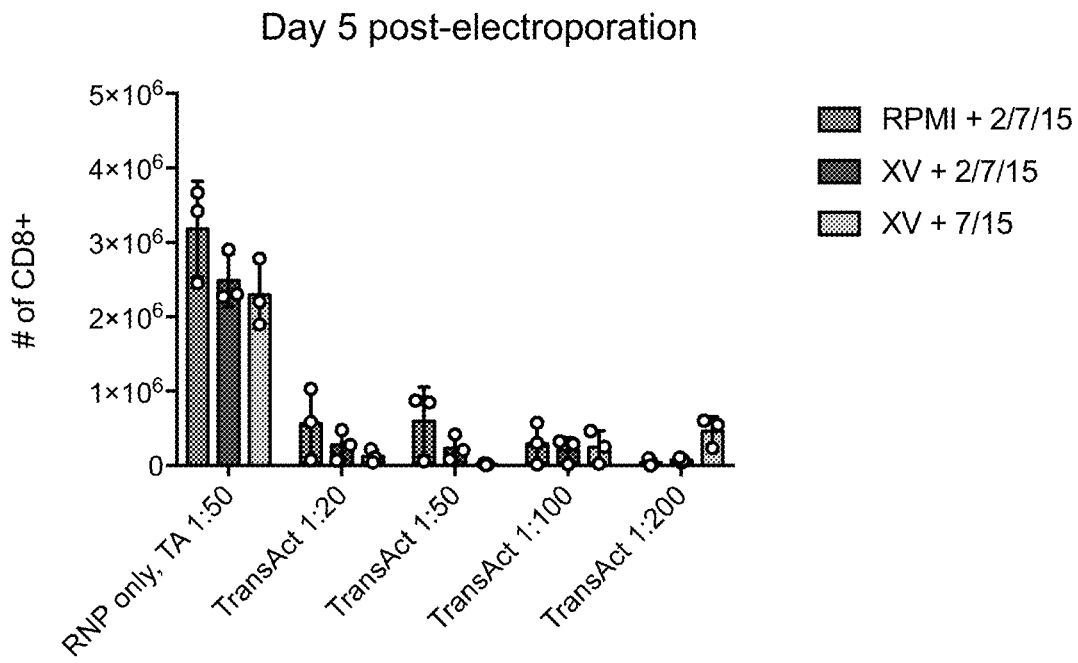
FIGS. 26A and 26B are graphs illustrating recovery and expansion of CD8+ cells following electroporation with TRAC3-mNeon.
Figure 26B:
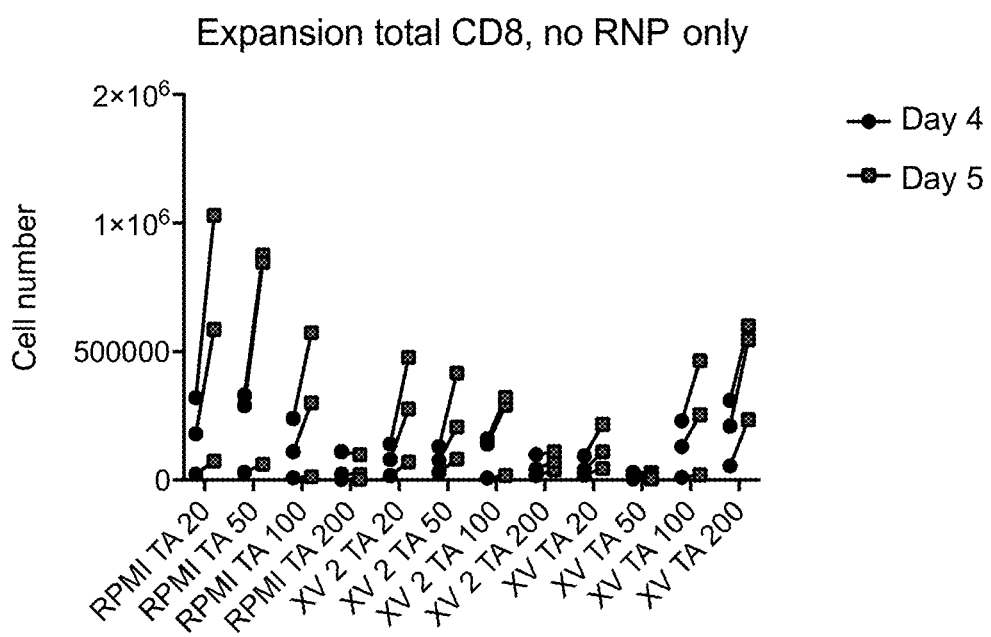
Figure 27A:
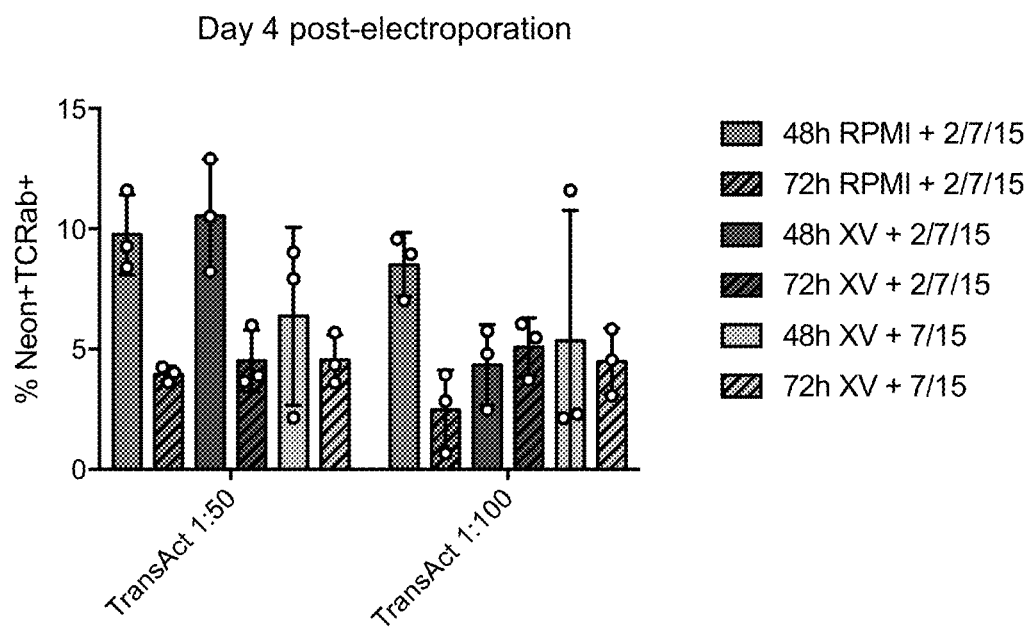
Figure 27B:
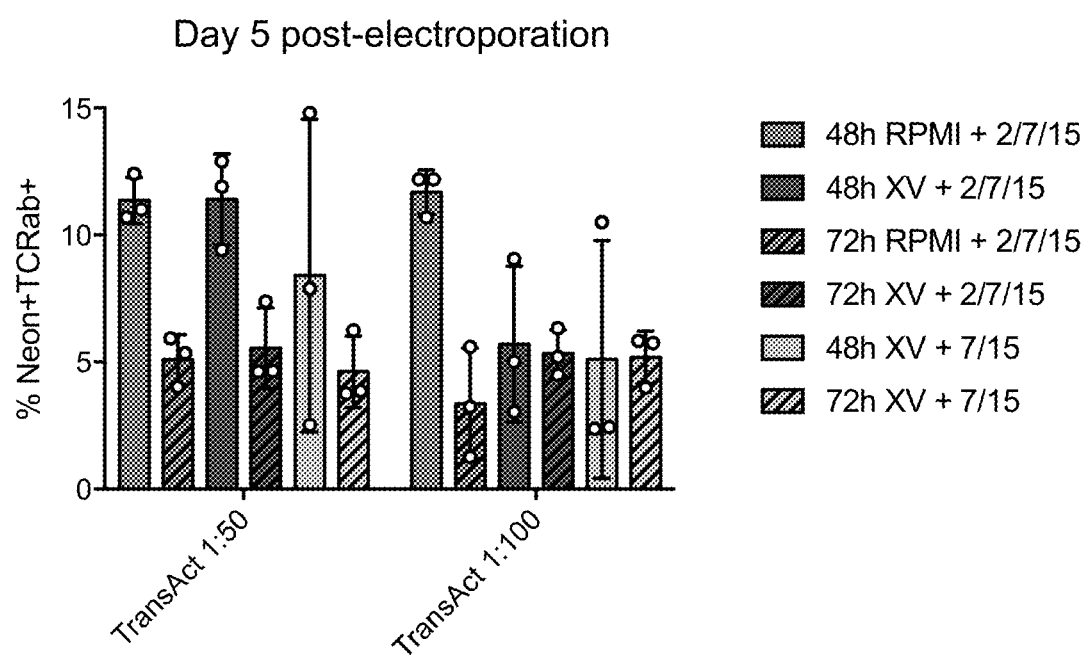

FIGS. 27A and 27B are bar graphs showing knock-in efficiency of TRAC3-mNeon for electroporations conducted at 48- or 72-hours post-activation using varying T cell activation conditions. FIG. 27A and FIG. 27B shows percent knock-in positive mNeon+TCRab+ cells 4 or 5 days post-electroporation, respectively. Media and cytokine conditions tested are as indicated for FIG. 24.

Figure 28:
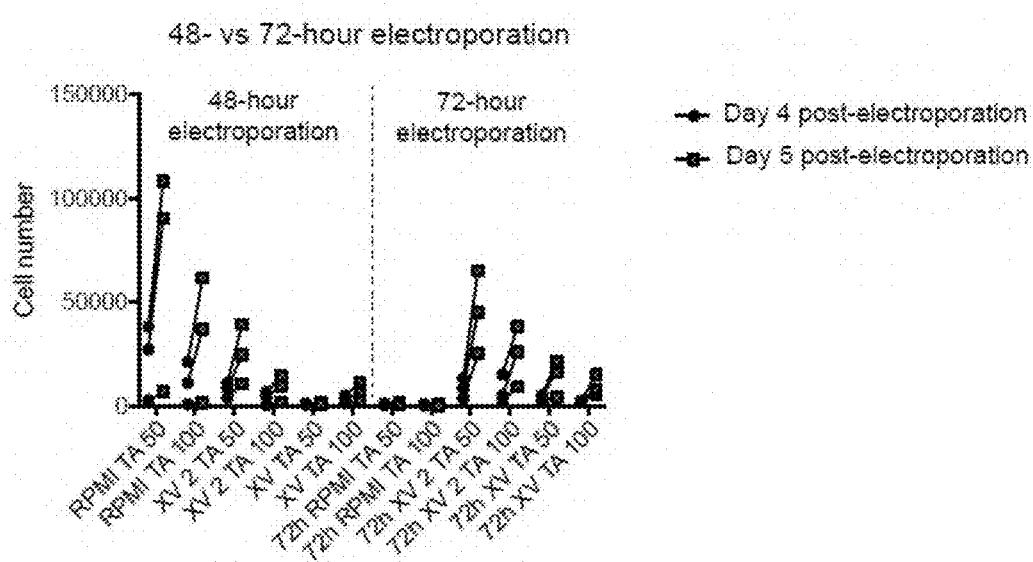

FIG. 28 shows graphs demonstrating expansion of knock-in positive (mNeon+TCRab+) CD8+ T cells following electroporation at 72 hours post-activation (left), and comparison of cell expansion following electroporation at 48 hours versus 72 hours post-activation (right). Varying media conditions and TRANSACT™ titrations were tested for T cell activation. 48h and 72h indicate data points for 48 and 72 hours post-activation, respectively; TA 20, TA 50, TA 100 and TA 200 indicate 1:20, 1:50, 1:100 and 1:200 TRANSACT™ titrations, respectively; RPMI and XV indicate RPMI media and X-VIVO media, respectively.

Figure 29A:
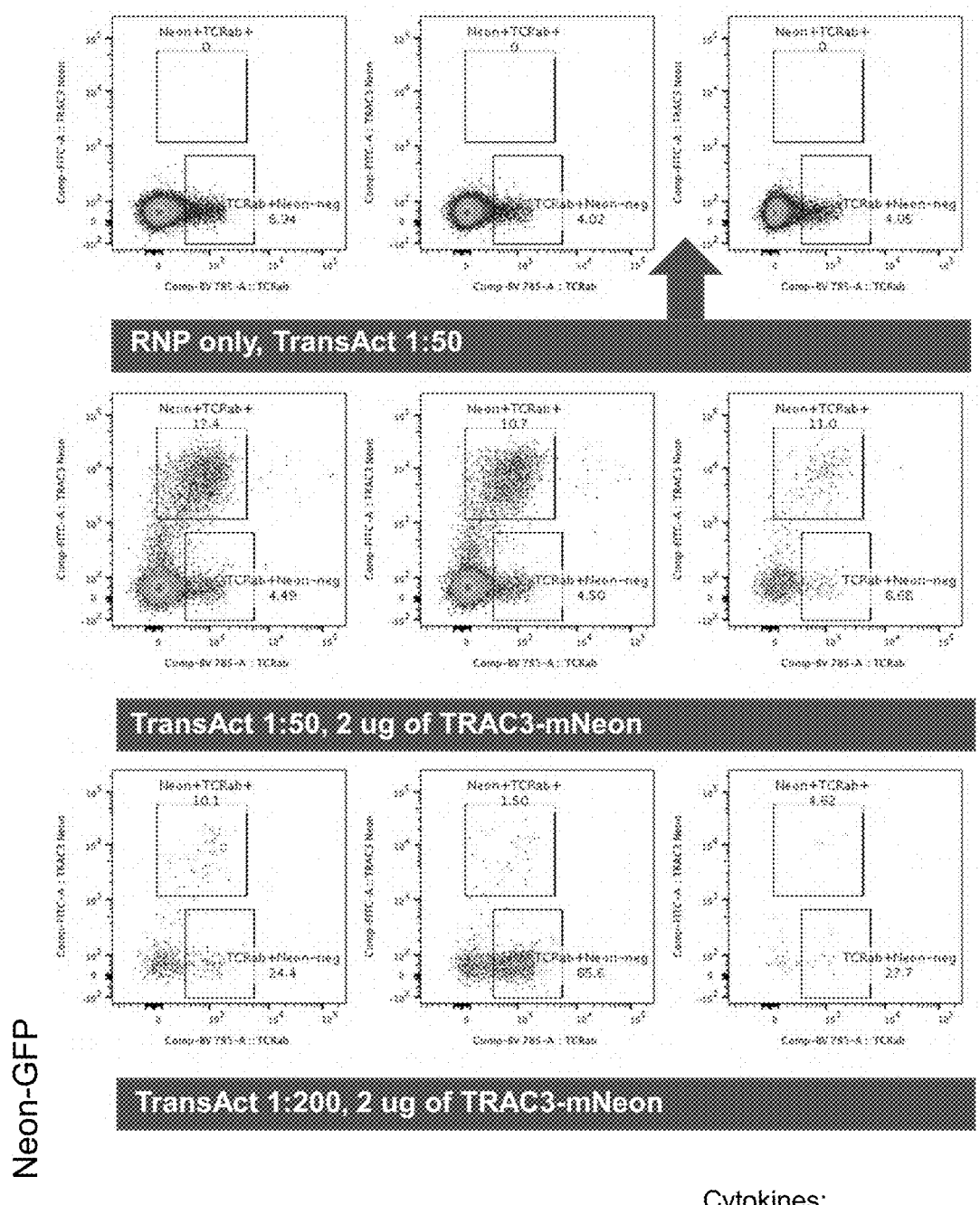
Figure 29B:
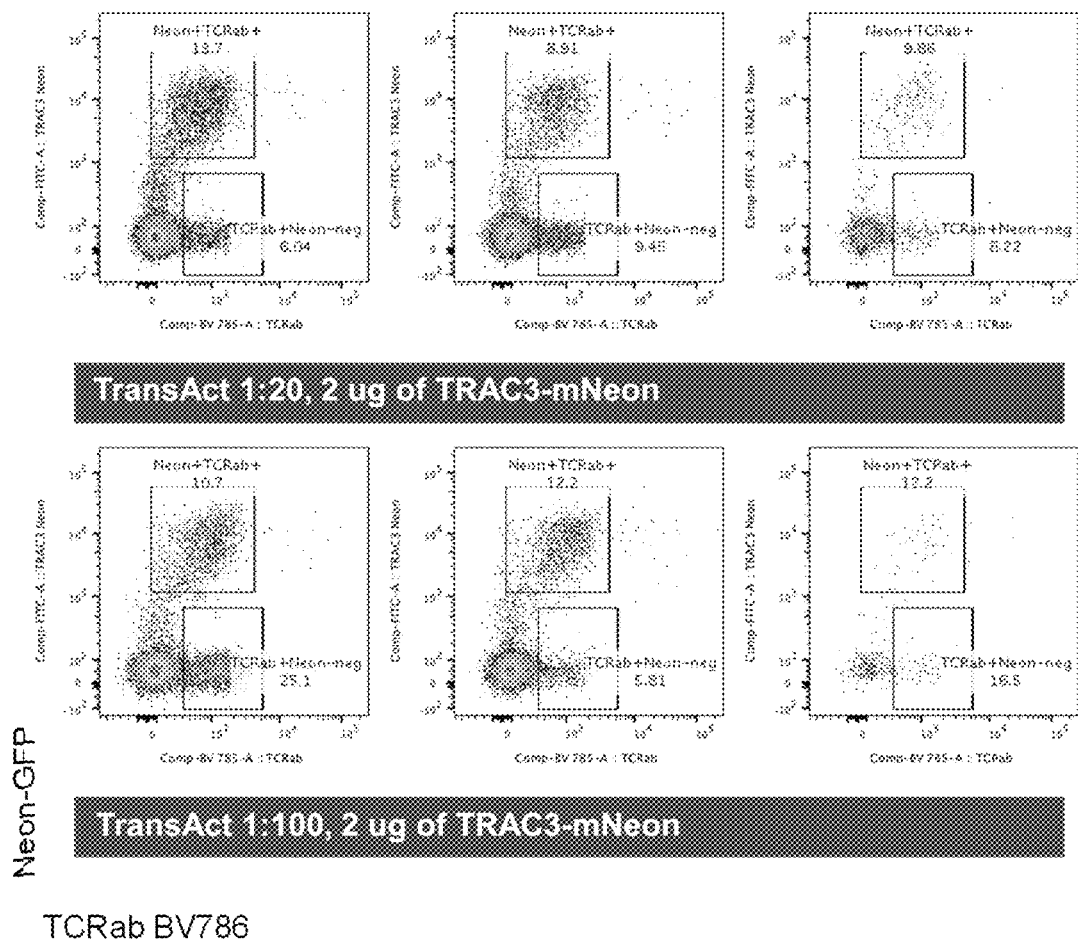

FIGS. 29A and 29B are flow-cytometry dot-plots showing detection of mNeon+TCRab+ T cells activated in RPMI media prior to electroporation. FIG. 29A shows analysis of cells activated with 1:50 TRANSACT™ and 1:200 TRANSACT™ and FIG. 29B shows analysis of cells activated with 1:20 and 1:100 TRANSACT™ titrations.

Figure 30A:
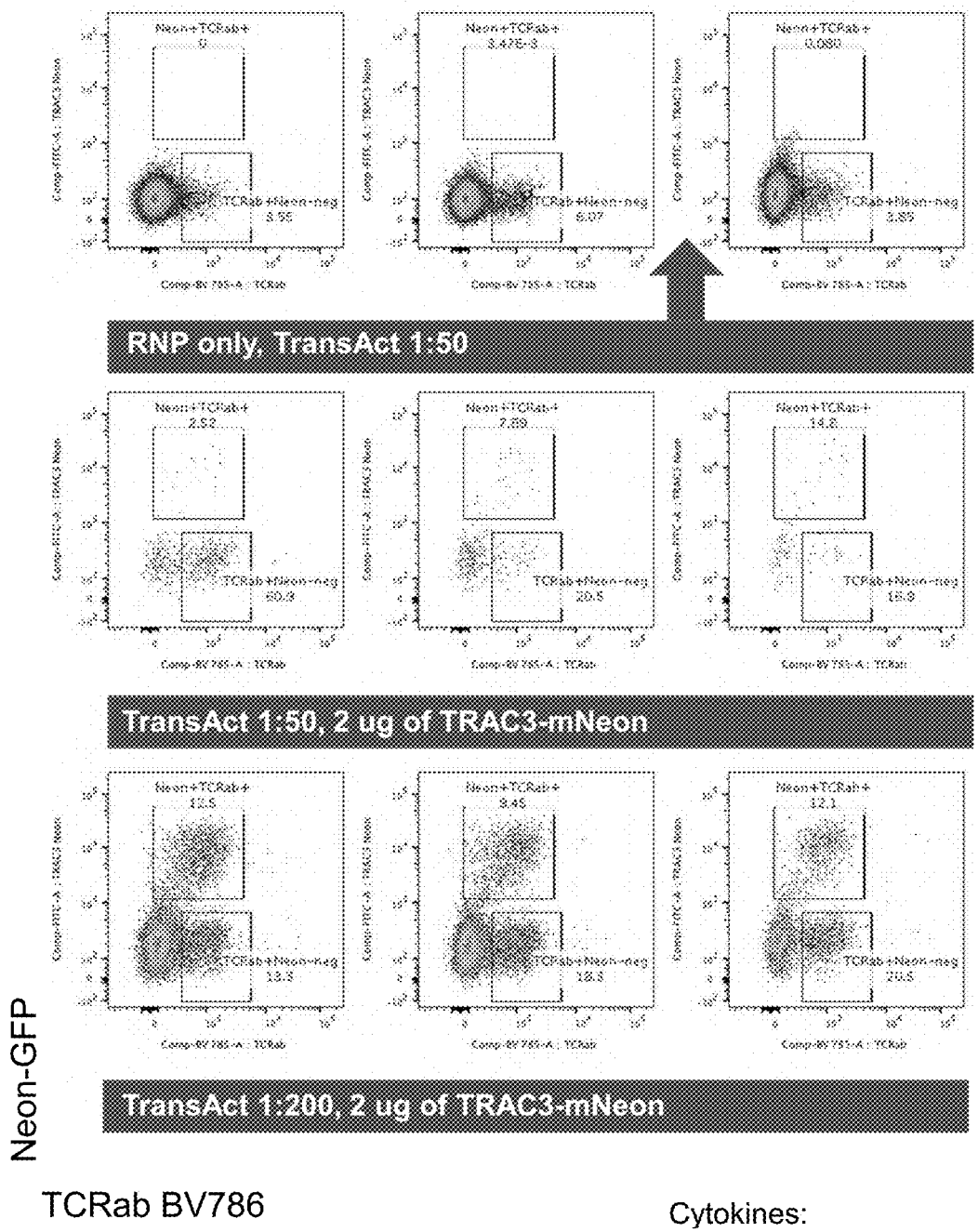
Figure 30B:
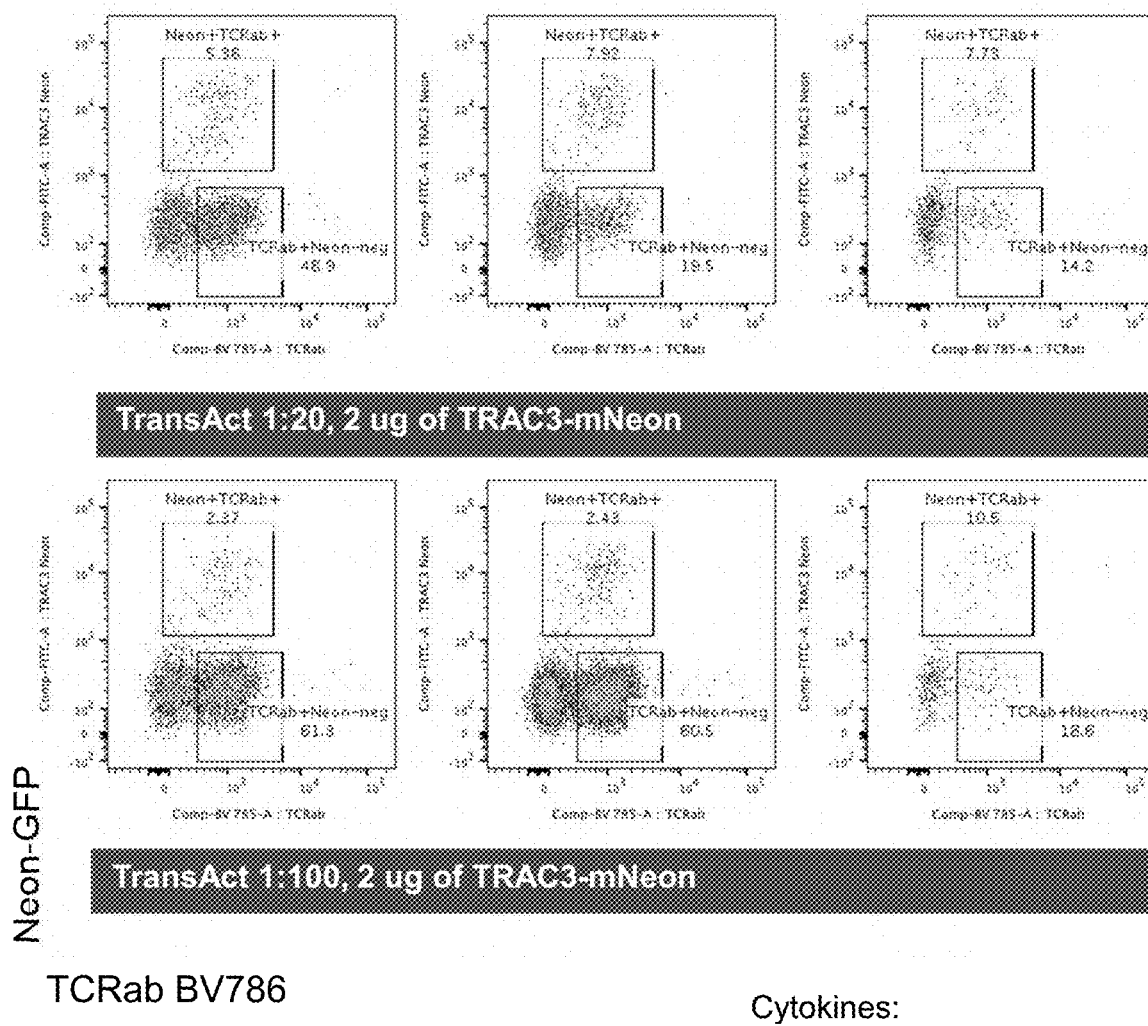

FIGS. 30A and 30B are flow-cytometry dot-plots showing detection of mNeon+TCRab+ T cells activated in X-VIVO™ media prior to electroporation. FIG. 30A shows analysis of cells activated with 1:50 TRANSACT™ and 1:200 TRANSACT™ and FIG. 30B shows analysis of cells activated with 1:20 and 1:100 TRANSACT™ titrations.

Figure 31A:
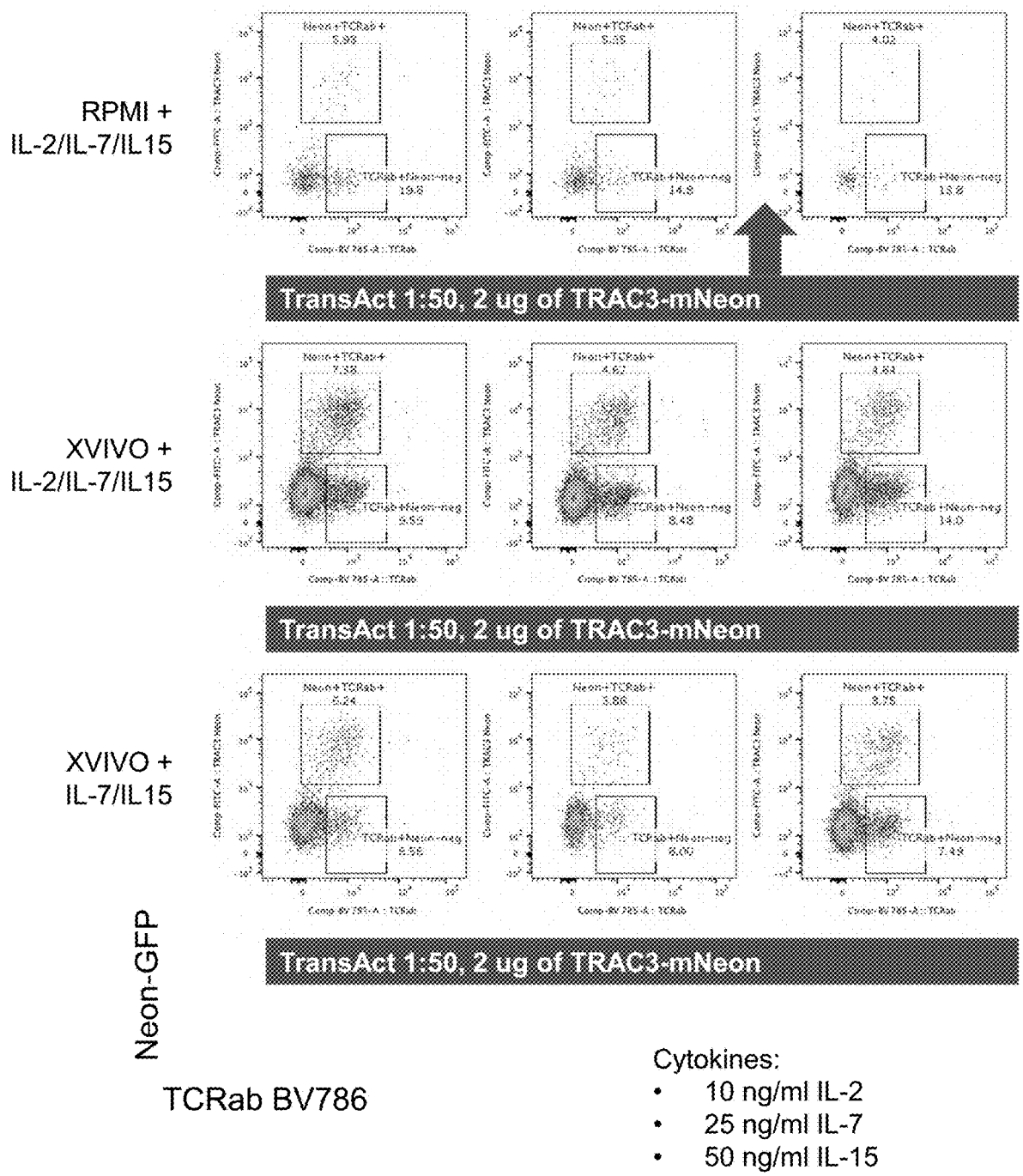
Figure 31B:
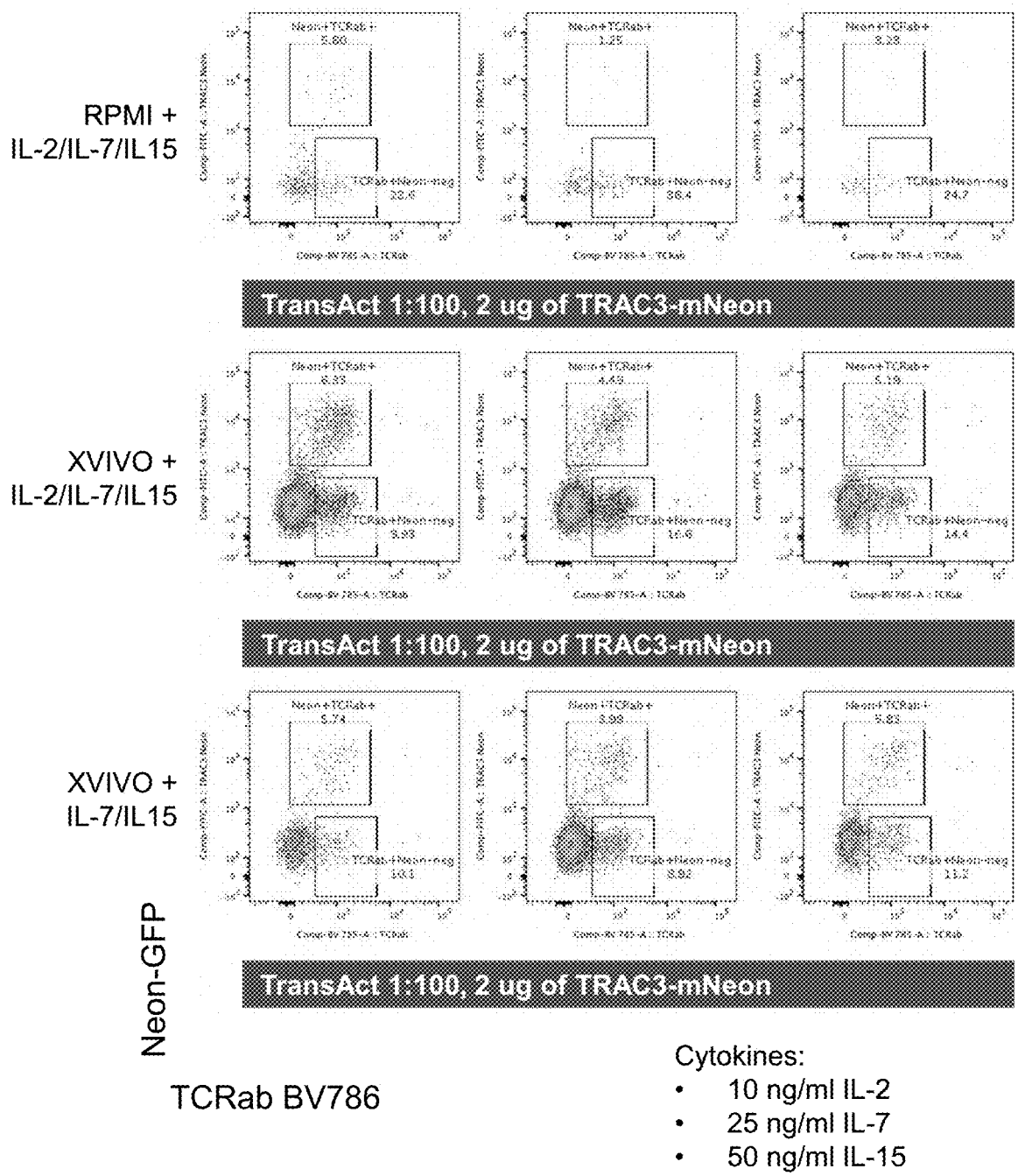

FIGS. 31A and 31B are flow-cytometry dot-plots showing detection of knock-in positive mNeon+TCRab+ cells activated in RPMI or X-VIVO™ media prior to electroporation. FIG. 31A shows analysis of cells activated with 1:50 TRANSACT™ and FIG. 31B shows analysis of cells activated with 1:100 TRANSACT™ titrations.

Figure 32:
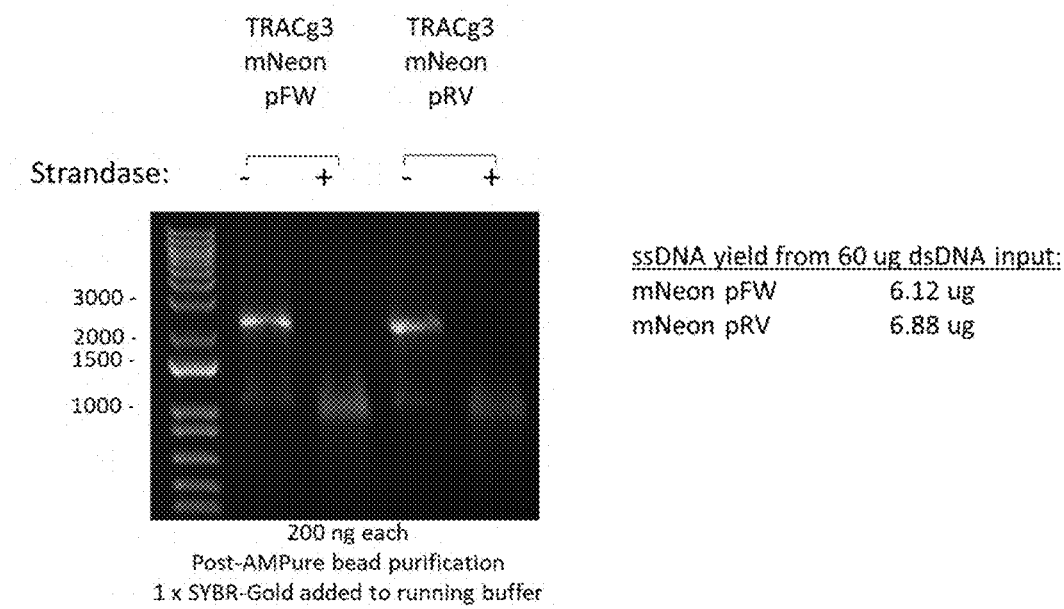

FIG. 32 is an image of an agarose gel showing forward (pFW) and reverse (pRV) ssDNA products generated from strandase reactions with double-stranded TRAC3-mNeon template. The left-most lane of the agarose gel is the molecular weight marker. ssDNA yields from the reactions are shown on the right.

Figure 33A:
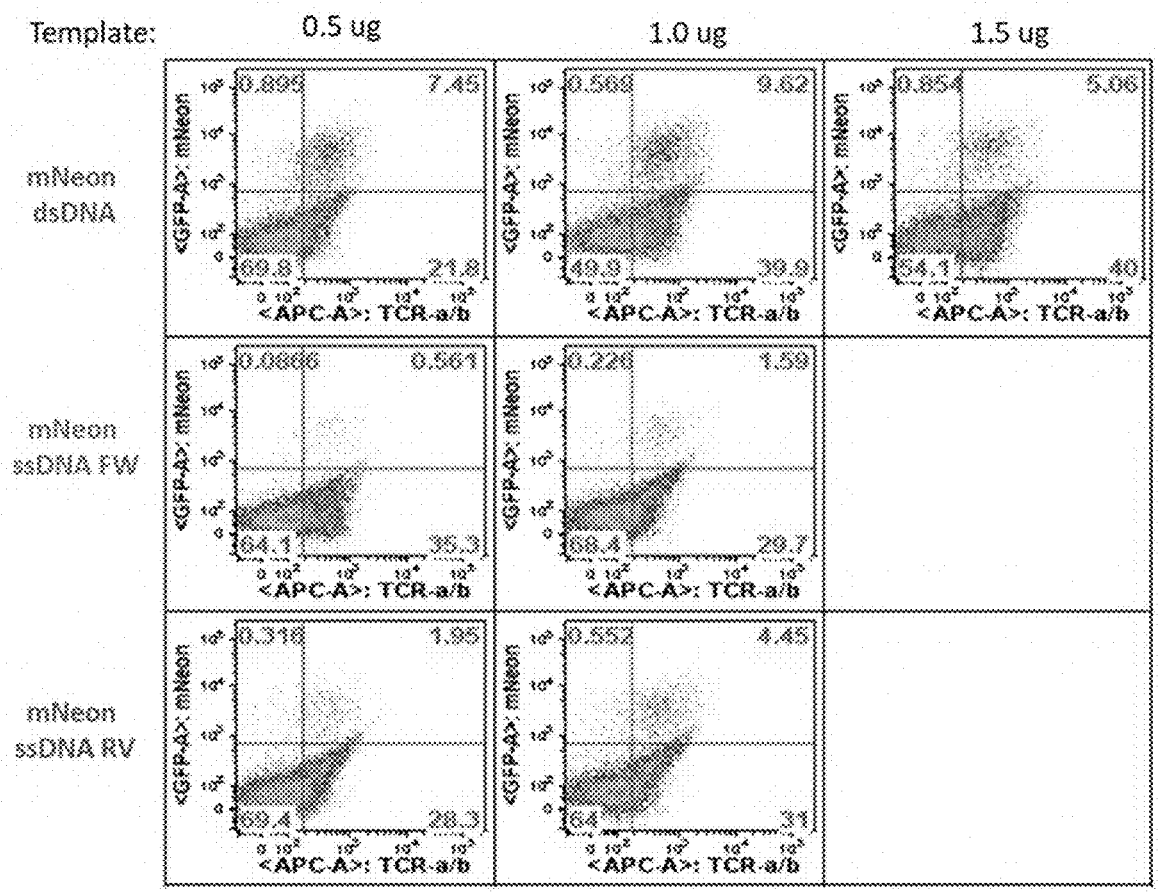
Figure 33B:
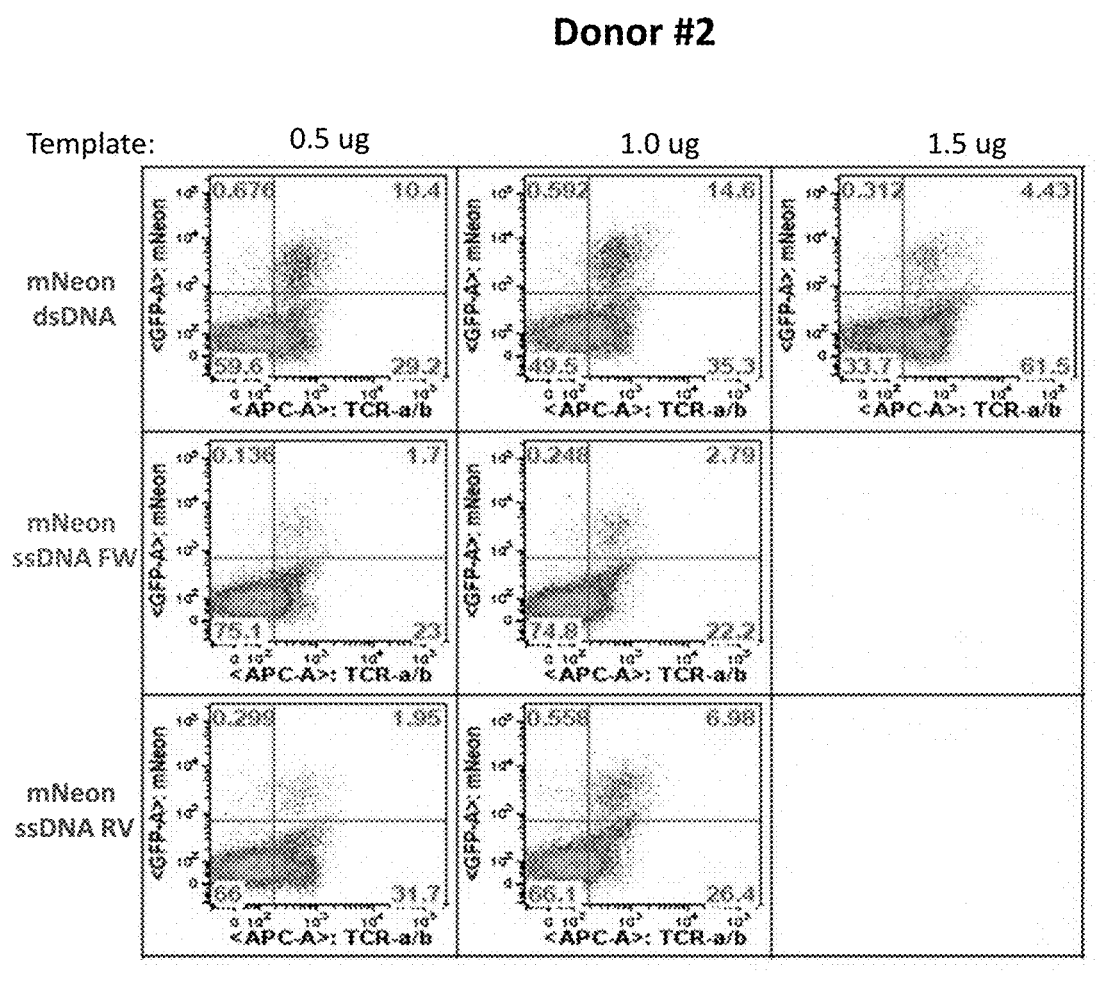

FIGS. 33A and 33B are flow-cytometry analysis illustrating knock-in efficiency of dsDNA, forward single stranded DNA (ssDNA FW) and reverse ssDNA (ssDNA RV) TRAC-mNeon template DNA by detection of mNeon+TCRab+ T cells. FIG. 33A shows analysis of cells from Donor 1 and FIG. 33B shows analysis of cells from Donor 2.

Figure 34A:
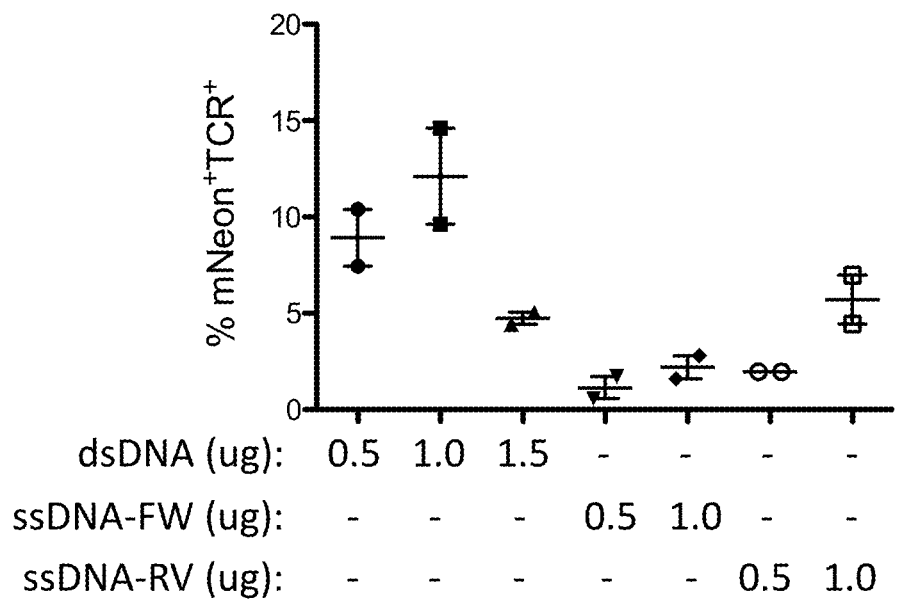
Figure 34B:
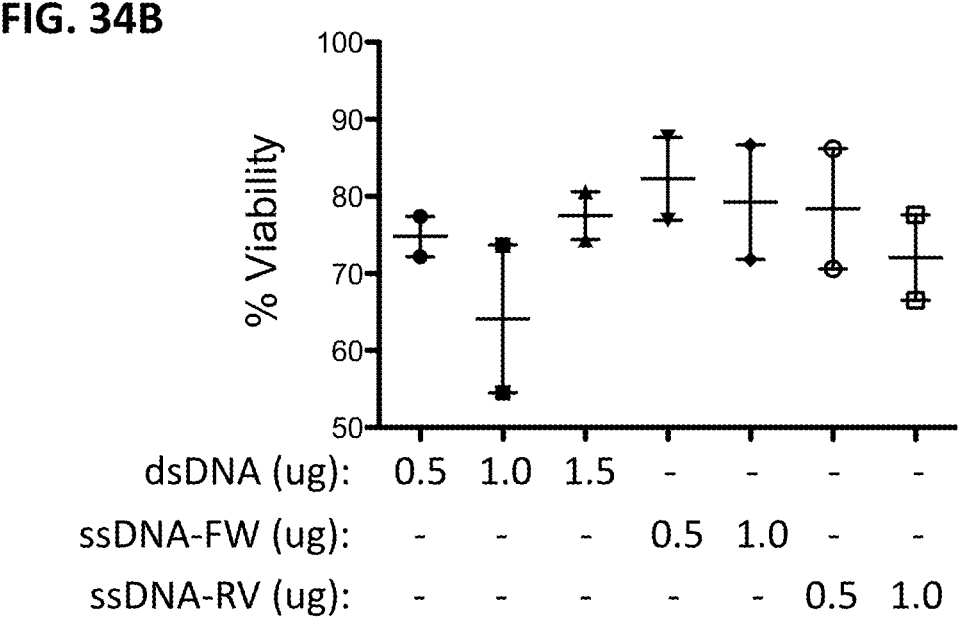

FIGS. 34A and 34B are graphs showing frequency of mNeon+TCRab+ T cells (FIG. 34A) and % viable cells (FIG. 34B), depending on varying amounts of either double stranded DNA (ds), forward ssDNA (ssDNA-FW) or reverse ssDNA (ssDNA-RV) TRAC-mNeon template used for electroporation.

Figure 35A:
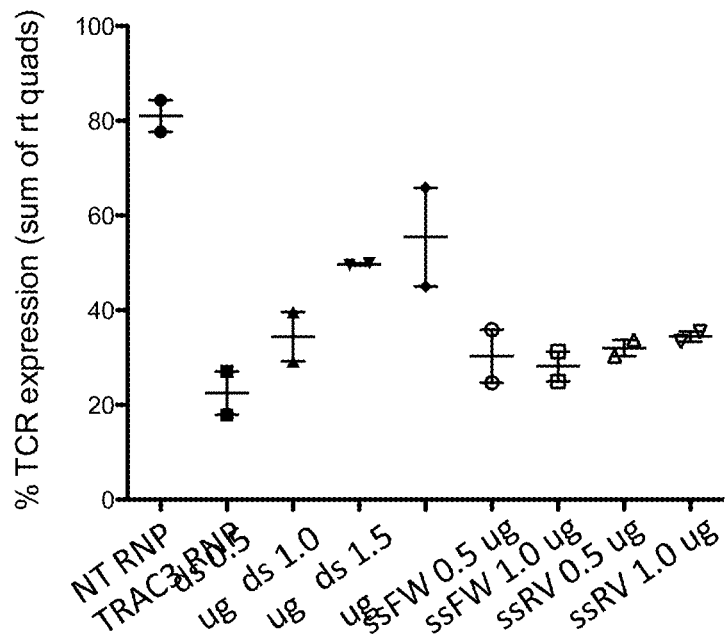
Figure 35B:
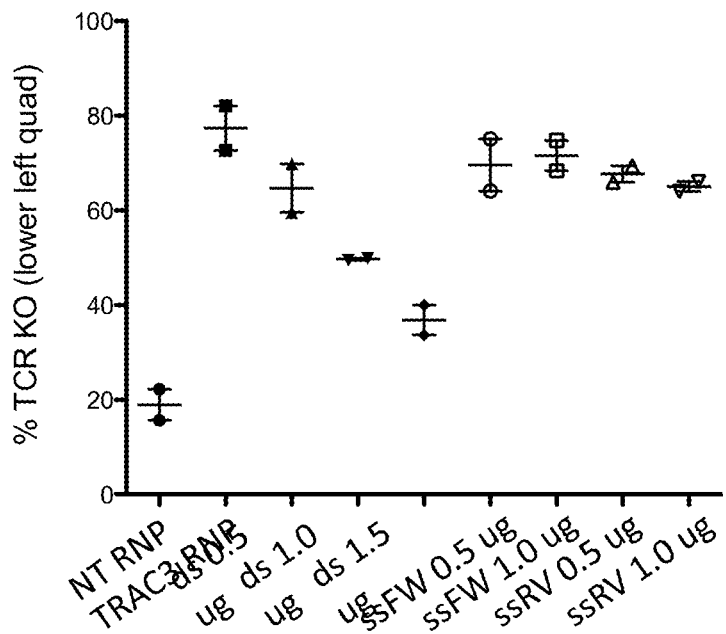

FIGS. 35A and 35B are graphs showing TCRab knock-out depending on interference of the template with knock-out efficiency. FIG. 35A illustrates percent TCRab expression, and FIG. 35B illustrates percent TCRab knock-out. ds indicates dsDNA, ssFW indicates ssDNA forward strand, and ssRV indicates ssDNA reverse strand.

Figure 36A:
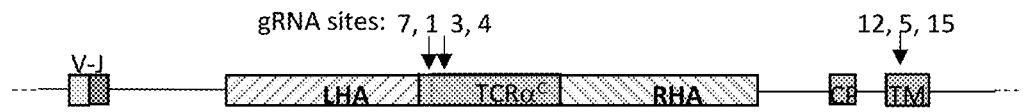
Figure 36B:
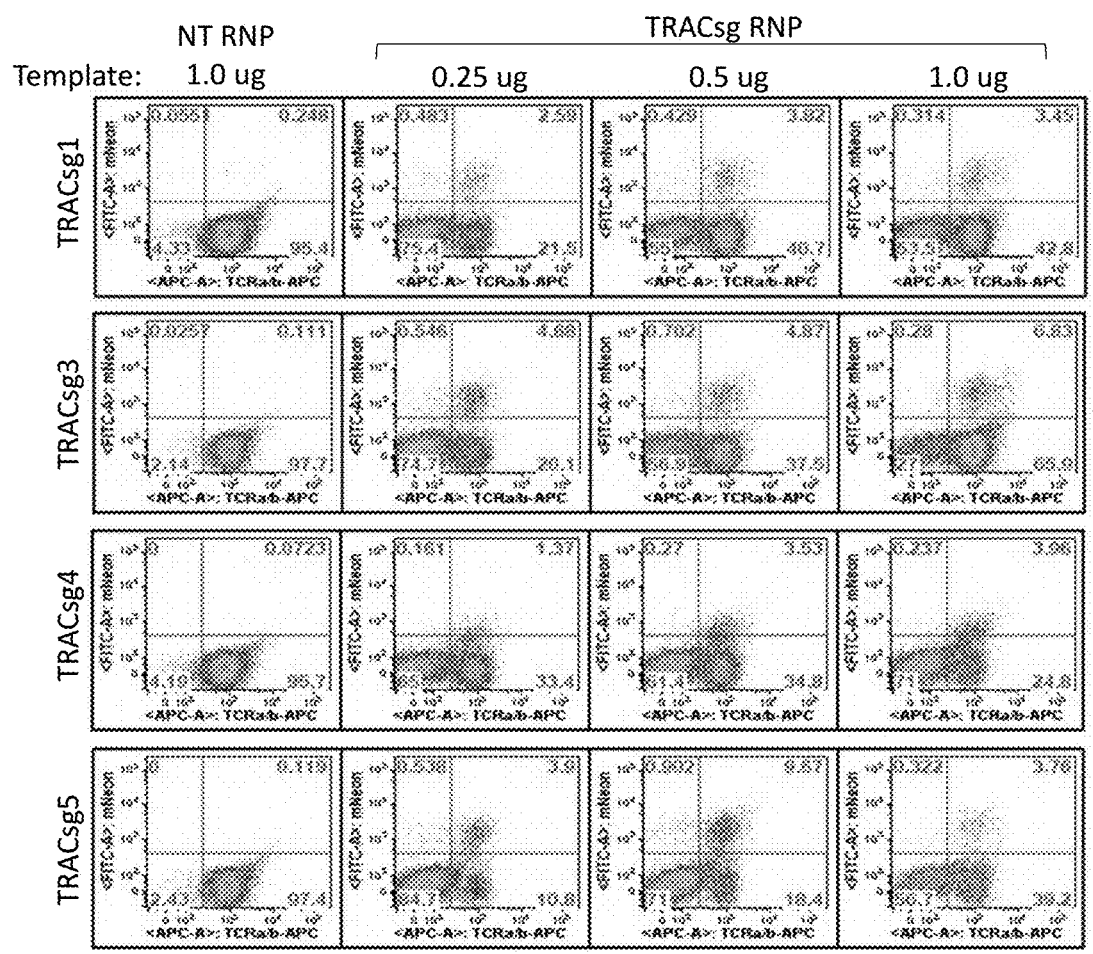
Figure 36C:
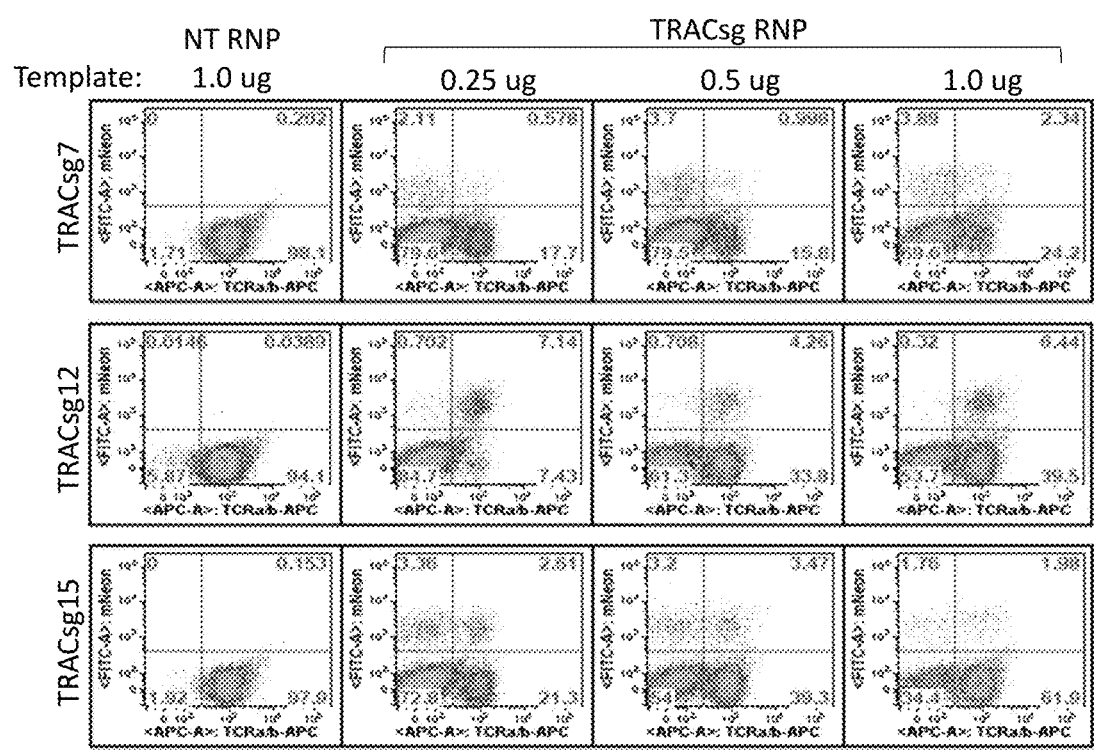

FIGS. 36A-36C illustrate TRAC-mNeon knock-in efficiency depending on various knock-in sites and different amounts of TRACsg RNP included in electroporation. FIG. 36A is a schematic of the TRAC locus with various sgRNA sites. FIG. 36B is flow cytometry analysis showing knock-in efficiency using TRACsg1, TRACsg3, TRACsg4, and TRACsg5 knock-in sites and FIG. 36C shows knock-in efficiency using TRACsg7, TRACsg12 and TRACsg15 knock-in sites.

Figure 37:
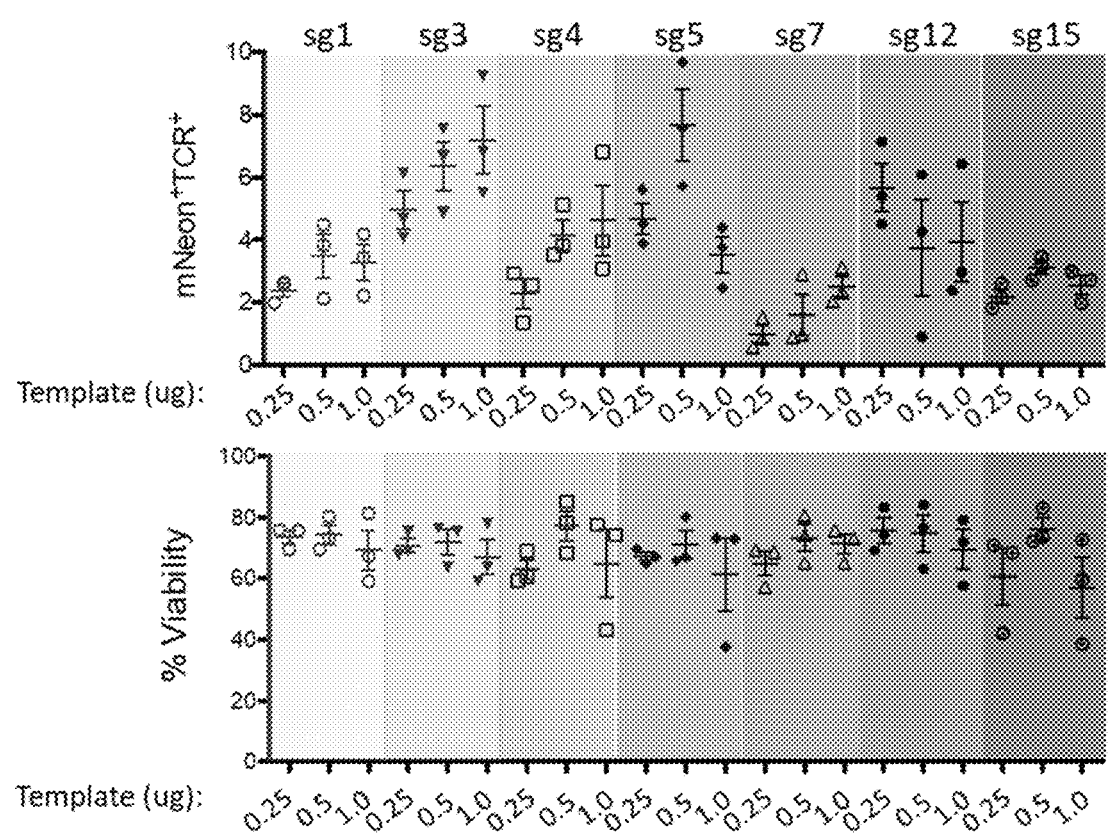

FIG. 37 are graphs showing mNeon knock-in efficiency by detection of mNeon+TCR+ cells (top) and cell viability following electroporation (bottom) using various amounts of each template as indicated.

Figure 38A:
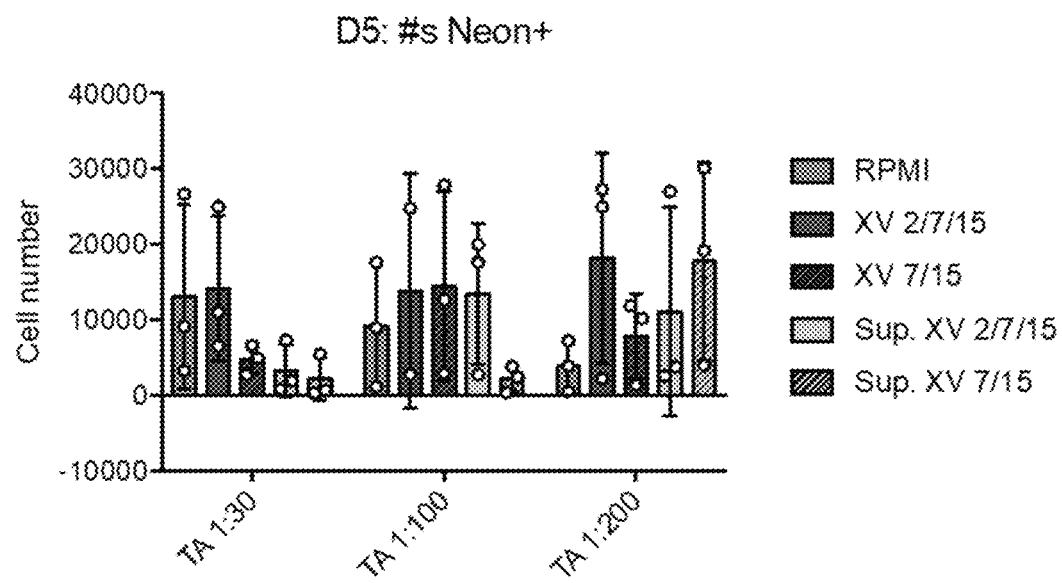
Figure 38B:
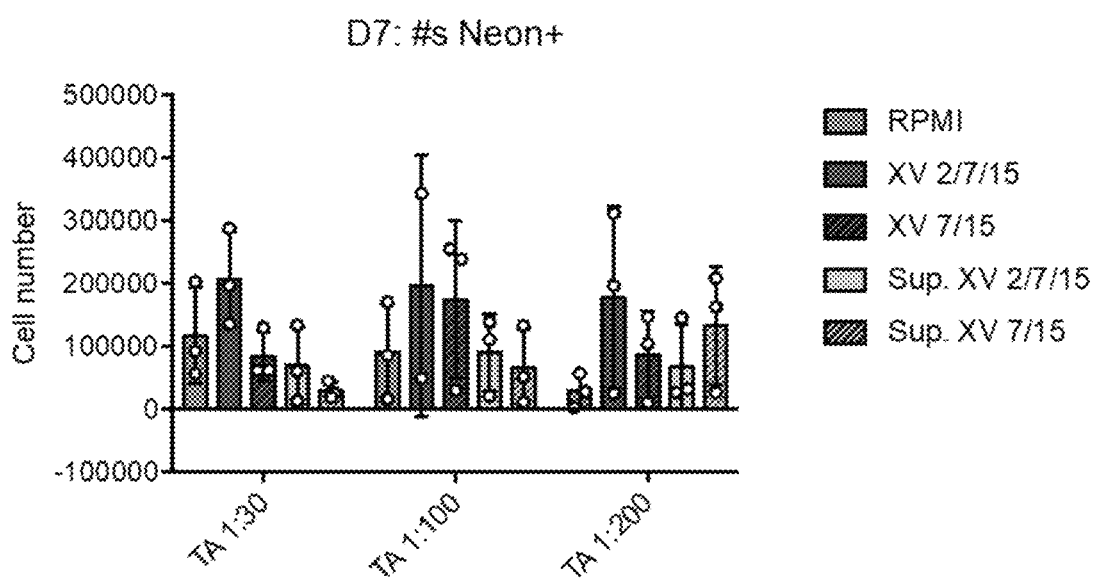
Figure 38C:
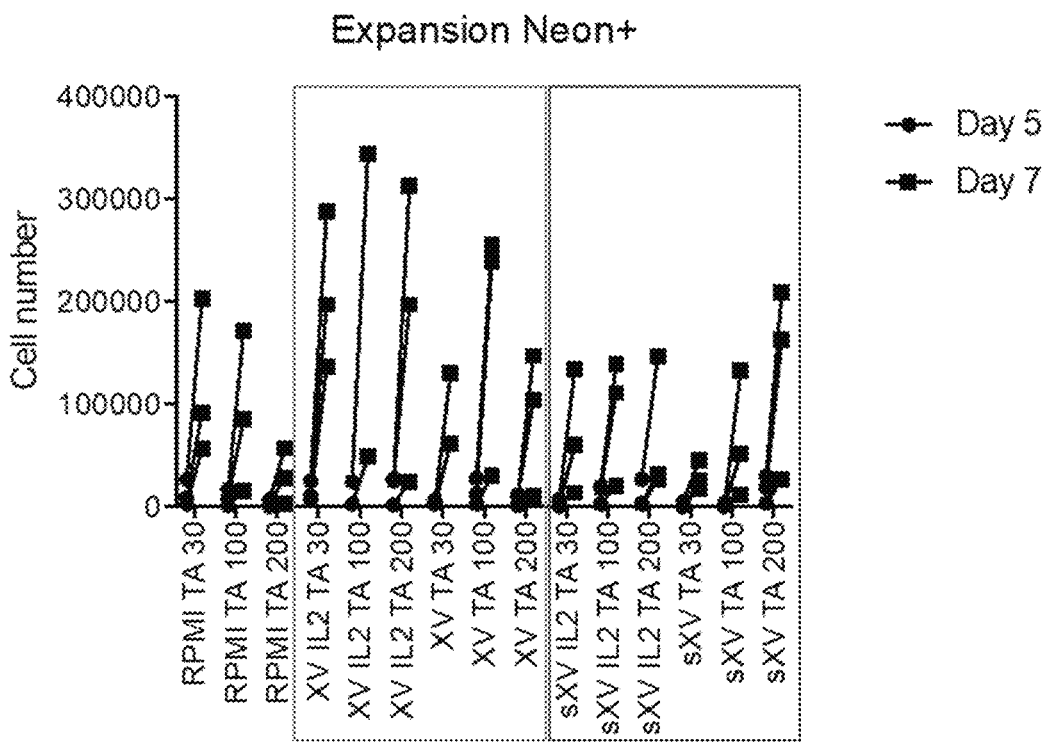

FIGS. 38A-38C illustrate the effect of media and supplements on mNeon+ knock-in in T cells following activation and electroporation. FIG. 38A is a bar graph showing cell recovery on Day 5 after initial T cell activation and FIG. 38B is a bar graph showing cell recovery on Day 7 after initial T cell activation. FIG. 38C is a graph showing T cell expansion between Days 5 and 7 for knock-in+ cells. Cells were cultured and activated in RPMI, X-Vivo (XV), supplemented X-Vivo (sXV or Sup. XV), with addition of either IL-2+IL-7+IL-15 (2/7/15) or IL-7+IL-15 (7/15). TA 30, TA 100 and TA 200 indicate TRANSACT™ titrations of 1:30, 1:100 and 1:200, respectively.

Figure 39A:
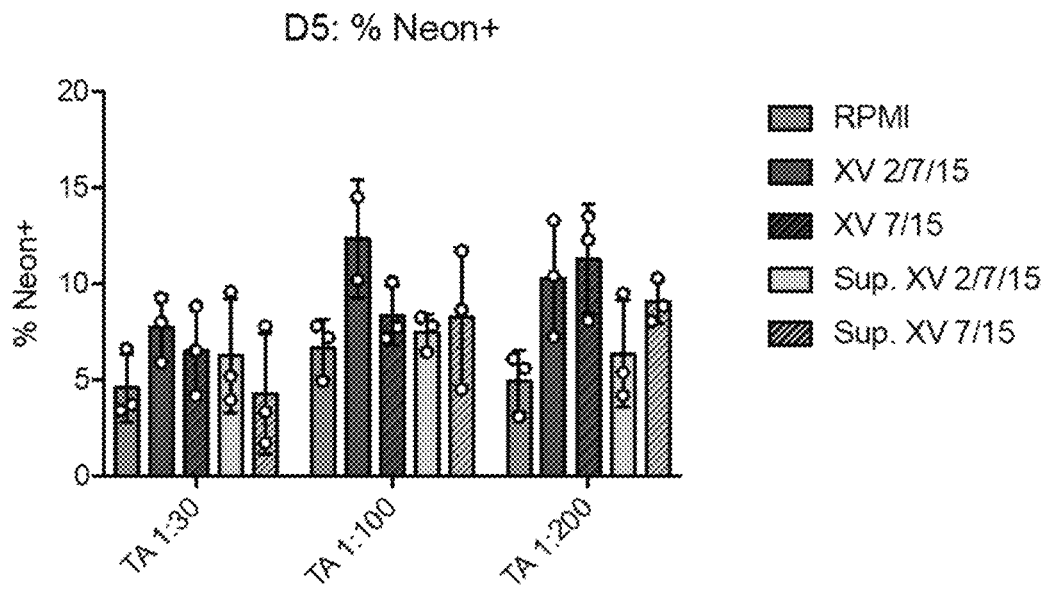
Figure 39B:
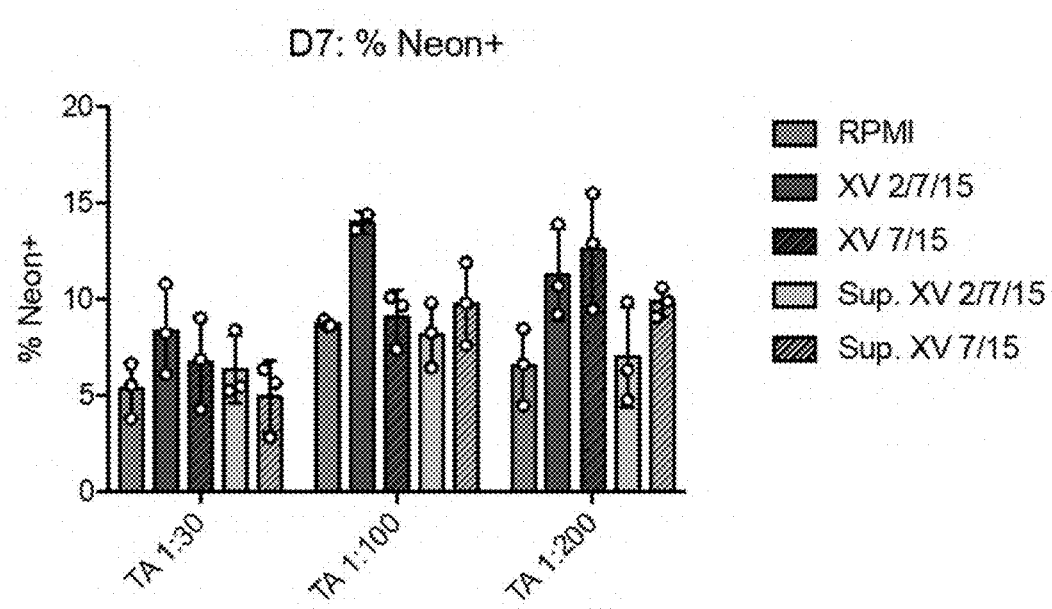

FIGS. 39A and 39B illustrate the effect of media and supplements on mNeon knock-in following T cell activation and electroporation. FIG. 39A is a bar graph showing frequency of knock-in positive mNeon+TCRab+ cells on Day 5 after initial T cell activation and FIG. 39B is a bar graph showing frequency of knock-in positive mNeon+TCRab+ cells on Day 7 after initial T cell activation. Cells were cultured and activated in conditions as indicated for FIG. 38.

Figure 40A:
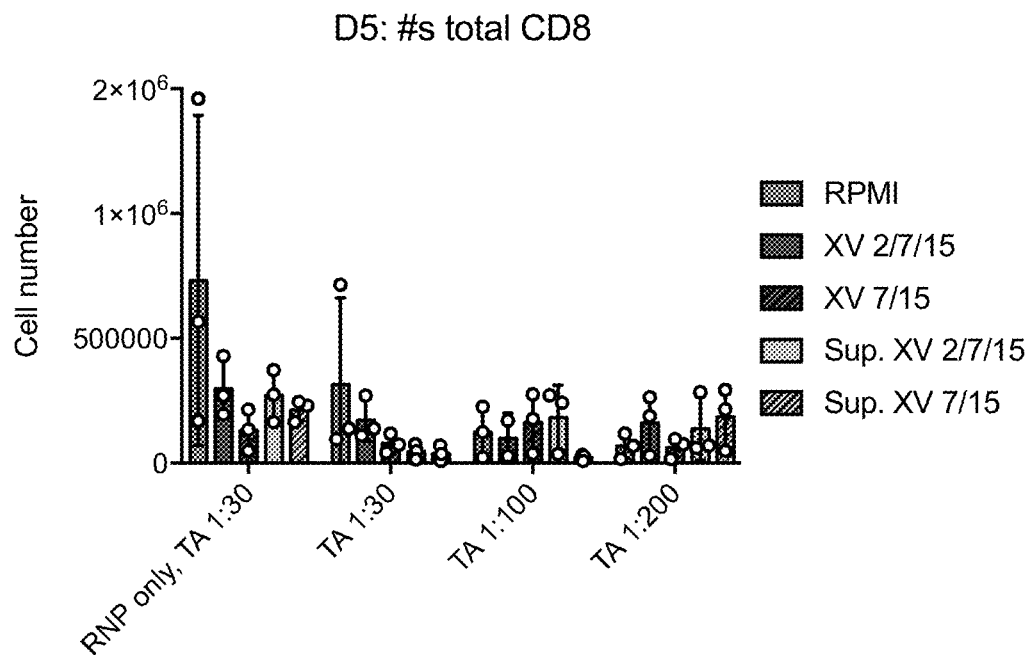
Figure 40B:
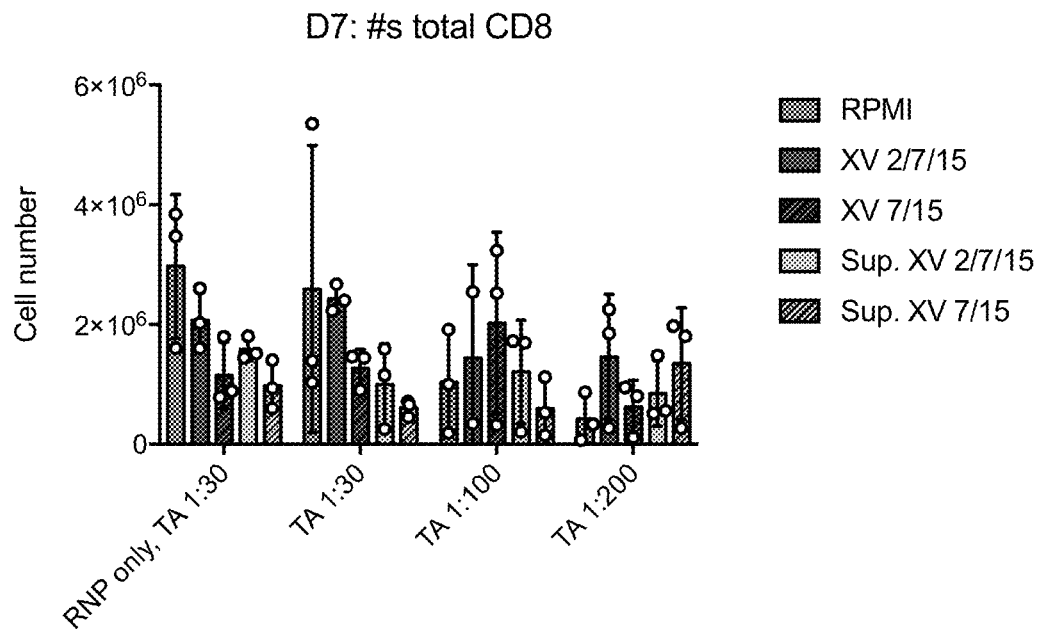

FIGS. 40A and 40B illustrate the effect of activation media and supplements on recovery of CD8+ T cells following electroporation. FIG. 40A is a bar graph showing cell recovery on Day 5 after initial T cell activation and FIG. 40B is a bar graph showing cell recovery on Day 7 after initial T cell activation. Cells were cultured and activated in conditions as indicated for FIG. 38.

Figure 41:
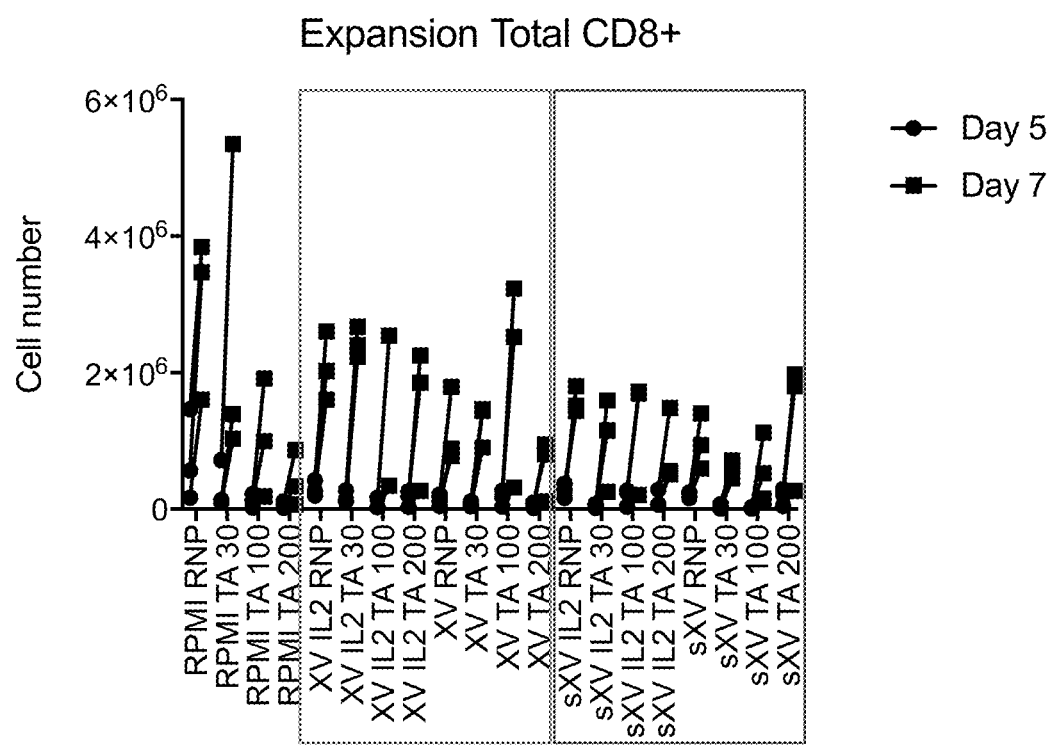

FIG. 41 is a graph showing total CD8+ cells expansion between days 5 and 7 post T cell activation. Cells were cultured and activated in conditions as indicated for FIG. 40.

Figure 42:
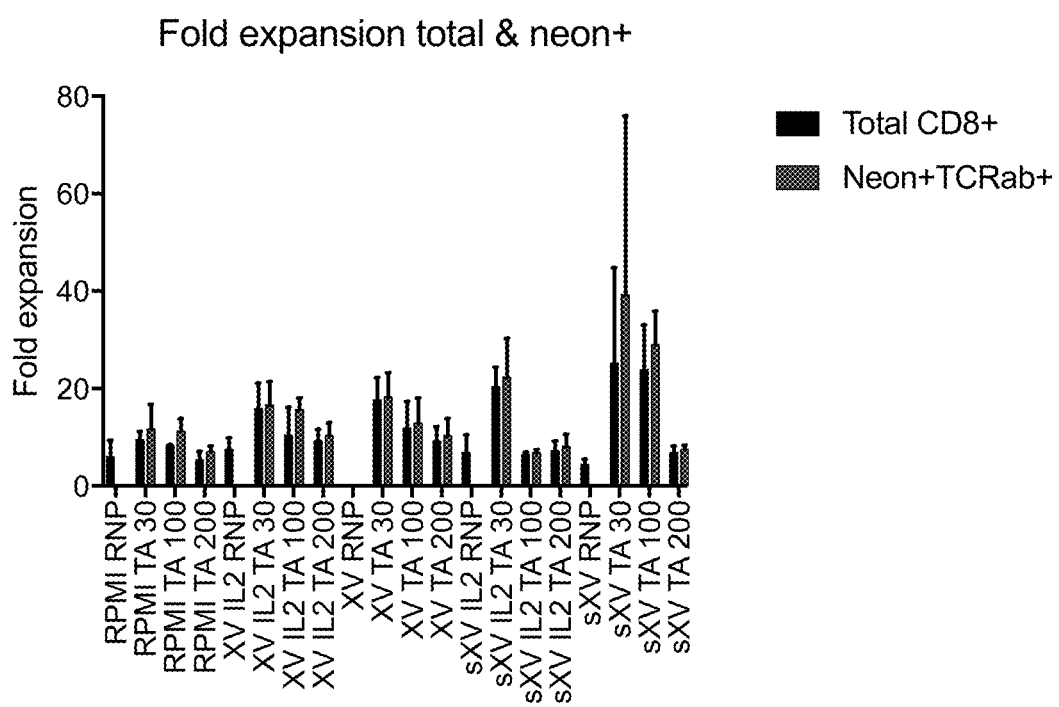

FIG. 42 is a bar graph illustrating fold-expansion of total CD8+ T cells (black bars) and knock-in positive Neon+TCRab+ cells (red bars) from the time of electroporation to day five post-electroporation. Cells were cultured and activated in conditions as indicated for FIG. 40.

Figure 43:
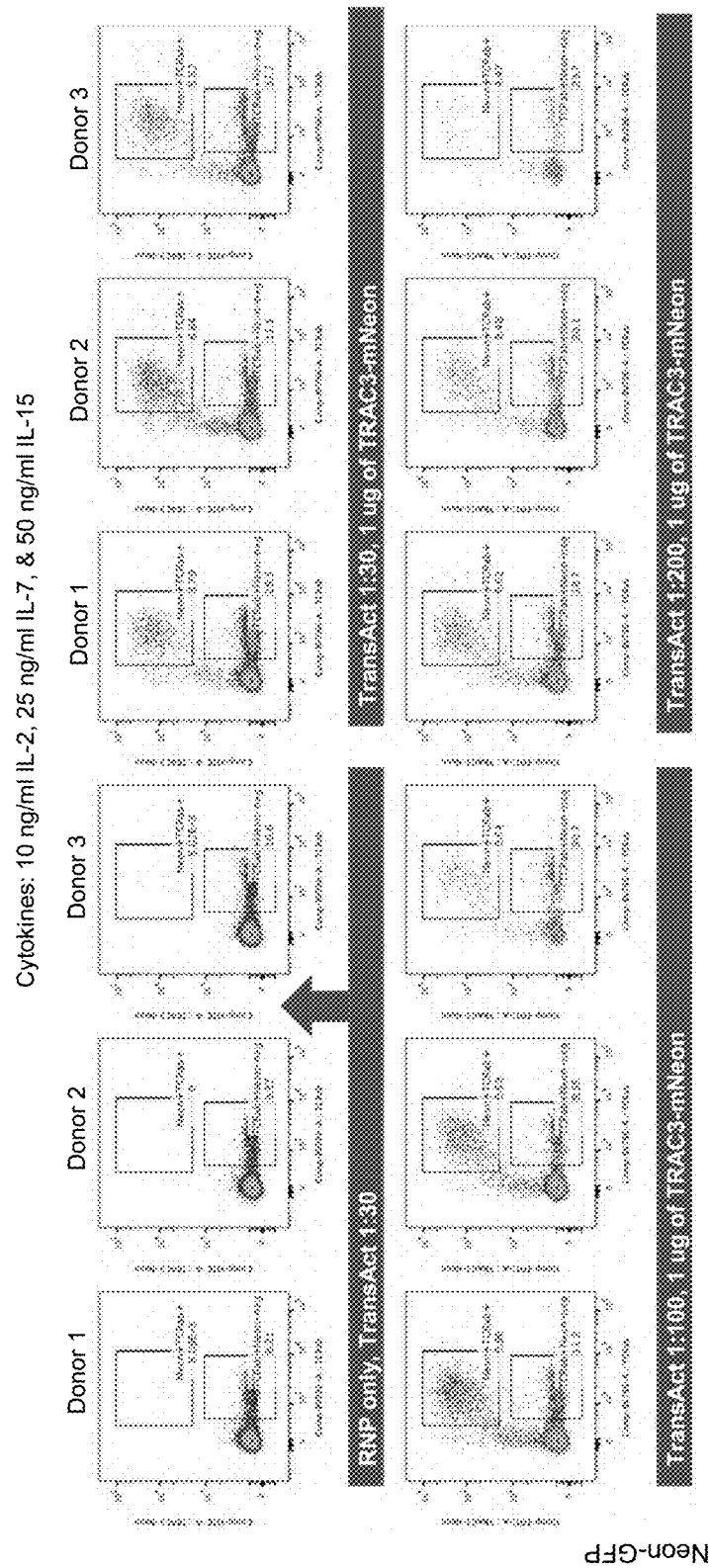

FIG. 43 shows flow-cytometry dot-plots illustrating the effect of TRANSACT™ titrations in RPMI media on mNeon knock-in efficiency. Media included IL-2, IL-7 and IL-15 cytokines.

Figure 44:
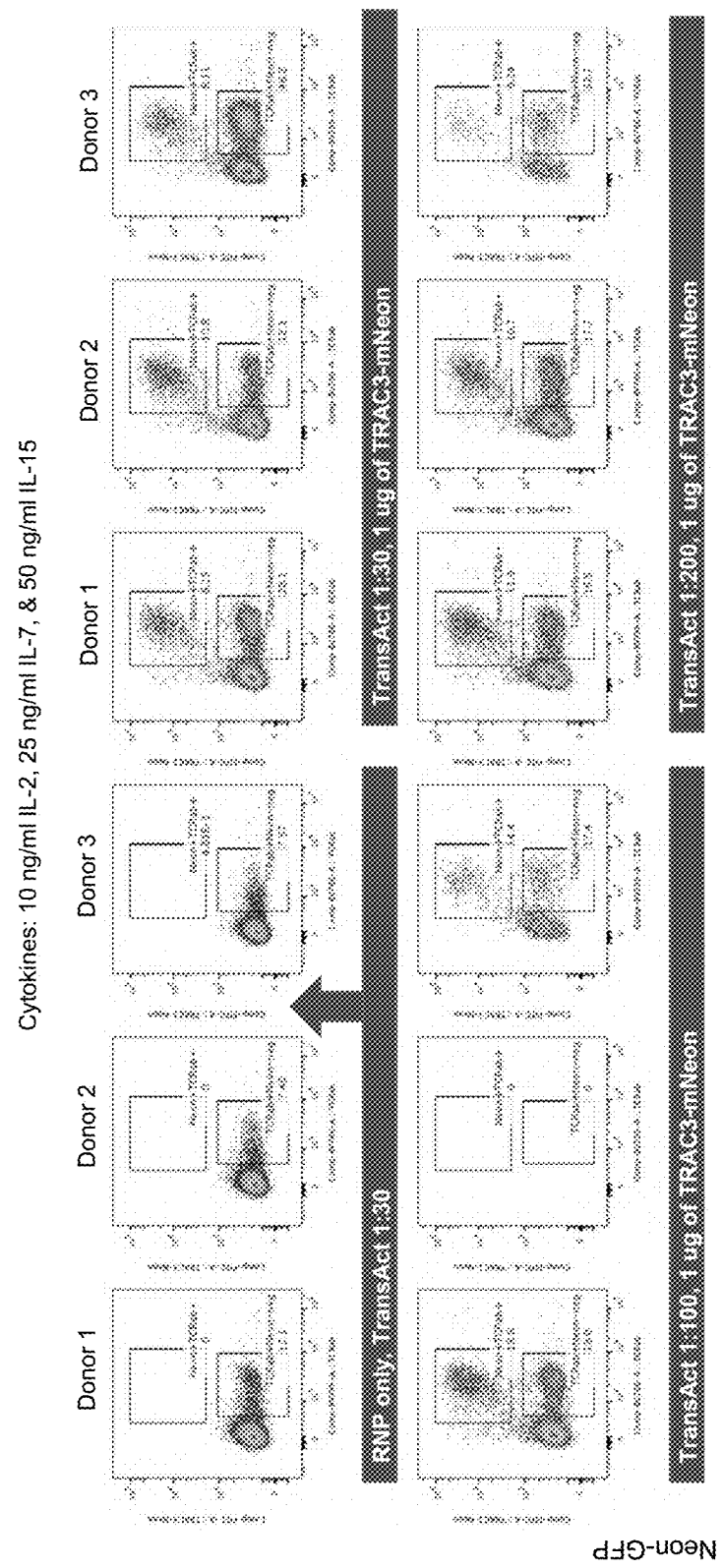

FIG. 44 shows flow-cytometry dot-plots illustrating the effect of TRANSACT™ titrations in X-VIVO™ media on mNeon knock-in efficiency for the representative TRAC locus donor DNA. Media included IL-2, IL-7 and IL-15 cytokines.

Figure 45:
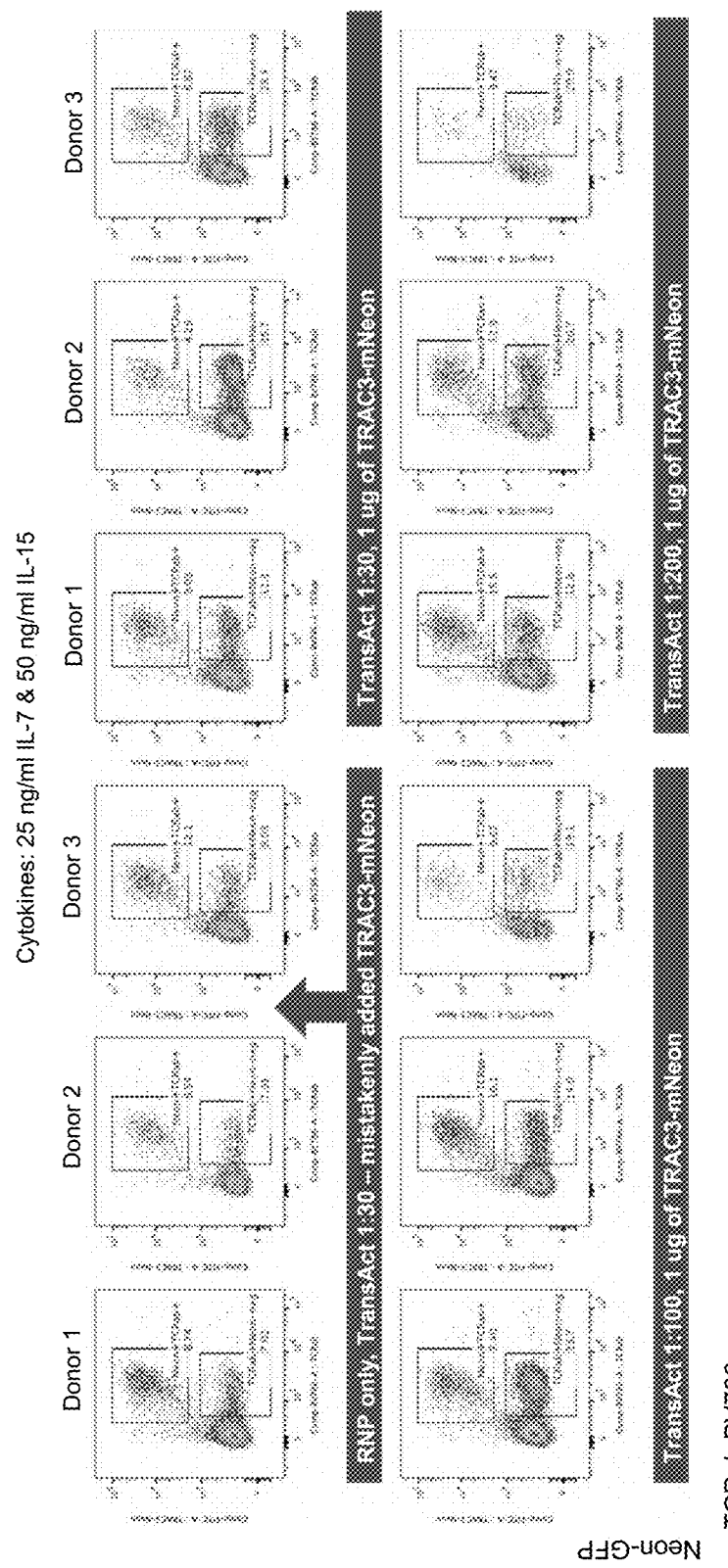

FIG. 45 shows flow-cytometry dot-plots illustrating the effect of TRANSACT™ titrations in X-VIVO™ media on mNeon knock-in efficiency. Media included IL-7 and IL-15 cytokines.

Figure 46:
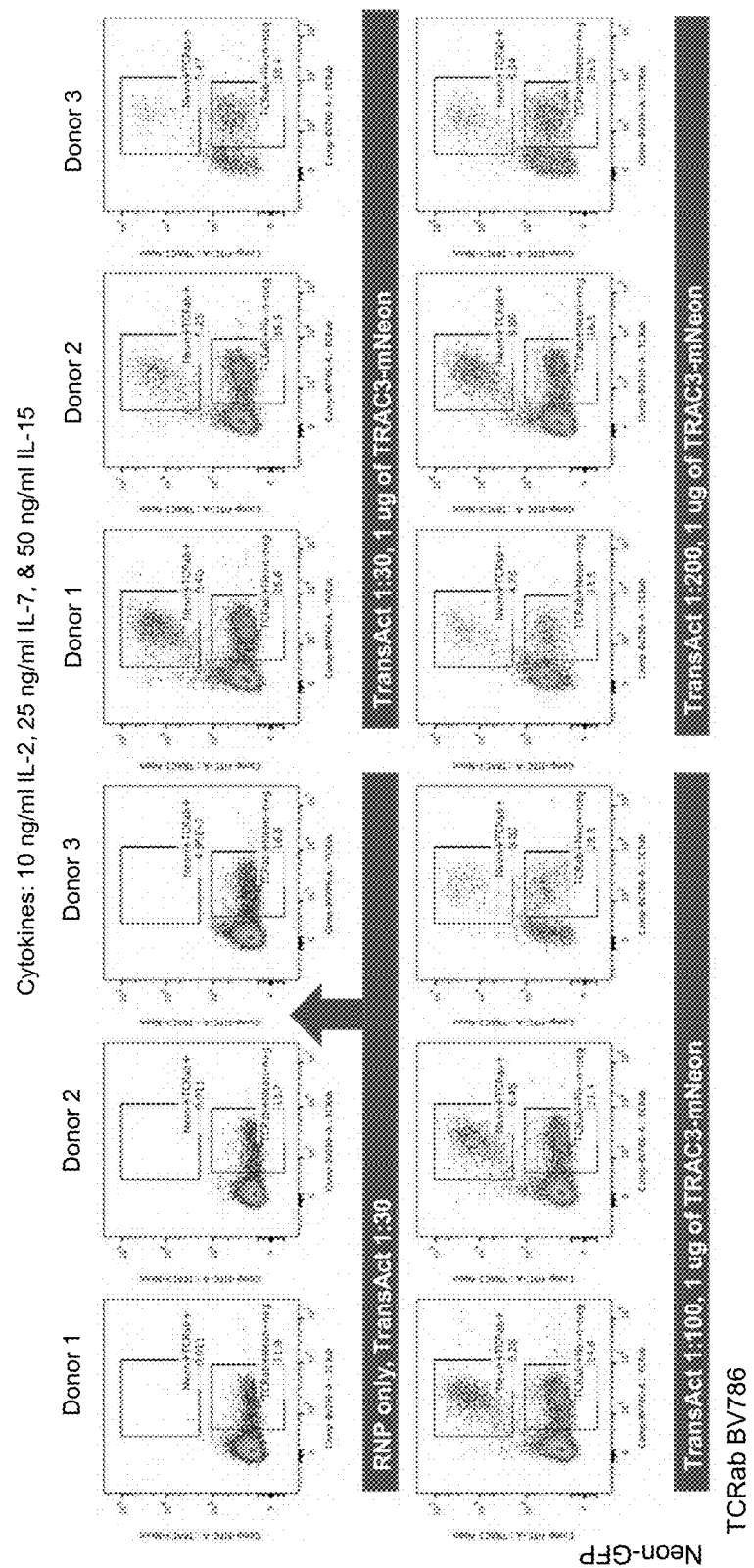

FIG. 46 shows flow-cytometry dot-plots illustrating the effect of TRANSACT™ addition in supplemented X-VIVO™ media on mNeon knock-in efficiency. Media included IL-2, IL-7 and IL-15 cytokines.

Figure 47:
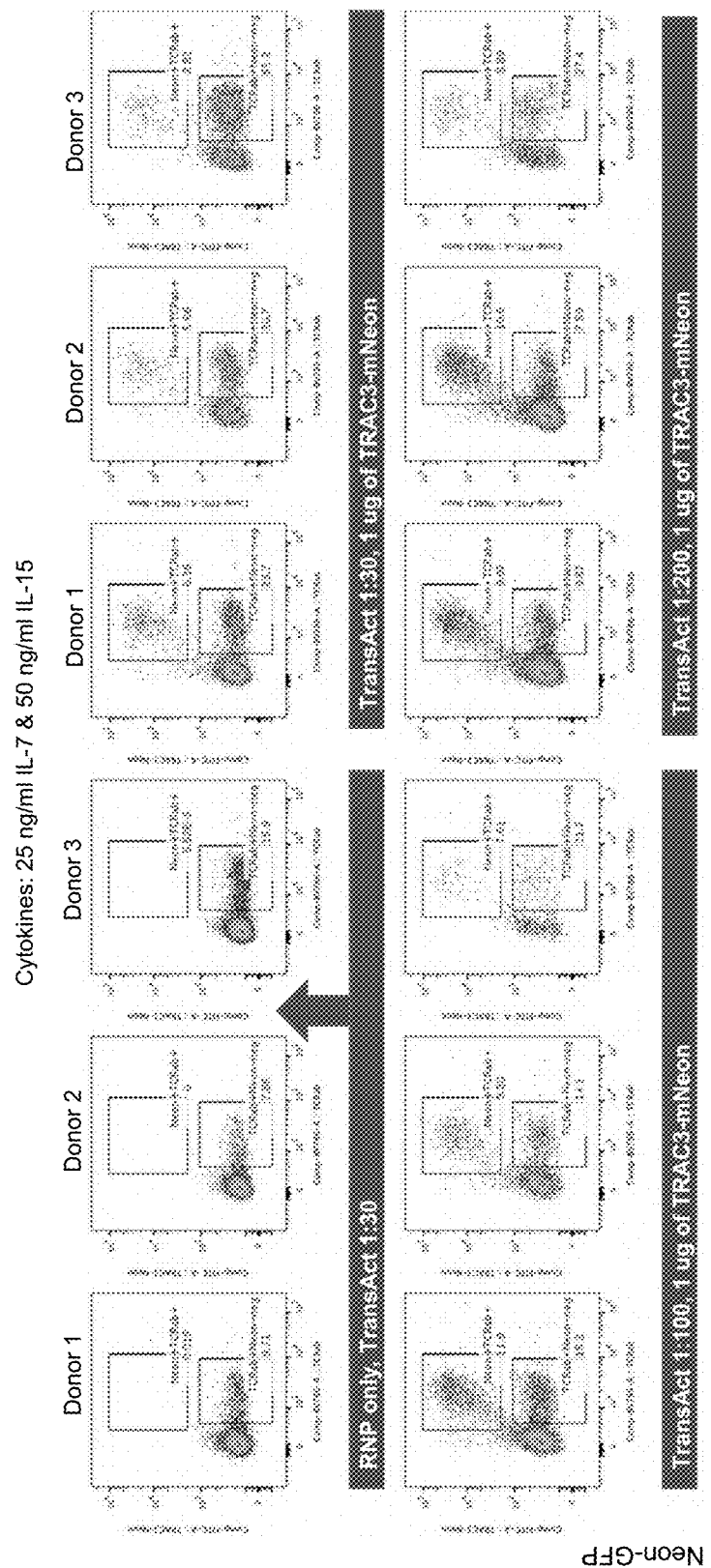

FIG. 47 show flow-cytometry analysis illustrating the effect of TRANSACT™ titrations in supplemented X-VIVO™ media on mNeon knock-in efficiency. Media included IL-7 and IL-15 cytokines.

Figure 48A:
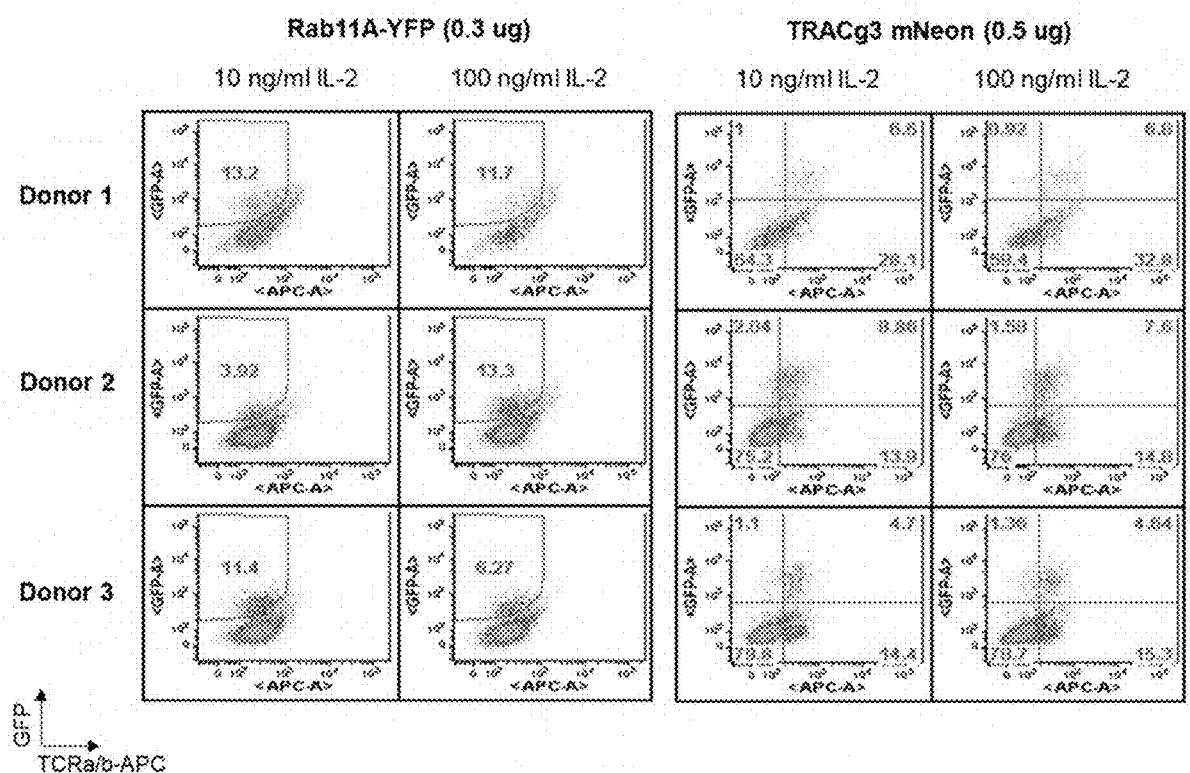
Figure 48B:
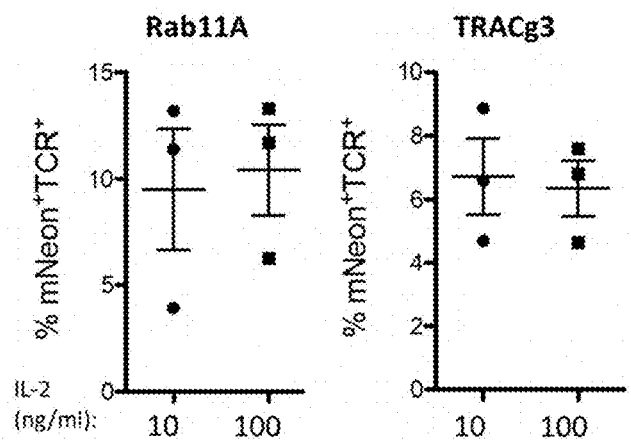

FIGS. 48A and 48B are flow-cytometry dot-plots illustrating the effect of IL-2 on knock-in efficiency in T cells (FIG. 48A) and frequency of knock-in positive mNeon+ TCR+ cells using the RAB11A-GFP (left) or TRAC3 (right) template (FIG. 48B).

Figure 49A:
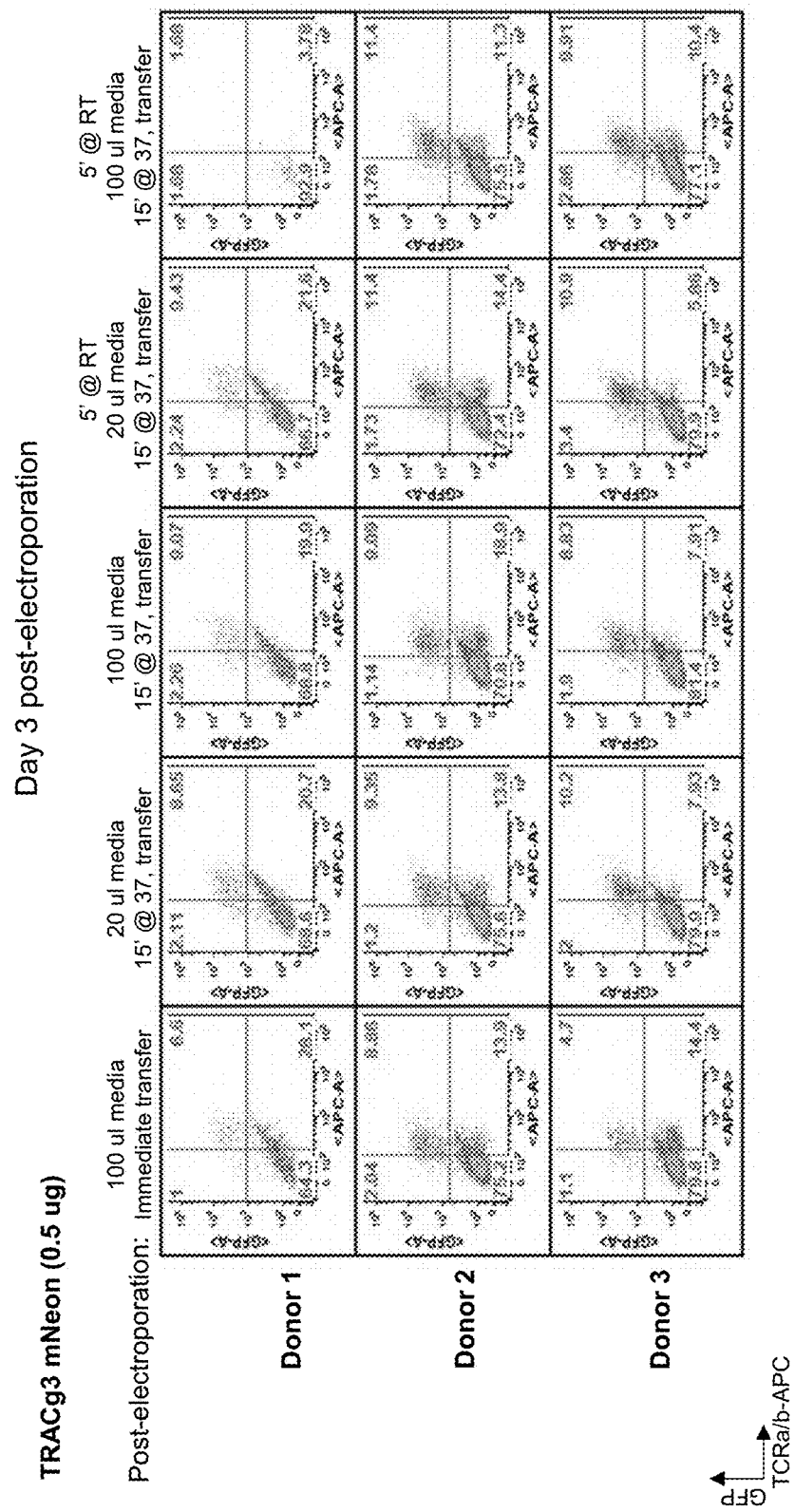
Figure 49B:
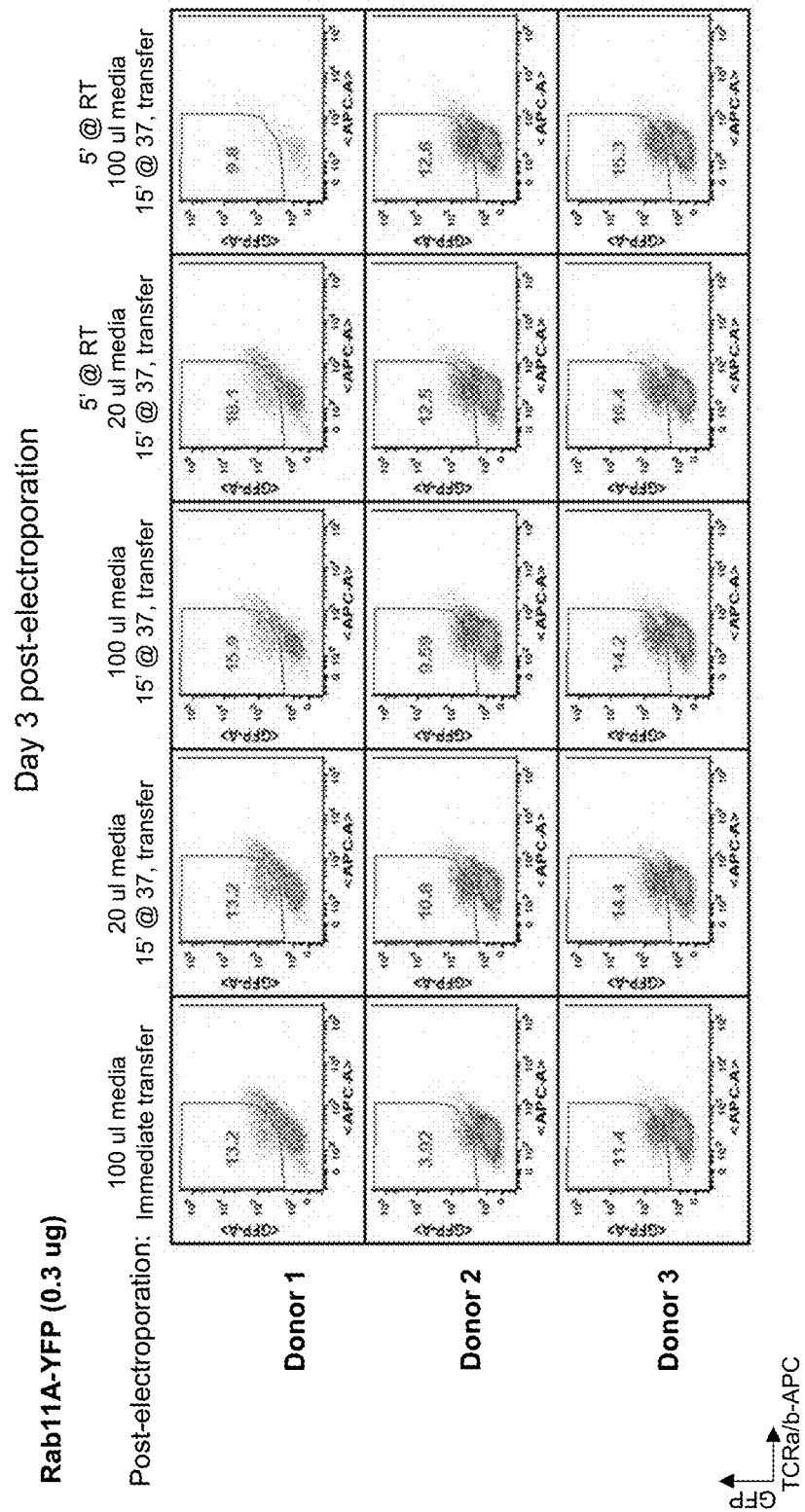

FIGS. 49A and 49B illustrate the effect of resting cells following electroporation on knock-in efficiency. FIG. 49A shows flow cytometry analysis three days after electroporation of cells electroporated with the mNeon-TRAC3 template; FIG. 49B shows flow cytometry analysis three days after electroporation of cells electroporated with the Rab11A-YFP template. Cells were subject to (from left to right) the following conditions following electroporation: addition of 100 µL buffer and transferred immediately; addition of 20 µL buffer and incubated for 15 minutes at 37° C.; addition of 100 µL buffer and incubated for 15 minutes at 37° C.; incubated for 5 minutes, followed by the addition of 20 µL of media, followed by a 15 minute incubation at 37° C.; or incubated for 5 minutes, followed by addition of 100 µL media, followed by a 15 minute incubation at 37° C.

Figure 50:
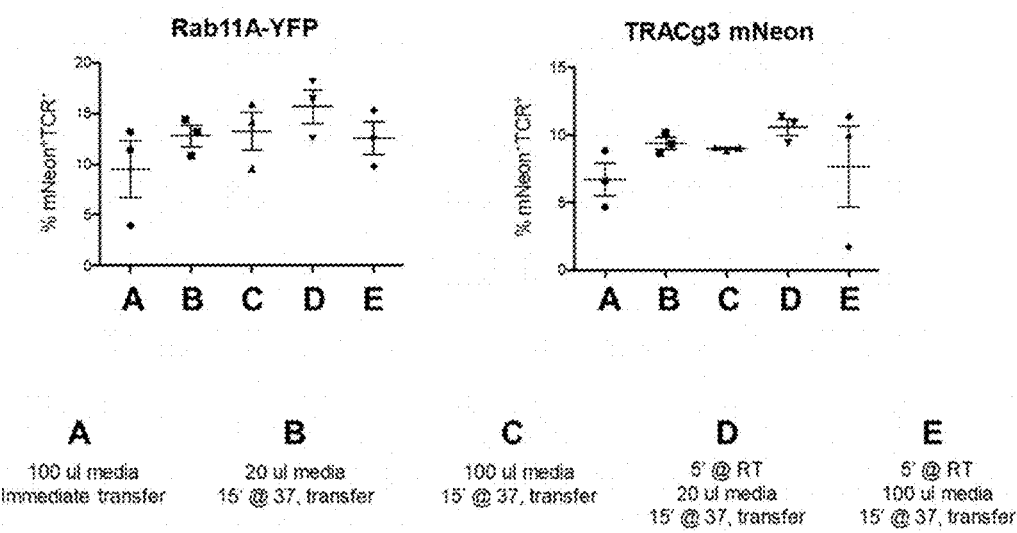

FIG. 50 are graphs illustrating frequency of knock-in positive mNeon+TCR+ cells under each condition tested in FIGS. 49A and 49B.

Figure 51A:
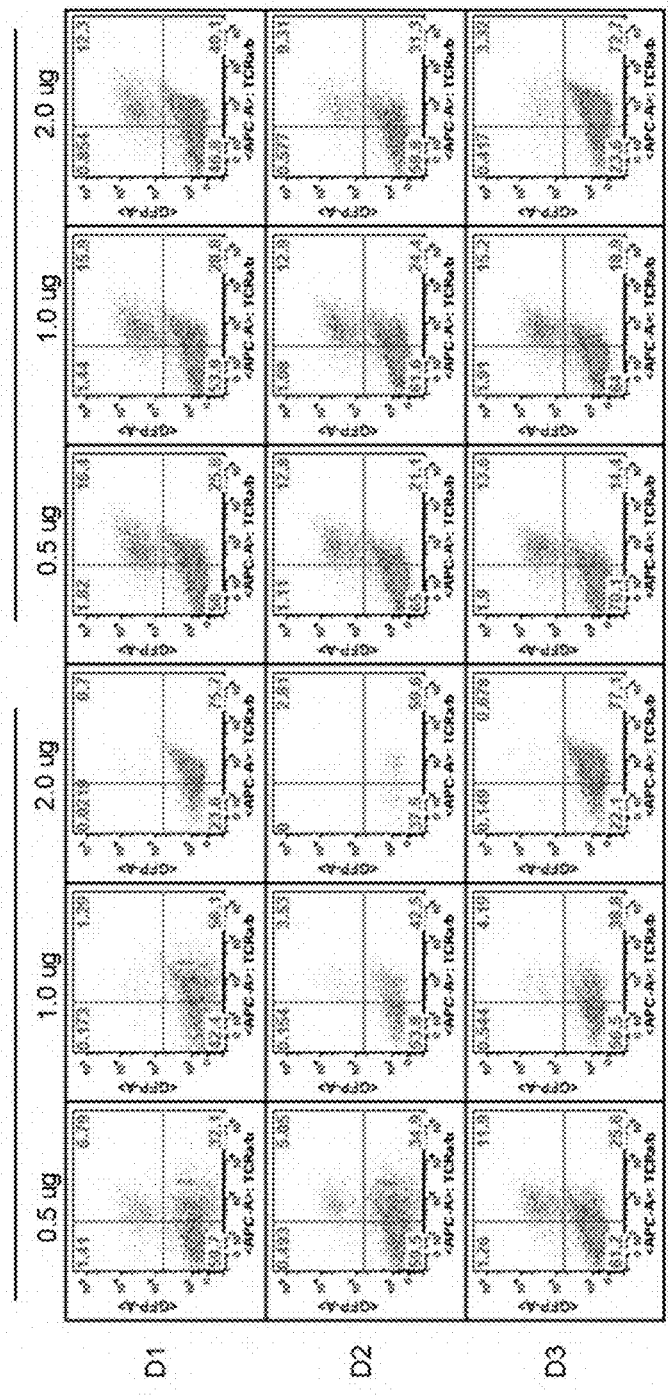
Figure 51B:
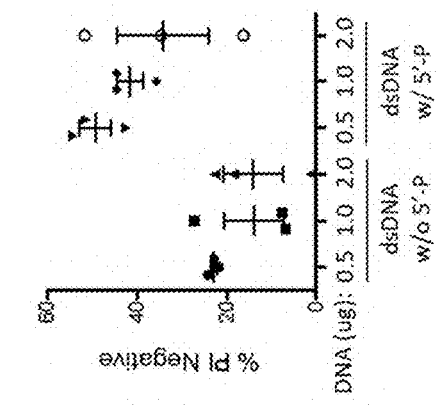
Figure 51C:
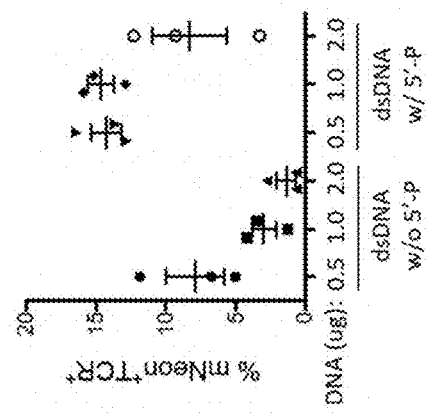

FIGS. 51A-51C illustrate knock-in efficiency depending on various amounts of either unmodified dsDNA template or 5'-phosphate modified dsDNA PCR template used for electroporation. FIG. 51A is flow-cytometry dot-plots showing detection of knock-in positive mNeon+TCRab+ cells, FIG. 51B is a graph showing frequency of mNeon+TCRab+ cells and FIG. 51C is a graph showing cell viability by analysis of PI negative cells following electroporation with the dsDNA template with (w/5'-P) or without (w/o 5'-P) 5'-phosphate.

Figure 52A:
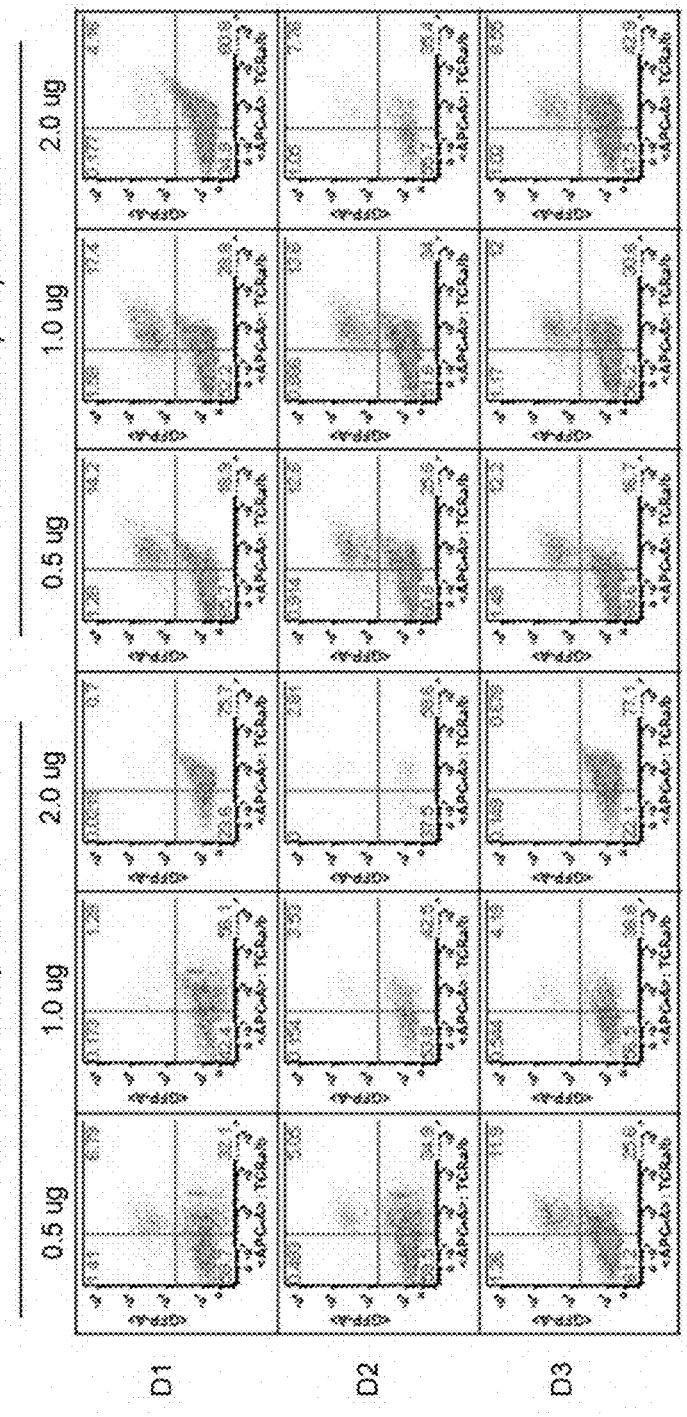
Figure 52B:
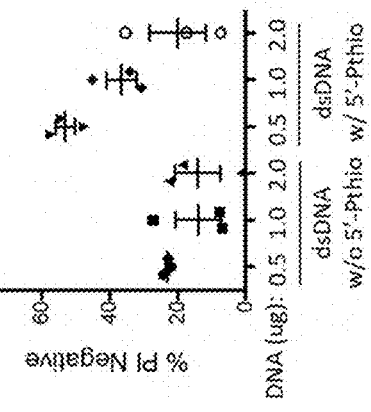
Figure 52C:
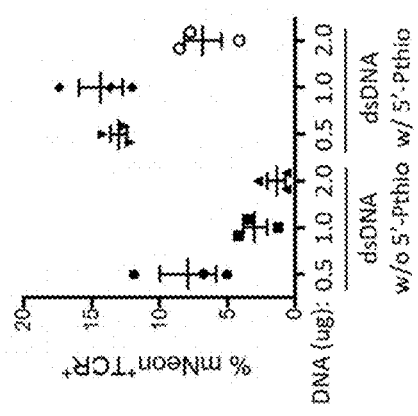

FIGS. 52A-52C illustrate knock-in efficiency using various amounts of either unmodified dsDNA template or 5'-phosphorthioate modified dsDNA template for electroporation. FIG. 52A is flow-cytometry analysis showing detection of knock-in positive mNeon+TCRab+ cells, FIG. 52B is a graph showing frequency of mNeon+TCRab+ cells and FIG. 52C is a graph showing cell viability by analysis of PI negative cells following electroporation with the dsDNA template with (w/5'-Pthio) or without (w/o 5'-Pthio) 5'-phosphorothioate.

Figure 53A:
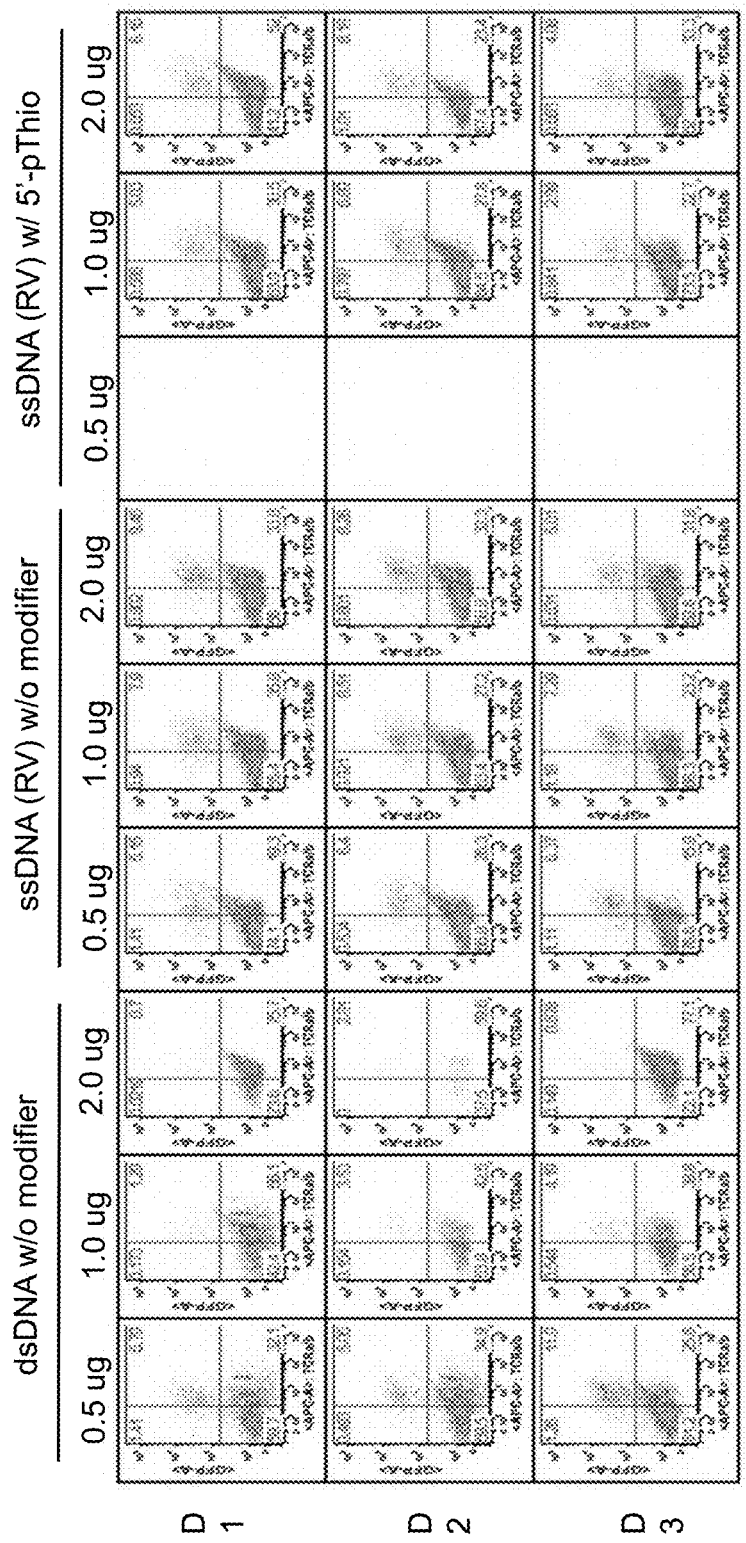
Figure 53B:
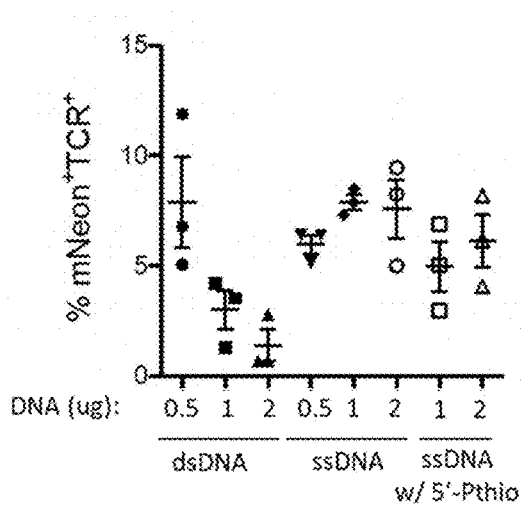
Figure 53C:
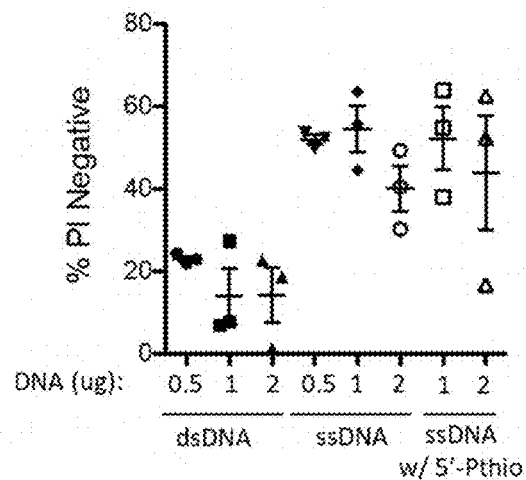

FIGS. 53A-53C illustrate knock-in efficiency using various amounts of unmodified reverse strand (RV) ssDNA template or 5'-phosphorthioate modified reverse strand (RV) ssDNA template, compared to unmodified ds DNA template for electroporation. FIG. 53A is flow-cytometry analysis showing detection of knock-in positive mNeon+TCRab+ cells, FIG. 53B is a graph showing frequency of mNeon+TCRab+ cells and FIG. 53C is a graph showing cell viability by analysis of PI negative cells following electroporation with the ssDNA template with (w/5'-Pthio) or without (w/o 5'-Pthio) 5'-phosphorothioate.

Figure 54:
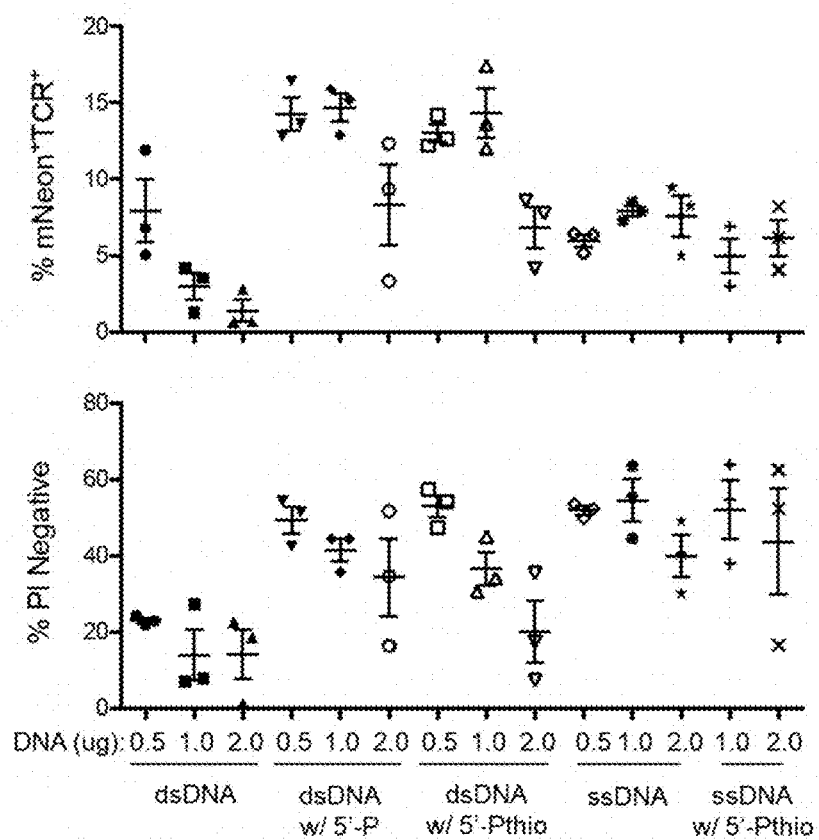

FIG. 54 are graphs comparing frequency of knock-in positive mNeon+TCRab+ (top) and viable cells (bottom) using varying amounts of dsDNA template, 5'-phosphate modified dsDNA template (w/5'-P), 5'-phosphorothioate modified dsDNA template (w/5'-Pthio), ssDNA template, or 5'-phosphorothioate modified ssDNA template (w/5'-Pthio) for electroporation.

Figure 55:
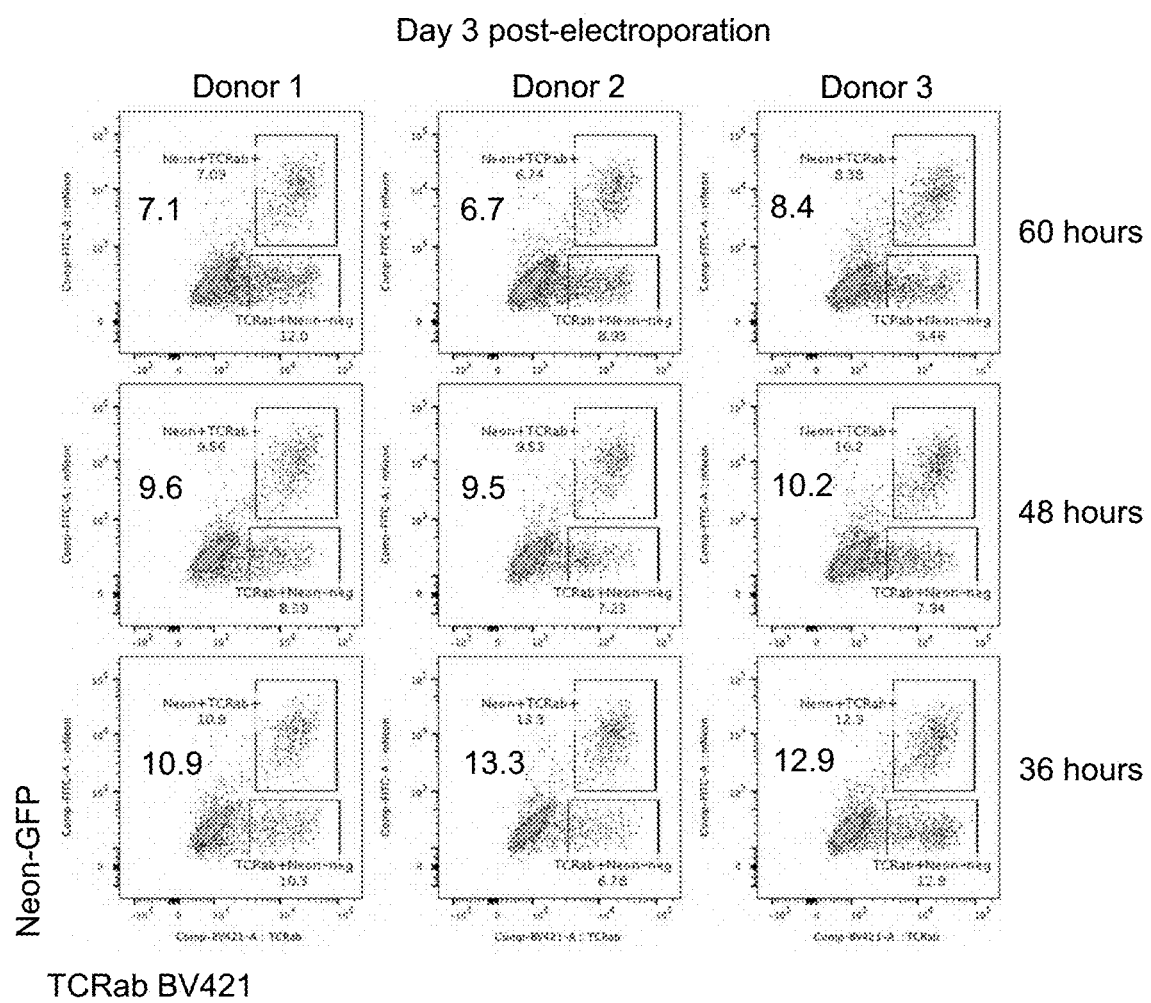

FIG. 55 is flow-cytometry analysis illustrating the effect of electroporation time points on template knock-in efficiency. Electroporation was conducted at either 60 (top row), 48 (middle row) or 36 (bottom row) hours following activation.

Figure 56:
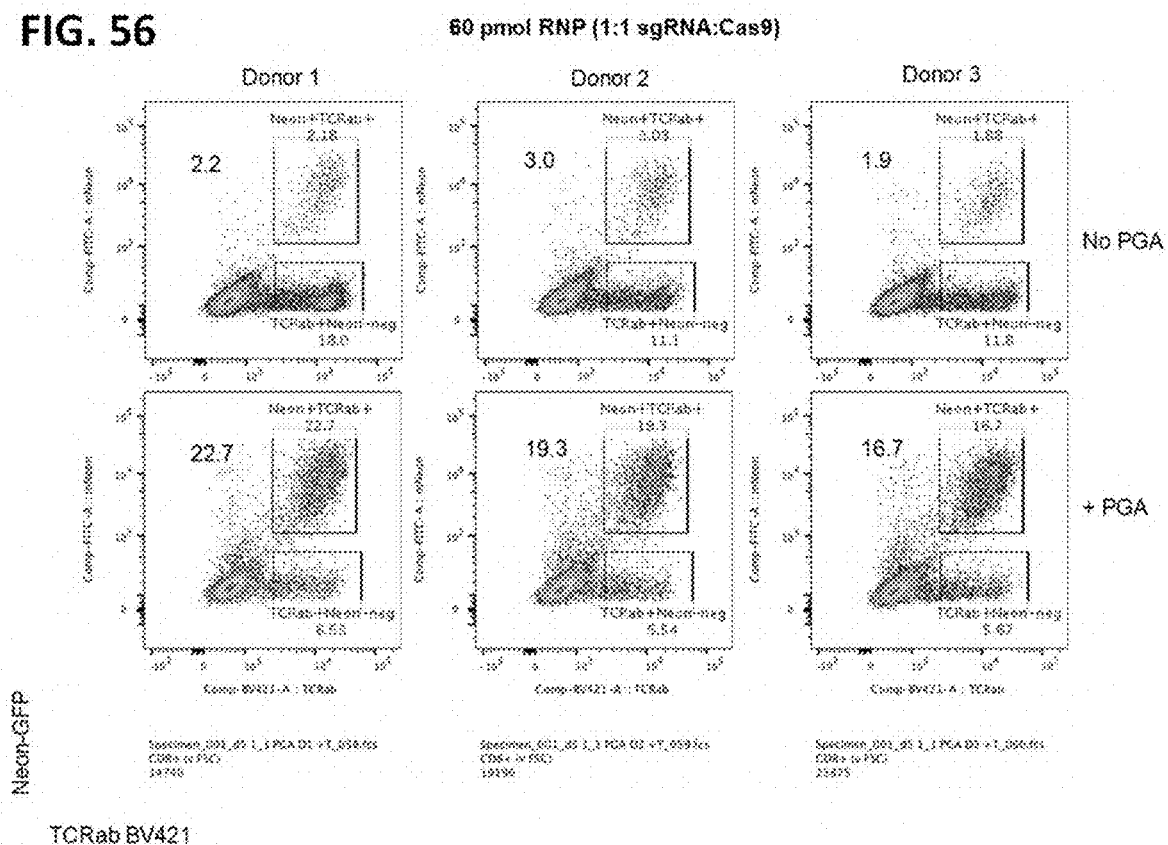

FIG. 56 is flow cytometry analysis illustrating the effect of PGA on knock-in efficiency by detection of knock-in positive mNeon+TCRab+ cells. Cells were electroporated with template DNA and 60 pmol RNP (1:1 sgRNA: Cas9), either in the presence (bottom row) or absence (top row) of PGA.

Figure 57:
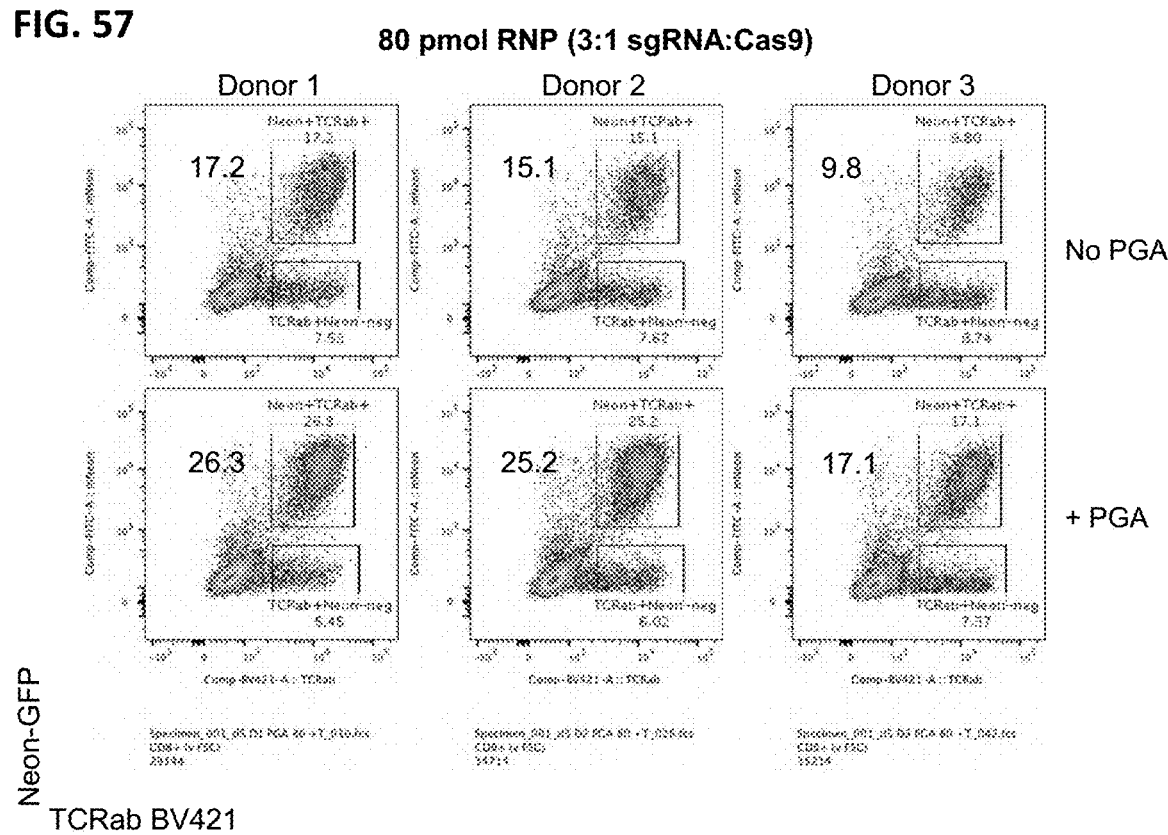

FIG. 57 is a flow-cytometry analysis showing the effect of PGA on knock-in efficiency by detection of knock-in positive mNeon+TCRab+ cells. Cells were electroporated with template DNA and 80 pmol RNP at 3:1 sgRNA: Cas9, either in the presence (bottom row) or absence (top row) of PGA.

Figure 58A:
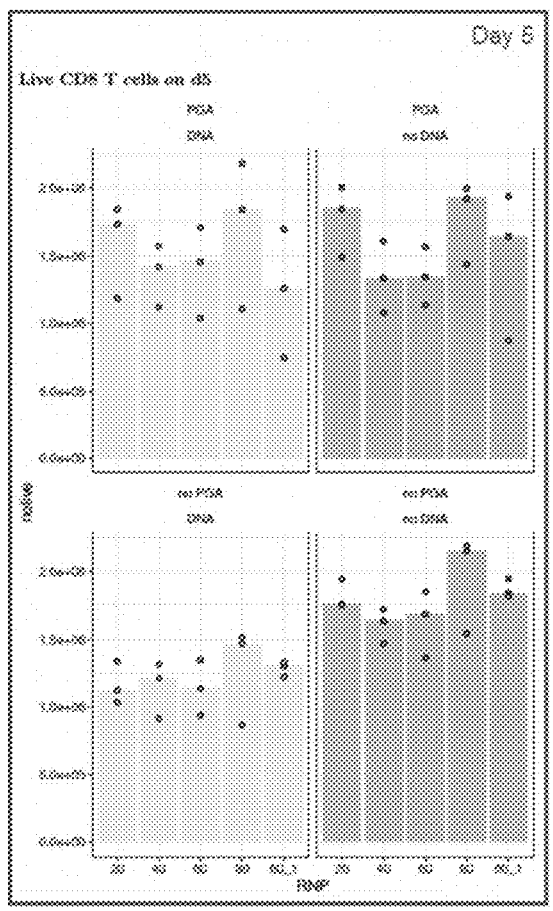
Figure 58B:
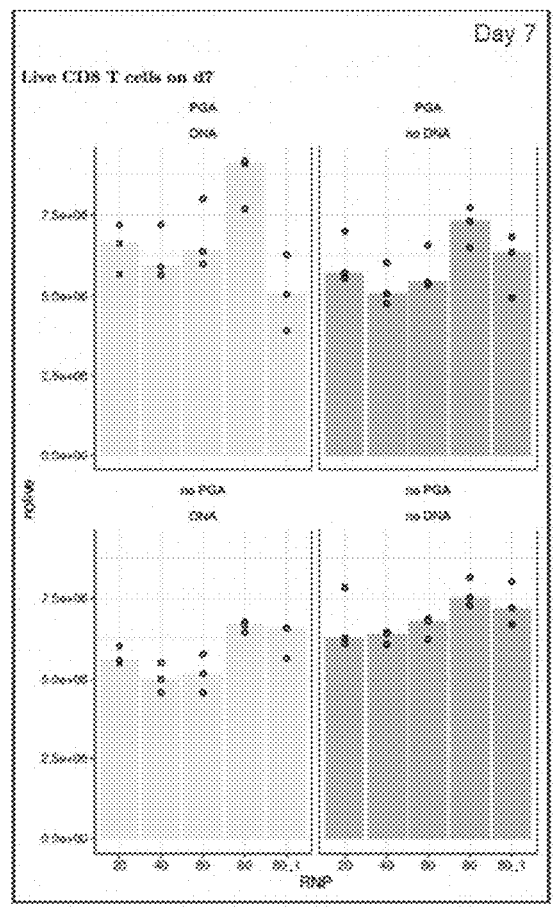

FIGS. 58A and 58B are bar graphs illustrating cell viability for CD8+ T cells electroporated in the presence or absence of PGA. Cell viability was assessed 3 days (FIG. 58A) and 5 days (FIG. 58B) post-electroporation (on days 5 and 7 of the cell culture) for samples electroporated with and without template DNA (control), and with or without PGA. Amounts of RNP (in pmol) used for electroporation are as indicated on the x-axis.

Figure 59A:
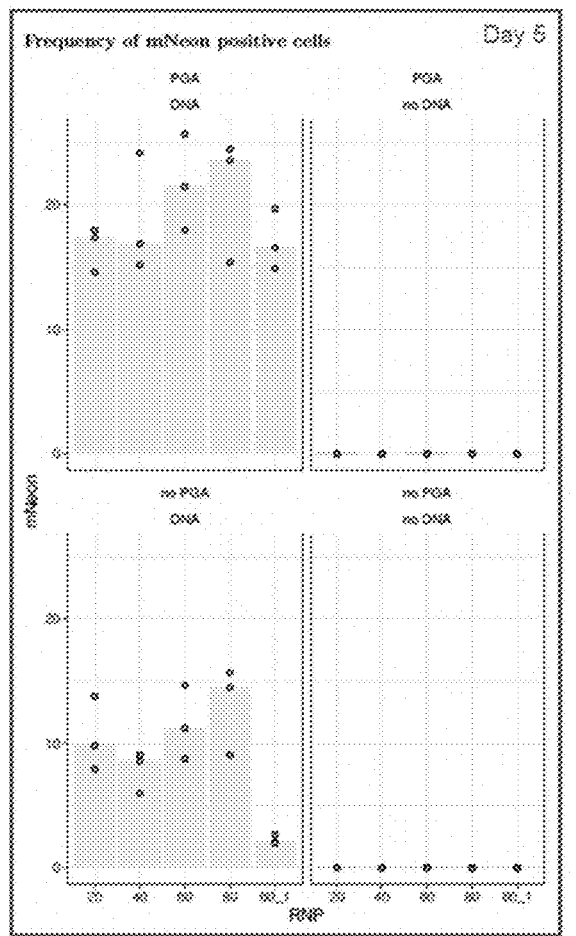
Figure 59B:
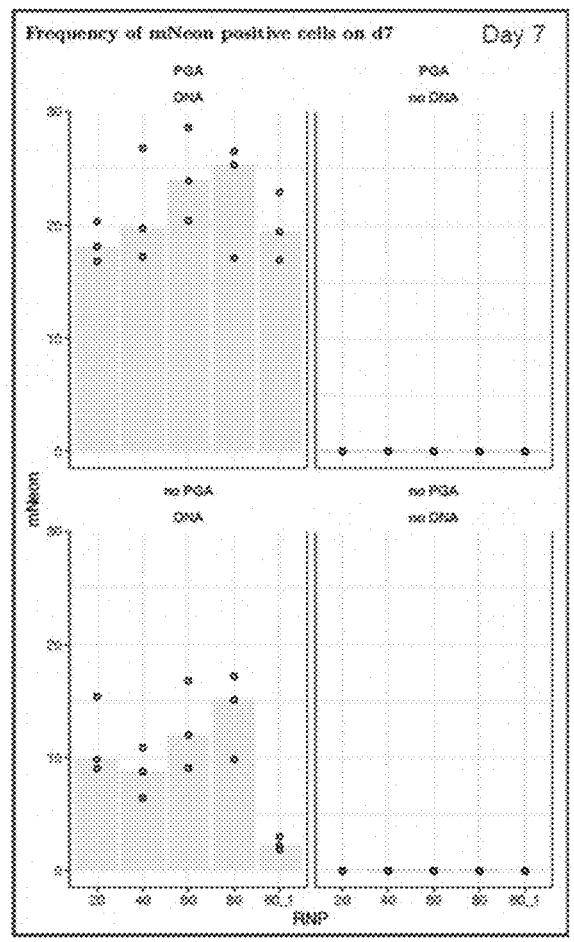

FIGS. 59A and 59B are bar graphs showing frequency of mNeon+ cells for T cells electroporated in the presence or absence of PGA. The frequency of knock-in positive cells was assessed 5 days (FIG. 59A) and 7 days (FIG. 59B) post-electroporation. Cells were electroporated with and without template DNA, and with or without PGA. Amounts of RNP (in pmol) used for electroporation are as indicated on the x-axis.

Figure 60A:
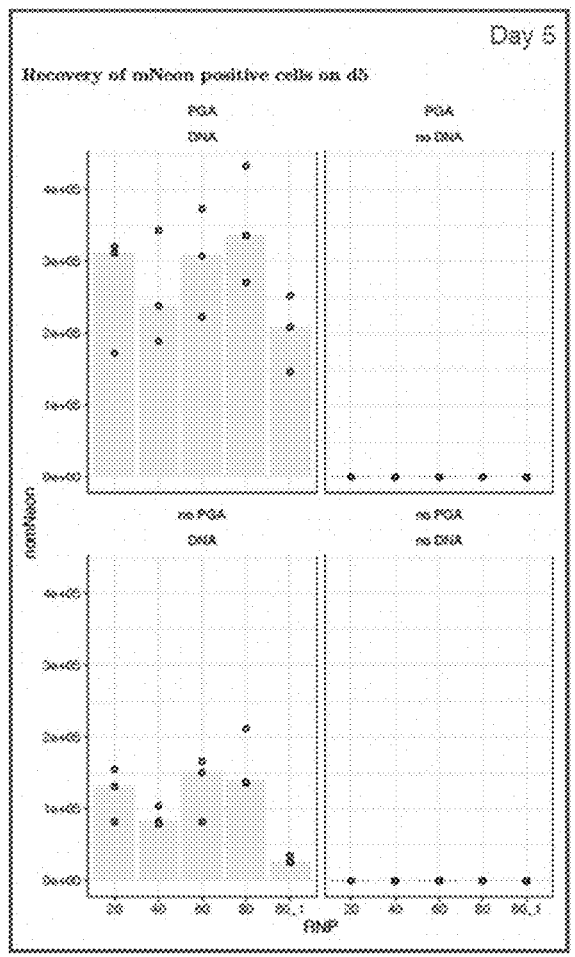
Figure 60B:
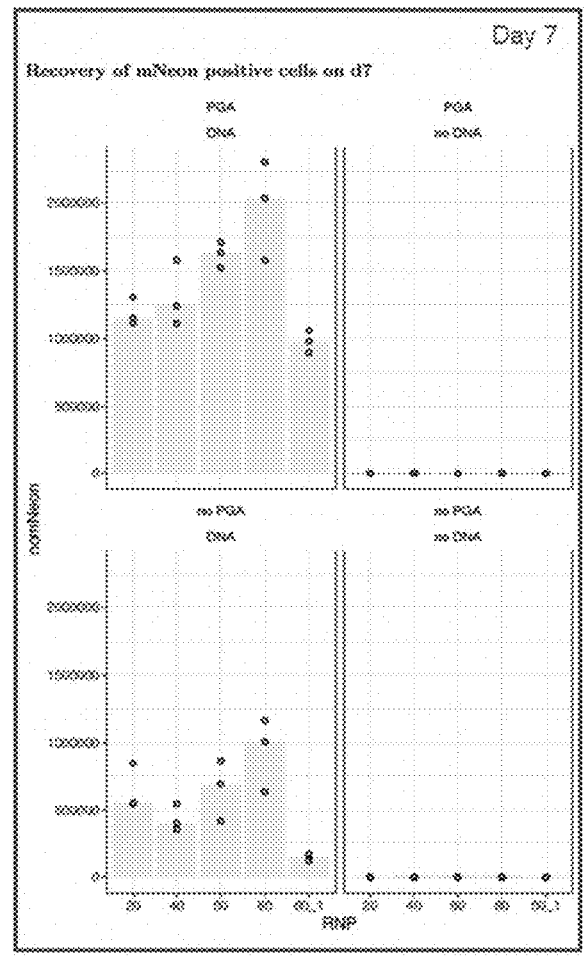

FIGS. 60A and 60B are bar graphs showing recovery of mNeon+ cells for T cells electroporated in the presence or absence of PGA. Cell recovery was assessed 5 days (FIG. 60A) and 7 days (FIG. 60B) post-electroporation. Cells were electroporated with and without template DNA, and with or without PGA. Amounts of RNP (in pmol) used for electroporation are as indicated on the x-axis.

Figure 61A:
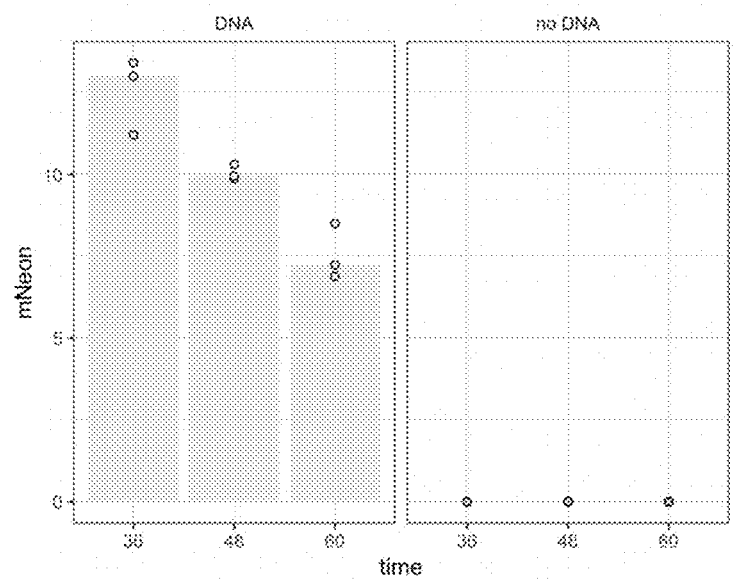
Figure 61B:
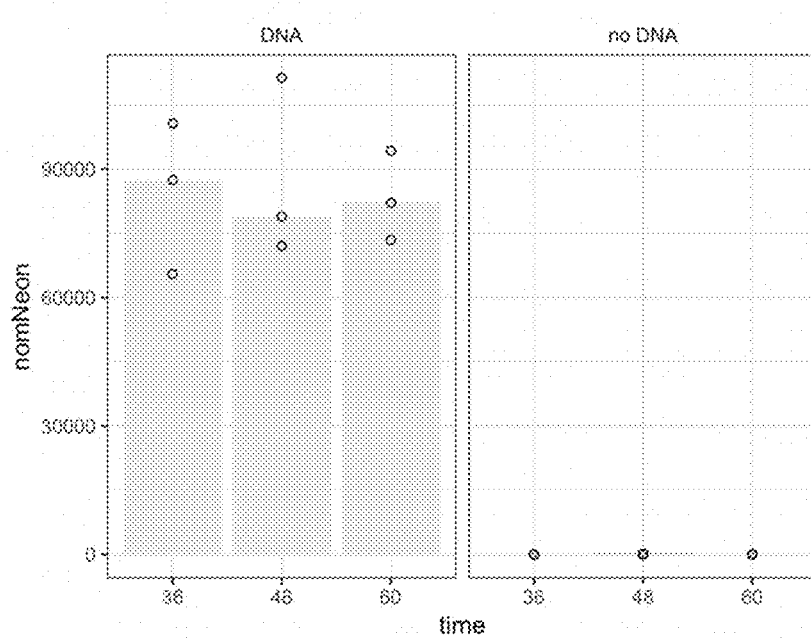

FIGS. 61A and 61B are bar graphs illustrating the effect of electroporation time on mNeon knock-in efficiency. Cells were electroporated at 36, 48, or 60 hours after T cell activation, with cells receiving no template during electroporation as controls. mNeon+ cell frequency (FIG. 61A) and recovery (FIG. 61B) were assessed 3 days post-electroporation.

Figure 62A:
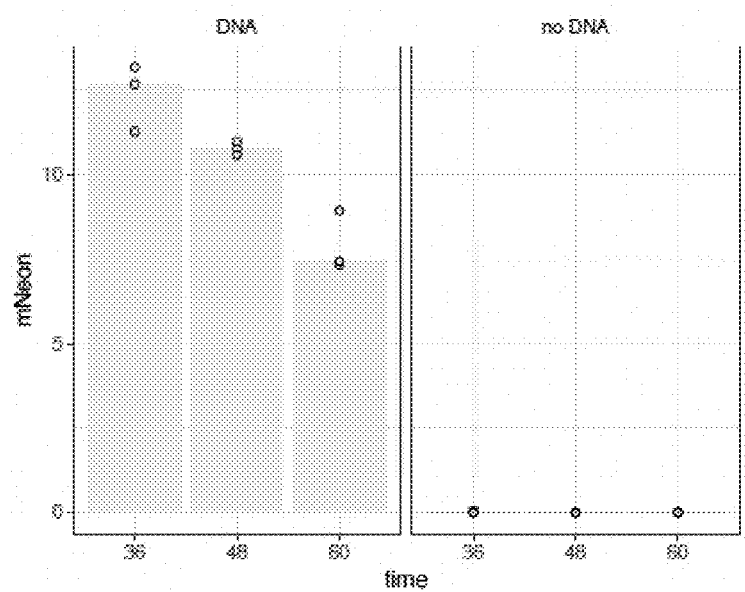
Figure 62B:
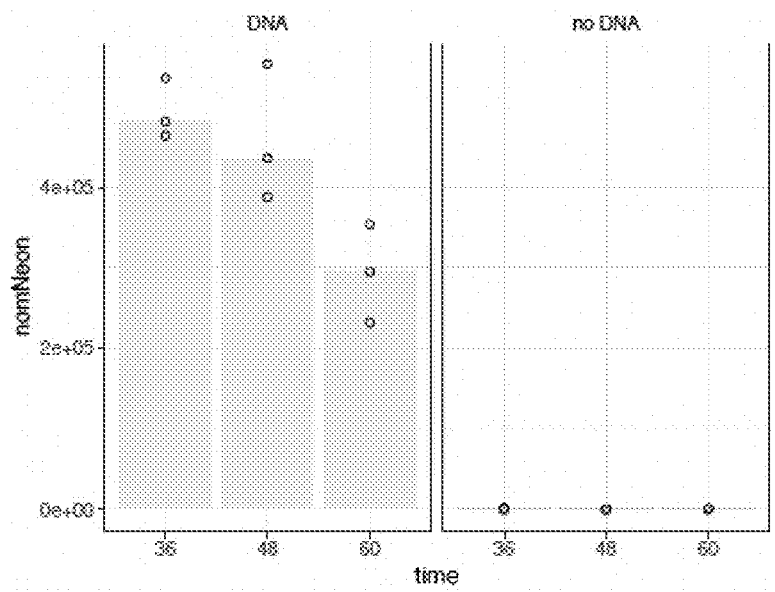

FIGS. 62A and 62B are bar graphs illustrating the effect of electroporation time on efficiency of mNeon knock-in to the TRAC locus. mNeon+ cell frequency (FIG. 62A) and recovery (FIG. 62B) were assessed 5 days post-electroporation. Cells were electroporated at 36, 48, or 60 hours after T cell activation with TransAct, with cells receiving no template during electroporation as controls.

Figure 63A:
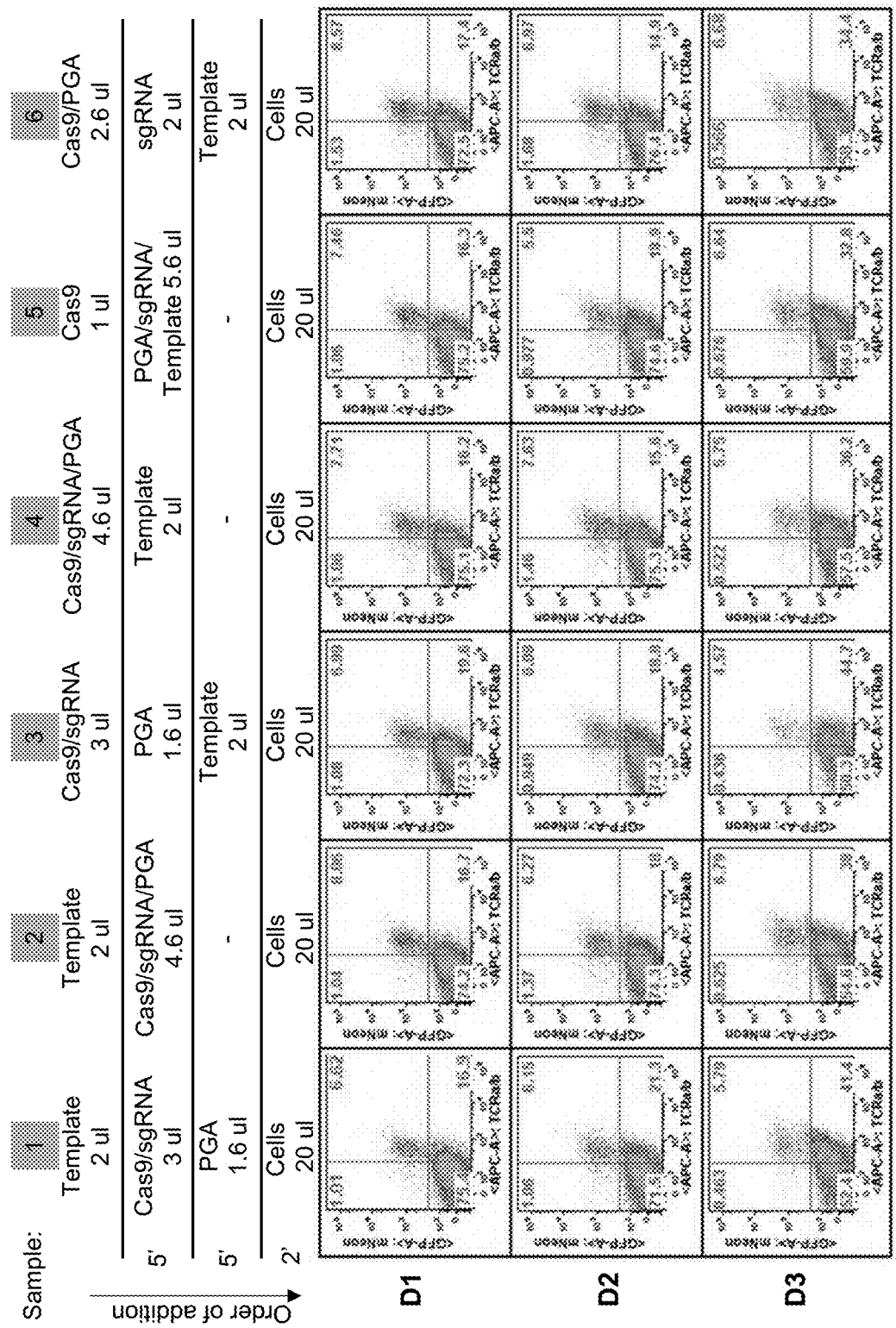
Figure 63B:
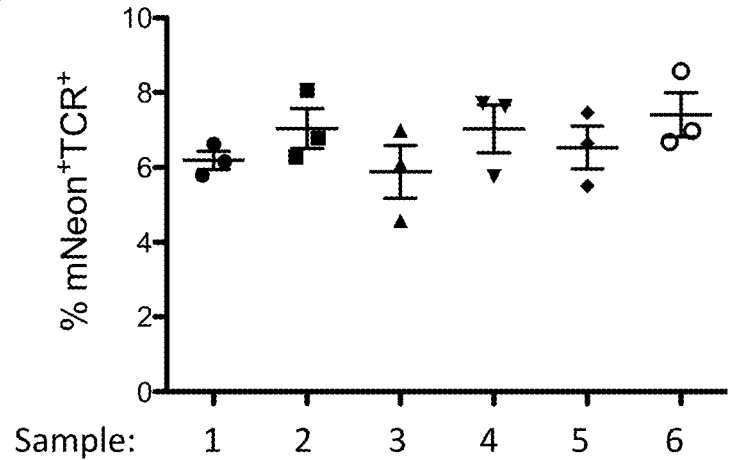
Figure 63C:
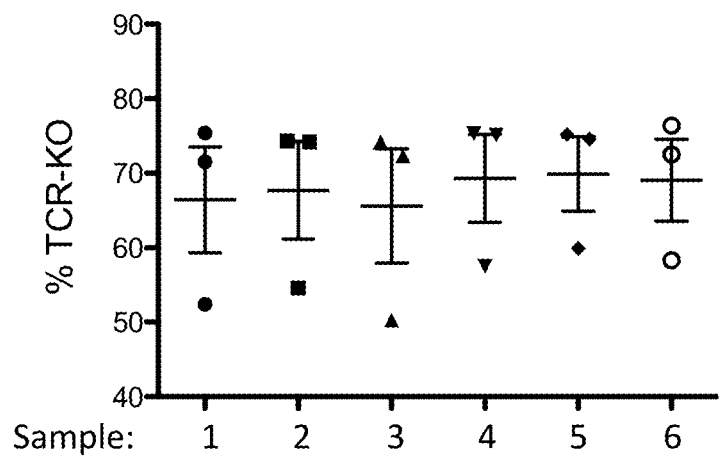
Figure 63D:
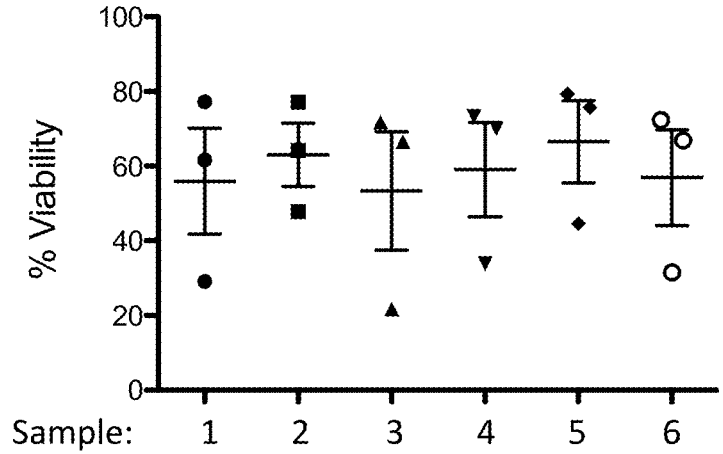

FIGS. 63A-63D show the effect of reagent order-of-addition on knock-in efficiency. FIG. 63A is flow cytometry analysis (bottom) of cells electroporated with varying order-of-addition of template, RNP and PGA to T cells, as indicated and numbered from 1 to 6 (top). Knock-in efficiency was assessed by detection of mNeon+TCRab+ cells. FIG. 63B is a graph showing frequency of mNeon+TCR+ cells, FIG. 63C is a graph showing frequency of TCR knock-out cells, and FIG. 63D is a graph showing frequency of viable cells for samples of cells undergoing electroporation with the varying order-of-additions as indicated on the x-axis of the graphs.

Figure 64A:
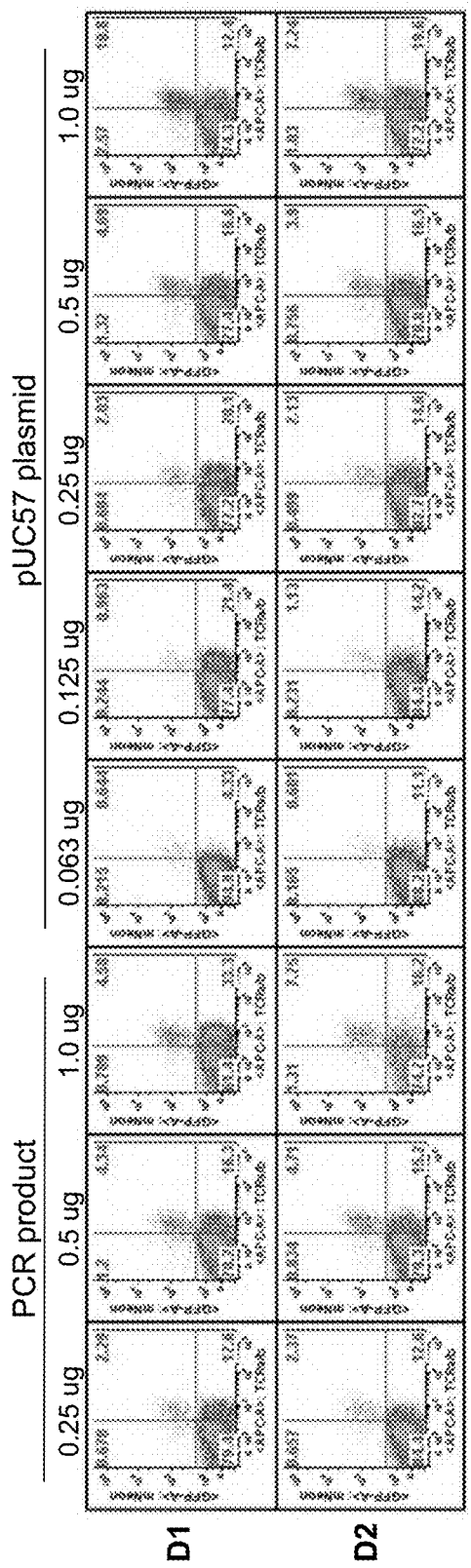
Figure 64B:
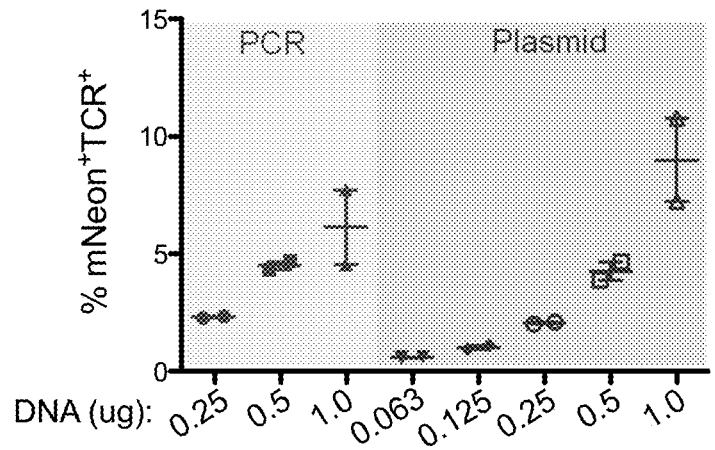
Figure 64C:
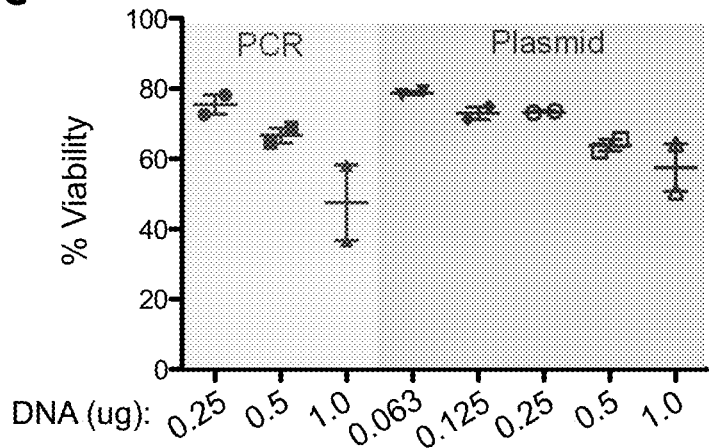
Figure 64D:
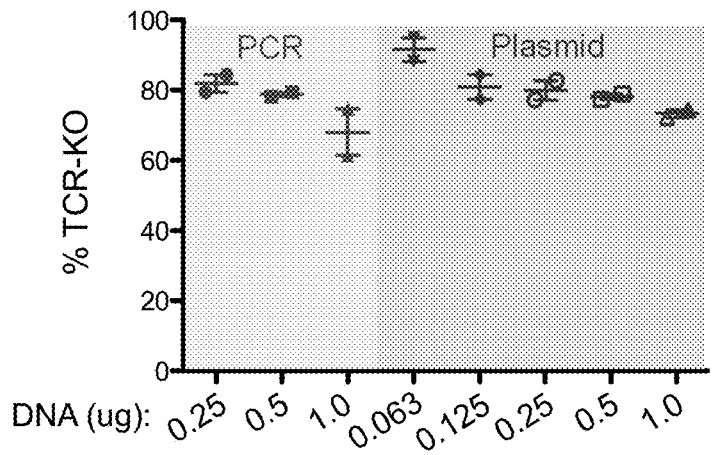

FIGS. 64A-64D show knock-in efficiency using a linear PCR product dsDNA template compared to a plasmid template for electroporation. FIG. 64A shows flow-cytometry dot-plots detecting mNeon+TCRab+ cells from cells electroporated with varying amounts of PCR product dsDNA or the pUC57 plasmid. FIG. 64B is a graph showing frequency of mNeon+TCR+ cells, FIG. 64C is a graph showing frequency of viable cells and FIG. 64D is a graph showing frequency of TCR knock-out cells for samples of cells undergoing electroporation with varying amounts of PCR product or pUC57 plasmid templates, as indicated on the x-axis of the graphs.

Figure 65A:
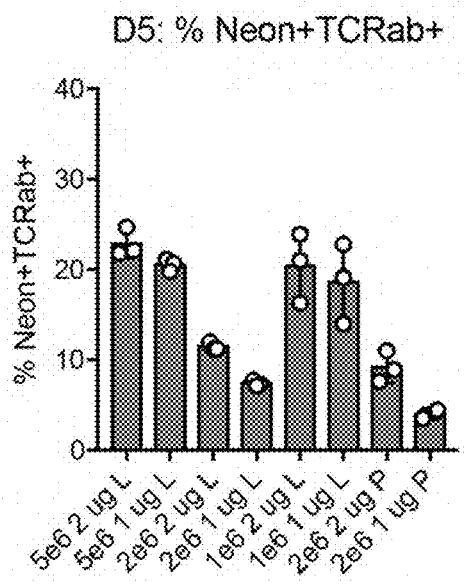
Figure 65B:
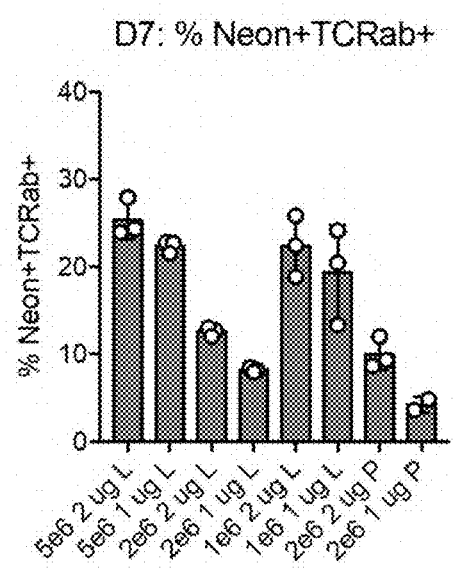
Figure 65C:
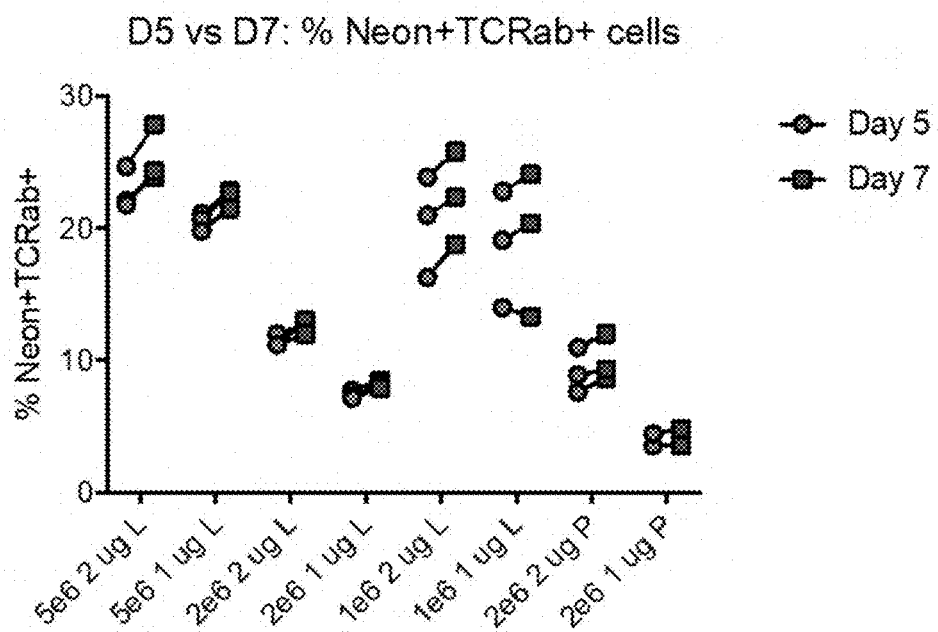

FIGS. 65A-65C illustrate the effect of cell density and type of donor template used for electroporation on knock-in efficiency. T cells were subject to electroporation with 1 μg or 2 μg of either linear PCR product ds DNA (L) or plasmid (P), and $5\times10^6$ (5e6), $2\times10^6$ (2e6), or $1\times10^6$ (1e6) cells. FIG. 65A is a graph showing frequency of mNeon+TCRab+ cells on Day 5 post-activation, FIG. 65B is a graph showing frequency of mNeon+TCRab+ cells on Day 7 post-activation and FIG. 65C is a graph showing mNeon+TCRab+ cell expansion from Day 5 to Day 7.

Figure 66A:
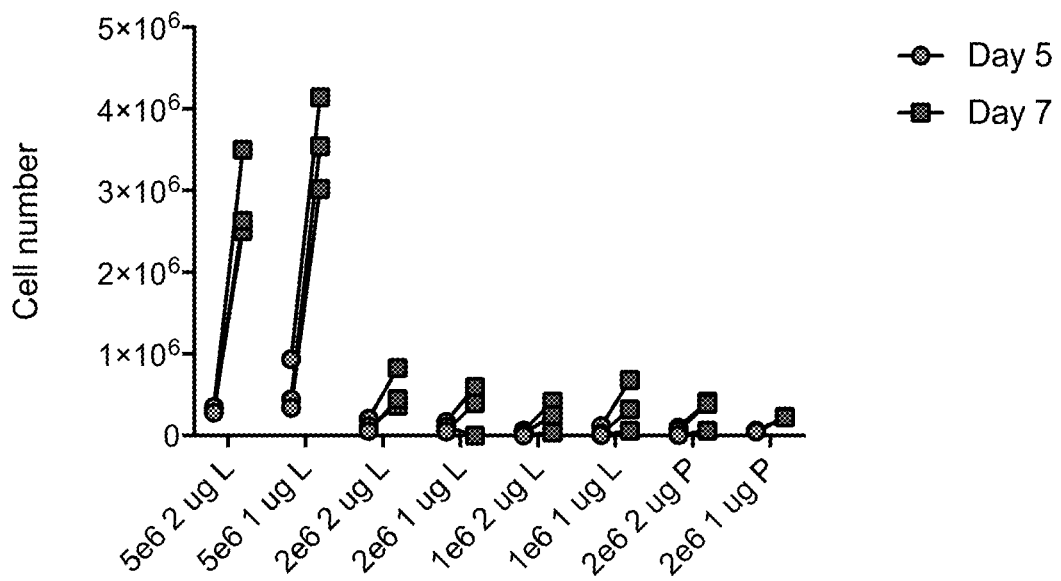
Figure 66B:
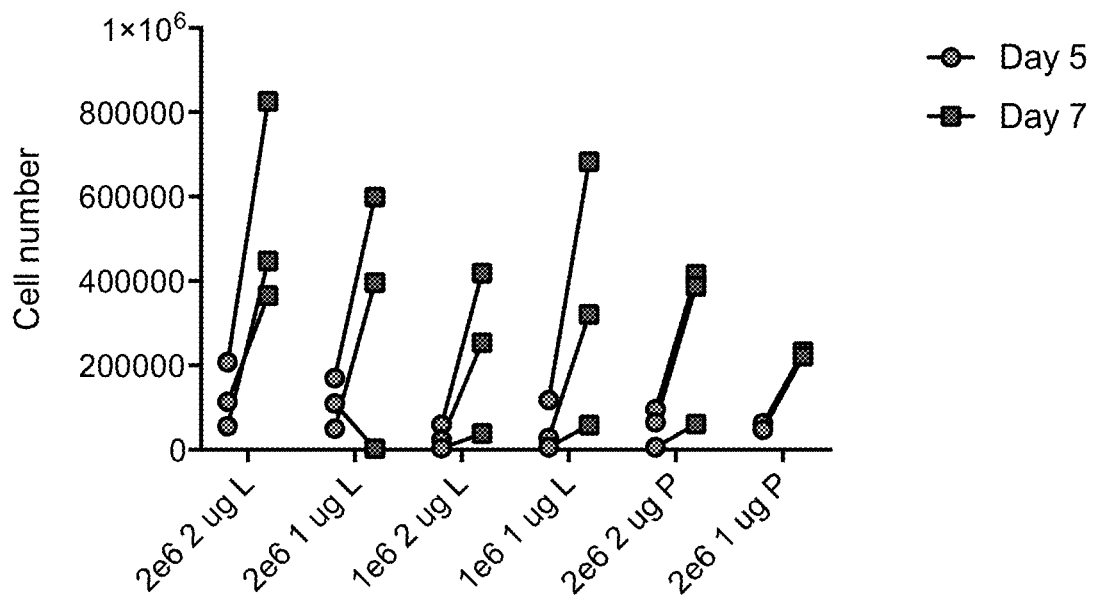

FIGS. 66A and 66B show mNeon+TCRab+ cell recovery depending on electroporation at varying cell densities with different amounts and types of donor template. T cells were subject to electroporation with 1 μg or 2 μg of either linear PCR product ds DNA (L) or plasmid (P), and $5\times10^6$ (5e6), $2\times10^6$ (2e6), or $1\times10^6$ (1e6) cells. FIG. 66A is a graph showing recovery of mNeon+TCRab+ cells on Day 7 post-activation, and FIG. 66B is a graph showing mNeon+TCRab+ cell expansion from Day 5 to Day 7. The 5e6 cell density conditions were excluded to better visualize expansion at lower cell densities.

Figure 67:
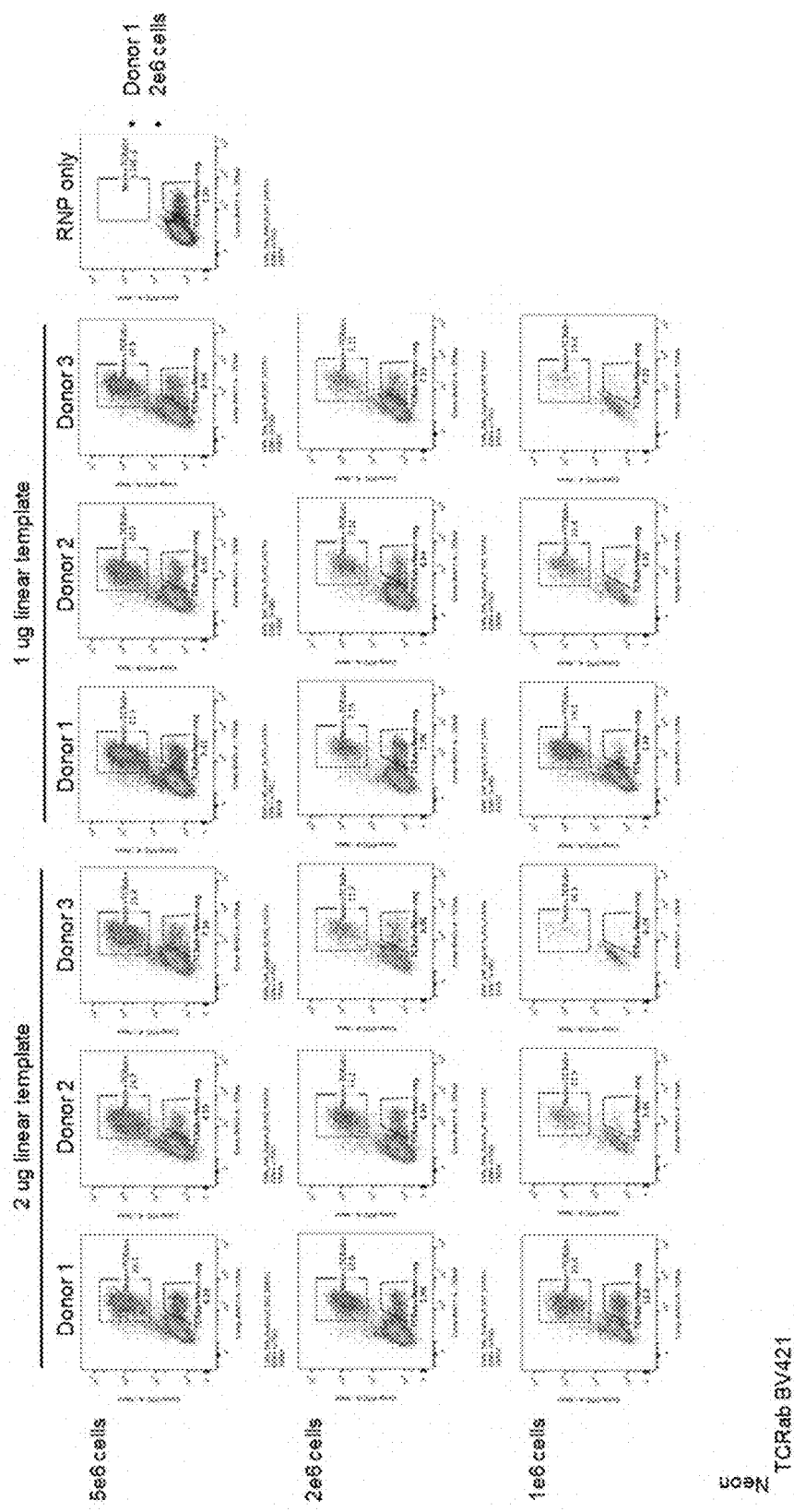

FIG. 67 is flow cytometry analysis showing detection of knock-in positive mNeon+TCRab+ T cells from cells electroporated with linear dsDNA template. Varying amounts of template and cell densities were used for electroporation.

Figure 68:
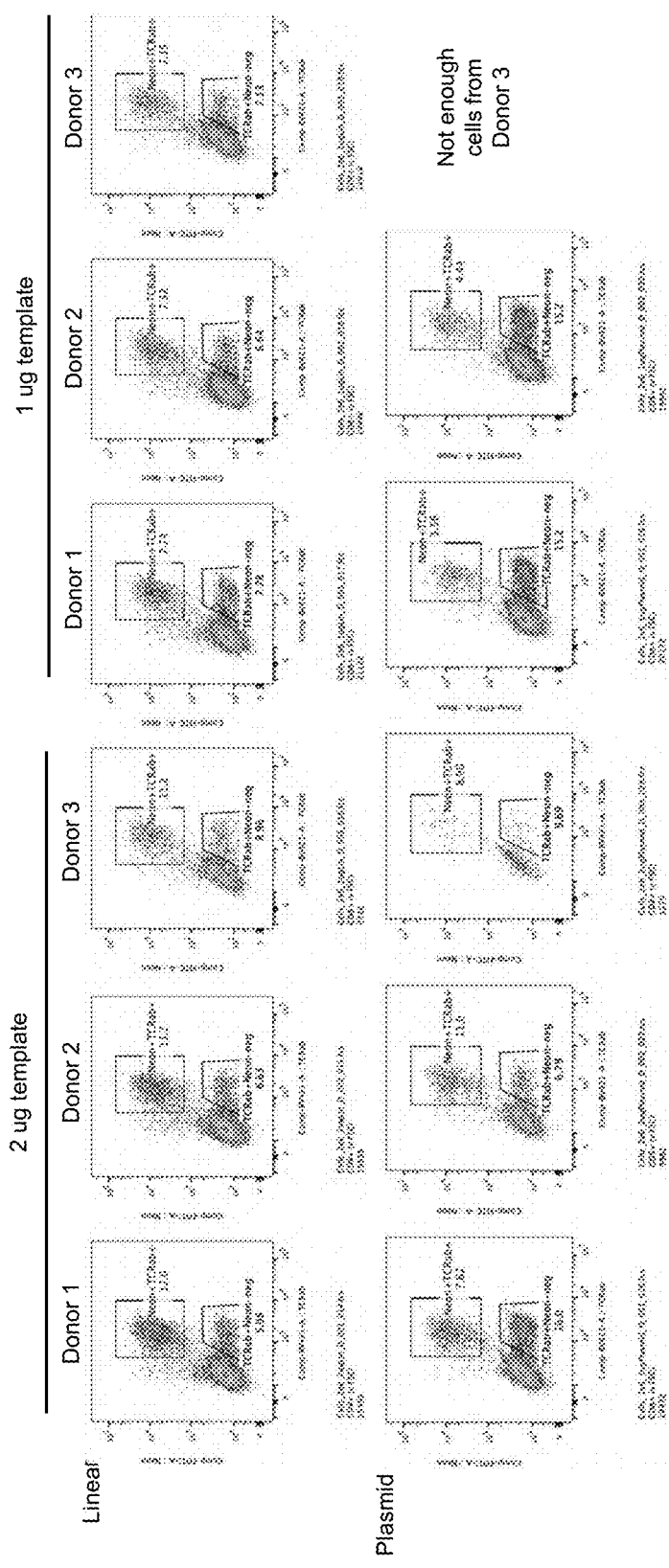

FIG. 68 is flow cytometry analysis of knock-in positive mNeon+TCRab+ T cells from cells electroporated with linear dsDNA template (top row) compared to cells electroporated with plasmid template (bottom row). Either 1 μg or 2 μg of template were used.

Figure 69:
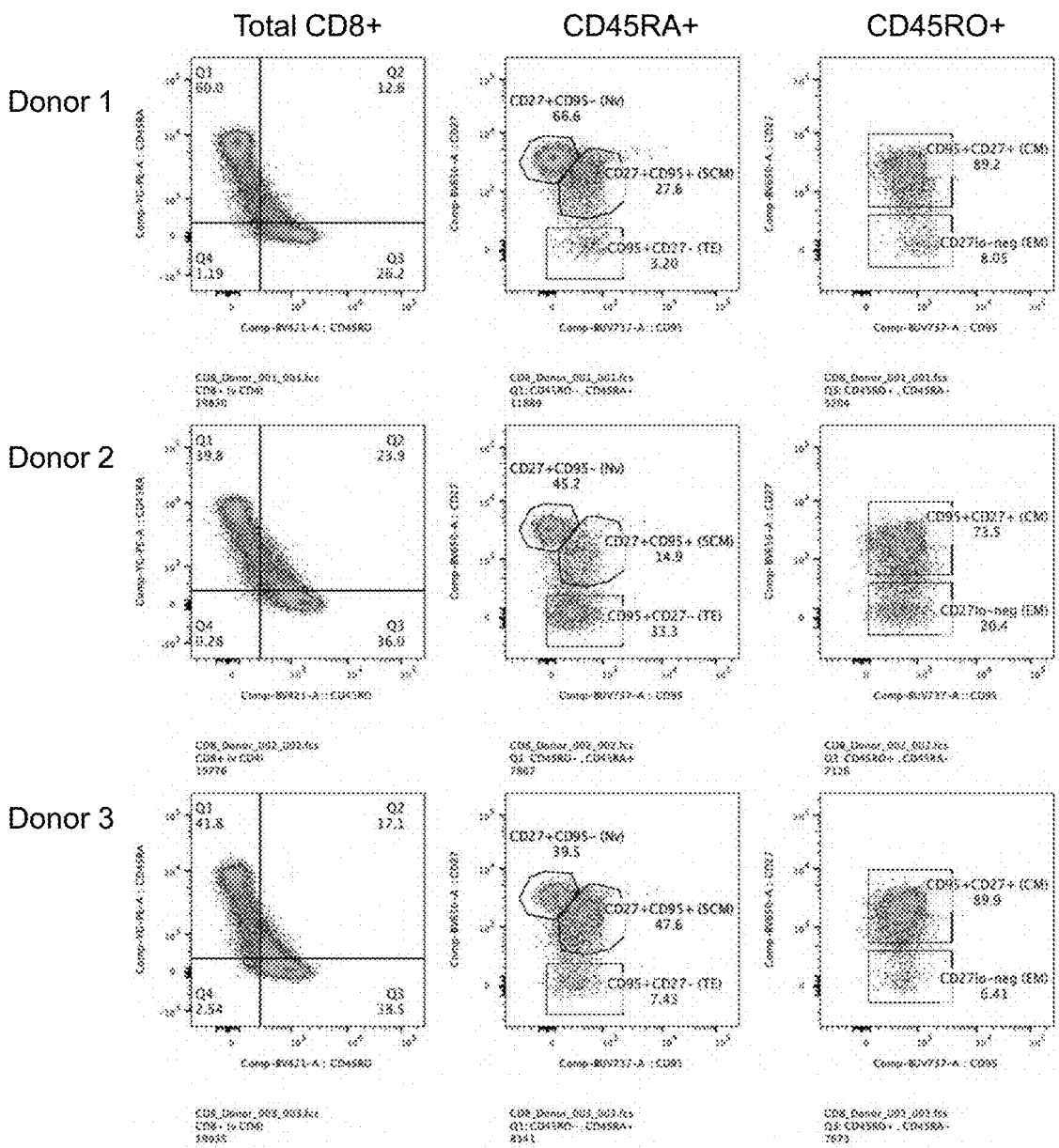

FIG. 69 is flow cytometry dot-plots showing detection of total CD8+ cells, CD45RA+ cells and CD45RO+ cells at Day 0 of T cell activation for three donors.

FIG. 70 is a schematic of T cell differentiation showing $T_{SCM}$ are minimally differentiated cells (top), and a table showing various cytokine combinations that may favor generation of T cell subsets (bottom).

Figure 71A:
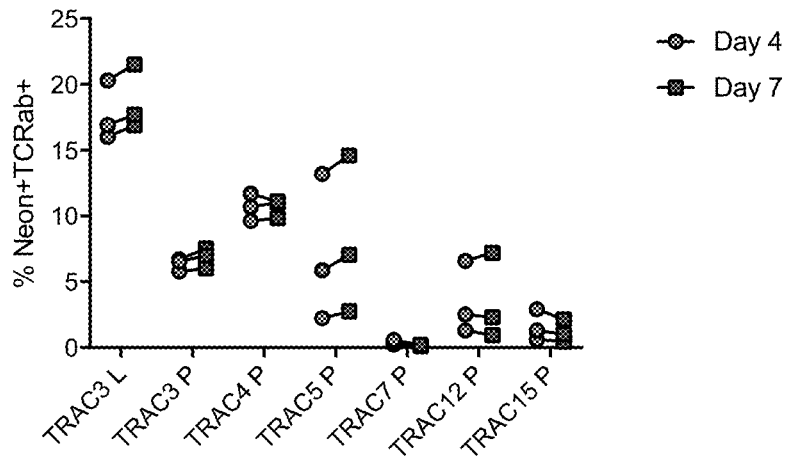
Figure 71B:
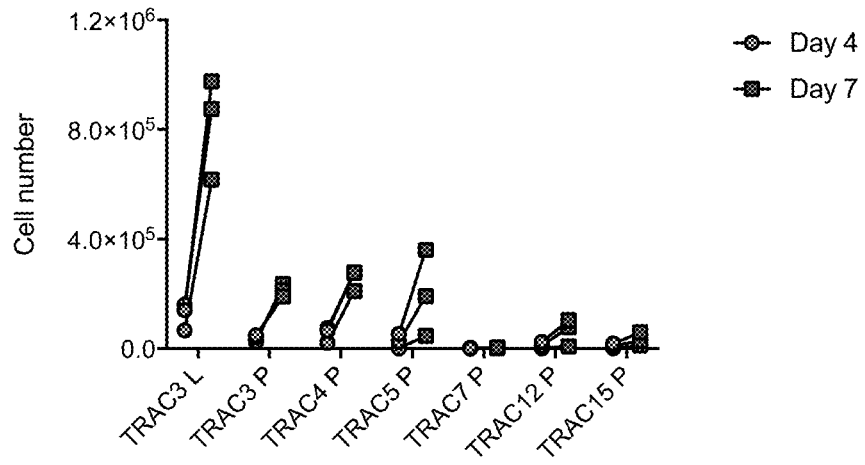
Figure 71C:
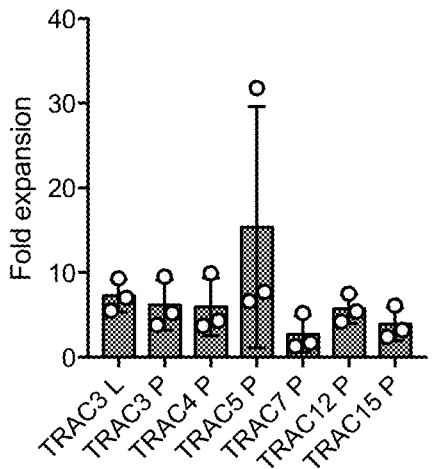

FIGS. 71A-71C illustrate knock-in efficiency using different TRAC loci, and either linear dsDNA or plasmid DNA as template. FIG. 71A is a graph showing frequency of knock-in positive mNeon+TCRab+ cells on day 4 compared to day 7 post T cell activation, FIG. 71B shows recovery of mNeon+TCRab+ cells on days 4 and 7 post-activation and FIG. 71C shows fold expansion of mNeon+TCRab+ cells. TRAC3, TRAC4, TRAC5, TRAC7, TRAC12 and TRAC15 templates in linear ds DNA (L) form or plasmid DNA (P) form were used for electroporation.

Figure 72:
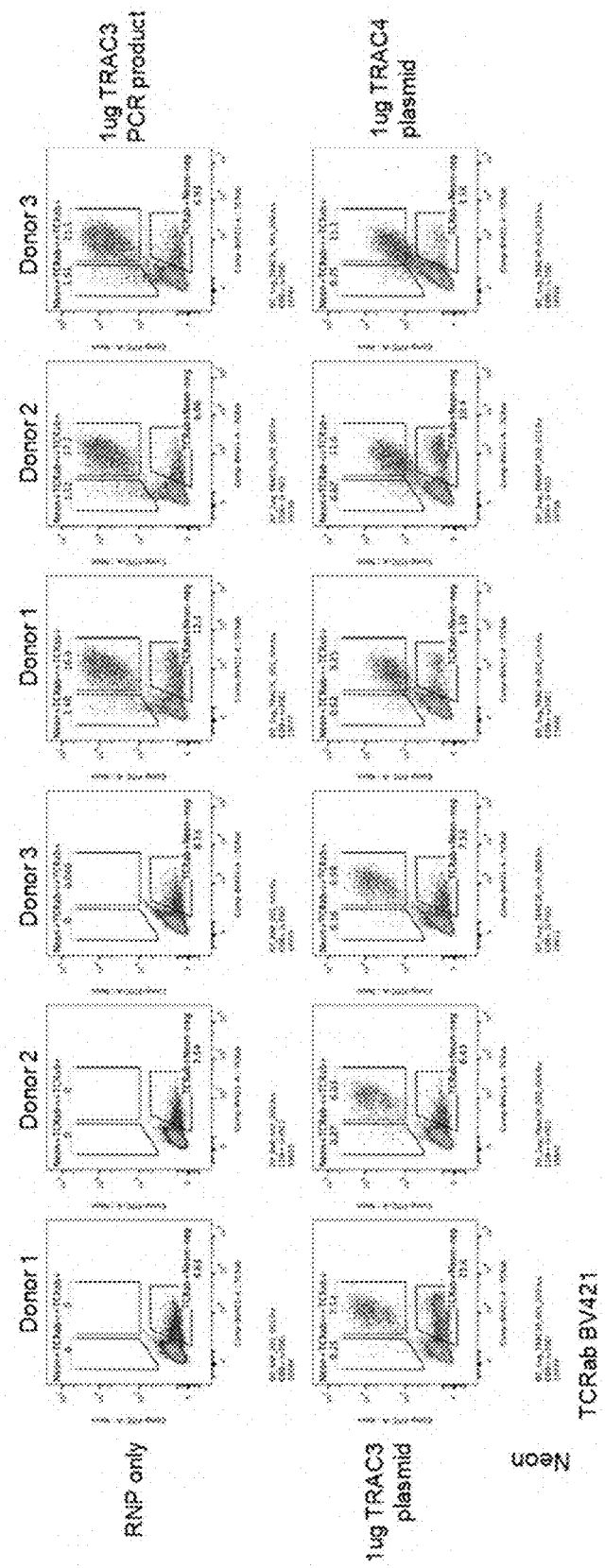

FIG. 72 is flow-cytometry analysis showing detection of knock-in positive mNeon+TCRab+ T cells electroporated with various templates. Cells were subject to electroporation with RNP only control (upper row, three panels on left), TRAC3 linear ds DNA template (upper row, three panels on right), TRAC3 plasmid (lower row, three panels on left), or TRAC4 plasmid (lower row, three panels on right).

Figure 73:
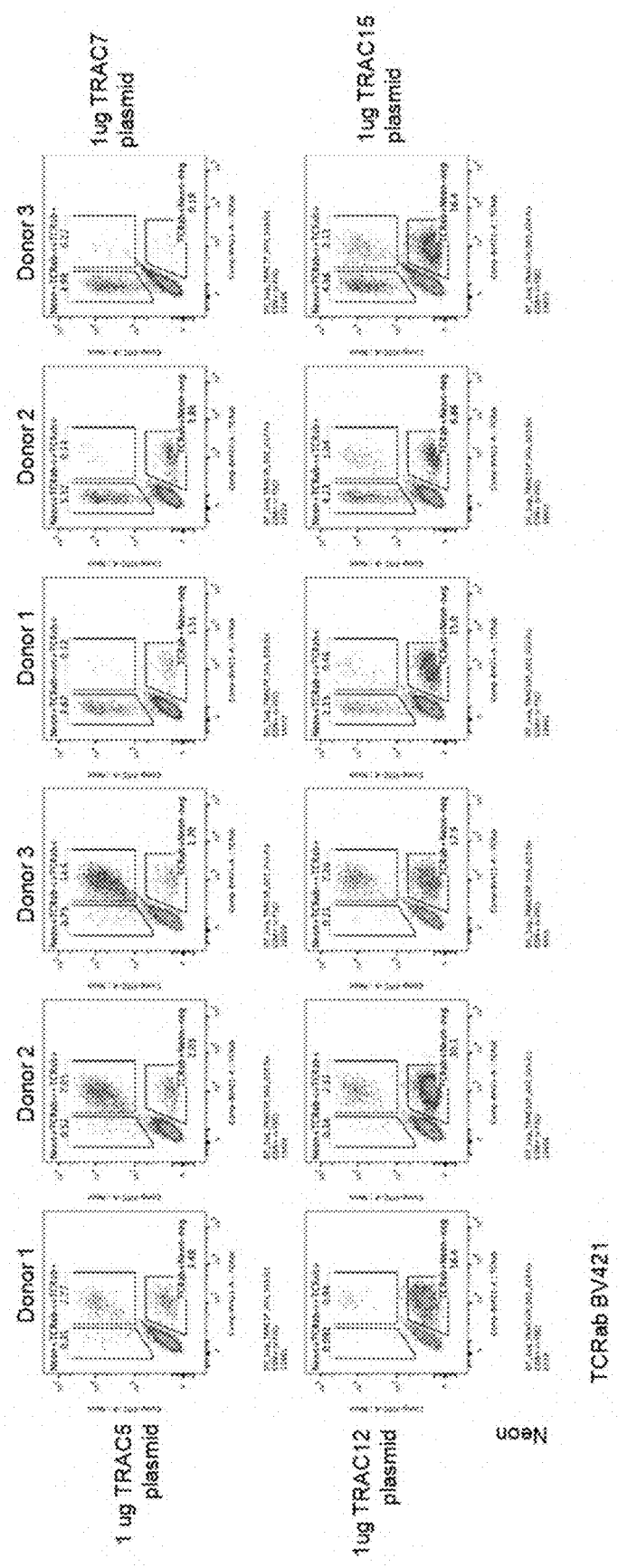

FIG. 73 is flow-cytometry analysis showing detection of knock-in positive mNeon+TCRab+ T cells electroporated with various templates. Cells were subject to electroporation with TRAC5 plasmid (upper row, three panels on left), TRAC7 plasmid (upper row, three panels on right), TRAC12 plasmid (lower row, three panels on left), or TRAC15 plasmid (lower row, three panels on right).

Figure 74:
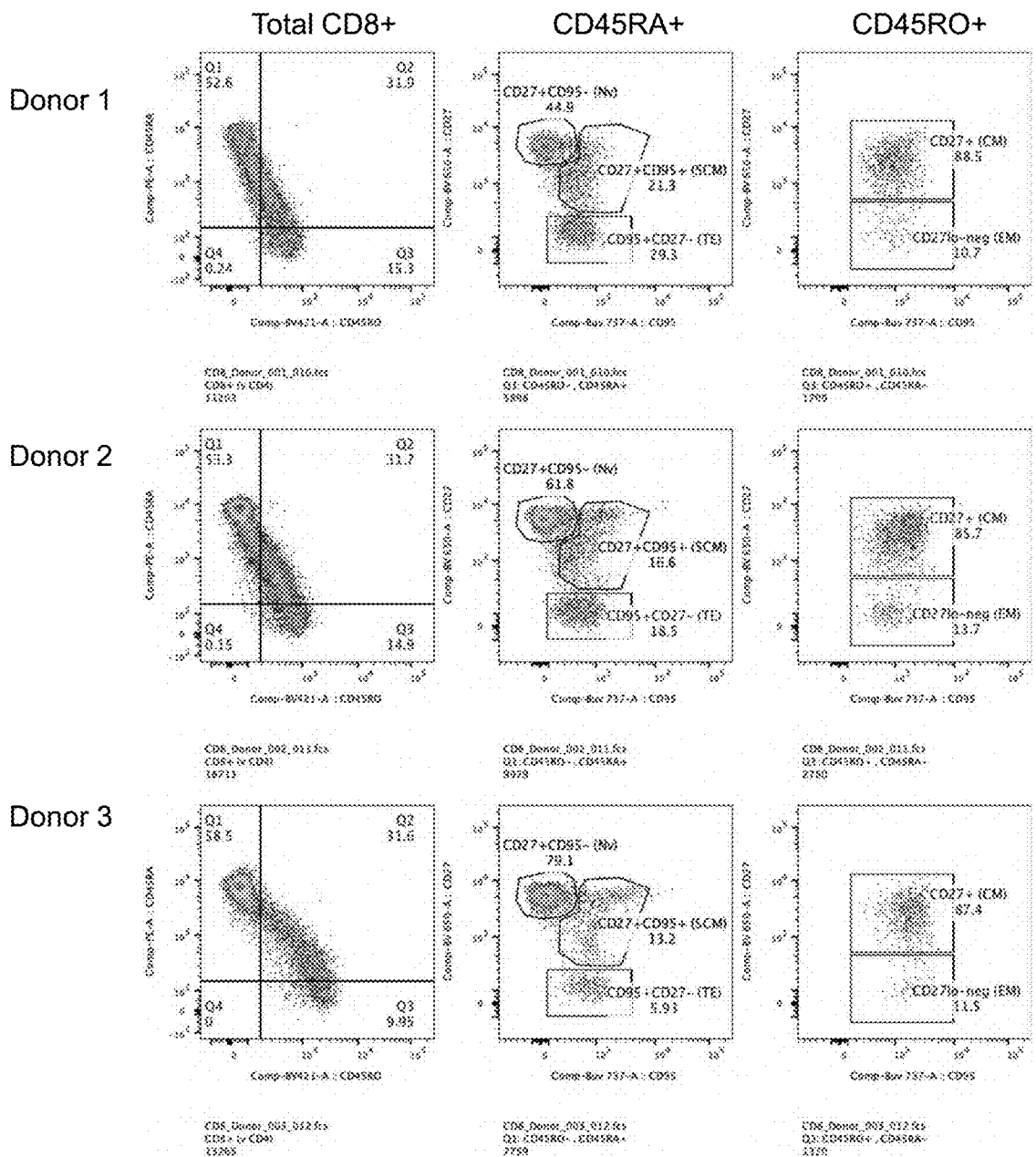

FIG. 74 is flow-cytometry analysis profiling total CD8+ (left column), CD45RA+ (middle column), and CD45RO+ (right column) T cells from donor samples used in experiments shown in FIGS. 72 and 73.

Figure 75:
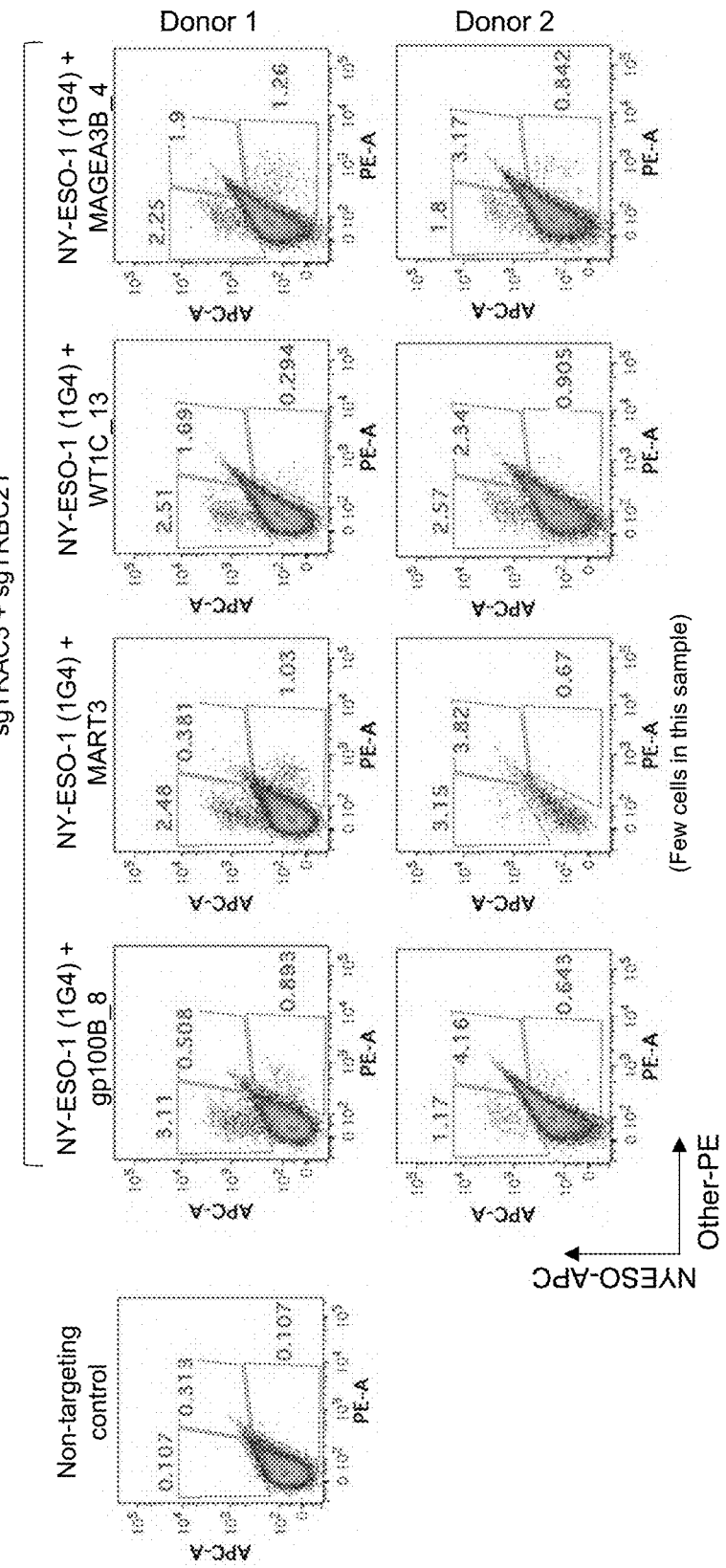

FIG. 75 is flow cytometry dot-plots showing knock-in efficiency of the NY-ESO1 TCR with either gp100 TCR, MART3 TCR, WT1C TCR, or MAGEAB3 TCR, as indicated. Plasmid templates encoding NY-ESO1 TCR were co-electroporated with templates encoding other TCRs. Flow cytometry data was collected 7 days post T cell activation. Cells were stained with Immudex peptide-MHC dextramers WB3247-APC (NY-ESO1 TCR) with WB3469-PE (WT1 TCR), WB2162-PE (MART TCR), WB3415_PE (MAGEA3 TCR) or WB2156_PE (gp100 TCR).

Figure 76A:
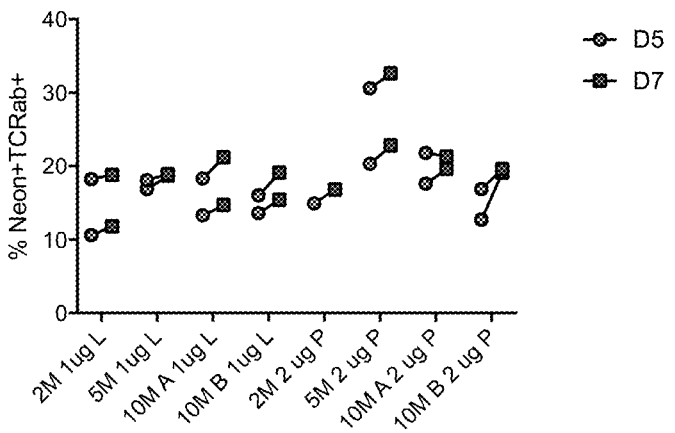
Figure 76B:
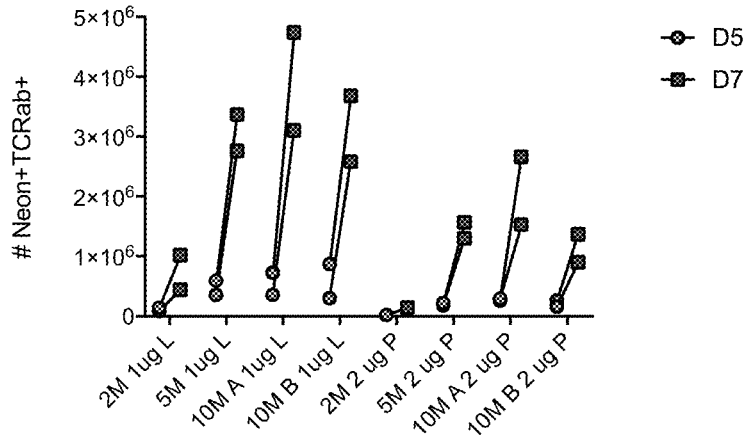
Figure 76C:
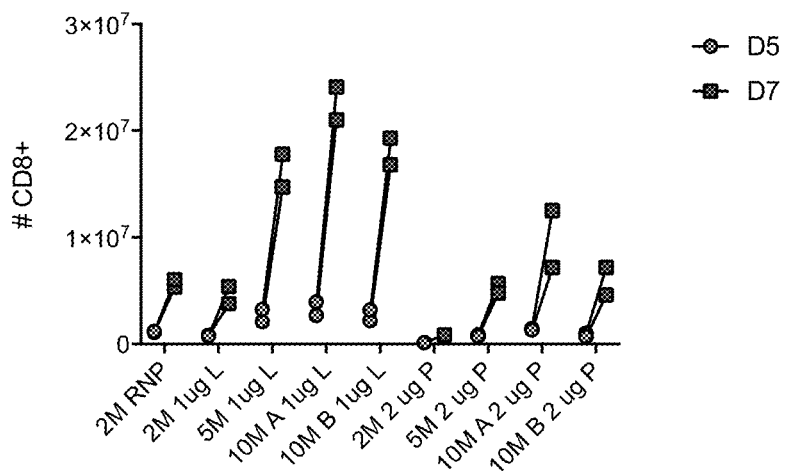

FIGS. 76A-76C are graphs showing the effect of linear versus plasmid template, template amount used, and cell density on knock-in efficiency. FIG. 76A is a graph illustrating frequency and FIG. 76B is a graph illustrating recovery of knock-in positive mNeon+TCRab+ cells at days 5 and 7 post-activation. FIG. 76C is a graph showing recovery of CD8+ T cells at days 5 and 7 post-activation. As indicated on the x-axis of the graphs, either 2 million (2M), 5 million (5M), or 10 million (10M) cells were used; and either 1 μg or 2 μg of linear dsDNA PCR product (L) or plasmid (P) template were used for electroporation for each group of cells.

Figure 77:
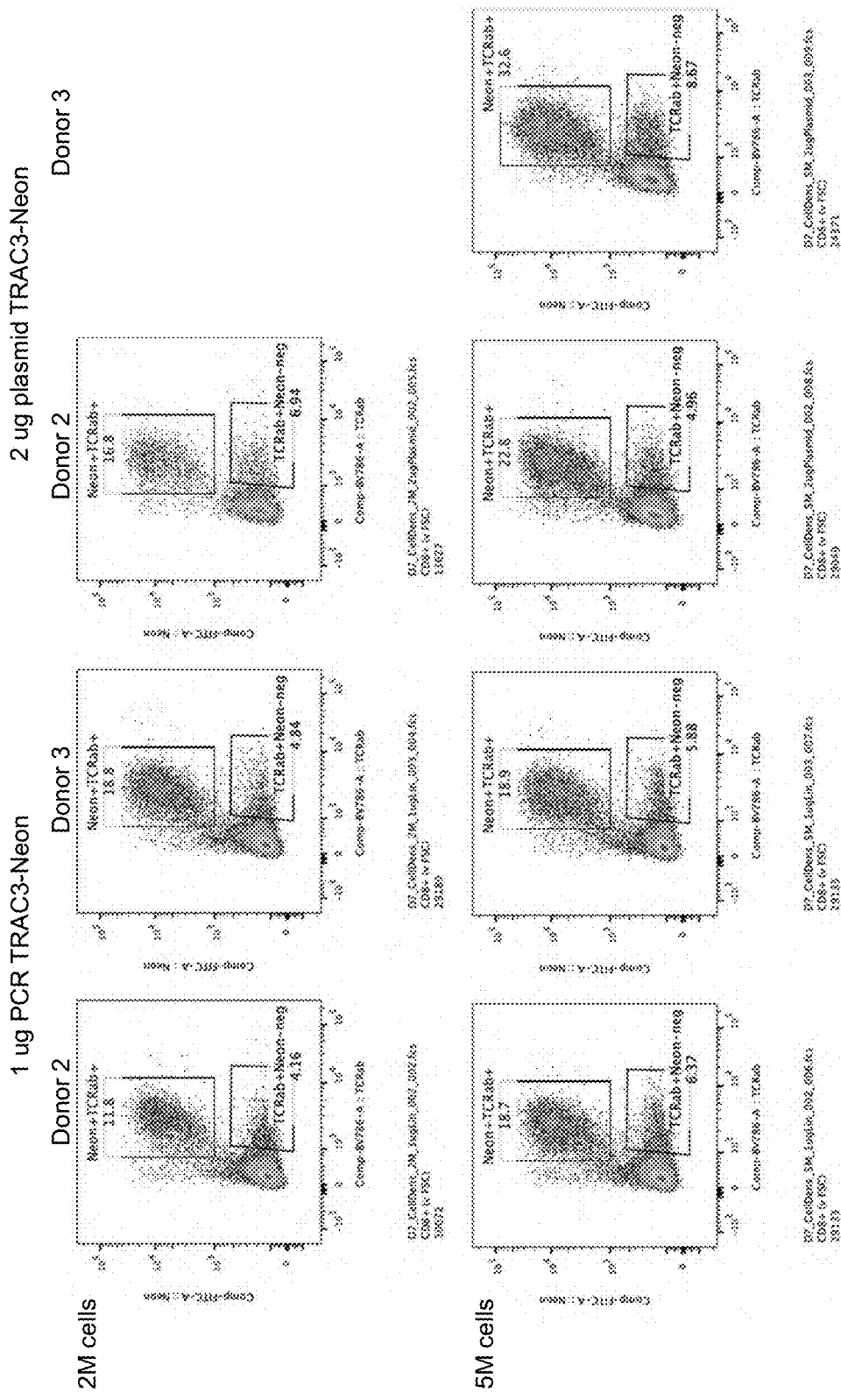

FIG. 77 is flow cytometry analysis showing detection of knock-in positive mNeon+TCRab+ T cells. Either 2 million (2M, top row) or 5 million cells (5M, bottom row), with 1 μg linear dsDNA or 2 μg plasmid DNA template was used for electroporation.

Figure 78:
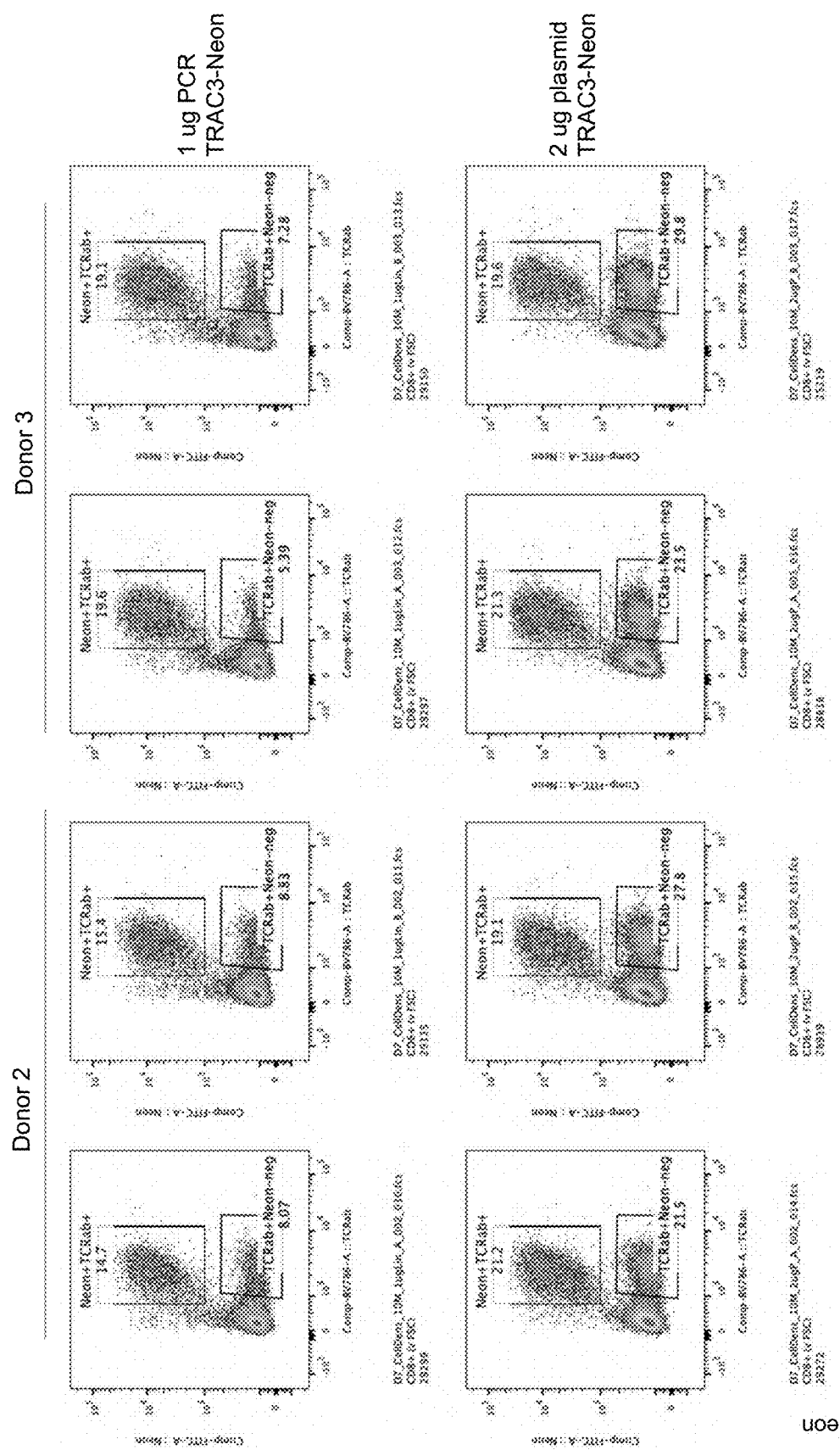
Figure 80A:
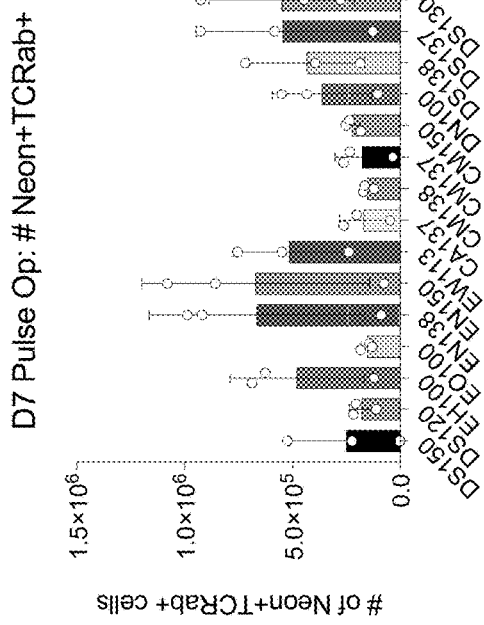
Figure 80B:
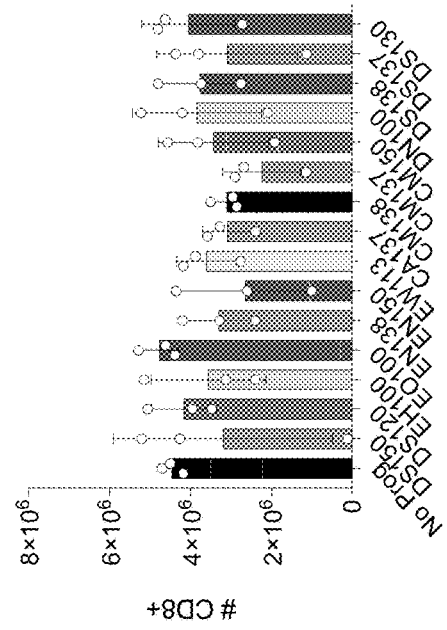
Figure 80C:
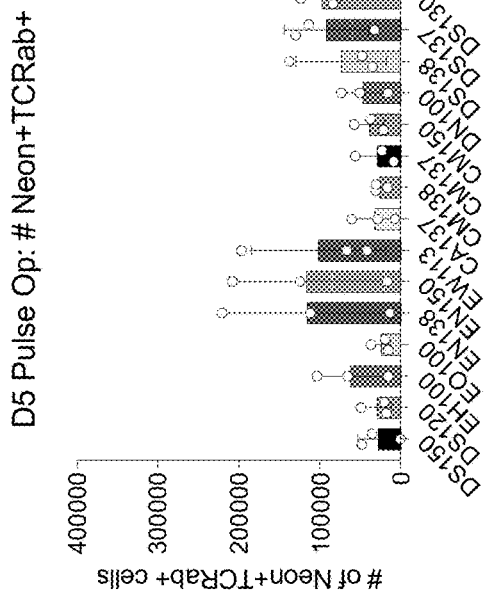
Figure 80D:
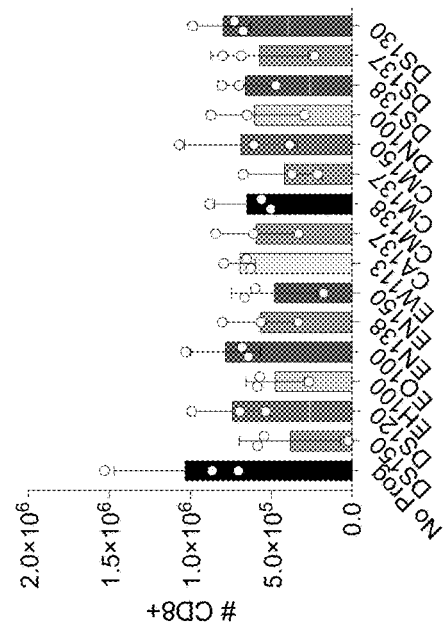

FIG. 78 is flow cytometry dot-plots detecting knock-in positive mNeon+TCRab+ T cells. Ten million cells were electroporated with either 1 μg linear dsDNA TRAC3-mNeon (top row) or 2 μg TRAC3-mNeon plasmid (bottom row) template.

FIGS. 79A-79D are bar graphs showing frequency of knock-in positive mNeon+TCRab+ cells on day 5 (FIG. 79A) and day 7 (FIG. 79C) after activation, and residual TCR expressing mNeon-TCRab+ cells on day 5 (FIG. 79B) and day 7 (FIG. 79D) after activation. All cell groups were electroporated in P3 buffer, and various pulse codes were tested, as indicated on the x-axis of the graphs.

FIGS. 80A-80D are bar graphs showing recovery of knock-in positive mNeon+TCRab+ cells on day 5 (FIG. 80A) and day 7 (FIG. 80C) after activation, and total CD8+ cells on day 5 (FIG. 80B) and day 7 (FIG. 80D) after activation. All cell groups were electroporated in P3 buffer, and various pulse codes were tested, as indicated on the x-axis of the graphs.

Figure 81A:
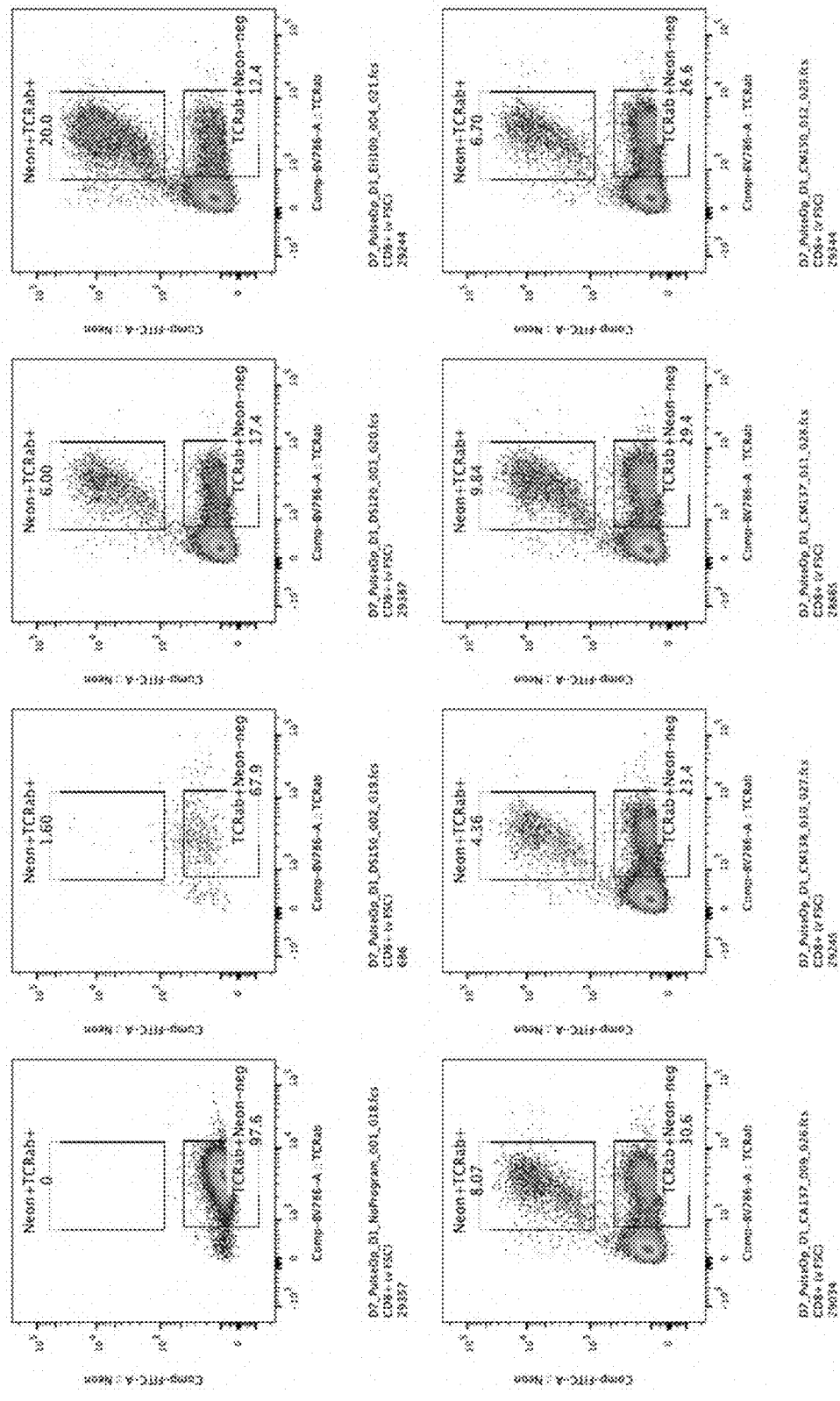
Figure 81B:
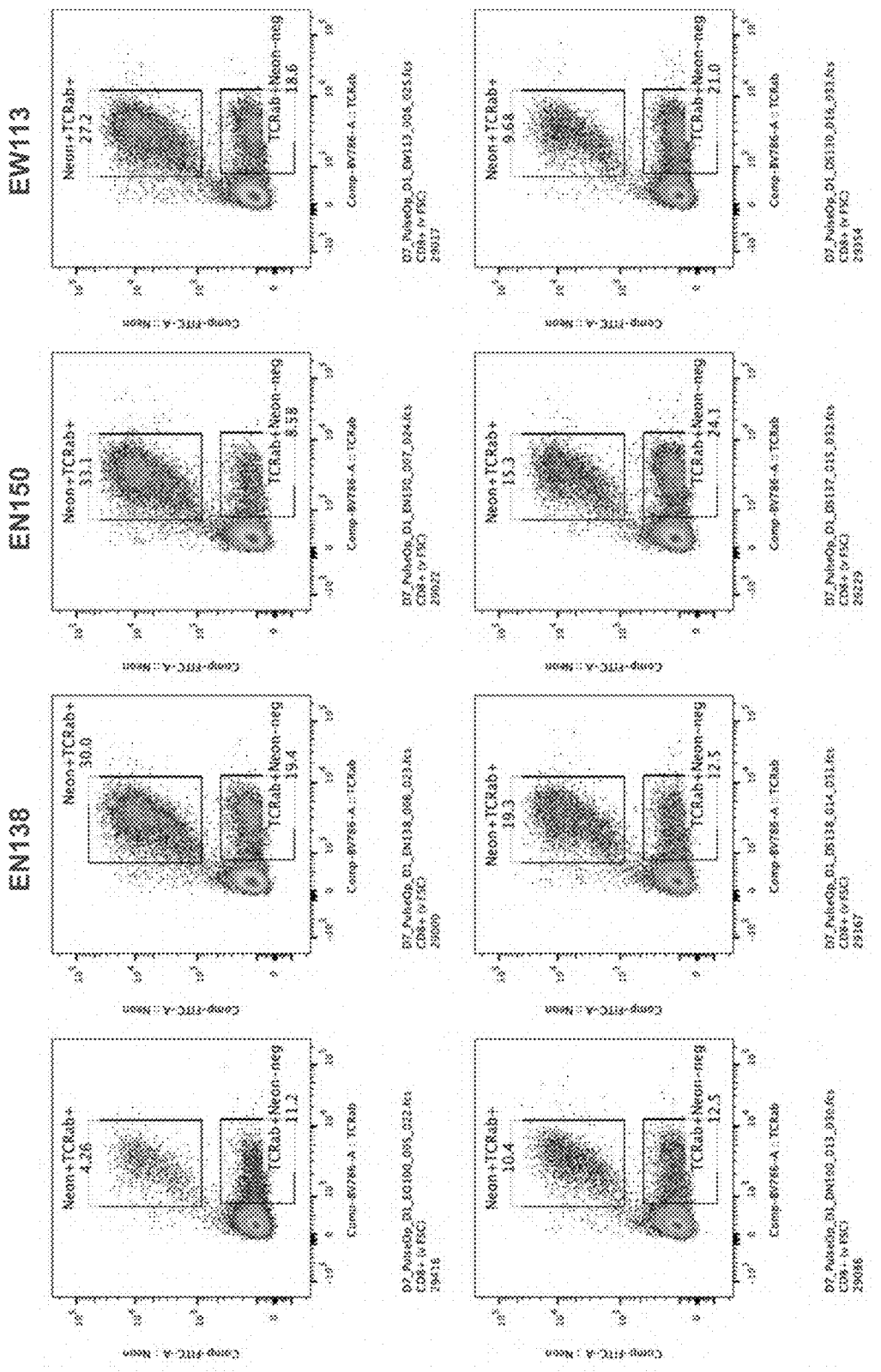

FIGS. 81A and 81B are flow cytometry analysis showing detection of knock-in positive mNeon+TCRab+ T cells on day 7 post-activation using samples from Donor 1. FIG. 81A shows data for cells electroporated using the pulse programs as follows for the top row from left to right: No Program, DS150, DS120, EH100; and for the bottom row from left to right CA137, CM138, CM137, and CM150. FIG. 81B shows data for cells electroporated using the pulse programs as follows for the top row from left to right: EO100, EN138, EN150, EN113; and for the bottom row from left to right DN100, DS138, DS137, DS130.

Figure 82A:
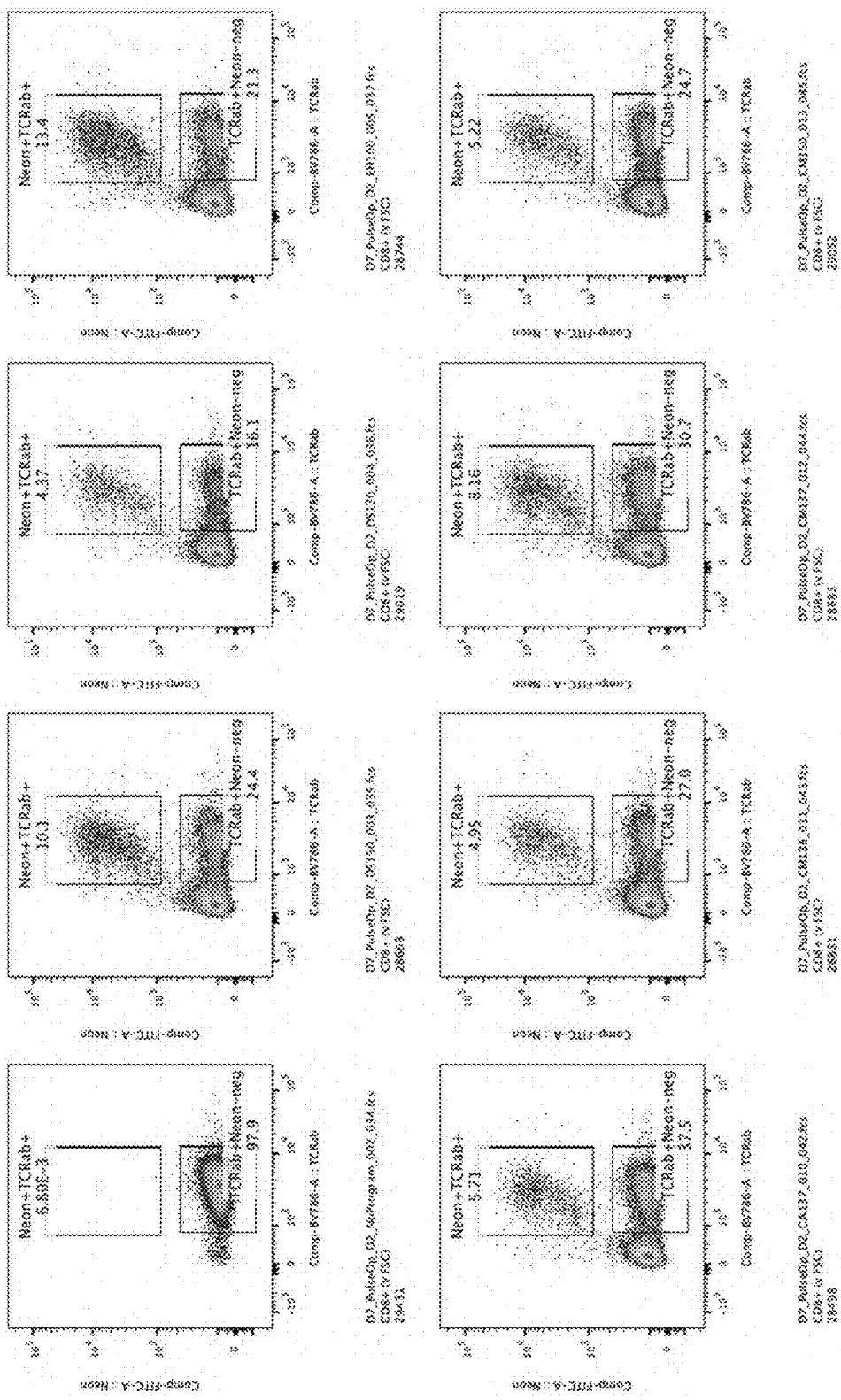
Figure 82B:
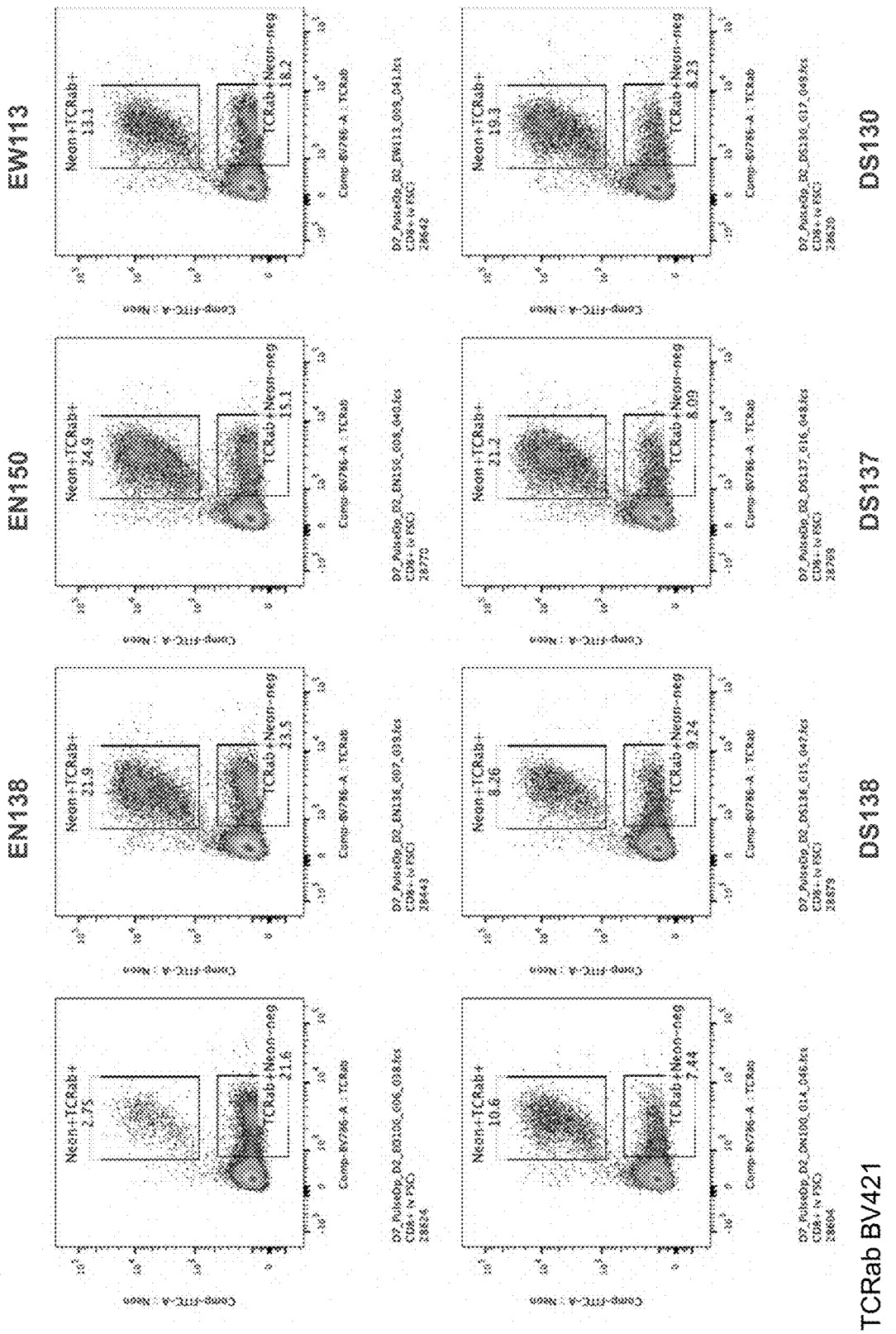

FIGS. 82A and 82B are flow cytometry analysis showing detection of knock-in positive mNeon+TCRab+ T cells on day 7 post-activation using samples from Donor 2. FIG. 82A shows data for cells electroporated using the pulse programs as follows for the top row from left to right: No Program, DS150, DS120, EH100; and for the bottom row from left to right CA137, CM138, CM137, and CM150. FIG. 82B shows data for cells electroporated using the pulse programs as follows for the top row from left to right: EO100, EN138, EN150, EN113; and for the bottom row from left to right DN100, DS138, DS137, DS130.

Figure 83A:
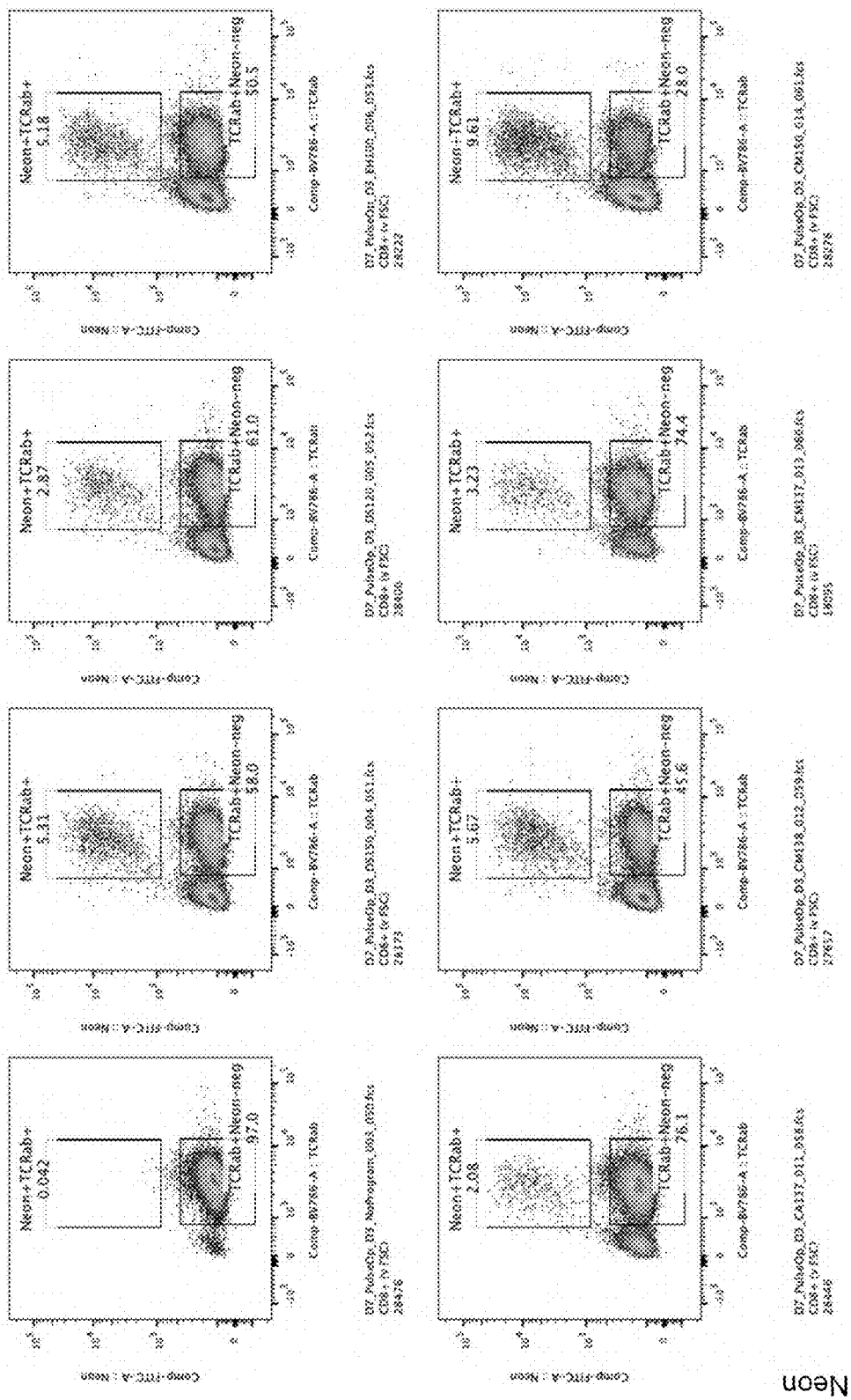
Figure 83B:
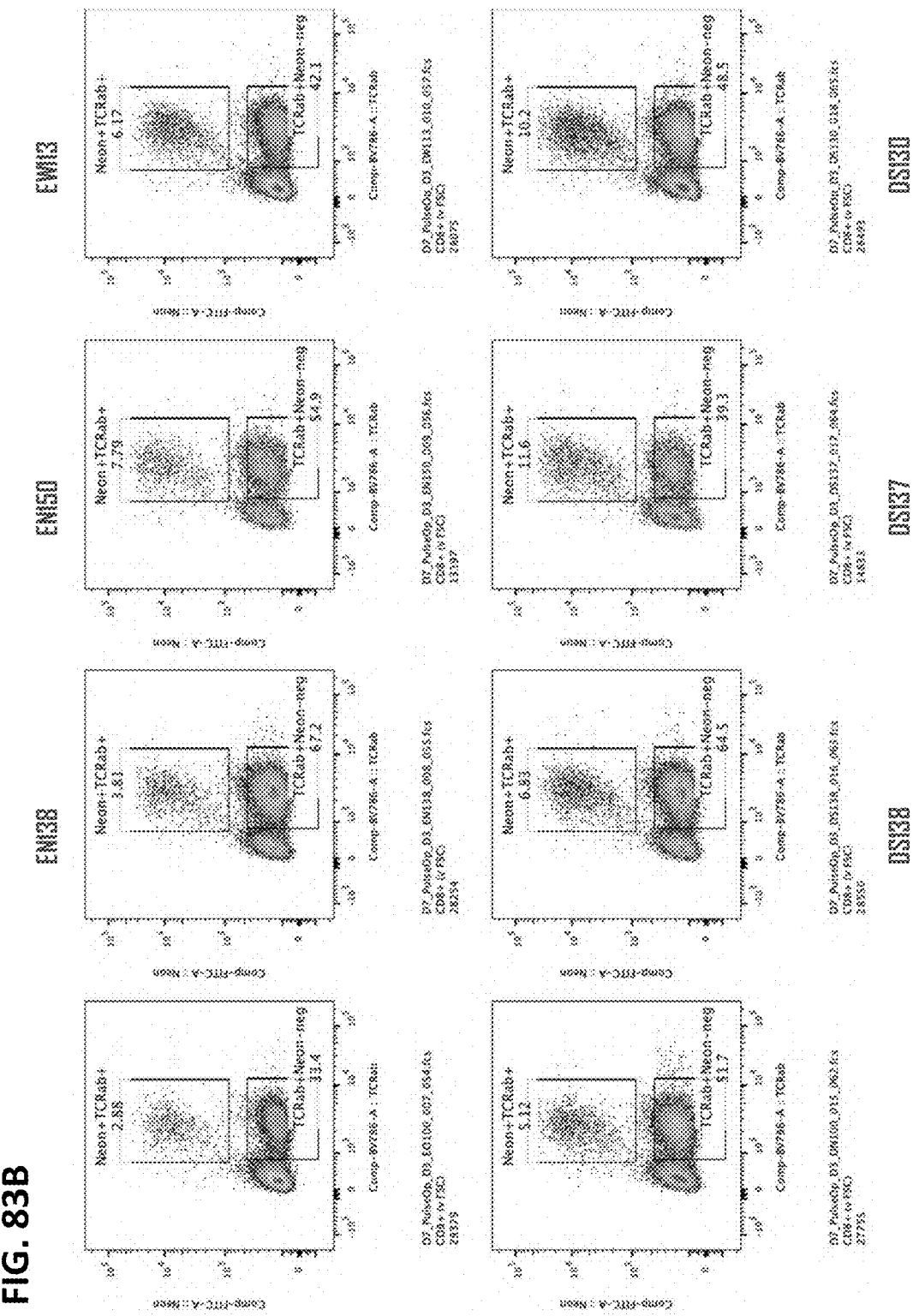

FIGS. 83A and 83B are flow cytometry analysis showing detection of knock-in positive mNeon+TCRab+ T cells on day 7 post-activation using samples from Donor 3. FIG. 83A shows data for cells electroporated using the pulse programs as follows for the top row from left to right: No Program, DS150, DS120, EH100; and for the bottom row from left to right CA137, CM138, CM137, and CM150. FIG. 83B shows data for cells electroporated using the pulse programs as follows for the top row from left to right: EO100, EN138, EN150, EN113; and for the bottom row from left to right DN100, DS138, DS137, DS130.

Figure 84:
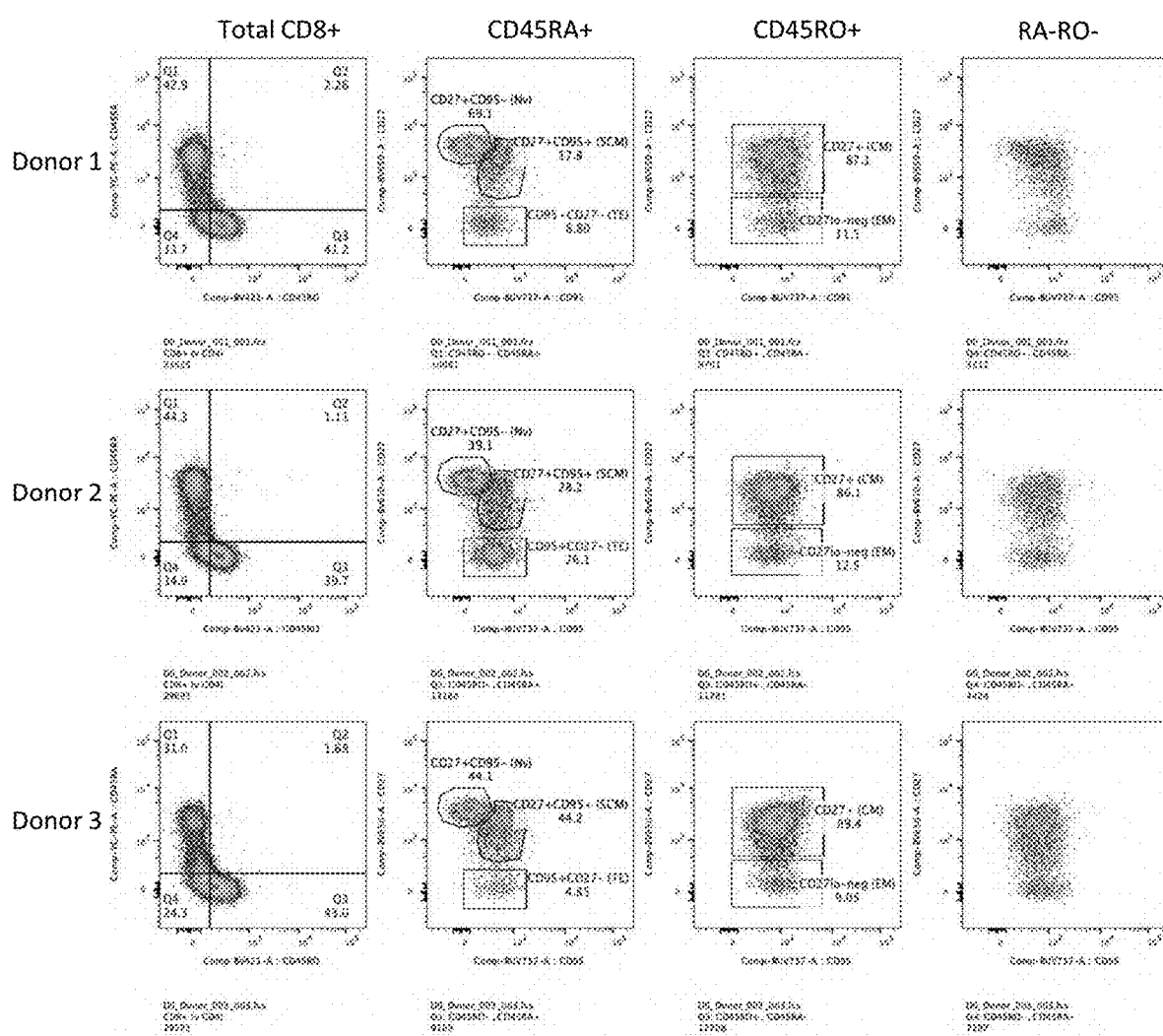
Figure 85A:
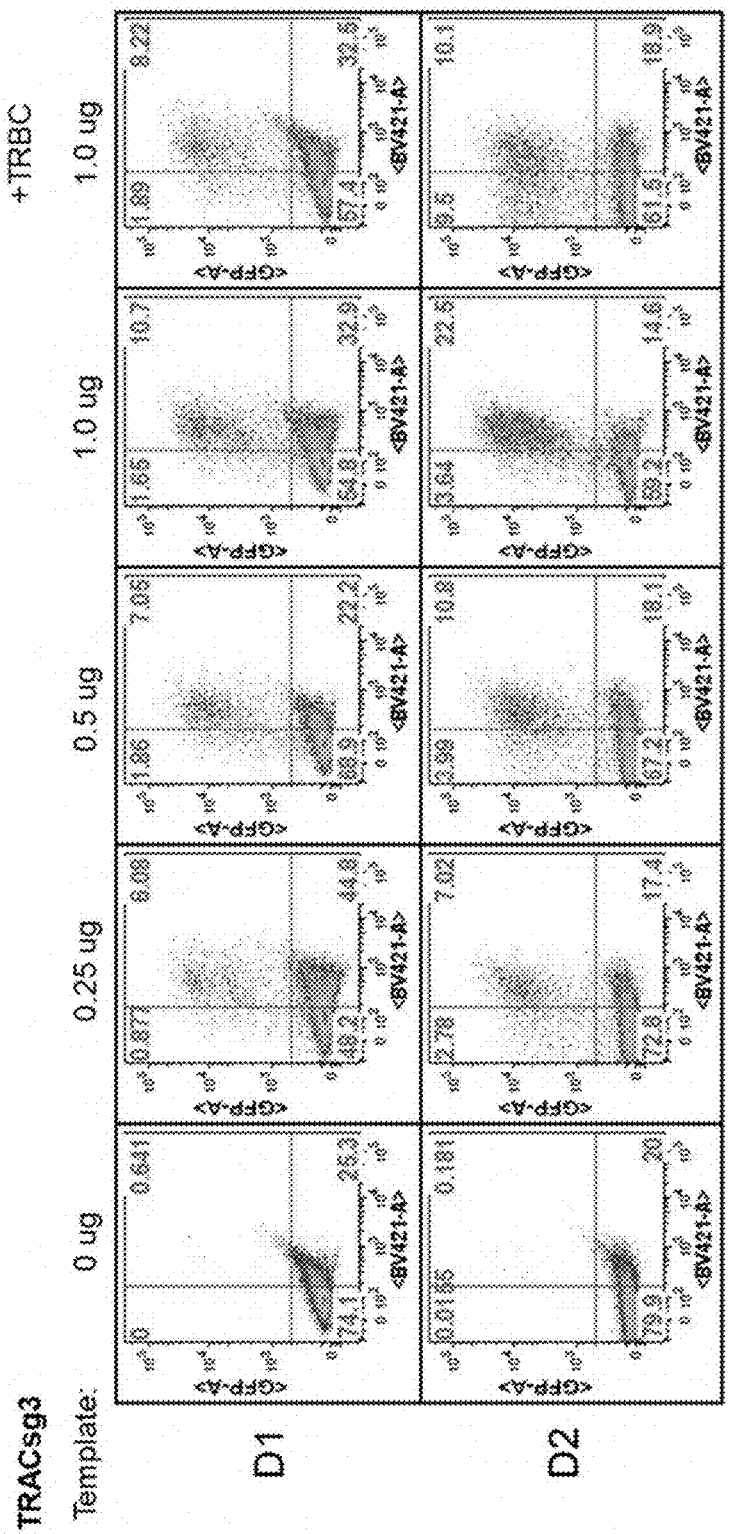
Figure 85B:
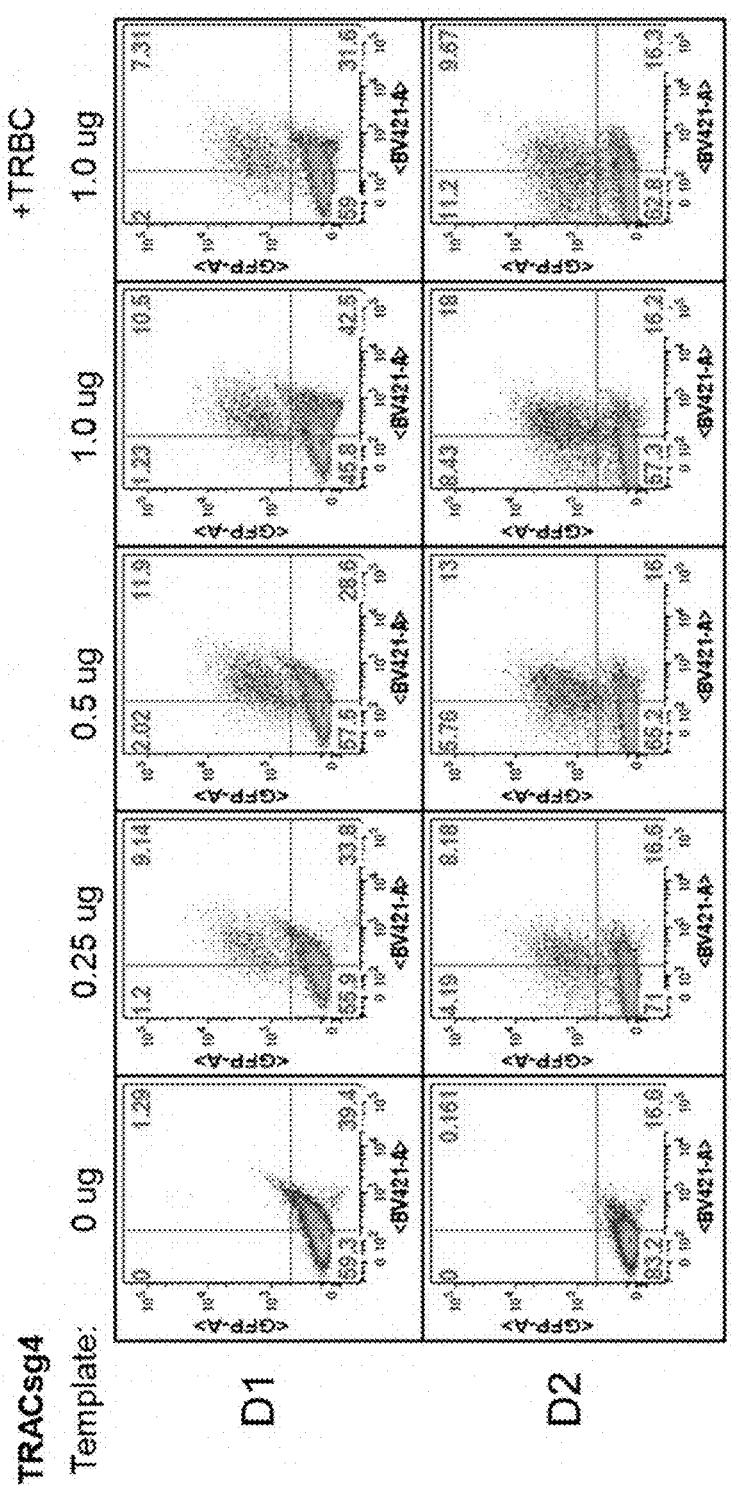
Figure 85C:
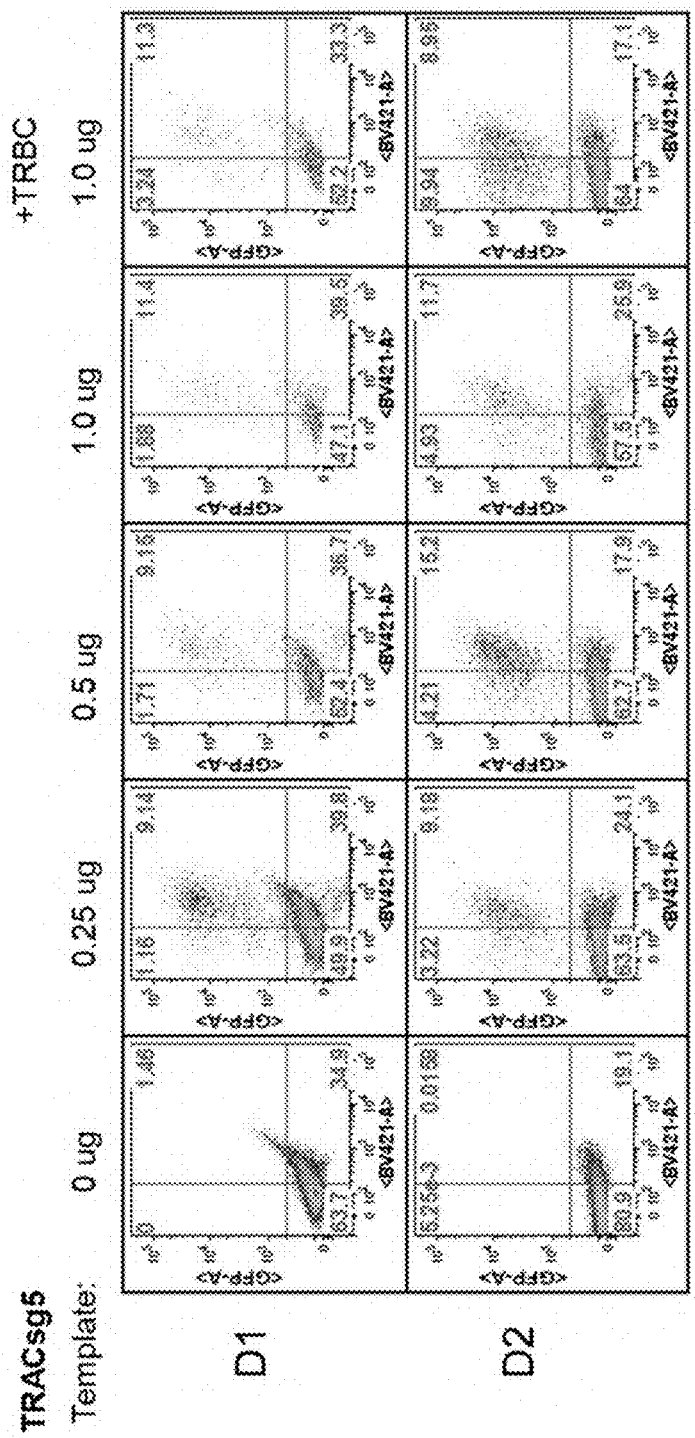

FIG. 84 shows flow cytometry dot-plots profiling donor samples used for experiments shown in FIGS. 81-83. Cells were analyzed on day 0 of activation. As indicated, plots showing total CD8+ cells, CD45RA+ cells, CD45RO+ cells and CD45RA–CD45RO– (RA–RO–) cells are shown.

Figure 85D:
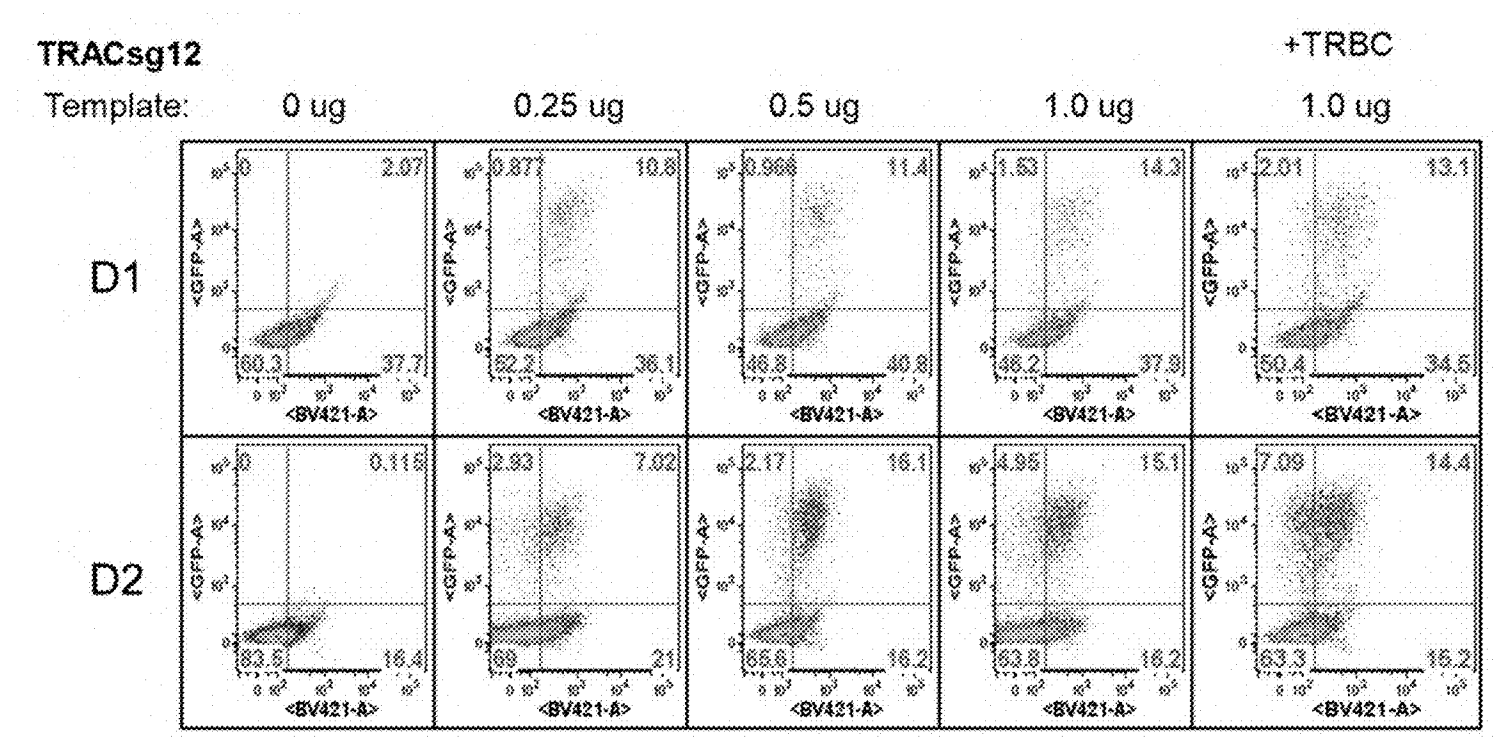

FIGS. 85A-85D are flow-cytometry analysis illustrating knock-in efficiency of various amounts of linear dsDNA TRAC templates mNeon-TRACsg3 (FIG. 85A), mNeon-TRACsg4 (FIG. 85B), mNeon-TRACsg5 (FIG. 85C), and mNeon-TRACsg12 (FIG. 85D) in T cells. The right-most column are dot-plots for cells electroporated with the addition of TRBC21 RNP.

Figure 86A:
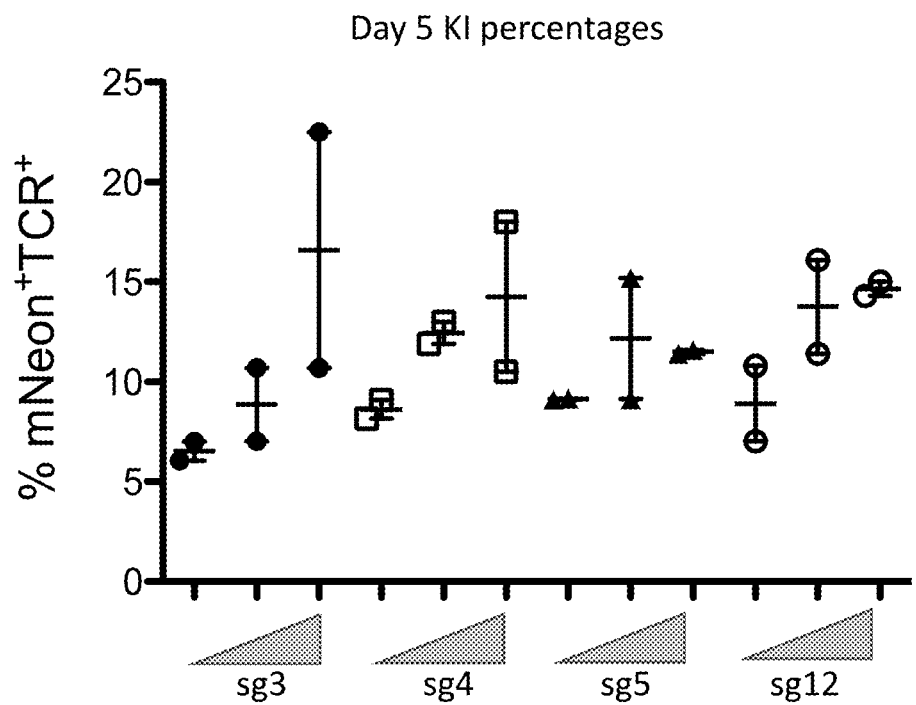
Figure 86B:
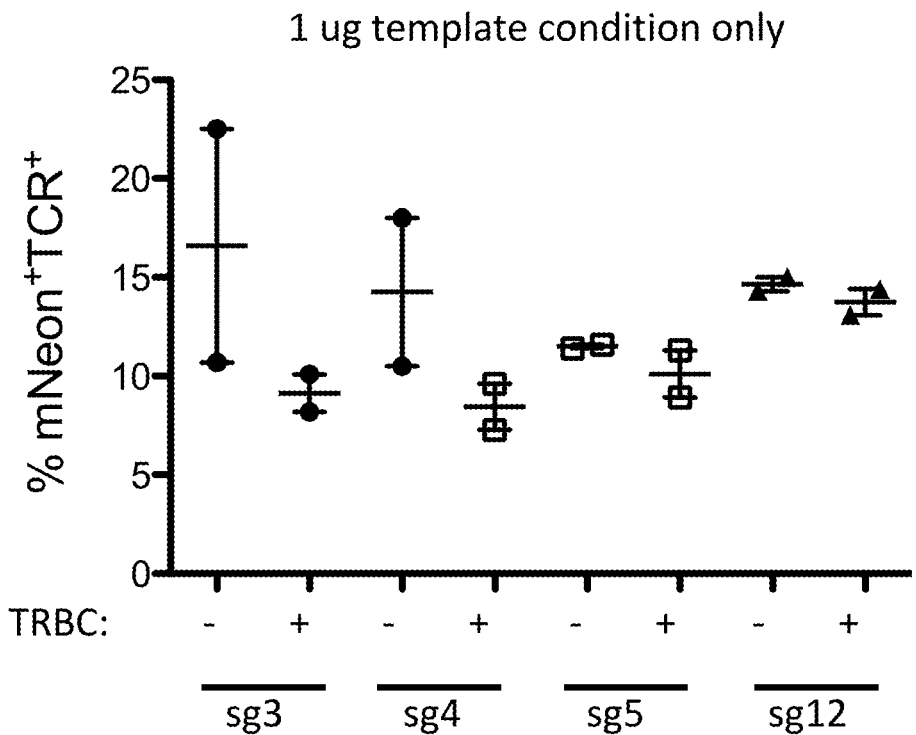

FIGS. 86A and 86B are graphs showing knock-in positive mNeon+TCR+ cells. FIG. 86A is a graph showing frequency of mNeon+TCRab+ cells using varying amounts of the mNeon-TRAC3, mNeon-TRAC4, mNeon-TRAC5 and mNeon-TRAC12 templates for electroporation. FIG. 86B is a graph showing frequency of mNeon+TCRab+ cells using 1 μg of mNeon-TRAC3, mNeon-TRAC4, mNeon-TRAC5 or mNeon-TRAC12 template for electroporation and with or without TRBC21 RNP.

Figure 87:
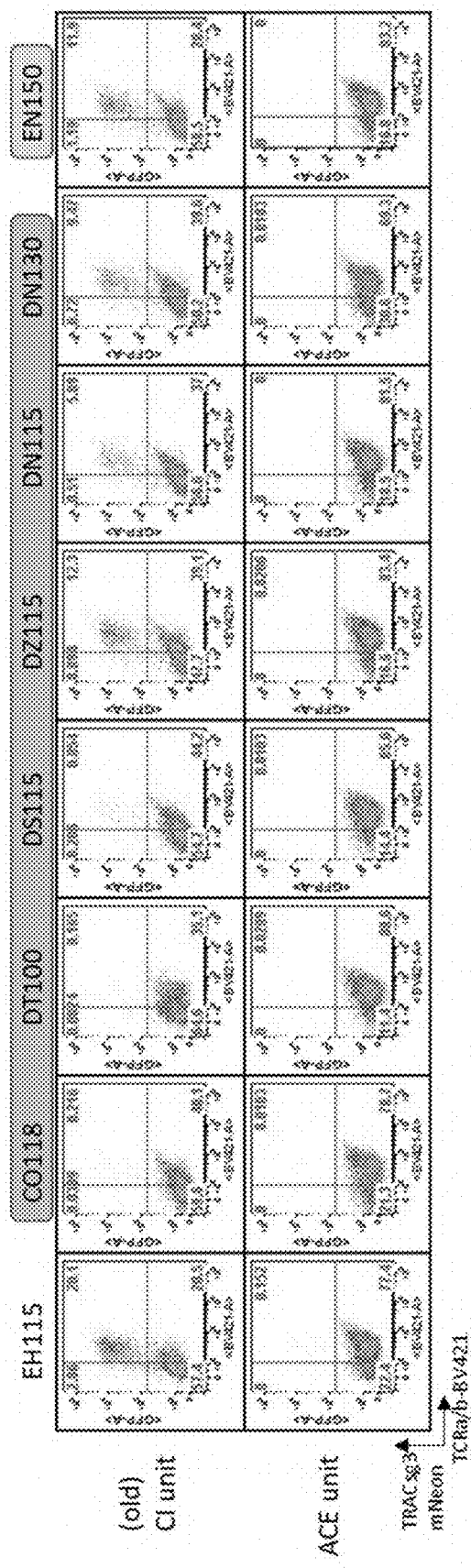

FIG. 87 is flow-cytometry analysis showing detection of knock-in positive mNeon+TCRab+ T cells for groups of cells electroporated with either CI unit electroporator (top row) or ACE electroporator (bottom row). Cells were analyzed 5 days post activation, and various pulse codes were tested.

Figure 88:
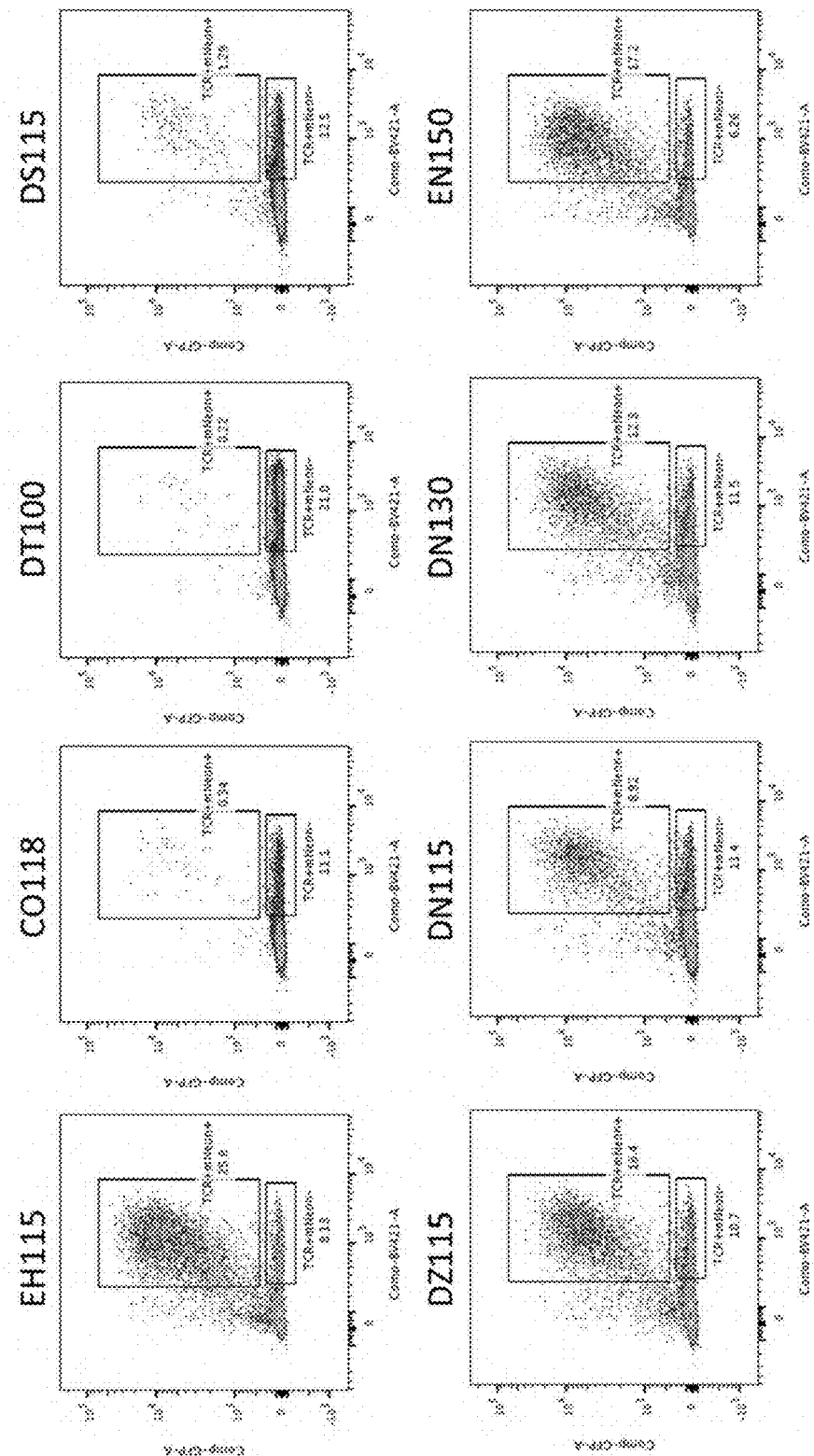

FIG. 88 are flow-cytometry analysis detecting knock-in positive mNeon+TCRab+ T cells for groups of cells electroporated with various pulse codes. Cells were analyzed 12 days post activation.

Figure 89A:
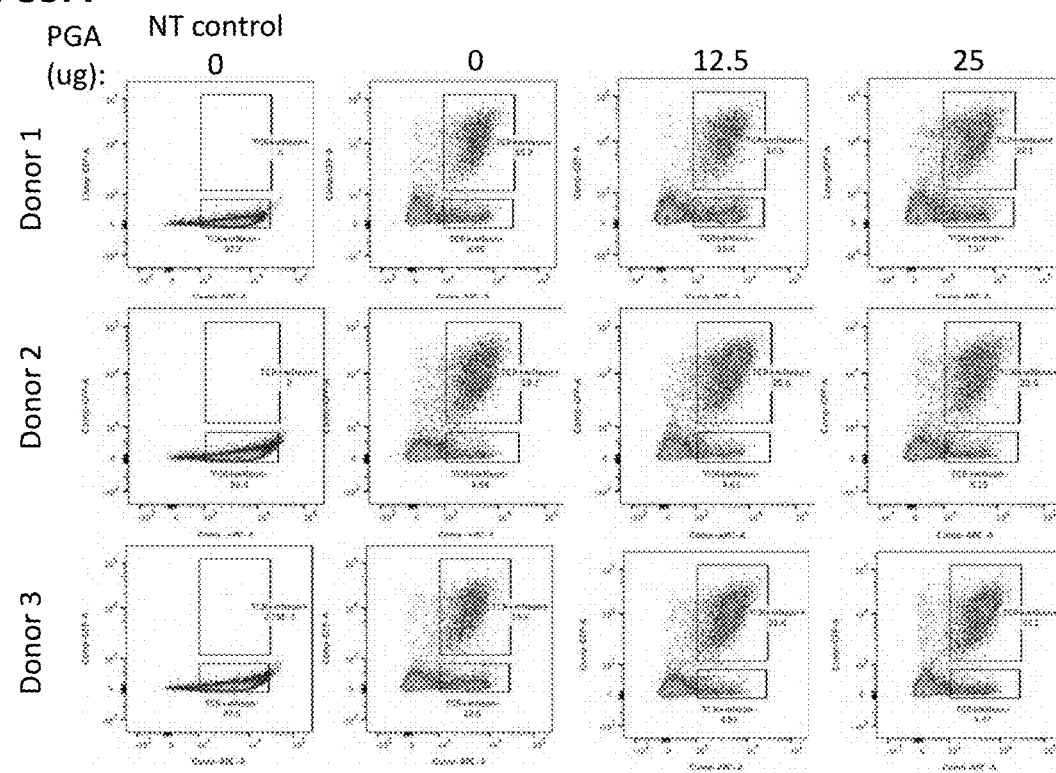
Figure 89B:
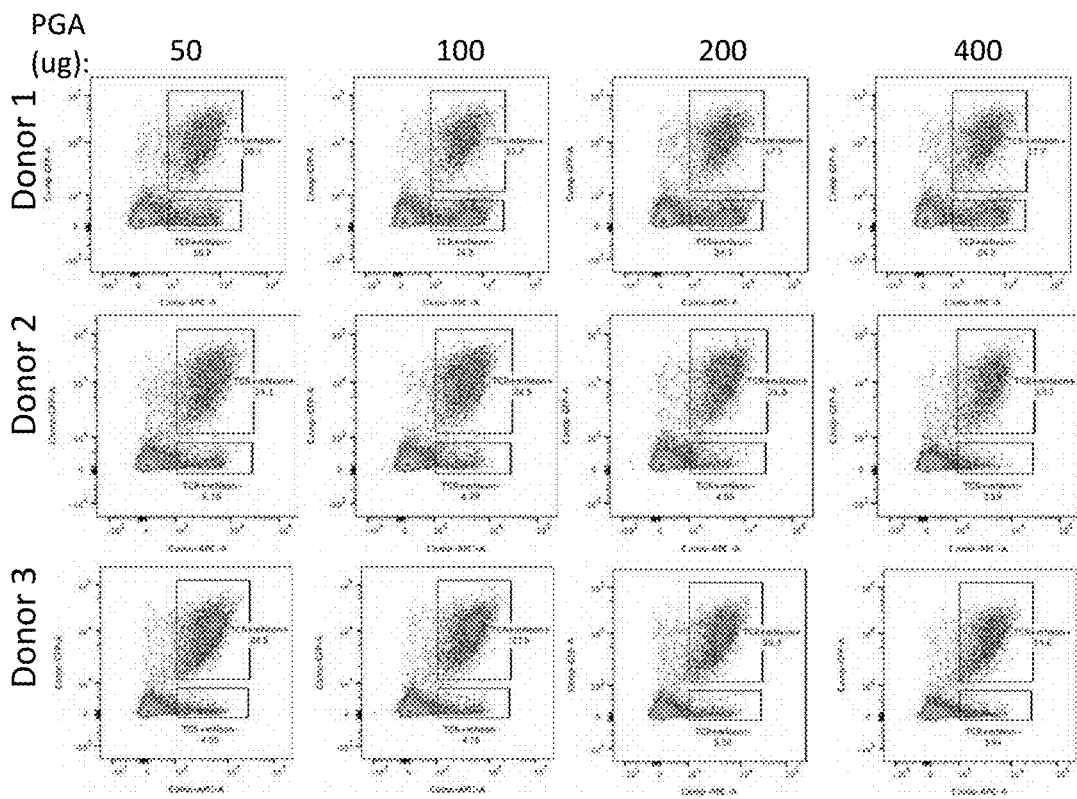

FIGS. 89A and 89B are flow-cytometry analysis showing the effect of varying concentrations of PGA on knock-in efficiency. FIG. 89A is flow-cytometry dot-plots for cells electroporated in the presence of 0, 12.5 or 254 μg PGA. Cells electroporated with NT (non-targeting guide control, i.e. no TCR knockout) RNP is a control group. FIG. 89B is flow-cytometry dot-plots for cells electroporated in the presence of 50, 100, 200 or 400 μg PGA.

Figure 90A:
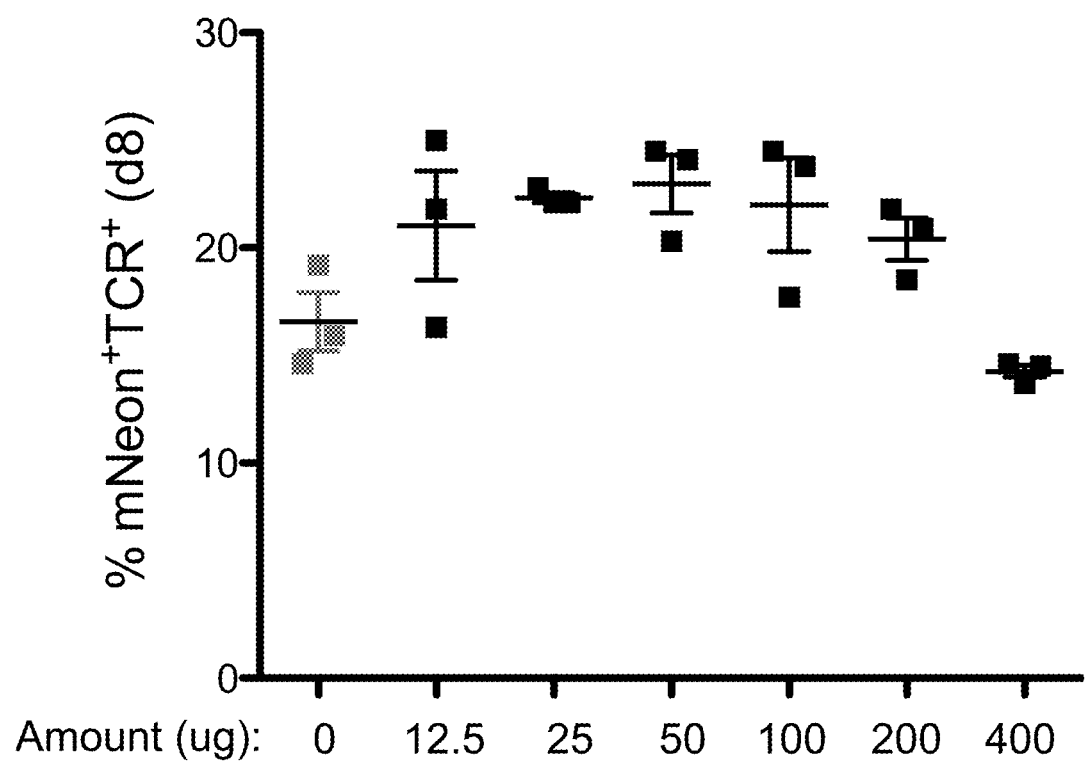
Figure 90B:
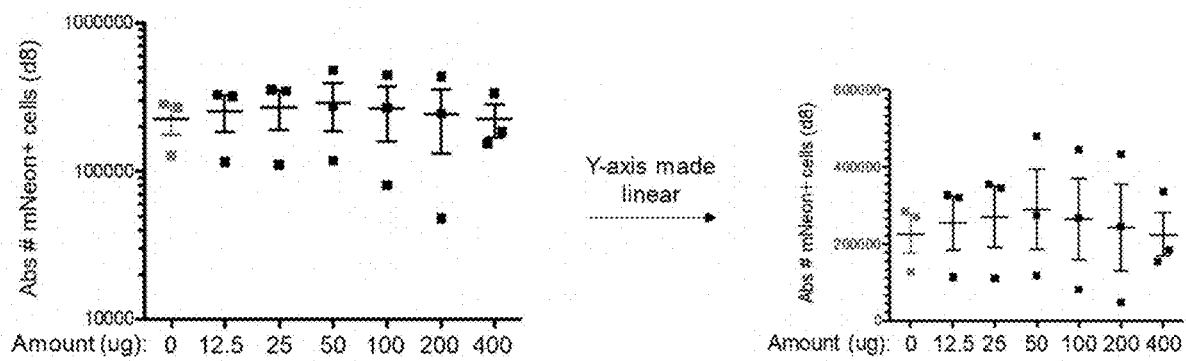

FIGS. 90A and 90B are graphs showing frequency of knock-in positive mNeon+TCRab+ cells (FIG. 90A) and recovery of mNeon+ cells (FIG. 90B) depending on the concentration of PGA used during electroporation.

Figure 91:
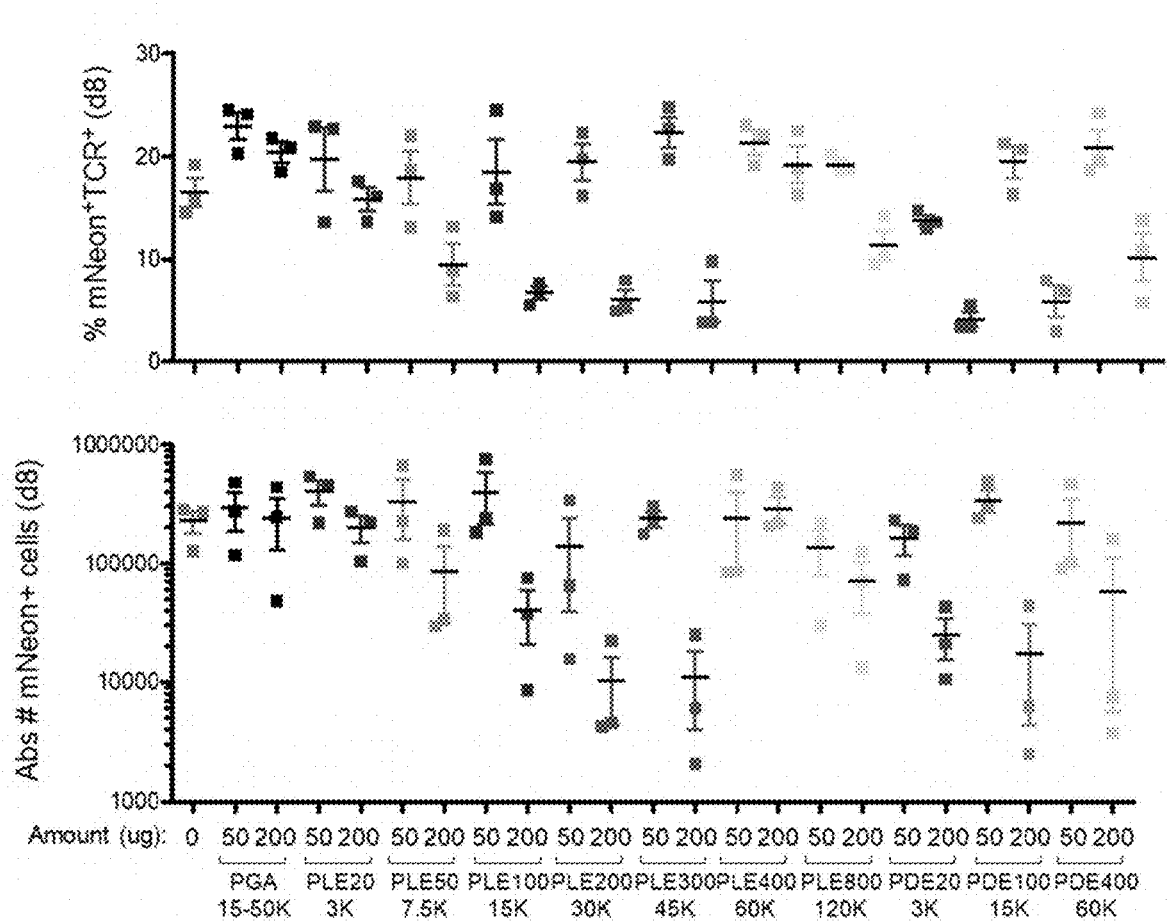
Figure 92A:
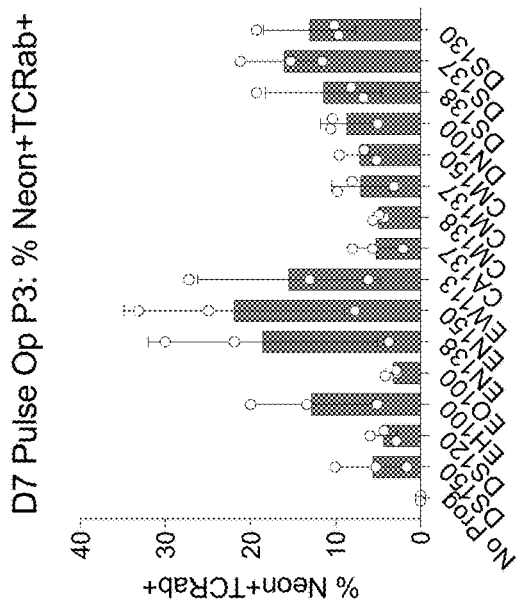
Figure 92C:
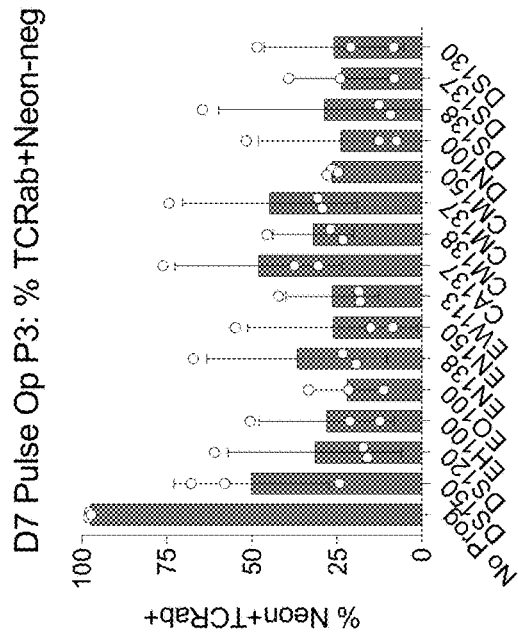
Figure 92B:
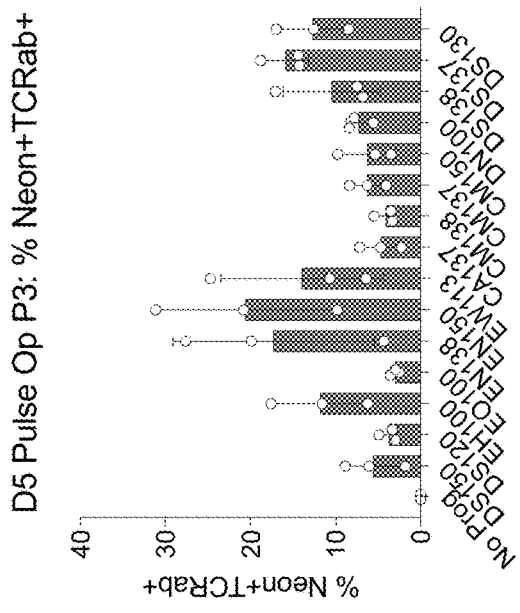
Figure 92D:
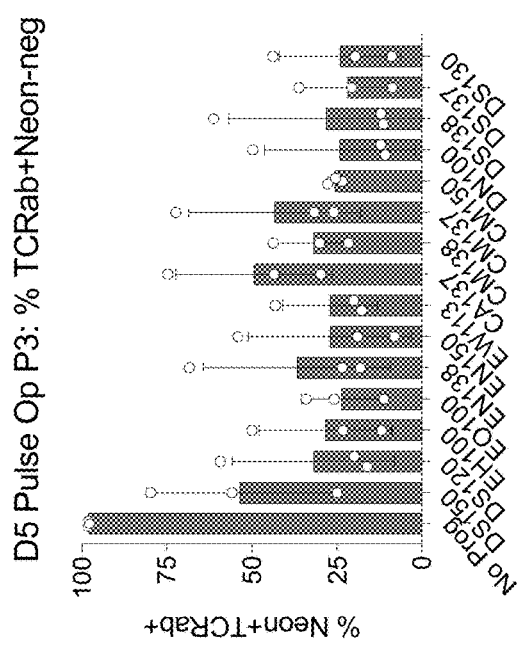

FIG. 91 shows the effects of PGA concentration and PGA variant on knock-in efficiency. Graphs illustrating frequency of knock-in positive mNeon+TCRab+ cells (top) and recovery of mNeon+ cells (bottom) are shown. PGA concentrations and variants are as indicated on the x-axis.

FIGS. 92A-92D are bar graphs illustrating the effect of electroporation pulse codes on knock-in efficiency of TRAC3-mNeon in T cells. Frequency of knock-in positive mNeon+TCRab+ cells on day 5 post activation (FIG. 92A) and day 7 post activation (FIG. 92C), and frequency of TCRab+mNeon-cells on day 5 post activation (FIG. 92B) and day 7 post activation (FIG. 92D) are shown.

Figure 93A:
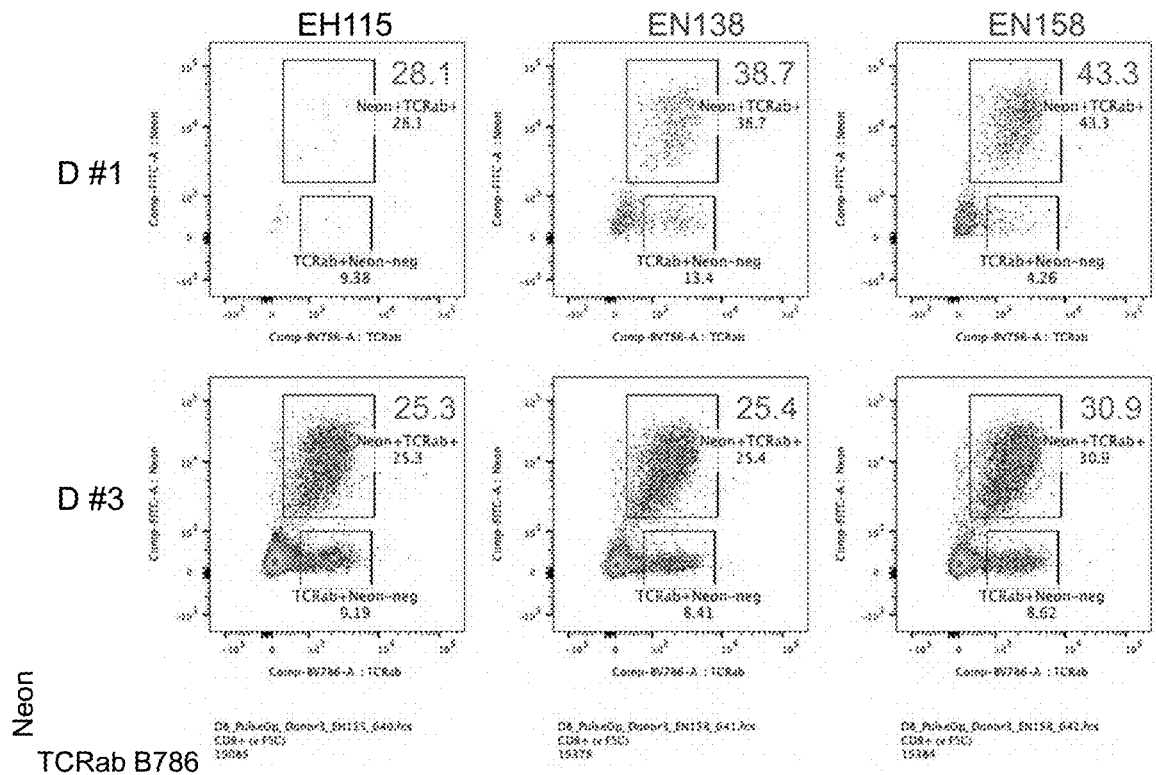
Figure 93B:
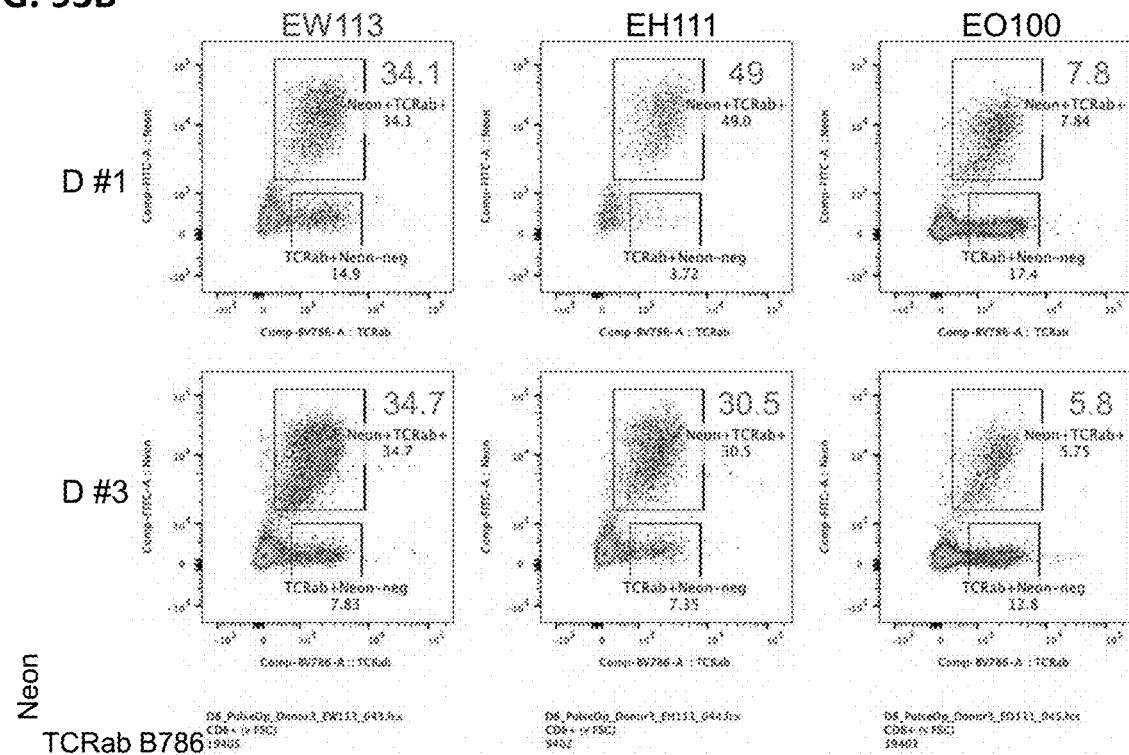

FIGS. 93A and 93B are flow-cytometry dot-plots illustrating the effect of electroporation pulse codes on TRAC3-mNeon knock-in efficiency in T cells. FIG. 93A shows flow-cytometry analysis for cells electroporated with EH115, EN138 and EN158 pulse codes. FIG. 93B shows flow-cytometry analysis for cells electroporated with EW113, EH111 and EO100 pulse codes. Percentage of mNeon+TCRab+ cells are as indicated on the top right corner of each plot.

Figure 94A:
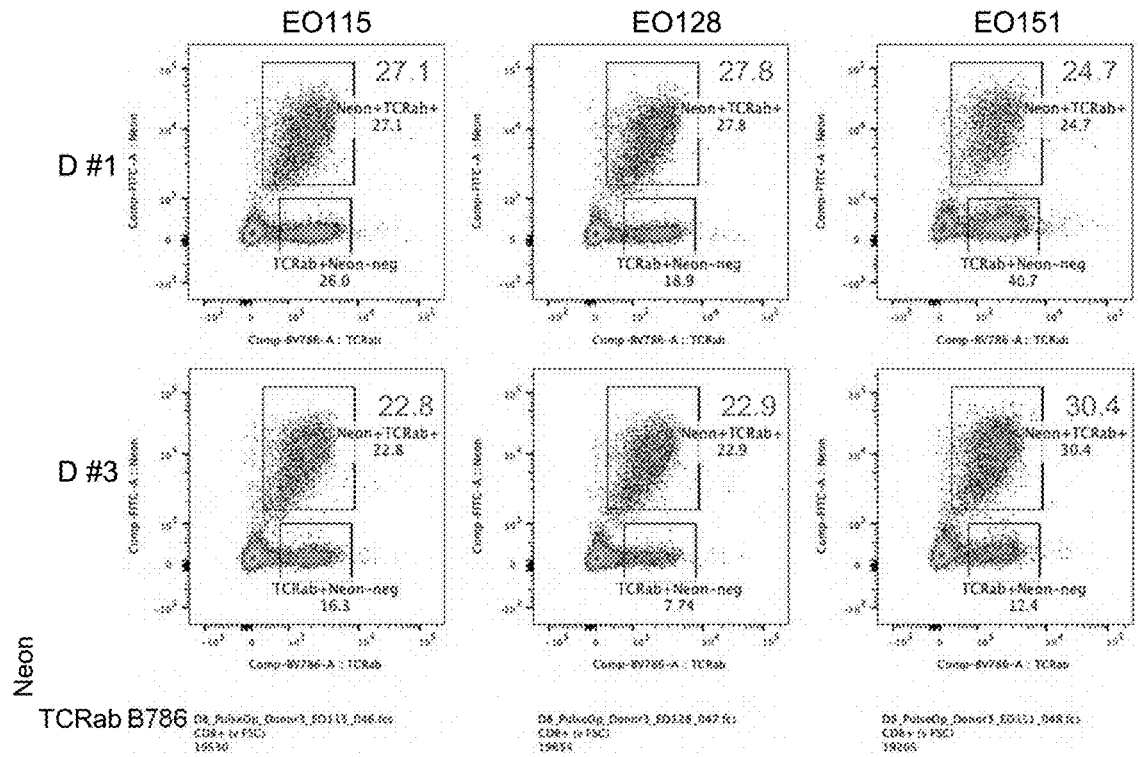
Figure 94B:
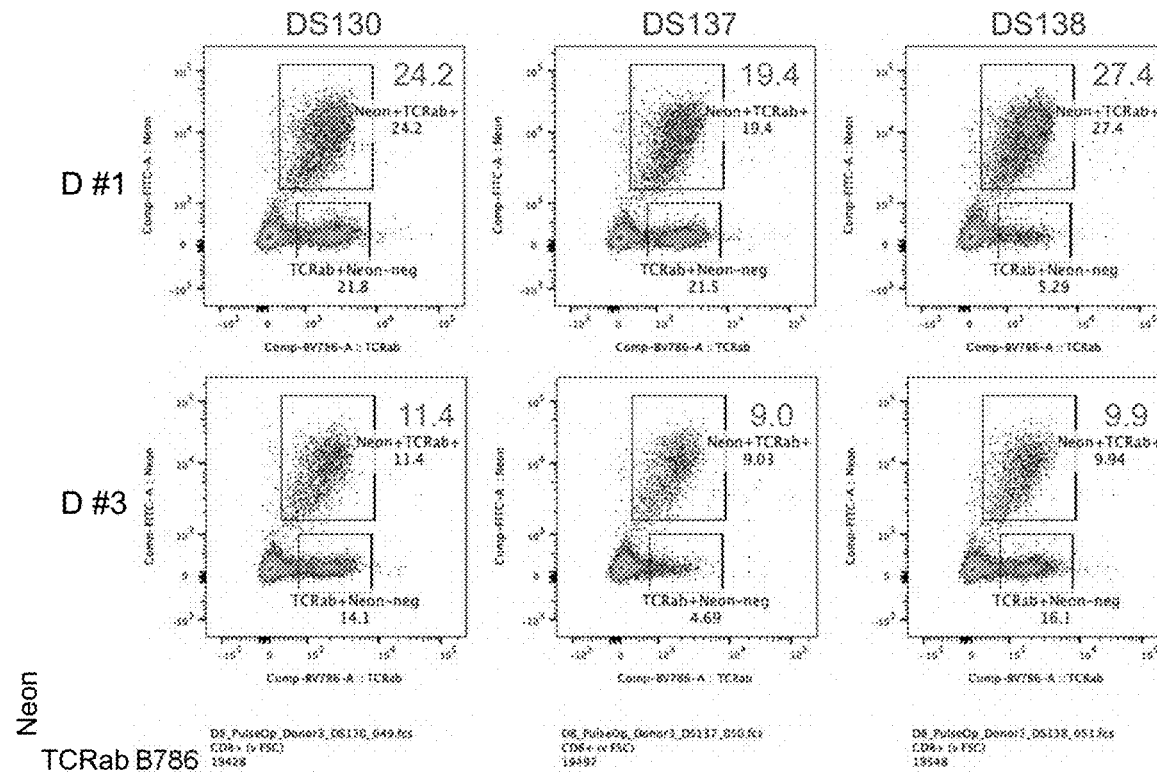
Figure 95A:
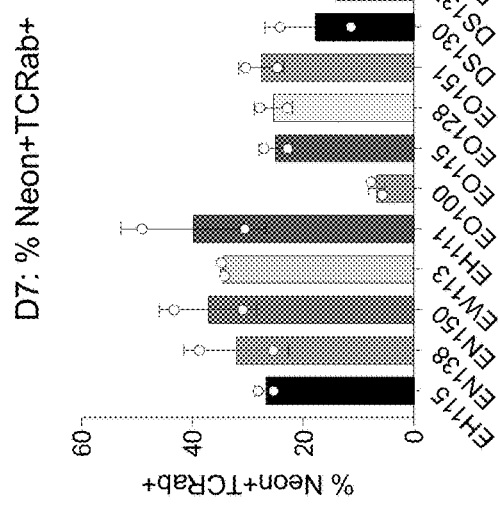
Figure 95C:
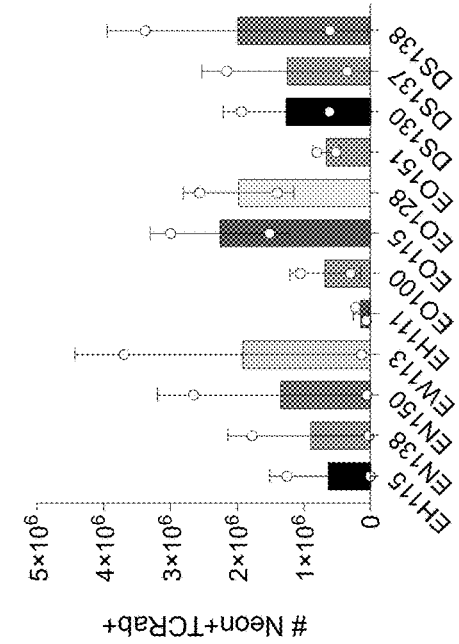
Figure 95B:
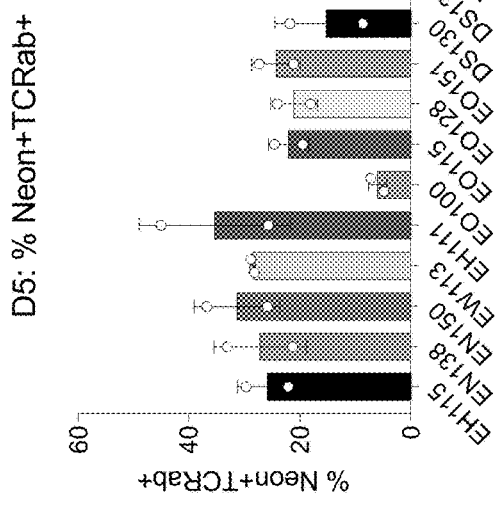
Figure 95D:
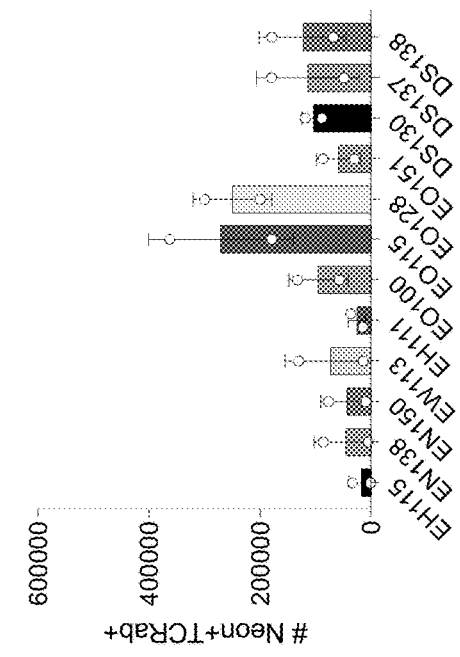

FIGS. 94A and 94B are flow-cytometry dot-plots illustrating the effect of electroporation pulse codes on TRAC3-mNeon knock-in efficiency in T cells. FIG. 94A shows flow-cytometry analysis for cells electroporated with EO115, EO128 and EO151 pulse codes. FIG. 94B shows flow-cytometry analysis for cells electroporated with DS130, DS137 and DS138 pulse codes. Percentage of mNeon+TCRab+ cells are as indicated on the top right corner of each plot.

FIGS. 95A-95D are bar graphs illustrating knock-in efficiency of TRAC3-mNeon in T cells depending on varying electroporation pulse codes, as indicated on the x-axis of the graphs. Frequency of knock-in positive mNeon+TCRab+ cells on day 5 post-activation (FIG. 95A) and day 7 post-activation (FIG. 95C), and recovery of mNeon+TCRab+ cells on day 5 post-activation (FIG. 95B) and day 7 post-activation (FIG. 95D) are shown.

Figure 96:
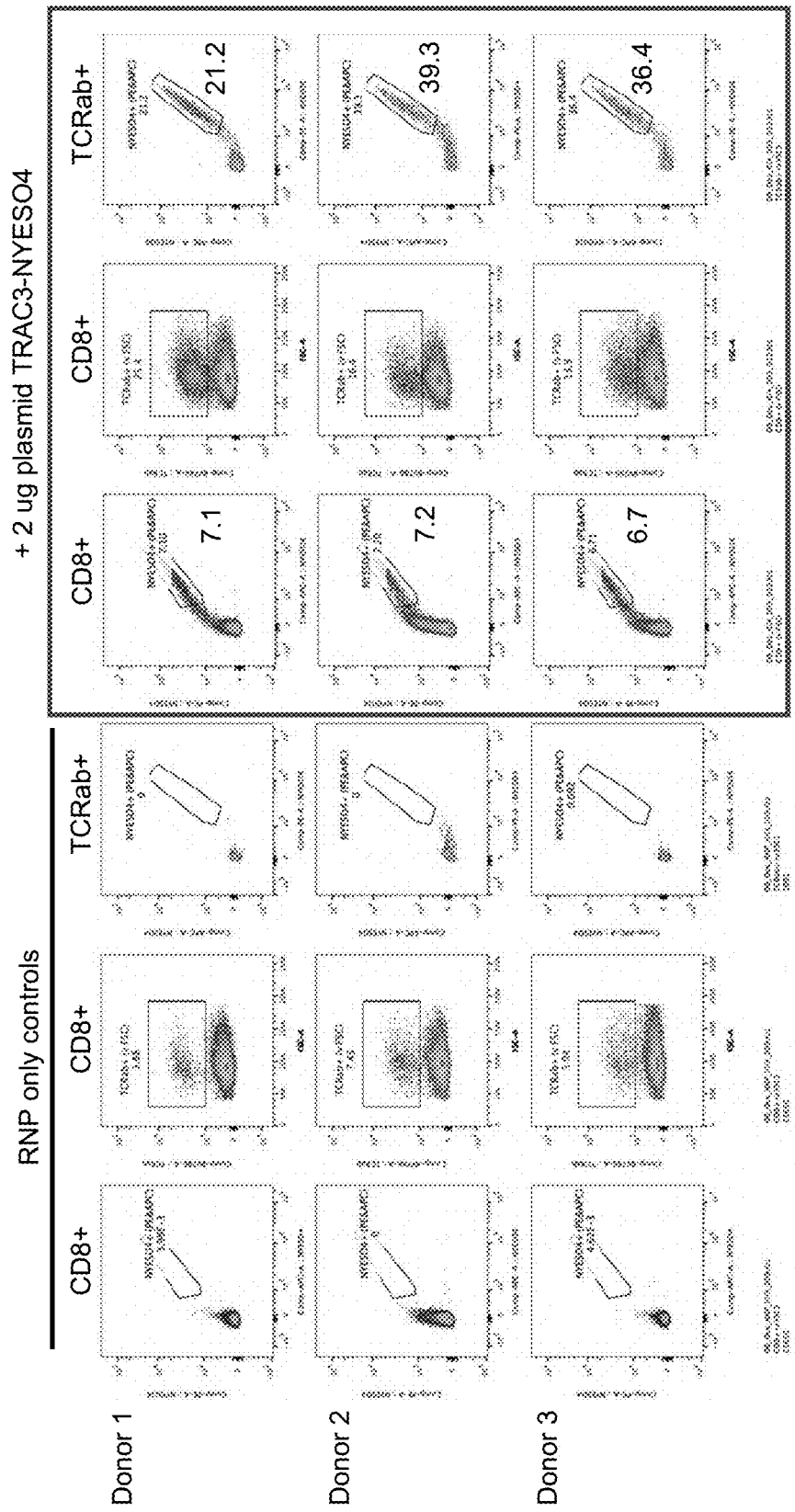

FIG. 96 is flow-cytometry analysis illustrating knock-in efficiency of TRAC3-NY-ESO-4 TCR plasmid template in T cells. Cells electroporated with RNP only (no template) are control groups (three left-most columns). From left to right for each three rows of plots, flow-cytometry analysis show detection of NY-ESO-4 TCR+ cells among total CD8+ T cells, TCRab+ cells among total CD8+ T cells, and NY-ESO-4 TCR+ cells among CD8+TCRab+ cells.

Figure 97A:
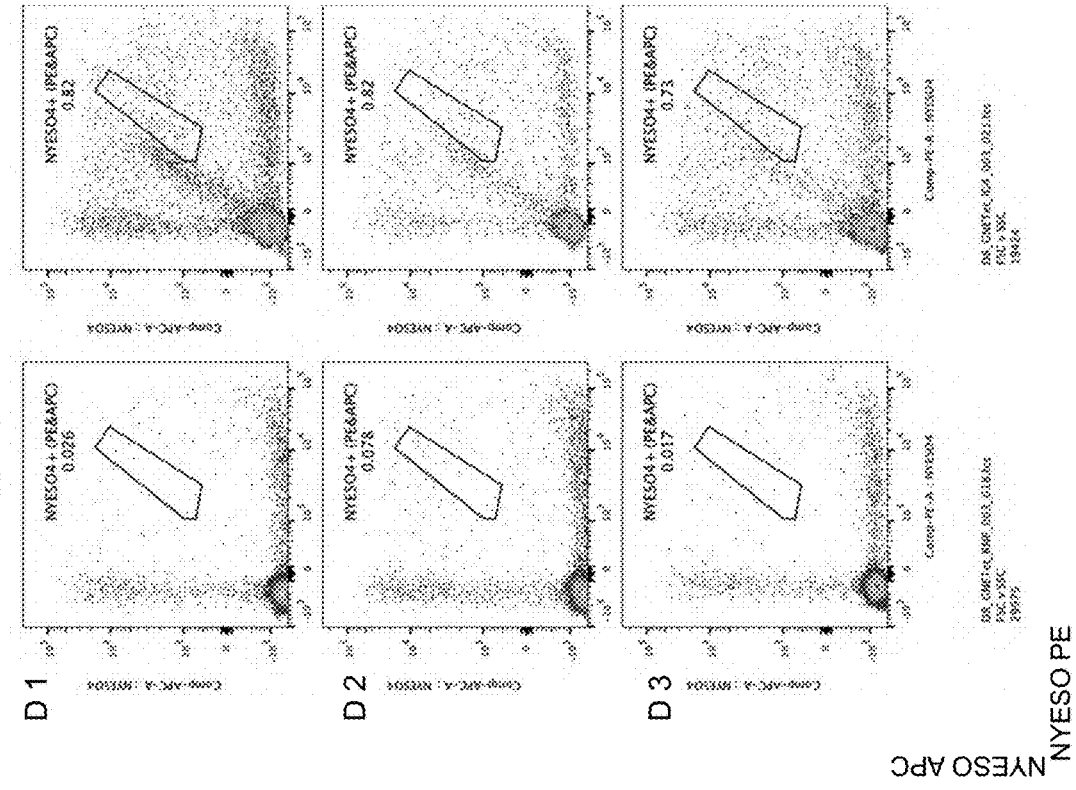
Figure 97B:
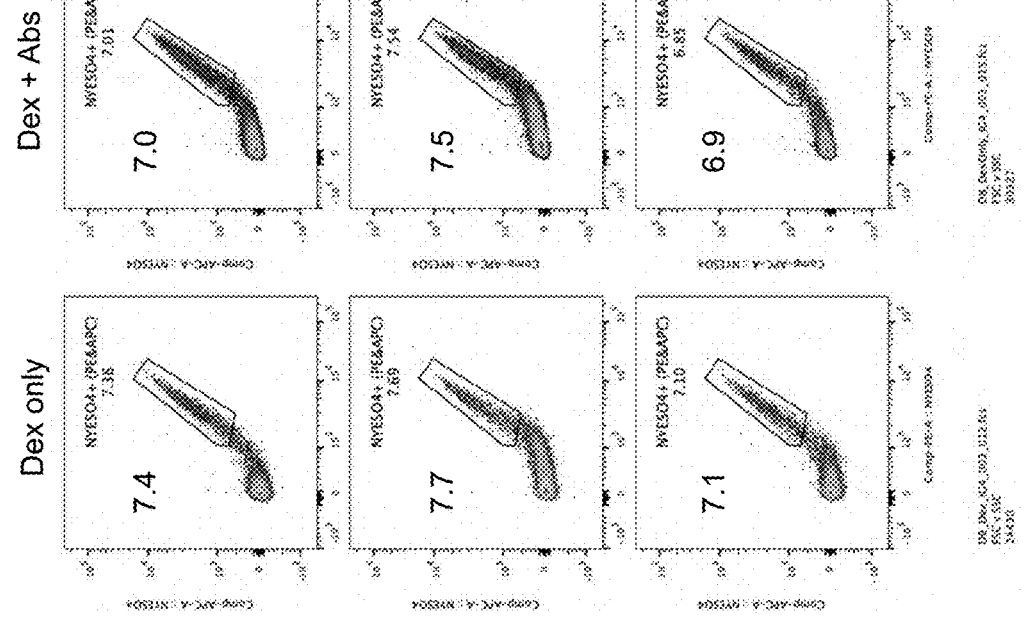

FIGS. 97A and 97B are flow-cytometry analysis illustrating effectiveness of various cell staining methods. FIG. 97A is flow-cytometry detection of NY-ESO-4 TCRab+ cells using Dextramer (Dex) stain (left) or Dextramer stain in the presence of other antibodies (right). FIG. 97B is flow-cytometry detection of NY-ESO-4 TCRab+ with GNE tetramers. Dot-plots for cells electroporated with RNP control are shown in the left column.

Figure 98:
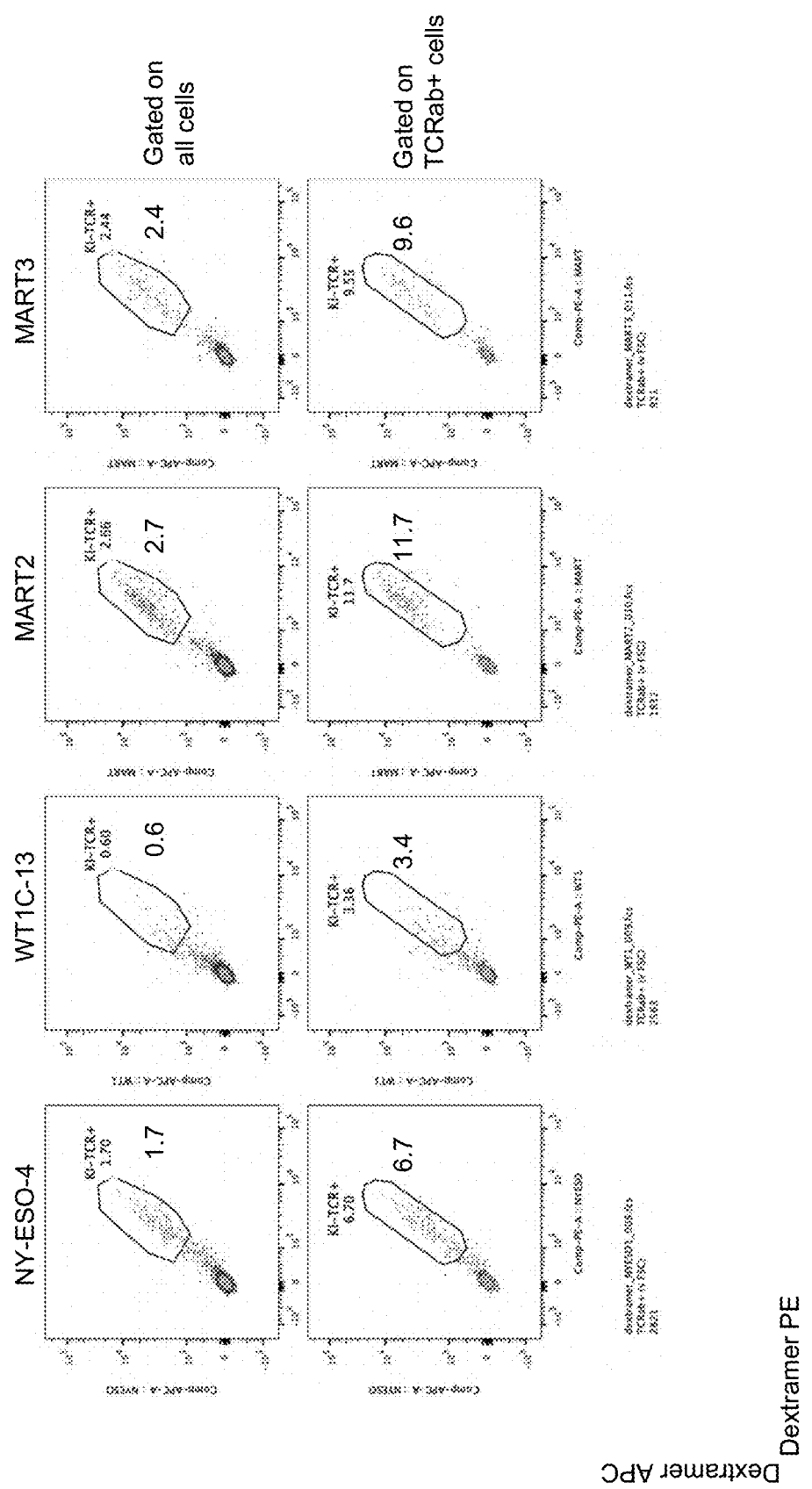

FIG. 98 is flow-cytometry analysis illustrating knock-in efficiency of various TCRs using the TRAC3 plasmid template in HLA-A0201 CD8+ T cells. TRAC3-NY-ESO-4, TRAC3-WT1C-13, TRAC3-MART2 and TRAC3-MART3 templates were used for electroporation.

Figure 99:
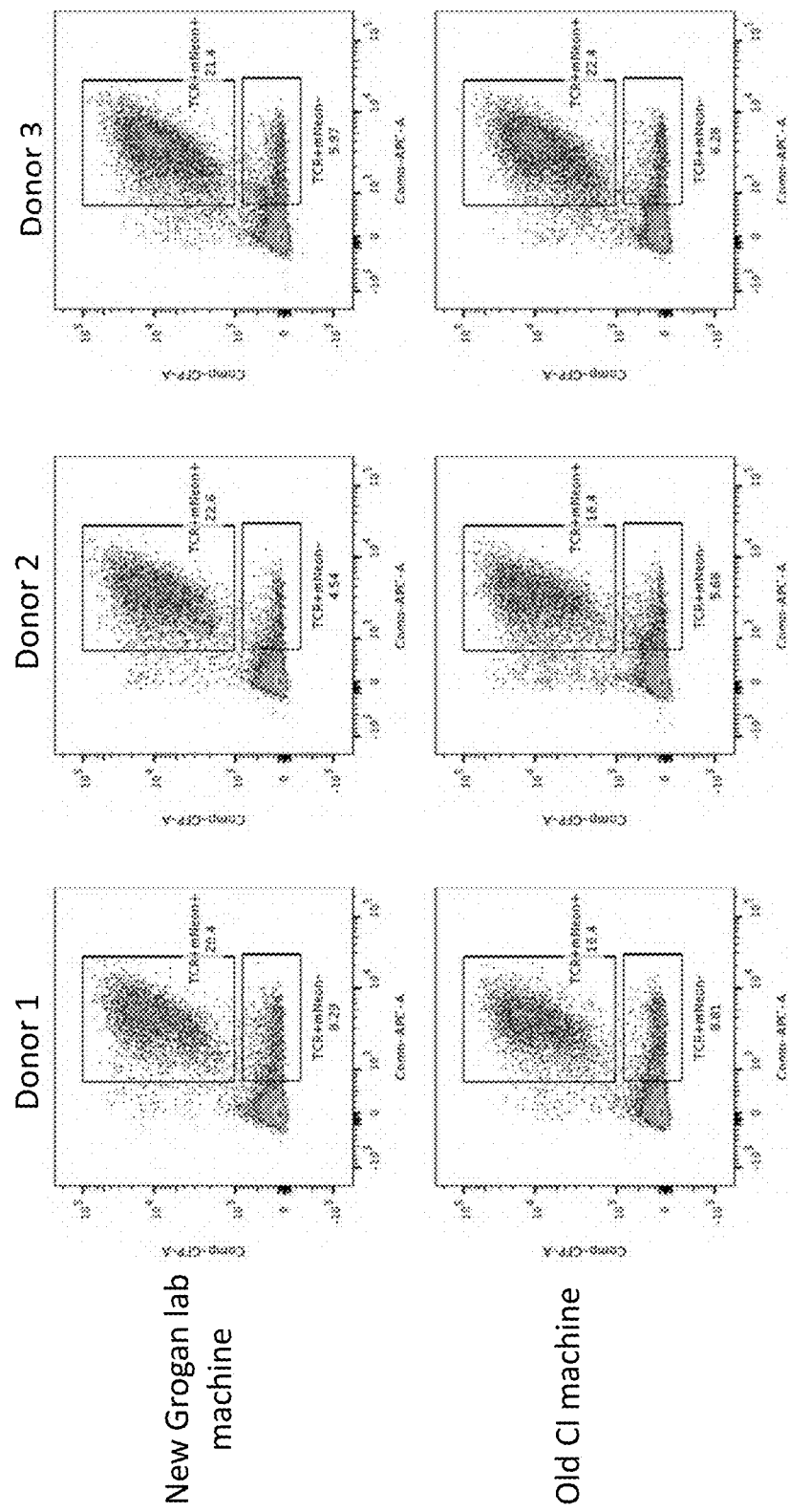

FIG. 99 is flow-cytometry analysis showing knock-in efficiency of the TRAC3-mNeon plasmid template using two different electroporators. In each dot-plot the upper box shows knock-in positive mNeon+TCRab+ cells and the lower box shows residual TCRab expressing cells.

Figure 100A:
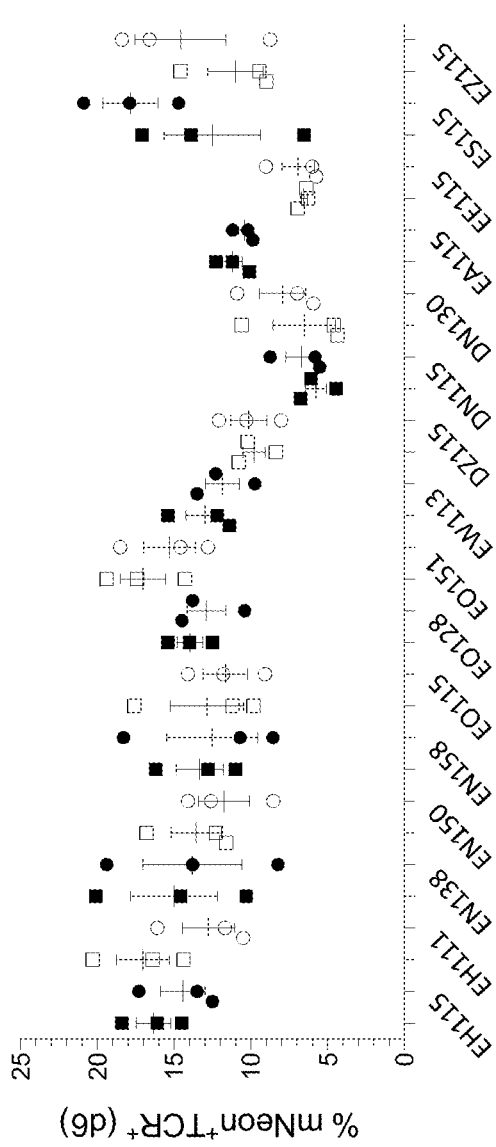
Figure 100B:
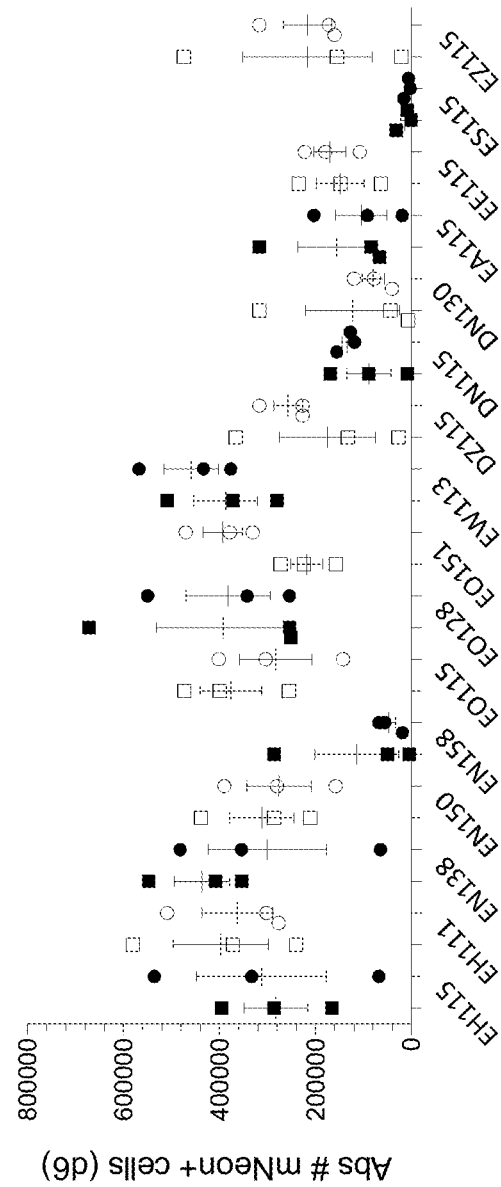

FIGS. 100A and 100B are graphs comparing frequency of knock-in positive mNeon+TCRab+ T cells (FIG. 100A) and number of mNeon+ T cells (FIG. 100B) on day 6 post-activation, depending on pulse code used for electroporation. Pulse codes used are as indicated on the x-axis and the four right-most pulse codes are made-up codes. The square and circle data markers represent data for cells electroporated with two different electroporators.

Figure 101A:
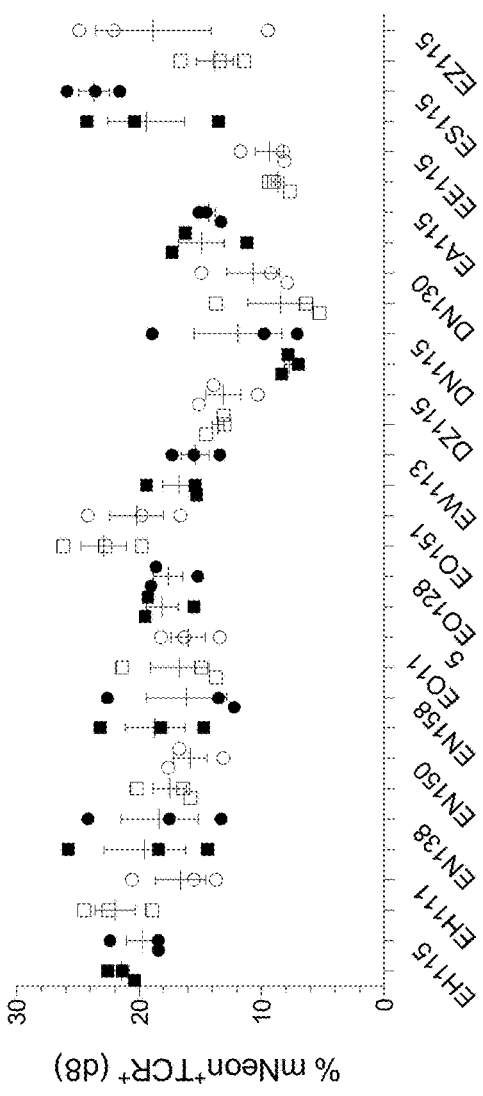
Figure 101B:
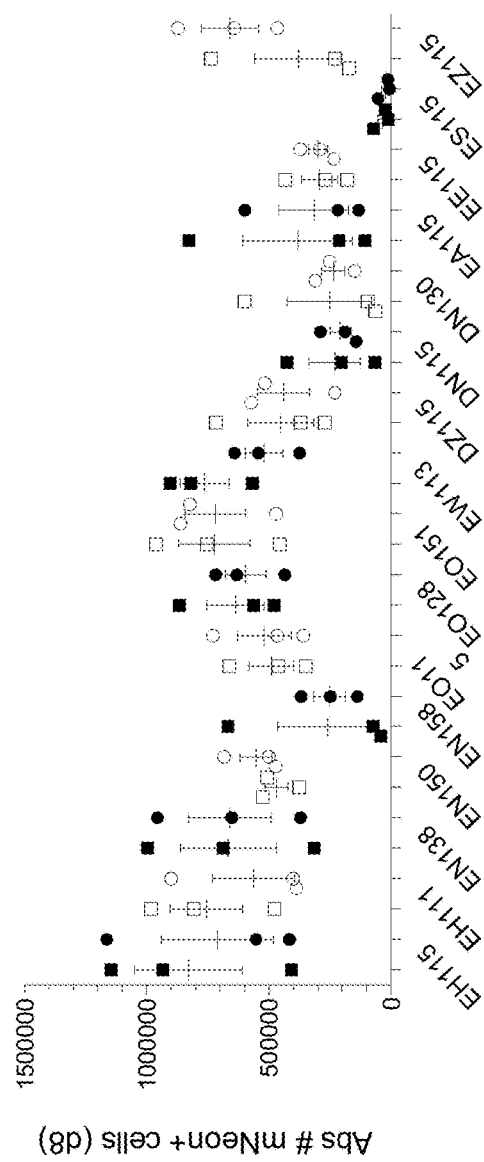

FIGS. 101A and 101B are graphs comparing frequency of knock-in positive mNeon+TCRab+ T cells (FIG. 101A) and number of mNeon+ T cells (FIG. 101B) on day 8 post-activation, depending on pulse code used for electroporation. Pulse codes used are as indicated on the x-axis and the four right-most pulse codes are made-up codes. The square and circle data markers represent data for cells elecroporated with two different electroporators.

Figure 102A:
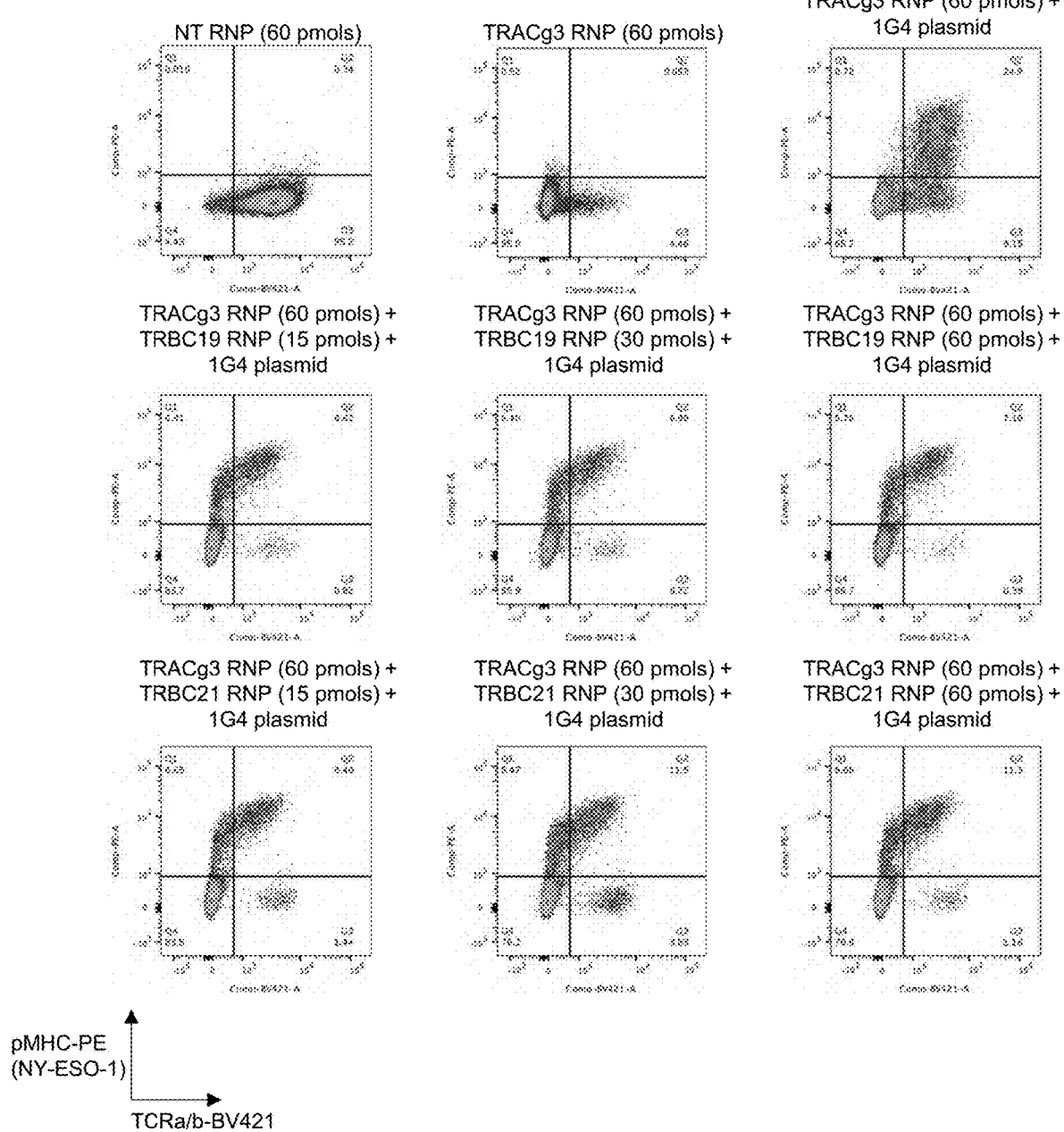
Figure 102B:
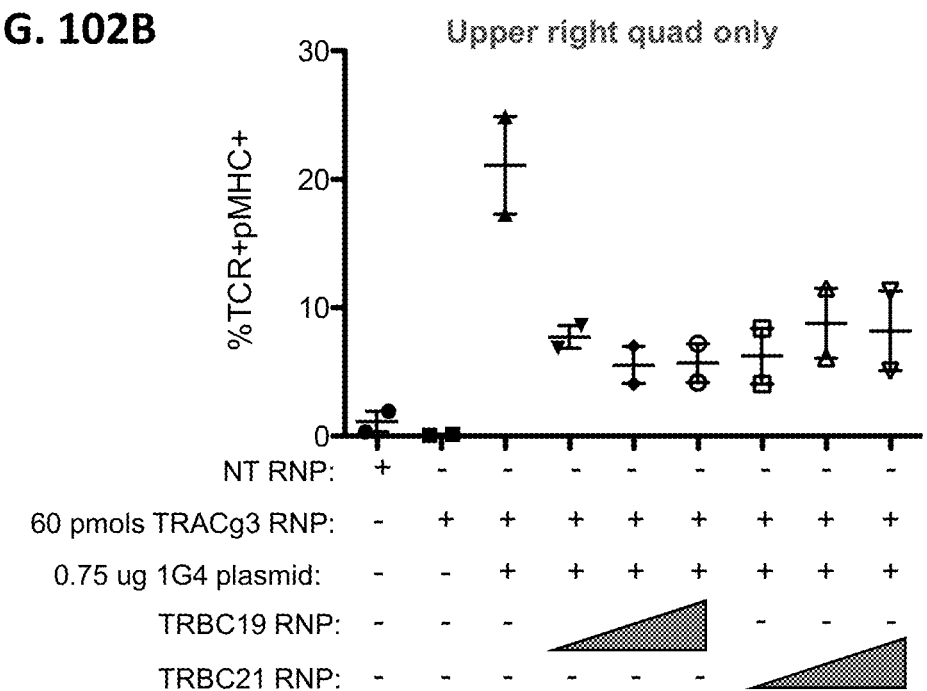
Figure 102C:
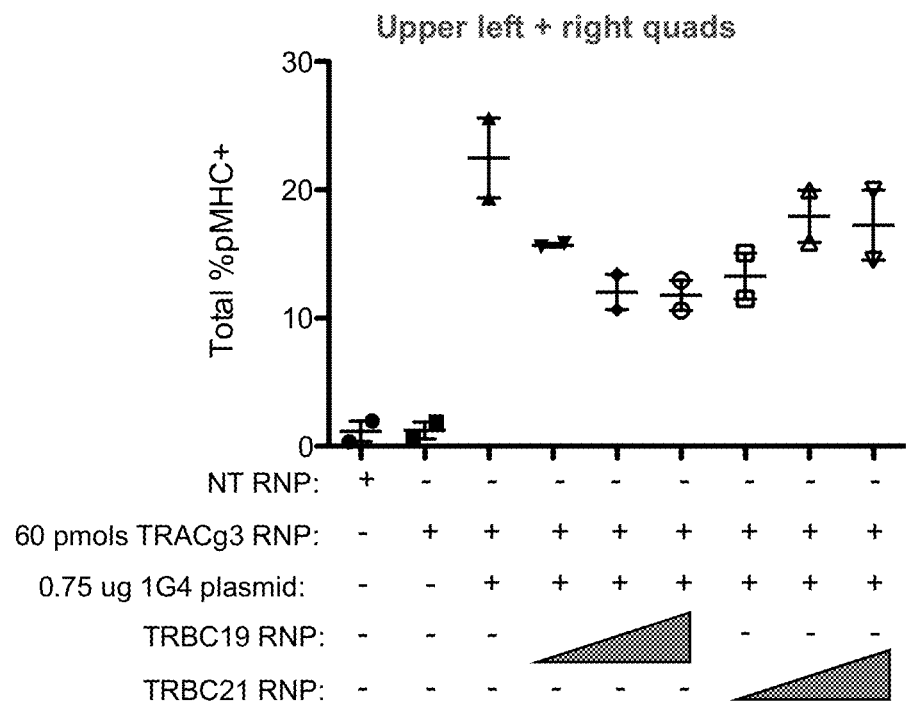

FIGS. 102A-102C illustrate the effect of TRBC RNP on knock-in efficiency of the NY-ESO1 TCR to the TRAC locus, using the TRAC3-1G4 (NY-ESO1) plasmid. FIG. 102A is flow-cytometry analysis of knock-in positive pMHC (NY-ESO1)+TCRab+ cells using various RNPs as indicated above each dot-plot. FIG. 102B is a graph showing frequency of TCRab+pMHC+ cells and FIG. 102C is a graph showing frequency of total pMHC+ cells. RNPs used for electroporation are as indicated under the graphs.

Figure 103A:
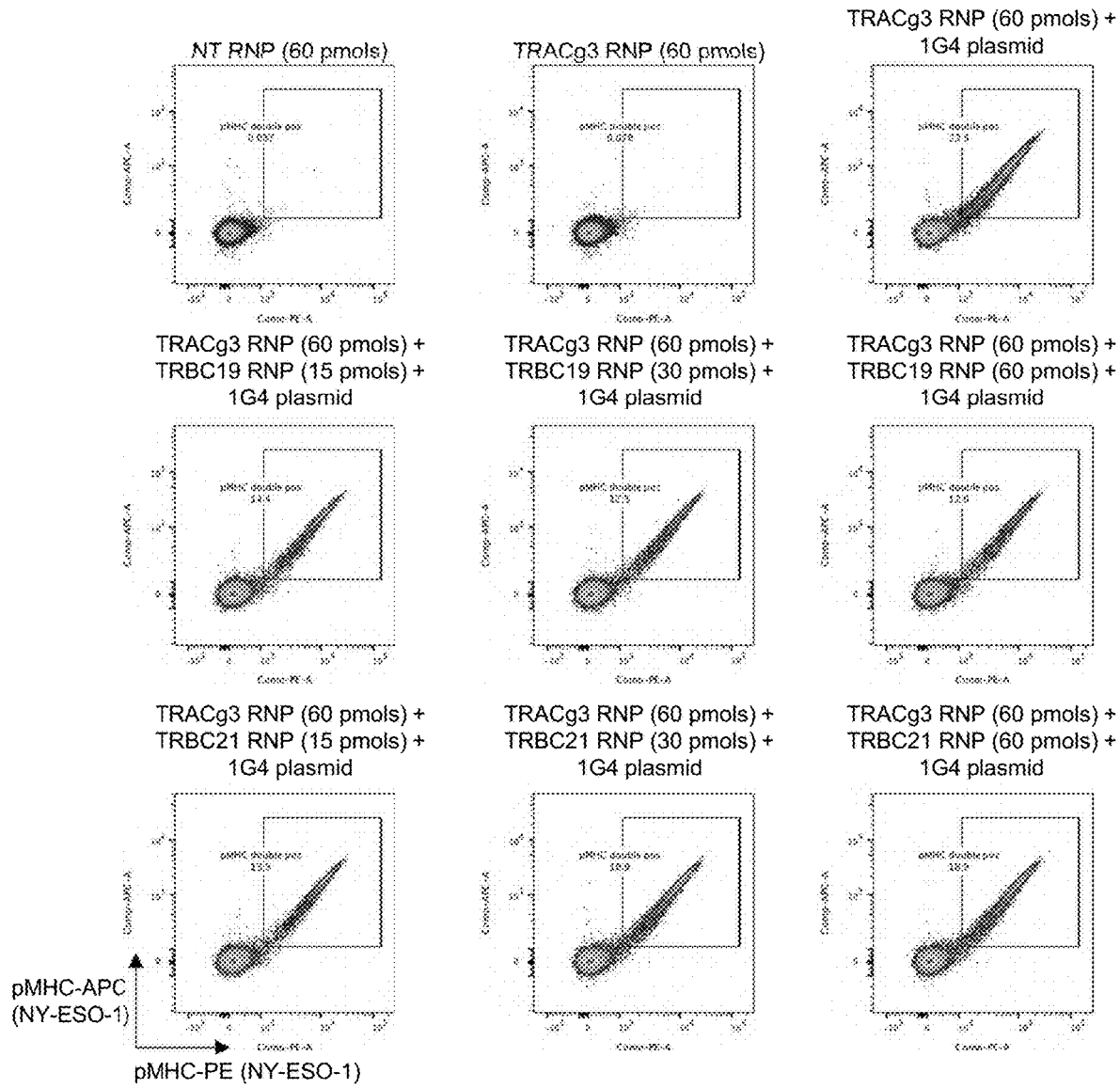
Figure 103B:
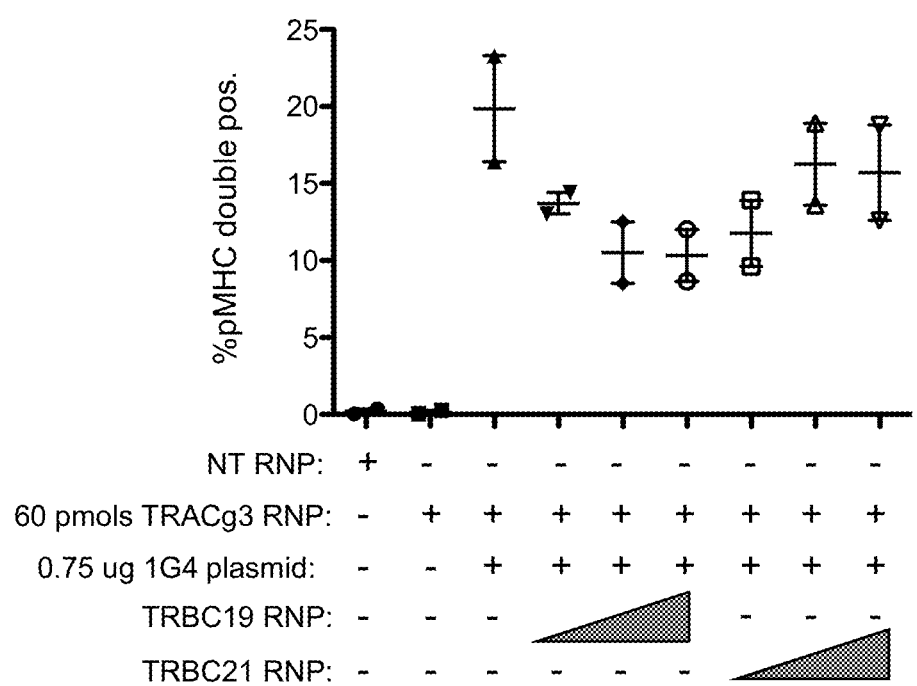

FIGS. 103A and 103B illustrate the effect of TRBC distinct TBBC RNPs on knock-in efficiency of the NY-ESO1 TCR to the TRAC locus in combination with the TRAC3 RNP, using the TRAC3-1G4 (NY-ESO1) plasmid. FIG. 103A is flow-cytometry analysis showing detection of double positive pMHC (NY-ESO1)+ cells using various RNPs as indicated above each dot-plot. FIG. 103B is a graph showing frequency of double positive pMHC+ cells. RNPs used for electroporation are as indicated under the graph.

Figure 104A:
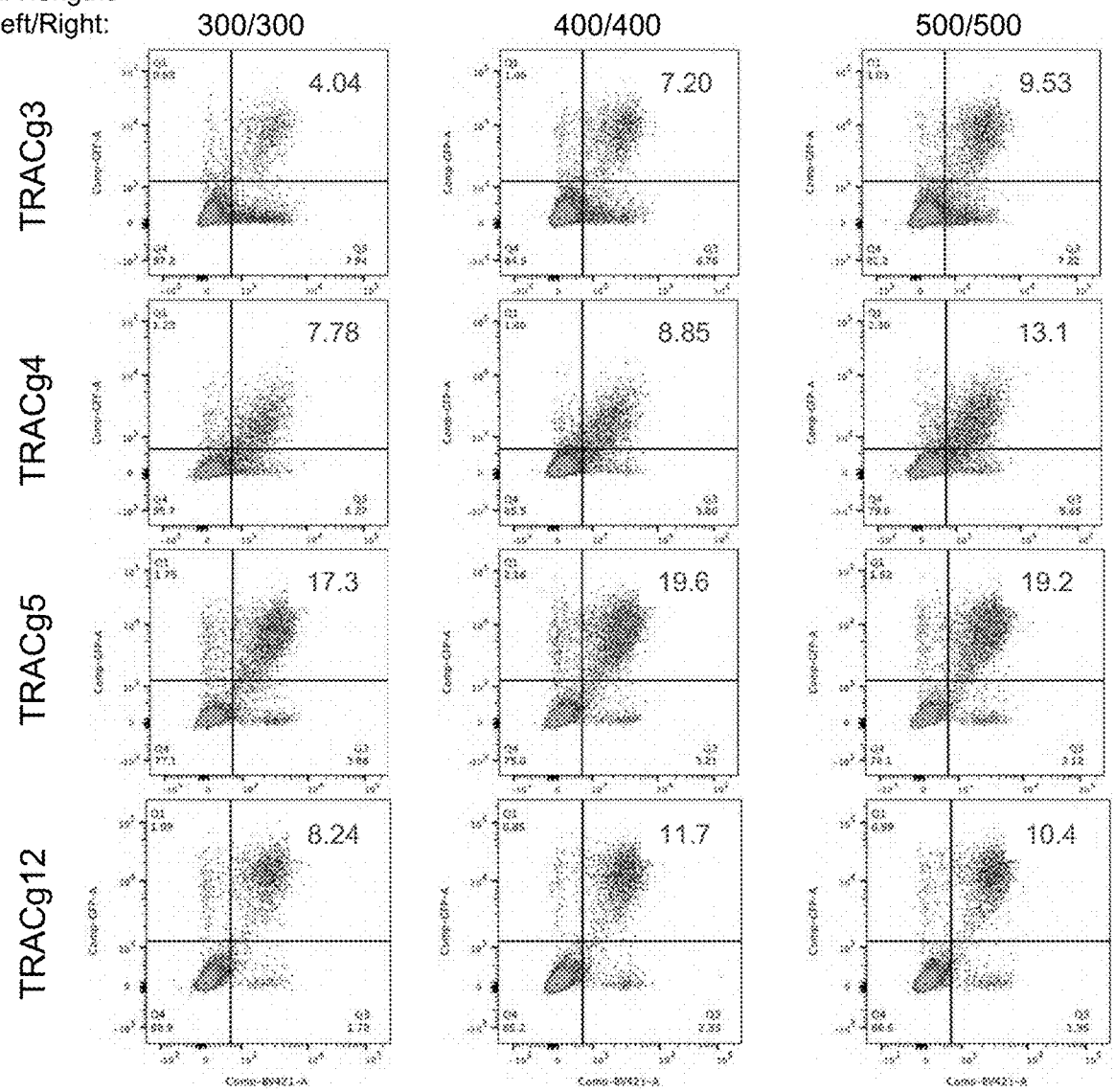
Figure 104B:
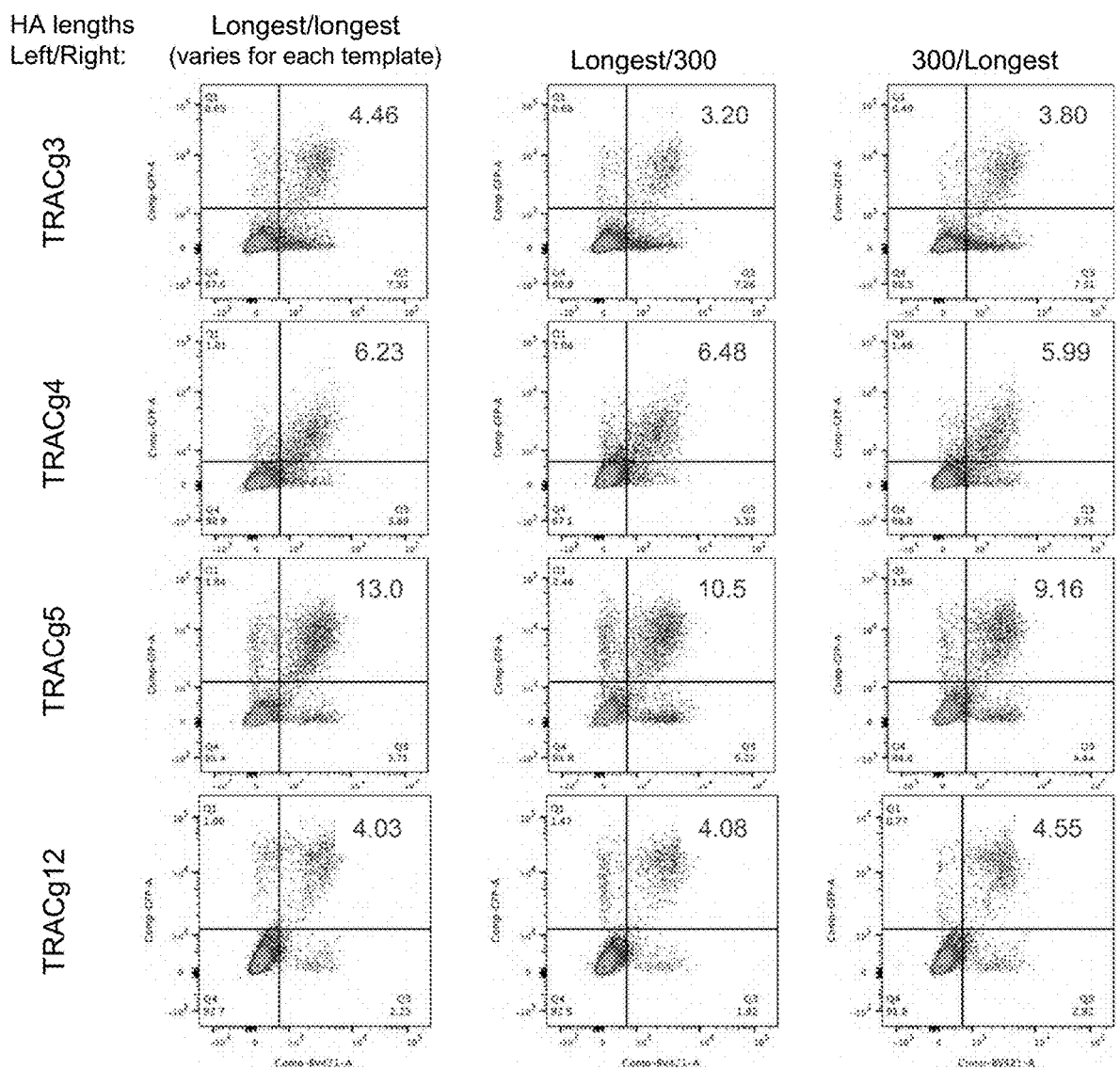
Figure 105A:
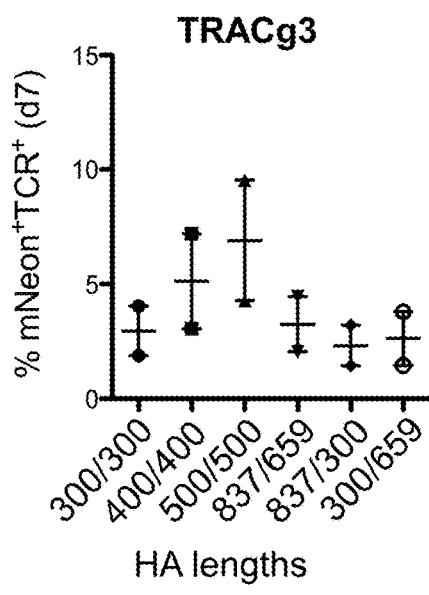
Figure 105C:
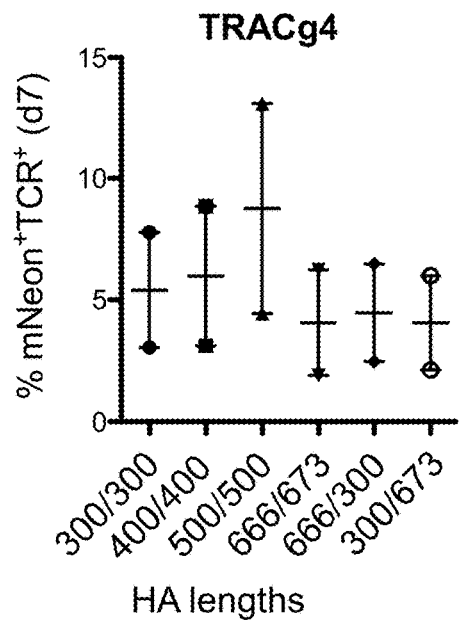
Figure 105B:
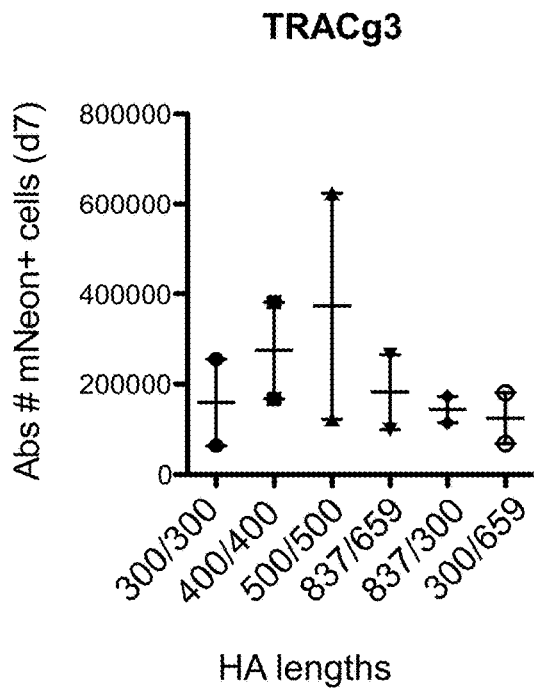
Figure 105D:
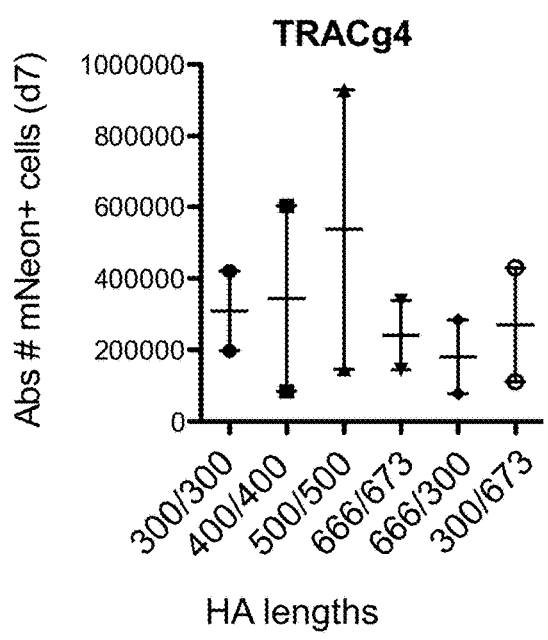
Figure 105E:
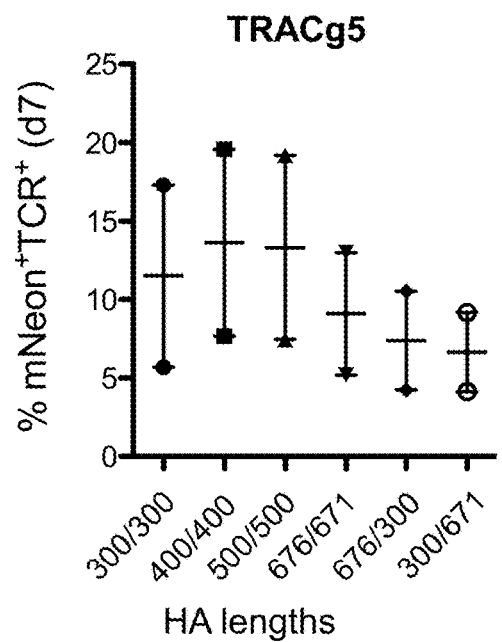
Figure 105G:
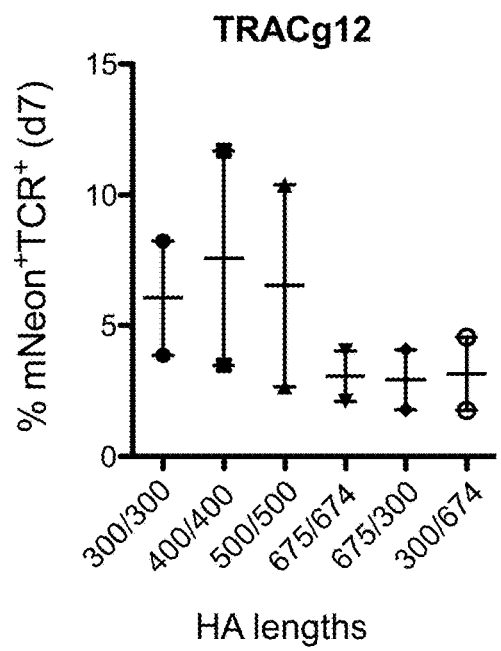
Figure 105F:
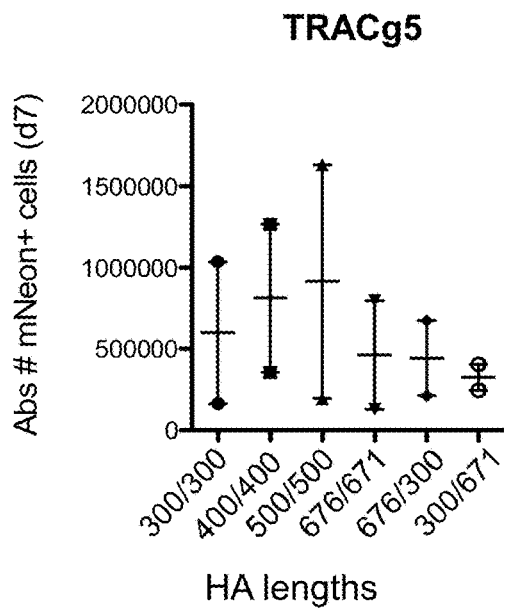
Figure 105H:
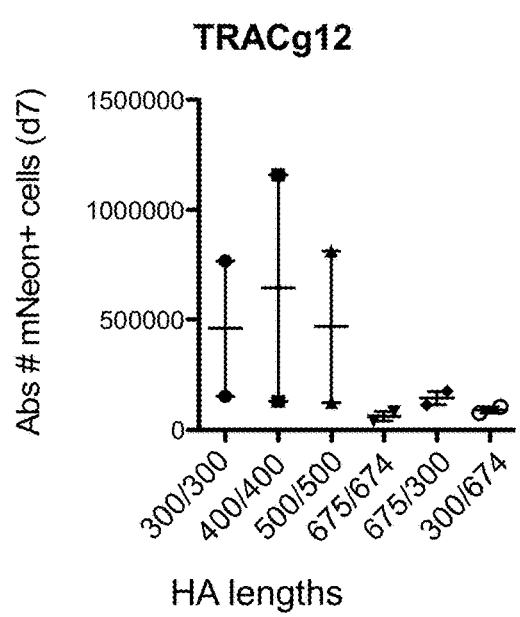

FIGS. 104A and 104B show the effect of different homology arm lengths on knock-in efficiency of TRACsg3-mNeon, TRACsg4-mNeon, TRACsg5-mNeon, and TRACsg12-mNeon templates in T cells. Flow-cytometry analysis showing knock-in efficiency as a function of homology arm lengths (HA lengths) for left/right arms 300/300, 400/400 and 500/500 (FIG. 104A) and longest/longest (varies for each template), longest/300 and 300/longest (FIG. 104B) are shown.

FIGS. 105A-105H are graphs illustrating the effect of different homology arm lengths on knock-in efficiency of TRACsg3-mNeon, TRACsg4-mNeon, TRACsg5-mNeon, and TRACsg12-mNeon templates in T cells. Frequency of knock-in positive mNeon+TCRab+ cells using the TRAC3-mNeon (FIG. 105A), TRAC4-mNeon (FIG. 105C), TRAC5-mNeon (FIG. 105E) or TRAC12-mNeon (FIG. 105G) templates for electroporation are shown. Numbers of mNeon+ cells using the TRAC3-mNeon (FIG. 105B) and TRAC4-mNeon (FIG. 105D) TRAC5-mNeon (FIG. 105F) or TRAC12-mNeon (FIG. 105H) templates for electroporation are shown. Varying homology arm (HA) lengths for left/right arms are as indicated on the x-axis.

Figure 106:
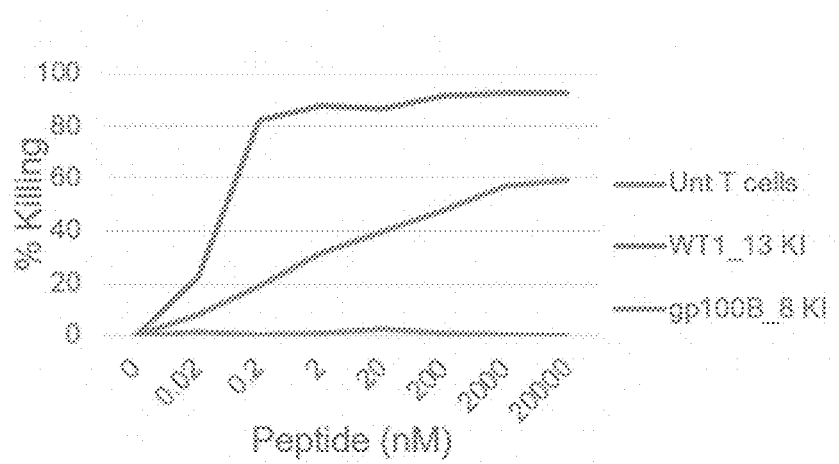

FIG. 106 is a graph illustrating T2 cell killing by WT1 and gp100B TCR knock-in cells. T2 cells were electroporated with varying concentrations of target peptides.

Figure 107A:
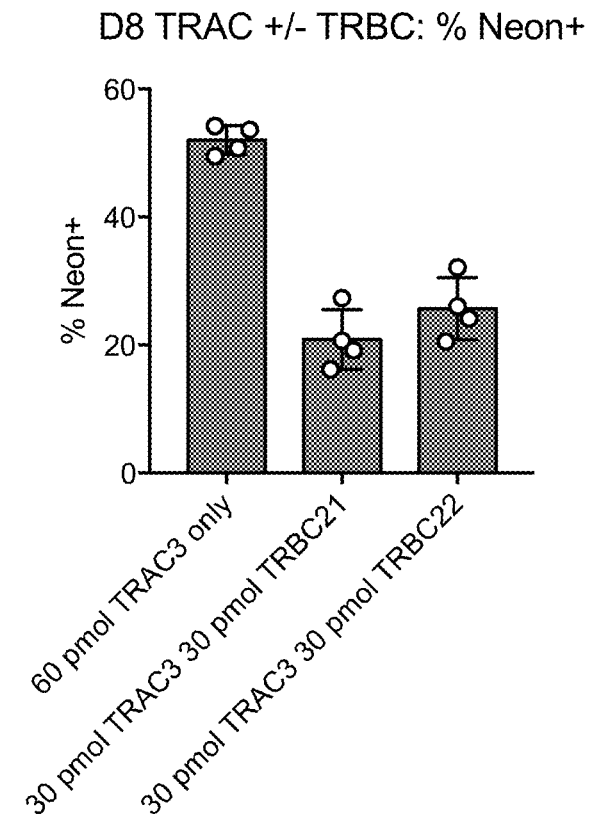
Figure 107B:
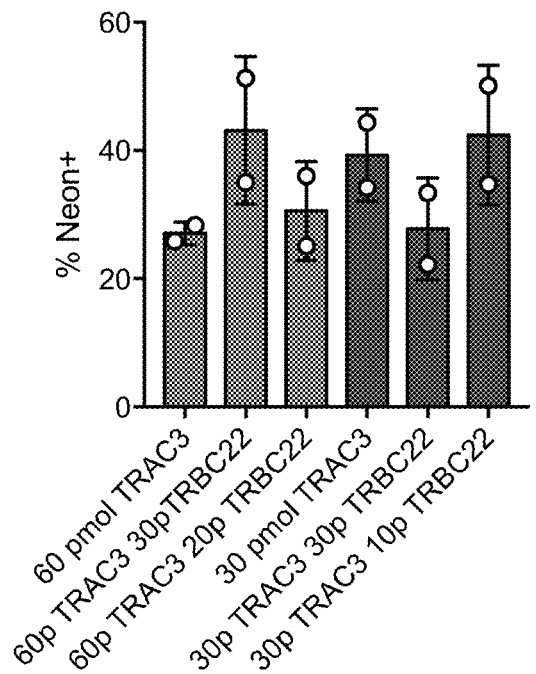
Figure 107C:
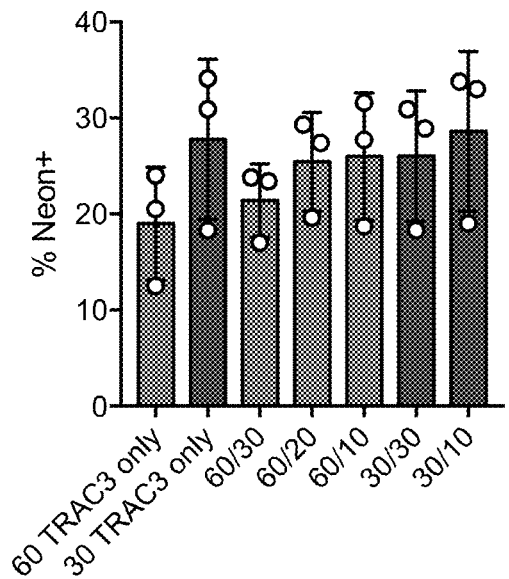
Figure 107D:
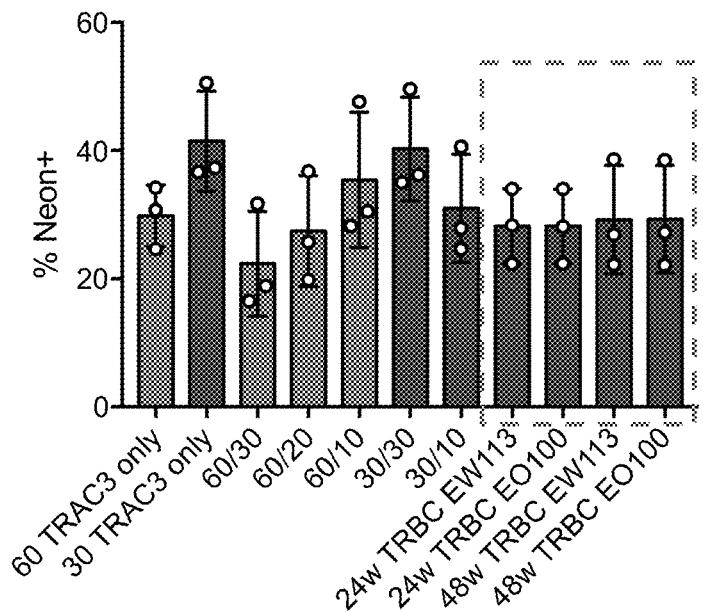

FIGS. 107A-107D are graphs showing the overall effect of TRBC22 RNP titration. FIG. 107A shows the percentage of Neon-positive TRAC+/−TRBC samples on Day 8 post-electroporation under the indicated conditions. FIG. 107B shows the percentage of Neon-positive samples on Day 8 post-electroporation under the indicated conditions. FIG. 107C shows the percentage of Neon-positive TRAC3/TRBC22 samples on Day 7 post-electroporation under the indicated conditions. FIG. 107D shows the percentage of Neon-positive TRAC3/TRBC22 samples on Day 7 post-electroporation under the indicated conditions. The dashed box in FIG. 107D shows the second electroporation with TRBC22 RNP 24 hours later, comparing EW113 and EO100. 24 w versus 48 w indicate whether cells were cultured in a 24-well or 48-well plate following the first electroporation (2×10$^6$ cells).

Figure 108A:
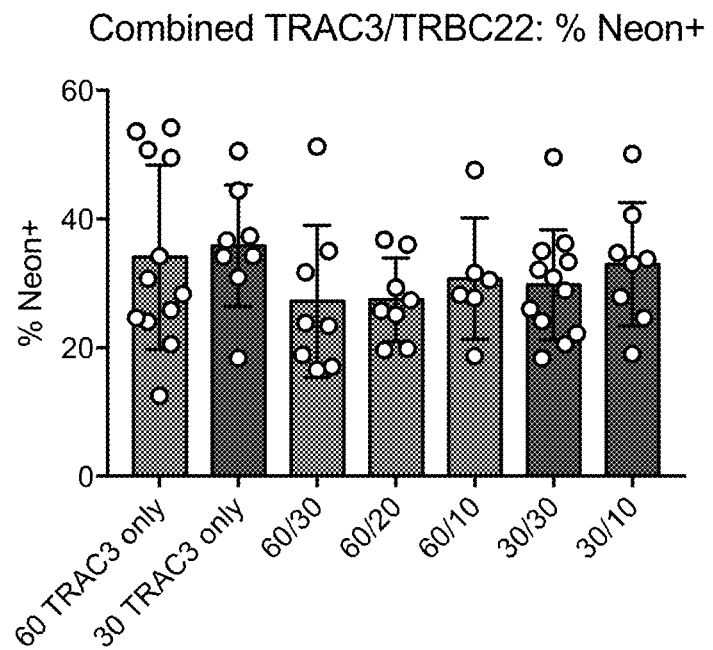
Figure 108B:
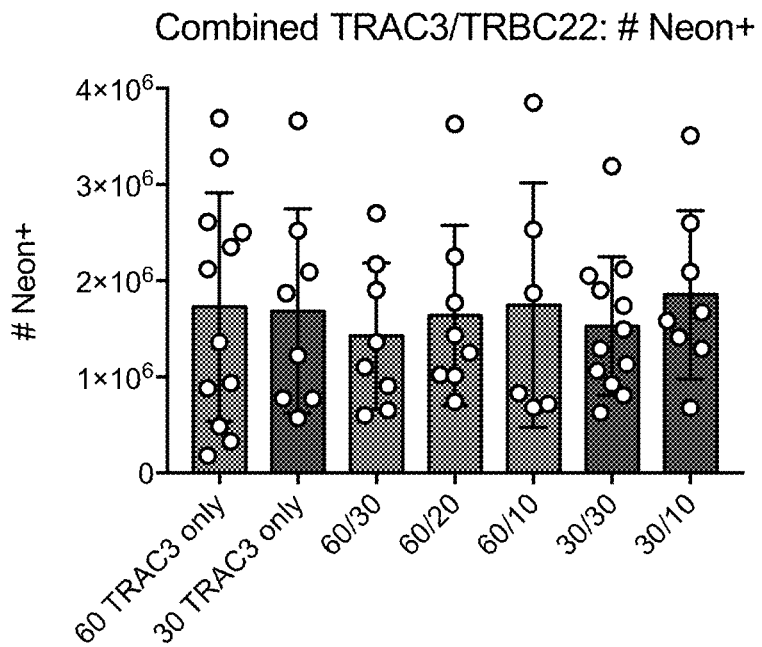

FIGS. 108A and 108B are graphs of combined data from all experiments showing that use of TRBC22 RNP appears to have minimal effect on Neon knock-in. FIG. 108A shows the percentage of Neon-positive samples. FIG. 108B shows the number of Neon-positive samples.

Figure 109A:
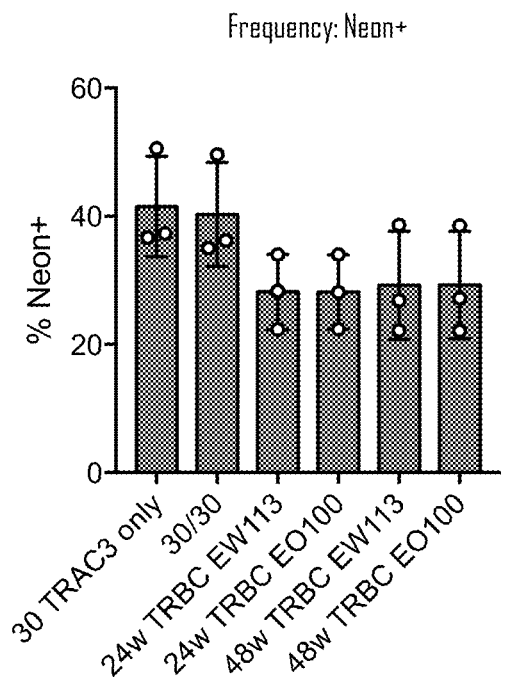
Figure 109B:
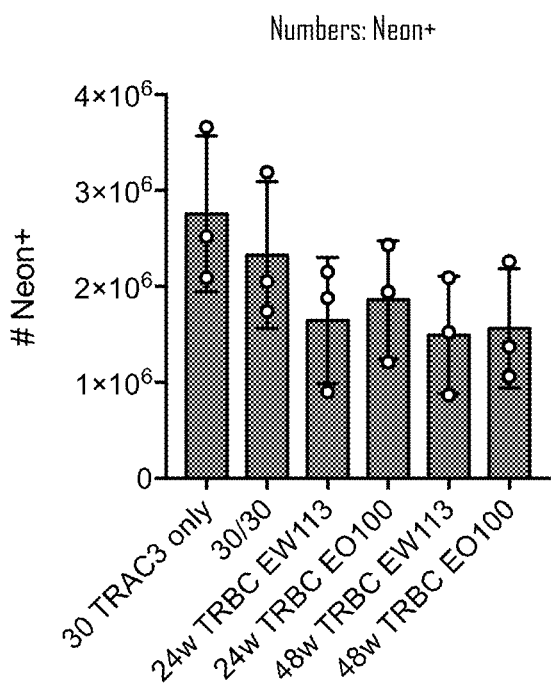
Figure 109C:
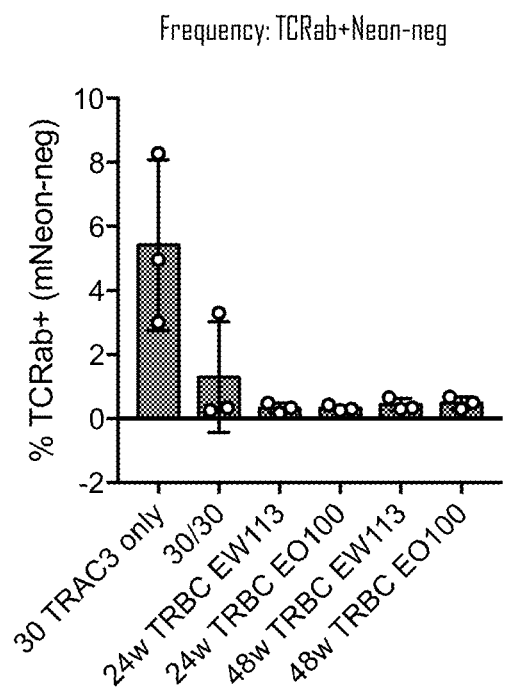

FIGS. 109A-109C are graphs showing the results of sets of sequential electroporations performed on TRAC3 RNP plus donor template, and TRBC22 RNP 24 hours later. FIG. 109A shows the percentage (or frequency) of Neon-positive samples. FIG. 109B shows the number of Neon-positive samples. FIG. 109C shows the frequency or percentage of TCRab+Neon-negative samples.

Figure 110A:
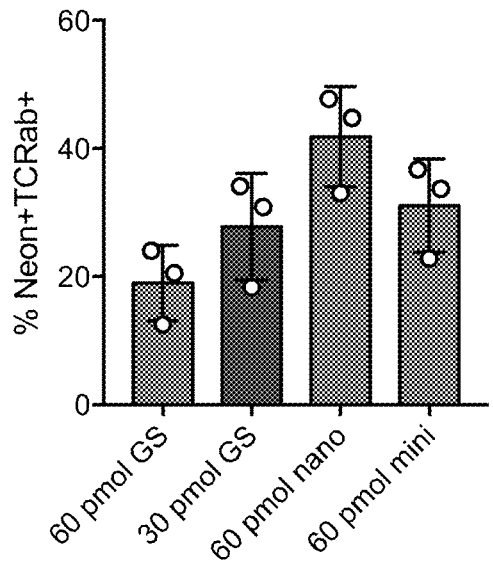
Figure 110B:
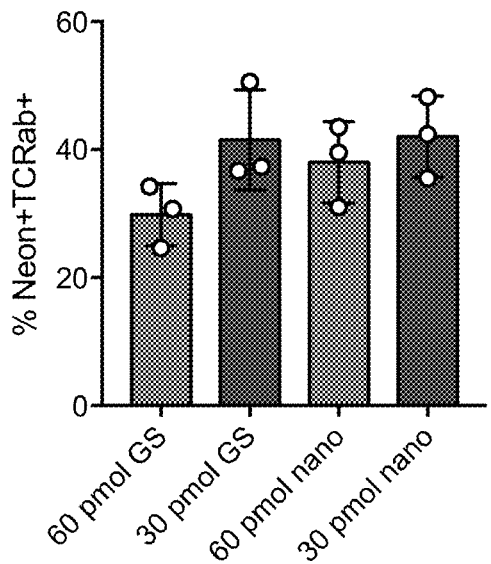
Figure 110C:
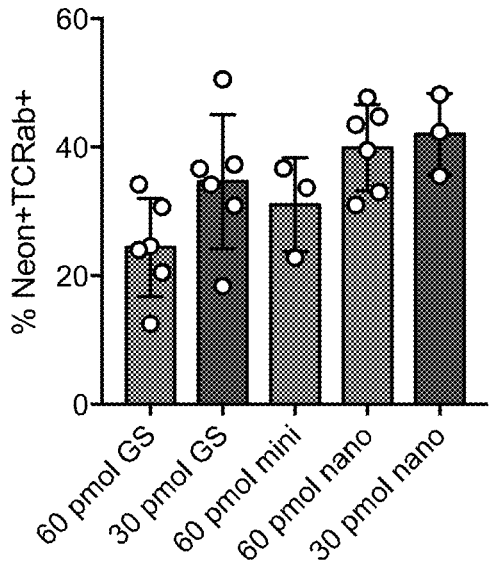
Figure 110D:
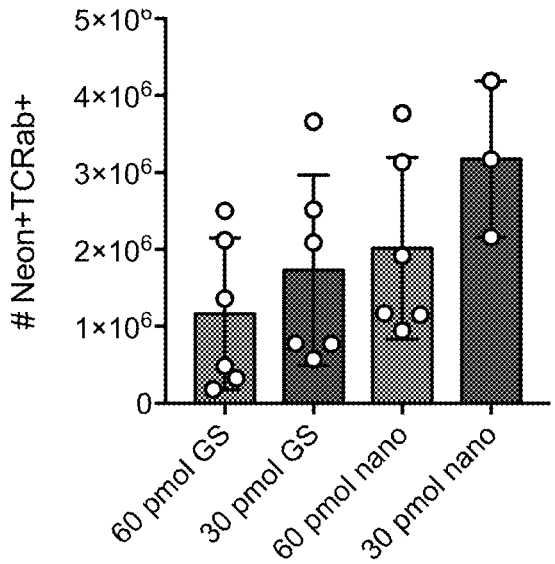

FIGS. 110A-110D are graphs showing the results of tests of knock-in frequencies for various templates. FIGS. 110A and 110B show the frequency of Neon-positive samples for two single experiments. FIGS. 110C-110D show combined data from both experiments, with FIG. 110C showing frequency of Neon-positive samples while FIG. 110D shows numbers of Neon-positive samples.

Figure 111:
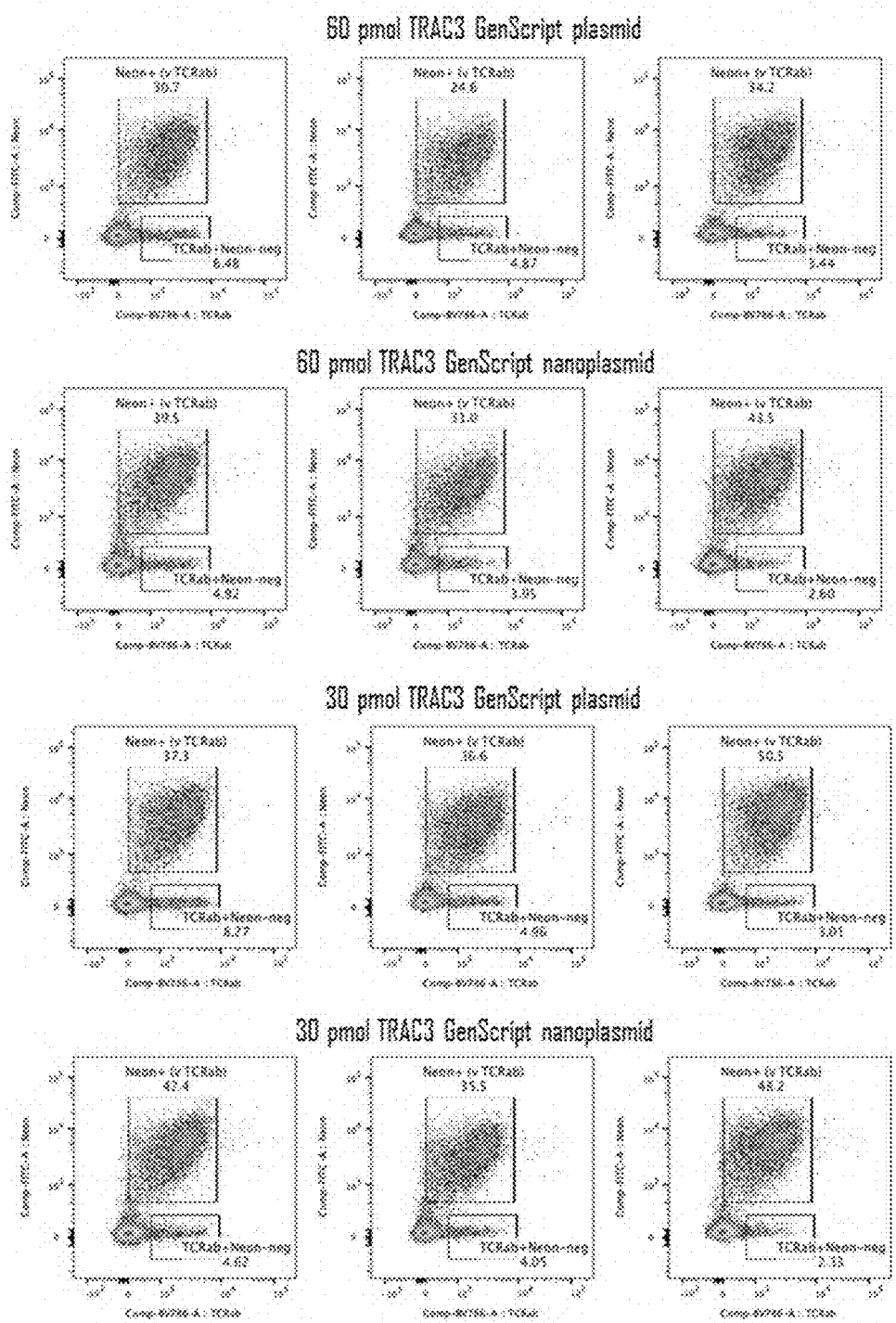

FIG. 111 is Day 7 flow cytometry data of TRAC3 RNP only (30 pmol or 60 μmol), with different donor templates, using plasmid or nanoplasmid.

Figure 112:
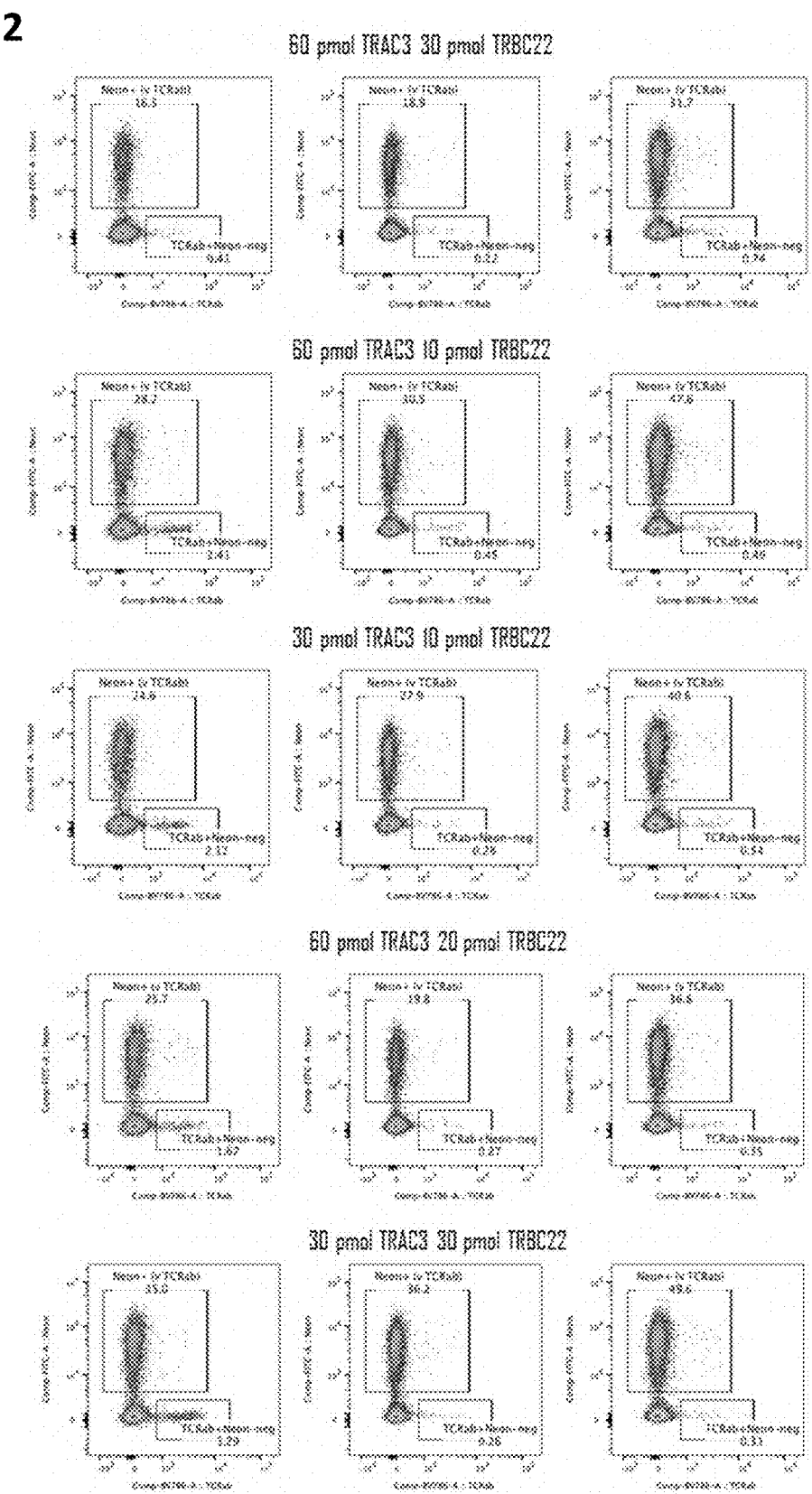

FIG. 112 is Day 7 flow cytometry data from a titration experiment using 30 pmol or 60 pmol TRAC3 RNP and 10 μmol, 20 μmol, or 30 pmol TRB22 RNP, as shown in FIG. 108.

Figure 113:
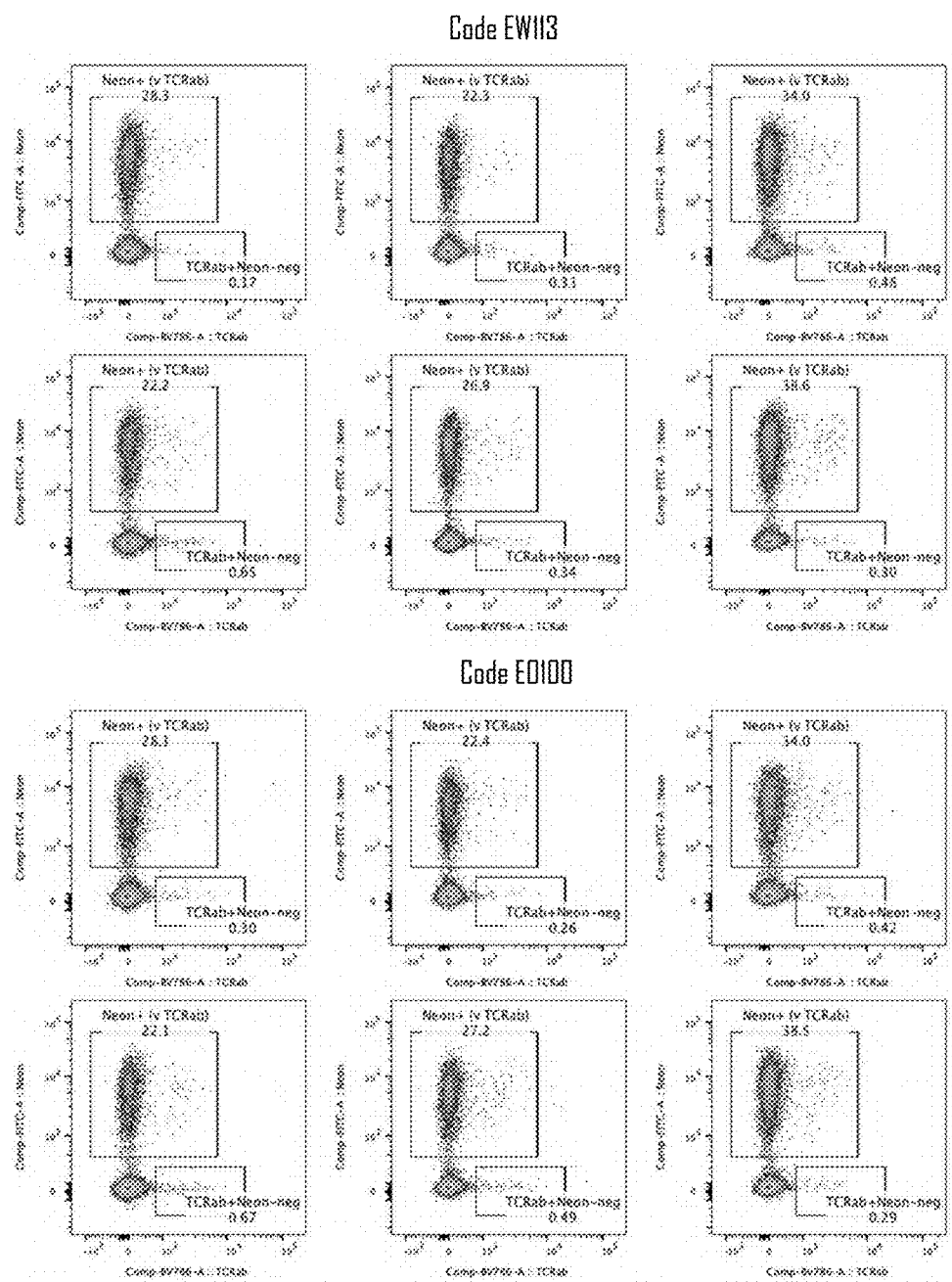

FIG. 113 is Day 7 post-electroporation flow cytometry data for sequential electroporations, all using 30 pmol TRAC3 RNP and 30 pmol TRBC22 RNP, with the indicated electroporation codes.

Figures 114A, 114B:
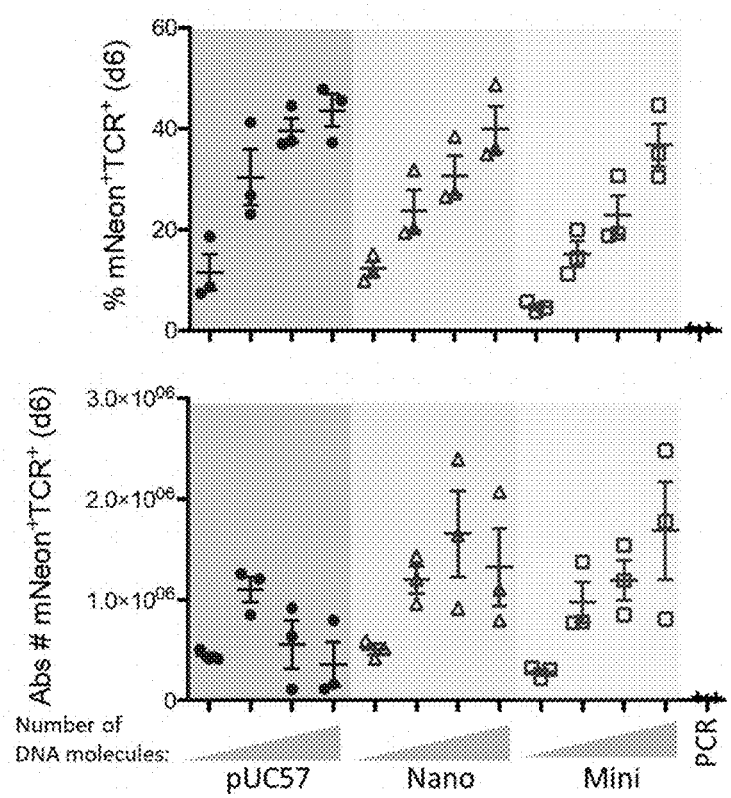

FIGS. 114A and 114B are graphs showing data for pUC57 versus nanoplasmid versus minicircle DNA on day 6 post-electroporation. FIG. 114A shows the percentage (top graph) and absolute number (bottom graph) of mNeon+TCR+ samples. FIG. 114B shows the quantities of DNA used in the experiment.

Figures 115A, 115B:
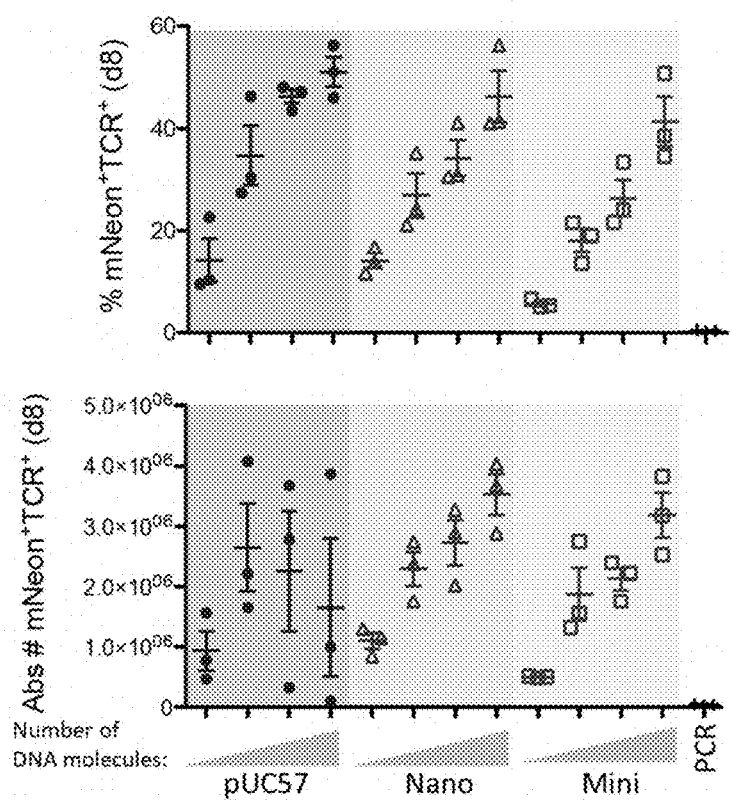

FIGS. 115A and 115B are graphs showing data for pUC57 versus nanoplasmid versus minicircle DNA on day 8 post-electroporation. FIG. 115A shows the percentage (top graph) and absolute number (bottom graph) of mNeon+TCR+ samples. FIG. 115B shows the quantities of DNA used in the experiment.

Figure 116A:
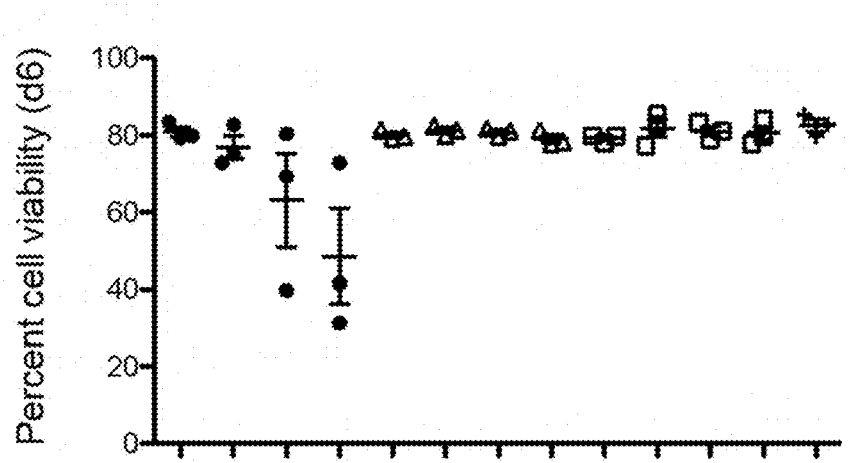
Figure 116B:
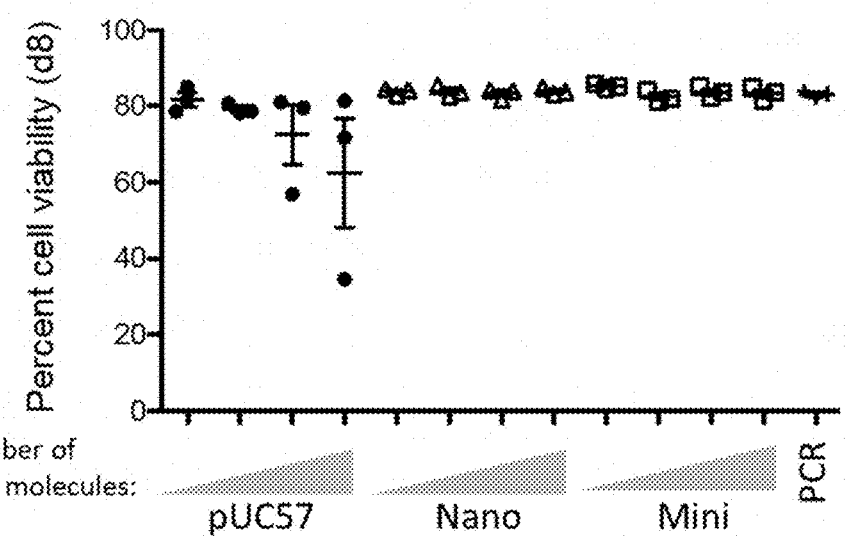

FIGS. 116A and 116B are graphs showing impacts on cell viability with equivalent molecules of each template on pUC57, nanoplasmid, or minicircle. FIG. 116A shows percentage of cell viability on day 6 post-electroporation, while FIG. 116B shows percentage of cell viability on day 8 post-electroporation.

Figure 117:
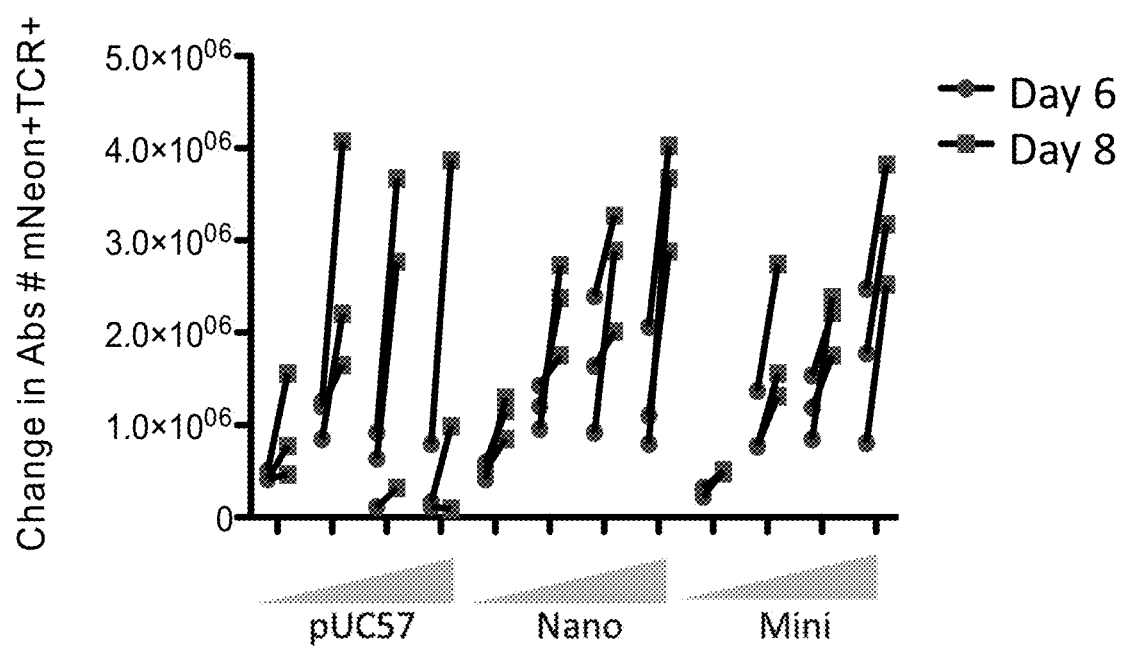

FIG. 117 is a graph of the change in knock-in cell numbers over time from day 6 to day 8 post-electroporation based on the data from FIGS. 116A and 116B.

Figure 118A:
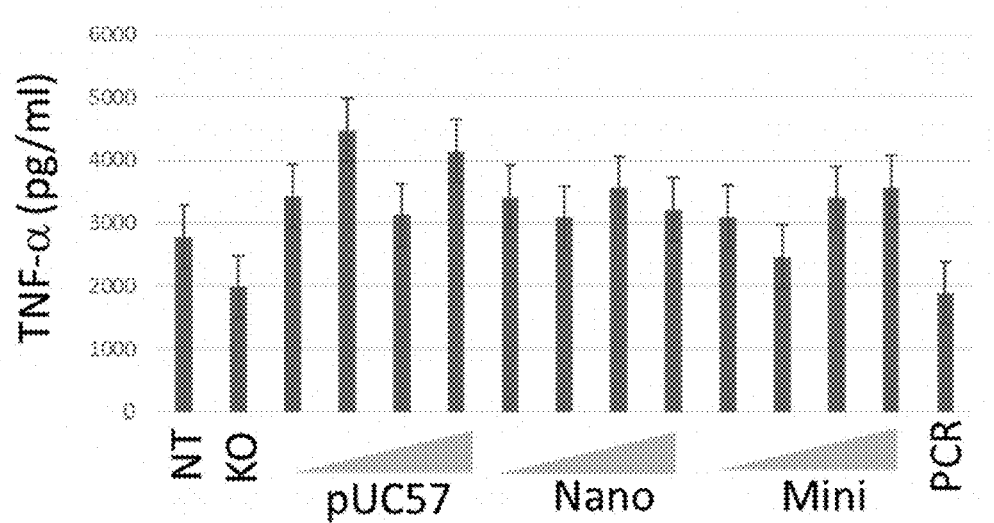
Figure 118B:
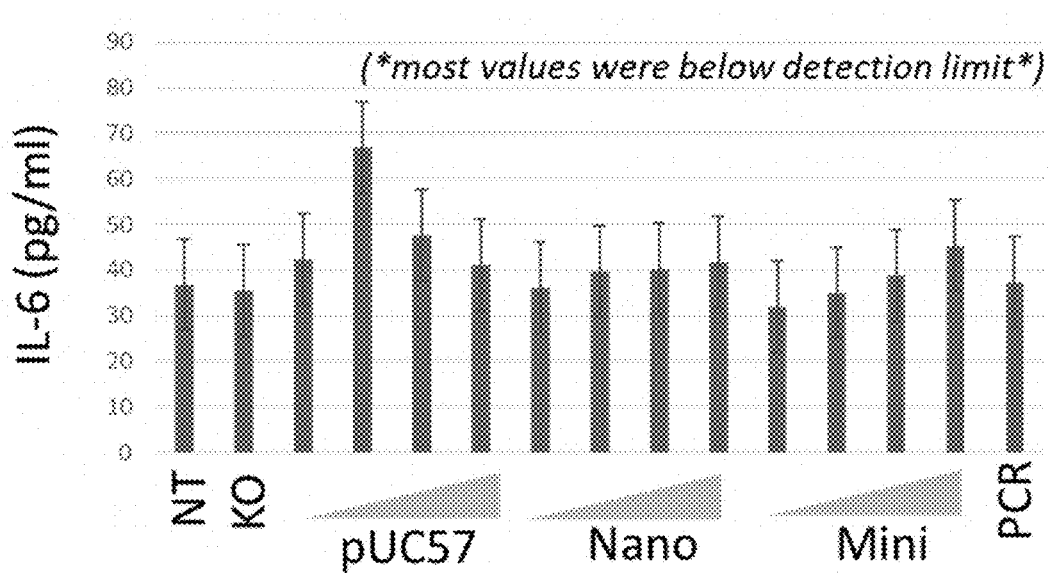

FIGS. 118A and 118B graphs summarizing cytokine readout monitoring. FIG. 118A shows the concentrations of TNF-alpha and FIG. 118B shows concentrations of IL-6 after electroporation with pUC57, nanoplasmid, or minicircle.

Figure 119:
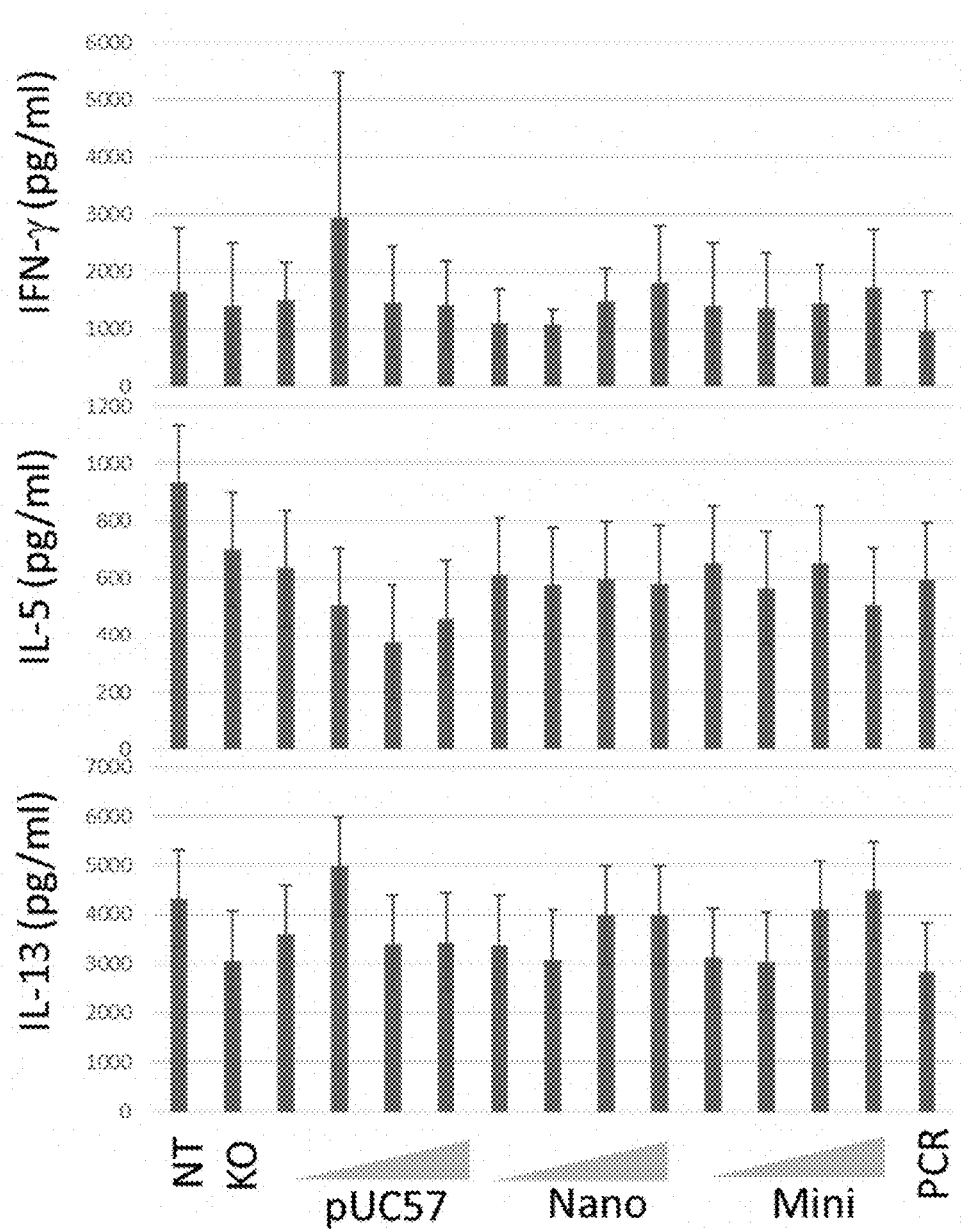

FIG. 119 shows the concentration of IFN-gamma (top graph), IL-5 (middle graph) and IL-13 (bottom graph) after electroporation with pUC57, nanoplasmid, or minicircle.

Figures 120A, 120B:
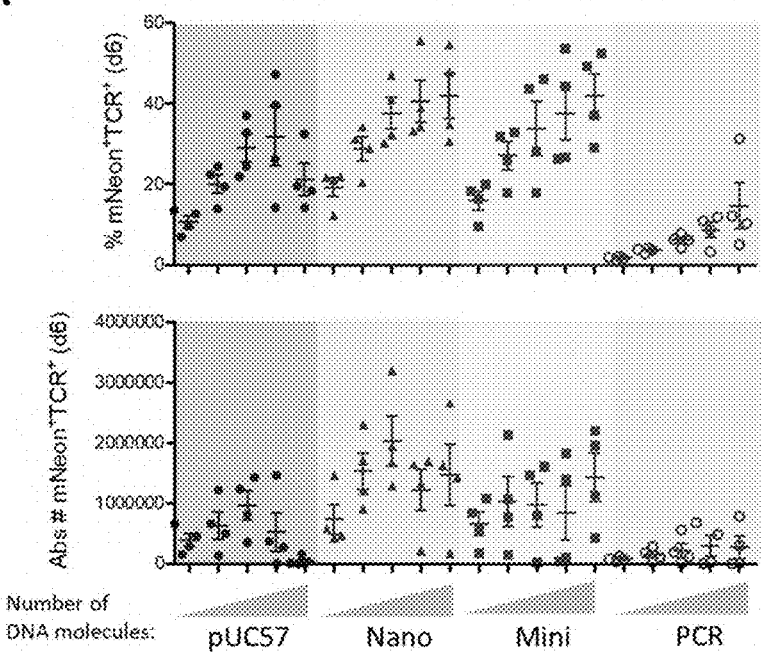

FIGS. 120A and 120B are graphs showing data for pUC57 versus nanoplasmid versus minicircle DNA on day 6. FIG. 120A shows the percentage (top graph) and the absolute numbers (bottom graph) of mNeon+TCR+ samples on day 6. FIG. 120B shows the quantities of DNA used in this experiment.

Figures 121A, 121B:
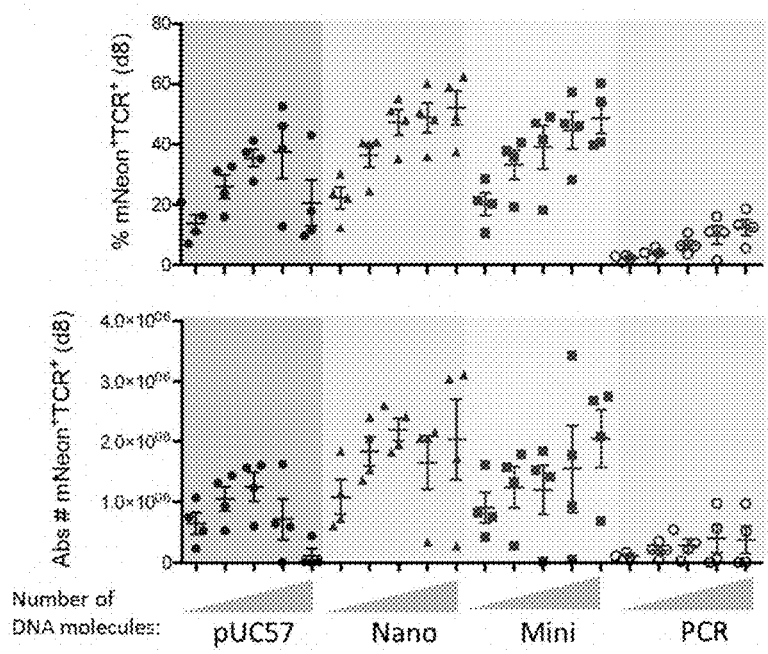

FIGS. 121A-121B are graphs showing data for pUC57 versus nanoplasmid versus minicircle DNA on day 8. FIG. 121A shows the percentage (top graph) and the absolute numbers (bottom graph) of mNeon+TCR+ samples on day 8. FIG. 121B shows the quantities of DNA used in this experiment.

Figure 122:
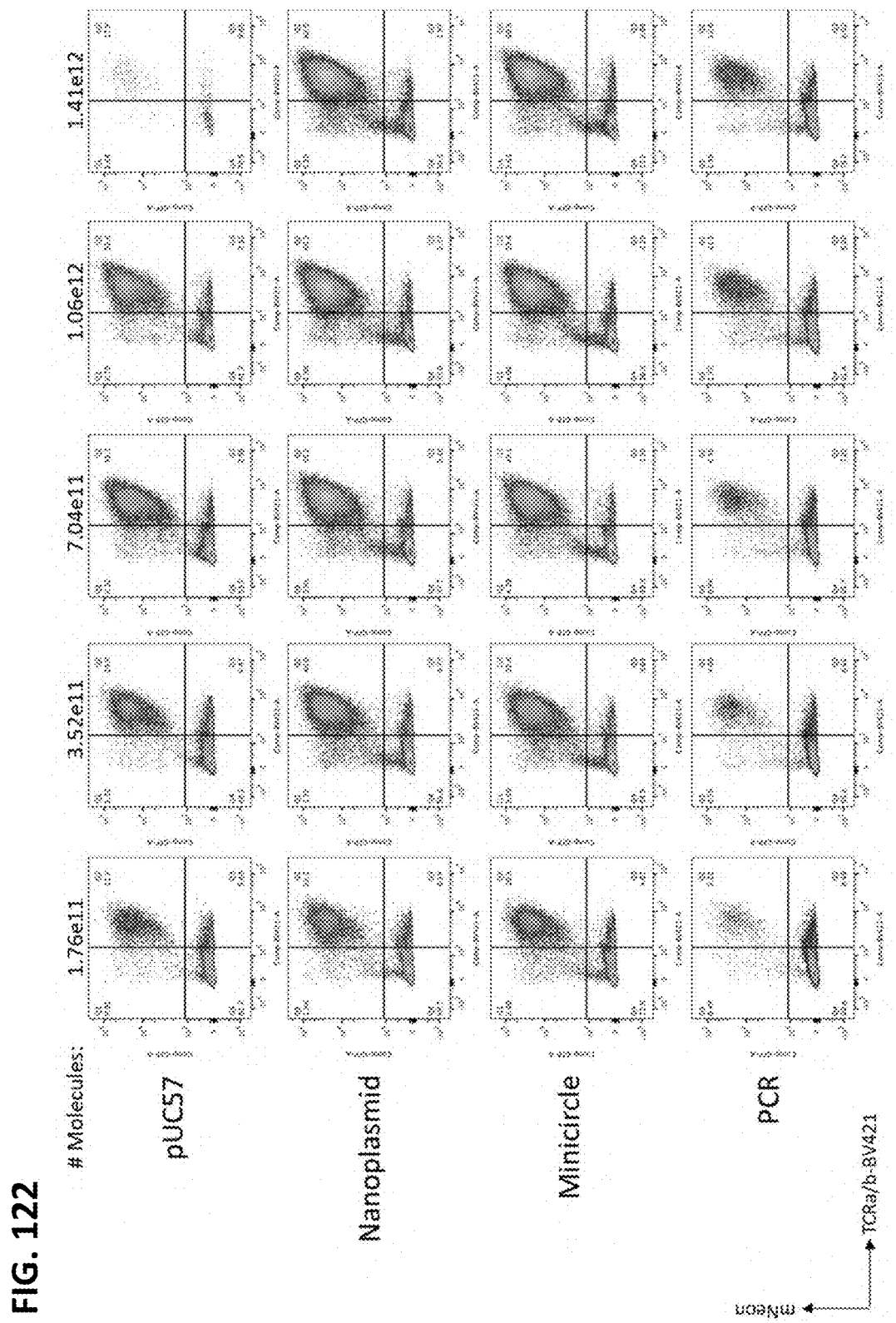

FIG. 122 is flow cytometry data of day 8 post-electroporation sample plots for T cells electroporated with pUC57, nanoplasmid, minicircle, and PCR samples.

Figure 123:
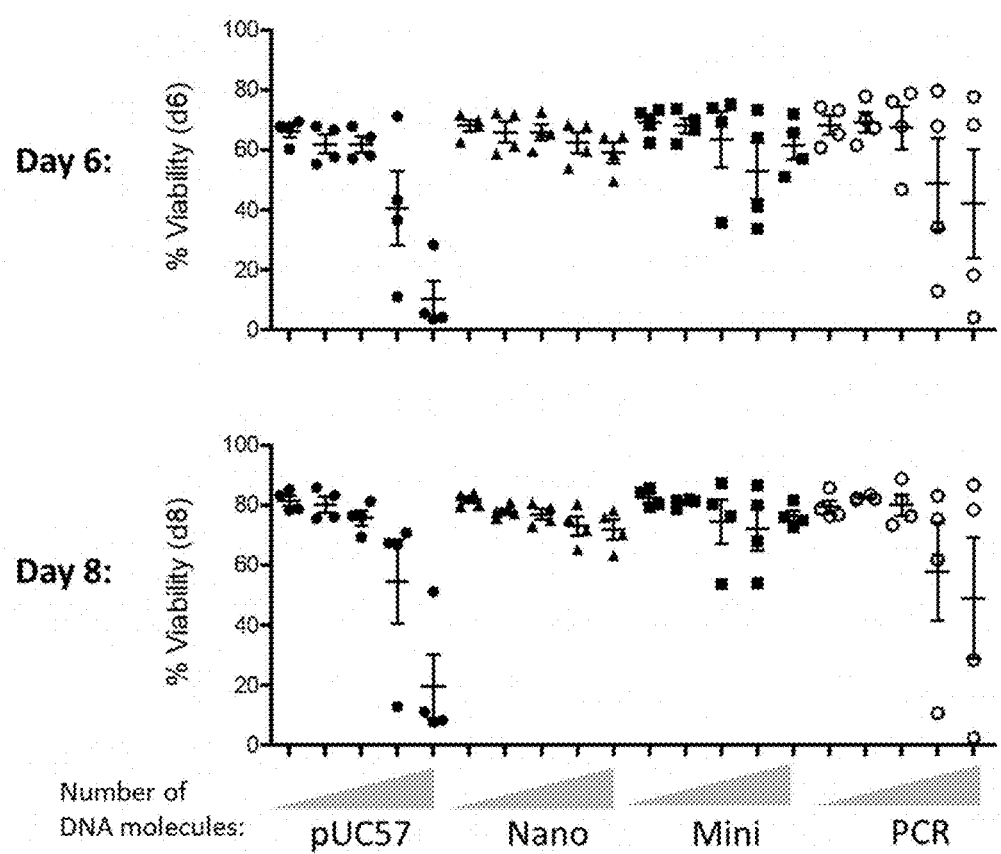

FIG. 123 is a pair of graphs showing impacts on cell viability after electroporation with equivalent molecules of the indicated template, with day 6 post-electroporation data shown in the top graph and day 8 data shown in the bottom graph.

Figure 124:
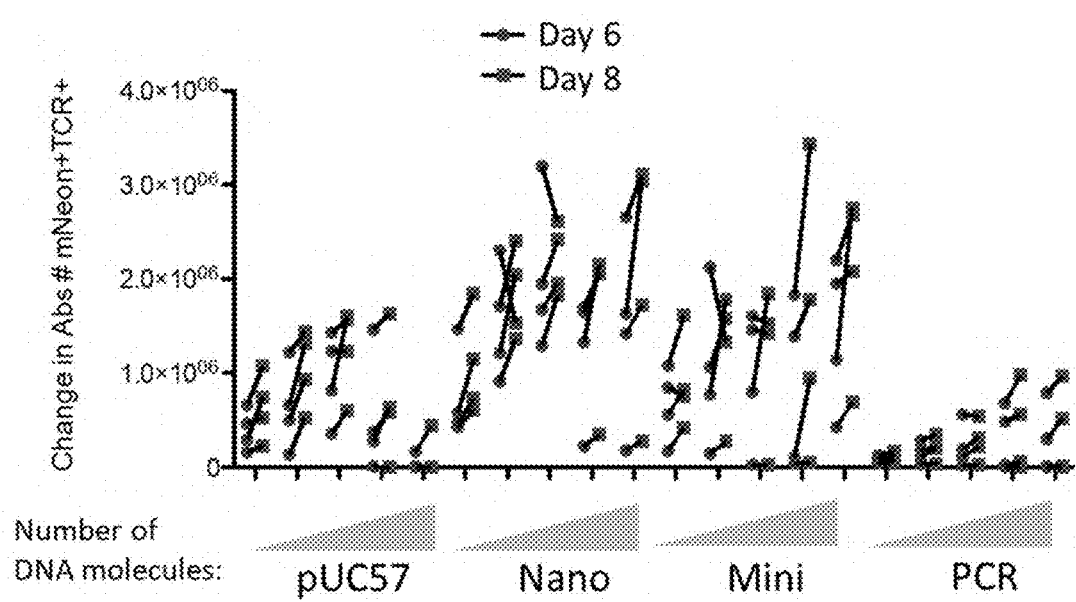

FIG. 124 is a graph showing the change in knock-in cell numbers over time from day 6 to day 8, based on the data in FIG. 123.

Figure 125:
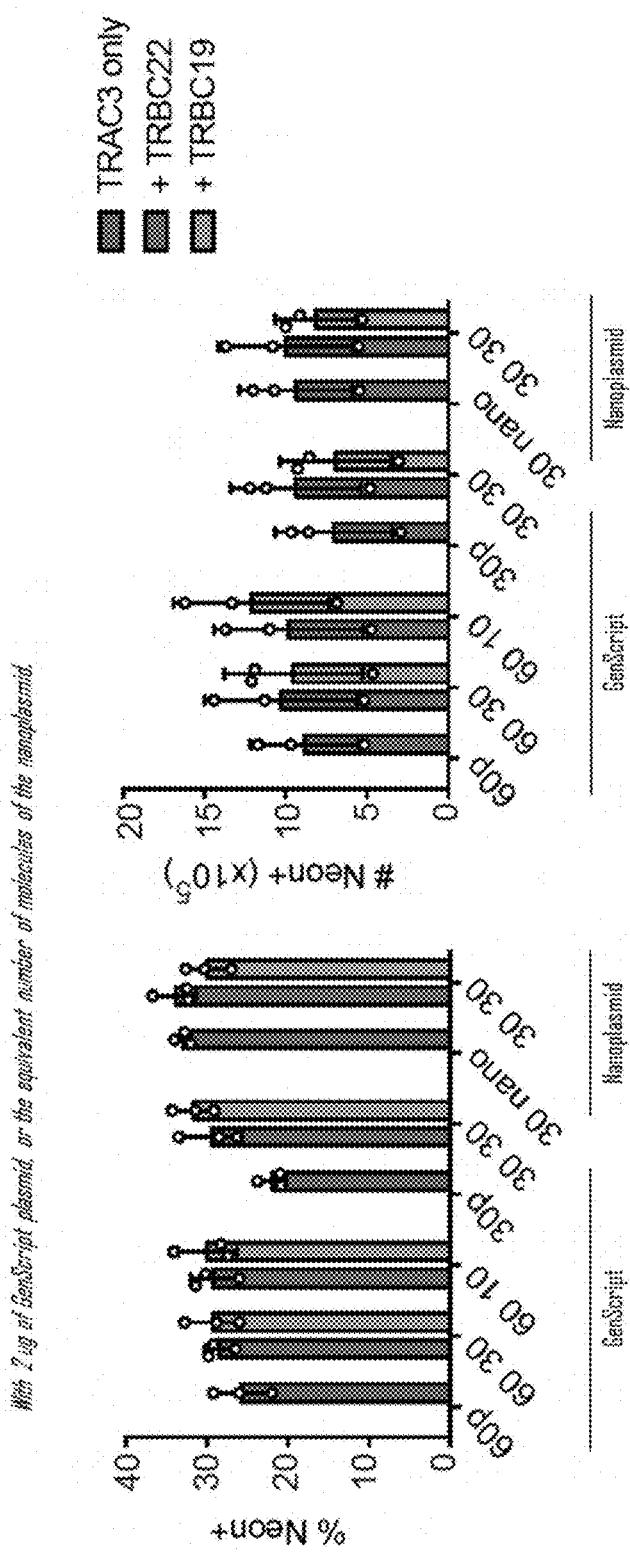

FIG. 125 are graphs showing that the addition of TRBC RNP does not reduce knock-in efficiency. Left graph shows the percentage of Neon-positive samples while the right graph shows the number of Neon-positive samples, after electroporation with template on a plasmid or nanoplasmid.

Figure 126A:
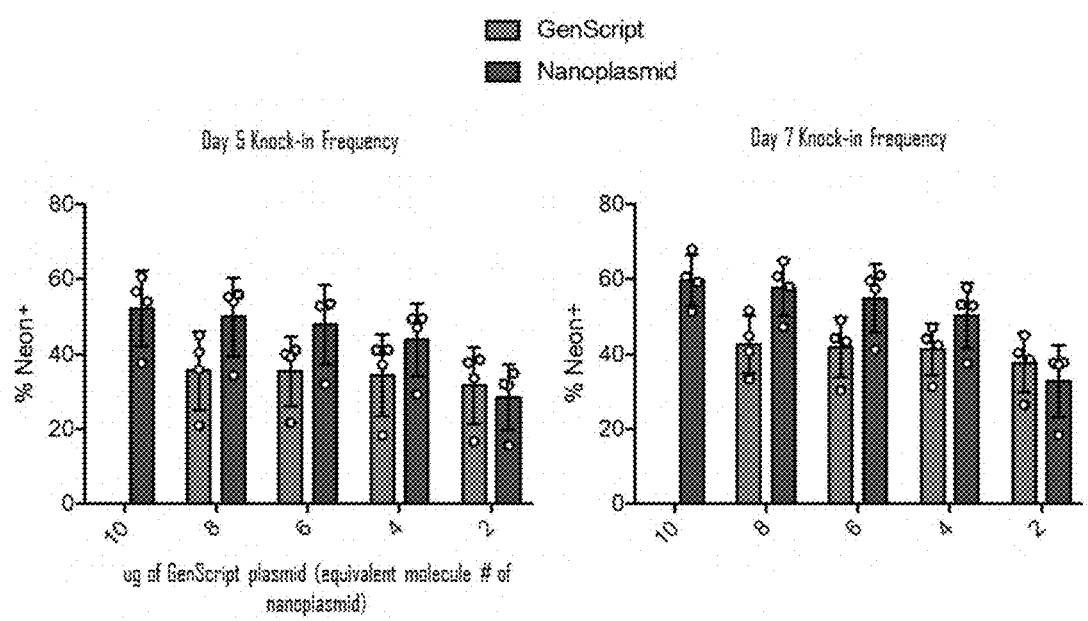
Figure 126B:
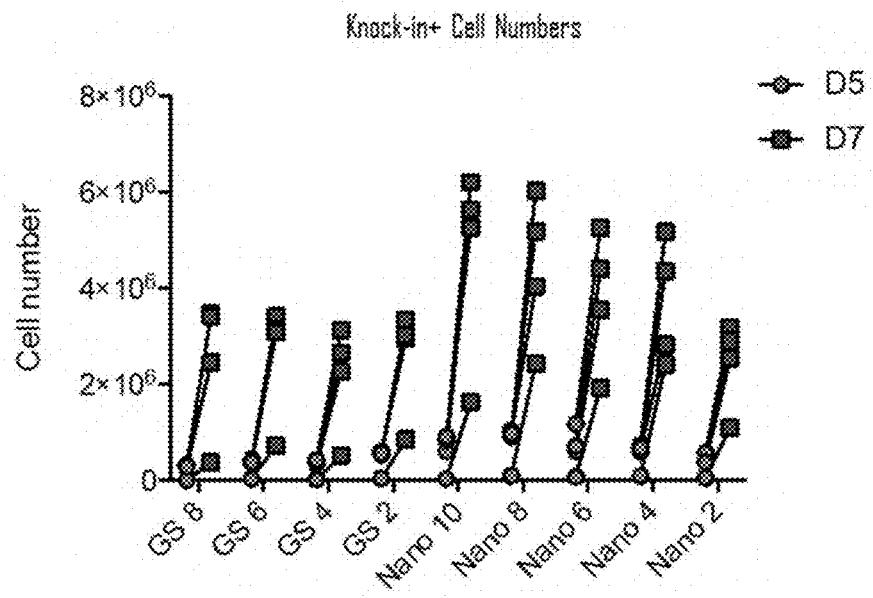

FIGS. 126A-126B are graphs showing show that knock-in efficiency increases with higher amounts of nanoplasmid. FIG. 126A shows the day 5 post-electroporation knock-in efficiency (left graph) and day 7 knock-in efficiency (right graph). FIG. 126B shows the change in knock-in cell numbers for day 5 and day 7 post electroporation.

Figure 127:
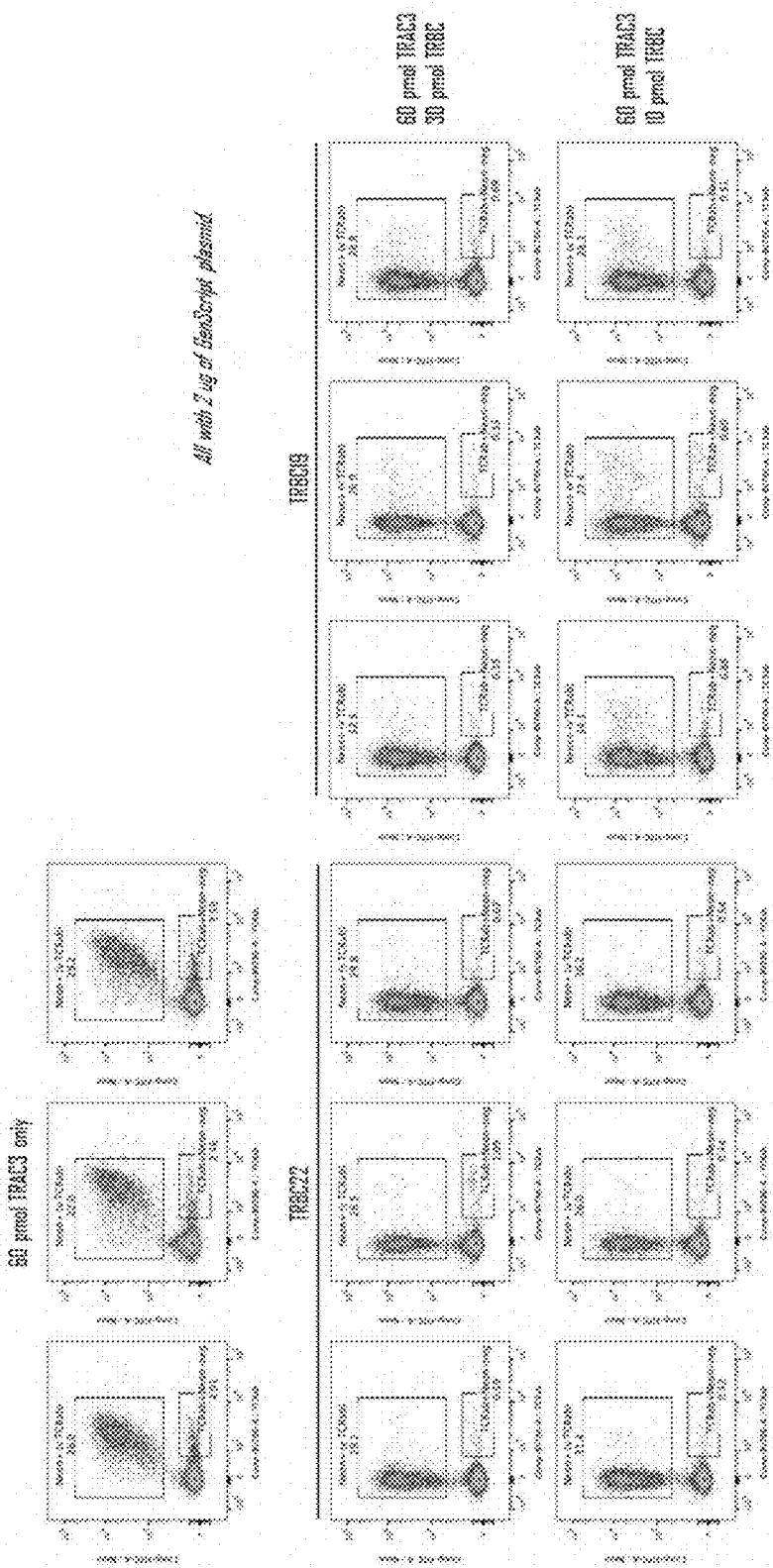

FIG. 127 is graphs of day 7 post-electroporation flow cytometry data for TRBC19 or TRBC22 plasmid titration (10 pmol or 30 μmol) with 60 pmol TRAC3.

Figure 128:
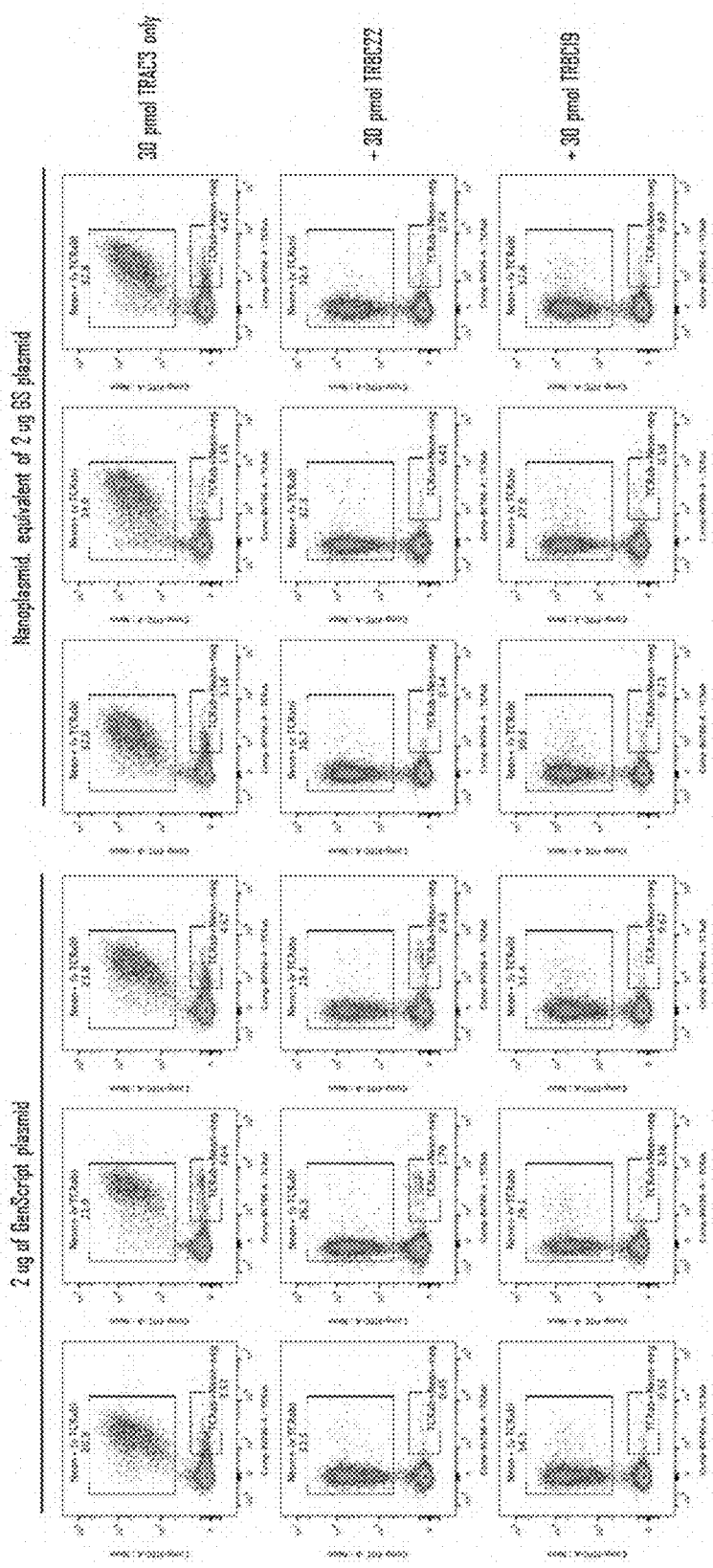

FIG. 128 is graphs of day 7 post-electroporation flow cytometry data for 30 pmol TRAC3 alone (top row), or with TRBC22 (30 μmol, middle row) or TRBC19 (30 μmol, bottom row) on plasmid (left 3 columns) or nanoplasmid (right 3 columns).

Figure 129:
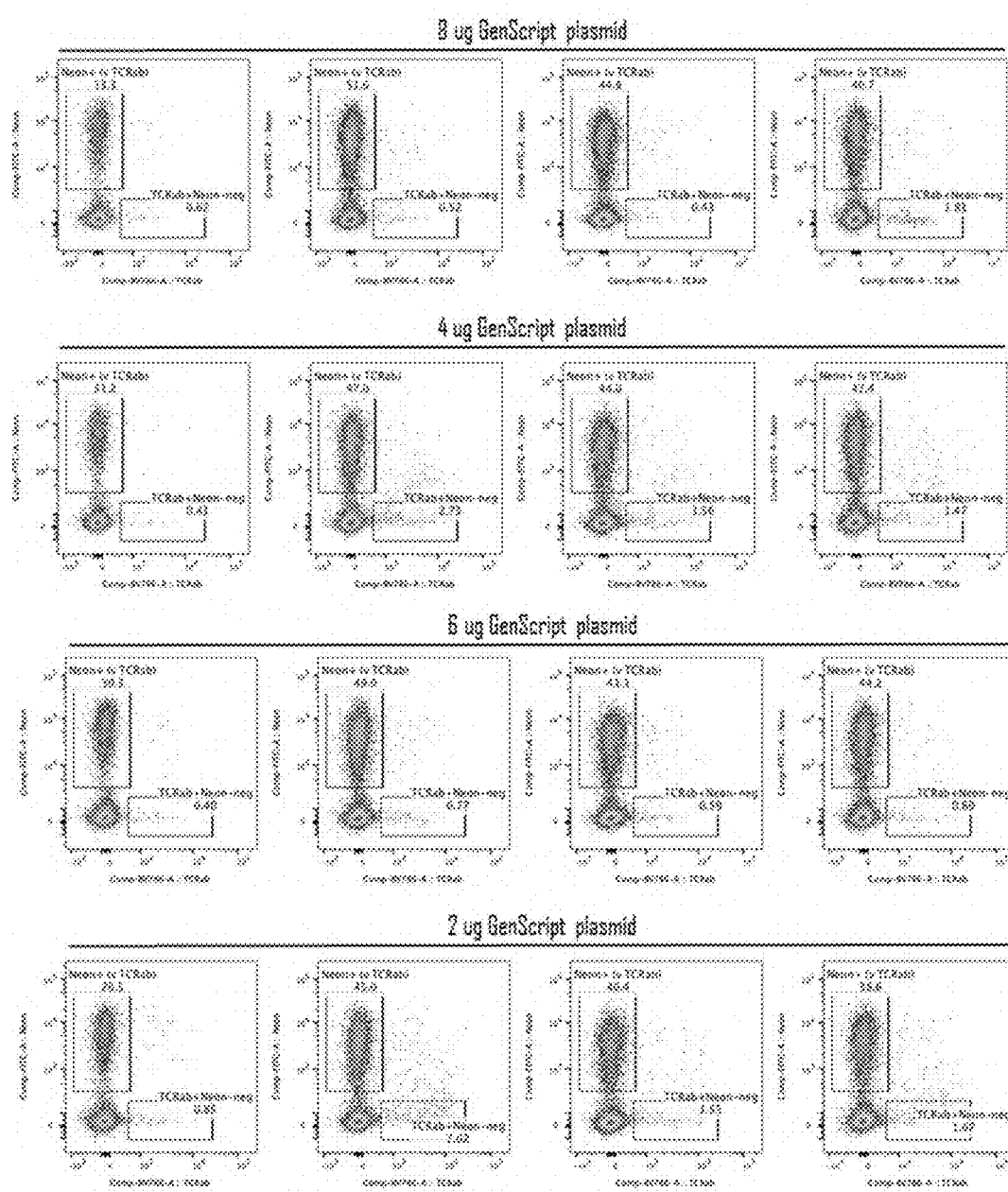

FIG. 129 is graphs of day 7 post-electroporation flow cytometry data for 2 μg, 4 μg, 6 μg, or 8 μg GenScript plasmid.

Figure 130:
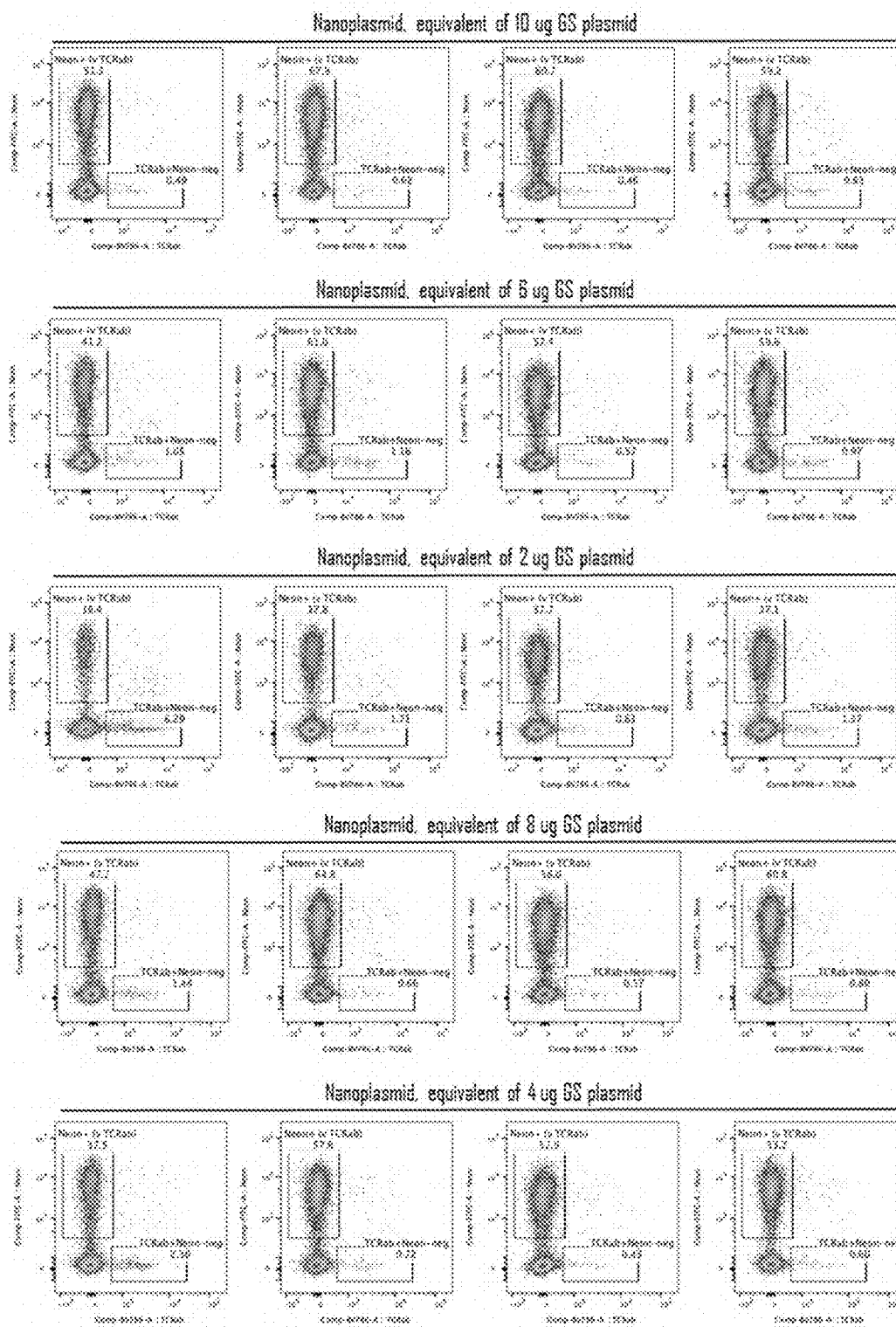

FIG. 130 is graphs of day 7 post-electroporation flow cytometry data for nanoplasmid titration.

Figure 131A:
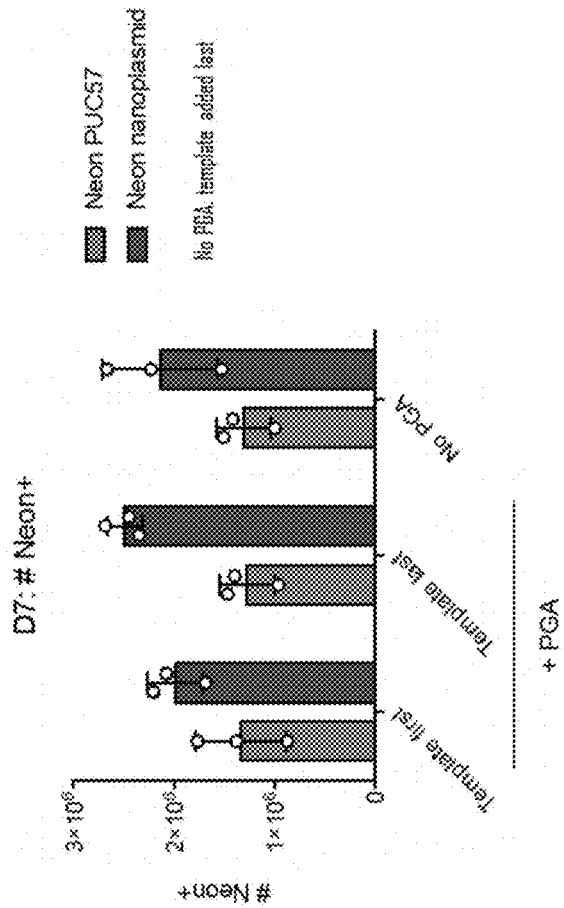
Figure 131B:
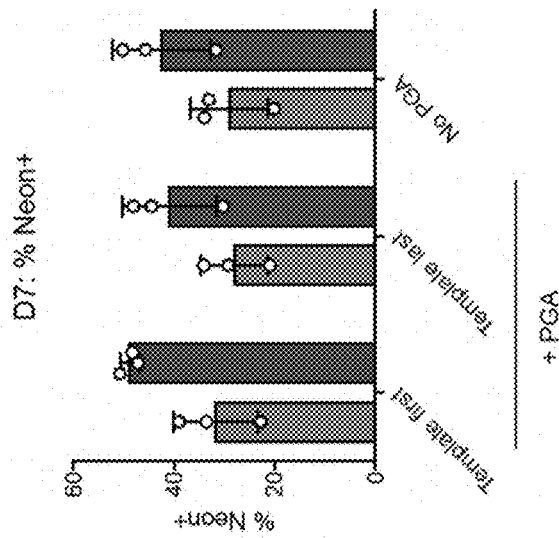

FIGS. 131A and 131B are graphs showing the results of Neon knock-in on day 7 post-electroporation using template on plasmid or nanoplasmid, with or without PGA and different order of addition of template. FIG. 131A shows percentage of Neon-positive cells, while FIG. 131B shows the number of Neon-positive cells.

FIGS. 132A-132C are graphs showing that codon optimization can dramatically reduce TCR knock-in efficiency, and effect of order of addition of template on knock-in efficiency. FIG. 132A shows the percentage of WT1+ (of total CD8+) samples on day 7 post-electroporation.

FIG. 132B shows the percentage of CD3+ samples on day 7 post-electroporation. FIG. 132C shows the percentage of WT1+ (of total CD3+) samples on day 7 post-electroporation.

Figure 133:
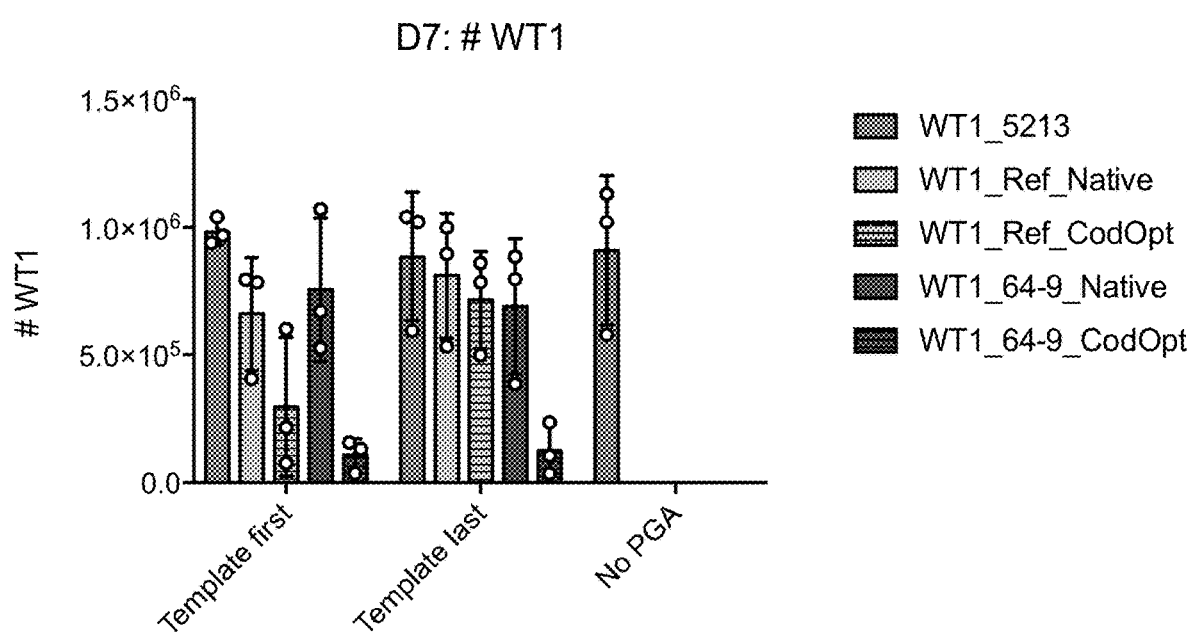

FIG. 133 is a graph showing the numbers of WT1 TCR+ cells on day 7 post-electroporation, based on the data in FIGS. 132A-132C. Conditions graphed are, from left to right, template added first, template added last, and no PGA.

Figure 134:
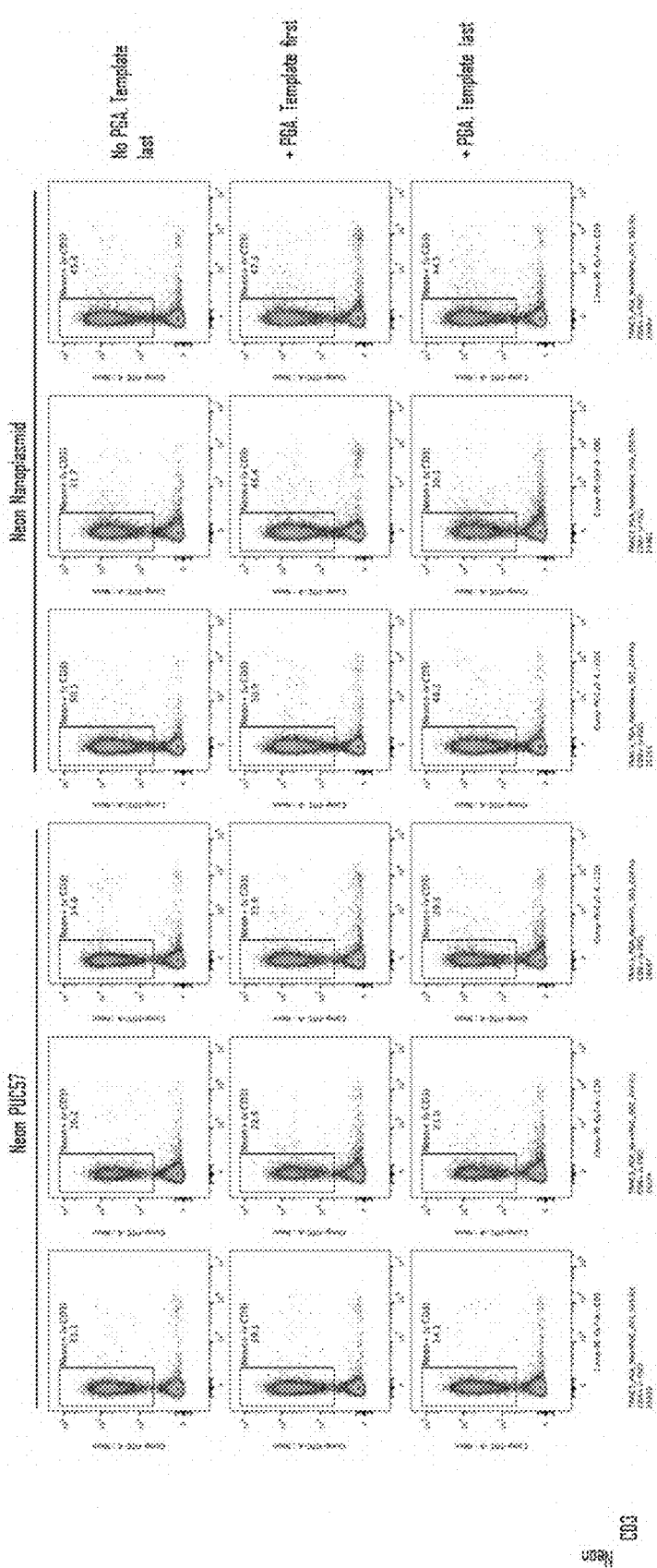

FIG. 134 is graphs of flow cytometry data for day 7 post-electroporation for Neon template knock-ins, with or without PGA and different order of addition of template.

Figure 135:
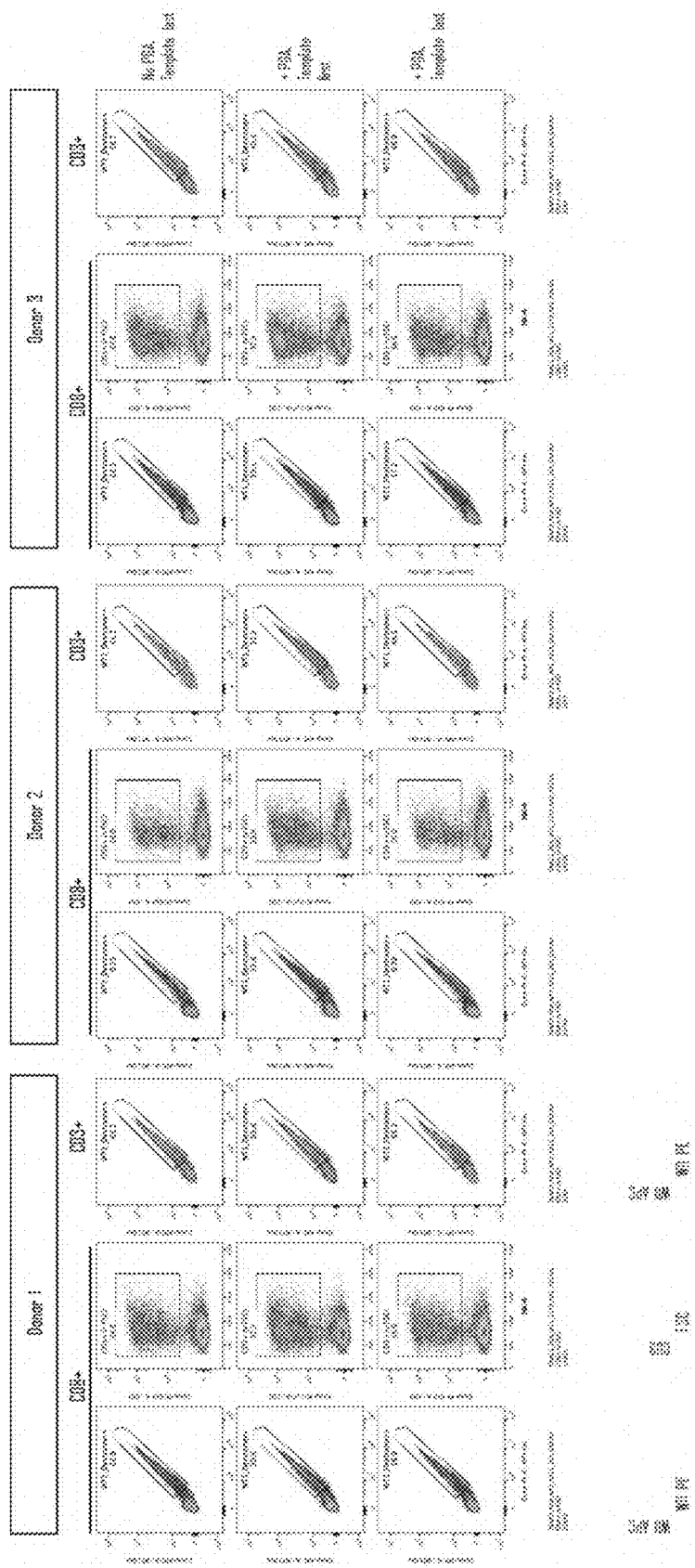

FIG. 135 is graphs of flow cytometry data for day 7 post-electroporation for WT1_5213, with or without PGA and different order of addition of template.

Figure 136:
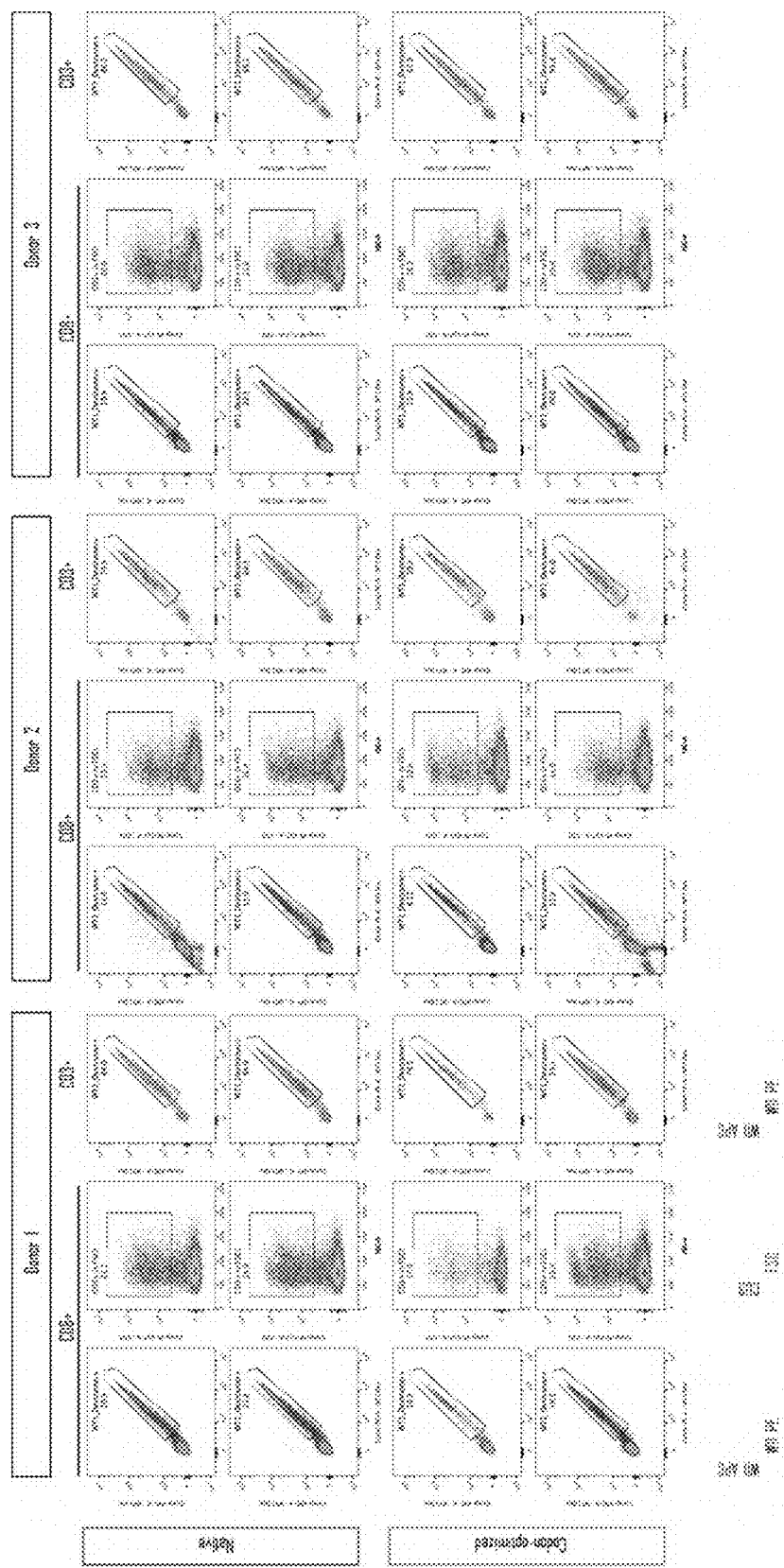

FIG. 136 is graphs of flow cytometry data for day 7 post-electroporation for WT1_Ref.

Figure 137:
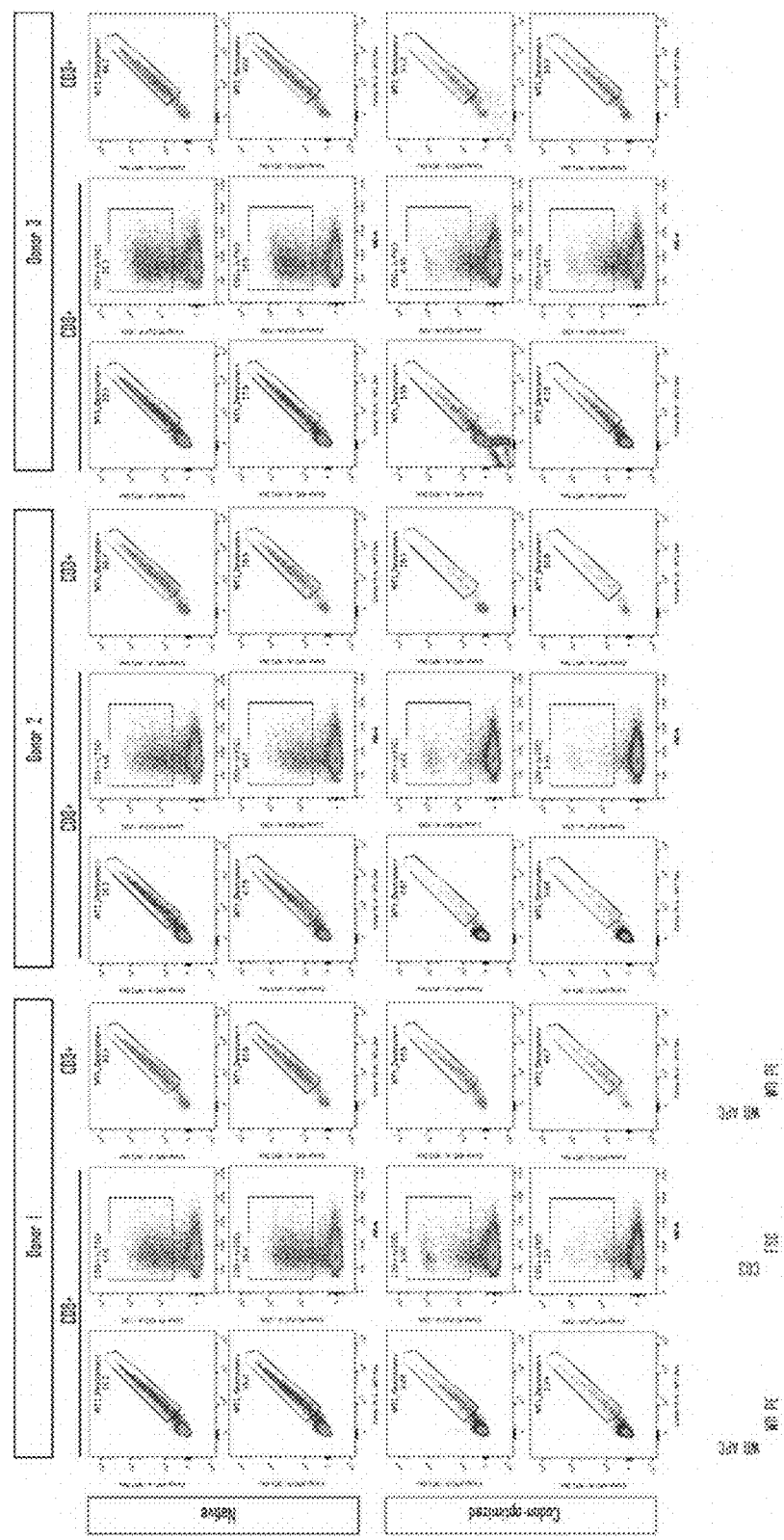

FIG. 137 is graphs of flow cytometry data for day 7 post-electroporation for WT1 64_9.

Figure 138:
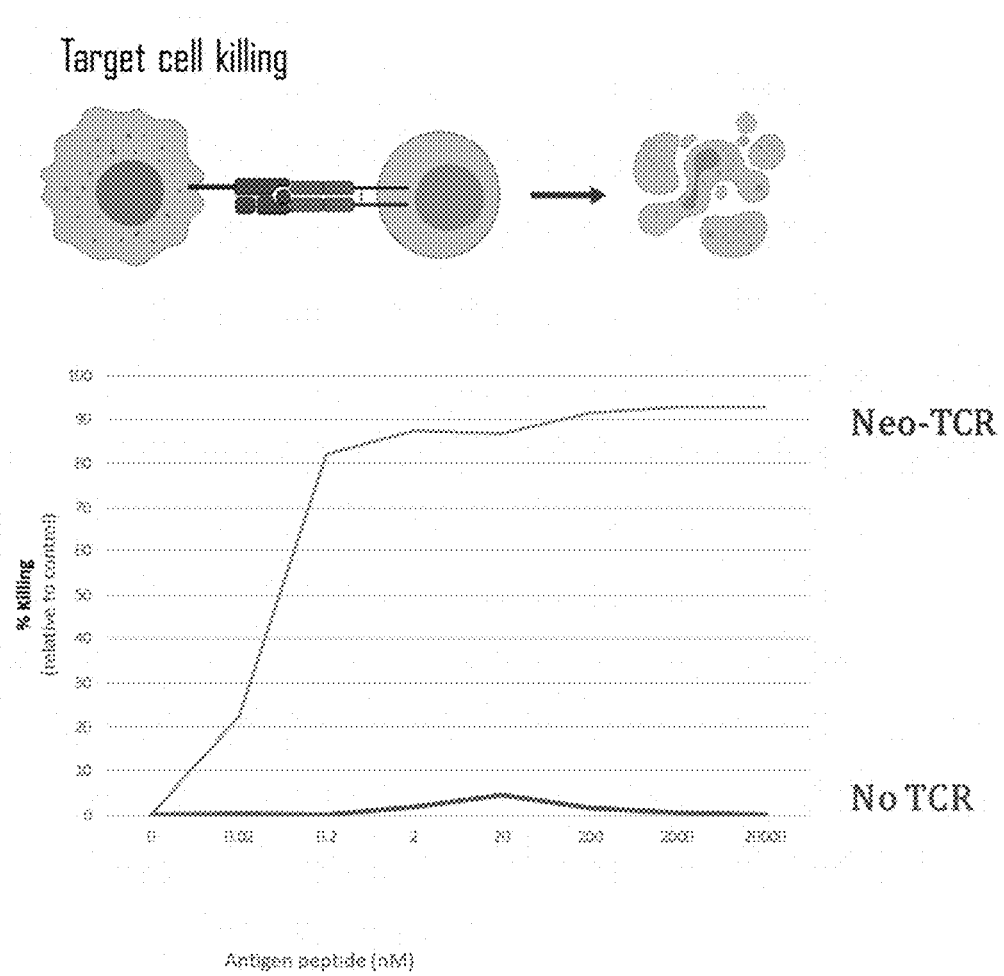

FIG. 138 is a cartoon representation of target cell killing (top) and a graph of the percent killing, relative to control, for neo-TCR and no TCR (bottom).

Figure 139:
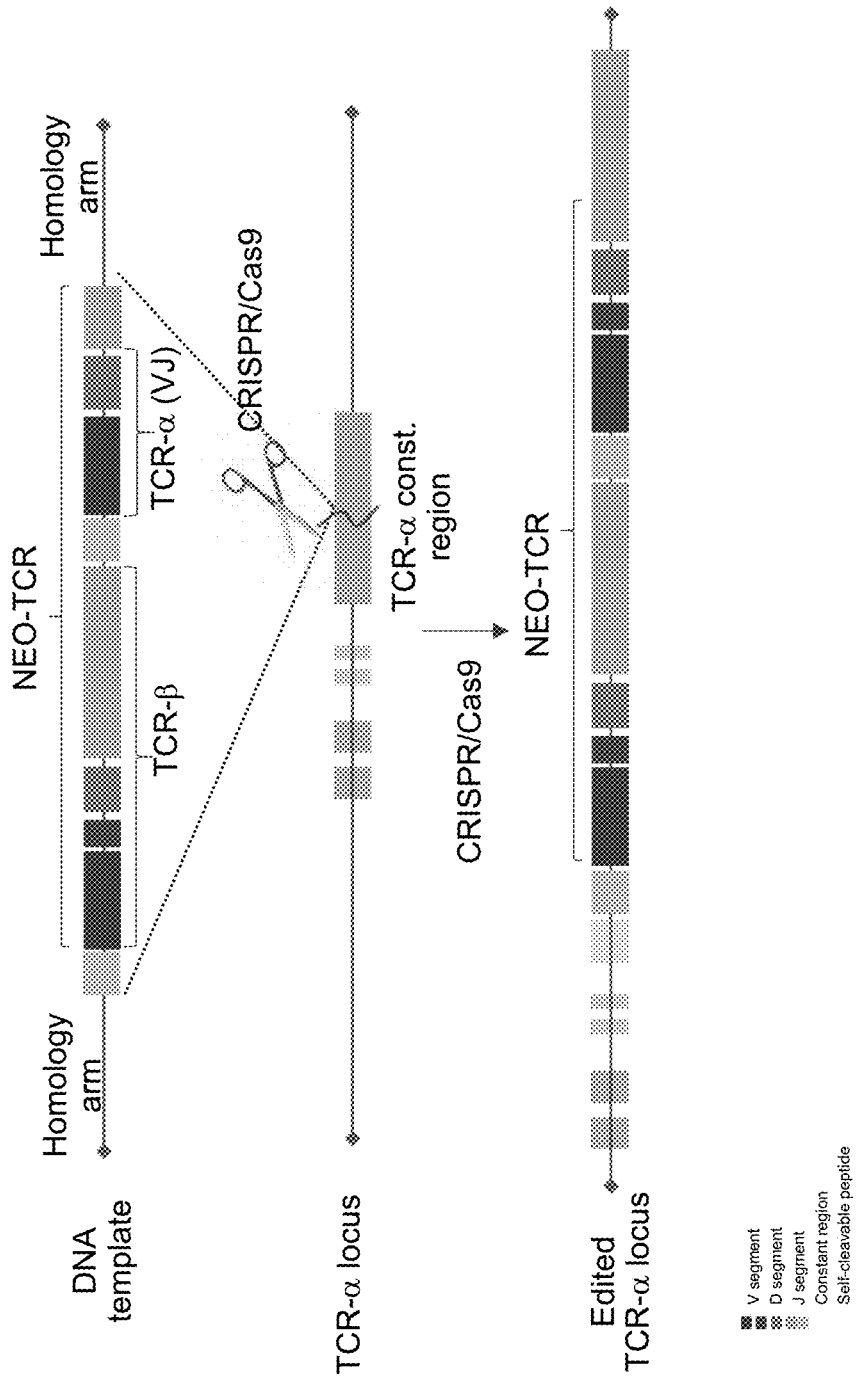

FIG. 139 is a cartoon representation of insertion of a DNA template as described herein into a TCR-alpha locus. The DNA template (top) includes (from 5' to 3'): a left (5') homology arm, the NEO-TCR (a first self-cleaving peptide (e.g., T2A), a TCR-beta V segment, a TCR-beta D segment, a TCR-beta J segment, a TCR-beta constant region, a second self-cleaving peptide (e.g., P2A), a TCR-alpha V segment, a TCR-alpha J segment, and a portion of a TCR-alpha constant region), and a right (3') homology arm. A nuclease or gene editing agent (e.g., CRISPR/Cas9) cleaves the endogenous TCR-alpha constant region in a T cell (middle) and promotes homologous recombination of the DNA template with the endogenous TCR-alpha locus, within the constant region. The resulting edited TCR-alpha locus (bottom) includes the NEO-TCR in frame with a portion of the endogenous TCR-alpha constant region.

FIGS. 140A-140I. Plasmid-based donor templates enable efficient non-viral gene editing of TRAC locus in primary T cells. (FIGS. 140A-C) Titration of linear dsDNA donor template (FIG. 140A) Diagram of linear dsDNA knock-in construct TRAC-mNG. (FIG. 140B) Bar graphs depicting knock-in efficiency, cell viability, total cell recovery and edited cell recovery (mNG-positive cells) three days post-electroporation with 1, 2, 4, 6, or 8 μg of linear dsDNA donor template together with Cas9-RNP targeting the TRAC locus (n=4). Circles represent individual donors; bars represent median values with range. (FIG. 140C) Representative contour plots showing the frequency of CD8 T cells expressing mNG. (FIGS. 140D-F), Titration of pUC57 plasmid donor template (FIG. 140D) Diagram of pUC57 knock-in construct TRAC-mNG. (FIG. 140E) Bar graphs showing the frequency of CD8 T cells expressing mNG, cell viability, total cell recovery and edited cell recovery (mNG-positive cells) three days post-electroporation with 1, 2, 4, 6, or 8 μg of pUC57 plasmid donor template together with Cas9-RNP targeting the TRAC locus (n=4). Circles represent individual donors; bars represent median values with range. (FIG. 140F) Representative contour plots showing the frequency of CD8 T cells expressing mNG. (FIGS. 140G-I) Titration of nanoplasmid donor template (FIG. 140G) Diagram of nanoplasmid knock-in construct TRAC-mNG. (FIG. 140H) Bar graphs showing the frequency of CD8 T cells expressing mNG, total cell recovery and edited cell recovery (mNG-positive cells) three days post-electroporation with 1, 2, 4, 6, or 8 μg of nanoplasmid donor template together with Cas9-RNP targeting the TRAC locus (n=4). Circles represent individual donors; bars represent median values with range. (FIG. 140I) Representative contour plots showing the frequency of CD8 T cells expressing mNG.

FIGS. 141A-141F. Optimization of CRISPR/Cas9-mediated gene knock-in with plasmid-based donor DNA in CD4 and CD8 T cells. (FIGS. 141A, B) Homology arm optimization for plasmid-based donor templates (FIG. 141A) Representative contour plots showing the frequency of CD8 T cells expressing mNG and (FIG. 141B) Bar graphs depicting knock-in efficiency, cell viability, total cell recovery and edited cell recovery (mNG-positive cells) three days post-electroporation with pUC57 plasmid or nanoplasmid donor templates with homology arm lengths between 100 bp and 2000 bp (amounts equimolar to 4 μg of 2000 bp constructs) together with Cas9-RNP targeting the TRAC locus (n=2). Circles represent individual donors; bars represent median values with range. (FIG. 141C) Frequency of CD8 T cells expressing mNG, cell viability, total cell recovery and edited cell recovery (mNG-positive cells) three days post-electroporation at 24, 36, 48, or 72 hours of culture with nanoplasmid donor template together with Cas9-RNP targeting the TRAC locus (n=4). Circles represent individual donors; bars represent median values with range. (FIG. 141D) Nucleofection pulse code optimization in CD8 T cells electroporated with nanoplasmid donor template and Cas9-RNP targeting the TRAC locus. Graph shows frequency of cells expressing mNG and edited cell recovery (mNG-positive cells) three days post-electroporation. Each circle represents a distinct pulse code. Data are representative of three independent CD8 T cell donors. (FIGS. 141E, F) Gene editing targeting the TRAC locus in CD4 T cells (FIG. 141E) Representative contour plot showing the frequency of CD4 T cells expressing mNG and (FIG. 141F) bar graphs depicting knock-in efficiency, cell viability, total cell recovery and edited cell recovery (mNG-positive cells) five days post-electroporation of CD4 T cells with TRAC-mNG nanoplasmid donor template together with Cas9-RNP targeting the TRAC locus (n=3). Circles represent individual donors; bars represent median values with range.

FIGS. 142A-142J. Non-viral T cell receptor editing using plasmid DNA donors (FIG. 142A) Diagram of TCR alpha and beta genomic loci. V gene (purple), D gene (red) and J gene (blue) and constant region (green) segments. sgTRAC and sgTRBC targeting sites are indicated. (FIG. 142B) Diagrams of nanoplasmid knock-in constructs TRAC-1G4TCR, TRAC-TCR6-2 and TRAC-CD19CAR. (FIGS. 142C, E, G) Representative contour plots (left) and bar graphs (right) showing the frequencies of CD8 T cells expressing (FIG. 142C) a NY-ESO1-specific 1G4 TCR, (FIG. 142E) a CMV-specific pp65 6-2 TCR, (FIG. 142G) a CD19-CAR five days post-electroporation using nanoplasmid donor templates together with Cas9-RNPs targeting the TRAC locus (n=3). Circles represent individual donors and bars represent median values with range. (FIGS. 142D, F, H) Bar graphs showing the cell viability, total cell recovery and edited cell recovery five days post-electroporation using nanoplasmid donor templates encoding (FIG. 142D) a NY-ESO1-specific 1G4 TCR, (FIG. 142F) a CMV-specific pp65 6-2 TCR, (FIG. 142H) a CD19-CAR together with Cas9-RNPs targeting the TRAC locus (n=3). Circles represent individual donors; bars represent median values with range. (FIG. 142I) Lactate levels in culture supernatant analyzed by luminescence using the Lactate-Glo Assay were measured one, three, five and seven days after transfection of CD8 T cells with sgTRAC/sgTRBC Cas9-RNP (RNP only) or sgTRAC/sgTRBC Cas9-RNP and nanoplasmid donor template targeting the TRAC locus (RNP+nanoplasmid) compared to non-transfected control T cells (No RNP). (FIG. 142J) Number of cells recovered from cultures seven days after transfection of CD8 T cells with sgTRAC/sgTRBC Cas9-RNP (RNP only) or sgTRAC/sgTRBC Cas9-RNP and nanoplasmid donor template targeting the TRAC locus (RNP+nanoplasmid) compared to non-transfected control T cells (No RNP).

Figure 143A:
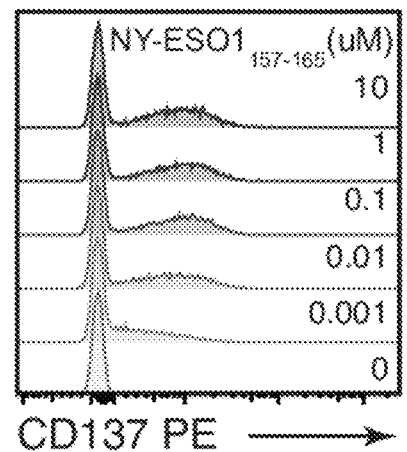
Figure 143B:
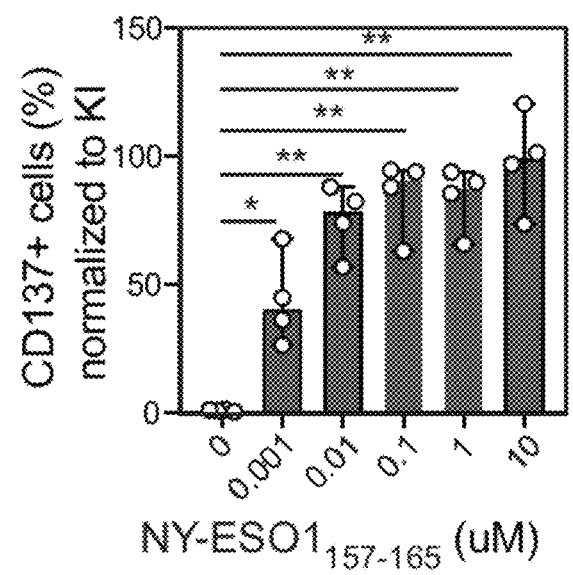
Figure 143C:
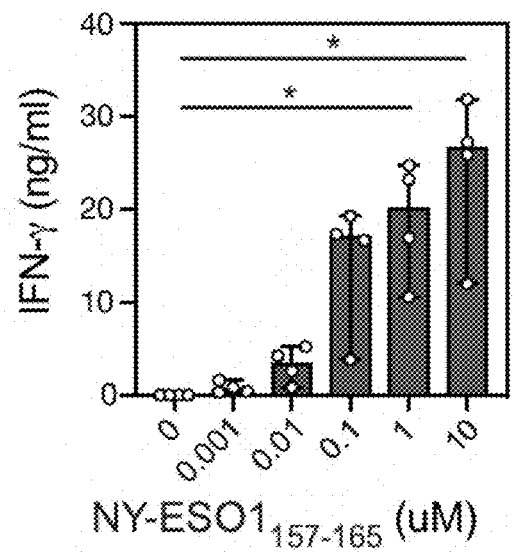
Figure 143D:
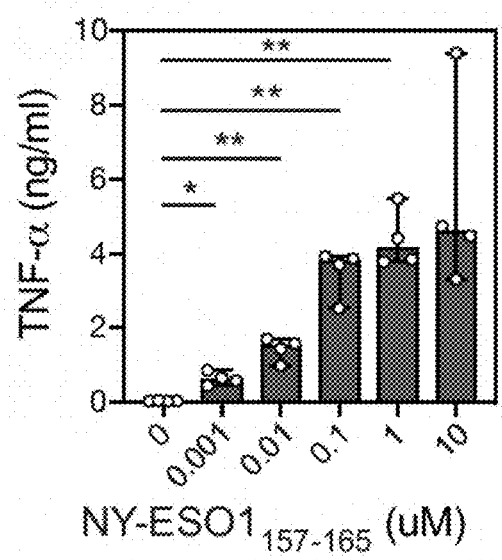
Figure 143E:
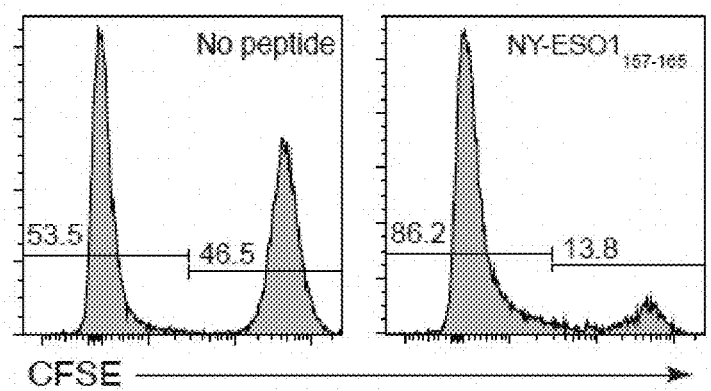
Figure 143F:
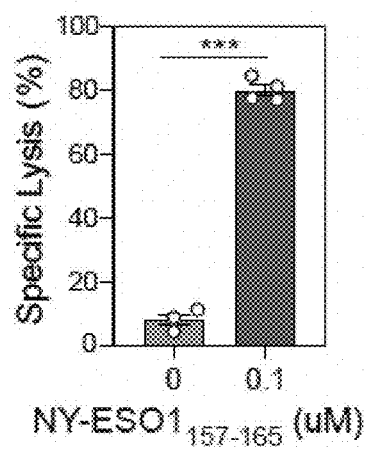
Figure 143G:
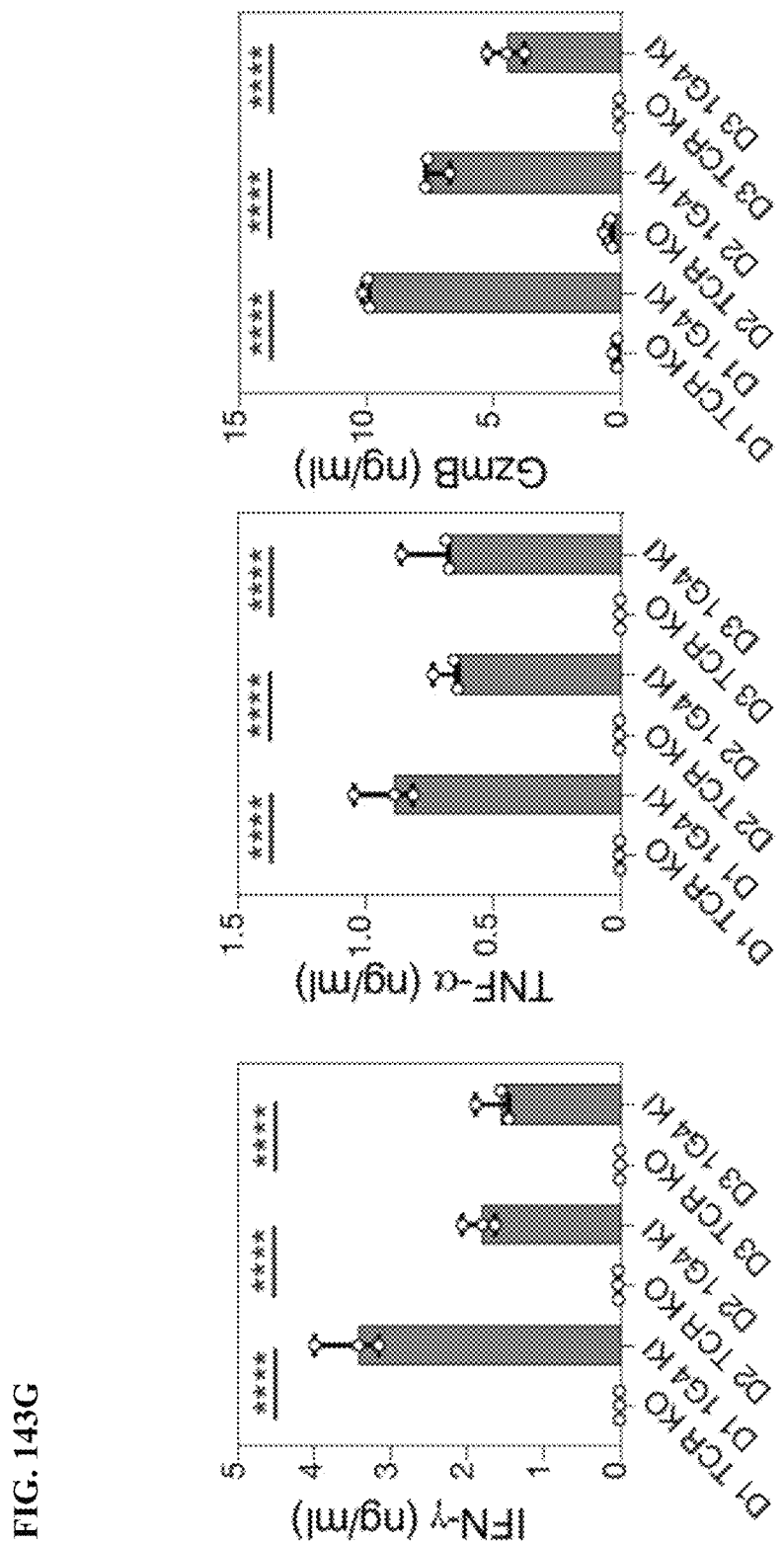

FIGS. 143A-143I: TCR-engineered T cells recognize and kill antigen-expressing target cells. (FIG. 143A) Representative histograms and (FIG. 143B) bar graphs showing CD137 frequencies of IG4 TCR knock-in CD8+ T cells activated with indicated doses of NY-ESO157-165 peptide (n=4). Circles represent individual donors and bars represent median values with range. (FIG. 143C) Representative histograms and (FIG. 143D) bar graphs showing CD137 frequencies of pp65 TCR knock-in CD8+ T cells activated with indicated doses of pp65495-503 peptide (n=3). Circles represent individual donors and bars represent median values with range. (FIG. 143E) Representative histograms showing the frequencies of CFSE-positive target cells to CFSE-negative reference cells in co-cultures with IG4 TCR knock-in CD8+ T cells in the absence or presence of the cognate peptide. (FIG. 143F) Graphs showing specific lysis calculated in the presence of no peptide or 0.1 µM of NY-ESO157-165 peptide. Circles represent individual donors and bars represent median values with range (n=4). This experiment was performed twice. (FIG. 143G). Bar graphs showing IFN-β, TNF-α and granzyme B (GzmB) production by TCR knock-out or 1G4 TCR knock-in CD8+ T cells from three donors co-cultured with A-375 cells that express the NY-ESO-1 antigen. Circles represent technical replicates and bars represent median values with range (n=3). This experiment was performed twice. (FIG. 143H) Representative images for A-375 cells that express the NY-ESO-1 antigen and were labeled with a cytoplasmic dye and co-cultured with TCR knock-out cells (left panels) or 1G4 TCR knock-in cells (right panels) at 2 and 18 hours post-culture seeding in the presence of Caspase 3/7-green apoptosis reagent. (FIG. 143I) Target cell killing over time as measured by the Cas3/7-positive object count in co-cultures of A-375 cells expressing the NY-ESO-1 antigen and labeled with a cytoplasmic dye and co-cultured with TCR knock-out cells (open circles) or 1G4 TCR knock-in cells (filled circles). Mean values±standard deviation of six technical replicates. This experiment was performed twice. *p<0.05, p<0.01, *p<0.001, ****p<0.0001 in RM one-way ANOVA with Geisser-Greenhouse correction (FIGS. 143B-D); paired t-test (FIG. 143F); one-way ANOVA (G) or Tukey's multiple comparisons test, 2-way ANOVA (FIG. 143I).

FIGS. 144A-144M. Generation of reporters of gene expression. (FIG. 144A) Diagram of nanoplasmid knock-in construct RAB11A-YFP. (FIG. 144B) Histogram overlay for YFP expression of CD8 T cells transfected with RAB11A-YFP nanoplasmid with or without RAB11A targeting Cas9-RNP ten days post electroporation. (FIG. 144C) Bar graphs showing the frequency of YFP expression (left) and cell viability (right) of CD8 T cells transfected with RAB11A-YFP nanoplasmid with or without RAB11A targeting Cas9-RNP ten days post electroporation (n=3). Circles represent individual donors and bars represent median values with range. (FIG. 144D) Diagram of nanoplasmid knock-in construct AAVS1-mNG. (FIG. 144E) Histogram overlay for mNG expression of CD8 T cells transfected with AAVS1-mNG nanoplasmid with or without AAVS1 targeting Cas9-RNP ten days post electroporation. (FIG. 144F) Bar graphs showing the frequency of mNG expression (left) and cell viability (right) of CD8 T cells transfected with AAVS1-mNG nanoplasmid with or without AAVS1 targeting Cas9-RNP ten days post electroporation (n=4). Circles represent individual donors and bars represent median values with range. (FIG. 144G) Diagram of nanoplasmid knock-in construct CD4-mNG. (FIG. 144H) Representative contour plots showing the frequency of CD4 and CD8 T cells expressing mNG ten days post-electroporation of a nanoplasmid donor template and Cas9/RNP targeting the CD4 locus. (FIG. 144I) Bar graphs showing the frequency of CD4 and CD8 T cells expressing mNG (top) and cell viability (bottom) ten days post-electroporation of a nanoplasmid donor template and Cas9/RNP targeting the CD4 locus (n=4 for CD4 T cells, n=3 for CD8 T cells). Circles represent individual donors and bars represent median values with range. (FIG. 144J) Histogram overlay for CD4 expression in CD4 T cells transfected with CD4-mNG nanoplasmid and either a non-targeting control Cas9-RNP (sgNTC) or a Cas9-RNP targeting the CD4 locus (sgCD4) ten days post electroporation. (FIG. 144K) Diagrams of nanoplasmid knock-in constructs TNFRSF9-mNG and RAB11A-YFP (left) and representative contour plots (right) showing the frequency of CD8 T cells expressing CD137 and mNG following electroporation with a nanoplasmid mNG reporter construct targeting the TNFRSF9 locus or a constitutive YFP expressing construct targeting the RAB11A locus together with the respective Cas9-RNP either without re-activation or 6h after reactivation with Transact. (FIG. 144L) Bar graphs showing the frequency of YFP (left) and mNG (right) expressing CD8 T cells over time following electroporation with a nanoplasmid mNG reporter construct targeting the TNFRSF9 locus or a constitutive YFP expressing construct targeting the RAB11A locus together with the respective Cas9-RNP and re-activation with Transact at time 0 h (n=4). Circles represent individual donors and bars represent median values with range. (FIG. 144M) Bar graphs showing the median fluorescent intensity (gMFI) of CD137 expression in CD8 T cells over time following electroporation with a nanoplasmid mNG reporter construct targeting the TNFRSF9 locus (right) or a constitutive YFP expressing construct targeting the RAB11A locus together (left) with the respective Cas9-RNP and re-activation with Transact at time 0 h (n=4). Circles represent individual donors and bars represent median values with range.

FIGS. 145A-145K. Multiplexed gene knock-in in human T cells. (FIGS. 145A-145C) Diagrams of nanoplasmid knock-in constructs are provided on the top. Representative contour plots (left) and bar graphs (right) showing the frequency of CD8 T cells expressing (FIG. 145A) mNG ten days post-electroporation with a nanoplasmid TRAC-mNG donor template and Cas9/RNPs targeting the TRAC locus (n=3), (FIG. 145B) mCherry ten days post-electroporation with a nanoplasmid TRAC-mCherry donor template and Cas9/RNPs targeting the TRAC locus (n=3), or (FIG. 145C) either mNG or mCherry ten days post-electroporation with two nanoplasmid donor templates (TRAC-mNG and TRAC-mCherry) and Cas9/RNPs targeting the TRAC locus (n=3). Graph on the right for (FIG. 145C) indicates proportion of transgene expressing cells that express either mNG (bottom right of histogram), mCherry (top left) or both (top right). In bar graphs, circles represent individual donors and bars represent median values with range. (FIG. 145D) Diagrams of nanoplasmids used in dual targeting study, RAB11A-YFP and TRAC-mCherry. (FIG. 145E) Representative contour plot showing the frequency of CD8 T cells expressing either YFP (bottom right), mCherry (top left) or both (top right) ten days post-electroporation with nanoplasmid donors RAB11A-YFP and TRAC-mCherry and Cas9/RNPs targeting the RAB11A and TRAC locus. (FIG. 145F) Bar graphs showing knock-in efficiency (left), cell viability (middle) and total cell recovery (right) of CD8 T cells both ten days post-electroporation with nanoplasmid donors RAB11A-YFP and TRAC-mCherry and Cas9/RNPs targeting the RAB11A and TRAC loci (n=4). Circles represent individual donors and bars represent median values with range. (FIG. 145G) Proportion of transgene expressing cells co-transfected with nanoplasmid donors RAB11A-YFP and TRAC-mCherry and Cas9/RNPs targeting the RAB11A and TRAC loci that express either YFP, mCherry or both (n=4). Circles represent individual donors and bars represent median values with range. (FIG. 145H) Diagrams of nanoplasmids used in dual targeting study, AAVS1-mNG and TRAC-mCherry. (FIG. 145I) Representative contour plot showing the frequency of CD8 T cells expressing either mNG, mCherry or both ten days post-electroporation with nanoplasmid donors AAVS1-mNG and TRAC-mCherry and Cas9/RNPs targeting the AAVS1 and TRAC loci. (FIG. 145J) Bar graphs showing knock-in efficiency (left), cell viability (middle) and total cell recovery (right) of CD8 T cells both ten days post-electroporation with nanoplasmid donors AAVS1-mNG and TRAC-mCherry and Cas9/RNPs targeting the AAVS1 and TRAC loci (n=4). Circles represent individual donors and bars represent median values with range. (FIG. 145K) Proportion of transgene expressing cells co-transfected with nanoplasmid donors AAVS1-mNG and TRAC-mCherry and Cas9/RNPs targeting the AAVS1 and TRAC loci that express either mNG, mCherry or both (n=4). Circles represent individual donors and bars represent median values with range.

FIG. 146A-146G. Non-viral CRISPR gene editing with large payloads. (FIG. 146A) Diagram of nanoplasmid knock-in constructs TRAC_NotchICD_mNG, TRAC_NotchICD_1G4 and TRAC_THEMIS_1G4. (FIGS. 146B, D, F) Representative contour plots showing the frequency of CD8 T cells expressing (FIG. 146B) mNG or (FIGS. 146D, F) 1G4 TCR five days post-electroporation of a (FIG. 146B) NotchICD_mNG, (FIG. 146D) NotchICD_1G4 or (FIG. 146F) THEMIS_1G4 nanoplasmid donor template together with Cas9/RNP targeting the TRAC locus (FIG. 146C, E, G) Bar graphs showing the frequency of CD8 T cells expressing (FIG. 146C) mNG or (FIG. 146E, G) 1G4 TCR and cell viability five days post-electroporation of a (FIG. 146C) NotchICD_mNG, (FIG. 146E) NotchICD_1G4 or (FIG. 146G) THEMIS_1G4 nanoplasmid donor template together with Cas9/RNP targeting the TRAC locus (n=3). Circles represent individual donors and bars represent median values with range.

FIG. 147A-147H. Optimization of non-viral gene editing in primary T cells using plasmid-based donor templates. (FIGS. 147A-F) Titration of linear dsDNA and nanoplasmid donor templates in RPMI/FBS media. (FIG. 147A) Diagram of linear dsDNA knock-in construct TRAC-mNG. (FIG. 147B) Bar graphs depicting knock-in efficiency, cell viability, total cell recovery and edited cell recovery (mNG-positive cells) of CD8 T cells cultured in RPMI/10% FBS three days post-electroporation with 1, 2, 4 μg of linear dsDNA donor template together with Cas9/RNP targeting the TRAC locus (n=4). (FIG. 147C) Representative contour plots showing the frequency of CD8 T cells expressing mNG (left), viability (second from left), total cell recovery (second from right), and edited cell recovery (right). Circles represent individual donors; bars represent median values with range. (FIG. 147D) Diagram of nanoplasmid knock-in construct TRAC-mNG. (FIG. 147E) Bar graphs depicting knock-in efficiency, cell viability, total cell recovery and edited cell recovery (mNG-positive cells) of CD8 T cells cultured in RPMI/10% FBS three days post-electroporation with 1, 2, 4 μg of nanoplasmid donor template together with Cas9/RNP targeting the TRAC locus (n=4). Circles represent individual donors; bars represent median values with range. (FIG. 147F) Representative contour plots showing the frequency of CD8 T cells expressing mNG (left), viability (second from left), total cell recovery (second from right), and edited cell recovery (right). (FIG. 147G) Bar graphs depicting knock-in efficiency (left), cell viability (second from left), total cell recovery (second from right) and edited cell recovery (right) three days post-electroporation with 2 μg of either linear dsDNA or nanoplasmid donor template together with Cas9-RNP targeting the TRAC locus. In the presence of absence of poly-L-glutamic acid (PGA) (n=3). Circles represent individual donors; bars represent median values with range. (FIG. 147H) Bar graphs depicting knock-in efficiency (left), cell viability (second from left), total cell recovery (second from right) and edited cell recovery (right) three days post-electroporation with 2 μg of either linear dsDNA or nanoplasmid donor template that either did (tCTS) or did not (w/o tCTS) contain truncated Cas9 target sequences together with Cas9-RNP targeting the TRAC locus (n=3). Circles represent individual donors; bars represent median values with range.

FIG. 148A-148H. Cytokine production and stress response induced in T cells following exposure to dsDNA donor templates. (FIG. 148A) IFN-α measured by SIMOA and IFN-γ, TNF-α and IL-2 measured by Luminex from CD8 T cells 18h after transfection with Cas9/RNP targeting the TRAC locus alone or together with nanoplasmid donor template compared to non-transfected control T cells (No RNP). Circles represent individual donors; bars represent median values with range. (n–3) (FIG. 148B) GSEA Enrichment analysis results from CD8 T cells after transfection with Cas9/RNP targeting the TRAC with nanoplasmid donor template compared to Cas9/RNP alone. Gene sets for Interferon-γ response, Interferon-α response, TNFα signaling, and inflammatory response were significantly enriched. (FIG. 148C) GSEA Enrichment analysis results from CD8 T cells after transfection with Cas9/RNP targeting the TRAC with linear dsDNA donor template compared to Cas9/RNP alone. Gene sets for Interferon-γ response, Interferon-α response, TNFα signaling, and inflammatory response were significantly enriched. (FIGS. 148B, C) The y-axis represents enrichment score and on the x-axis are genes (vertical black lines) represented in gene sets. The colored band at the bottom represents the degree of differentially-expressed genes (red for upregulation and blue for downregulation). (FIG. 148D) GSEA of all 375 upregulated genes in both Nanoplasmid/Cas9-RNP and linear dsDNA/Cas9-RNP over Cas9-RNP-only using the GSEA MSigDB Hallmark 2020. (FIGS. 148E-H) Heatmaps showing upregulated genes in Nanoplasmid/Cas9-RNP and linear dsDNA/Cas9-RNP over Cas9-RNP-only that mostly contributed to (FIG. 148E) Interferon-α response, (FIG. 148F) TNFα response, (FIG. 148G) Apoptosis or (FIG. 148H) Inflammatory Response (all MSigDB Hallmark). Color-coded by the normalized RNA-seq count data with variance stabilizing transformation (VST).

Figure 149A:
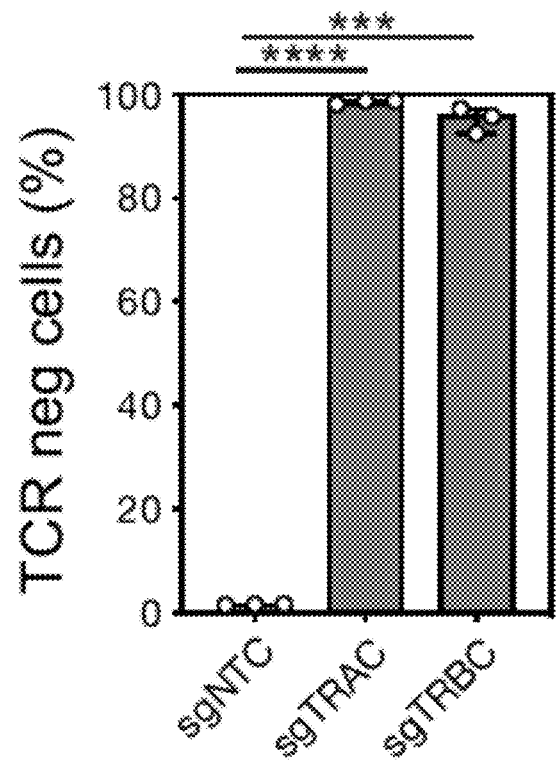
Figure 149B:
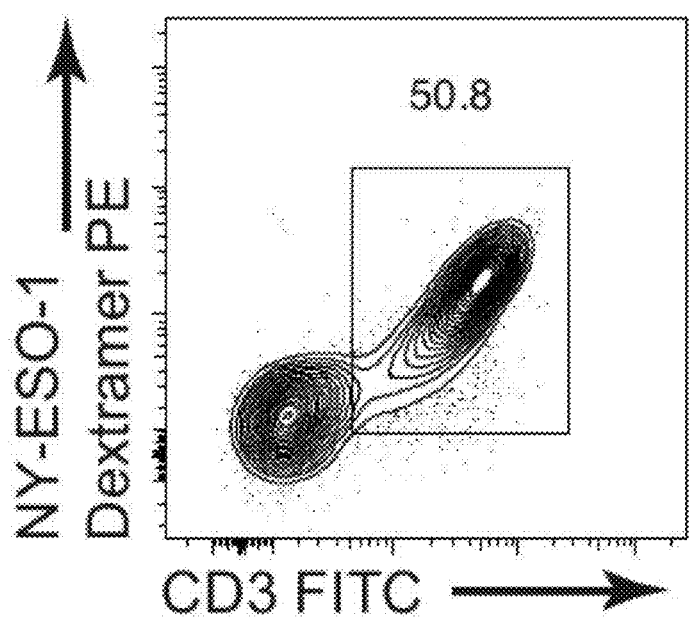
Figure 149C:
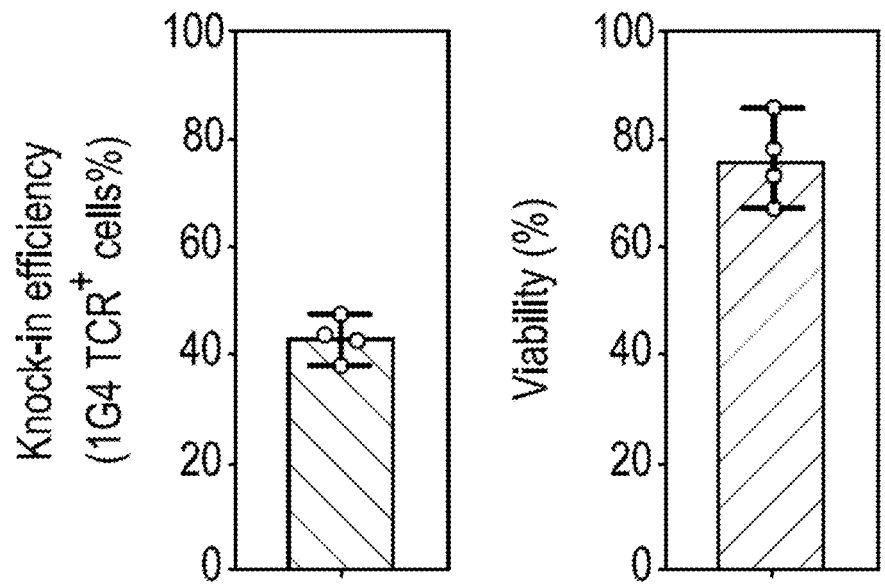
Figure 149D:
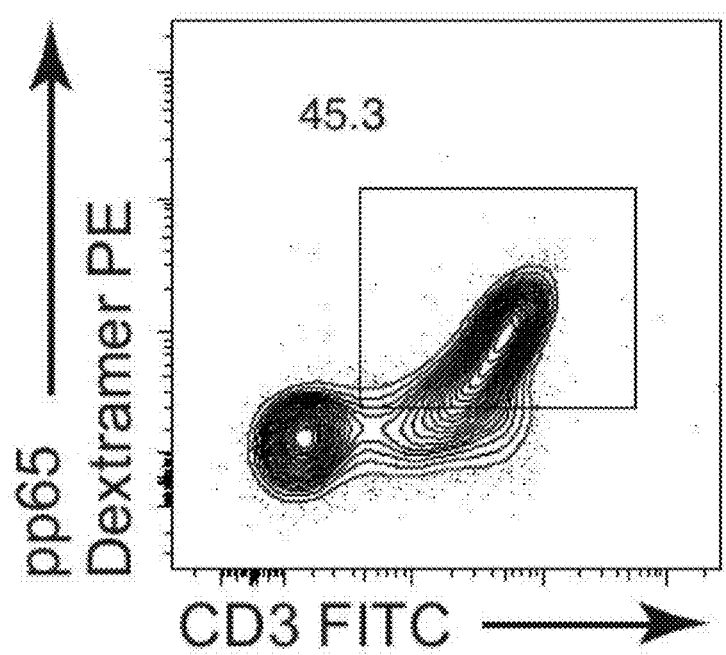
Figure 149E:
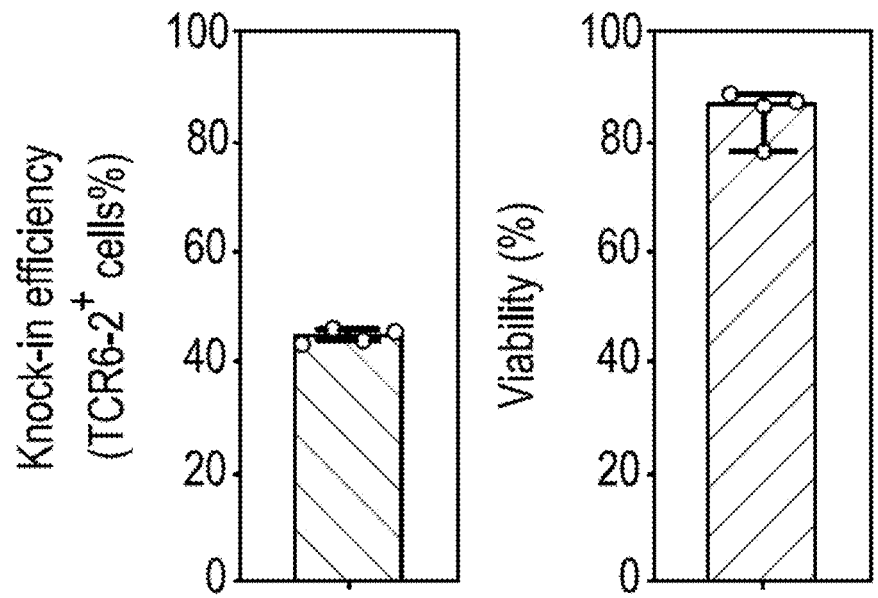
Figure 149F:
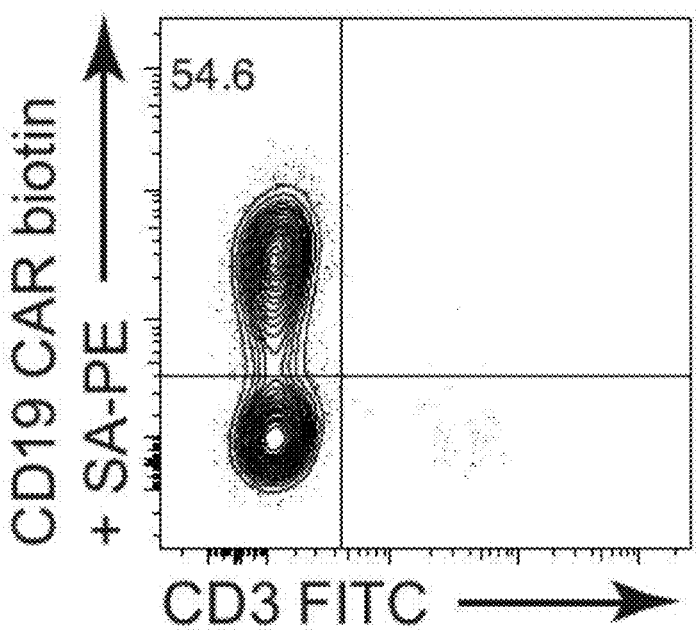
Figure 149G:
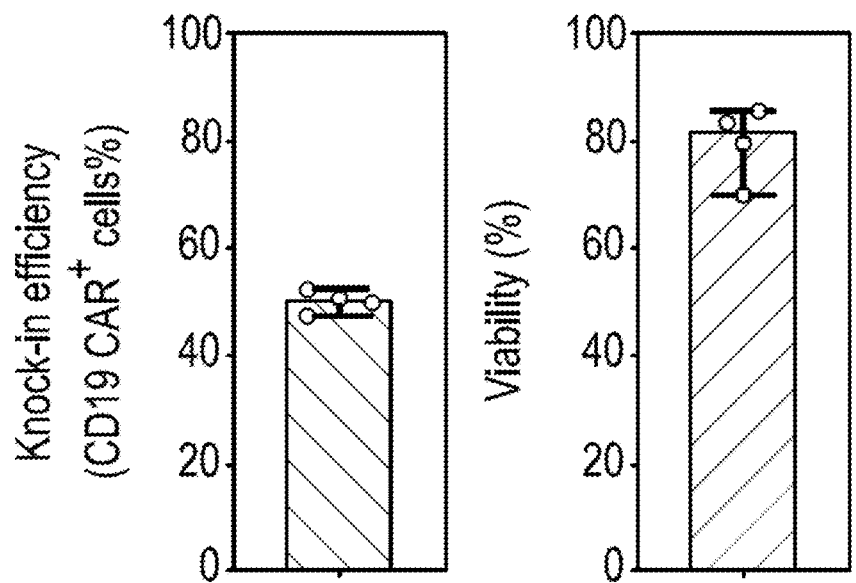

FIGS. 149A-149O. Non-viral T cell receptor editing in CD4+ and CD8+ T cells using plasmid DNA donors. (FIG. 149A) TCR expression on the cell surface by flow cytometry of CD8 T cells 48h after transfection with Cas9-RNP targeting the TRAC (sgTRAC) or TRBC (sgTRBC) loci (FIGS. 149B-G) TCR editing in CD4 T cells. Representative contour showing the frequencies of CD8 T cells expressing (FIG. 149B) a NY-ESO1-specific 1G4 TCR, (FIG. 149D) a CMV-specific pp65 6-2 TCR, (FIG. 149F) a CD19-CAR five days post-electroporation using nanoplasmid donor templates together with Cas9-RNPs targeting the TRAC locus. Bar graphs showing the knock-in efficiency and cell viability five days post-electroporation using nanoplasmid donor templates encoding (FIG. 149C) a NY-ESO1-specific 1G4 TCR, (FIG. 149E) a CMV-specific pp65 6-2 TCR, (FIG. 149G) a CD19-CAR together with Cas9-RNPs targeting the TRAC locus (n=4). Circles represent individual donors; bars represent median values with range. (FIG. 149H) Diagram depicting all possible translocation events between the TRAC, TRBC1 and TRBC2 genomic loci (FIG. 149I) Bar graph showing the frequencies of individual translocation events between the TRAC, TRBC1 and TRBC2 genomic loci quantified by ddPCR in CD8 T cells co-transfected with Cas9-RNPs targeting the TRAC and TRBC loci or in non-transfected control T cells (n=4). Circles represent individual donors; bars represent median values with range. This experiment was performed twice. (FIG. 149J) Representative histograms and (FIG. 149K) bar graphs showing CD137 frequencies of pp65 TCR knock-in CD8+ T cells stimulated with indicated concentrations of $pp65_{495\text{-}503}$ peptide. Circles represent individual donors and bars represent median values with range (n=3). This experiment was performed twice. (FIG. 149L) Bar graphs showing IFN-β (left) and TNF-α (right) production by pp65 TCR knock-in CD8+ T cells stimulated with indicated concentrations of $pp65_{495\text{-}503}$ peptide. Circles represent individual donors and bars represent median values with range (n=3). This experiment was performed twice. (FIG. 149M) Representative histograms showing the frequencies of CFSE-positive target cells and CFSE-negative reference cells in co-cultures with pp65 TCR knock-in CD8+ T cells in the absence or presence of the cognate peptide. (FIG. 149N) Graphs showing specific lysis calculated in the absence of peptide or with 0.1 μM of $pp65_{495\text{-}503}$ peptide. Circles represent individual donors and bars represent median values with range (n=3). This experiment was performed twice. (FIG. 149O) Bar graphs showing IFN-β and TNF-α production by TCR6-2 (irrelevant TCR) or CD19-CAR knock-in CD4+ T cells from two donors (D1, D2) in co-cultures with CD19-expressing B cells. Circles represent technical replicates; bars: represent median values with range (n=9). This experiment was performed twice. *p<0.05, p<0.01, *p<0.001, ****p<0.0001 in RM one-way ANOVA with Geisser-Greenhouse correction (FIGS. 149A, K), paired t-test (FIG. 149N) one-way ANOVA (FIG. 149O).

FIGS. 150A-150I. Kinetics of gene expression following transient transfection of dsDNA, plasmid and nanoplasmid. (FIG. 150A) Diagram of nanoplasmid knock-in construct RAB11A-YFP. (FIG. 150B) Representative histograms showing the frequencies of CD8 T cells expressing YFP three, five or seven days after electroporation with promoter-containing nanoplasmid donor template together with (red/right bar of pair) or without (blue/left bar or pair) Cas9/RNPs targeting the RAB11A locus. (FIG. 150C) Graphs depicting frequency of YFP expression, cell viability, total cell recovery and edited cell recovery three, five or seven days after electroporation with promoter-containing nanoplasmid donor template together with (red/right bar) or without (blue/left bar) Cas9/RNPs targeting the RAB11A locus (n=3) (FIG. 150D) Diagram of linear dsDNA knock-in construct RAB11A-YFP. (FIG. 150E) Representative histograms showing the frequencies of CD8 T cells expressing YFP three, five or seven days after electroporation with promoter-containing linear dsDNA donor templates together with (top) or without (bottom) Cas9/RNPs targeting the RAB11A locus. (FIG. 150F) Graphs depicting frequency of YFP expression, cell viability, total cell recovery and edited cell recovery three, five or seven days after electroporation with promoter-containing linear dsDNA donor templates together with (red/right bar of pair) or without (blue/left bar of pair) Cas9/RNPs targeting the RAB11A locus (n=3). (FIG. 150G) Diagram of pUC57 plasmid knock-in construct RAB11A-YFP. (FIG. 150H) Representative histograms showing the frequencies of CD8 T cells expressing YFP three, five or seven days after electroporation with promoter-containing pUC57 plasmid donor templates together with (top) or without (bottom) Cas9/RNPs targeting the RAB11A locus. (FIG. 150I) Graphs depicting frequency of YFP expression, cell viability, total cell recovery and edited cell recovery three, five or seven days after electroporation with promoter-containing pUC57 plasmid donor templates together with (red/right bar of pair) or without (blue/left bar of pair) Cas9/RNPs targeting the RAB11A locus (n=3).

FIGS. 151A-151G. Multiplexed gene knock-in in human T cells. (FIGS. 151A-C) Diagrams of pUC57 plasmid knock-in constructs are provided on the top. Representative contour plots (left) and bar graphs (right) showing the frequency of CD8 T cells expressing (FIG. 151A) mNG ten days post-electroporation with a pUC57 plasmid TRAC-mNG donor template and Cas9/RNPs targeting the TRAC locus (n=3), (FIG. 151B) mCherry ten days post-electroporation with a pUC57 plasmid TRAC-mCherry donor template and Cas9/RNPs targeting the TRAC locus (n=3), or (FIG. 151C) either mNG or mCherry ten days post-electroporation with two pUC57 plasmid donor templates (TRAC-mNG and TRAC-mCherry) and Cas9/RNPs targeting the TRAC locus (n=3). Graph on the right for (FIG. 151C) indicates proportion of transgene expressing cells that express either mNG (green/bottom right of histogram), mCherry (red/top left) or both (blue/top right). Circles represent individual donors and bars represent median values with range. (FIG. 151D) Diagrams of pUC57 plasmids used in dual targeting study, RAB11A-YFP and TRAC-mCherry. (FIG. 151E) Representative contour plot showing the frequency of CD8 T cells expressing either YFP, mCherry or both ten days post-electroporation with pUC57 donors RAB11A-YFP and TRAC-mCherry and Cas9/RNPs targeting the RAB11A and TRAC locus. (FIG. 151F) Bar graphs showing knock-in efficiency, cell viability and total cell recovery of CD8 T cells both ten days post-electroporation with pUC57 donors RAB11A-YFP and TRAC-mCherry and Cas9/RNPs targeting the RAB11A and TRAC loci (n=4). Circles represent individual donors and bars represent median values with range. (FIG. 151G) Proportion of transgene expressing cells co-transfected with pUC57 donor templates RAB11A-YFP and TRAC-mCherry and Cas9/RNPs targeting the RAB11A and TRAC loci that express either YFP, mCherry or both (n=4). Circles represent individual donors and bars represent median values with range. This experiment was performed three times. *p<0.05 **p<0.01 in RM one-way ANOVA with Geisser-Greenhouse correction.

Figure 152:
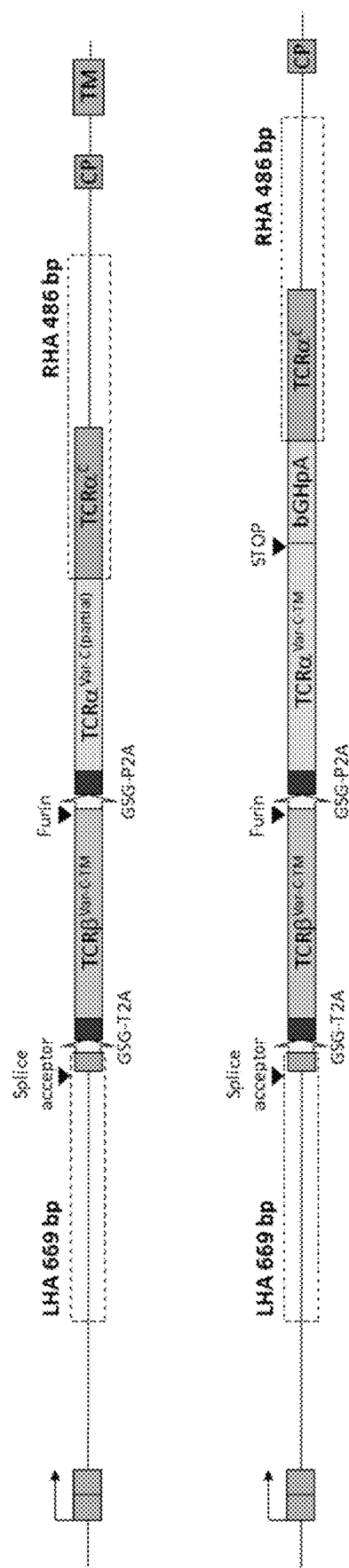

FIG. 152. Two TCR knock-in constructs, with and without a polyadenylation (bGHpA) sequence. The TRACg3_WT1C13_pUC57 construct contains a truncated TCR-alpha sequence consisting of the entire variable region, plus a small segment of the constant region prior to the right homology arm. Once copied into the TRAC3 cut site within the genome, the truncated TCR-alpha within the construct is made whole through an in-frame fusion with the genomic DNA, which supplies the remainder of the TCR-alpha constant chain sequence. The construct named Schober_TRACg3_WT1C13_pUC57 differs from TRACg3_WT1C13_pUC57 in that it contains a full-length TCR-alpha sequence, followed by a STOP codon, and then a polyadenylation sequence from the bovine growth hormone gene (bGHpA) prior to the right homology arm. It does not require an in-frame fusion with the remaining TCR-alpha constant chain sequence in the genome for TCR-alpha expression.

Figure 153:
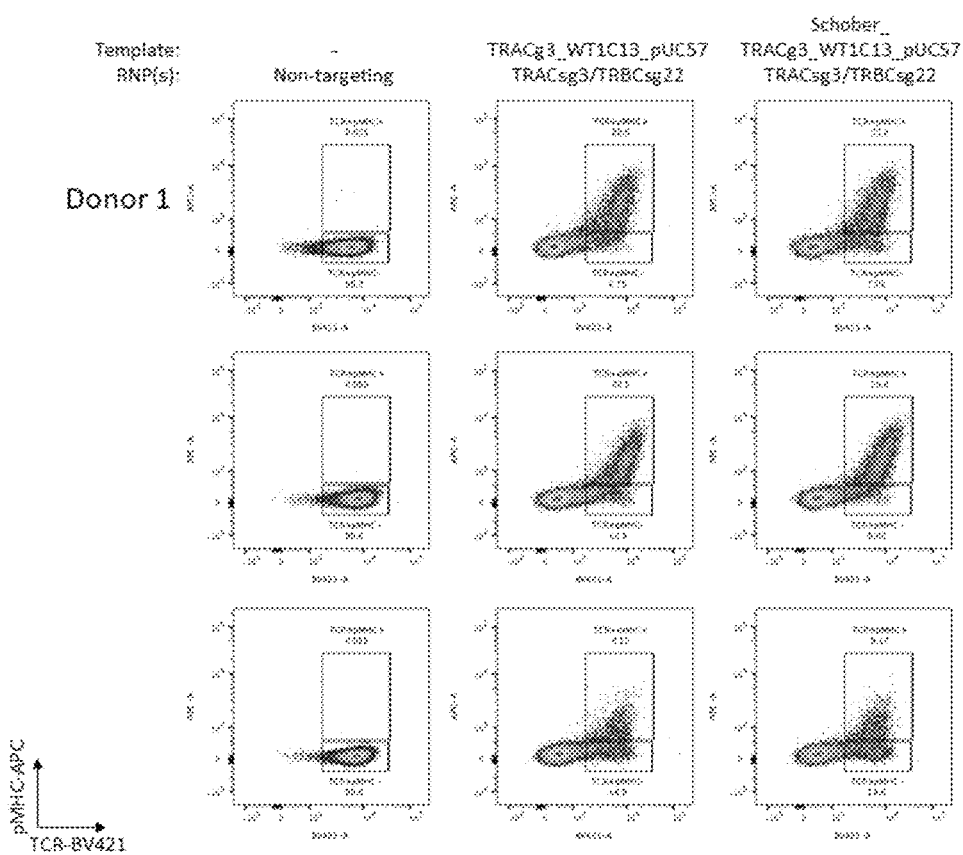

FIG. 153. Flow cytometry scatter plots of donor primary cells electroporated with two TCR knock-in construct RNPs, with and without a polyadenylation (bGHpA) sequence (Schober_TRACg3_WT1C13_pUC57 and TRACg3_WT1C13_pUC57).

Figure 154:
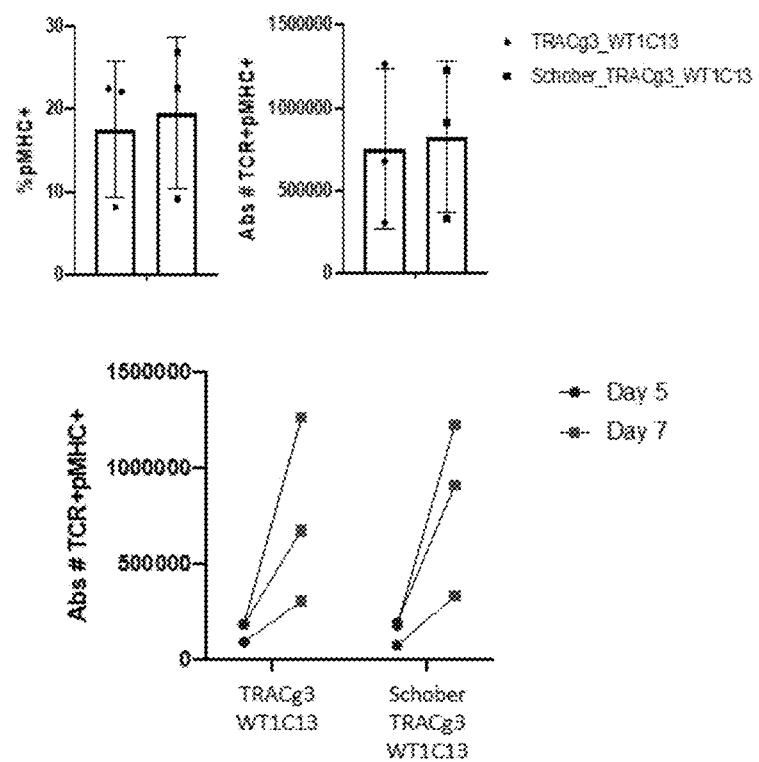

FIG. 154. Bar graph comparison (% pMHC+ and TCR+ pMHC+) of donor primary cells electroporated with two TCR knock-in construct RNPs, with and without a polyadenylation (bGHpA) sequence (Schober_TRACg3_WT1C13_pUC57 and TRACg3_WT1C13_pUC57).

Figure 155:
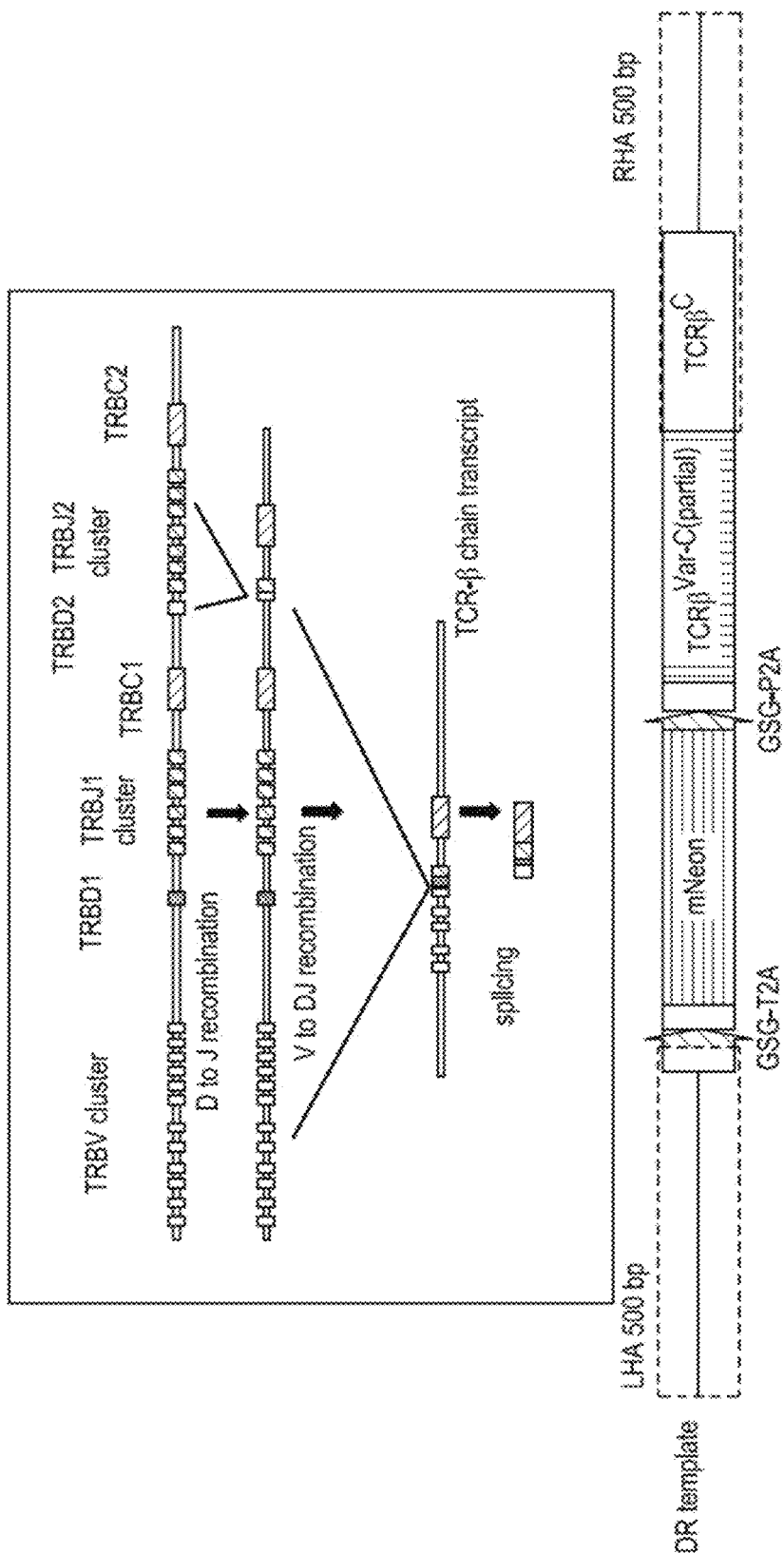

FIG. 155. Schematic representation of knock-in at TCRB1 and TCRB2 loci nanoplasmid constructs.

Figure 156:
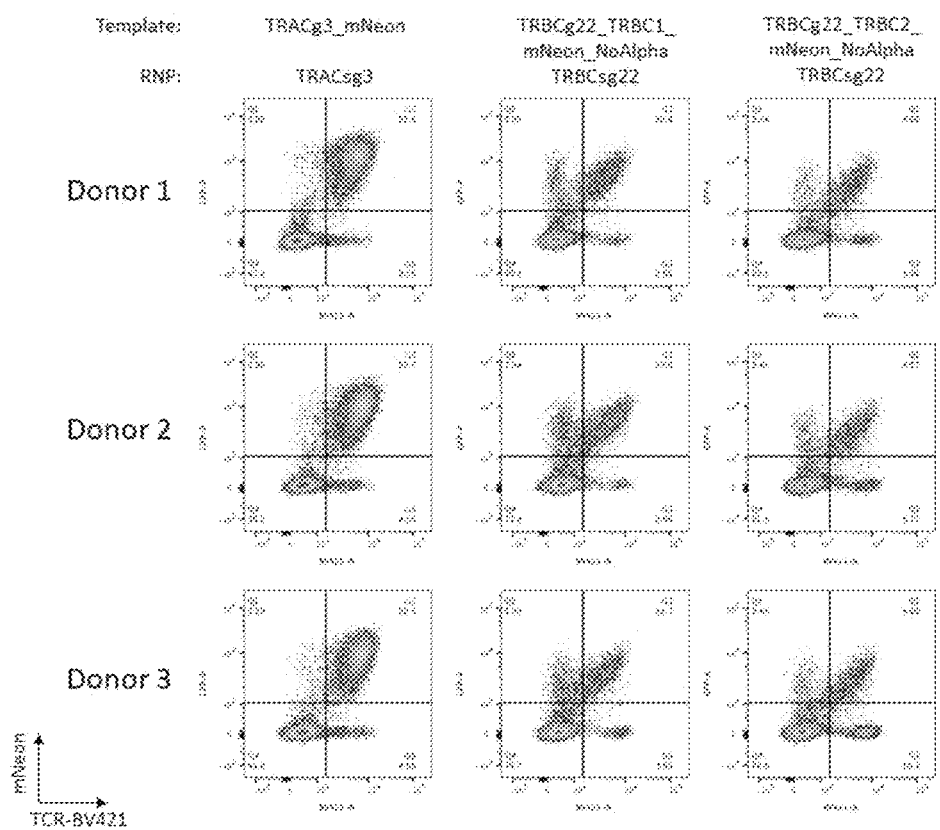

FIG. 156. Flow cytometry scatter plots of donor primary cells electroporated with two knock-in at TCRB1 and TCRB2 loci nanoplasmid constructs, without a TCR alpha sequence.

Figure 157:
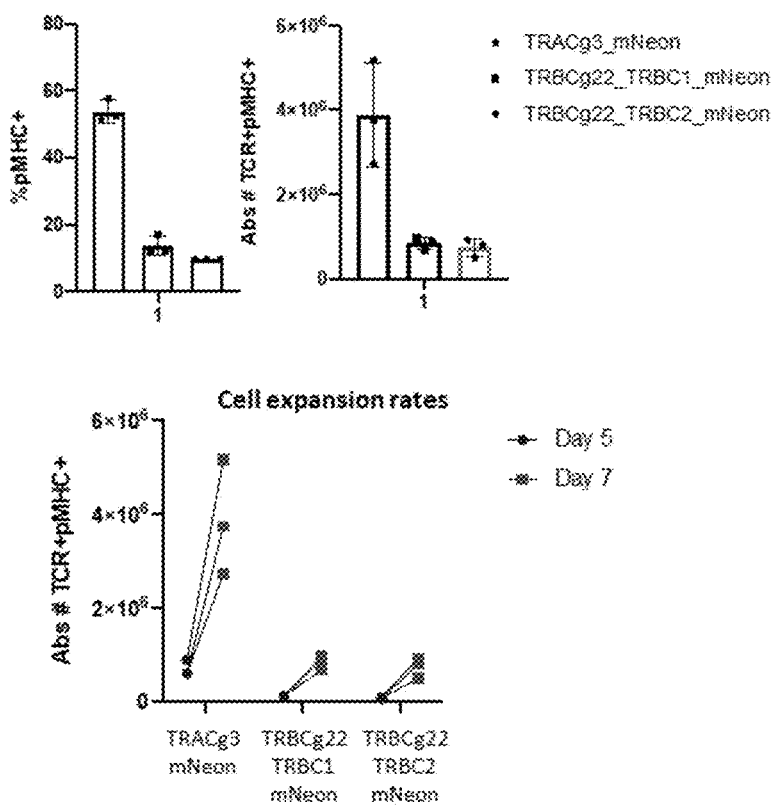

FIG. 157. Bar graph comparison (% pMHC+ and TCR+ pMHC+) of donor primary cells electroporated with two knock-in at TCRB1 and TCRB2 loci nanoplasmid constructs, without a TCR alpha sequence.

Figure 158:
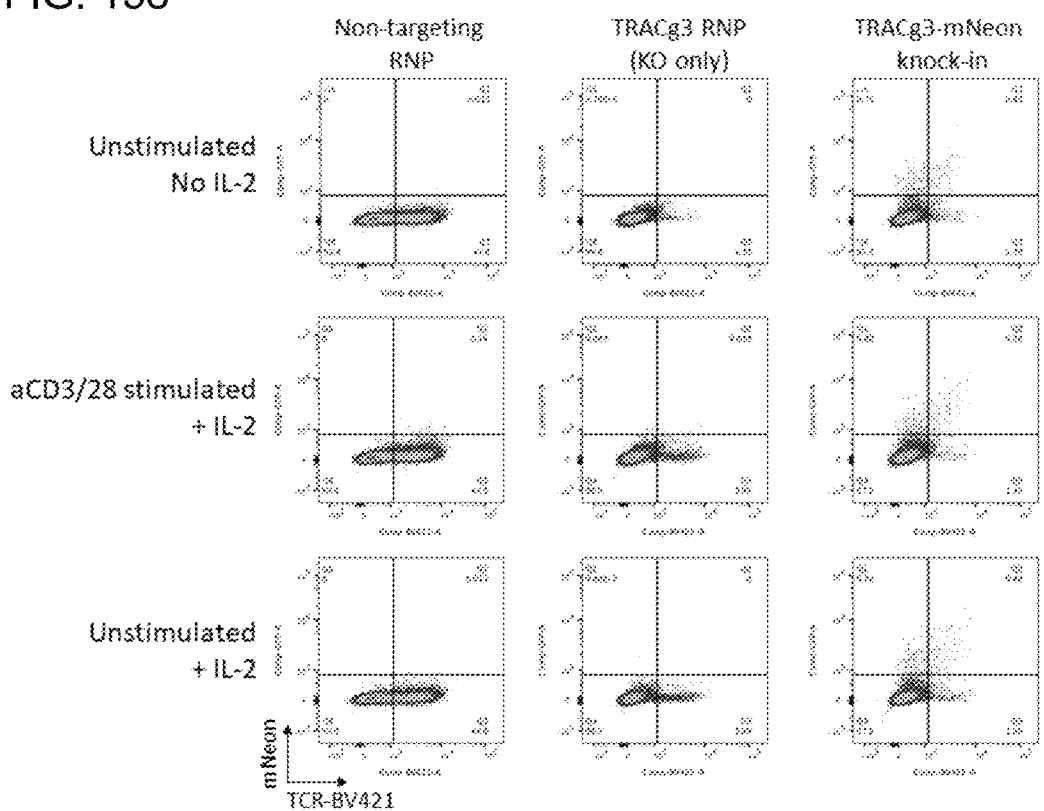

FIG. 158. Scatter plots of cell expansion rates at days 5 and 7 of the donor primary cells electroporated with two knock-in at TCRB1 and TCRB2 loci nanoplasmid constructs, without a TCR alpha sequence.

Figure 159:
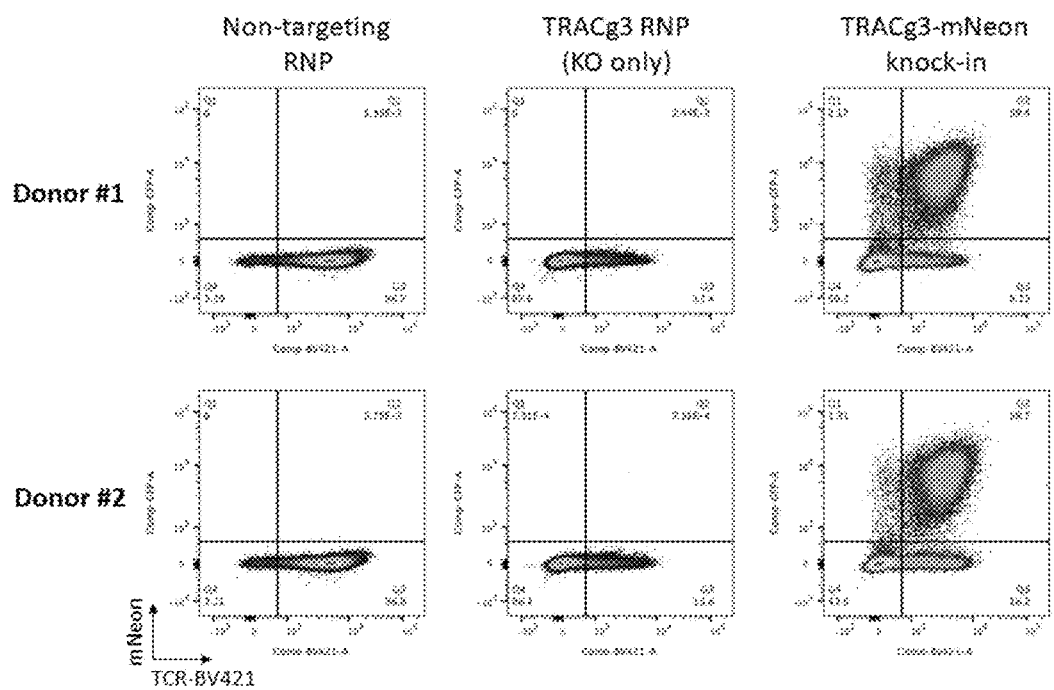

FIG. 159. Flow cytometry scatter plots of non-viral TCR knock-in using Jurkat cells at day 7, with and without activation with IL-2.

Figure 160:
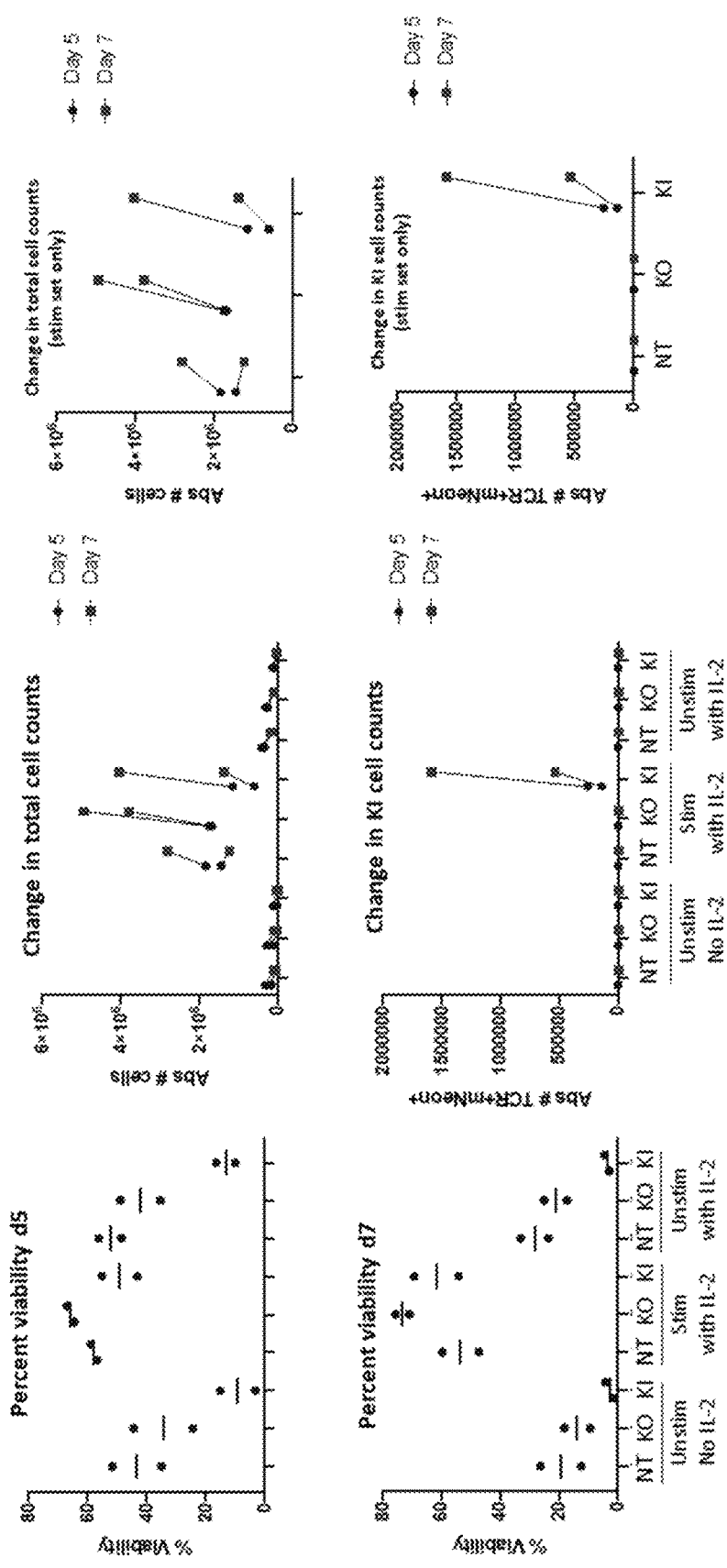

FIG. 160. Flow cytometry scatter plots of non-viral TCR knock-in using primary CD4+ cells, without activation with IL-2.

Figure 161:
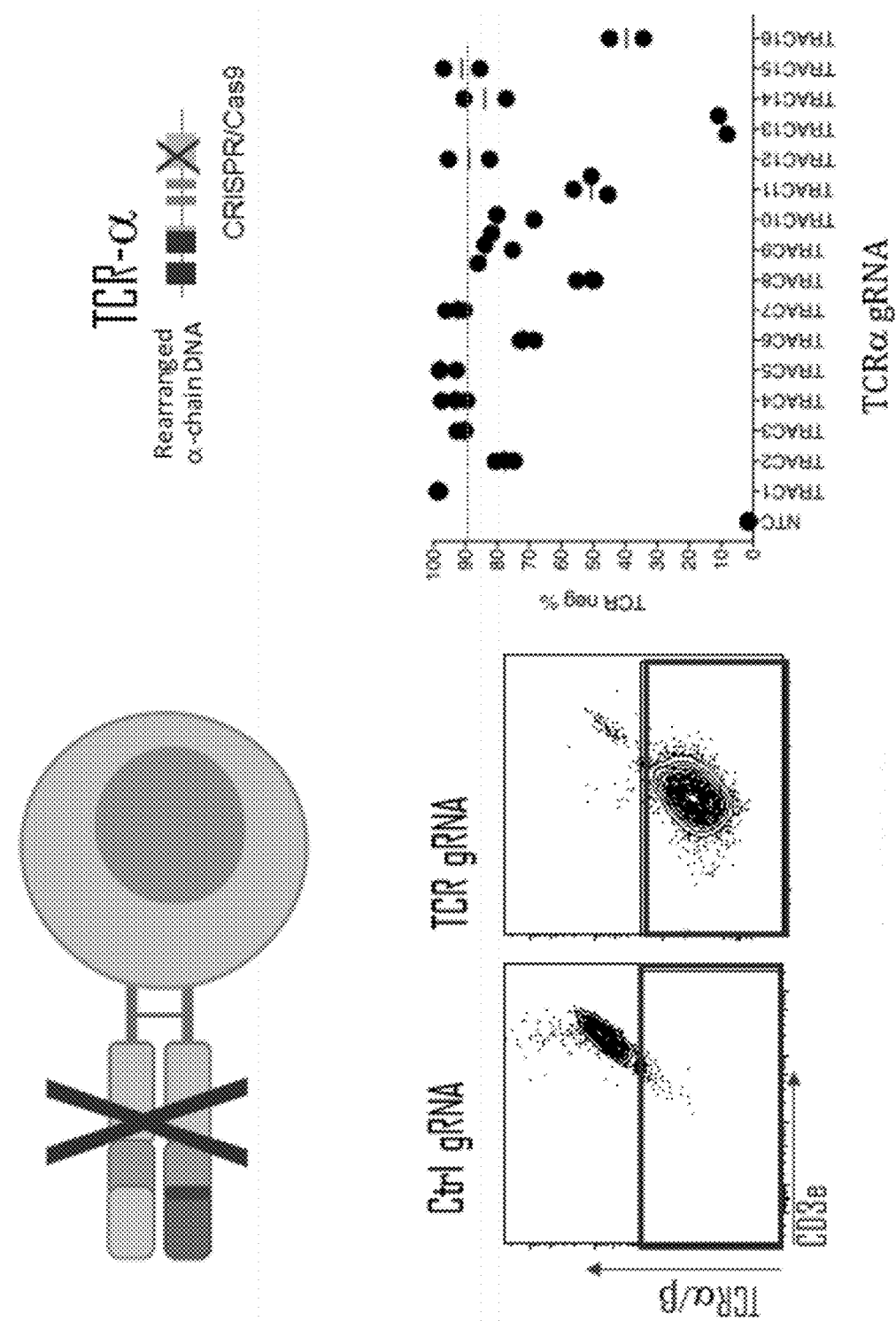
Figure 161:
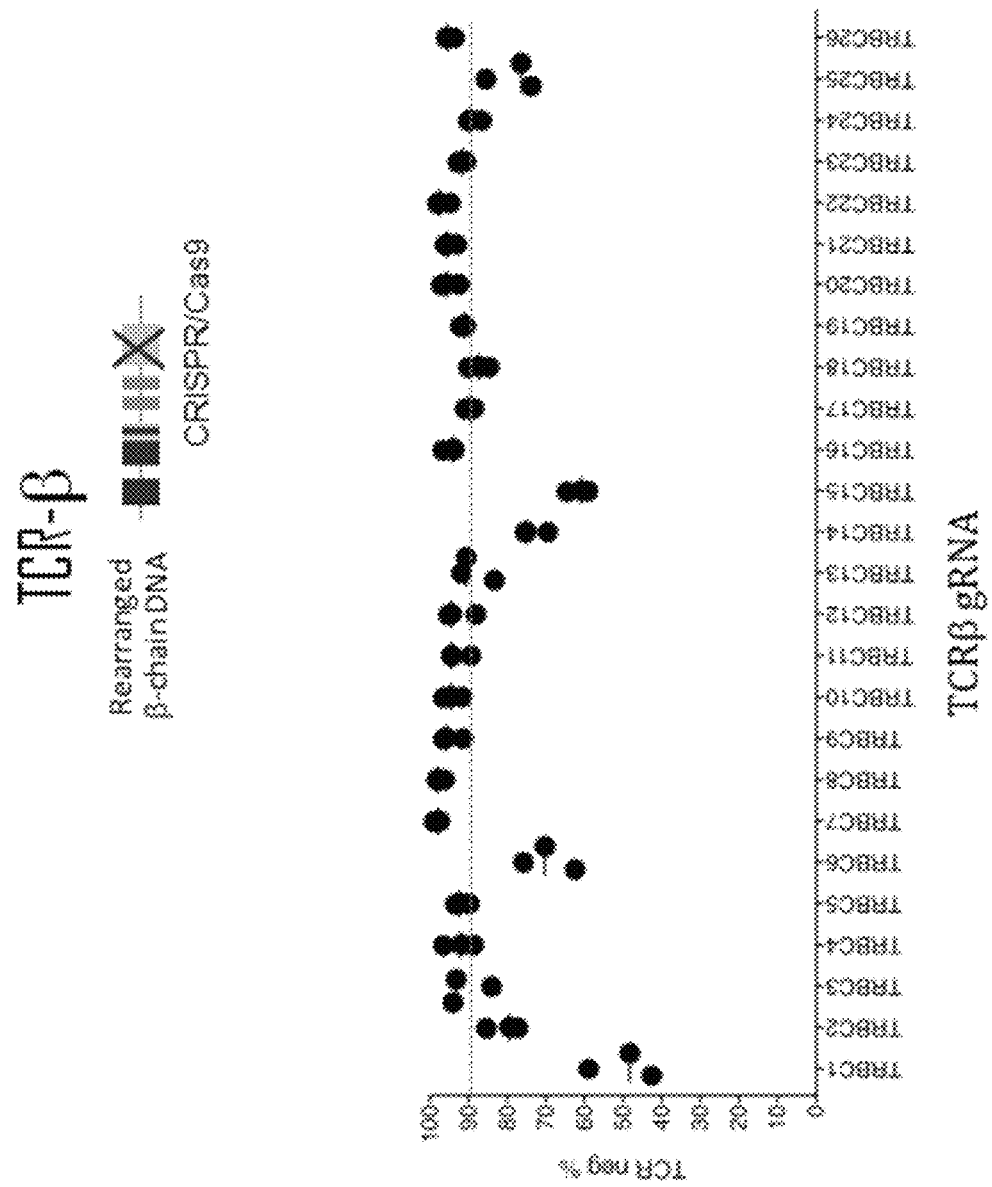

FIG. 161. Overview schematic of the knock-out of either TCR-alpha and TCR-beta loci using TCRA1-TCRA16 and TCRB1-TCRB26 guide RNA, including a plot of the % negative T cells for TCR-alpha or beta by flow cytometry.

Figure 162:
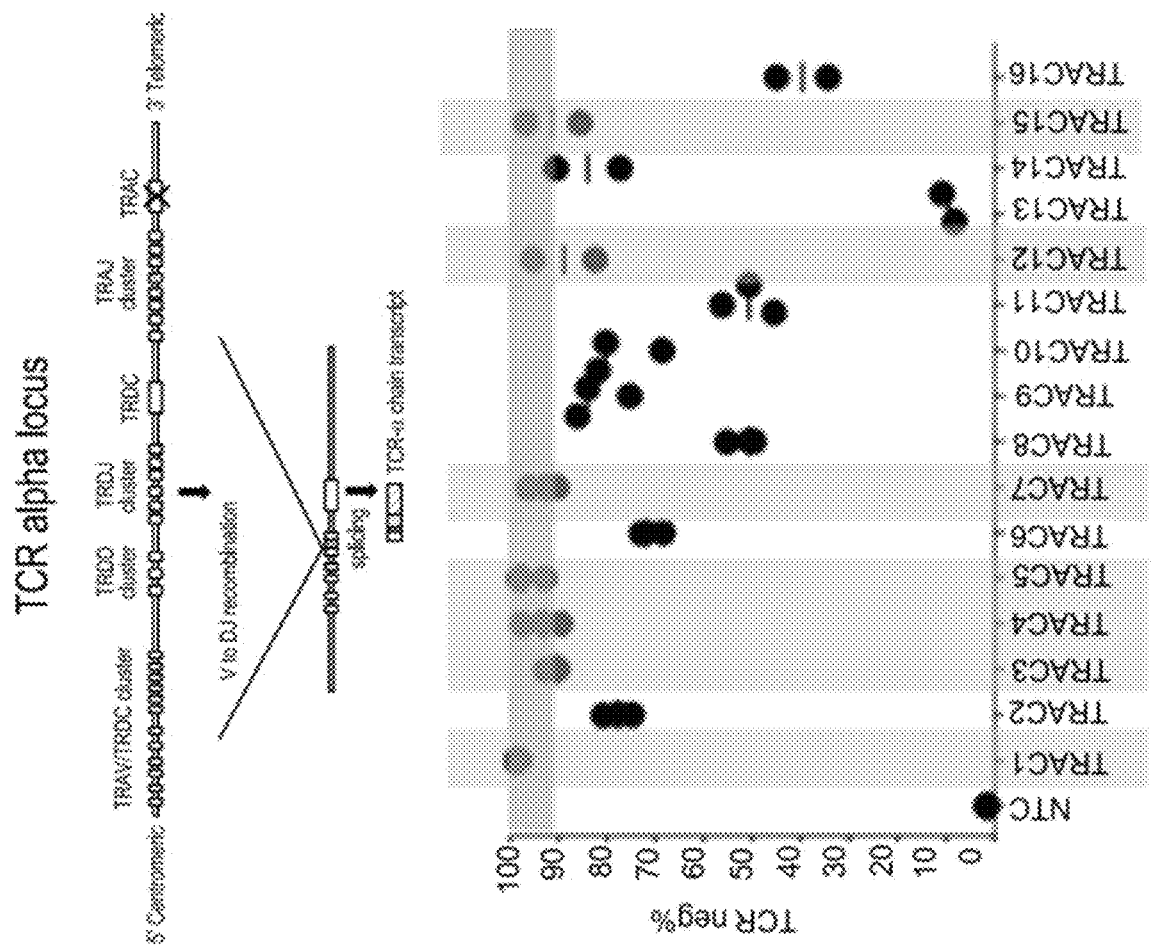
Figure 162:
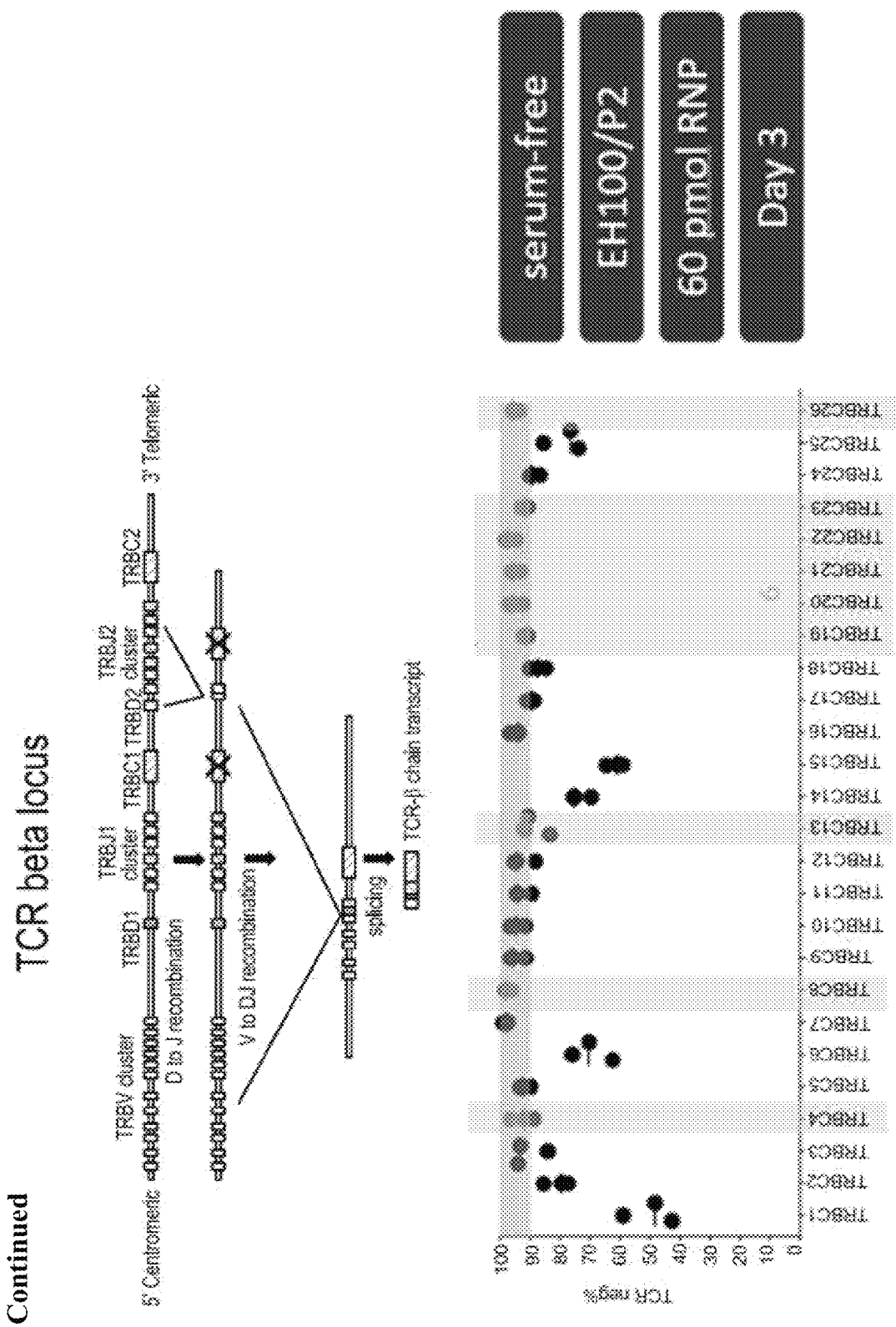

FIG. 162. Overview schematic of the knock-out of either TCR-alpha and TCR-beta loci using TCRA1-TCRA16 and TCRB1-TCRB26 guide RNA, including a plot of the % negative T cells for TCR-alpha or beta by flow cytometry. Boxed sequences indicate guide RNA sequences with >90% knock-out efficiency.

Figure 163:
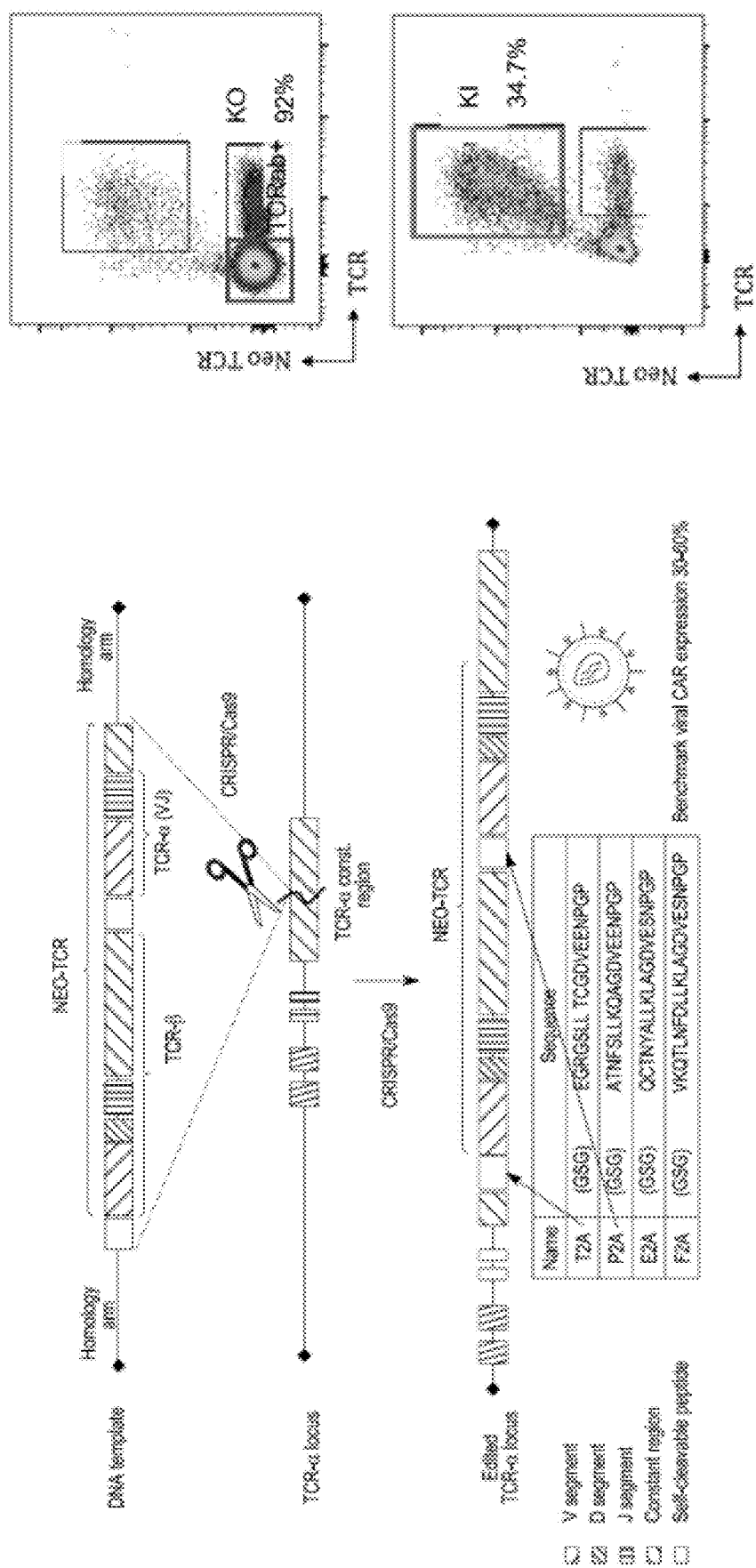

FIG. 163. Overview schematic of construct with a Self-Cleaving Peptide (SCP). The SCP upstream of the TCRb gene is T2A, and the second SCP sequence upstream of the TCRa gene is P2A. The two sequential SCPs in this example are not 100% identical to prevent erroneous recombination (i.e., each of the up- or downstream P2A-encoding sequences could recombine with each other, leading to non-functional recombined locus). By using different nucleic acid sequences to encode each P2A site, the only homologous regions of the TCR donor and acceptor sites are the 5' and 3' arms. In this example, different up- and downstream SCP sequences are used (T2A and P2A, respectively, and are not limited to T2A and P2A sequences only). Alternatively, the nucleic acid sequences encoding each the two SCPs can be codon-diverged, but encode the same SCP peptide sequence The short neutral GSG sequence is optionally added upstream of each SCP sequence.

DETAILED DESCRIPTION

After reading this description it will become apparent to one skilled in the art how to implement the present disclosure in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present disclosure as set forth herein.

Before the present technology is disclosed and described, it is to be understood that the aspects described below are not limited to specific compositions, methods of preparing such compositions, or uses thereof as such may, of course, vary.

It is also to be understood that the terminology used herein is for the purpose of describing particular aspects only and is not intended to be limiting.

The detailed description divided into various sections only for the reader's convenience and disclosure found in any section may be combined with that in another section. Titles or subtitles may be used in the specification for the convenience of a reader, which are not intended to influence the scope of the present disclosure.

I. Definitions

Unless defined otherwise, all technical and scientific terms used herein have the same meaning as commonly understood by one of ordinary skill in the art to which this disclosure belongs. In this specification and in the claims that follow, reference will be made to a number of terms that shall be defined to have the following meanings:

The terminology used herein is for the purpose of describing particular embodiments only and is not intended to be limiting. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" means that the amount may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this disclosure.

"T cells" or "T lymphocytes" as used herein are a type of lymphocyte (a subtype of white blood cell) that plays a central role in cell-mediated immunity. They can be distinguished from other lymphocytes, such as B cells and natural killer cells, by the presence of a T-cell receptor on the cell surface. T cells include, for example, natural killer T (NKT) cells, cytotoxic T lymphocytes (CTLs), regulatory T (Treg) cells, and T helper cells. Different types of T cells can be distinguished by use of T cell detection agents.

A "memory T cell" is a T cell that has previously encountered and responded to its cognate antigen during prior infection, encounter with cancer or previous vaccination. At a second encounter with its cognate antigen memory T cells can reproduce (divide) to mount a faster and stronger immune response than the first time the immune system responded to the pathogen.

A "regulatory T cell" or "suppressor T cell" is a lymphocyte which modulates the immune system, maintains tolerance to self-antigens, and prevents autoimmune disease.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide or nucleic acid, i.e., a monomer. Nucleotides can be ribonucleotides, deoxyribonucleotides, or modified versions thereof. Examples of nucleic acids contemplated herein include single and double stranded DNA, single and double stranded RNA, and hybrid molecules having mixtures of single and double stranded DNA and RNA. Examples of nucleic acid, e.g. nucleic acids contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of nucleic acids refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, "left homology arm" and "right homology arm" are used to define the 5' and 3', respectively, genomic DNA fragments flanking a DNA sequence of interest (gene, partial gene or other DNA segment to be introduced into the genome). For example, gene targeting via homologous recombination can include transfecting cells with a targeting vector, which is typically designed and constructed so as to contain a gene, transgene, gene fragment or other DNA of interest flanked with two genomic DNA fragments, the 5' or left homology arm, and the 3' or right homology arm. After transfection, these two arms are used to facilitate homologous recombination between the DNA donor and the endogenous target locus.

As used herein, "unmodified donor DNA" is defined as DNA which has not been altered from its original state. As used herein, "chemically modified donor DNA" is defined as DNA upon which some form of chemical modification, e.g. addition or subtraction of a bond or moiety, has been performed. Examples of chemical modifications include, without limitation, phosphorothioation, phosphorylation, methylation, acetylation, etc.

As used herein, the terms "ribonucleoprotein" or "RNP" are used to refer to a complex of ribonucleic acid and RNA-binding protein, such as Cas9.

As used herein, the term "CRISPR" or "clustered regularly interspaced short palindromic repeats" is used in accordance with its plain ordinary meaning and refers to a genetic element that bacteria use as a type of acquired immunity to protect against viruses. CRISPR includes short sequences that originate from viral genomes and have been incorporated into the bacterial genome. Cas (CRISPR associated proteins) process these sequences and cut matching viral DNA sequences. Thus, CRISPR sequences function as a guide for Cas to recognize and cleave DNA that are at least partially complementary to the CRISPR sequence. By introducing plasmids including Cas genes and specifically constructed CRISPRs into eukaryotic cells, the eukaryotic genome can be cut at any desired position.

As used herein, the term "Cas9" or "CRISPR-associated protein 9" is used in accordance with its plain ordinary meaning and refers to an enzyme that uses CRISPR sequences as a guide to recognize and cleave specific strands of DNA that are at least partially complementary to the CRISPR sequence. Cas9 enzymes together with CRISPR sequences form the basis of a technology known as CRISPR-Cas9 that can be used to edit genes within organisms. This editing process has a wide variety of applications including basic biological research, development of biotechnology products, and treatment of diseases.

A "CRISPR associated protein 9," "Cas9," "Csn1" or "Cas9 protein" as referred to herein includes any of the recombinant or naturally-occurring forms of the Cas9 endonuclease or variants or homologs thereof that maintain Cas9 endonuclease enzyme activity (e.g. within at least 50%, 80%, 90%, 95%, 96%, 97%, 98%, 99% or 100% activity compared to Cas9). In aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cas9 protein. In aspects, the Cas9 protein is substantially identical to the protein identified by the UniProt reference number Q99ZW2 or a variant or homolog having substantial identity thereto. In aspects, the Cas9 protein has at least 75% sequence identity to the amino acid sequence of the protein identified by the UniProt reference number Q99ZW2. In aspects, the Cas9 protein has at least 80% sequence identity to the amino acid sequence of the protein identified by the UniProt reference number Q99ZW2. In aspects, the Cas9 protein has at least 85% sequence identity to the amino acid sequence of the protein identified by the UniProt reference number Q99ZW2. In aspects, the Cas9 protein has at least 90% sequence identity to the amino acid sequence of the protein identified by the UniProt reference number Q99ZW2. In aspects, the Cas9 protein has at least 95% sequence identity to the amino acid sequence of the protein identified by the UniProt reference number Q99ZW2.

A "CRISPR-associated endonuclease Cas12a," "Cas12a," "Cas12" or "Cas12 protein" as referred to herein includes any of the recombinant or naturally-occurring forms of the Cas12 endonuclease or variants or homologs thereof that maintain Cas12 endonuclease enzyme activity (e.g. within at least 50%, 80%, 90%, 95%, 96%, 97%, 98%, 99% or 100% activity compared to Cas12). In aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cas12 protein. In aspects, the Cas12 protein is substantially identical to the protein identified by the UniProt reference number A0Q7Q2 or a variant or homolog having substantial A "guide RNA" or "gRNA" as provided herein refers to an RNA sequence having sufficient complementarity with a target nucleic acid sequence to hybridize with the target sequence and direct sequence-specific binding of a CRISPR complex to the target sequence. For example, a gRNA can direct Cas to the target nucleic acid. In embodiments, the gRNA includes the crRNA and the tracrRNA. For example, the gRNA can include the crRNA and tracrRNA hybridized by base pairing. Thus, in embodiments, the crRNA and tracrRNA are two RNA molecules which then form an RNA/RNA complex due to complementary base pairing between the crRNA and tracrRNA to form the gRNA. In embodiments, the gRNA is a single gRNA (sgRNA), with both the crRNA and tracrRNA in a single RNA molecule. In aspects, the degree of complementarity between a guide RNA sequence and its corresponding target sequence, when optimally aligned using a suitable alignment algorithm, is about 50%, 60%, 75%, 80%, 85%, 90%, 95%, 97.5%, 99%, or more. In aspects, the degree of complementarity between a guide RNA sequence and its corresponding target sequence, when optimally aligned using a suitable alignment algorithm, is at least about 50%, 60%, 75%, 80%, 85%, 90%, 95%, 97.5%, 99%.

Non-limiting examples of CRISPR enzymes include Cas1, Cas1B, Cas2, Cas3, Cas4, Cas5, Cas6, Cas7, Cas8, Cas9 (also known as Csn1 and Csx12), Cas10, Cas12, Cas13, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, fusion proteins thereof, or modified versions thereof. In embodiments, the CRISPR enzyme is a Cas9 enzyme. In embodiments, the Cas9 enzyme is *S. pneumoniae, S. pyogenes* or *S. thermophilus* Cas9, or mutants derived thereof in these organisms. In embodiments, the CRISPR enzyme is codon-optimized for expression in a eukaryotic cell. In embodiments, the CRISPR enzyme directs cleavage of one or two strands at the location of the target sequence. In embodiments, the CRISPR enzyme lacks DNA strand cleavage activity.

As used herein, the terms "nuclear localization signal," "nuclear localization sequence," or "NLS" are used to refer to an amino acid sequence that marks or tags a protein for import into the cell nucleus by nuclear transport. Typically, this signal consists of one or more short sequences of positively-charged lysines or arginines exposed on the protein surface.

As used herein, the terms "non-viral" or "non-viral gene therapy" refers to any nucleic acid sequence that does not comprise a virus, viral vector, or virus-mediated delivery of nucleic acid. Examples of non-viral methods of nucleic acid delivery include, but are not limited to, injection by needle, ballistic DNA, electroporation, sonoporation, photoporation, magnetofection, hydroporation, mechanical massage, chemical carrier, inorganic particles, cationic lipids, lipid emulsions, solid lipid nanoparticles, peptide-based complexes, polymer-based complexes, or mixtures thereof.

As used herein, the term "nanoplasmid" is used to refer to an engineered circular nucleic acid containing at minimum a nucleic acid(s) sequence of interest, an miniature origin of replication (e.g. R6K), and an selectable marker (e.g. a small RNA selectable marker, RNA-OUT). A nanoplasmid contains less than 500 bp of prokaryotic DNA.

As used herein, the term "antigen" is used to describe a compound, composition, or chemical that is capable of inducing an immune response, e.g., cytotoxic T lymphocyte (CTL) response, T helper cell response, a B cell response (for example, production of antibodies that specifically bind the epitope), an NK cell response or any combinations thereof, when administered to an immunocompetent subject. Thus, an immunogenic or antigenic composition is a composition capable of eliciting an immune response in an immunocompetent subject.

As used herein, the term "neoantigen" is used to describe newly formed antigens that have not been previously recognized by the immune system. Neoantigens can arise from altered tumor proteins formed as a result of tumor mutations, or from viral proteins. Non-limiting examples of neoantigens are listed in Table 2.

As used herein, the terms "tumor associated antigen" or "TAA" are used to describe proteins that are significantly over-expressed in cancer compared to normal cells, and are therefore also abundantly presented on the cancer cell's surface. Non-limiting examples of TAAs are listed in Table 1.

TABLE 1

| Tumor-Associated Antigens |
|---|
| WT1 |
| MAGEA1 |
| MSLN |
| PRAME |
| CTAG1A (NY-ESO) |

TABLE 2

| Shared neoantigens | | |
|---|---|---|
| JAK2 V617F | PIK3CA H1047R | IDH2 R140Q |
| BRAF V600E | EGFR L858R | FLT3 D835Y |
| BRAF V600M | EGFR E746_A750del | ERBB2 S310F |
| KRAS G12V | TP53 R175H | FGFR3 S249C |
| KRAS G12C | TP53 R248Q | PTEN R130Q |
| KRAS G12D | TP53 R273C | PTEN R130G |
| KRAS G12R | TP53 R273H | SF3B1 R625H |
| KRAS G13D | TP53 R273L | SF3B1 R625C |
| NRAS Q61R | TP53 R282W | GTF2I L424H |
| NRAS Q61K | MYD88 L265P | GNAQ Q209P |
| PIK3CA E542K | DNMT3A R882H | GNAQ Q209L |
| PIK3CA E545K | IDH1 R132H | GNA11 Q209L |

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

As used herein, the terms "population of cells" or "plurality of cells" can be used interchangeably and refer to more than one cell.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenia purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

II. Engineered T Cells

In an aspect, an engineered T cell is provided. The engineered T cell includes a nucleic acid sequence encoding a polypeptide comprising an exogenous TCR-beta and an exogenous TCR-alpha. In embodiments, the engineered T cell includes a nucleic acid sequence encoding a polypeptide comprising an exogenous TCR-beta and an exogenous TCR-alpha (VJ) domain. In embodiments, the nucleic acid sequence is inserted into a TCR-alpha locus of the engineered T cell.

In another interrelated aspect, a composition comprising isolated T cells is provided, wherein at least 5% of the cells are engineered T cells, each engineered T cell including a nucleic acid sequence encoding a polypeptide comprising an exogenous TCR-beta and an exogenous TCR-alpha. In embodiments, the nucleic acid sequence is inserted into a TCR-alpha locus of the engineered T cell.

In embodiments, at least 10% of the cells are engineered T cells. In embodiments, at least 15% of the cells are engineered T cells. In embodiments, at least 20% of the cells are engineered T cells. In embodiments, at least 25% of the cells are engineered T cells. In embodiments, at least 30% of the cells are engineered T cells. In embodiments, at least 40% of the cells are engineered T cells. In embodiments, at least 50% of the cells are engineered T cells. In embodiments, at least 60% of the cells are engineered T cells. In embodiments, between about 5% and 100% of the cells are engineered T cells. In embodiments, between about 5% and about 50% of the cells are engineered T cells. In embodiments, between about 5% and about 25% of the cells are engineered T cells. In embodiments, between about 5% and about 20% of the cells are engineered T cells. In embodiments, between about 5% and about 15% of the cells are engineered T cells. The percentage may be any value or subrange within the recited ranges, including endpoints.

In embodiments, the engineered T cell does not express a functional endogenous TCR-beta protein. In embodiments, less than about 50% of the engineered T cells express a functional endogenous TCR-beta protein. For In embodiments, less than about 40% of the engineered T cells express a functional endogenous TCR-beta protein. In embodiments, less than about 30% of the engineered T cells express a functional endogenous TCR-beta protein. In embodiments, less than about 20% of the engineered T cells express a functional endogenous TCR-beta protein. In embodiments, less than about 10% of the engineered T cells express a functional endogenous TCR-beta protein. In embodiments, less than about 5% of the engineered T cells express a functional endogenous TCR-beta. In embodiments, less than about 4% of the engineered T cells express a functional endogenous TCR-beta protein. In embodiments, less than about 3% of the engineered T cells express a functional endogenous TCR-beta protein. In embodiments, less than about 2% of the engineered T cells express a functional endogenous TCR-beta protein. In embodiments, less than about 1% of the engineered T cells express a functional endogenous TCR-beta protein. In embodiments, between about 0% and about 50% of the engineered T cells express a functional endogenous TCR-beta protein. In embodiments, between about 0% and about 25% of the engineered T cells express a functional endogenous TCR-beta protein. In embodiments, between about 1% and about 25% of the engineered T cells express a functional endogenous TCR-beta protein. The percentage may be any value or subrange within the recited ranges, including endpoints.

In embodiments, at least about 50% of the engineered T cells have a disrupted and non-functional TCR-beta locus across all alleles. In embodiments, at least about 40% of the engineered T cells have a disrupted and non-functional TCR-beta locus across all alleles. In embodiments, at least about 60%, 70%, 80%, or 90% of the engineered T cells have a disrupted and non-functional TCR-beta locus across all alleles. In embodiments, at least about 95%, 96%, 97%, 98%, or 99% of the engineered T cells have a disrupted and non-functional TCR-beta locus across all alleles. In embodiments, between about 50% and about 100% of the engineered T cells, have a disrupted and non-functional TCR-beta locus across all alleles. In embodiments, between about 60% and about 95% of the engineered T cells have a disrupted and non-functional TCR-beta locus across all alleles. The percentage may be any value or subrange within the recited ranges, including endpoints.

In embodiments, less than about 50% of the engineered T cells express a functional endogenous TCR-alpha protein. In embodiments, less than about 40% of the engineered T cells express a functional endogenous TCR-alpha protein. In embodiments, less than about 30% of the engineered T cells express a functional endogenous TCR-alpha protein. In embodiments, less than about 20% of the engineered T cells express a functional endogenous TCR-alpha protein. In embodiments, less than about 10% of the engineered T cells express a functional endogenous TCR-alpha protein. In embodiments, less than about 5% of the engineered T cells express a functional endogenous TCR-alpha protein. In embodiments, less than about 4% of the engineered T cells express a functional endogenous TCR-alpha protein. In embodiments, less than about 3% of the engineered T cells express a functional endogenous TCR-alpha protein. In embodiments, less than about 2% of the engineered T cells express a functional endogenous TCR-alpha protein. In embodiments, less than about 1% of the engineered T cells express a functional endogenous TCR-alpha protein. In embodiments, between about 0% and about 50% of the engineered T cells express a functional endogenous TCR-alpha protein. In embodiments, between about 0% and about 25% of the engineered T cells express a functional endogenous TCR-alpha protein. In embodiments, between about 1% and about 25% of the engineered T cells express a functional endogenous TCR-alpha protein. The percentage may be any value or subrange within the recited ranges, including endpoints.

In embodiments, at least about 50% of the engineered T cells have a disrupted and non-functional TCR-alpha locus across all alleles. In embodiments, at least about 40% of the engineered T cells have a disrupted and non-functional TCR-alpha locus across all alleles. In embodiments, at least about 60%, 70%, 80%, or 90% of the engineered T cells have a disrupted and non-functional TCR-alpha locus across all alleles. In embodiments, at least about 95%, 96%, 97%, 98%, or 99% of the engineered T cells have a disrupted and non-functional TCR-alpha locus across all alleles. In embodiments, between about 50% and about 100% of the engineered T cells, have a disrupted and non-functional TCR-alpha locus across all alleles. In embodiments, between about 60% and about 95% of the engineered T cells have a disrupted and non-functional TCR-alpha locus across all alleles. The percentage may be any value or subrange within the recited ranges, including endpoints.

In embodiments, the exogenous TCR-alpha (VJ) domain forms part of a heterologous TCR-alpha comprising at least a portion of the endogenous TCR-alpha of the T cell. In embodiments, the TCR-alpha locus is a TCR-alpha constant region. In embodiments, the exogenous TCR-beta and the heterologous TCR-alpha are expressed from the nucleic acid and form a functional TCR. In embodiments, at least 40% of the engineered T cells express heterologous TCR-alpha. In embodiments, at least 50% of the engineered T cells express heterologous TCR-alpha. In embodiments, at least 60% of the engineered T cells express heterologous TCR-alpha. In embodiments, at least 70% of the engineered T cells express heterologous TCR-alpha. In embodiments, at least 80% of the engineered T cells express heterologous TCR-alpha. In embodiments, at least 90% of the engineered T cells express heterologous TCR-alpha.

In embodiments, the engineered T cell is bound to an antigen. In embodiments, the engineered T cell is bound to a cancer cell. In embodiments, the TCR binds to the antigen presented on a major histocompatibility complex class I (MHCI) molecule.

In embodiments, the antigen is a neoantigen or a tumor-associated antigen (TAA). In embodiments, the antigen is a neoantigen. In embodiments, the antigen is a TAA. In embodiments, the neoantigen or TAA is selected from WT1, JAK2, NY-ESO1, PRAME, KRAS, HPV or an antigen from Table 1 or Table 2. In embodiments, the antigen is WT1. In embodiments, the antigen is specific to a cancer of a subject to be administered the engineered T cell. In embodiments, the antigen is expressed by or associated with a cancer of a subject to be administered the engineered T cell.

In embodiments, the nucleic acid sequence further encodes a self-cleaving peptide. In embodiments, the self-cleaving peptide is a self-cleaving viral peptide. In embodiments, the self-cleaving viral peptide is T2A. In embodiments, the self-cleaving viral peptide is P2A. In embodiments, the self-cleaving viral peptide is E2A. In embodiments, the self-cleaving viral peptide is F2A.

In embodiments, the nucleic acid sequence further encodes a protease cleavage site. In embodiments, the protease cleavage site is a furin cleavage site.

In embodiments, the nucleic acid further contains a polyadenylation (polyA) sequence. In embodiments, the polyadenylation sequence can be located immediately 3'-adjacent from the TCR-encoding sequence. In embodiments, the polyadenylation sequence can be located immediately 5'adjacent to the second homology arm. In embodiments, the polyadenylation sequence is a bovine growth hormone polyadenylation sequence (bgh-polyA).

In embodiments, the engineered T cell expresses CD45RO, C—C chemokine receptor type 7 (CCR7), and L-selectin (CD62L). In embodiments, the engineered T cell has a central memory (CM) T cell phenotype. In embodiments, the engineered T cell has a naïve T cell phenotype. In embodiments, the engineered T cell having a naïve T cell phenotype is CD45RA+CD45RO−CD27+CD95− (that is, the cell expresses CD45RA and CD27 and does not express detectable levels of CD45RO and CD95). In embodiments, the engineered T cell has a stem cell memory T cell phenotype. In embodiments, the engineered T cell having a stem cell memory T cell phenotype is CD45RA+CD45RO−CD27+CD95+CD58+CCR7-Hi TCF1+. In embodiments, the engineered T cell has a central memory T cell phenotype. In embodiments, the engineered T cell having a central memory T cell phenotype is CD45RO+CD45RA−CD27+CD95+CD58+. In embodiments, the engineered T cell has a progenitor exhausted T cell phenotype. In embodiments, the engineered T cell having a progenitor exhausted T cell phenotype is PD-1+SLAMF6+TCF1+TIM3−CD39−. In embodiments, the engineered T cell having a progenitor exhausted T cell phenotype expresses PD-1 at a low or intermediate level compared to PD-1 high exhausted T cells, or recently activated T cells. In embodiments, the engineered T cell having a progenitor exhausted T cell phenotype expresses PD-1 at a low or intermediate level compared to PD-1 level expressed in recently activated T cells. In embodiments, the T cell is autologous to a subject in need thereof.

In another interrelated aspect, a pharmaceutical composition is provided. The pharmaceutical composition includes a population of the engineered T cells as described herein, including embodiments, and a pharmaceutically acceptable excipient.

In embodiments, at least 10% of the cells in the composition comprising isolated T cells are engineered T cells. In embodiments, at least 20% of the cells are engineered T cells. In embodiments, at least 30% of the cells are engineered T cells. In embodiments, at least 40% of the cells are engineered T cells. In embodiments, at least 50% of the cells are engineered T cells. In embodiments, at least 60% of the cells are engineered T cells. In embodiments, at least 70% of the cells are engineered T cells. In embodiments, at least 80% of the cells are engineered T cells. In embodiments, at least 90% of the cells are engineered T cells.

In embodiments, the composition includes between about $0.1 \times 10^5$ and about $1 \times 10^9$ engineered T cells. In embodiments, the composition includes at least $1 \times 10^8$ engineered T cells. In embodiments, the composition includes at least $1 \times 10^9$ engineered T cells. In embodiments, the composition includes between $1 \times 10^9$ and $1 \times 10^{11}$ engineered T cells. In embodiments, the composition includes at least $1 \times 10^{10}$ engineered T cells. In embodiments, the composition includes at least $1 \times 10^{11}$ engineered T cells. The number of cells may be any value or subrange between the recited ranges, including endpoints.

In embodiments, the composition further includes a pharmaceutically acceptable excipient. The means of making such a composition or an implant have been described in the art (see, for instance, Remington's Pharmaceutical Sciences, 16th Ed., Mack, ed. (1980)). Where appropriate, the engineered T cells can be formulated into a preparation in semisolid or liquid form, such as a capsule, solution, injection, inhalant, or aerosol, in the usual ways for their respective route of administration. In embodiments, the excipient is a balanced salt solution, such as Hanks' balanced salt solution, or normal saline. It will also be understood that, if desired, the compositions of the invention may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

In another interrelated aspect, a T cell comprising an RNA transcript having a structure as described herein is provided. In embodiments, a T cell comprising an RNA transcript, wherein the mRNA transcript is transcribed from a TCR transgene inserted into the TCR-alpha and/or TCR-beta locus.

III. Methods for Making

In another, interrelated aspect, a method for making an engineered T cell is provided. The method includes: a) contacting a T cell with a first ribonucleoprotein particle (RNP) and a donor DNA, wherein the first RNP comprises a first guide RNA that targets an endogenous TCR-alpha locus, and wherein the donor DNA comprises a nucleic acid sequence comprising a gene encoding a polypeptide comprising an exogenous TCR-beta and an exogenous TCR-alpha, under conditions to allow the RNP and the donor DNA to enter the cell; b) incubating the T cell for a period of time; and c) culturing the cell in a medium for a period of time to allow the donor DNA to be inserted into the endogenous TCR-alpha locus, thereby forming an engineered T cell.

In embodiments, the first RNP comprises a first gene editing protein, and a first guide RNA at a molar excess of the latter. In embodiments, the first RNP comprises a first gene editing protein, and the ratio of the first guide RNA to the first gene editing protein is between the molar ratios of about 1:1 and about 100:1. In embodiments, the ratio of the first guide RNA to the first gene editing protein is between the molar ratio of about 1:1 and of about 75:1. In embodiments, the ratio of the first guide RNA to the first gene editing protein is between the molar ratio of about 1:1 and of about 50:1. In embodiments, the ratio of the first guide RNA to the first gene editing protein is between the molar ratio of about 1:1 and of about 25:1. In embodiments, the ratio of the first guide RNA to the first gene editing protein is between the molar ratio of about 1:1 and of about 10:1. In embodiments, the ratio of the first guide RNA to the first gene editing protein is between the molar ratio of about 1:1 and of about 5:1. In embodiments, the ratio of the first guide RNA to the first gene editing protein is between the molar ratio of about 1:1 and of about 4:1. In embodiments, the ratio of the first guide RNA to the first gene editing protein is the molar ratio of about 1:1. In embodiments, the ratio of the first guide RNA to the first gene editing protein is the molar ratio of about 2:1. In embodiments, the ratio of the first guide RNA to the first gene editing protein is the molar ratio of about 3:1. In embodiments, the ratio of the first guide RNA to the first gene editing protein is the molar ratio of about 4:1. In embodiments, the ratio of the first guide RNA to the first gene editing protein is the molar ratio of about 5:1. In embodiments, the ratio of the first guide RNA to the first gene editing protein is the molar ratio of about 6:1. In embodiments, the ratio of the first guide RNA to the first gene editing protein is the molar ratio of about 7:1. In embodiments, the ratio of the first guide RNA to the first gene editing protein is the molar ratio of about 8:1. In embodiments, the ratio of the first guide RNA to the first gene editing protein is the molar ratio of about 9:1. In embodiments, the ratio of the first guide RNA to the first gene editing protein is the molar ratio of about 10:1. In embodiments, the ratio of the first guide RNA to the first gene editing protein is the molar ratio of about 25:1. In embodiments, the ratio of the first guide RNA to the first gene editing protein is the molar ratio of about 50:1. In embodiments, the ratio of the first guide RNA to the first gene editing protein is the molar ratio of about 75:1. In embodiments, the ratio of the first guide RNA to the first gene editing protein is the molar ratio of about 100:1. The molar ratio may be any value or subrange within the recited ranges, including endpoints.

In embodiments, the T cell is contacted with a second RNP comprising a second guide RNA that targets an endogenous TCR-beta locus. In embodiments, the second RNP comprises a second gene editing protein, and a second guide RNA at a molar excess of the latter. In embodiments, the second RNP comprises a second gene editing protein, and the molar ratio of the second guide RNA to the second gene editing protein is between 1:1 and 100:1. In embodiments, the second RNP comprises a second gene editing protein, and the molar ratio of the second guide RNA to the second gene editing protein is between 1:1 and 75:1. In embodiments, the second RNP comprises a second gene editing protein, and the molar ratio of the second guide RNA to the second gene editing protein is between 1:1 and 50:1. In embodiments, the second RNP comprises a second gene editing protein, and the molar ratio of the second guide RNA to the second gene editing protein is between 1:1 and 25:1. In embodiments, the second RNP comprises a second gene editing protein, and the molar ratio of the second guide RNA to the second gene editing protein is between 1:1 and 10:1. In embodiments, the second RNP comprises a second gene editing protein, and the molar ratio of the second guide RNA to the second gene editing protein is between 1:1 and 5:1. In embodiments, the molar ratio of the second guide RNA to the second gene editing protein is between 1:1 and 4:1. In embodiments, the molar ratio of the second guide RNA to the second gene editing protein is about 1:1. In embodiments, the molar ratio of the second guide RNA to the second gene editing protein is about 2:1. In embodiments, the molar ratio of the second guide RNA to the second gene editing protein is about 3:1. In embodiments, the molar ratio of the second guide RNA to the second gene editing protein is about 4:1. In embodiments, the molar ratio of the second guide RNA to the second gene editing protein is about 5:1. In embodiments, the ratio of the first guide RNA to the first gene editing protein is the molar ratio of about 10:1. In embodiments, the ratio of the first guide RNA to the first gene editing protein is the molar ratio of about 25:1. In embodiments, the ratio of the first guide RNA to the first gene editing protein is the molar ratio of about 50:1. In embodiments, the ratio of the first guide RNA to the first gene editing protein is the molar ratio of about 75:1. In embodiments, the ratio of the first guide RNA to the first gene editing protein is the molar ratio of about 100:1. The molar ratio may be any value or subrange within the recited ranges, including endpoints.

In embodiments, the T cell is contacted with the second RNP comprising the second guide RNA simultaneously with the first RNP comprising the first guide RNA. In embodiments, the T cell is contacted with the second RNP comprising the second guide RNA prior to the first RNP comprising the first guide RNA. In embodiments, the T cell is contacted with the second RNP comprising the second guide RNA after the first RNP comprising the first guide RNA.

In embodiments, the first guide RNA is discovered through methods known to one skilled in the art such that it targets the exon 1, exon 2 or exon 3 region of the TCR constant alpha region locus (TRAC). In embodiments, the first guide RNA targets one of the following sequences from the TCR-alpha loci: TRAC1 (SEQ ID NO: 7), TRAC2 (SEQ ID NO: 8), TRAC3 (SEQ ID NO: 9), TRAC4 (SEQ ID NO: 10), TRAC5 (SEQ ID NO: 11), TRAC6 (SEQ ID NO: 12), TRAC7 (SEQ ID NO: 13), TRAC8 (SEQ ID NO: 14), TRAC9 (SEQ ID NO: 15), TRAC10 (SEQ ID NO: 16), TRAC11 (SEQ ID NO: 17), TRAC12 (SEQ ID NO: 18), TRAC13 (SEQ ID NO: 19), TRAC14 (SEQ ID NO: 20), TRAC15 (SEQ ID NO: 21), or TRAC16 (SEQ ID NO: 22). In embodiments, the first guide RNA targets one of the following sequences: TRAC1, TRAC3, TRAC4, TRAC5, TRAC7, TRAC12, or TRAC15. In embodiments, the first guide RNA targets the sequence TRAC1. In embodiments, the first guide RNA targets the sequence TRAC3. In embodiments, the first guide RNA comprises a nucleic acid sequence in Table 10. Any one or more of the guide RNAs may be expressly excluded.

In embodiments, the second guide RNA is discovered through methods known to one skilled in the art such that it targets the exon I regions of both TCR constant beta region loci (TRBC). In embodiments, the second guide RNA targets one of the following sequences from the TCR-beta loci: TRBC1 (SEQ ID NO: 23), TRBC2 (SEQ ID NO: 24), TRBC3 (SEQ ID NO: 25), TRBC4 (SEQ ID NO: 26), TRBC5 (SEQ ID NO: 27), TRBC6 (SEQ ID NO: 28), TRBC7 (SEQ ID NO: 29), TRBC8 (SEQ ID NO: 30), TRBC9 (SEQ ID NO: 31), TRBC10 (SEQ ID NO: 32), TRBC11 (SEQ ID NO: 33), TRBC12 (SEQ ID NO: 34), TRBC13 (SEQ ID NO: 35), TRBC14 (SEQ ID NO: 36), TRBC15 (SEQ ID NO: 37), TRBC16 (SEQ ID NO: 38), TRBC17 (SEQ ID NO: 39), TRBC18 (SEQ ID NO: 40), TRBC19 (SEQ ID NO: 41), TRBC20 (SEQ ID NO: 42), TRBC21 (SEQ ID NO: 43), TRBC22 (SEQ ID NO: 44), TRBC23 (SEQ ID NO: 45), TRBC24 (SEQ ID NO: 46), TRBC25 (SEQ ID NO: 47), or TRBC26 (SEQ ID NO: 48). In embodiments, the second guide RNA targets one of the following loci: TRBC4, TRBC8, TRBC13, TRBC19, TRBC20, TRBC21, TRBC22, TRBC23, or TRBC26. In embodiments, the second guide RNA comprises the nucleic acid sequence in Table 11. Any one or more of the guide RNAs may be expressly excluded.

In embodiments, the RNP comprises a CRISPR-associated (CAS) protein. In embodiments, the CAS protein is Cas9. In embodiments the Cas9 is *Streptococcus pyogenes* (Sp) Cas9. In embodiments, the SpCas9 is wild-type SpCas9. In embodiments, the SpCas9 is a mutant SpCas9.

In embodiments, the RNP comprises a guide RNA. In embodiments, the guide RNA is a synthetic nucleic acid. In embodiments, the guide RNA contains non-naturally occurring bases and/or backbone linkages known in the art. In embodiments, the guide RNA is a single guide (sg) RNA. In embodiments, the guide RNA comprises a tracer (tr) RNA and a crispr (cr) RNA. In embodiments, the guide RNA comprises phosphodiester derivatives including, but not limited to, phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages.

In embodiments, the conditions to allow the RNP and the donor DNA to enter the cell include electroporation. In embodiments, in method step b), the T cell is incubated for at least 10 minutes. In embodiments, the T cell is incubated at about 37° C. In embodiments, the T cell is incubated at less than about 37° C. In embodiments, the medium comprises cytokines. In embodiments, the cytokines comprise IL-2, IL-7, and/or IL-15. In embodiments, the cytokines comprise IL-2. In embodiments, the cytokines comprise IL-7. In embodiments, the cytokines comprise IL-15. In embodiments, the cytokines comprise IL-7 and IL-15. Any one or more of the recited cytokines may be expressly excluded.

In embodiments, method step a) is performed in the presence of a negatively charged polymer. In embodiments, the polymer is poly(glutamic acid) (PGA) or variant thereof, poly(aspartic acid), heparin, or poly(acrylic acid). In embodiments, the PGA is poly(L-glutamic acid) or variant thereof. In embodiments, the PGA is poly(D-glutamic acid) or variant thereof. In embodiments, the PGA or variant thereof has an average molecular weight between 15 kilo-Daltons (kDa) and 50 kDa. Any one or more of the polymers may be expressly excluded.

In embodiments, about 0.4 µg/µL to about 20 µg/µL of the polymer is added. In embodiments, about 2 µg/µL to about 12 µg/µL of the polymer is added. In embodiments, about 2 µg/µL to about 8 µg/µL of the polymer is added. In embodiments, about 4 µg/µL to about 8 µg/µL of the polymer is added. In embodiments, about 6 µg/µL to about 8 µg/µL of the polymer is added. In embodiments, about 6 µg/µL of the polymer is added. In embodiments, about 8 µg/µL of the polymer is added. The amount may be any value or subrange within the recited ranges, including endpoints. In embodiments, a polymer is not added.

In embodiments, the amount of RNP is about 0.04 pmol/µL to about 20 pmol/µL. In embodiments, the amount of RNP is about 0.2 pmol/µL to about 8 pmol/µL. In embodiments, the amount of RNP is about 0.6 pmol/µL to about 8 pmol/µL. In embodiments, the amount of RNP is about 0.8 pmol/µL to about 8 pmol/µL. In embodiments, the amount of RNP is about 1.2 pmol/µL to about 8 pmol/µL. In embodiments, the amount of RNP is about 2 pmol/µL to about 8 pmol/µL. In embodiments, the amount of RNP is about 3 pmol/µL to about 8 pmol/µL. In embodiments, the amount of RNP is about 4 pmol/µL to about 8 pmol/µL. In embodiments, the amount of RNP is about 0.2 pmol/µL to about 6 pmol/µL. In embodiments, the amount of RNP is about 0.2 pmol/µL to about 4 pmol/µL. In embodiments, the amount of RNP is about 0.2 pmol/µL to about 2 pmol/µL. In embodiments, the amount of RNP is about 0.2 pmol/µL to about 1 pmol/µL. The amount may be any value or subrange within the recited ranges, including endpoints.

In embodiments, the amount of donor DNA is about 0.0002 pmol/µL to about 2 pmol/µL. In embodiments, the amount of donor DNA is about 0.0004 pmol/µL to about 0.4 pmol/µL. In embodiments, the amount of donor DNA is about 0.0004 pmol/µL to about 0.2 pmol/µL. In embodiments, the amount of donor DNA is about 0.0004 pmol/µL to about 0.04 pmol/µL. In embodiments, the amount of donor DNA is about 0.0004 pmol/µL to about 0.02 pmol/µL. In embodiments, the amount of donor DNA is about 0.0004 pmol/µL to about 0.004 pmol/µL. In embodiments, the amount of donor DNA is about 0.0002 pmol/µL to about 0.4 pmol/µL. In embodiments, the amount of donor DNA is about 0.004 pmol/µL to about 0.4 pmol/µL. In embodiments, the amount of donor DNA is about 0.02 pmol/µL to about 0.4 pmol/µL. In embodiments, the amount of donor DNA is about 0.04 pmol/µL to about 0.4 pmol/µL. In embodiments, the amount of donor DNA is about 0.08 pmol/µL to about 0.4 pmol/µL. In embodiments, the amount of donor DNA is about 0.2 pmol/µL to about 0.4 pmol/µL. The amount may be any value or subrange within the recited ranges, including endpoints.

Amounts of polymer, RNP, donor DNA, and any other component of the embodiments described herein can be scaled up, as needed, for example to prepare engineered T cells for clinical use.

In embodiments, the donor DNA recombines into an endogenous TCR-alpha locus. In embodiments, the TCR-alpha locus is a TCR-alpha constant chain. In embodiments, the donor DNA recombines into an endogenous TCR-beta locus.

In embodiments, the donor DNA comprises a left homology arm and a right homology arm. In embodiments, the left homology arm and right homology arm are homologous to an endogenous TCR-alpha locus. In embodiments, the left homology arm is about 50 bases to about 2000 bases long. In embodiments, the left homology arm is about 100 bases to about 1000 bases long. In embodiments, the left homology arm is about 200 bases to about 800 bases long. In embodiments, the right homology arm is about 200 bases to about 2000 bases long. In embodiments, the right homology arm is about 100 bases to about 1000. In embodiments, the left homology arm and right homology arm are homologous to an endogenous TCR-beta locus. In embodiments, the left homology arm is about 200 bases to about 800 bases long.

In embodiments, the left homology arm is about 250 bases to about 700 bases long. In embodiments, the right homology arm is about 200 bases to about 800 bases long. In embodiments, the right homology arm is about 250 bases to about 700 bases long. The length may be any value or subrange within the recited ranges, including endpoints.

In embodiments, the donor DNA comprises double stranded DNA (dsDNA). In embodiments, the donor DNA is on a plasmid, nanoplasmid, or minicircle. In embodiments, the donor DNA is on a plasmid. In embodiments, the donor DNA is on a nanoplasmid. In embodiments, the donor DNA is on a minicircle. In embodiments, the donor DNA is linear. In embodiments, the donor DNA comprises single stranded DNA (ssDNA). In embodiments, the donor DNA is not chemically modified. In embodiments, the donor DNA comprises a chemical modification. In embodiments, the modification comprises a 5' phosphate or a 5' phosphorothioate.

In embodiments, the donor DNA and RNP are incubated together prior to contacting the T cell with the first RNP and donor DNA. In embodiments, the gene editing protein of the RNP comprises a nuclear localization sequence (NLS).

In embodiments, the T cell is cultured in media. In embodiments, the media is selected from RPMI, PRIME-XV, and/or X-VIVO.

In embodiments, the T cell is activated prior to contacting the T cell with the first RNP and donor DNA. In embodiments, the T cell is activated for between 24 hours and 96 hours. In embodiments, the T cell is activated in the presence of cytokines. In embodiments, the cytokines comprise IL-2, IL-7, and/or IL-15.

In embodiments, the T cell is activated with IL-2. In embodiments, the T cell is activated in the presence of between about 0 ng/mL and about 50 ng/ml IL-2. In embodiments, the T cell is activated in the presence of between about 5 ng/ml and about 50 ng/mL IL-2. In embodiments, the T cell is activated in the presence of between about 1 ng/mL and about 5 ng/ml IL-2. In embodiments, the T cell is activated in the presence of between about 5 ng/ml and about 25 ng/mL IL-2. In embodiments, the T cell is activated in the presence of between about 5 ng/ml and about 20 ng/ml IL-2. In embodiments, the T cell is activated in the presence of between about 5 ng/ml and about 15 ng/ml IL-2. In embodiments, the T cell is activated in the presence of about 10 ng/ml IL-2. The amount may be any value or subrange within the recited ranges, including endpoints.

In embodiments, the T cell is activated with IL-2. In embodiments, the T cell is activated in the presence of between about 0 units/mL and about 1000 units/mL IL-2. In embodiments, the T cell is activated in the presence of between about 25 units/mL and about 500 units/mL IL-2. In embodiments, the T cell is activated in the presence of between about 125 units/mL and about 500 units/mL IL-2. In embodiments, the T cell is activated in the presence of between about 125 units/mL and about 400 units/mL IL-2. In embodiments, the T cell is activated in the presence of between about 125 units/mL and about 300 units/mL IL-2. In embodiments, the T cell is activated in the presence of about 200 units/mL IL-2. The amount may be any value or subrange within the recited ranges, including endpoints.

In embodiments, the T cell is activated with IL-7. In embodiments, the T cell is activated in the presence of between about 0 ng/mL and about 200 ng/ml IL-7. In embodiments, the T cell is activated in the presence of between about 5 ng/ml and about 200 ng/ml IL-7. In embodiments, the T cell is activated in the presence of between about 10 ng/ml and about 200 ng/ml IL-7. In embodiments, the T cell is activated in the presence of between about 5 ng/ml and about 150 ng/mL IL-7. In embodiments, the T cell is activated in the presence of between about 5 ng/ml and about 100 ng/ml IL-7. In embodiments, the T cell is activated in the presence of between about 5 ng/mL and about 50 ng/ml IL-7. In embodiments, the T cell is activated in the presence of between about 10 ng/mL and about 100 ng/ml IL-7. In embodiments, the T cell is activated in the presence of between about 10 ng/ml and about 50 ng/ml IL-7. In embodiments, the T cell is activated in the presence of about 25 ng/ml IL-7. The amount may be any value or subrange within the recited ranges, including endpoints.

In embodiments, the T cell is activated with IL-7. In embodiments, the T cell is activated in the presence of between about 0 units/mL and about 4000 units/mL IL-7. In embodiments, the T cell is activated in the presence of between about 20 units/mL and about 2000 units/mL IL-7. In embodiments, the T cell is activated in the presence of between about 20 units/mL and about 1000 units/mL IL-7. In embodiments, the T cell is activated in the presence of between about 20 units/mL and about 500 units/mL IL-7. In embodiments, the T cell is activated in the presence of between about 100 units/mL and about 500 units/mL IL-7. In embodiments, the T cell is activated in the presence of about 500 units/mL IL-7. The amount may be any value or subrange within the recited ranges, including endpoints.

In embodiments, the T cell is activated with IL-15. In embodiments, the T cell is activated in the presence of between about 0 ng/ml and about 500 ng/ml IL-15. In embodiments, the T cell is activated in the presence of between about 0 ng/ml and about 200 ng/mL IL-15. In embodiments, the T cell is activated in the presence of between about 5 ng/ml and about 200 ng/ml IL-15. In embodiments, the T cell is activated in the presence of between about 10 ng/ml and about 200 ng/mL IL-15. In embodiments, the T cell is activated in the presence of between about 15 ng/ml and about 200 ng/mL IL-15. In embodiments, the T cell is activated in the presence of between about 25 ng/ml and about 200 ng/ml IL-15. In embodiments, the T cell is activated in the presence of between about 5 ng/mL and about 150 ng/mL IL-15. In embodiments, the T cell is activated in the presence of between about 5 ng/ml and about 100 ng/mL IL-15. In embodiments, the T cell is activated in the presence of between about 10 ng/mL and about 100 ng/ml IL-15. In embodiments, the T cell is activated in the presence of between about 25 ng/mL and about 100 ng/mL IL-15. In embodiments, the T cell is activated in the presence of about 50 ng/mL IL-15. The amount may be any value or subrange within the recited ranges, including endpoints.

In embodiments, the T cell is activated with IL-15. In embodiments, the T cell is activated in the presence of between about 0 units/mL and about 500 units/mL IL-15. In embodiments, the T cell is activated in the presence of between about 25 units/mL and about 500 units/mL IL-15. In embodiments, the T cell is activated in the presence of between about 125 units/mL and about 500 units/mL IL-15. In embodiments, the T cell is activated in the presence of between about 125 units/mL and about 400 units/mL IL-15. In embodiments, the T cell is activated in the presence of between about 125 units/mL and about 300 units/mL IL-15. In embodiments, the T cell is activated in the presence of about 200 units/mL IL-15. The amount may be any value or subrange within the recited ranges, including endpoints.

In embodiments, the T cell is activated in the presence of anti-CD3 antibody and/or anti-CD28 antibody. In embodiments, the T cell is activated in the presence of CD3 agonist and/or CD28 agonist. In embodiments, the anti-CD3 antibody and/or anti-CD28 antibody is conjugated to a substrate. In embodiments, the CD3 agonist and/or CD28 agonist is conjugated to a substrate. In embodiments, the substrate is a colloidal polymeric nanomatrix. In embodiments, the substrate is a superparamagnetic particle. In embodiments, the T cells are activated in the presence of T cell TRANSACT™ (Miltenyi Biotech). In embodiments, the T cells are activated in the presence of DYNABEADS® Human T-Activator CD3/CD28 (Thermo Fisher Scientific). In embodiments, method step a) is performed no more than about 24 hours after activation. In embodiments, method step a) is performed between about 24 hours and about 72 hours after activation. In embodiments, method step a) is performed between about 36 hours and about 60 hours after activation.

In another interrelated aspect, a method for making a population of engineered T cells is provided, comprising performing the method described herein, including embodiments, on a population of T cells. In embodiments, at least about 5% of the population of T cells are recovered as engineered T cells. In embodiments, about 5% to about 100% of the population of T cells are recovered as engineered T cells. In embodiments, at least about 50% of the population of T cells are recovered as engineered T cells. In embodiments, at least about 60% of the population of T cells are recovered as engineered T cells. The percentage may be any value or subrange within the recited ranges, including endpoints.

In embodiments, the engineered T cells are expanded after genetic modification. In embodiments, the engineered T cells are expanded by at least about 2-fold relative to the day 1 post-electroporation cell count. In embodiments, the engineered T cells are expanded by at least about 5-fold, at least about 10-fold, at least about 15-fold, at least about 20-fold, at least about 50-fold, at least about 100-fold, at least about 200-fold, at least about 500-fold, at least about 1000-fold, relative to the day 1 post-electroporation cell count.

In embodiments, between about 5% and about 100% of the population of T cells are viable after method step c). In embodiments, between about 10% and about 100% of the population of T cells are viable after method step c). In embodiments, between about 15% and about 100% of the population of T cells are viable after method step c). In embodiments, between about 20% and about 100% of the population of T cells are viable after method step c). In embodiments, between about 25% and about 100% of the population of T cells are viable after method step c). In embodiments, at least about 5% of the population of T cells are viable after method step c). In embodiments, at least about 10% of the population of T cells are viable after method step c). In embodiments, at least about 15% of the population of T cells are viable after method step c). In embodiments, at least about 20% of the population of T cells are viable after method step c). In embodiments, at least about 25% of the population of T cells are viable after method step c). In embodiments, at least about 50% of the population of T cells are viable after method step c). In embodiments, at least about 75% of the population of T cells are viable after method step c). The percentage may be any value or subrange within the recited ranges, including endpoints.

In embodiments, the method further includes contacting the cell with a second RNP comprising a guide RNA that targets an endogenous TCR-beta locus, and wherein at least about 5% of the population of T cells are recovered as engineered T cells. In embodiments, less than about 30% of the engineered T cells express functional endogenous TCR-beta protein. In embodiments, less than about 20% of the engineered T cells express functional endogenous TCR-beta protein. In embodiments, less than about 10% of the engineered T cells express functional endogenous TCR-beta protein. In embodiments, less than about 5% of the engineered T cells express functional endogenous TCR-beta protein. The percentage may be any value or subrange within the recited ranges, including endpoints.

In embodiments, about 10% to about 100% of the population of T cells are recovered as engineered T cells. In embodiments, at least about 20% of the population of T cells are recovered as engineered T cells. In embodiments, at least about 30% of the population of T cells are recovered as engineered T cells. In embodiments, at least about 40% of the population of T cells are recovered as engineered T cells. In embodiments, at least about 50% of the population of T cells are recovered as engineered T cells. In embodiments, at least about 60% of the population of T cells are recovered as engineered T cells. In embodiments, at least about 70% of the population of T cells are recovered as engineered T cells. In embodiments, at least about 80% of the population of T cells are recovered as engineered T cells. In embodiments, at least about 90% of the population of T cells are recovered as engineered T cells. The percentage may be any value or subrange within the recited ranges, including endpoints. In embodiments, the percentage of engineered T cells is determined prior to expansion. In embodiments, the percentage of engineered T cells is determined after expansion.

In embodiments, method step a) comprises the following steps in any order: (i) adding the donor DNA to a chamber; (ii) adding the RNP to the chamber; (iii) adding a negatively charged polymer to the chamber; and (iv) adding the T cell to the chamber. In embodiments, method step a) comprises the following steps in any order: (i) combining the RNP and negatively charged polymer to form a RNP-PGA mixture; (ii) adding the donor DNA to a chamber; (iii) adding the RNP-PGA mixture to the chamber; and (iv) adding the T cell to the chamber. In embodiments, method step a) comprises the following steps in any order: (i) adding the RNP to a chamber; (ii) adding the donor DNA to the chamber; and (iii) adding the T cell to the chamber. In embodiments, the T cell is not pipetted during method steps a) and b). In embodiments, the method includes adding a negatively charged polymer to the chamber. In embodiments, the method expressly excludes adding a negatively charged polymer to the chamber.

In another interrelated aspect, an engineered T cell is provided. The engineered T cell is made by the methods described herein including embodiments. In another interrelated aspect, a population of engineered T cells is provided. The population of engineered T cells are made by the methods described herein including embodiments.

IV. Methods of Using

The engineered T cells described herein may be used for any suitable purpose. For example, the engineered T cells may be administered to treat a disease in a subject in need thereof. The disease may be a neoplasia, an infection, or an inflammatory disease.

In embodiments, the neoplasia is a cancer. In embodiments, the infection is a viral infection, a bacterial infection, a fungal infection, a protozoan infection, or a helminth infection. In embodiments, the viral infection is caused by Human Immunodeficiency Virus, Hepatitis C Virus, Hepatitis B Virus, Human Cytomegalovirus, or a coronavirus. In embodiments, the inflammatory disease is an autoimmune disorder, an allergy, arthritis, psoriasis, diabetes, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

In another, interrelated aspect, a method for treating a subject having cancer is provided. The method includes: a) providing a population of T cells; b) engineering at least a subset of the population of T cells to express an exogenous T cell receptor (TCR) and to knock out an endogenous TCR-beta, thereby forming a population of engineered T cells, wherein the exogenous TCR binds to an antigen expressed by the cancer; c) expanding the population of engineered T cells; and d) administering the expanded population of engineered T cells to the subject.

In another interrelated aspect, a method for treating a subject having cancer is provided. The method includes: a) providing a first population of T cells isolated from the subject; b) engineering at least a subset of the first population of T cells to express a first exogenous T cell receptor (TCR) and to knock out an endogenous TCR-beta, thereby forming a first population of engineered T cells, wherein the exogenous TCR binds to a first antigen expressed by the cancer; c) expanding the first population of engineered T cells; d) administering the expanded first population of engineered T cells to the subject; e) providing a second population of T cells isolated from the subject; f) engineering at least a subset of the second population of T cells to express a second exogenous TCR and to knock out the endogenous TCR-beta, thereby forming a second population of engineered T cells, wherein the exogenous TCR binds to a second antigen expressed by the cancer; g) expanding the second population of engineered T cells; and h) administering the expanded second population of engineered T cells to the subject. In embodiments, any number of pluralities of engineered T cells, each containing a different TCR, can be prepared and administered to the subject. In embodiments, each TCR binds to a different antigen. In embodiments, two or more TCRs bind to the same antigen. The pluralities of T cells may be administered in any order, including simultaneously.

In another interrelated aspect, a method for treating a subject having cancer is provided. The method includes: a) providing a first population of T cells isolated from the subject; b) engineering at least a subset of the first population of T cells to express a first exogenous T cell receptor (TCR) and to knock out an endogenous TCR-alpha, thereby forming a first population of engineered T cells, wherein the exogenous TCR binds to a first antigen expressed by the cancer; c) expanding the first population of engineered T cells; d) administering the expanded first population of engineered T cells to the subject; e) providing a second population of T cells isolated from the subject; f) engineering at least a subset of the second population of T cells to express a second exogenous TCR and to knock out the endogenous TCR-alpha, thereby forming a second population of engineered T cells, wherein the exogenous TCR binds to a second antigen expressed by the cancer; g) expanding the second population of engineered T cells; and h) administering the expanded second population of engineered T cells to the subject.

In embodiments, a method for treating a subject having cancer, wherein the subject is treated with any one or combination thereof of the population of engineered T cells expressing exogenous TCR-beta and/or TCR-alpha.

In embodiments, the expanded population of engineered T cells comprises between $1 \times 10^5$ and $1 \times 10^{11}$ engineered T cells. In embodiments, the expanded population of engineered T cells comprises at least $1 \times 10^8$ engineered T cells. In embodiments, the expanded population of engineered T cells comprises at least $1 \times 10^9$ engineered T cells. In embodiments, the expanded population of engineered T cells comprises at least $1 \times 10^{10}$ engineered T cells. In embodiments, the expanded population of engineered T cells comprises at least $1 \times 10^{11}$ engineered T cells. The number may be any value or subrange within the recited ranges, including endpoints.

In embodiments, the T cells are autologous to the subject. In embodiments, the T cells are allogeneic to the subject.

In embodiments, the antigen is a neoantigen or a TAA. In embodiments, at least a portion of the genome and/or transcriptome of the cancer was sequenced to determine the presence of the antigen. In embodiments, the engineered T cells are made using the methods described herein including embodiments. In embodiments, the antigen is WT1, JAK2, NY-ESO1, PRAME, or mutant KRAS, HPV. In embodiments, the antigen is an antigen from Table 1 or Table 2. In embodiments, the antigen is specific for the cancer. In embodiments, the TCR binds to the antigen presented on a major histocompatibility complex class I (MHCI) molecule.

In embodiments, the first expanded population of engineered T cells comprises between $1 \times 10^5$ and $1 \times 10^{11}$ engineered T cells. In embodiments, the first expanded population of engineered T cells comprises at least $1 \times 10^8$ engineered T cells. In embodiments, the first expanded population of engineered T cells comprises at least $1 \times 10^9$ engineered T cells. In embodiments, the first expanded population of engineered T cells comprises at least $1 \times 10^{10}$ engineered T cells. In embodiments, the first expanded population of engineered T cells comprises at least $1 \times 10^{11}$ engineered T cells. In embodiments, the second expanded population of engineered T cells comprises between $1 \times 10^5$ and $1 \times 10^{11}$ engineered T cells. In embodiments, the second expanded population of engineered T cells comprises at least $1 \times 10^8$ engineered T cells. In embodiments, the second expanded population of engineered T cells comprises at least $1 \times 10^9$ engineered T cells. In embodiments, the second expanded population of engineered T cells comprises at least $1 \times 10^{10}$ engineered T cells. In embodiments, the second expanded population of engineered T cells comprises at least $1 \times 10^{11}$ engineered T cells. The number may be any value or subrange within the recited ranges, including endpoints.

In embodiments, an additional population of engineered T cells is administered to the patient, and the T cells in the additional population of engineered T cells express a third exogenous TCR that binds to a third antigen expressed by the cancer. In embodiments, an additional population of engineered T cells is administered to the patient, and the T cells in the additional population of engineered T cells express a fourth exogenous TCR that binds to a fourth antigen expressed by the cancer. In embodiments, an additional population of engineered T cells is administered to the patient, and the T cells in the additional population of engineered T cells express a fifth exogenous TCR that binds to a fifth antigen expressed by the cancer. In embodiments, an additional population of engineered T cells is administered to the patient, and the T cells in the additional population of engineered T cells express a sixth exogenous TCR that binds to a sixth antigen expressed by the cancer. In embodiments, an additional population of engineered T cells is administered to the patient, and the T cells in the additional population of engineered T cells express a seventh exogenous TCR that binds to a seventh antigen expressed by the cancer. In embodiments, an additional population of engineered T cells is administered to the patient, and the T cells in the additional population of engineered T cells express an eighth exogenous TCR that binds to an eighth antigen expressed by the cancer. One of skill in the art would understand that any number of additional pluralities of T cells expressing any number of additional TCRs fall within the scope of this disclosure.

In another interrelated aspect, a method of treating cancer is provided. The method includes administering a T cell, composition, or pharmaceutical composition as described herein including embodiments, to a patient having a cancer. In embodiments, the method further comprises administering an anti-cancer therapy to the subject. In embodiments, a patient who has undergone an anti-cancer therapy is administered a T cell, composition, or pharmaceutical composition as described herein. In embodiments, a patient who has undergone an anti-cancer therapy is selected for administration of a T cell, composition, or pharmaceutical composition as described herein. In embodiments, the anti-cancer therapy comprises immunotherapy, chemotherapy, and/or radiation.

In embodiments, the patient undergoes lymphodepletion prior to administration of a T cell, composition, or pharmaceutical composition as described herein. In embodiments, a patient who has undergone lymphodepletion is administered a T cell, composition, or pharmaceutical composition as described herein. In embodiments, a patient who has undergone lymphodepletion is selected for administration of a T cell, composition, or pharmaceutical composition as described herein.

V. Nucleic Acids and Kits

In another interrelated aspect, a guide RNA is provided. The guide RNA is discovered through methods known to one skilled in the art such that it targets the exon 1, exon 2 or exon 3 region of the TCR constant alpha region locus (TRAC). In embodiments, the guide RNA targets an endogenous TCR-alpha locus at one of the following sites: TRAC1 (SEQ ID NO: 7), TRAC2 (SEQ ID NO: 8), TRAC3 (SEQ ID NO: 9), TRAC4 (SEQ ID NO: 10), TRAC5 (SEQ ID NO: 11), TRAC6 (SEQ ID NO: 12), TRAC7 (SEQ ID NO: 13), TRAC8 (SEQ ID NO: 14), TRAC9 (SEQ ID NO: 15), TRAC10 (SEQ ID NO: 16), TRAC11 (SEQ ID NO: 17), TRAC12 (SEQ ID NO: 18), TRAC13 (SEQ ID NO: 19), TRAC14 (SEQ ID NO: 20), TRAC15 (SEQ ID NO: 21), or TRAC16 (SEQ ID NO: 22). In embodiments, the guide RNA that targets an endogenous TCR-alpha locus includes a nucleic acid sequence as set forth in Table 10. In embodiments, the endogenous TCR-alpha locus is an endogenous TCR-alpha constant region.

In another interrelated aspect, a guide RNA is provided. The guide RNA is discovered through methods known to one skilled in the art such that it targets the exon 1 regions of both TCR constant beta region loci (TRBC). In embodiments, the guide RNA targets an endogenous TCR-beta locus that targets one of the following sequences: TRBC1 (SEQ ID NO: 23), TRBC2 (SEQ ID NO: 24), TRBC3 (SEQ ID NO: 25), TRBC4 (SEQ ID NO: 26), TRBC5 (SEQ ID NO: 27), TRBC6 (SEQ ID NO: 28), TRBC7 (SEQ ID NO: 29), TRBC8 (SEQ ID NO: 30), TRBC9 (SEQ ID NO: 31), TRBC10 (SEQ ID NO: 32), TRBC11 (SEQ ID NO: 33), TRBC12 (SEQ ID NO: 34), TRBC13 (SEQ ID NO: 35), TRBC14 (SEQ ID NO: 36), TRBC15 (SEQ ID NO: 37), TRBC16 (SEQ ID NO: 38), TRBC17 (SEQ ID NO: 39), TRBC18 (SEQ ID NO: 40), TRBC19 (SEQ ID NO: 41), TRBC20 (SEQ ID NO: 42), TRBC21 (SEQ ID NO: 43), TRBC22 (SEQ ID NO: 44), TRBC23 (SEQ ID NO: 45), TRBC24 (SEQ ID NO: 46), TRBC25 (SEQ ID NO: 47), or TRBC26 (SEQ ID NO: 48). In embodiments, the guide RNA that targets an endogenous TCR-beta locus includes a nucleic acid sequence as set forth in Table 11.

In another interrelated aspect, a nucleic acid is provided. The nucleic acid includes a nucleic acid sequence comprising an exogenous TCR-beta encoding sequence and an exogenous TCR-alpha encoding sequence, wherein the nucleic acid sequence further comprises a first self-cleaving peptide encoding sequence. In embodiments, the nucleic acid further includes a first homology arm and a second homology arm. In embodiments, the nucleic acid further includes a second self-cleaving peptide encoding sequence. In embodiments, the nucleic acid includes, in order from 5' to 3': (i) the first homology arm; (ii) the first self-cleaving viral peptide encoding sequence; (iii) the exogenous TCR-beta encoding sequence; (iv) the second self-cleaving viral peptide encoding sequence; (v) the exogenous TCR-alpha encoding sequence; (vi) optionally, a polyA sequence; and (vii) the second homology arm. In embodiments, the exogenous TCR-alpha encoding sequence encodes an exogenous TCR-alpha VJ domain.

In embodiments, the first homology arm is homologous to an endogenous TCR-alpha locus in a human T cell. In embodiments, the second homology arm is homologous to an endogenous TCR-alpha locus in a human T cell. In embodiments, the endogenous TCR-alpha locus is a TCR-alpha constant region. In embodiments, the first homology arm is homologous to an endogenous TCR-beta locus in a human T cell. In embodiments, the second homology arm is homologous to an endogenous TCR-beta locus in a human T cell.

In embodiments, the first self-cleaving viral peptide is T2A, P2A, E2A, or F2A. In embodiments, the second self-cleaving viral peptide is T2A, P2A, E2A, or F2A. In embodiments, the first self-cleaving viral peptide and the second self-cleaving viral peptide are different. In embodiments, the first self-cleaving viral peptide and the second self-cleaving viral peptide are the same. In embodiments, the first self-cleaving peptide encoding sequence is 5' of the exogenous TCR-alpha encoding sequence (e.g., exogenous TCR-alpha VJ domain encoding sequence). In embodiments, the second self-cleaving peptide encoding sequence is 5' of the exogenous TCR-beta encoding sequence. In embodiments, the first self-cleaving peptide encoding sequence is 5' of the exogenous TCR-beta encoding sequence. In embodiments, the second self-cleaving peptide encoding sequence is 5' of the exogenous TCR-alpha encoding sequence (e.g., exogenous TCR-alpha VJ domain encoding sequence). In embodiments, the nucleic acid sequence comprises a polyA signal. In embodiments, the polyA signal is 3' of a full-length TCR-alpha encoding sequence. In embodiments, the polyA signal is 3' of a full-length TCR-beta encoding sequence.

In embodiments, the nucleic acid is a plasmid, nanoplasmid, or minicircle. In embodiments, the nucleic acid is a plasmid. In embodiments, the nucleic acid is a nanoplasmid. In embodiments, the nucleic acid is a minicircle.

In another, interrelated aspect, a kit for producing engineered T cells is provided. The kit includes a TCR-alpha-targeting guide RNA as described herein including embodiments. In embodiments, the kit further includes a TCR-beta-targeting guide RNA as described herein including embodiments. In embodiments, the kit further includes a gene editing reagent or nucleotide encoding a gene editing reagent. In embodiments, the gene editing reagent is a CRISPR system. In embodiments, the kit further includes a donor DNA. In embodiments, the donor DNA comprises a nucleic acid sequence encoding a polypeptide comprising an exogenous TCR-beta and an exogenous TCR-alpha domain. In embodiments, the exogenous TCR-beta and the heterologous TCR-alpha form a TCR capable of binding to an antigen. In embodiments, the TCR binds to the antigen presented on a major histocompatibility complex class I (MHCI) molecule. In embodiments, the antigen is WT1, JAK2, NY-ESO1, PRAME, mutant KRAS, or an antigen from Table 1 or Table 2. In embodiments, the antigen is a neoantigen. In embodiments, the kit further includes poly (glutamic acid) (PGA) or variant thereof. In embodiments, the kit further includes a nucleic acid as described herein including embodiments.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

One skilled in the art would understand that descriptions of making and using the particles described herein is for the sole purpose of illustration, and that the present disclosure is not limited by this illustration.

Example 1. T Cell Purification and Activation

To purify T cells, the following reagents were used: STRAIGHTFROM® Buffy Coat CD8 MicroBeads (Miltenyi, Catalog #130-114-978), MACS Buffer (PBS/0.5% BSA/2 mM EDTA), QUADROMACS™ Separator (Miltenyi), X-VIVO™ 15 without gentamicin & phenol red (Lonza, Catalog #04-744Q), and red blood cell lysis buffer.

Buffy Coat from each donor was diluted to 80 mL with PBS/0.5% BSA/2 mM EDTA and 4 mL STRAIGHTFROM® Buffy Coat CD8 MicroBeads were added per buffy coat (i.e. 4 mL beads per 80 mL volume of blood). Tubes were inverted 5-8 times to mix and incubated for 15 minutes in the refrigerator (2-8° C.).

For magnetic separation, the whole blood column was placed in the magnetic field of the QUADROMACS™ Separator. The column was prepared by rinsing with 3 mL of separation (MACS) buffer and the magnetically labeled cell suspension applied onto the prepared whole blood column. The flow-through contained unlabeled cells. The whole blood column was washed twice with 2 mL separation buffer, then removed from the separator and placed on a new collection tube. Magnetically labeled cells were eluted by applying elution buffer followed by firmly pushing the plunger into the column. Cells were pelleted by centrifuging for 5 min at 300 g and the supernatant removed. The cells were resuspended by pipetting up and down in 5 mL of red blood cell lysis buffer, and incubated for 5 minutes at room temperature. Cells were washed with PBS and centrifuged again before resuspending the resulting cell pellet by pipetting in 5 mL of X-VIVO™ media containing 50 µM 2-mercaptoethanol and 10 µM N-Acetyl-L-Cysteine. Cells were counted; target is $1 \times 10^6$ cells/mL in X-VIVO™ 15 media for culture.

To activate T cells, the following reagents were used: TRANSACT™ (Miltenyi, Catalog #130-111-160), 25 ng/mL research-grade Human IL-7 (Miltenyi, Catalog #130-095-367), 50 ng/mL research-grade Human IL-15 (Miltenyi, Catalog #130-095-760), 10 ng/mL research grade Human IL-2 (Miltenyi, Catalog #130-097-743), X-VIVO™ 15 without gentamicin & phenol red (Lonza, Catalog #04-744Q), N-Acetyl-L-cysteine (Catalog #A9165), and b-Mercaptoethanol (Catalog #21985-023).

Plating was performed in tissue culture plates, according to the following protocol. First, cells were plated in X-VIVO™ 15 containing 50 µM 2-mercaptoethanol and 10 µM N-Acetyl-L-Cysteine, at a concentration of $1 \times 10^6$ cells/mL in 12-well-plate (4 mL per well), or $5 \times 10^{\hat{}}6$ cells in a 6-well-plate (5 mL per well). T Cell TRANSACT™ reagent (1:100) was added to each well, along with 10 ng/ml IL-2, 25 ng/ml IL-7, and 50 ng/ml IL-15. Cells were incubated for 36 h to 48 h at 37° C., 5% CO2, humidified.

Example 2. T Cell Electroporation

For electroporation of T cells, the following reagents and equipment were used: SpyFi™ Cas9 (Aldevron, Catalog #9214-5 mg), sgRNAs targeting TCR (for examples see Tables 3 and 4; and NTC), donor DNA template, Nuclease-Free Duplex Buffer (IDT, Catalog #1072570), poly-L-glutamic acid sodium salt with molecular weight 15,000-50,000 (Sigma, Catalog #P4761-100 MG), PCR tubes, P3 Primary Cell Kit (Lonza V4SP-3096, 96 reactions), 4D-Nucleofector™ Core Unit (Lonza, cat. no. AAF-1002B), and 4D-Nucleofector™ X Unit (Lonza, cat. no. AAF-1002X).

T cell electroporation. Unless otherwise noted, sgRNA was reconstituted to 50 UM in Nuclease-Free Duplex Buffer, vortexed briefly, and incubated at room temperature (RT) for 5 minutes, then vortexed again. If crRNA+tracrRNA were used, each was reconstituted at 100 µM. crRNA and tracRNA (20 µL each) was added to a tube, vortexed briefly, and spun down. RNAs were allowed to anneal at 95° C. for 5 minutes and to cool down slowly to RT (about 5 minutes).

X-VIVO™ 15 (900 µL) containing 50 µM 2-mercaptoethanol and 10 µM N-Acetyl-L-Cysteine, 10 ng/ml IL-2, 25 ng/ml IL-7 and 50 ng/ml IL-15 was dispensed into each well, and incubated at 37° C. to warm the medium.

Separately, recovery medium (X-VIVO™ 15 media containing 50 µM 2-mercaptoethanol and 10 UM N-Acetyl-L-Cysteine, without added cytokines) was pre-warmed.

RNP complex was prepared immediately before transfection as follows: 1. added 3.5 µl (180 µmol) of the sgRNA to a RNAse/DNAse-free PCR tube; 2. Added 1 µl of the High Fidelity Cas9 (60 µmol) and mixed gently by repeatedly pipetting the solution (3:1 ratio); and 3. incubated for 15 min at room temperature to obtain 4.5 µl of RNP mix ready for transfection.

Activated T cells were harvested and centrifuged at 300 g. The activated T cells were washed with PBS and counted (by Vi-CELL). Cells were again centrifuged at 300 g, then resuspended at $1 \times 10^{\hat{}}6$ cells per 20 µl of P3 nucleofection buffer with supplement and mixed by pipetting 2-3 times. Donor template (2 µl, containing a total of 1 µg) was added to a PCR tube. RNP (4.5 µl) was added to the PCR tube and incubated for 1 minute at room temperature. If used, 2 µl of PGA (resuspended at 100 mg/mL) was added to PCR tube and incubated for 1-2 minutes at room temperature. Cells (20 µL) were added to PCR tube, mixed by pipetting up and down gently. The mixture was transferred to a cuvette strip, the lid added, and incubated in cuvette strip for 3-5 min.

Cuvette strips were placed in the 4D-Nucleofector™ machine, and electroporated using the indicated program (e.g., Primary Cell P3 program and EH115 pulse code). 80 µl pre-warmed X-VIVO™ 15 containing 50 µM 2-mercaptoethanol and 10 UM N-Acetyl-L-Cysteine (without cytokines) was added per nucleofection cell and the cuvette transferred to a 37° C. incubator for a minimum of 15 minutes. After 15-minute incubation, cells were transferred to appropriate wells in 48-well plate (X-VIVO™ 15 media containing cytokines).

On day 3, cells were transferred to a 24-well plate and 1 mL fresh X-VIVO™ 15 media containing 50 µM 2-mercaptoethanol and 10 UM N-Acetyl-L-Cysteine with 10 ng/mL IL-2, 25 ng/ml IL-7 and 50 ng/ml IL-15 was added. On day 5, cells were resuspended by pipetting. An aliquot (100 µL) was set aside for analysis, the rest transferred to a 12-well plate and 2 mL fresh X-VIVO™ 15 media containing 50 µM 2-mercaptoethanol and 10 UM N-Acetyl-L-Cysteine with 10 ng/mL IL-2, 25 ng/mL IL-7 and 50 ng/mL IL-15 was added. On day 7, the cells were resuspended by pipetting and another 100 µL aliquot taken for analysis.

Example 3. Flow Cytometry Analysis

100 µl of post-transfection cell culture were transferred to a 96-well V-bottom well. 100 µl of cold FACS buffer (0.5% Bovine Serum Albumin (BSA)+sodium azide in PBS) was added, and cells were spun down at 300×g at 4° C. for 5 minutes. Cells were resuspended in 200 µl of FACS buffer and spun at 300×g at 4° C. for 5 minutes. Cells were then resuspended in a 100 µl working solution of a fixable viability dye (e.g. eBioscience Fixable Viability Dye eFluor 506, Thermo Fisher Catalog #65-0866-14) that was generated by diluting the dye at 1:1000 in PBS (azide- and serum/protein-free). Cells were mixed well and incubated at 4° C. for 30 minutes in the dark. Cells were washed twice with cold FACS buffer, first by adding 100 µL of FACS buffer to the mixture of cells in the working solution of the fixable viability dye and spinning down at 300× g at 4° C. for 5 minutes, and then by resuspending in 200 µl of FACS buffer and spinning down at 300× g at 4° C. for 5 minutes. Cells were then resuspended in a working solution of appropriate fluorochrome-conjugated antibodies. For most surface antibodies, cells were incubated for 30 minutes at 4° C. in the dark. If assessing expression of an exogenous T cell receptor by dextramer or tetramer staining, cells were first incubated with a 50 µL working solution of the dextramer/tetramer reagent for 15 minutes at room temperature in the dark. Following this incubation, a 50 µl working solution of the other fluorochrome-conjugated antibodies (e.g. CD8, CD3, etc.) was added to the cells, and the cells were incubated for an additional 15 minutes at 4° C. in the dark. Cells were then resuspended in a working solution of appropriate fluorochrome-conjugated antibodies. For most surface antibodies, cells were incubated for 30 minutes at 4° C. in the dark. If assessing expression of an exogenous T cell receptor by dextramer or tetramer staining, cells were first incubated with a 50 µL working solution of the dextramer/tetramer reagent for 15 minutes at room temperature in the dark. Following this incubation, a 50 µL working solution of the other fluorochrome-conjugated antibodies (e.g. CD8, CD3, etc.) was added to the cells, and the cells were incubated for an additional 15 minutes at 4° C. in the dark. Following the incubation with antibodies, cells were washed twice with cold FACS buffer. After the second wash, cells were resuspended in 100 µL of FACS buffer and analyzed on a flow cytometer. For counting cells, 10 µL of CountBright Absolute Counting Beads (Molecular Probes Catalog #402-ML-020) were added to the stained cells. A minimum of 1000 beads was collected on the flow cytometer to determine an accurate concentration number, and cell counts were determined using the calculation provided by the manufacturer.

Example 4. Donor DNA Titration and Electroporation Conditions

A donor DNA encoding a first 2A peptide, a mNeon fluorescent protein, a second 2A peptide and a TCRa VJ domain was used to determine experimental conditions. T cells were activated using TRANSACT™ (1:30) in RPMI+10% FBS, Glutamax, HEPES, non-essential amino acids, sodium pyruvate, beta-mercaptoethanol and cytokines (10 ng/ml IL-2, 25 ng/ml IL-7, and 50 ng/ml IL-15). Cells were electroporated 48 hours post-activation using Lonza P2 buffer and pulse code EH100 or P3 buffer and EH115 pulse code.

RNP was prepared as follows: 1.6 µL of PGA (15-50 kDa at 100 mg/mL in water)+2 µL TRAC1 sgRNA (100 µmol)+1 µL Cas9 (50 µmol); 10 minute incubation for RNP and additional 5 minute incubation with TRAC1-mNeon construct (both incubations at room temperature). The PCR product TRAC1-mNeon construct was titrated: 6 µg, 4 µg, 2 µg, or 1 µg.

Electroporation conditions: TRAC1 RNP+titrated amounts of TRAC1-mNeon (6 µg, 4 µg, 2 µg, and 1 µg); NTC (non-targeting guide control, i.e. no TCR knockout) RNP+4 µg TRAC1-mNeon; TRAC1 RNP+2 µg TRAC1-mNeon+P3 buffer+EH115 pulse. Following electroporation, cells were split in half: (1) 37° C. for the entire culture period, and (2) "cold shock"–24 hours at 32° C. followed by transfer to 37° C.

Results are shown in FIGS. 1A through 7.

Example 5. Targeting Different TRAC Loci and Titration of Donor DNA

A donor DNA encoding a first 2A peptide, a mNeon fluorescent protein, a second 2A peptide and a TCRa VJ domain was used.

T cells were activated using TRANSACT™ (1:30) in RPMI+10% FBS, Glutamax, HEPES, non-essential amino acids, sodium pyruvate, beta-mercaptoethanol and cytokines (10 ng/ml IL-2, 25 ng/ml IL-7, and 50 ng/ml IL-15). Cells were electroporated 48 hours post-activation using Lonza P3 buffer and EH115 pulse code. Cells were incubated at 37° C. immediately after electroporation.

RNP was prepared as follows: 1.6 µL of PGA (15-50 kDa at 100 mg/mL in water)+2 µL TRAC1 or TRAC3 sgRNA+1 µL Cas9. Ten minute incubation for RNP and additional 5 minute incubation with appropriate PCR product donor template (TRAC1-mNeon or TRAC3-mNeon); all incubations at room temperature. Cells were electroporated with TRAC1 or TRAC3 RNP+titrated amounts of corresponding TRAC-Neon template (6 µg, 4 µg, 2 µg, and 1 µg), or TRAC1 RNP+titrated amounts of NY-ESO TCR template.

Results are provided in FIGS. 10A through 16.

Example 6. Titration of the RNP

A donor DNA encoding a first 2A peptide, a mNeon fluorescent protein, a second 2A peptide and a TCRa VJ domain was used.

T cells were activated using TRANSACT™ (1:30) in RPMI+10% FBS, L-glutamine, non-essential amino acids, BME, and cytokines (10 ng/mL IL-2, 25 ng/ml IL-7, and 50 ng/ml IL-15). Cells were electroporated 48 hours post-activation using P3 buffer and EH115 pulse code.

RNP was prepared as follows: 1.6 µL of PGA (15-50 kDa at 100 mg/mL in water)+RNP+IDT duplex buffer to equalize volumes across samples. Ten minute incubation for RNP and additional 5 minute incubation with template (TRAC3 mNeon dsDNA (1 µg or 2 µg)) at room temp. TRAC3 only (no TRBC) at 0, 10, 20, 40, 80, or 120 pmols RNP. On day 4 after electroporation, cells were stained with TCRa/b-APC (BioLegend clone IP26) and flow cytometry analysis performed. Results are shown in FIGS. 7-21.

Example 7. Single-Stranded DNA Templates and Double-Stranded DNA Donor Templates A donor DNA encoding a first 2A peptide, a mNeon fluorescent protein, a second 2A peptide and a TCRa VJ domain was used. T cells were activated using TRANSACT™ (1:30) in RPMI+10% FBS, L-glutamine, non-essential amino acids, BME, and cytokines (10 ng/mL IL-2, 25 ng/ml IL-7, and 50 ng/ml IL-15). Cells were electroporated 48 hours post-activation using P3 buffer and EH115 pulse code.

Figure 22:
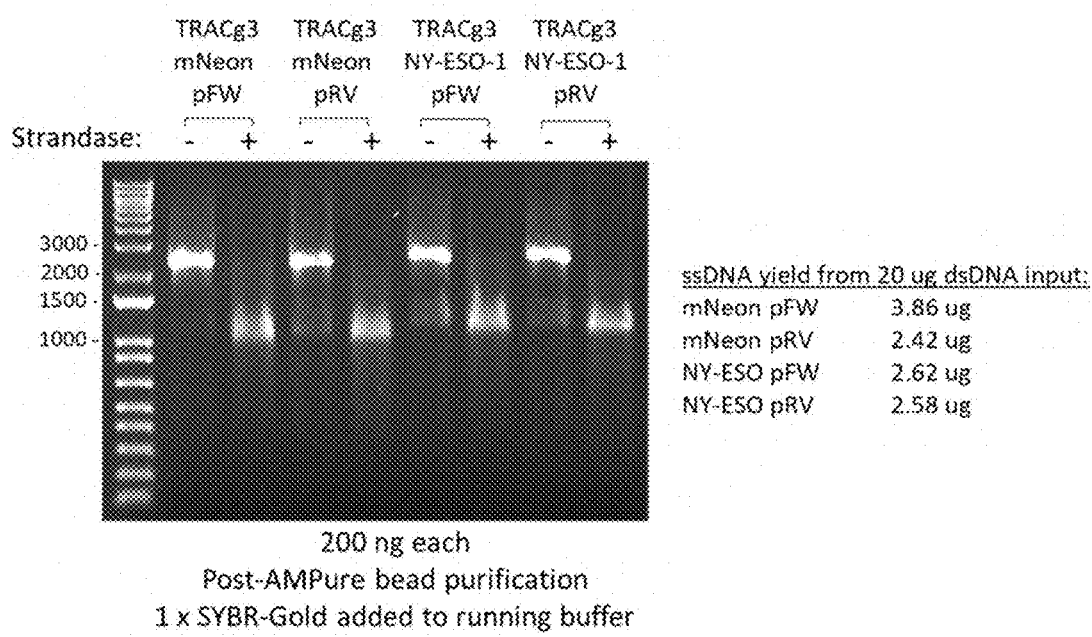
FIG. 22 is an image of an agarose gel showing forward (pFW) and reverse (pRV) ssDNA products generated from strandase reactions with dsDNA template. Strandase reactions were completed with 20 µg of double-stranded TRAC3-mNeon and TRAC3-NY-ESO1. The left-most lane shows the molecular weight marker. ssDNA yields from the reactions are shown on the right.
Figure 23A:
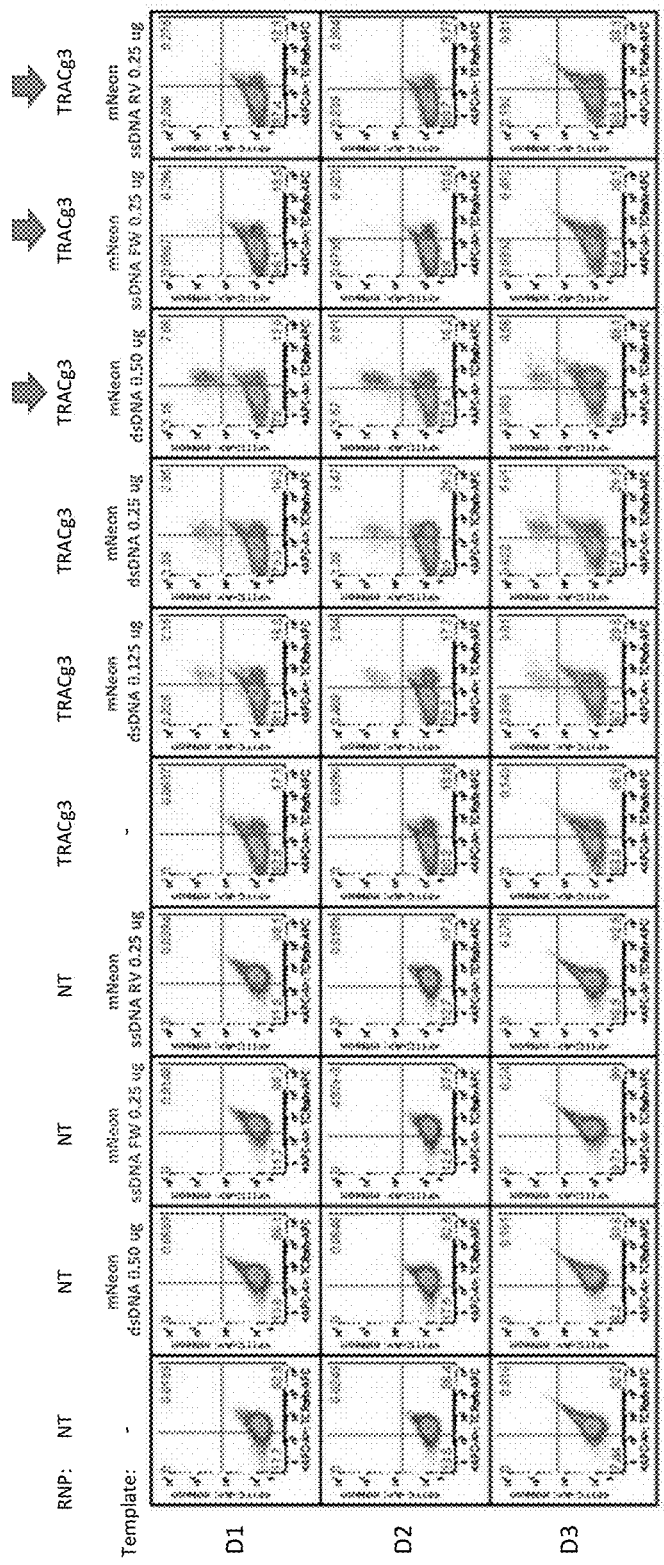
FIGS. 23A-23C illustrate knock-in efficiency and cell viability following electroporation with either ss or ds TRAC3-mNeon template.
Figure 23B:
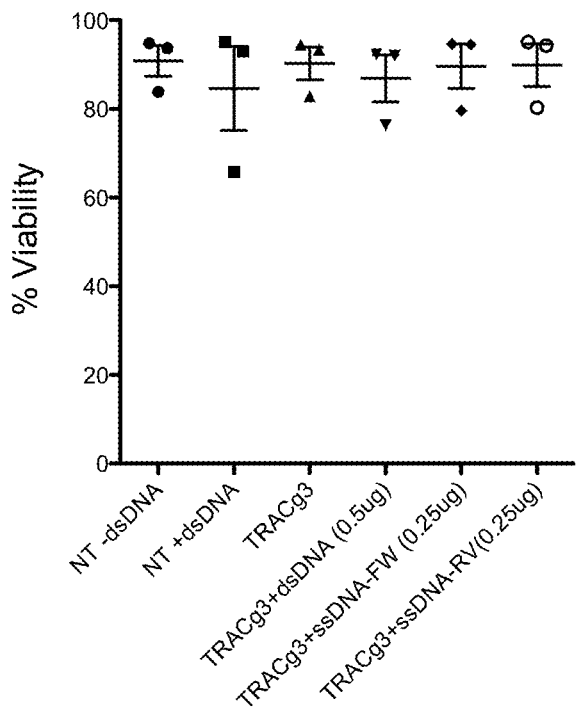
Figure 23C:
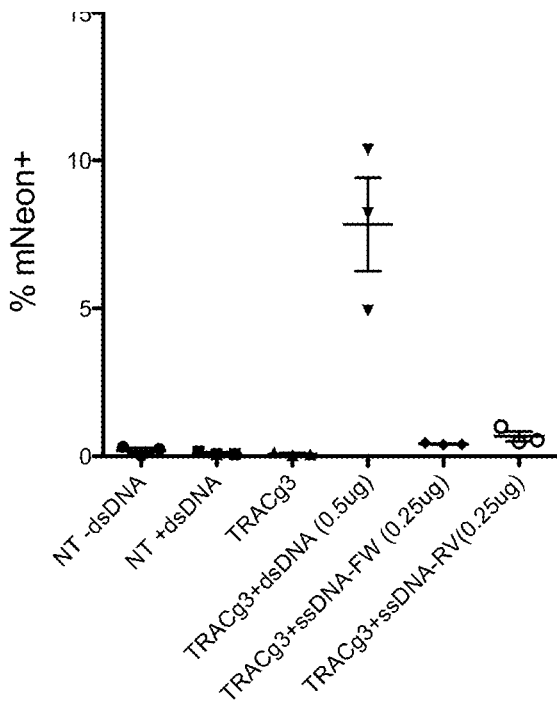

RNP was prepared as follows: Cas9+gRNA (10 min, RT), followed by 1.6 µL of PGA (15-50 kDa at 100 mg/mL in water), then template and incubated for 5 min at RT. Template was TRAC3 mNeon dsDNA (0.125, 0.25, 0.50 µg) or TRAC3 ssDNA forward (FW) or reverse (RV). RNPs: NT or TRAC3 only (no TRBC) at 10 pmols. On day 4 after electroporation, cells were stained with TCRa/b-APC (BioLegend clone IP26) and flow cytometry analysis performed. Results are provided in FIGS. 22 through 23C.

Example 8. Activation and Electroporation Conditions

A donor DNA encoding a first 2A peptide, a mNeon fluorescent protein, a second 2A peptide and a TCRa VJ domain was used. T cells were activated in RPMI+10% FBS, Glutamax, HEPES, non-essential amino acids, sodium pyruvate, beta-mercaptoethanol and cytokines (10 ng/ml IL-2, 25 ng/mL IL-7, and 50 ng/ml IL-15); X-VIVO 15 with 10 ng/ml IL-2, 25 ng/ml IL-7, and 50 ng/ml IL-15; or X-VIVO 15 with 25 ng/ml IL-7 and 50 ng/ml IL-15. For each set of media/cytokine conditions tested, TRANSACT™ was titrated (1:20, 1:50, 1:100, 1:200). Cells were electroporated 48 or 72 hours after activation.

RNP was prepared as follows: 10 minute incubation at RT for RNP (2 µL sgRNA+1 µL Cas9, used 40 pmol per reaction); additional 5 minute incubation at RT with 1.6 µL of PGA (15-50 kDa at 100 mg/mL in water)+2 µg of TRAC3-mNeon construct.

Results are provided in FIGS. 24A through 31B.

Example 9. Single-Stranded DNA Templates (Forward and Reverse) and Double-Stranded DNA A donor DNA encoding a first 2A peptide, a mNeon fluorescent protein, a second 2A peptide and a TCRa VJ domain was used. T cells were activated using TRANSACT™ (1:30) in X-VIVO media+L-glutamine, non-essential amino acids, BME, and cytokines (10 ng/ml IL-2, 25 ng/ml IL-7, and 50 ng/ml IL-15). Cells were electroporated 48 hours post-activation using P3 buffer and EH115 pulse code.

RNP was prepared as follows: SpyFi Cas9+sgRNA+PGA (1.6 µL/sample), 10 minute incubation. Template added (TRAC mNeon dsDNAs (0.5, 1.0, 1.5 µg) and ssDNAs (0.5, 1.0 µg), see FIG. 34), incubate an additional 5 minutes at RT. 40 pmols RNPs were electroporated (no TRBC). On day 4 after electroporation, cells were stained with TCRa/b-APC (BioLegend clone IP26) and flow cytometry analysis performed. Results are shown in FIGS. 33 through 35B.

Example 10. Targeting Additional TRAC Loci for TCR Knock-In

Donor DNA encoding a first 2A peptide, a mNeon fluorescent protein, a second 2A peptide and a TCRa VJ domain were used. T cells were activated using TRANSACT™ (1:30) in X-VIVO media+L-glutamine, non-essential amino acids, BME, and cytokines (10 ng/ml IL-2, 25 ng/ml IL-7, and 50 ng/mL IL-15). Cells were electroporated 48 hours post-activation using P3 buffer and EH115 pulse code.

RNP was prepared as follows: SpyFi Cas9+sgRNA+PGA (1.6 µL/sample), 10 minute incubation. Template added (TRAC mNeon dsDNAs at 0.25, 0.5, or 1.0 µg), incubated an additional 5 minutes at RT. 40 pmols RNPs were electroporated (no TRBC). On day 4 after electroporation, cells were stained with TCRa/b-APC (BioLegend clone IP26) and flow cytometry analysis performed. Corresponding gRNA sites within the TCR-alpha locus are shown in FIG. 36A. Results are shown in FIGS. 36B, 36C, and 37.

Example 11. Cytokine Conditions and Titration of TCR Activation

A donor DNA encoding a first 2A peptide, a mNeon fluorescent protein, a second 2A peptide and a TCRa VJ domain was used.

T cells were activated using TRANSACT™ (1:30, 1:100, or 1:200) in the following media conditions:

| Media | IL-2 (10 ng/mL) | IL-7 (25 ng/mL) | IL-15 (50 ng/mL) |
| --- | --- | --- | --- |
| RPMI + supplements | x | x | x |
| X-VIVO 15 | x | x | x |
| X-VIVO 15 |   | x | x |
| X-VIVO 15 + supplements | x | x | x |
| X-VIVO 15 + supplements |   | x | x |

Supplements added: Glutamax, non-essential amino acids, sodium pyruvate, and beta-mercaptoethanol. Cells were electroporated 48 hours post-activation using P3 buffer and EH115 pulse code.

RNP was prepared as follows: SpyFi Cas9+sgRNA+PGA (1.6 µL/sample) (3:1 sgRNA to Cas9 ratio), 10 minute incubation. Template added (1 µg TRAC3-mNeon), incubated an additional 5 minutes at RT. 40 pmols RNPs were electroporated (no TRBC). On day 4 after electroporation, cells were stained with TCRa/b-APC (BioLegend clone IP26) and flow cytometry analysis performed. Results are shown in FIGS. 38A through 47.

Example 12. Post-Electroporation Cell Handling

A donor DNA encoding a first 2A peptide, a mNeon fluorescent protein, a second 2A peptide and a TCRa VJ domain was used. Activation was performed using X-VIVO media with supplements, 1:100 TRANSACT™, 10 ng/ml IL-2, 25 ng/ml IL-7, and 50 ng/ml IL-15. After 48 hours, electroporation was performed. Electroporation was carried out according to the following steps: 1) 2:1 sgRNA: Cas9 (SpyFi) plus PGA for 15 minutes; 2) addition of 0.5 µg mNeon template for 5 minutes; 3) add cells; 4) P3 buffer, pulse code EH115; and 5) add 100 µL prewarmed X-VIVO with cytokines and pipette once to mix.

The following three conditions were performed following post-electroporation: 1) addition of 100 µL X-VIVO with cytokines and immediate transfer to a 24-well plate; 2) addition of 20 or 100 µL X-VIVO with cytokines without pipetting, wait 15 minutes at 37° C., then transfer to a 24-well plate; 3) wait 5 minutes at room temperature, addition of 20 µL or 100 µL X-VIVO with cytokines without pipetting, wait 15 minutes at 37 C, then transfer to a 24-well plate. Results are shown in FIGS. 48A-50.

Example 13. Double- and Single-Stranded DNA Templates with 5'-Phosphate, Phosphorothioates PCR products which have been used as templates in the above mentioned experiments are generated with primers lacking a 5' phosphate. Here we used templates with added 5' phosphates, or added phosphorothioates to the ends of the primers. A donor DNA encoding a first 2A peptide, a mNeon fluorescent protein, a second 2A peptide and a TCRa VJ domain was used.

Experimental setup included a new order of addition and RNP formulation. Plating was performed using X-VIVO with 10 ng/ml IL-2, 25 ng/ml IL-7, 50 ng/ml IL-15, and TRANSACT™ 1:100. Electroporation was performed at 42 hours post-activation using P3 buffer and EH115 pulse. Templates used were 0.5 µg, 1.0 µg, and 2.0 µg TRAC3 mNeon dsDNA and 40 pmol RNP. RNP formulation involved SpyFi Cas9 and TRACsg3 at a 2:1 ratio, and 15 minute incubation at room temperature.

The order of addition was as follows: 1) 2 µL of template, 2) 2 µL of RNP, 3) 1.6 µL of 10 mg/mL stock PGA, and 4) 20 µL cells. Time to pipette each ingredient across all tubes was approximately 7-10 minutes. Post-electroporation, samples were rested 5 minutes at room temperature, followed by addition of 20 µL plain X-VIVO without pipetting, a 15 minute incubation at 37 C, and transfer to a 24-well plate containing 1 mL X-VIVO media with cytokines. Staining conditions 4 days post-electroporation included TCRa/b-APC (BioLegend clone IP26) and PI. Results are shown in FIGS. 51A-54.

Example 14. Timing of Transfection and RNP Titration

A donor DNA encoding a first 2A peptide, a mNeon fluorescent protein, a second 2A peptide and a TCRa VJ domain was used. Activation conditions included X-VIVO media, 1:100 TRANSACT™, 10 ng/mL IL-2, 25 ng/ml IL-7, and 50 ng/ml IL 15. Cells were electroporated at 36, 48, or 72 hours post-activation. Approximately 1×10$^6$ cells were used, in P3 buffer with EH115 pulse. For RNP generation, appropriate volumes of sgRNA and Cas9 were mixed and incubated at room temperature for 10 minutes. Cas9 used was IDT HiFi Cas9. The order of adding reagents was as follows: 1) donor template, 2) RNP, 3) PGA, and 4) cells. 80 µL of prewarmed X-VIVO media with no cytokines was added directly to a cuvette, without pipetting cells, and incubated at 37° C. for 15 minutes before transfer to larger plates.

TABLE 3

Samples for experimental design testing how RNP amount and PGA impact knock-in efficiency and cell recovery.

| | 3:1 sgRNA to Cas9 |
|---|---|
| 1. | RNP only 80 pmol |
| 2. | RNP only 60 pmol |
| 3. | RNP only 40 pmol |
| 4. | RNP only 20 pmol |
| 5. | 80 pmol RNP + 1 ug donor template |
| 6. | 60 pmol RNP + 1 ug donor template |
| 7. | 40 pmol RNP + 1 ug donor template |
| 8. | 20 pmol RNP + 1 ug donor template |
| 9. | PGA RNP only 80 pmol |
| 10. | PGA RNP only 60 pmol |
| 11. | PGA RNP only 40 pmol |
| 12. | PGA RNP only 20 pmol |
| 13. | PGA 80 pmol RNP + 1 ug donor template |
| 14. | PGA 60 pmol RNP + 1 ug donor template |
| 15. | PGA 40 pmol RNP + 1 ug donor template |
| 16. | PGA 20 pmol RNP + 1 ug donor template |
| | 1:1 sgRNA to Cas9 |
| 1. | RNP only 60 pmol |
| 2. | PGA RNP only 60 pmol |
| 3. | 60 pmol RNP + 1 ug donor template |
| 4. | PGA 60 pmol RNP + 1 ug donor template |

Results are shown in FIGS. 55-62B.

Example 15. Order of Addition of Reagents During Transfection

A donor DNA encoding a first 2A peptide, a mNeon fluorescent protein, a second 2A peptide and a TCRa VJ domain was used. Experimental setup for the order of addition testing. Plating included X-VIVO with gentamicin, 10 ng/ml IL-2, 25 ng/ml IL-7, 50 ng/ml IL-15, and TRANSACT™ 1:100. Electroporation was performed at 48-52 hours post activation using P3 buffer and EH115 pulse. Template used was 0.5 µg TRAC3 mNeon dsDNA, SEC purified. RNP formulation and orders of addition are shown in FIG. 63A. Post-electroporation, samples were rested 5 minutes at room temperature, followed by addition of 20 µL plain X-VIVO without gentamicin without pipetting, 15 minute incubation at 37 C, and transfer to a 24-well plate containing 1 mL X-VIVO media with cytokines. Staining conditions on day 4 post-electroporation included TCRa/b-APC (BioLegend clone IP26) and PI. Results are shown in FIGS. 63B-63D.

Example 16. dsPCR Versus Plasmid Templates

A donor DNA encoding a first 2A peptide, a mNeon fluorescent protein, a second 2A peptide and a TCRa VJ domain was used.

Plating was performed using X-VIVO with gentamicin, 10 ng/ml IL-2, 25 ng/ml IL-7, 50 ng/ml IL-15, and TRANSACT™ 1:100. Electroporation was performed at 48-52 hours post activation using P3 buffer and EH115 pulse. Template used was TRAC3 mNeon dsDNA, SEC purified, or GenScript pUC57 TRAC3 mNeon plasmid. RNP formulation was performed using SpyFi Cas9 plus TRACsg3 at a 2:1 ratio, followed by 15 minutes incubation at room temperature. Order of addition was as follows: 1) 2 µL template, 2) 2 µL RNP, 3) 1.6 µL of 10 mg/mL stock PGA, and 4) 20

µL cells. Post-electroporation, samples were rested 5 minutes at room temperature, followed by addition of 20 µL plain X-VIVO without gentamicin without pipetting, a 15 minute incubation at 37 C, and transfer to a 24-well plate containing 1 mL X-VIVO media with cytokines. Staining conditions 4 days post-electroporation included TCRa/b-APC (BioLegend clone IP26) and PI. Results are shown in FIGS. 64A-64D.

Example 17. Cell Density and Linear Versus Plasmid Donor Templates

A donor DNA encoding a first 2A peptide, a mNeon fluorescent protein, a second 2A peptide and a TCRa VJ domain was used. Parameters tested were: 1) cell density for electroporation, and 2) PCR product versus plasmid as donor template. Culture conditions included X-VIVO media, without gentamicin or phenol red, supplemented with 50 µM 2-mercaptoethanol and 10 µM N-Acetyl-L-Cysteine, as well as 1:100 TRANSACT™ with 25 ng/mL IL-7 and 50 ng/mL IL-15 (no IL-2 added). Electroporation was performed at 48 hours post-activation using P3 buffer and EH115 pulse code, using TRAC3-Neon template. The order of addition of reagents was as follows: 1) donor template, 2) 60 pmol RNP (3:1 pmol ratio sgRNA:SpyFi Cas9, incubated at room temperature for 15 minutes), and 3) 2 µL of PGA (100 mg/mL). Post-electroporation, 80 µL of prewarmed media without cytokines was added to the electroporation cuvettes, and cells were incubated at 37 C for 15 minutes before transfer to larger cell culture plates. Test conditions are shown in Table 4 below, and included a plasmid comparison for the 2×10$^6$ cell density condition.

TABLE 4

Test conditions for testing impact of cell density on knock-in efficiency.

| Cells per electroporation | 2 ug of linear TRAC3-Neon | 1 ug of linear TRAC3-Neon | 2 ug of plasmid TRAC3-Neon | 1 ug of plasmid TRAC3-Neon |
|---|---|---|---|---|
| 5e6 | x | x | | |
| 2e6 | x | x | x | x |
| 1e6 | x | x | | |

Results are shown in FIGS. 65A-70.

Example 18. Targeting Different TRAC Loci with Plasmid Donor Templates

Donor DNA encoding a first 2A peptide, a mNeon fluorescent protein, a second 2A peptide and a TCRa VJ domain were used. Parameters tested were: 1) different TRAC loci for knock-in and 2) PCR product versus plasmid as donor template. Culture conditions included X-VIVO media without gentamicin or phenol red, supplemented with 50 µM 2-mercaptoethanol and 10 µM N-Acetyl-L-Cysteine, as well as 1:100 TRANSACT™ with 25 ng/ml IL-7 and 50 ng/ml IL-15 (no IL-2 added). Electroporation was performed at 48 hours post-activation using P3 buffer and EH115 pulse code, using TRAC3-mNeon template. The order of addition of reagents was as follows: 1) donor template, 2) 60 pmol RNP (3:1 pmol ratio sgRNA:SpyFi Cas9, incubated at room temperature for 15 minutes), and 3) 2 µL of PGA (100 mg/mL). Post-electroporation, 80 µL of prewarmed media without cytokines was added to the electroporation cuvettes, and cells were incubated at 37 C for 40 minutes before transfer to larger cell culture plates. Test conditions included 1 µg of the following templates: TRAC3 L (TRAC3 PCR product), TRAC3 plasmid, TRAC4 plasmid, TRAC5 plasmid, TRAC7 plasmid, TRAC12 plasmid, and TRAC15 plasmid. Results are shown in FIGS. 71A-74.

Example 19. Co-Transfection with Two TCR Constructs

Parameters tested were cotransfection of two different plasmid-based TCR templates. Culture conditions included X-VIVO media without gentamicin or phenol red, supplemented with 50 µM 2-mercaptoethanol and 10 µM N-Acetyl-L-Cysteine, as well as 1:100 TRANSACT™ with 25 ng/ml, IL-7 and 50 ng/ml IL-15 (no IL-2 added). Electroporation was performed at 44 hours post-activation using P3 buffer and EH115 pulse code, using templates NYESO1_TRAC3 (SEQ ID NO: 2), eRT80_gp100B_8_TRAC3 (SEQ ID NO: 3), eRT76_MART_3_TRAC3 (SEQ ID NO: 4), eJH52_WT1C_13_TRAC3 (SEQ ID NO: 5), and eRT76_MAGEA3B_4_TRAC3 (SEQ ID NO: 6).

The order of addition of reagents was as follows: 1) 0.5 µg of each donor template; 2) 40 pmol TRAC3 RNP (3:1 pmol ratio sgRNA:SpyFi Cas9, that had been preassembled at room temperature for 15 minutes before adding 1 µL of PGA at 100 mg/mL); 3) 40 pmol TRBCg21 RNP (3:1 pmol ratio sgRNA:SpyFi Cas9, that had been preassembled at room temperature for 15 minutes before adding 1 µL of PGA at 100 µg/µL); 4) 1 million cells resuspended in 20 µL of P3 buffer.

Post-electroporation, 80 µl of prewarmed media without cytokines was added to the electroporation cuvettes, and cells were incubated at 37 C for 15 minutes before transfer to larger cell culture plates. Results are shown in FIG. 75.

Plasmids encoding the NY-ESO1 TCR were electroporated with several other TCRs and analyzed by flow cytometry on day 7 post-activation.

Results are shown in FIG. 75.

Example 20. Cell Density and Electroporation Conditions

A donor DNA encoding a first 2A peptide, a mNeon fluorescent protein, a second 2A peptide and a TCRa VJ domain was used.

Culture conditions included X-VIVO media without gentamicin or phenol red, supplemented with 50 µM 2-mercaptoethanol and 10 µM N-Acetyl-L-Cysteine, as well as 1:100 TRANSACT™ with 25 ng/ml IL-7 and 50 ng/ml IL-15. Electroporation was performed at 48 hours post-activation, using TRAC3-mNeon template. The order of addition of reagents was as follows: 1) donor template, 2) 60 pmol RNP (3:1 pmol ratio sgRNA:Aldevron SpyFi Cas9, incubated at room temperature for 15 minutes), and 3) 2 µL of PGA (100 mg/mL). Post-electroporation, 80 µL of prewarmed media without cytokines was added to the electroporation cuvettes, and cells were incubated at 37 C for 40 minutes before transfer to larger cell culture plates. Cell density was 2M, 5M, and 10M cells. Testing knock-in efficiencies was performed using 1 µg linear PCR product template or 2 µg plasmid template (TRAC3-mNeon) to standardize for number of molecules used per electroporation. A pulse optimization program was performed using P3 buffer and 2 µg plasmid template, TRAC3-mNeon, research grade, using 1.5M cells per condition to allow for testing of all conditions for each donor. Results are shown in FIGS. 76A-84.

Example 21. Knock-In at TRAC Locus with Disruption of Endogenous TCR Beta Chain

Here we compared the knock-in efficiency of various TRAC templates as PCR products, and tested whether the addition of TRBCsg21 RNP has any negative effects on knock-in efficiency or staining pattern. A donor DNA encoding a first 2A peptide, a mNeon fluorescent protein, a second 2A peptide and a TCRa VJ domain was used. Parameters tested were titrations of four different PCR-based mNeon constructs targeting different regions of the TRAC locus, comparing TRAC RNP without and with TRBC RNP. Culture conditions included X-VIVO media without gentamicin or phenol red, supplemented with 50 µM 2-mercaptoethanol and 10 µM N-Acetyl-L-Cysteine, as well as 1:100 TRANSACT™ with 25 ng/ml IL-7 and 50 ng/ml IL-15 (no IL-2 added). Electroporation was performed at 44 hours post-activation using P3 buffer and EH115 pulse code. The templates were the following double-stranded PCR products: TRAC3_mNeon, TRAC4_mNeon, TRAC5_mNeon, and TRAC12_mNeon.

The order of addition of reagents was as follows: 1) 0.25, 0.5, or 1 µg of each donor template; 2) 60 pmol TRACsg3 RNP (2.5:1 pmol ratio sgRNA:SpyFi Cas9, that had been preassembled at room temperature for 15 minutes before adding 1 µL of PGA at 100 mg/ml); 3) duplicate 1 µg template set only: 60 pmol TRBCsg21 RNP (2.5:1 pmol ratio sgRNA:SpyFi Cas9, that had been preassembled at room temperature for 15 minutes before adding 1 µL of PGA at 100 µg/µL); 4) cells resuspended in 20 µL of P3 buffer. A duplicate set for the 1 µg template condition was created and only this set received both TRACsg3 and TRBCsg21 RNPs. All other samples received TRACsg3 RNP only.

Post-electroporation, cells were rested for 10 min in a 37 C incubator. Then, 80 µL of prewarmed media without cytokines was added to the electroporation cuvettes, and cells were incubated an additional 10 min in the 37 C incubator before transfer to larger cell culture plates.

Results are shown in FIGS. 85A-86B.

Example 22. Poly(L-Glutamic) and Poly(D-Glutamic) Molecular Weights Variants

A donor DNA encoding a first 2A peptide, a mNeon fluorescent protein, a second 2A peptide and a TCRa VJ domain was used. We used a 2.5:1 gRNA: Cas9 ratio, and we titrated the 15-50 kDa PGA to better define its optimal range. Plating was performed using X-VIVO without gentamicin, with 25 ng/ml IL-7, 50 ng/mL IL-15, b-Me, L-Cys, and 1:100 TRANSACT™ Electroporation was performed at 42 hours post-activation in P3 buffer, EH115. Template used was 0.75 µg TRAC3 mNeon plasmid (GenScript industrial grade, endotoxin free maxiprep). RNP used was 60 pmol with 2.5:1 sgRNA3: Cas9 ratio. Cells were added to the master mix after 1 hour, then electroporated. The order of addition of reagents was as follows: 1) RNP preincubated for 15 minutes, 2) template, 3) PGA, and 4) 1.5 million cells per cuvette. Post-electroporation, 80 µL plain X-VIVO was added without pipetting, followed by 1 hour incubation at 37 C and transfer to a 48-well plate containing 1 mL X-VIVO media with cytokines. Staining conditions on days 6 and 8 post-activation included TCRa/b-APC (BioLegend clone IP26), 5 µL stain, and PI 1:200 per stain.

Results are shown in FIGS. 89-90.

The structure of poly(L-glutamic acid) is shown below.

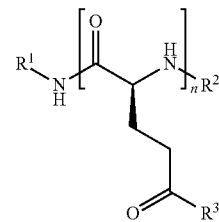

Other uses of PGA and its derivatives include: thermoplastic, fiber, film, and membrane compositions; cryoprotectants; super absorbent polymer when cross-linked. PGA also has an affinity for binding a variety of metal ions. Table 5 below lists the poly(L-glutamic acid) variants used in this study.

TABLE 5

| | PGA variants. | | |
|---|---|---|---|
| Variant # | Variant Name | Variant Size | Lot Number |
| 1 | PLE20 | 3000 | 000-E020-104 |
| 2 | PLE50 | 7500 | 000-E050-105 |
| 3 | PLE100 | 15000 | |
| 4 | PLE200 | 30000 | 000-E200-106 |
| 5 | PLE300 | 45000 | 0000-E300-102 |
| 6 | PLE400 | 60000 | 000-E400-107 |
| 7 | PLE800 | 120000 | 000-E800-105 |
| 8 | PDE20 | 3000 | 000-DE020-102 |
| 9 | PDE100 | 15000 | 000-DE100-103 |
| 10 | PDE400 | 60000 | 000-DE400-102 |

Example 23. TCR Knock-In

Culture conditions included X-VIVO media without gentamicin or phenol red, supplemented with 50 µM 2-mercaptoethanol and 10 µM N-Acetyl-L-Cysteine, and 1:100 TRANSACT™ with 25 ng/mL IL-7 and 50 ng/mL IL-15. Electroporation was performed at 48 hours post-activation using P3 buffer. The order of addition of reagents was as follows: 1) TRAC3-Neon or TRAC3-TCRs donor template, 2) 60 pmol RNP (3:1 pmol ratio sgRNA:Aldevron SpyFi Cas9, incubated at room temperature for 15 minutes), and 3) 2 µL of PGA 100 mg/mL. Post-electroporation, 80 µL of pre-warmed media without cytokines was added to the electroporation cuvettes, and cells were incubated at 37 C for 40 minutes before transfer to larger cell culture plates. Results are shown in FIGS. 92A-98.

Example 24. Electroporation Conditions

A donor DNA encoding a first 2A peptide, a mNeon fluorescent protein, a second 2A peptide and a TCRa VJ domain was used. Plating was performed using X-VIVO media without gentamicin, 25 ng/ml IL-7, 50 ng/ml IL-15, b-Me, L-Cys, and 1:100 TRANSACT™. Electroporation was performed at 44 hours post-activation in P3 buffer, using 16 different pulse codes and two different machines. Template used was 0.75 µg TRAC3 mNeon plasmid (GenScript industrial grade endotoxin free maxiprep). RNP used was 60 pmol with 2.5:1 sgRNA3: Cas9 ratio. The order of addition of reagents was as follows: 1) RNP preincubated for 15 minutes, 2) template, 3) PGA, and 4) 1.5 million cells per cuvette. Enough master mix was made to cover all reactions. Aliquots of the mix, enough for 4 reactions, were pipetted into each tube of a PCR 8-strip per donor (n=3, or one strip for each donor). Enough donor cells for 4 reactions were added to each tube. The cell mixture was multichannel pipetted from the PCR strip directly into two cuvettes for a total of 32 wells. Pairs of cuvettes were electroporated on two different machines simultaneously. Post-electroporation, 80 µL of plain X-VIVO was added without pipetting, followed by 1 hour incubation at 37 C and transfer to a 48-well plate containing 1 mL X-VIVO media with cytokines. Staining conditions at days 6 and 8 post-activation included TCRa/b-APC (BioLegend clone IP26), 5 µL stain, and PI 1200 per stain. Table 6 below gives donor information.

TABLE 6

Donor Information.

| Donor # | Donor ID | Buffy cell count | CD8 counts post purification (3/4 buffy) | Stimulate how many | Day 2 counts |
|---|---|---|---|---|---|
| 1 | R42584 | 2.9 billion | 192 million | 120 million | 73 million |
| 2 | R42587 | 3 billion | 131 million | 120 million | 98 million |
| 3 | R42580 | 3.8 billion | 258 million | 120 million | 103 million |

Results are shown in FIGS. 103-105B. Tables 7 and 8 below show percent knock-in versus mNeon+ cell numbers for days 6 and 8.

TABLE 7

Day 6 comparison of percent knock-in versus mNeon+ cell numbers.

| Code | Donor 1 New | Donor 1 Old | Donor 2 New | Donor 2 Old | Donor 3 New | Donor 3 Old |
|---|---|---|---|---|---|---|
| mNeon knock-in percentages: | | | | | | |
| P3, EH115 | 14.5 | 12.5 | 18.4 | 13.5 | 16.1 | 17.3 |
| P3, EH111 | 14.4 | 11.7 | 20.3 | 10.5 | 16.4 | 16.1 |
| P3, EN138 | 10.3 | 8.23 | 20.1 | 19.4 | 14.6 | 13.8 |
| P3, EN150 | 12.3 | 8.54 | 16.8 | 14.1 | 11.6 | 12.6 |
| P3, EN158 | 11 | 8.58 | 16.2 | 18.3 | 12.8 | 10.7 |
| P3, EO115 | 11.2 | 9.09 | 17.6 | 11.8 | 9.83 | 14.1 |
| P3, EO128 | 12.5 | 10.4 | 15.4 | 14.5 | 14 | 13.8 |
| P3, EO151 | 17.4 | 12.8 | 19.4 | 18.5 | 14.3 | 14.6 |
| P3, EW113 | 15.4 | 12.3 | 12.2 | 13.5 | 11.4 | 9.75 |
| P3, DZ115 | 8.38 | 8.03 | 10.2 | 12.1 | 10.8 | 10.3 |
| P3, DN115 | 4.45 | 5.51 | 6.76 | 8.74 | 6.1 | 5.83 |
| P3, DN130 | 4.36 | 5.93 | 4.6 | 10.9 | 10.6 | 6.99 |
| P3, EA115 | 11.2 | 9.89 | 10.1 | 11.2 | 12.3 | 10.2 |
| P3, EE115 | 6.28 | 5.75 | 6.39 | 9.02 | 6.97 | 6.01 |
| P3, ES115 | 13.9 | 14.7 | 6.53 | 20.9 | 17.1 | 17.9 |
| P3, EZ115 | 9 | 18.4 | 14.6 | 8.74 | 9.44 | 16.6 |
| mNeon+ cell numbers expressed as fold above EH115: | | | | | | |
| P3, EH115 | 1 | 1 | 1 | 1 | 1 | 1 |
| P3, EH111 | 2.24879167 | 4.4421943 | 0.83935905 | 0.8309172 | 1.46696873 | 0.9507813 |
| P3, EN138 | 2.46972064 | 0.94838449 | 1.23577813 | 1.44840749 | 1.3841744 | 0.66139745 |
| P3, EN150 | 1.73141699 | 2.31957171 | 0.7348929 | 1.17201602 | 1.10777879 | 0.52309875 |
| P3, EN158 | 0.3050737 | 0.81375058 | 0.01583056 | 0.05640351 | 0.72295501 | 0.12632723 |
| P3, EO115 | 2.86361052 | 4.46341808 | 1.39669141 | 0.42958452 | 0.64512788 | 0.74953894 |
| P3, EO128 | 4.06481798 | 5.02818643 | 0.88635905 | 0.76341335 | 0.63494232 | 1.02629978 |
| P3, EO151 | 1.64850395 | 5.55853248 | 0.54942733 | 0.99315936 | 0.56615941 | 0.8782369 |
| P3, EW113 | 2.25108961 | 6.36701999 | 0.97819993 | 1.13066259 | 1.28734031 | 1.05939728 |
| P3, DZ115 | 0.16232461 | 3.32982396 | 0.4634985 | 0.6815603 | 0.92599674 | 0.59172633 |
| P3, DN115 | 0.05053786 | 1.74036246 | 0.30998418 | 0.38256707 | 0.42658046 | 0.29008458 |
| P3, DN130 | 0.04247055 | 1.76200877 | 0.15325705 | 0.23512857 | 0.80094387 | 0.0752365 |
| P3, EA115 | 0.50690853 | 0.28628206 | 0.23266891 | 0.27524554 | 0.80143626 | 0.37910335 |
| P3, EE115 | 0.89258053 | 1.58274586 | 0.22108651 | 0.66861184 | 0.59389249 | 0.3353445 |
| P3, ES115 | 0.05188307 | 0.03594673 | 0.00310532 | 0.01871239 | 0.07920091 | 0.02953448 |
| P3, EZ115 | 0.93674004 | 2.35340749 | 0.07321235 | 0.51850632 | 1.19933553 | 0.59126035 |

TABLE 8

Day 8 comparison of percent knock-in versus mNeon+ cell numbers.

| Code | Donor 1 | | Donor 2 | | Donor 3 | |
|---|---|---|---|---|---|---|
| | New | Old | New | Old | New | Old |
| mNeon knock-in percentages: | | | | | | |
| P3, EH115 | 20.4 | 18.4 | 22.6 | 18.4 | 21.4 | 22.4 |
| P3, EH111 | 18.9 | 15.5 | 24.5 | 13.7 | 22.5 | 20.6 |
| P3, EN138 | 14.4 | 13.3 | 25.8 | 24.2 | 18.4 | 17.5 |
| P3, EN150 | 16.4 | 13.1 | 20.2 | 17.6 | 15.8 | 16.7 |
| P3, EN158 | 14.7 | 12.2 | 23.2 | 22.6 | 18.2 | 13.5 |
| P3, EO115 | 14.9 | 13.4 | 21.4 | 16.3 | 13.7 | 18.2 |
| P3, EO128 | 15.5 | 15.2 | 19.3 | 19 | 19.5 | 18.6 |
| P3, EO151 | 22.8 | 16.6 | 26.2 | 24.2 | 19.8 | 19.8 |
| P3, EW113 | 19.4 | 15.5 | 15.3 | 17.3 | 15.4 | 13.4 |
| P3, DZ115 | 13 | 10.3 | 13.1 | 15.1 | 14.5 | 13.9 |
| P3, DN115 | 6.98 | 7.1 | 7.83 | 9.77 | 8.35 | 18.9 |
| P3, DN130 | 6.38 | 7.9 | 5.27 | 14.9 | 13.7 | 9.26 |
| P3, EA115 | 16.2 | 15.1 | 11.2 | 13.3 | 17.3 | 14.5 |
| P3, EE115 | 8.99 | 8.24 | 7.68 | 11.7 | 9.4 | 8.15 |
| P3, ES115 | 20.4 | 21.6 | 13.5 | 23.6 | 24.3 | 25.9 |
| P3, EZ115 | 11.4 | 24.9 | 16.6 | 9.49 | 13.4 | 22.1 |
| mNeon+ cell numbers expressed as fold above EH115: | | | | | | |
| P3, EH115 | 1 | 1 | 1 | 1 | 1 | 1 |
| P3, EH111 | 1.17039078 | 0.72704741 | 0.8638642 | 0.93010505 | 0.85731041 | 0.77449285 |
| P3, EN138 | 0.77494303 | 0.67058639 | 1.06569408 | 2.29138369 | 0.6005241 | 0.56119934 |
| P3, EN150 | 0.92306606 | 0.90481221 | 0.56285398 | 1.13525407 | 0.44272394 | 0.58858515 |
| P3, EN158 | 0.17672842 | 0.45239043 | 0.04512087 | 0.88431557 | 0.58275908 | 0.11791251 |
| P3, EO115 | 0.85835508 | 0.64941531 | 0.7085308 | 1.11959918 | 0.40290453 | 0.62764349 |
| P3, EO128 | 1.17495567 | 0.78858889 | 0.60336655 | 1.51599145 | 0.7569908 | 0.61728633 |
| P3, EO151 | 1.1243684 | 0.85030418 | 0.80636286 | 2.06724138 | 0.8399462 | 0.70871943 |
| P3, EW113 | 2.00655718 | 0.67876709 | 0.60784598 | 1.30199039 | 0.78884201 | 0.55054792 |
| P3, DZ115 | 0.66647803 | 0.41701645 | 0.39706798 | 1.24127234 | 0.6262055 | 0.49308107 |
| P3, DN115 | 0.162305 | 0.2569525 | 0.21688185 | 0.69640463 | 0.37300566 | 0.16119488 |
| P3, DN130 | 0.15523576 | 0.26531128 | 0.10079164 | 0.74580815 | 0.52310704 | 0.21716146 |
| P3, EA115 | 0.25873055 | 0.23849515 | 0.22697259 | 0.52233485 | 0.72294447 | 0.51574991 |
| P3, EE115 | 0.43726988 | 0.42289802 | 0.28866449 | 0.70169573 | 0.37901651 | 0.31994102 |
| P3, ES115 | 0.05569148 | 0.02161601 | 0.01077317 | 0.01521078 | 0.06241362 | 0.04546989 |
| P3, EZ115 | 0.56467854 | 1.1580516 | 0.18251292 | 1.11865757 | 0.64387668 | 0.75012626 |

Example 25. NY-ESO TCR Knock-In with Disruption of Endogenous TCR Beta Chain

Plating was performed using X-VIVO without gentamicin, 25 ng/mL IL-7, 50 ng/ML IL-15, b-Me, L-Cys, and 1:100 TRANSACT™. Electroporation was performed at 48 hours post-activation in P3 buffer, code EH115. Template used was 0.75 μg TRAC3 164 (NY-ESO1) plasmid (GenScript industrial grade endotoxin free maxiprep), and RNP used was variable with 2.5:1 sgRNA3: Cas9 ratio. Order of addition of reagents was as follows: 1) 0.75 μg template, 2) 60 pmol NT or TRAC RNP (preincubated 15 minutes), 3) 1 μL PGA, 4) 15, 30, or 60 pmol TRBC RNP (preincubated 15 minutes separately to make RNP), and 5) 2 million cells per cuvette. Post-electroporation, 80 μL plain X-VIVO was added without pipetting, followed by 20 minutes incubation at 37 C and transfer for a 48-well plate containing 1 mL X-VIVO media with cytokines. Staining conditions 8 days post-activation included TCRa/b-BV421, 5 μL/stain, and PI 1:200 per stain. Table 9 below lists donor information.

TABLE 9

Donor information

| Donor # | Donor ID | Buffy cell count | CD8 counts post purification (3/4 buffy) | Stimulate how many | Day 2 counts |
|---|---|---|---|---|---|
| 1 | R42584 | 2.9 billion | 192 million | 120 million | 73 million |
| 2 | R42587 | 3 billion | 131 million | 120 million | 98 million |
| 3 | R42580 | 3.8 billion | 258 million | 120 million | 103 million |

Example 26. Different Homology Arm Lengths

Plating was performed using X-VIVO without gentamicin, 25 ng/ml IL-7, 50 ng/ml IL-15, b-Me, L-Cys, and 1:100 TRANSACT™. Electroporation was performed at 43 hours post-activation in P3 buffer, code EH115. Template used was variable amounts of double-stranded PCR product used to achieve the same number of DNA molecules ($3.34 \times 10^{11}$) across samples. RNP used was 60 pmol with 2.5:1 sgRNA3: Cas9 ratio. Order of addition of reagents was as follows: 1)

RNP (pre-incubated 15 minutes), 2) template, 3) 0.5 μL PGA per sample, and 4) one million cells per cuvette. Post-electroporation, 80 μL plain X-VIVO was added without pipetting, followed by 20 minutes incubation at 37 C and transfer for a 48-well plate containing 1 mL X-VIVO media with cytokines. Staining conditions 7 days post-activation included TCRa/b-BV421, 5 μL/stain, and PI 1:200 per stain. Results are shown in FIGS. 104A-105H.

Example 27. Titration of TRBC Targeting Guide RNA and Different Donor DNA Formats A donor DNA encoding a first 2A peptide, a mNeon fluorescent protein, a second 2A peptide and a TCRa VJ domain was used. T cells were activated in Prime media with TRANSACT™ (1:100)+25 ng/ml IL-7 and 50 ng/mL IL-15. TRAC3 and TRBC22 RNPs were generated by mixing TRAC3 or TRBC22 sgRNAs and Cas9 at a 3:1 sgRNA:Cas9 molar ratio and incubating at room temperature for 15 minutes. 2 μL of 100 mg/mL PGA was used per electroporation reaction. A master mix of PGA, TRAC3 RNP, TRBC22 RNP, and donor template was generated for each reaction. Different amounts of the TRAC3 RNP (60 or 30 μmol) and/or TRBC22 RNP (60, 30, 20, or 10 μmol) were used to determine the effect of TRBC22 RNP on knock-in efficiency. The appropriate volume of mastermix (varies depending on the pmol of TRAC3 and/or TRBC22 RNPs used) was added per well, followed by the addition of 2×10⁶ cells per reaction.

Electroporation conditions were all at 48-hours post-activation in Lonza P3 buffer with code EW113. For sequential electroporations: (1) TRAC3 RNP and the donor template (PUC57 vector) were electroporated first (following 48 hours of T cell activation) using code EW113 and (2) TRBC22 RNP was electroporated 24 hours electroporation 24 hours after first electroporation using code EW113 or EO100. RNP conditions used are as follows: TRAC3 RNP only 60 or 30 μmol, TRAC3 RNP/TRBC22 RNP in the following combinations: 60 pmol/30 pmol 60 pmol/20 μmol, 60 pmol/10 μmol, 30 pmol/30 μmol, or 30 pmol/10 pmol. Following each electroporation, cells were incubated at 37 degrees Celsius for 15 minutes (in only P3 buffer) activation Results are shown in FIGS. 111-123. FIG. 111A shows the percentage of Neon-positive TRAC+/−TRBC samples on Day 8 for (from left to right): 60 pmol TRAC3 only, 30 pmol TRAC3 plus 30 pmol TRBC21, and 30 pmol TRAC3 plus 30 pmol TRBC22. FIG. 111B shows the percentage of Neon-positive samples on Day 8 for (from left to right): 60 pmol TRAC3, 60 pmol TRAC3 plus 30 pmol TRBC22, 60 pmol TRAC3 plus 20 pmol TRBC22, 30 pmol TRAC3, 30 pmol TRAC3 plus 30 pmol TRBC22, and 30 pmol TRAC3 plus 10 pmol TRBC22. FIG. 112 shows the percentage (FIG. 108A) and numbers (FIG. 108B) of Neon-positive samples for (from left to right) 60 pmol TRAC3 RNP only, 30 pmol TRAC3 RNP only, a 60 pmol/30 pmol mix of TRAC3 RNP/TRBC22 RNP, a 60 pmol/20 pmol mix of TRAC3 RNP/TRBC22 RNP, a 60 pmol/10 pmol mix of TRAC3 RNP/TRBC22 RNP, a 30 pmol/30 pmol mix of TRAC3 RNP/TRBC22 RNP, and a 30 pmol/10 pmol mix of TRAC3 RNP/TRBC22 RNP. Tests of sequential electroporations were performed by first electroporating TRAC3 RNP and the donor template (PUC57 vector) using pulse code EW113, followed by electroporation of the TRBC22 RNP 24 hours later using pulse code EW113 or EO100. The data are shown in FIGS. 109A-109C. FIG. 109A shows the percentage (or frequency) of Neon-positive samples. FIG. 109B shows the number of Neon-positive samples. FIG. 109C shows the frequency of TCRab+Neon-negative cells. Following the sequential electroporation, cells were cultured in 24-well (24 w) or 48-well (48 w) plates.

Example 28. Different Donor DNA Formats

T cells were activated using Prime media with TRANSACT™ (1:100)+25 ng/ML IL-7 and 50 ng/ml IL-15. TRAC3 and TRBC22 RNPs were generated by mixing TRAC3 sgRNAs (IDT GMP-grade) and Cas9 at a 3:1 sgRNA: Cas9 molar ratio and incubating at room temperature for 15 minutes. 2 μL of 100 mg/mL PGA was used per electroporation reaction. A master mix of PGA, TRAC3 RNP, and donor template was generated for each reaction. Order of addition was as follows: 1) RNP (preincubated 15 min at RT); 2) Template; 3) PGA (1 μL of 100 μg/μL stock); 4) Cells (1.5 million per cuvette). Different template formats were tested: PUC57 plasmid, nanoplasmid, and minicircle. Template amounts were normalized to yield similar numbers of molecules for comparison. Electroporation conditions were all at 48-hours post-activation in Lonza P3 buffer with code EW113. Post-electroporation, samples were left for 15 min at 37 C (in P3 buffer only or with the addition of 75 μL plain prewarmed Prime-XV without pipetting), and following this incubation, cells were transferred to 24- or 48-well plates containing Prime-XV media with cytokines.

Figure 11A:
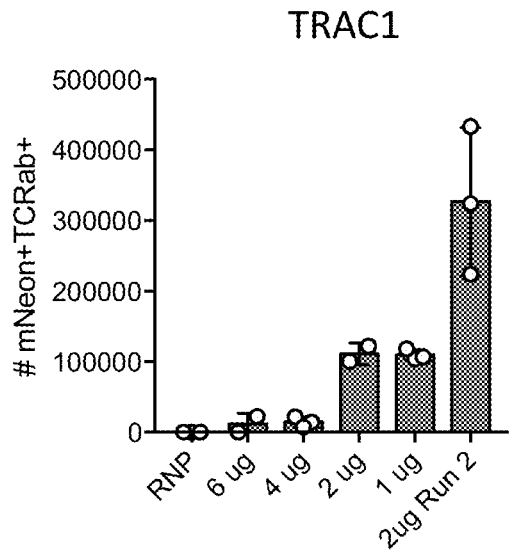
FIGS. 11A-11D are bar graphs showing recovery of knock-in positive mNeon+TCRab+ T cells depending on amount of template used.
Figure 11B:
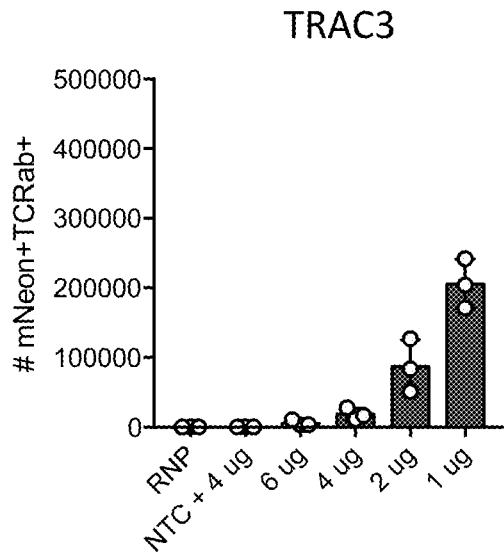
Figure 11C:
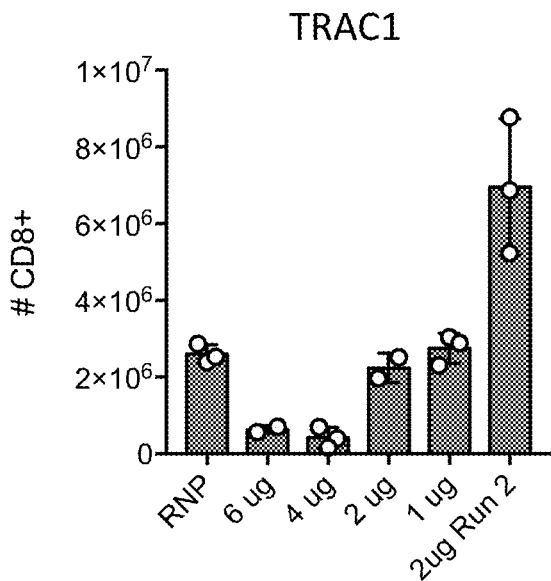
Figure 11D:
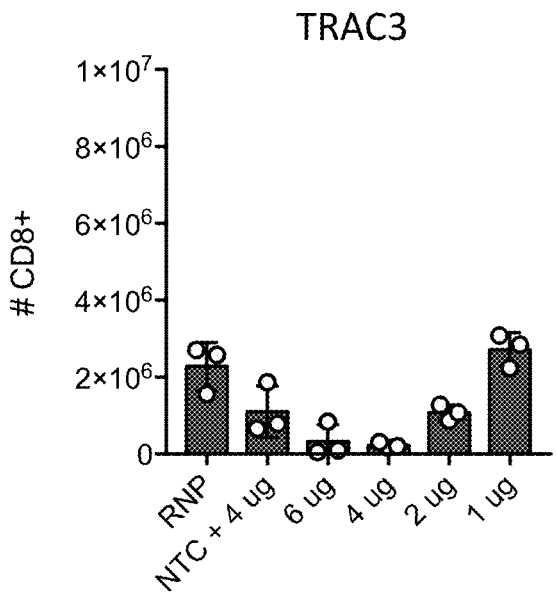
Figure 12A:
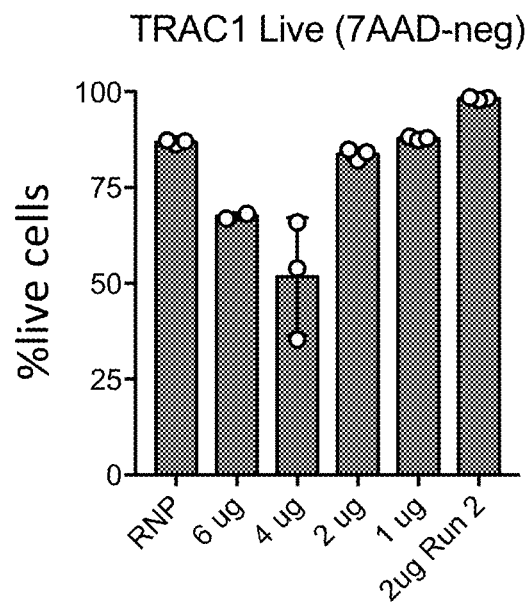
FIGS. 12A and 12B are bar graphs showing cell viability (percentage live cells) following electroporation with various amounts of TRAC1-mNeon (FIG. 14A) or TRAC3-mNeon (FIG. 14B) templates. Cell viability was assessed by absence of 7AAD stain.
Figure 12B:
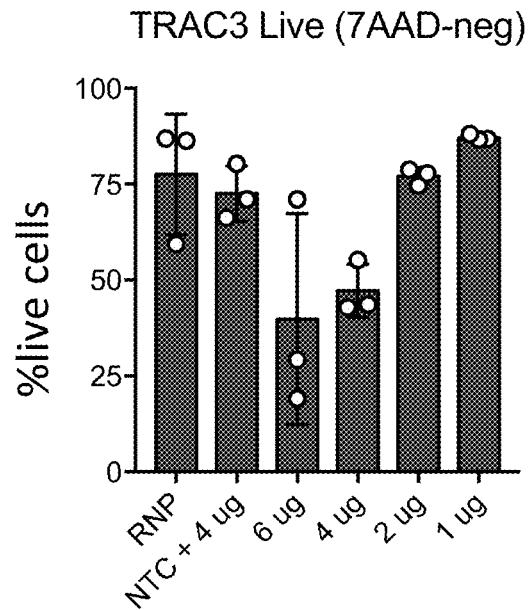
Figure 13:
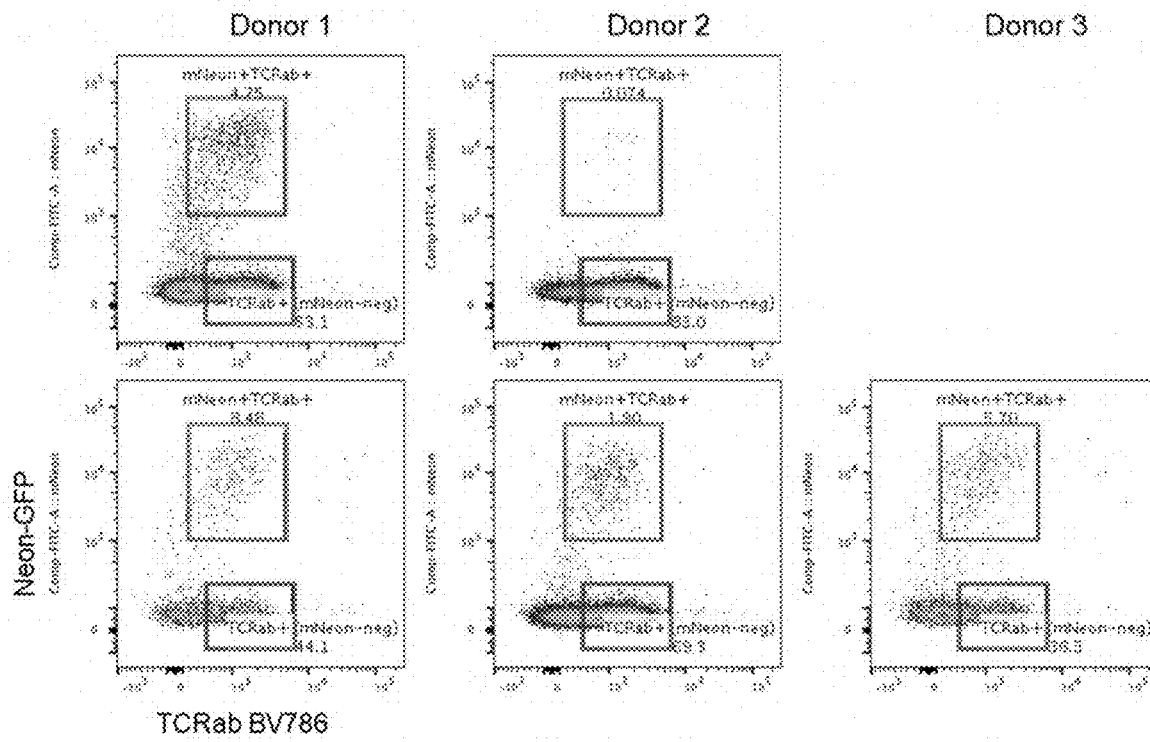
FIG. 13 is flow cytometry analysis illustrating knock-in of TRAC1-mNeon (top row) and TRAC3-mNeon (bottom row) templates. For electroporation 6 µg of template was used. The green (top) box shows detection of knock-in cells and the red (lower) box shows detection of residual TCRab-expressing cells.
Figure 14:
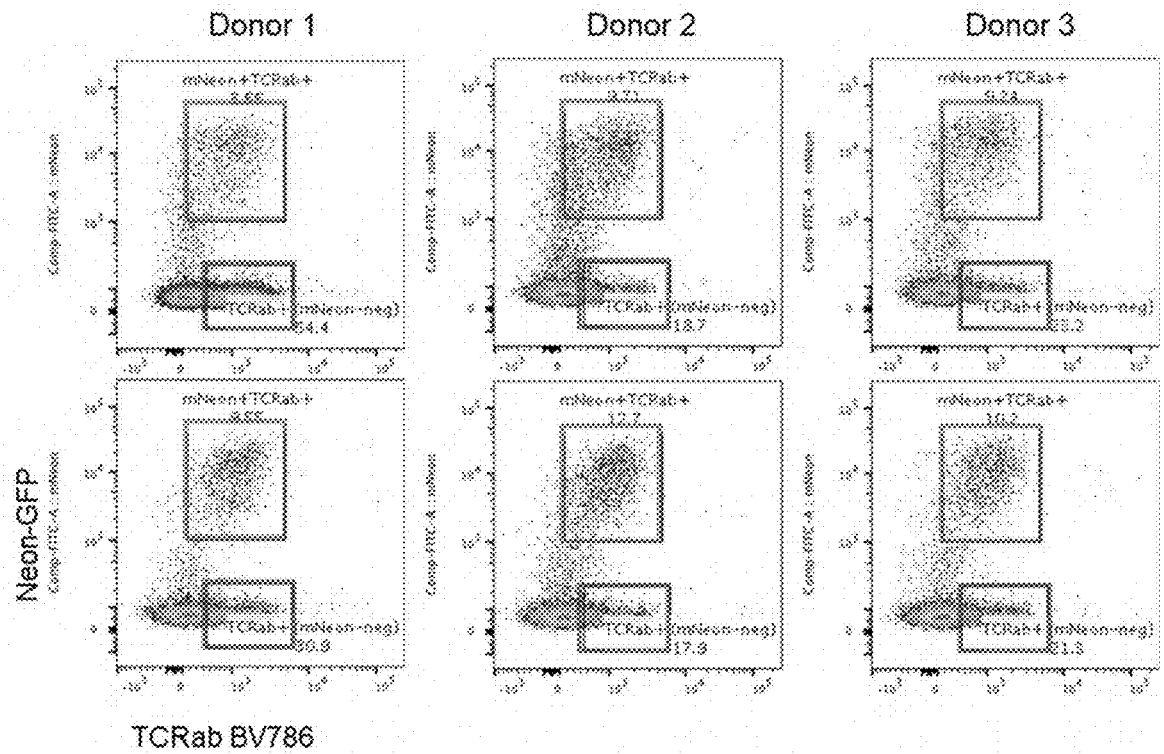
FIG. 14 are flow cytometry dot-plots illustrating knock-in of TRAC1-mNeon (top row) and TRAC3-mNeon (bottom row) templates. For electroporation, 4 µg of each template was used. The green (top) box shows detection of knock-in cells and the red (lower) box shows detection of residual TCRab-expressing cells.
Figure 15:
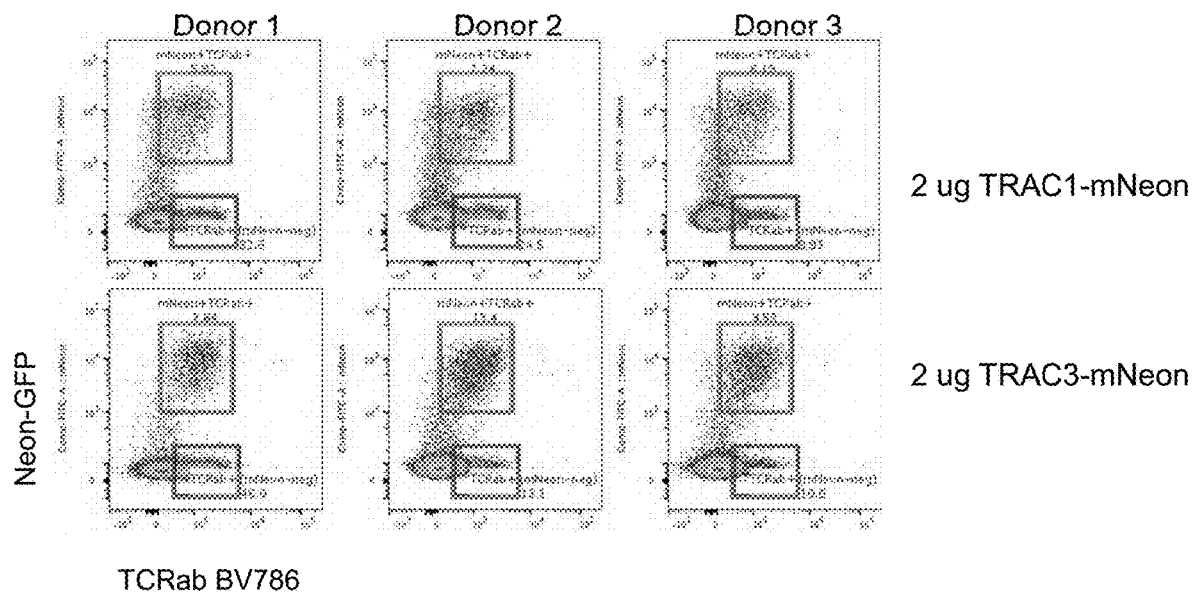
FIG. 15 are flow cytometry dot-plots illustrating knock-in of TRAC1-mNeon (top row) and TRAC3-mNeon (bottom row) templates; 2 µg of each template was used for electroporation. The green (top) box shows detection of knock-in cells and the red (lower) box shows detection of residual TCRab-expressing cells.
Figure 16:
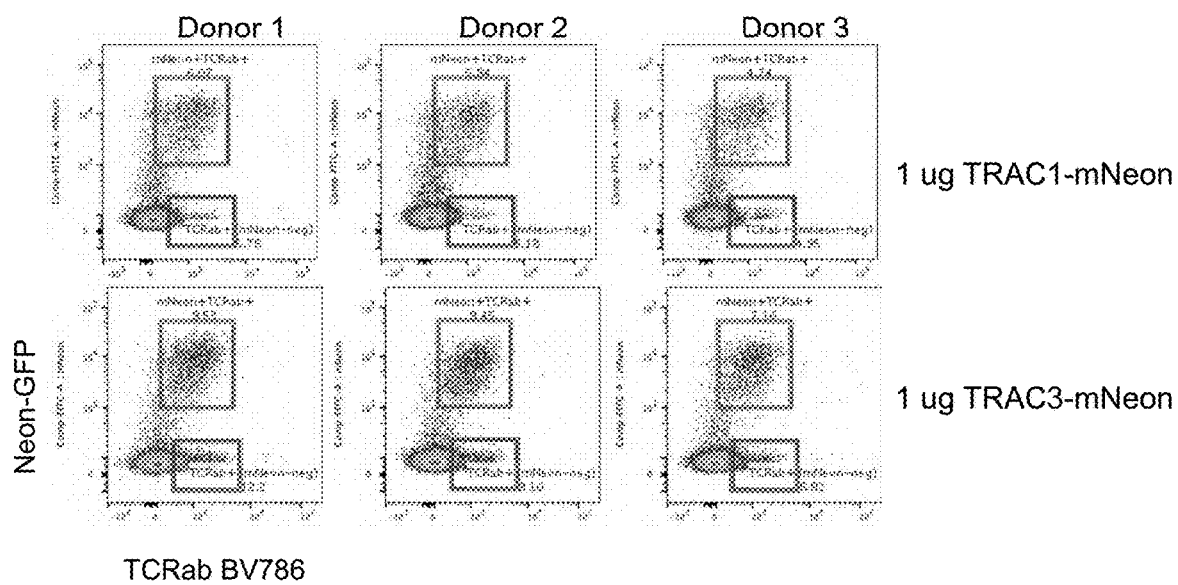
FIG. 16 are flow cytometry dot-plots illustrating knock-in of TRAC1-mNeon (top row) and TRAC3-mNeon (bottom row) template; 1 µg of each template was used for electroporation. The green (top) box shows detection of knock-in cells and the red (lower) box shows detection of residual TCRab-expressing cells.
Figure 17:
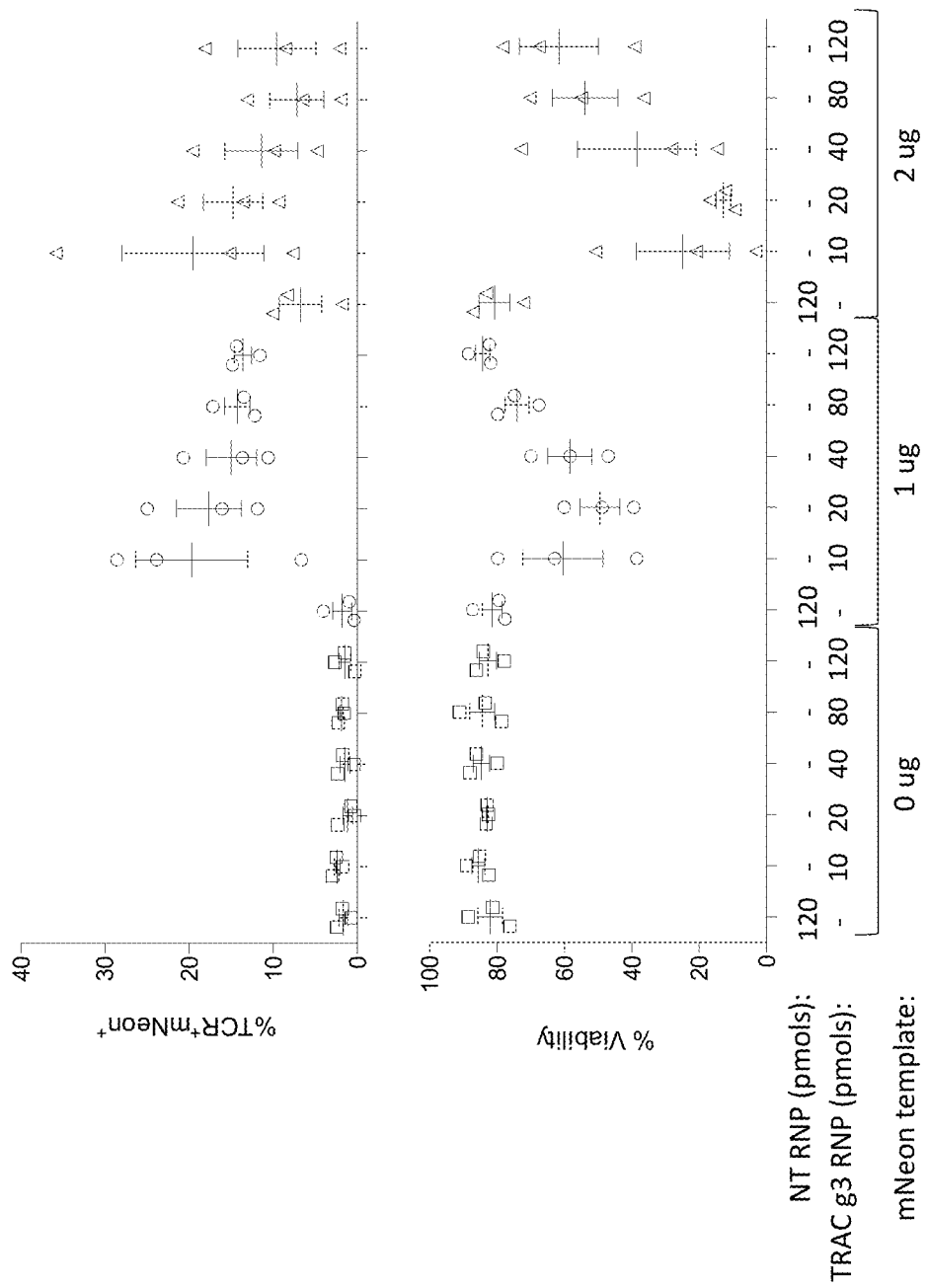
FIG. 17 are graphs illustrating knock-in of TRAC3-mNeon template in T cells (top) and cell viability after electroporation (bottom), depending on amounts of RNP used for electroporation. T cells were electroporated with varying amounts of TRAC3 RNP and fixed amounts of TRAC3-mNeon template. Groups of cells electroporated with no template RNP (NT RNP) served as negative controls.
Figure 18:
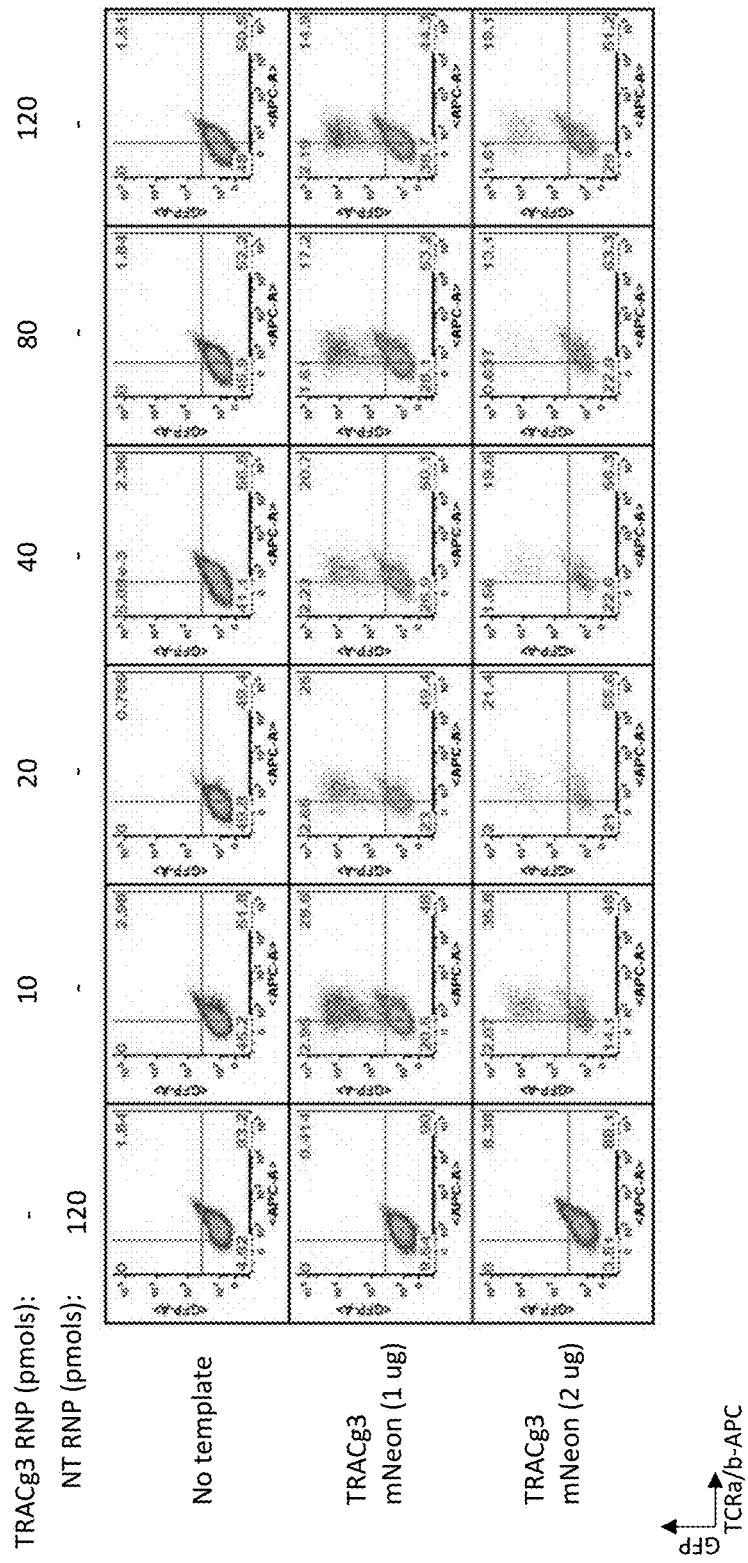
FIG. 18 are flow cytometry dot-plots showing knock-in of TRAC3-mNeon template in T cells, depending on amounts of TRAC3-mNeon template and TRAC3 RNP used for electroporation, for a sample from a first donor.
Figure 19:
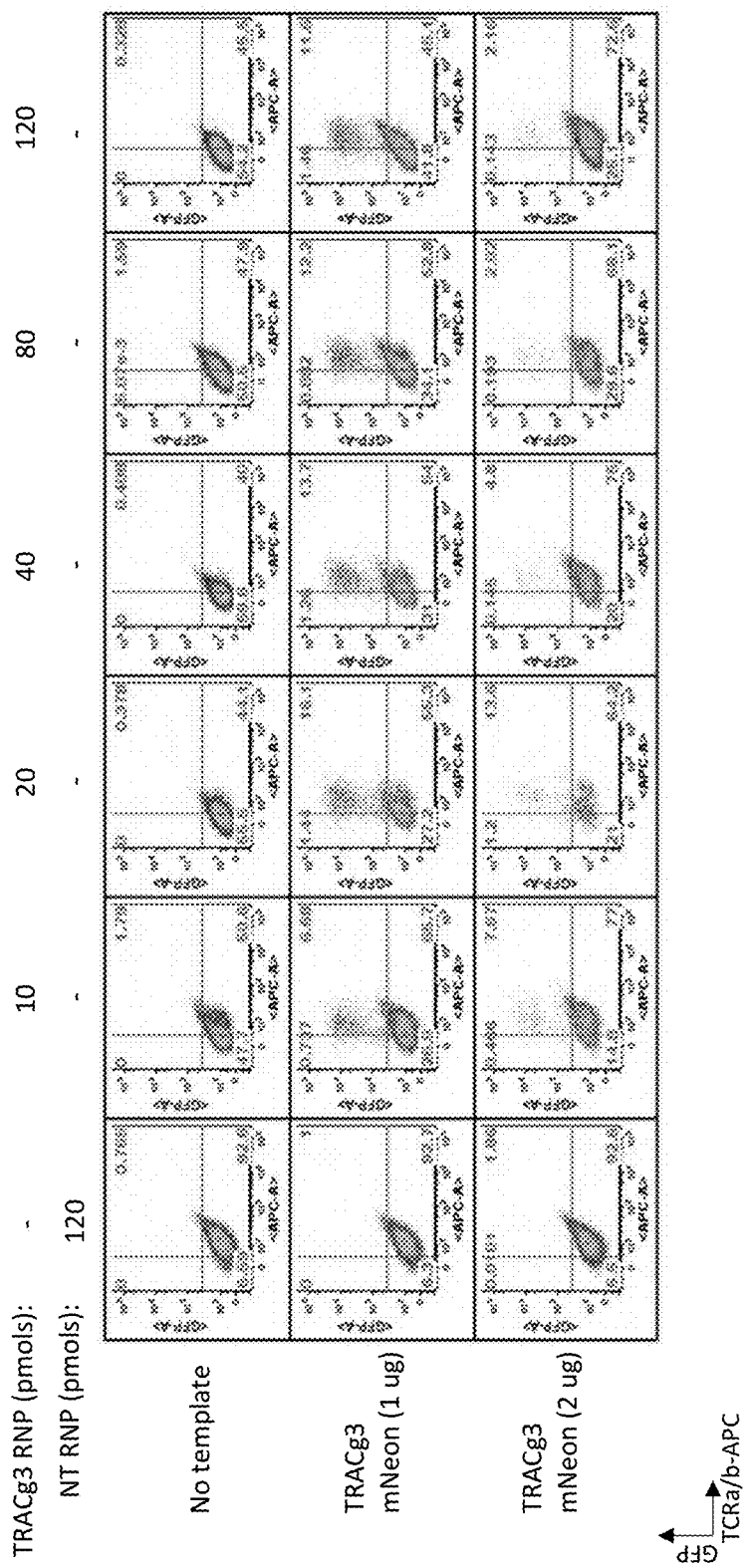
FIG. 19 are flow cytometry dot-plots showing knock-in of TRAC3-mNeon template in T cells, depending on amounts of TRAC3-mNeon template and TRAC3 RNP used for electroporation, for a sample from a second donor.
Figure 20:
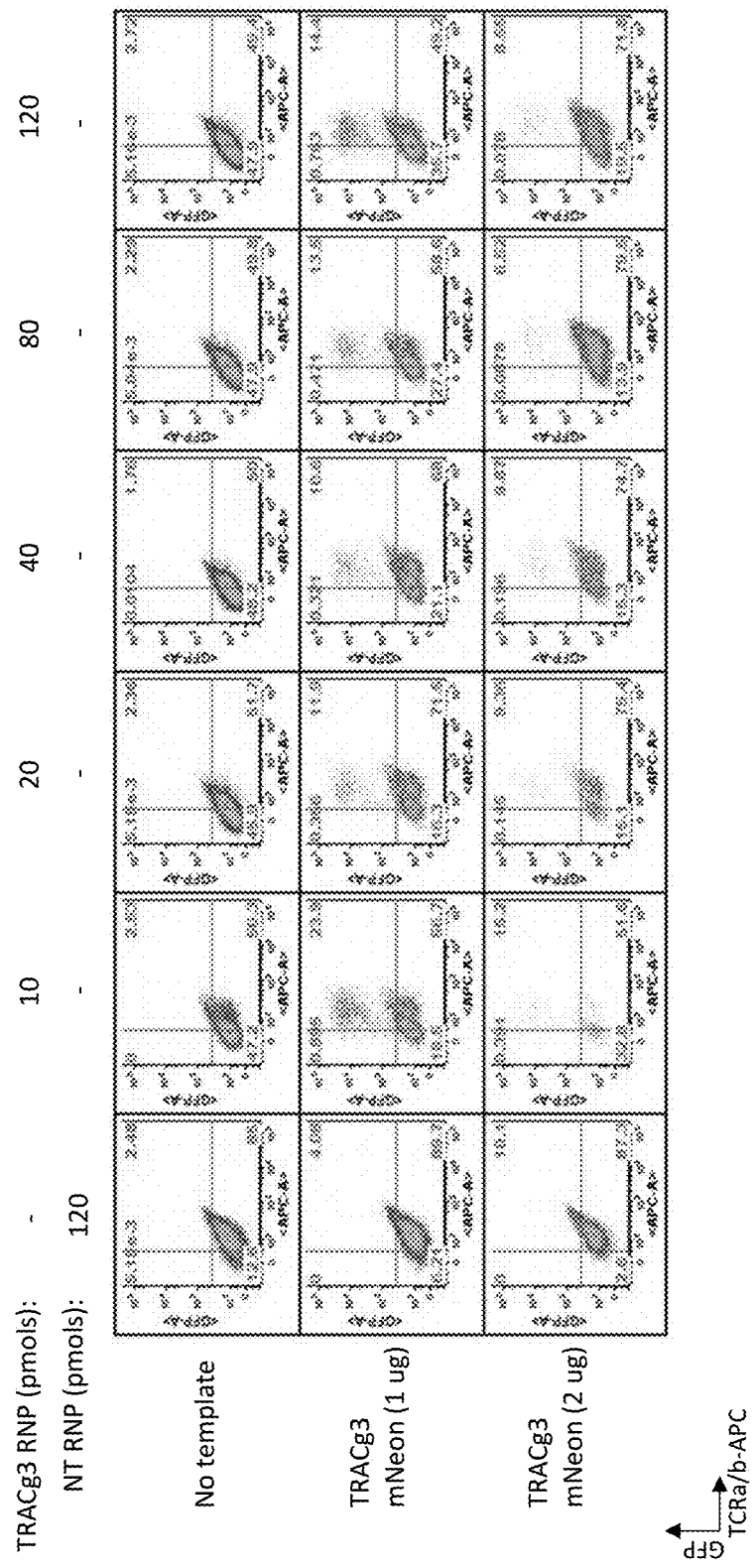
FIG. 20 are flow cytometry dot-plots showing knock-in of TRAC3-mNeon template in T cells, depending on amounts of TRAC3-mNeon template and TRAC3 RNP used for electroporation, for a sample from a third donor.
Figure 21:
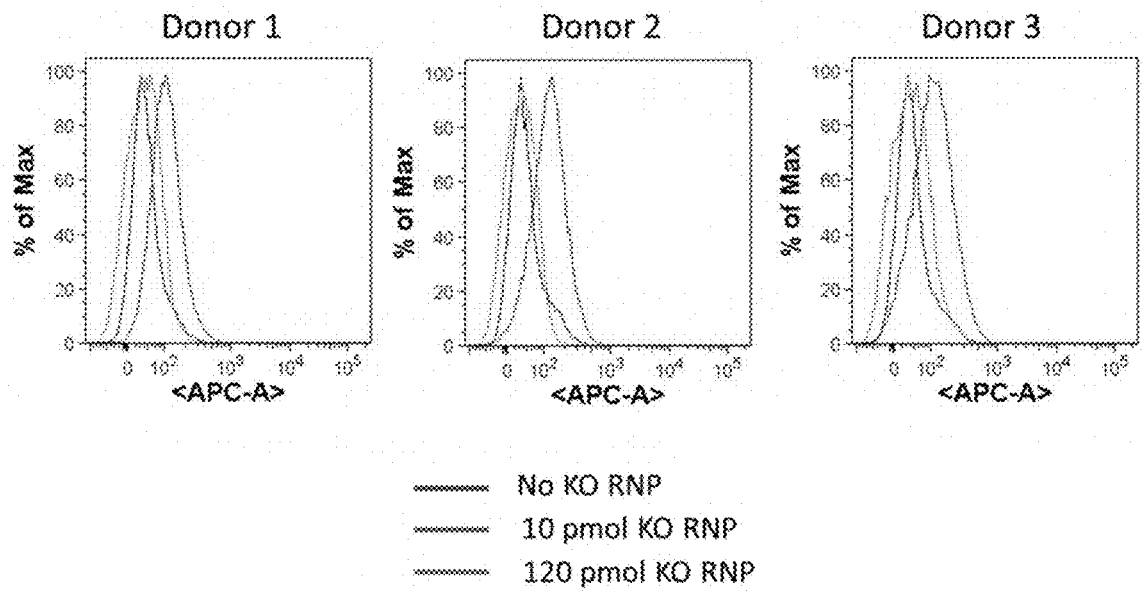
FIG. 21 show flow cytometry histograms illustrating TCRab knock-out using various amounts of TRAC3 RNP (KO RNP).

FIGS. 110C and 11D shows the frequency (FIG. 110C) and number (FIG. 110D) of Neon-positive cells. Experiments were conducted with TRAC3 RNP only. Templates used were the PUC57 vector (GS), nanoplasmid (nano), and minicircle (mini).

Data for pUC57 versus nanoplasmid versus minicircle DNA on day 6 is shown in FIGS. 114A-114B. FIG. 114A shows the percentage (top graph) and absolute number (bottom graph) of mNeon+TCR+ samples. FIG. 114B shows the quantities of DNA used in the experiment. Data for pUC57 versus nanoplasmid versus minicircle DNA on day 8 is shown in FIGS. 115A-115B. FIG. 115A shows the percentage (top graph) and absolute number (bottom graph) of mNeon+TCR+ samples. FIG. 115B shows the quantities of DNA used in the experiment. FIG. 116A shows percentage of cell viability on day 6, while FIG. 116B shows percentage of cell viability on day 8. The change in knock-in cell numbers over time from day 6 to day 8 is shown in FIG. 117.

Example 29. pUC57 Plasmid, Minicircle (Mini), Nanoplasmid (Nano), and PCR Templates A donor DNA encoding a first 2A peptide, a mNeon fluorescent protein, a second 2A peptide and a TCRa VJ domain was used.

Data for pUC57 versus nanoplasmid versus minicircle DNA on day 6 is shown in FIGS. 120A-120B. FIG. 120A shows the percentage (top graph) and the absolute numbers (bottom graph) of mNeon+TCR+ samples on day 6. FIG. 120B shows the quantities of DNA used in this experiment. Data for pUC57 versus nanoplasmid versus minicircle DNA on day 8 is shown in FIGS. 121A-121B. FIG. 125A shows the percentage (top graph) and the absolute numbers (bottom graph) of mNeon+TCR+ samples on day 8. FIG. 121B shows the quantities of DNA used in this experiment. Day 8 sample plots for pUC57, nanoplasmid, minicircle, and PCR samples are shown in FIG. 122. Cell viability with equivalent molecules of each template are shown in FIG. 123, with day 6 data shown in the top graph and day 8 data shown in the bottom graph. FIG. 124 shows the change in knock-in cell numbers over time from day 6 to day 8.

Example 30. TCR-Beta Targeting Guide RNAs, and Plasmid Versus Nanoplasmid Templates A donor DNA encoding a first 2A peptide, a mNeon fluorescent protein, a second 2A peptide and a TCRa VJ domain was used.

T cell activation conditions: Prime, TRANSACT™ (1:100)+25 ng/mL IL-7 and 50 ng/mL IL-15. RNPs were generated by mixing sgRNA and Cas9 at a 3:1 sgRNA: Cas9 ratio, and incubating at room temperature for 15 minutes. TRAC3, TRBC22, and TRBC19 sgRNAs were resuspended at 200 µM; A mastermix for electroporations was generated by mixing the following: (1) 2 µL of 100 mg/mL PGA per reaction, (2) TRBC22 or TRBC19 RNP, (3) TRAC3 RNP, and (4) donor template. The exact amounts of reagents varied based on the pmol of RNP and amount of donor template used per electroporation condition. The following RNP conditions were used: TRAC3 only 60 or 30 µmol, TRAC RNP/TRBC RNP 60 pmol/30 µmol, 60 pmol/10 µmol, 30 pmol/30 pmol (TRBC22 or TRBC19 RNPs). For titration of donor templates, the following amounts of PUC57 (GenScript) and nanoplasmid templates were used: PUC57 (GenScript): 8, 6, 4, and 2 µg, and nanoplasmid: 10, 8, 6, 4, and 2 µg. An equal number of molecules of nanoplasmid was used for electroporations, using the PUC57 (GenScript) µg amount as a reference. Cells were electroporated at 48-hours post-activation in Lonza P3 buffer with code EW113. Following electroporation, cells were incubated at 37 C for 15 minutes (in only P3 buffer) before being transferred to culture plates containing pre-warmed PRIME media and cytokines.

FIG. 125 (left) shows the percentage of Neon-positive samples while (right) shows the number of Neon-positive samples, for (from left to right): 60 pmol TRAC3 RNP only with PUC57 template (GenScript), 60 pmol TRBC22 RNP and 30 pmol TRBC19 RNP with PUC57 template (GenScript), 60 pmol TRBC22 RNP and 10 pmol TRBC19 RNP with PUC57 template (GenScript), 30 pmol TRAC3 RNP only with PUC57 template (GenScript), 30 pmol TRBC22 RNP and 30 pmol TRBC19 RNP with PUC57 template (GenScript), 30 pmol TRAC3 RNP only with nanoplasmid, and 30 pmol TRAC3 RNP with 30 pmol TRBC22 RNP and 30 pmol TRBC19 RNP with nanoplasmid.

FIG. 126A shows the day 5 knock-in efficiency (left graph) and day 7 knock-in efficiency (right graph) for GenScript versus nanoplasmid templates. Samples were electroporated with 30 pmol TRAC3 RNP and 30 pmol TRBC22 RNP. FIG. 126B shows the knock-in cell numbers for day 5 and day 7.

Day 7 flow cytometry data of TRBC RNP titration, 60 µmol, is shown in FIG. 127. Day 7 flow cytometry data of TRBC RNP titration, 30 µmol, is shown in FIG. 128. Day 7 flow cytometry data for the PUC57 (GenScript) plasmid titration is shown in FIG. 129. Day 7 flow cytometry data for nanoplasmid titration is shown in FIG. 130.

Example 31. TCR Knock-In with pUC57 and Nanoplasmid

T cell activation conditions: Prime, TRANSACT™ (1:100)+25 ng/ml IL-7 and 50 ng/ml IL-15. RNP+/−PGA preparation included: 15 minute room temperature incubation for RNP generation (3:1 sgRNA: Cas9) with all sgRNAs at 200 µM and 30 pmol each of TRAC3 RNP and TRBC22 RNP; and 2 µL of 100 mg/mL PGA. Templates used were PUC57 (Neon, WT1 TCRs) or nanoplasmid (Neon). We used equivalent numbers of nanoplasmid molecules with 4 µg of PUC57 as a reference. Following electroporation, incubation at 37 C for 15 minutes (in only P3 buffer). Electroporation conditions (all at 48-hours post-activation in Lonza P3 buffer with code EW113) included: test of PGA requirement (+/−PGA for the following templates: Neon PUC57, Neon nanoplasmid, and WT1_5213 PUC57); test of order of template addition (template added first with RNP/PGA mix, or template added last); and test of native (non-codon optimized) versus codon optimized WT1 TCRs (WT1_Ref and WT1_64-9).

The results of Neon knock-in are shown in FIGS. 131A-131B. 4 µg of PUC57 plasmid, or the equivalent number of molecules of the nanoplasmid, were used. FIG. 131A shows percentage of Neon-positive samples on day 7, while FIG. 131B shows the number of Neon-positive samples.

FIG. 132A shows the percentage of WT1+ (of total CD8+) samples on day 7. FIG. 132B shows the percentage of CD3+ samples among CD8+ cells on day 7. FIG. 132C shows the percentage of WT1+among total CD3+CD8+ cells on day 7. For "No PGA" conditions, the template was added last. 4 µg of PUC57 plasmid was used.

FIG. 133 shows the numbers of WT1 TCR+ cells on day 7. Conditions graphed are, from left to right, template first, template last, and no PGA. For each condition, data is given for, from left to right, WT1_5213, WT1_Ref_Native, WT1_Ref_CodOpt, WT1_64_9_Native, and WT1_64_9_CodOpt.

FIG. 134 shows day 7 flow cytometry data for Neon template knock-ins. FIG. 135 shows day 7 flow cytometry data for WT1_5213. FIG. 136 shows day 7 flow cytometry data for WT1_Ref (all with PGA). FIG. 137 shows day 7 flow cytometry data for WT1 64_9 (all with PGA).

TABLE 10

TRAC sgRNA

| | Sequence | PAM | Exon | KO efficiency | targeted locus |
|---|---|---|---|---|---|
| TRAC_1 (SEQ ID NO: 7) | AGAGTCTCTCAGCTGGTACA | CGG | 1 | 98.8 | chr14:22547530-22547549 |
| TRAC_2 (SEQ ID NO: 8) | TGGATTTAGAGTCTCTCAGC | TGG | 1 | 77.7 | chr14:22547537-22547556 |
| TRAC_3 (SEQ ID NO: 9) | ACAAAACTGTGCTAGACATG | AGG | 1 | 90.3 | chr14:22547641-22547660 |

TABLE 10-continued

TRAC sgRNA

| | Sequence | PAM | Exon | KO efficiency | targeted locus |
|---|---|---|---|---|---|
| TRAC_4 (SEQ ID NO: 10) | CTTCAAGAGCAACAGTGCTG | TGG | 1 | 93.2 | chr14:22547672-22547691 |
| TRAC_5 (SEQ ID NO: 11) | TAAACCCGGCCACTTTCAGG | AGG | 3 | 98 | chr14:22550609-22550628 |
| TRAC_6 (SEQ ID NO: 12) | TTAATCTGCTCATGACGCTG | CGG | 3 | 71.9 | chr14:22550626-22550645 |
| TRAC_7 (SEQ ID NO: 13) | GCTGGTACACGGCAGGGTCA | GGG | 1 | 92.5 | chr14:22547519-22547538 |
| TRAC_8 (SEQ ID NO: 14) | CTCTCAGCTGGTACACGGCA | GGG | 1 | 50.6 | chr14:22547525-22547544 |
| TRAC_9 (SEQ ID NO: 15) | TAGGCAGACAGACTTGTCAC | TGG | 1 | 84 | chr14:22547557-22547576 |
| TRAC_10 (SEQ ID NO: 16) | AAGTTCCTGTGATGTCAAGC | TGG | 2 | 80.2 | chr14:22549639-22549658 |
| TRAC_11 (SEQ ID NO: 17) | GTCGAGAAAAGCTTTGAAAC | AGG | 2 | 50.7 | chr14:22549661-22549680 |
| TRAC_12 (SEQ ID NO: 18) | TTCGGAACCCAATCACTGAC | AGG | 3 | 88.935 | chr14:22550582-22550601 |
| TRAC_13 (SEQ ID NO: 19) | CCGAATCCTCCTCCTGAAAG | TGG | 3 | 9.6 | chr14:22550597-22550616 |
| TRAC_14 (SEQ ID NO: 20) | TCCTCCTCCTGAAAGTGGCC | GGG | 3 | 83.915 | chr14:22550602-22550621 |
| TRAC_15 (SEQ ID NO: 21) | CGTCATGAGCAGATTAAACC | CGG | 3 | 91.225 | chr14:22550623-22550642 |
| TRAC_16 (SEQ ID NO: 22) | CTGCGGCTGTGGTCCAGCTG | AGG | 3 | 39.7 | chr14:22550643-22550662 |

TABLE 11

TRBC sgRNA

| | Sequence | PAM | Exon | KO efficiency | targeted locus | Targeted locus |
|---|---|---|---|---|---|---|
| TRBC_1 (SEQ ID NO: 23) | GAAAAACGTGTTCCCACCCA | AGG | 1 | 48.3 | chr7:142801048-142801067 | |
| TRBC_2 (SEQ ID NO: 24) | CAAACACAGCGACCTTGGGT | GGG | 1 | 79.5 | chr7:142801063-142801082 | |
| TRBC_3 (SEQ ID NO: 25) | CCACACCCAAAAGGCCACAC | TGG | 1 | 93.3 | chr7:142791758-142791777 | chr7:142801105-142801124 |
| TRBC_4 (SEQ ID NO: 26) | TGTGGCCAGGCACACCAGTG | TGG | 1 | 92 | chr7:142801122-142801141 | |
| TRBC_5 (SEQ ID NO: 27) | GTGGTCGGGGTAGAAGCCTG | TGG | 1 | 92.4 | chr7:142801140-142801159 | |
| TRBC_6 (SEQ ID NO: 28) | AGGCTTCTACCCCGACCACG | TGG | 1 | 70.3 | chr7:142801141-142801160 | |
| TRBC_7 (SEQ ID NO: 29) | CCCACCAGCTCAGCTCCACG | TGG | 1 | 97.9 | chr7:142791812-142791831 | chr7:142801159-142801178 |
| TRBC_8 (SEQ ID NO: 30) | CCACGTGGAGCTGAGCTGGT | GGG | 1 | 98.1 | chr7:142791809-142791828 | chr7:142801156-142801175 |

TABLE 11-continued

TRBC sgRNA

| | Sequence | PAM | Exon | KO efficiency | targeted locus | Targeted locus |
|---|---|---|---|---|---|---|
| TRBC_9 (SEQ ID NO: 31) | GAGCTGGTGGGTGAATGGGA | AGG | 1 | 95.9 | chr7:142791821-142791840 | chr7:142801168-142801187 |
| TRCB_10 (SEQ ID NO: 32) | CTGGTGGGTGAATGGGAAGG | AGG | 1 | 94.7 | chr7:142791824-142791843 | chr7:142801171-142801190 |
| TRBC_11 (SEQ ID NO: 33) | AATGGGAAGGAGGTGCACAG | TGG | 1 | 94.4 | chr7:142791834-142791853 | chr7:142801181-142801200 |
| TRBC_12 (SEQ ID NO: 34) | TGGGAAGGAGGTGCACAGTG | GGG | 1 | 94.4 | chr7:142791836-142791855 | chr7:142801183-142801202 |
| TRBC_13 (SEQ ID NO: 35) | TATCTGGAGTCATTGAGGGC | GGG | 1 | 90.7 | chr7:142791894-142791913 | chr7:142801241-142801260 |
| TRBC_14 (SEQ ID NO: 36) | GTATCTGGAGTCATTGAGGG | CGG | 1 | 75.2 | chr7:142791895-142791914 | chr7:142801242-142801261 |
| TRBC_15 (SEQ ID NO: 37) | GGCAGTATCTGGAGTCATTG | AGG | 1 | 60.8 | chr7:142791899-142791918 | chr7:142801246-142801265 |
| TRBC_16 (SEQ ID NO: 38) | AGGTGGCCGAGACCCTCAGG | CGG | 1 | 94 | chr7:142791929-142791948 | chr7:142801276-142801295 |
| TRBC_17 (SEQ ID NO: 39) | GACAGCGGAAGTGGTTGCGG | GGG | 1 | 89.6 | chr7:142791962-142791981 | chr7:142801309-142801328 |
| TRBC_18 (SEQ ID NO: 40) | CGTAGAACTGGACTTGACAG | CGG | 1 | 87.4 | chr7:142791977-142791996 | chr7:142801324-142801343 |
| TRBC_19 (SEQ ID NO: 41) | GGCTCTCGGAGAATGACGAG | TGG | 1 | 91 | chr7:142791997-142792016 | chr7:142801344-142801363 |
| TRBC_20 (SEQ ID NO: 42) | GGAGAATGACGAGTGGACCC | AGG | 1 | 95.8 | chr7:142792004-142792023 | chr7:142801351-142801370 |
| TRBC_21 (SEQ ID NO: 43) | CACCCAGATCGTCAGCGCCG | AGG | 1 | 95.6 | chr7:142792043-142792062 | chr7:142801390-142801409 |
| TRBC_22 (SEQ ID NO: 44) | TGGCTCAAACACAGCGACCT | TGG | 1 | 97.6 | chr7:142791721-142791740 | chr7:142801068-142801087 |
| TRBC_23 (SEQ ID NO: 45) | AGAGATCTCCCACACCCAAA | AGG | 1 | 91.7 | chr7:142791749-142791768 | chr7:142801096-142801115 |
| TRBC_24 (SEQ ID NO: 46) | ACCACGTGGAGCTGAGCTGG | TGG | 1 | 89.5 | chr7:142791808-142791827 | chr7:142801155-142801174 |
| TRBC_25 (SEQ ID NO: 47) | TGACAGCGGAAGTGGTTGCG | GGG | 1 | 76.5 | chr7:142791963-142791982 | chr7:142801310-142801329 |
| TRBC_26 (SEQ ID NO: 48) | ATCGTCAGCGCCGAGGCCTG | GGG | 1 | 95.7 | chr7:142792050-142792069 | chr7:142801397-142801416 |

TABLE 12

Neoantigens

| Mutation | Indications with highest prevalence |
|---|---|
| KRAS-p.G12D | Pancreatic Adenocarcinoma |
| KRAS-p.G12D | Colorectal Adenocarcinoma |
| KRAS-p.G12D | Lung Adenocarcinoma |
| KRAS-p.G12V | Pancreatic Adenocarcinoma |
| KRAS-p.G12V | Colorectal Adenocarcinoma |
| KRAS-p.G12V | Lung Adenocarcinoma |
| KRAS-p.G12C | Lung Adenocarcinoma |
| KRAS-p.G12C | Colorectal Adenocarcinoma |
| KRAS-p.G12R | Pancreatic Adenocarcinoma |
| IDH1-p.R132H | Low-Grade Glioma |
| BRAF-p.V600E | Papillary Thyroid Cancer |
| BRAF-p.V600E | Cutaneous Melanoma |
| BRAF-p.V600E | Colorectal Adenocarcinoma |
| BRAF-p.V600M | Cutaneous Melanoma |
| GTF2I-p.L424H | Thymoma |
| GNAQ-p.Q209P | Uveal Melanoma |
| GNAQ-p.Q209L | Uveal Melanoma |
| GNA11-p.Q209L | Uveal Melanoma |
| NRAS-p.Q61R | Cutaneous Melanoma |
| NRAS-p.Q61K | Cutaneous Melanoma |
| PTEN-p.R130Q | Uterine Endometrioid Carcinoma |
| PTEN-p.R130G | Uterine Endometrioid Carcinoma |

TABLE 12-continued

Neoantigens

| Mutation | Indications with highest prevalence |
|---|---|
| SF3B1-p.R625H | Uveal Melanoma |
| SF3B1-p.R625C | Uveal Melanoma |
| PIK3CA-p.H1047R | Breast Carcinoma |
| DNMT3A-p.R882H | Acute Myeloid Leukemia |
| PIK3CA-p.E545K | Cervical Squamous Cell Carcinoma |
| PIK3CA-p.E545K | Breast Carcinoma |
| PIK3CA-p.E545K | Bladder Urothelial Carcinoma |
| KRAS-p.G13D | Colorectal Adenocarcinoma |
| TP53-p.R273C | Low-Grade Glioma |
| TP53-p.R273H | Low-Grade Glioma |
| TP53-p.R273H | Colorectal Adenocarcinoma |
| TP53-p.R273L | Low-Grade Glioma |
| TP53-p.R175H | Colorectal Adenocarcinoma |
| TP53-p.R175H | Esophageal Adenocarcinoma |
| TP53-p.R175H | Breast Carcinoma |
| FGFR3-p.S249C | Bladder Urothelial Carcinoma |
| TP53-p.R248Q | Uterine Carcinosarcoma |
| TP53-p.R248Q | Esophageal Adenocarcinoma |
| TP53-p.R248Q | Bladder Urothelial Carcinoma |
| TP53-p.R248Q | Colorectal Adenocarcinoma |
| PIK3CA-p.E542K | Cervical Squamous Cell Carcinoma |
| PIK3CA-p.E542K | Bladder Urothelial Carcinoma |
| PIK3CA-p.E542K | Breast Carcinoma |
| HRAS-p.Q61R | Pheochromocytoma |
| IDH2-p.R140Q | Acute Myeloid Leukemia |
| FLT3-p.D835Y | Acute Myeloid Leukemia |
| EGFR-p.L858R | Lung Adenocarcinoma |
| MYD88-p.L265P | Diffuse Large B-Cell Lymphoma |
| ERBB2-p.S310F | Bladder Urothelial Carcinoma |
| TP53-p.R282W | Colorectal Adenocarcinoma |
| EGFR E746_A750del | Lung Adenocarcinoma |

Example 32. Functional Characterization of TCR Engineered T Cells

This assay determines the potency of TCR T cells by measuring the ability of engineered T cells to induce specific target cell cytolysis as measured by % specific loss of target cells using FACS. On the day of the assay, target cell peptide-pulsing (3-4 hrs) and bystander cell CellTrace staining were set up in the morning. Killing assay was prepared by incubating T cells with previously prepared target/bystander cells. Cell killing was measured using FACS approximately 18 hrs later. Assay diluent was T cells growth media (X-VIVO or PRIME-XV plus IL-7 and IL-15).

Reagent preparation. Peptide stock solution preparation: peptide was diluted to 10 mM in DMSO. CellTrace™ stock solution was prepared following manufacturer's protocol, i.e., reconstituted CellTrace™ solution by adding the appropriate volume (e.g., 20 µL) of DMSO (Component B) to one vial of CellTrace™ reagent (Component A) and mix. Further dilutions were made in DMSO and stored at ≤−20° C. after reconstitution. LIVE/DEAD™ stock solution was prepared following manufacturer's protocol, i.e., LIVE/DEAD™ stock solution was reconstituted immediately prior to use by adding the appropriate volume (e.g., 50 µL) of DMSO (Component B) to one vial of LIVE/DEAD™ reagent (Component A) and mixing.

Assay Procedure. Peptide dilutions were prepared in target cell growth media in a deep-well 96-well plate as shown in Table 13.

TABLE 13

| Tube | Dilution Number | Nominal Concentration of Peptide | Volume of Peptide (µL) | Volume of Assay Diluent (µL) |
|---|---|---|---|---|
| A | stock | 10 mM stock | N/A | N/A |
| B | 1 | 100 µM | 5 of stock | 495 |
| C | 2 | 20 µM | 100 of 1 | 400 |
| D | 3 | 2 µM | 50 of 2 | 450 |
| E | 4 | 200 nM | 50 of 3 | 450 |
| F | 5 | 20 nM | 50 of 4 | 450 |
| G | 6 | 2 nM | 50 of 5 | 450 |
| H | 7 | 200 pM | 50 of 6 | 450 |
| I | 8 | 20 pM | 50 of 7 | 450 |
| J | 9 | 0 | — | 500 |

Preparation of Cells for the Assay: all steps were performed in a biosafety cabinet. Preparation of Target cells: 0.05M target cells per well; 1) cell viability and cell concentration were determined. Cells were centrifuged in conical tube at 300× g for 5 minutes at ambient temperature and supernatant discarded. Cell pellet was re-suspended in target cell growth media in a total volume cell seeding suspension calculated for the assay and 50 µL of cell suspension seeded per well into a round-bottom 96-well plate, overlaid with appropriate peptide dilutions, mixed gently by pipetting up/down and incubated for 3-4 hrs at 37° C.

Preparation of Bystander cells: this format uses 0.05M bystander cells per well; CellTrace™ Far red was used at final concentration of 0.1 nM. Cells were centrifuged at 300×g for 5 minutes at ambient temperature and resuspend in PBS at $1 \times 10^6$/mL density in a 15 or 50 mL conical tube. CellTrace (1 µl of 100 nM working solution in DMSO) was added per mL of cell suspension in PBS. Cells were mixed and incubated for 20 minutes at room temperature, protected from light. Five times the original staining volume of culture medium (containing at least 1% protein) was added to the cells and incubated for 5 minutes. This step removes any free dye remaining in the solution. Cells were pelleted by centrifugation (300×g for 5 minutes at ambient temperature) and resuspended in fresh pre-warmed complete culture medium at $1 \times 10^6$/mL density. Cells were incubated for at least 10 minutes before analysis to allow the CellTrace™ reagent to undergo acetate hydrolysis.

Wash target cells: After 3-4 hrs incubation, cells were washed to remove the free peptide, 2 times with PBS. Cells were resuspended in 50 µL assay diluent, ready to mix with bystander and effector T cells.

Transfer of Bystander Cells to Plate: Bystander cell suspension was resuspended in assay diluent (at $1 \times 10^6$/mL density) by centrifuging at 300× g for 5 minutes, ambient temperature; 50 µL was added into the plate(s) containing 50 µL of the peptide loaded target cells; and mixed by pipetting up and down approximately 2 times.

Preparation of Effector cells: KI TCR T cells recognizing specific peptides were provided after transfection. KI TCR T cells and non-transfected (or mock) control cells were counted and the volume of cell suspension required was calculated (for a 1:1 T: E ratio, $0.1 \times 10^6$ T cells per reaction). Cells were centrifuged at 300×g for 5 minutes at ambient temperature and resuspended in assay diluent ($1 \times 10^6$/mL density)

Transfer Effector Cells to Plate: 100 µL T cell suspension was added into the plate containing the peptide loaded target and bystander cells. Plate(s) were incubated overnight at 37° C. in a humidified incubator.

Assay Readout: Plate was centrifuged at 300×g for 5 minutes and 180 µL of the supernatant transferred to another 96 well plate and stored at −80° C. for later analysis. LIVE/DEAD reconstituted dye was diluted into FACS buffer at 1:1000 ratio (e.g. 5 μL of LIVE/DEAD reconstituted dye+5 mL of FACS Buffer), 100 μL of LIVE/DEAD working solution added to each well and mixed gently pipetting up and down 2-3 times. Plate was incubated for 10 minutes in the dark at 4° C. FcR blocking solution was diluted into FACS buffer at 1:20 ratio. To wash away Live/Dead dye, 100 μL of FACS buffer was added to each well and centrifuged plate at 300× g for 5 minutes, room temperature. The supernatant was decanted and 50 μL of the FcR blocking solution added to each well and mixed. Plate was incubated for 10 minutes in the dark at 4° C.

CD8 and CD137 antibody cocktail solution was prepared by: combining CD8, CD137, and FACS buffer to make 2× staining antibody mix, for example for 80 wells: 4000 μL of FACS buffer+40 μL of CD8+400 μL of CD137. At the end of FcR blocking incubation, 50 μL of the antibody cocktail was added to each well and mixed by pipetting. The plate was incubated for 30 minutes in the dark at 4° C., then the cells washed twice to remove free antibodies. 100 μL of FACS buffer was added to each well and centrifuged plate at 300× g for 5 minutes, room temperature, the supernatant decanted. 200 μL of FACS buffer was added to each well and centrifuge plate at 300× g for 5 minutes, room temperature, then the supernatant was decanted. 100 μL of FACS buffer was added to each well, and mixed by pipetting up and down approximately 2-3 times.

Samples were analyzed immediately using the BD FACS-Lyric (Gating strategy: Lymphocytes>Single cells>Live cells>nonT (CD8−) and T cells (CD8+): nonT cells: Farred+/Farred−; T cells: CD137+). FlowJo was used for FACS gating, analysis.

A flow cytometry-based cell killing assay was used to determine the percent cell killing of T2 target cells when co-incubated with neo-TCR T cells. T2 cells (from ATCC, CRL-1992) were pre-loaded with the target peptide WT1 (VLDFAPPGA, SEQ ID NO: 71) (0-100 μM) by incubating cells in the presence of peptide for 3-4 hours at 37° C. and washed twice with PBS before being exposed to WT1 TCR-T cells in the cell-killing assay. A no-peptide or irrelevant peptide-pulsed target cell population was used as a negative control. Then the target cells were mixed with neo-TCR T cells in a 1:1 ratio for ~20 hrs to allow for the occurrence of T cell induced cell killing.

To measure percent cell killing, the cell mixtures from each assay well were stained with antibodies to label CD8+ (Anti-CD8, Biolegend: 406515) and CD137+ (Anti-CD137, Biolegend: 309822) cells, and a viability dye (Fixable Aqua stain, Thermofisher: L34965) to label dead cells. After selecting live cells, cells were further divided into CD8+ T cells, and CD8-target cells. The % loss of peptide-pulsed target cells per reaction was calculated based on the negative control. Also, peptide-specific T cell activation during cell killing assay was assessed by determining the % CD137+ signal in the CD8+ T cell population.

FIG. 138 shows a cartoon representation of target cell killing, as well as a graph of the percent killing, relative to control, for neo-TCR and no-TCR.

Example 33. Electroporation Pulse Codes

Table 14 below shows a summary of percent knock-in across three donors for various buffers/codes.

TABLE 14

NeoT Pulse Code Summary.

| Buffer/Code | % Knock-in Donor 1 | % Knock-in Donor 2 | % Knock-in Donor 3 | % Knock-in Donor 1 | % Knock-in Donor 1 | % Knock-in Donor 2 | % Knock-in Donor 3 | % Knock-in Donor 1 | % Knock-in Donor 2 | % Knock-in Donor 3 | % Knock-in Donor 1 | % Knock-in Donor 2 | % Knock-in Donor 3 | Average % Knock-in across all experiments | Std Deviation across all experiments |
|---|---|---|---|---|---|---|---|---|---|---|---|---|---|---|---|
| P2/EH100 | 1.5 | 2.7 | 1.9 | | 5.00 | 5.00 | 5.00 | | | | | | | 3.52 | 1.67 |
| P3/EH115 | 4 | 5 | 6 | 25.8 | 28.10 | 25.30 | | 20.00 | 22.60 | 21.40 | 39.9 | 45.3 | 58.4 | 25.15 | 16.53 |
| P3/DS150 | 1.6 | 10.1 | 5.31 | | | | | | | | | | | 5.67 | 4.26 |
| P3/DS120 | 6.00 | 4.40 | 2.90 | | | | | | | | | | | 4.43 | 1.55 |
| P3/EH100 | 20.00 | 13.40 | 5.20 | | | | | | | | | | | 12.87 | 7.41 |
| P3/EO100 | 4.30 | 2.80 | 2.90 | | 7.80 | 5.80 | | | | | | | | 4.7 | 2.11 |
| P3/EN138 | 30.00 | 21.90 | 7.80 | | 38.70 | 25.40 | | 14.40 | 25.80 | 18.40 | 53.6 | 58.2 | 55.7 | 31.81 | 17.40 |
| P3/EN150 | 33.00 | 24.90 | 11.60 | 17.20 | | | | 16.40 | 20.20 | 15.80 | | | | 19.87 | 7.09 |
| P3/EW113 | 27.20 | 13.10 | 6.20 | | 34.10 | 34.70 | | 19.40 | 15.30 | 15.40 | 45.3 | 48 | 48.5 | 27.93 | 15.14 |
| P3/CA137 | 8.10 | 5.70 | 2.10 | | | | | | | | | | | 5.30 | 3.02 |
| P3/CM138 | 4.40 | 5.00 | 5.70 | | | | | | | | | | | 5.03 | 0.65 |
| P3/CM137 | 9.80 | 8.20 | 3.20 | | | | | | | | | | | 7.07 | 3.44 |
| P3/CM150 | 6.70 | 5.20 | 9.60 | | | | | | | | | | | 7.17 | 2.2 |
| P3/CO118 | | | | 0.30 | | | | | | | | | | 0.30 | N/A |
| P3/DN100 | 10.40 | 10.60 | 5.10 | | | | | | | | | | | 8.70 | 3.1 |
| P3/DN115 | | | | 8.90 | | | | 7.00 | 7.80 | 8.40 | 56.5 | 62.7 | 58.5 | 29.97 | 27.44 |
| P3/DN130 | | | | 12.30 | | | | 6.40 | 5.30 | 13.70 | | | | 9.43 | 4.19 |
| P3/DS115 | | | | 1.30 | | | | | | | | | | 1.30 | N/A |
| P3/DS138 | 19.30 | 8.30 | 6.80 | | 27.40 | 9.90 | | | | | | | | 14.34 | 8.78 |
| P3/DS137 | 15.30 | 21.20 | 11.60 | | 19.40 | 9.00 | | | | | | | | 15.30 | 5.12 |
| P3/DS130 | 9.70 | 19.30 | 10.20 | | 24.20 | 11.40 | | | | | | | | 14.96 | 6.47 |
| P3/DT100 | | | | 0.20 | | | | | | | | | | 0.20 | N/A |
| P3/DZ115 | | | | 16.40 | | | | 13.00 | 13.10 | 14.50 | | | | 14.25 | 1.59 |
| P3/EH111 | | | | | 49.00 | 30.50 | | 18.90 | 24.50 | 22.50 | | | | 29.08 | 11.90 |
| P3/EN158 | | | | | 43.30 | 30.90 | | 14.70 | 23.20 | 18.20 | | | | 26.06 | 11.40 |
| P3/EO115 | | | | | 27.10 | 22.80 | | 14.90 | 21.40 | 13.70 | | | | 19.98 | 5.61 |
| P3/EO128 | | | | | 27.80 | 22.90 | | 15.50 | 19.30 | 19.50 | 48.9 | 54.4 | | 29.76 | 15.50 |

TABLE 14-continued

NeoT Pulse Code Summary.

| Buffer/Code | % Knock-in Donor 1 | Donor 2 | Donor 3 | % Knock-in Donor 1 | % Knock-in Donor 1 | Donor 2 | Donor 3 | % Knock-in Donor 1 | Donor 2 | Donor 3 | % Knock-in Donor 1 | Donor 2 | Donor 3 | Average % Knock-in across all experiments | Std Deviation across all experiments |
|---|---|---|---|---|---|---|---|---|---|---|---|---|---|---|---|
| P3/EO151 | | | | | 24.70 | 30.40 | | 22.80 | 26.20 | 19.80 | | | | 24.78 | 3.95 |
| P3/EA115 | | | | | | | | 16.20 | 11.20 | 17.30 | | | | 14.90 | 3.25 |
| P3/EE115 | | | | | | | | 9.00 | 7.70 | 9.40 | | | | 8.70 | 0.89 |
| P3/ES115 | | | | | | | | 20.40 | 13.50 | 24.30 | | | | 19.40 | 5.47 |
| P3/EZ115 | | | | | | | | 11.40 | 16.60 | 13.40 | | | | 13.80 | 2.62 |

Example 34. Knock-Out of TCR-Alpha or TCR-Beta

Purified (non-activated) CD8+ T cells were electroporated using Lonza P2 buffer and pulse code EH100. RNPs were generated by incubating the respective sgRNA and Cas9 (at a 3:1 ratio) for 15 minutes at room temperature. 60 pmol of RNP was added per electroporation. Following electroporation, the cells were cultured in X-VIVO media supplemented with IL-7 and IL-15. Two days following electroporation, the cells were collected and surface expression of the TCR was analyzed by flow cytometry.

Example 35. High Efficiency Non-Viral CRISPR/Cas9-Mediated Gene Editing of Human T Cells Using Plasmid Donor DNA CRISPR-mediated gene knockout using Cas9-ribonucleoprotein (RNP) delivery into primary human T cells represents a rapid and versatile approach for introducing genetic loss-of-function perturbations in this clinically relevant cell type (Schumann et al., 2015; Hendel et al., 2015; Scki and Rutz, 2018; Oh et al., 2019). However, methods for gain-of-function studies and stable expression of therapeutic transgenes in T cells rely mainly on viral delivery techniques that do not allow for the precise editing of genes.

Lentiviruses or retroviruses are widely used by the research community, and are also applied for the introduction of chimeric antigen receptors (CARs) or T cell receptors (TCRs) in the manufacturing of adoptive T cell therapies (Wang and Rivière, 2016; Zhang et al., 2017). Transposon-based gene delivery methods, for example, the piggyBac and Sleeping Beauty systems, have been developed as non-viral alternatives (Monjezi et al., 2017; Kebriaei et al., 2016; Hudecek and Ivics, 2018). While these approaches allow for highly efficient and stable gene delivery, they insert the transgene into the genome through random integration and are not amenable to precision gene editing. Further, the random nature of the integration process poses a risk for insertional mutagenesis (Hacein-Bey-Abina et al., 2008, 2003; Modlich et al., 2009).

Homology-directed repair (HDR) of double-strand breaks introduced by targeted gene editing methods, such as transcription activator-like effector nucleases (TALEN), zinc finger nucleases (ZFN) or CRISPR/Cas9, can be utilized to make intentional, specified changes to a genomic sequence, including the insertion of longer stretches of DNA at a defined location in the T cell genome (Li et al., 2020; Singh et al., 2017). Viral vectors, in particular adeno-associated viruses (AAV), have been used to deliver donor DNA templates for HDR-mediated target gene knock-in in T cells (Sather et al., 2015; Wang et al., 2016; Eyquem et al., 2017; Choi et al., 2019). This approach facilitated integration of a CAR into the T cell receptor alpha constant (TRAC) region locus (Eyquem et al., 2017), which put the CAR under the transcriptional control of the endogenous TCR promotor leading to improved CAR performance (Eyquem et al., 2017). Several groups have subsequently reported high editing efficiencies using AAV-based repair templates (Choi et al., 2019; Vakulskas et al., 2018; Dai et al., 2019). However, production and purification of AAV not only represents a significant clinical manufacturing challenge (Loo and Wright, 2016; Halbert et al., 2018; Davidsson et al., 2020), it also limits more widespread use of this approach in the research community.

Recently, a series of papers demonstrated that linear double-stranded (ds) DNA donor templates can be co-delivered with Cas9-RNPs for directed insertion of full-length coding sequences within the T cell genome (Nguyen et al., 2019; Roth et al., 2018; Schober et al., 2019), thus not only facilitating the generation of point mutants, but also the targeted integration of one or several expression constructs, including CARs or TCRs. In particular the need to produce and purify linear dsDNA of sufficient quantity and quality, in addition to the modest knock-in efficiencies observed with this donor DNA format, constitute serious limitations to the utility and scalability of this method. Here, we addressed these challenges by developing an efficient and scalable protocol for CRISPR/Cas9-mediated non-viral gene editing in primary human T cells using readily-available plasmid-based donor templates.

Improved CRISPR-Mediated Gene Knock-In Efficiency and Cell Recovery with Plasmid-Based Homology Donors Compared to Linear DNA Templates.

Building on previous work, including a protocol for CRISPR-Cas9-mediated gene perturbation in human and murine T cells (Seki and Rutz, 2018; Oh et al., 2019), and a report describing the use of linear double-stranded DNA as repair template (Roth et al., 2018), we set out to develop a robust, efficient and scalable protocol for non-viral CRISPR/Cas9-mediated gene knock-in in primary human T cells. To circumvent the labor-intensive steps involved in the generation and purification of PCR-based linear dsDNA and to facilitate engineering with sequence-verified templates, we investigated the use of plasmid DNA.

In addition to conventional plasmid backbones, which are ~2.5 kb in size (i.e. pUC57), several smaller circularized DNA backbones including minicircles, midges and nanoplasmids have been described for cell engineering applications (Hardee et al., 2017). Commercially available nanoplasmids consist of a <0.5 kb backbone (Luke et al., 2009; Williams et al., 2006). Since double-stranded DNA is toxic to T cells, the use of these minimal vectors can maximize the donor element-to-plasmid backbone sequence ratio and reduce the overall amount of DNA needed for transfection. We designed a donor template to encode the alpha chain of the NY-ESO1 specific T cell receptor 1G4 (Li et al., 2005) as well as the fluorescent protein mNeonGreen (mNG) targeting the T cell receptor alpha constant region (TRAC).

Figure 1A:
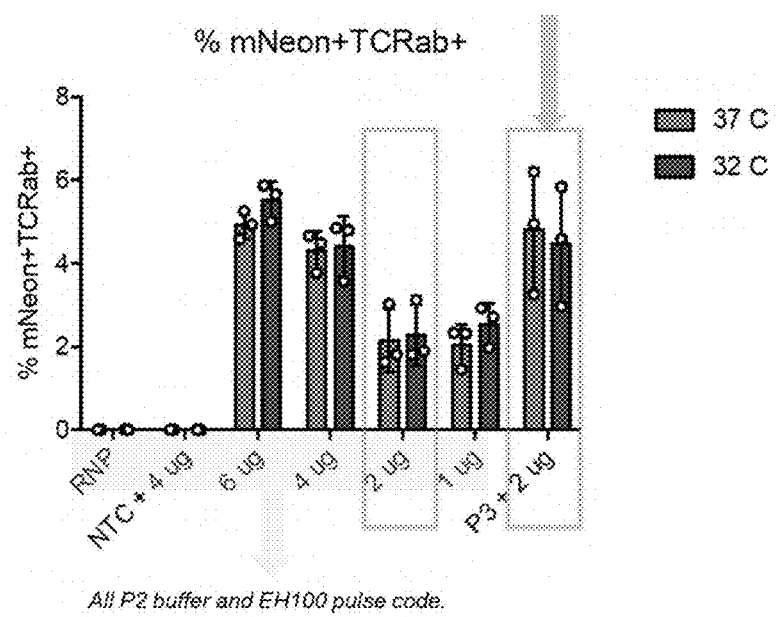
FIGS. 1A and 1B are bar graphs showing knock-in efficiency of the TRAC1-mNeon template depending on varying electroporation conditions.
Figure 1B:
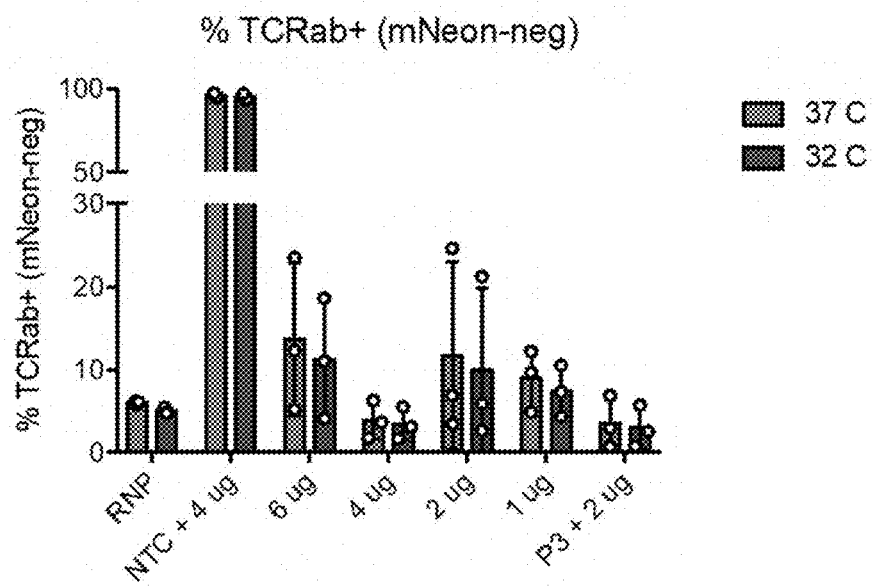
Figure 2A:
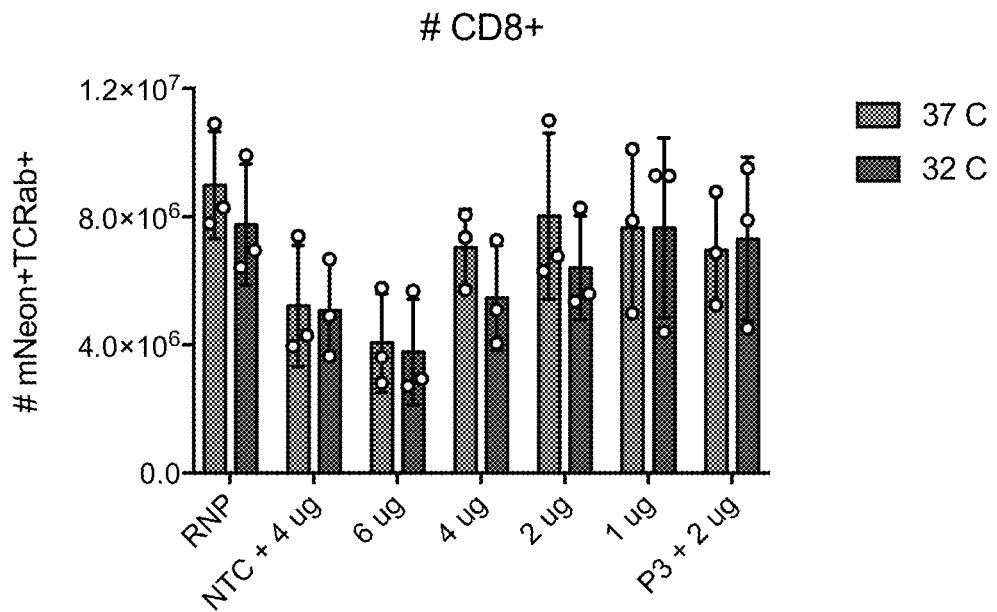
FIGS. 2A and 2B are bar graphs showing recovery of total CD8+ cells (FIG. 2A) and knock-in positive CD8+ T cells (FIG. 2B), depending on the amount of template used for electroporation. Groups of cells electroporated with RNP only (RNP) or NTC+4 μg template (NTC+4 μg) were control groups. Post-electroporation, cells were incubated at either 37° C. or 32° C.
Figure 2B:
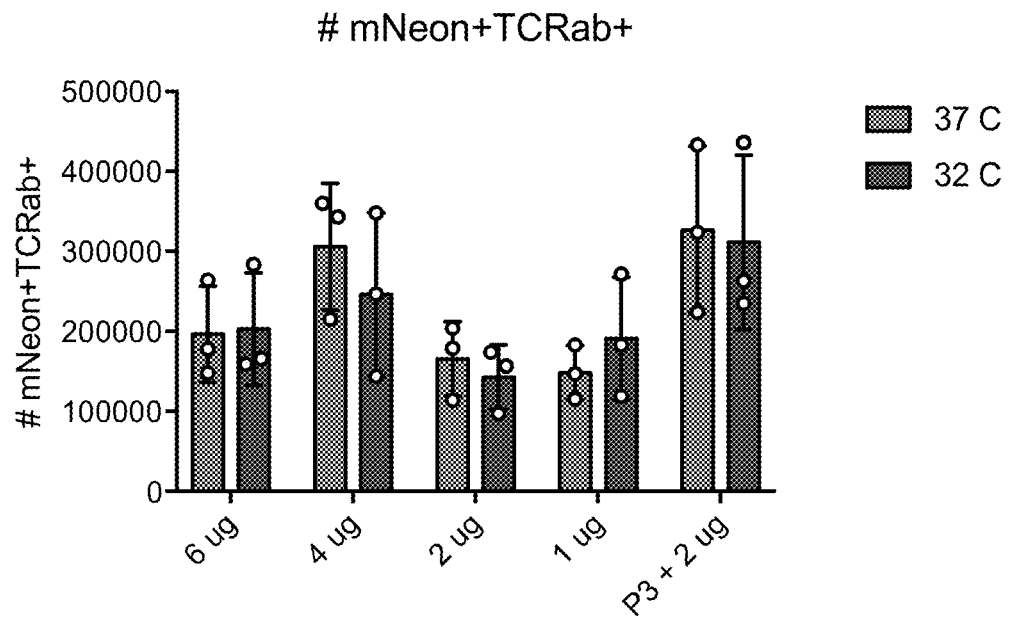
Figure 3:
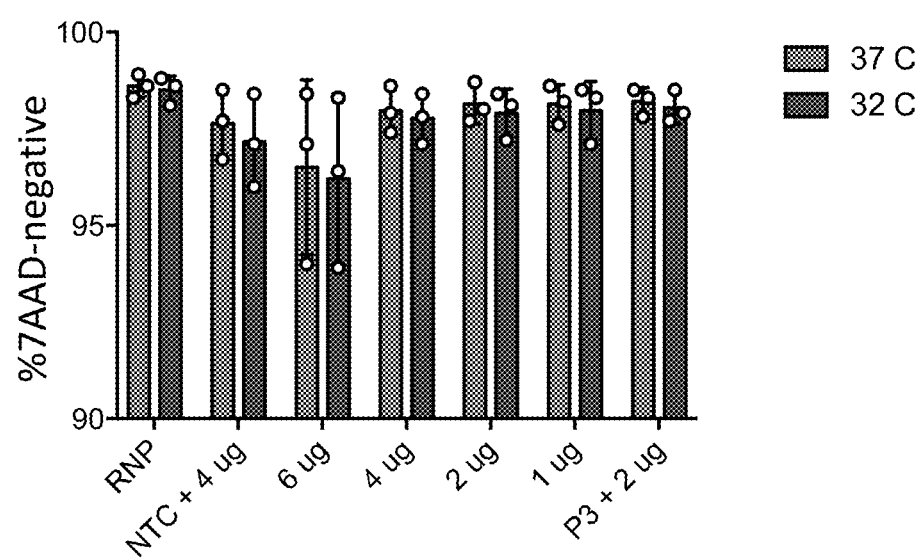
FIG. 3 is a bar graph illustrating cell viability following electroporation for the data of FIGS. 2A-2B.
Figure 4:
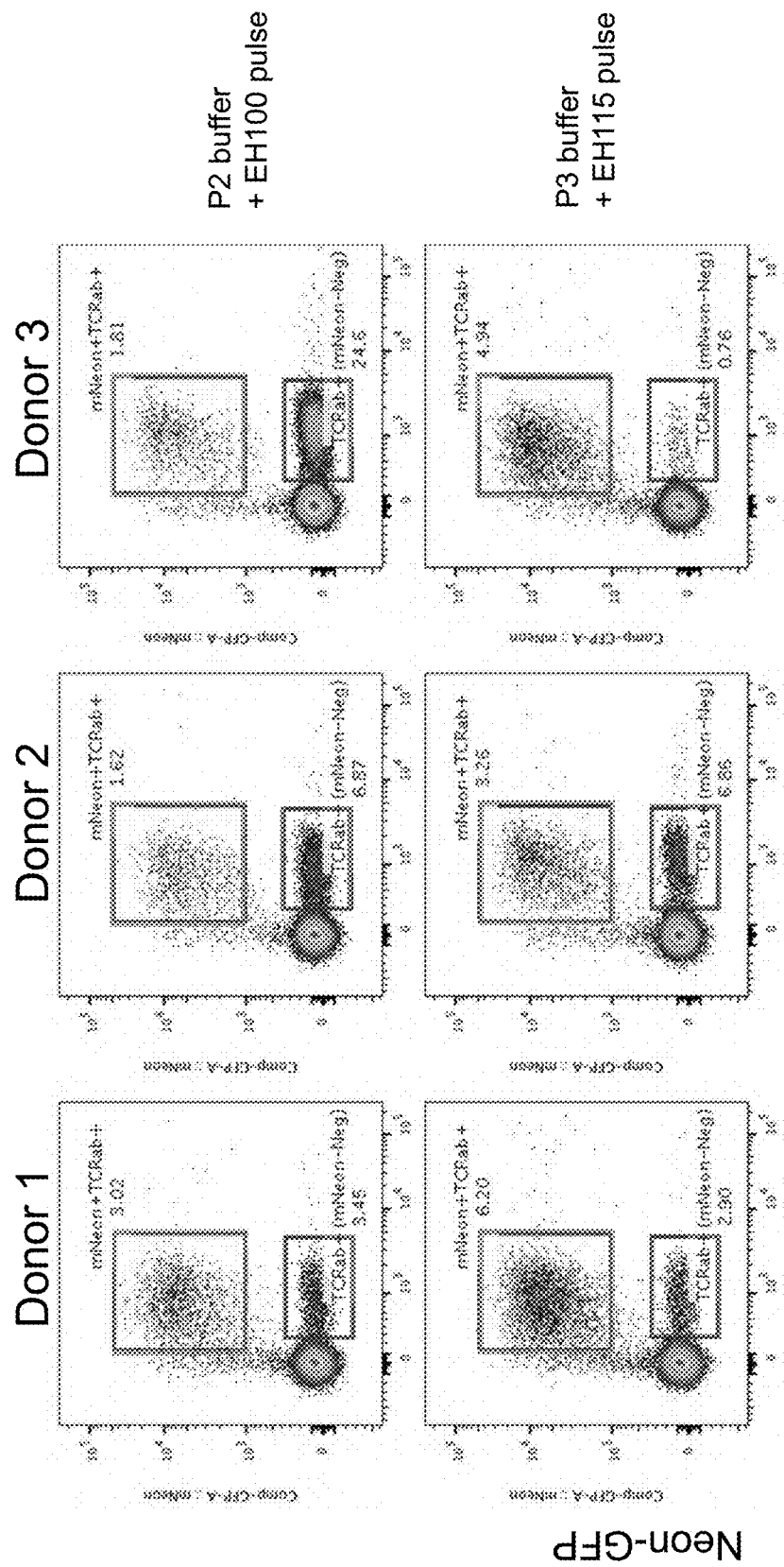
FIG. 4 is flow cytometry analysis illustrating knock-in of the TRAC1-mNeon template. The top row shows analysis of cells electroporated in P2 buffer using the EH100 pulse code and the bottom row shows analysis of cells electroporated in P3 buffer using the EH115 pulse code. The green (top) box in each plot shows detection of TRAC1-mNeon knock-in cells and the red (lower) box shows detection of residual TCRab-expressing cells. T cells from three different donors were evaluated.
Figure 5:
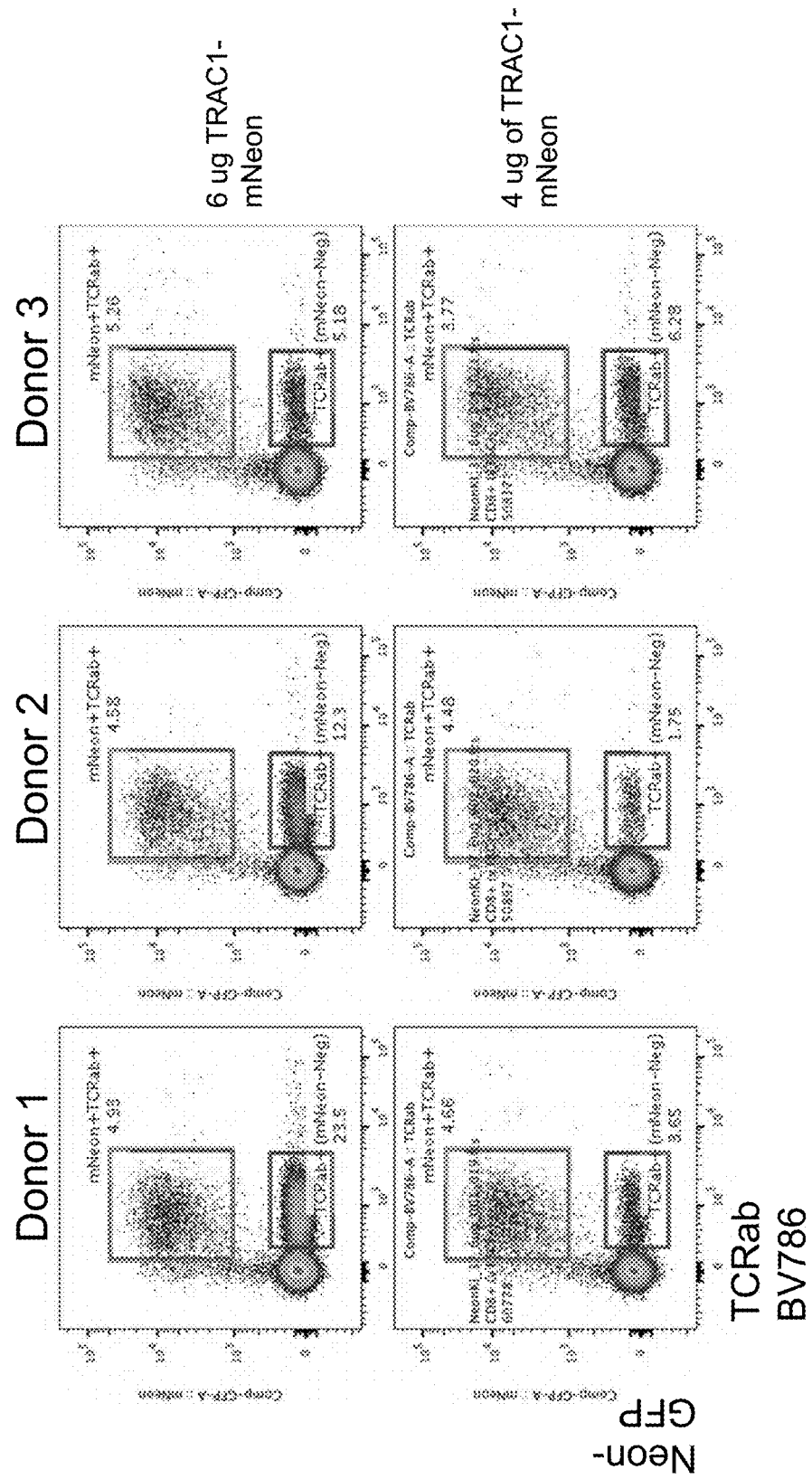
FIG. 5 are flow cytometry dot-plots illustrating knock-in of the TRAC1-mNeon template. The top and bottom rows are dot-plots representing groups of cells electroporated with 6 μg or 4 μg of template, respectively. The green (top) box in each plot shows detection of TRAC1-mNeon knock-in cells and the red (lower) box shows detection of residual TCRab-expressing cells. T cells from three different donors were evaluated.
Figure 6:
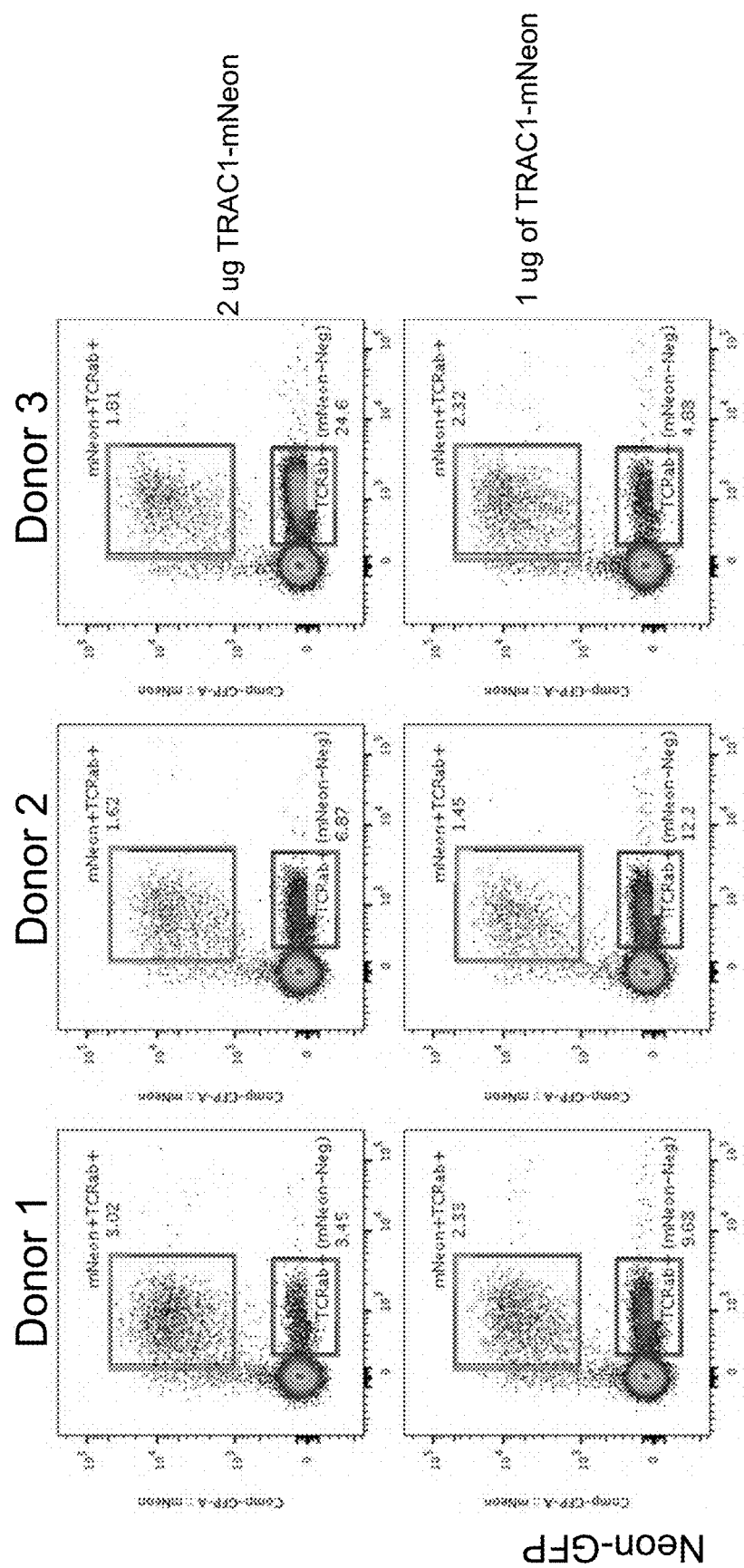
FIG. 6 is flow cytometry analysis illustrating knock-in of the TRAC1-mNeon template. The top and bottom rows are dot-plots representative of cells electroporated with 2 μg or 1 μg of template, respectively. The green (top) box in each plot shows detection of TRAC1-mNeon knock-in cells and the red (lower) box shows detection of residual TCRab-expressing cells. T cells from three different donors were evaluated.
Figure 7:
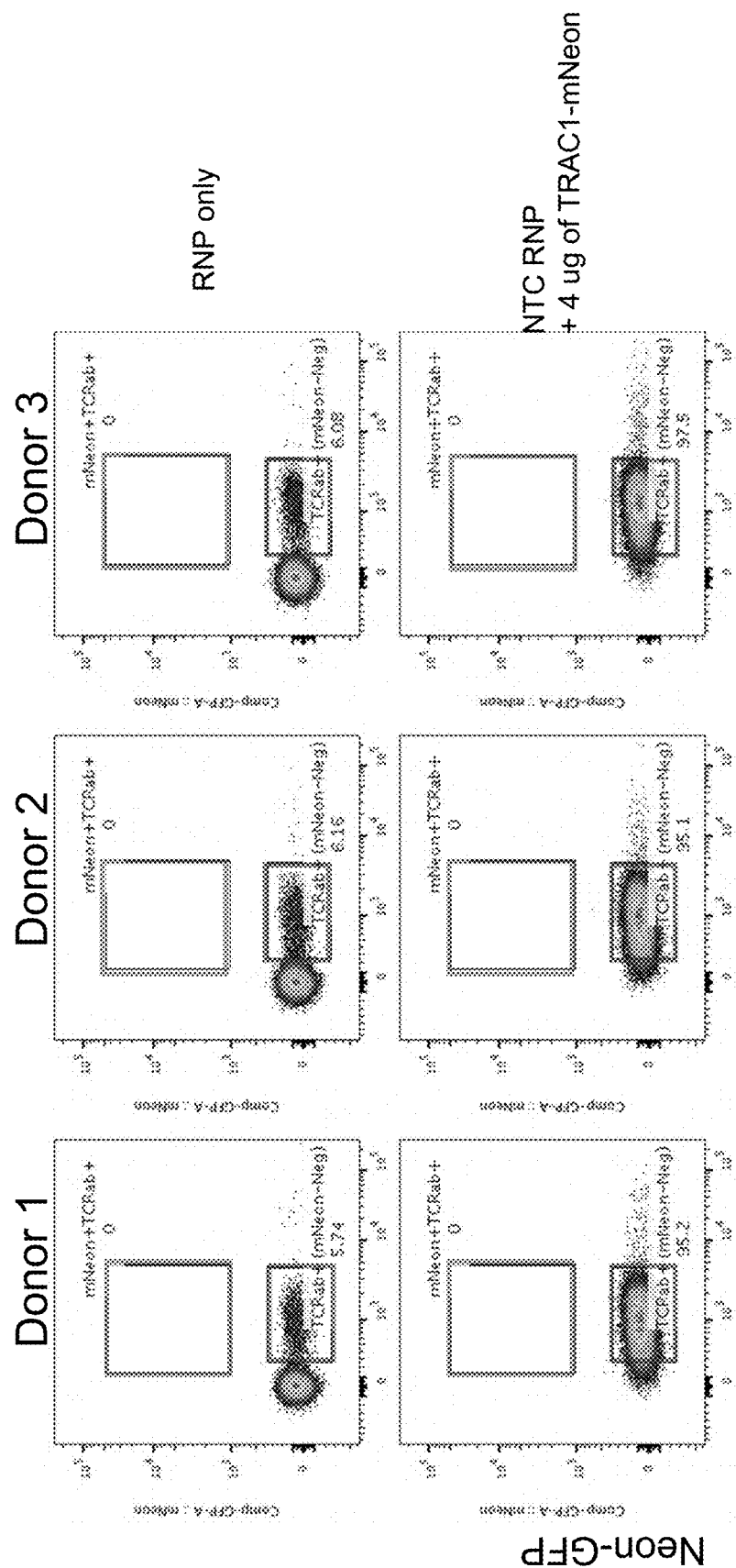
FIG. 7 is flow cytometry analysis illustrating non-significant off-target integration. The top and bottom rows show dot-plots representing groups of cells electroporated with RNP only or NTC RNP+4 μg TRAC1-mNeon, respectively. The green (top) box in each plot shows detection of TRAC1-mNeon knock-in cells and the red (lower) box shows detection of TCRab-expressing cells. T cells from three different donors were evaluated.
Figure 8A:
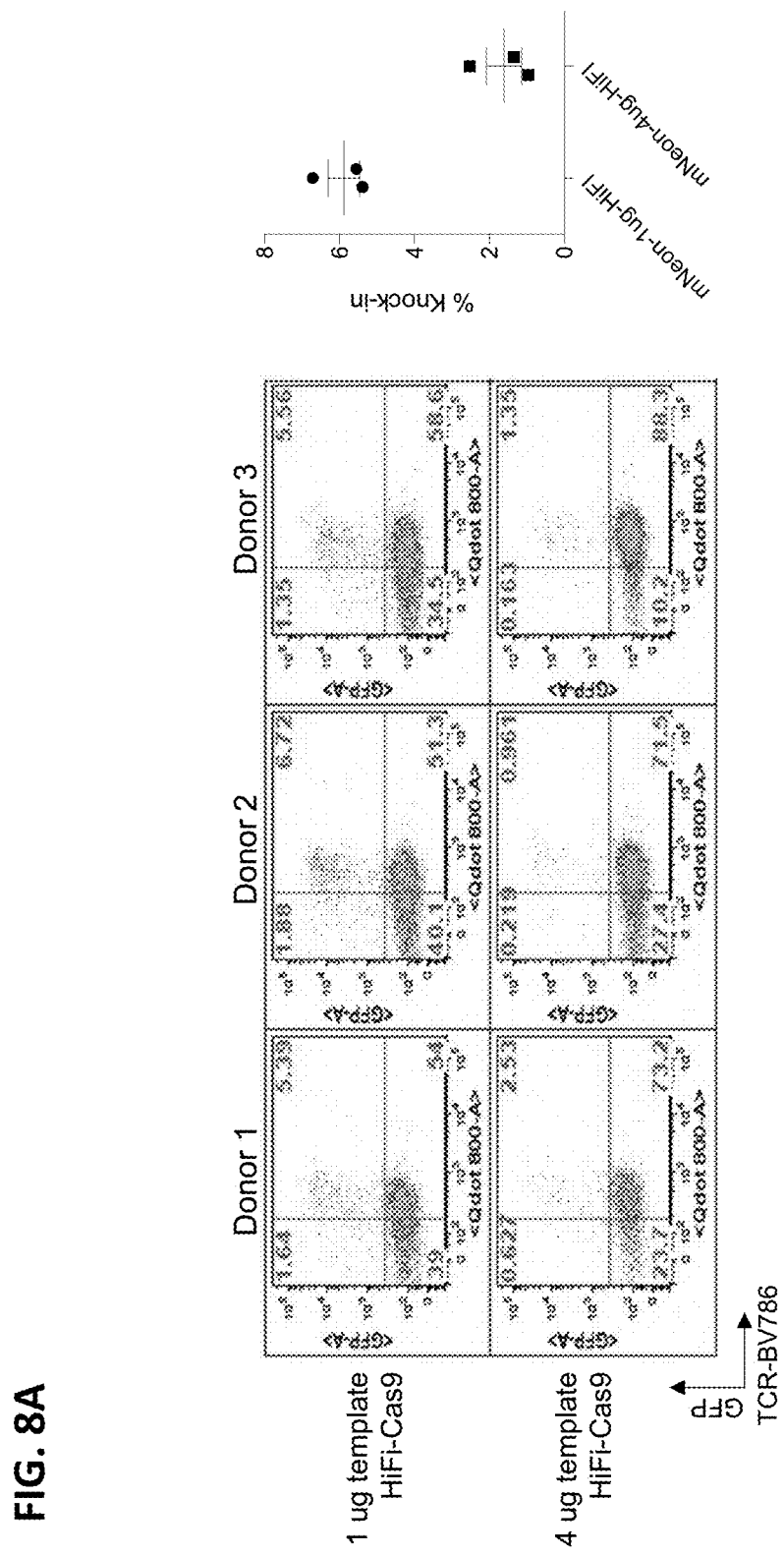
FIGS. 8A and 8B illustrate knock-in of the TRAC1-mNeon (FIG. 8A) and Rab11A-YFP (FIG. 8B) templates in T cells. The left panel shows flow cytometry analysis detecting knock-in positive cells, and the right panel is a graph showing percent knock-in depending on amount of template used for electroporation. T cells from three different donors were evaluated.
Figure 8B:
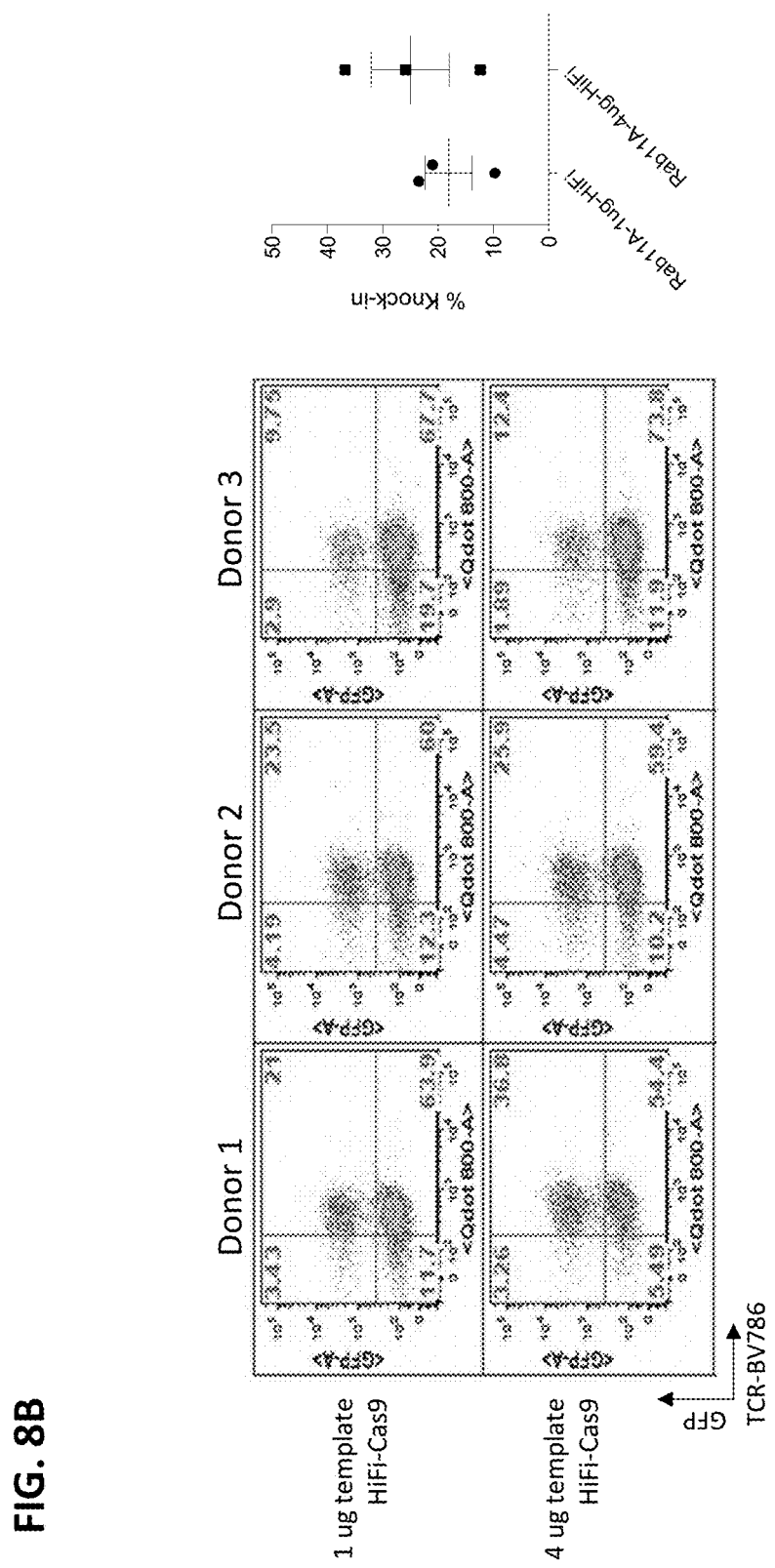
Figure 8C:
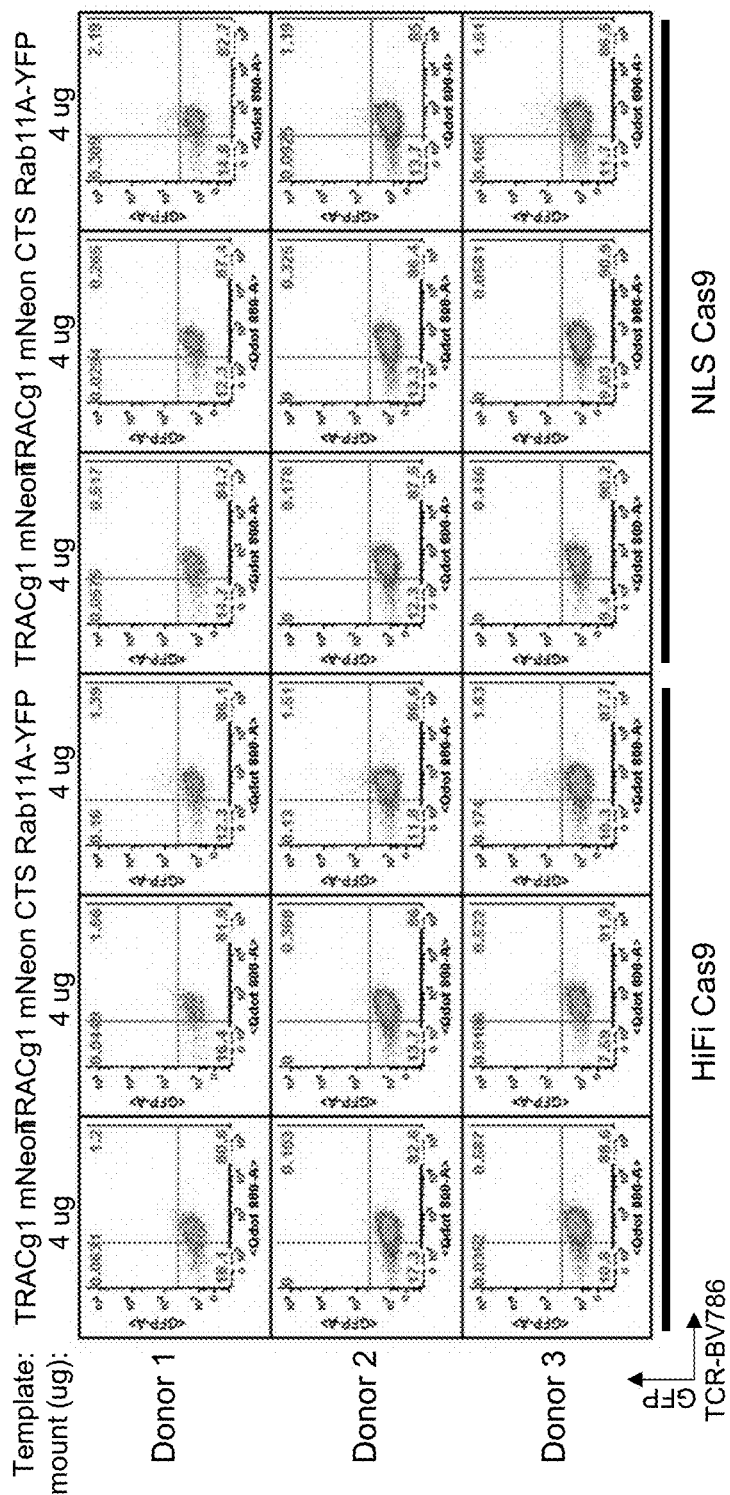
FIG. 8C are flow cytometry plots illustrating non-significant off-target integration with NTC RNP. Various donor templates and Cas9 enzymes were tested. T cells from three different donors were evaluated.
Figure 8D:
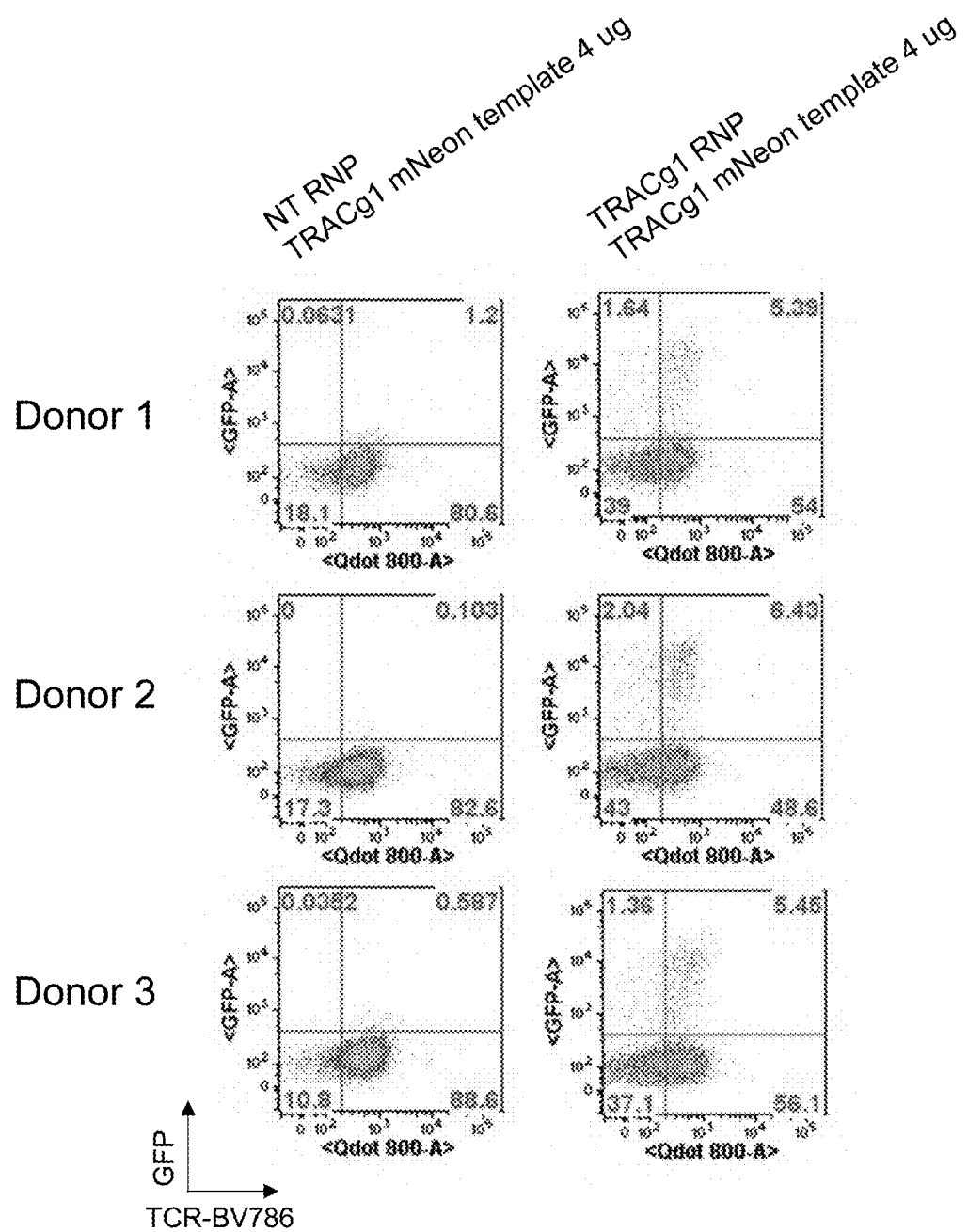
FIG. 8D is flow cytometry analysis of T cells electroporated with TRAC1 RNP+4 µg TRAC1-mNeon template (right) and NTC RNP+4 µg TRAC1-mNeon template (left).
Figure 9A:
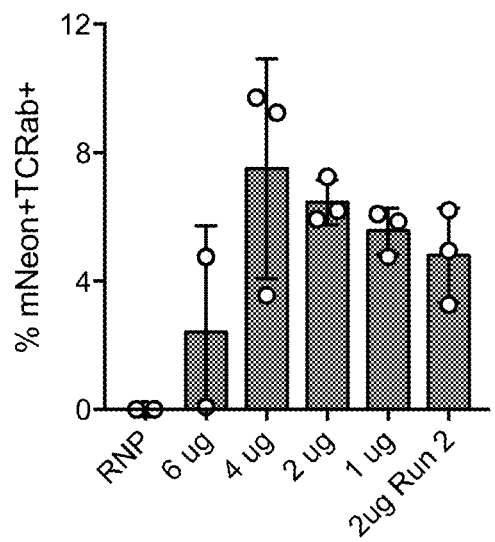
FIGS. 9A and 9B are bar graphs illustrating knock-in efficiency depending on TRAC locus used for knockout and amount of template DNA used for electroporation.
Figure 9B:
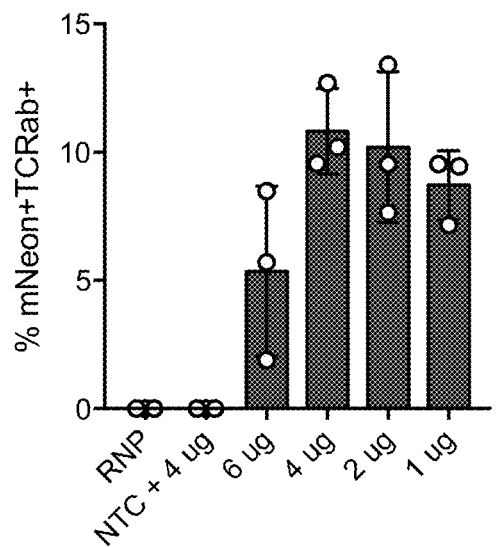
Figure 10A:
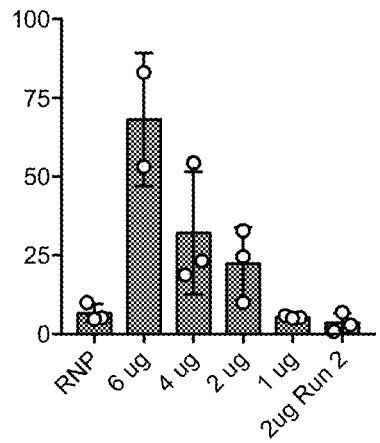
FIGS. 10A-10C are bar graphs illustrating TCRab knock-out efficiency. The graphs show frequency of TCR+Neon− cells following electroporation with varying amounts of TRAC1-mNeon template (FIG. 10A), TRAC3-mNeon template (FIG. 10B), or no template (FIG. 10C).
Figure 10B:
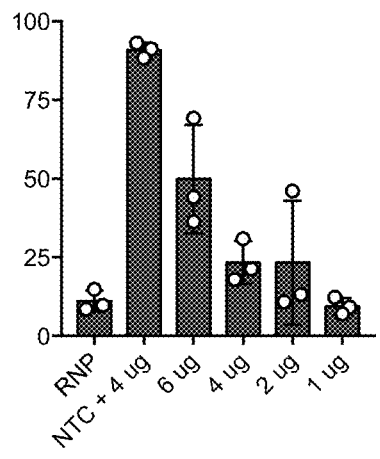
Figure 10C:
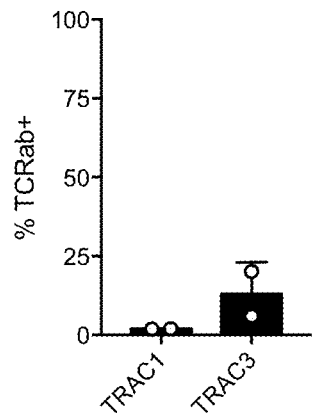

Here, the transgene and TRAC homology arms (~500 base pairs, bps) were encoded as linear dsDNA, pUC57 conventional plasmid or as a nanoplasmid (FIG. 1A, D, G). Similar to our previous approach to CRISPR/Cas9 knockout in T cells (Seki and Rutz, 2018), we optimized the process individually for CD4 and CD8 T cells, rather than working with a mixed cell population. Here, we isolated human CD8+ T cells in PRIME-XV media, supplemented with the cytokines IL-7 and IL-15, and activated them with TransAct, a bead-free colloidal polymeric nano-matrix conjugated to humanized CD3 and CD28 agonists. The CD8+ T cells were cultured for 48h before being nucleofected (Lonza Biosciences 4D nucleofection system) with Cas9-RNPs containing a chemically-synthesized single guide (sg) RNA targeting the TRAC locus together with the respective donor DNA template. Importantly, all studies were performed using the R691A HiFi-Cas9 variant in order to minimize CRISPR/Cas9 off-target events (Vakulskas et al., 2018). Further, we titrated the amount of linear and plasmid DNA side-by-side and determined knock-in efficiency, cell viability and cell recovery by flow cytometry three days post electroporation.

Figure 140C:
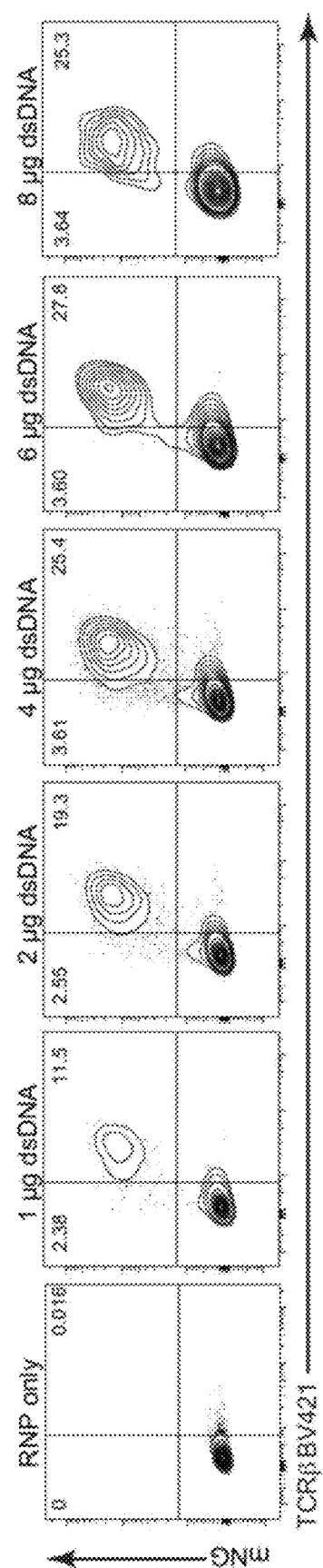
Figure 140D:
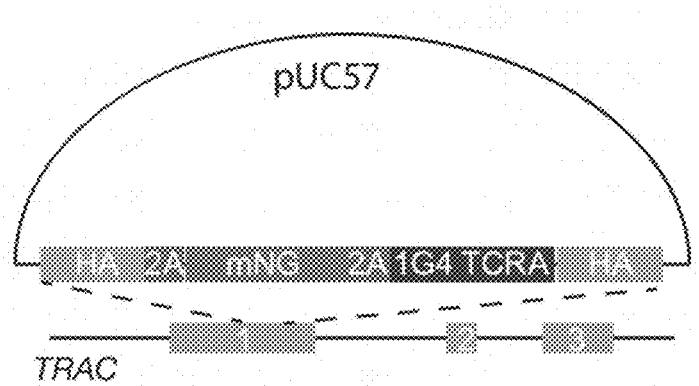
Figure 140E:
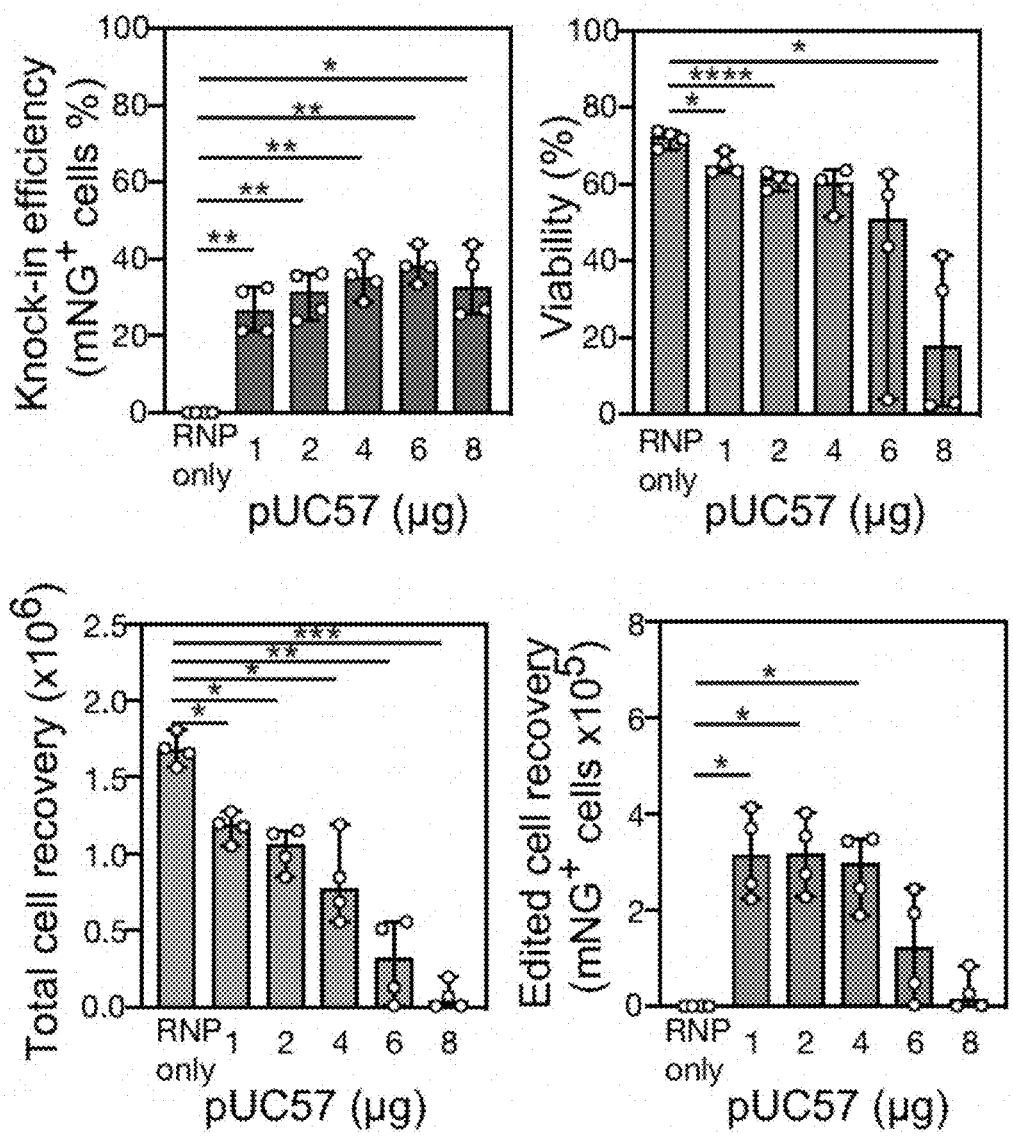
Figure 140F:
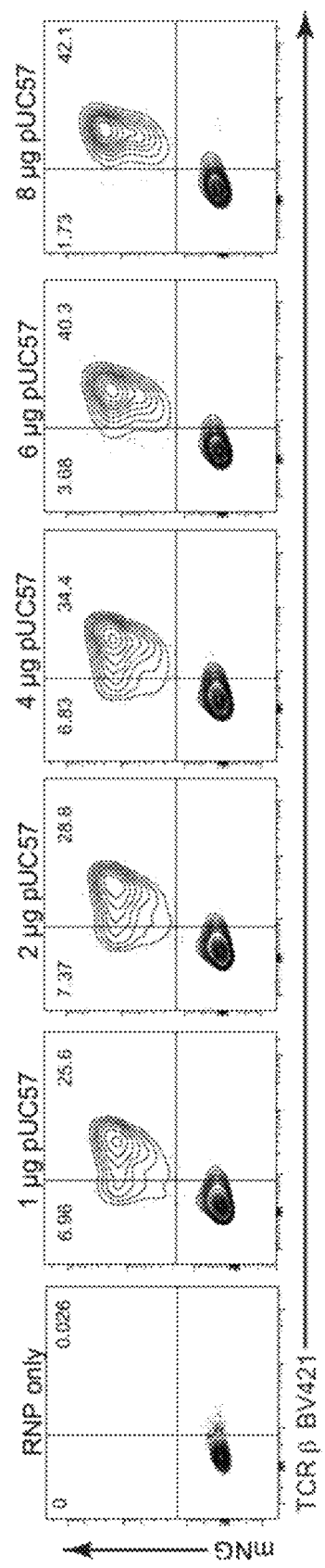
Figure 140G:
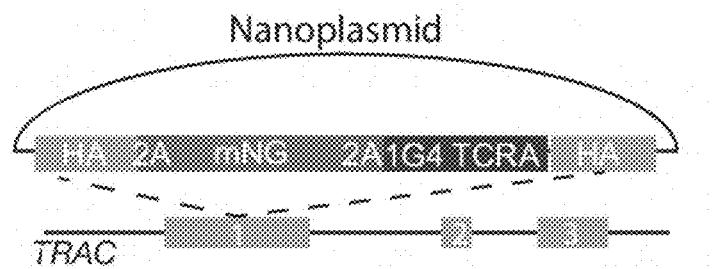
Figure 140H:
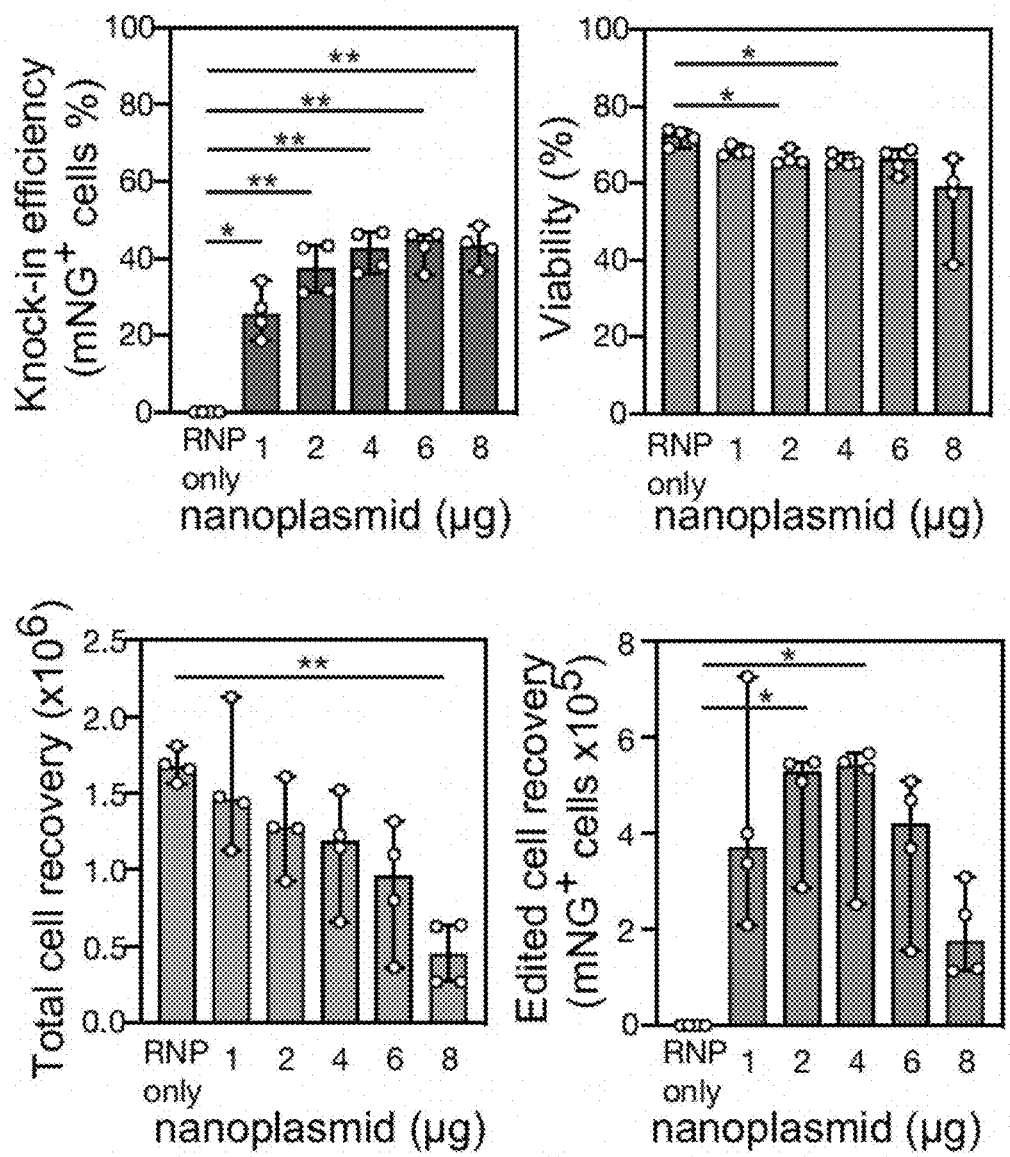
Figure 140I:
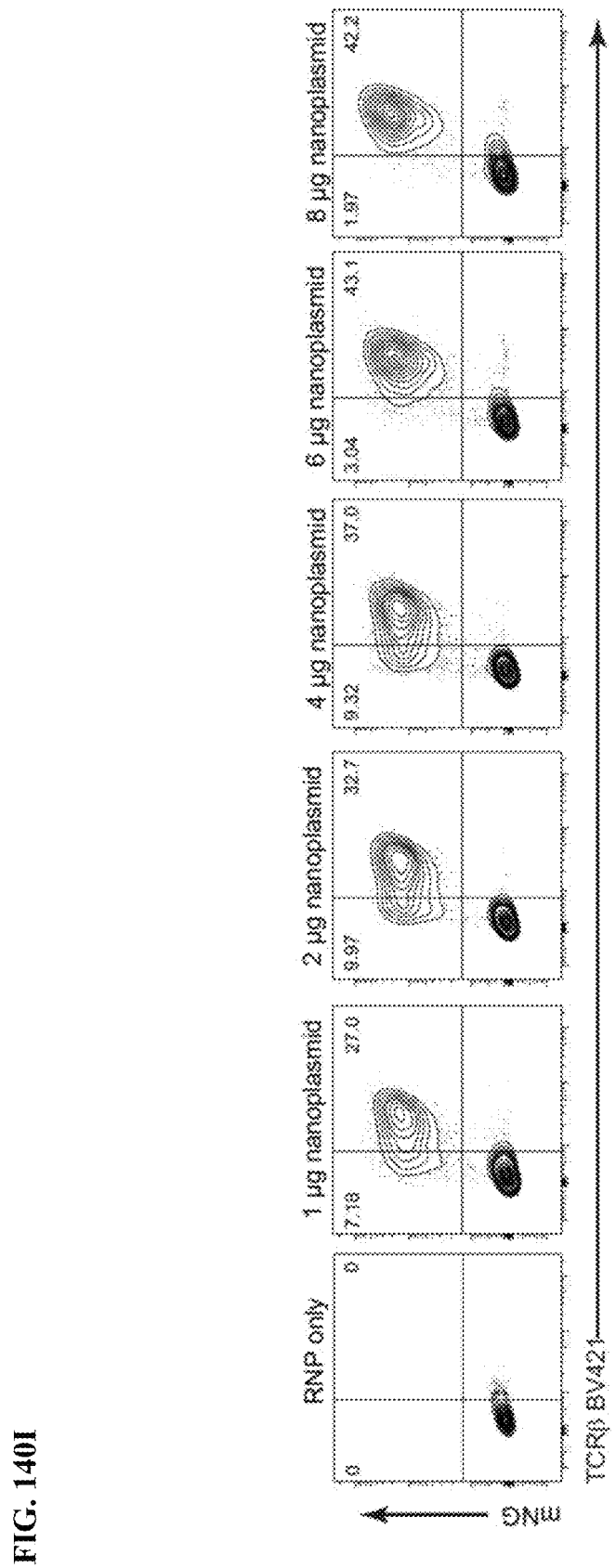

Under these conditions, we found that 4 µg of linear DNA resulted in the maximum knock-in rate of 28.8-32.1% across four independent human T cell donors (FIG. 140B, C). However, this amount of DNA impaired cell viability and resulted in low T cell recovery (FIG. 140B). When using 1 µg linear DNA instead, knock-in rates were slightly lower with 13.9-20%, but cell viability and recovery were comparable to transfection with Cas9-RNP without DNA (FIG. 140B,C). Titration of the pUC57 plasmid DNA revealed higher knock-in rates compared to linear dsDNA, with 33.5-44% when using as much as 6 µg plasmid (FIG. 140E, F). However, this condition resulted in sub-optimal viability and cell recovery, whereas 2 µg plasmid DNA generated a 24-36.2% knock-in rate with minimally impaired cell viability resulting in an optimal recovery of edited cells (FIG. 140E, F). The nanoplasmid format enabled knock-in rates of 36.2-46.6% at 4 µg DNA with minimal impact on cell viability and recovery when compared to a Cas9-RNP only condition (FIG. 140H, I). We also evaluated knock-in efficiency, cell viability and recovery when the T cells were cultured in RPMI-1640 supplemented with 10% FBS (R10), which is a more widely used and accessible culture media for T cells. Experiments performed in R10 yielded results largely comparable to cultures in PRIME XV media for linear dsDNA templates but somewhat lower knock-in rates (29.5-37.4%) for nanoplasmid templates (147A-F), demonstrating that R10 may be used as an alternative to PRIME-XV media. Addition of the negatively charged poly-L-glutamic acid (PGA) or encoding truncated Cas9 target sequences (tCTS) in the donor template, as previously described (Nguyen et al., 2019) did not impact targeting efficiency (147G,H).

Figure 148A:
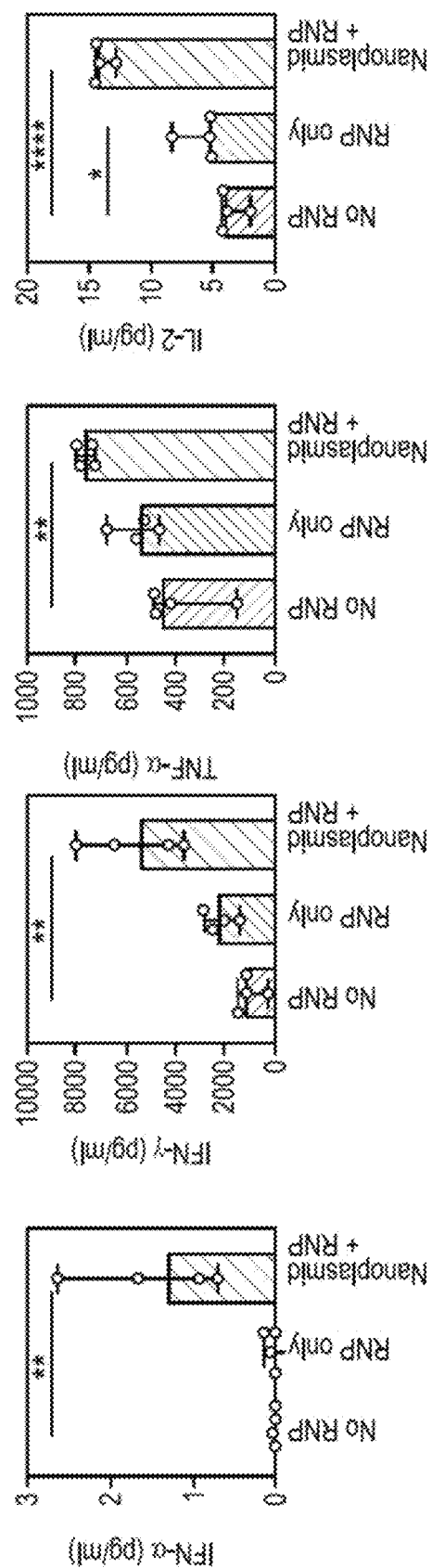
Figure 148B:
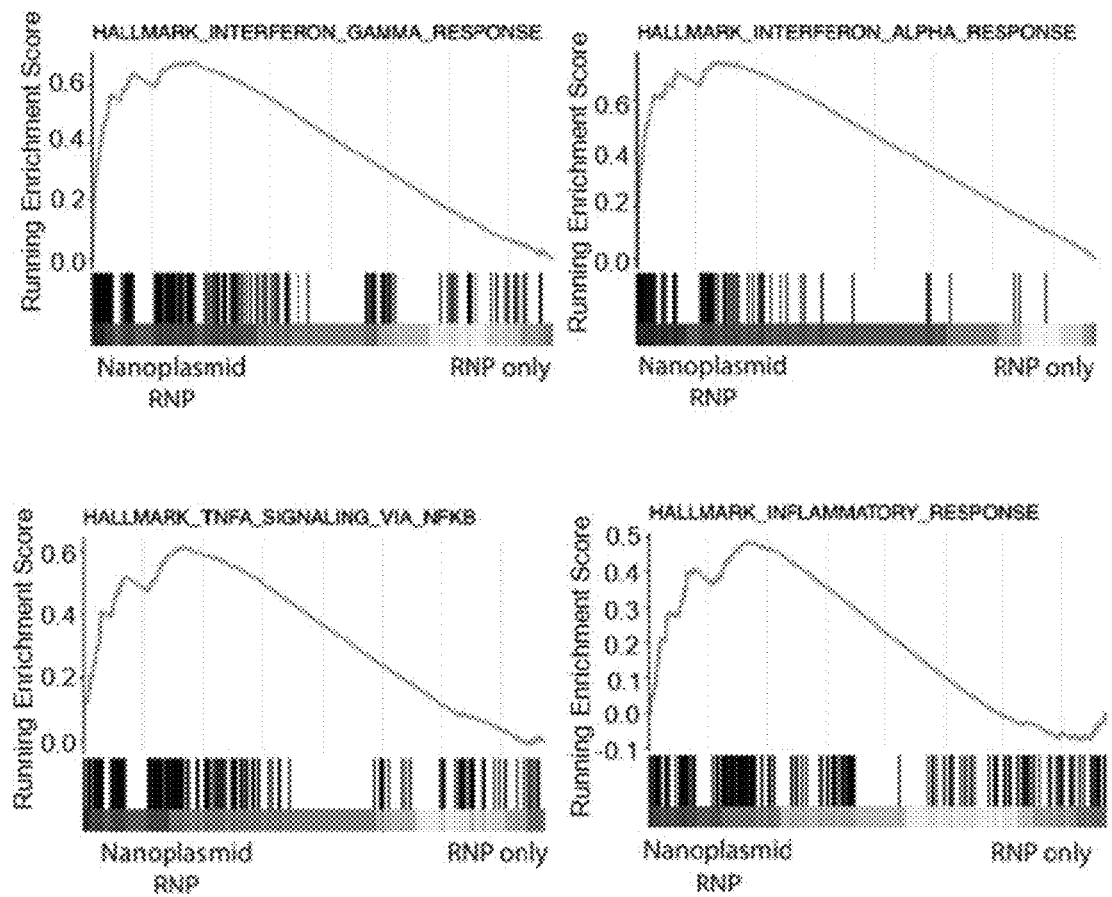
Figure 148C:
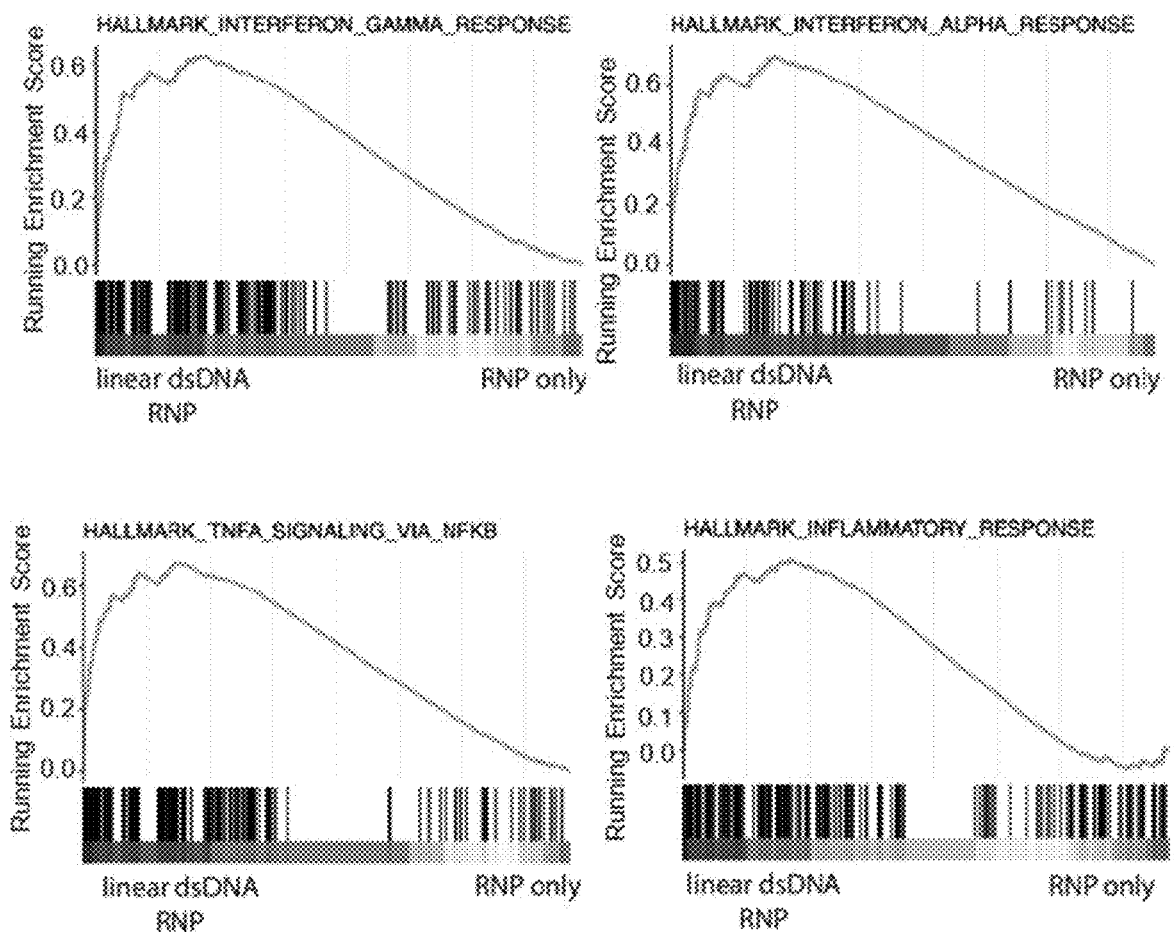
Figures 148D, 148E, 148F:
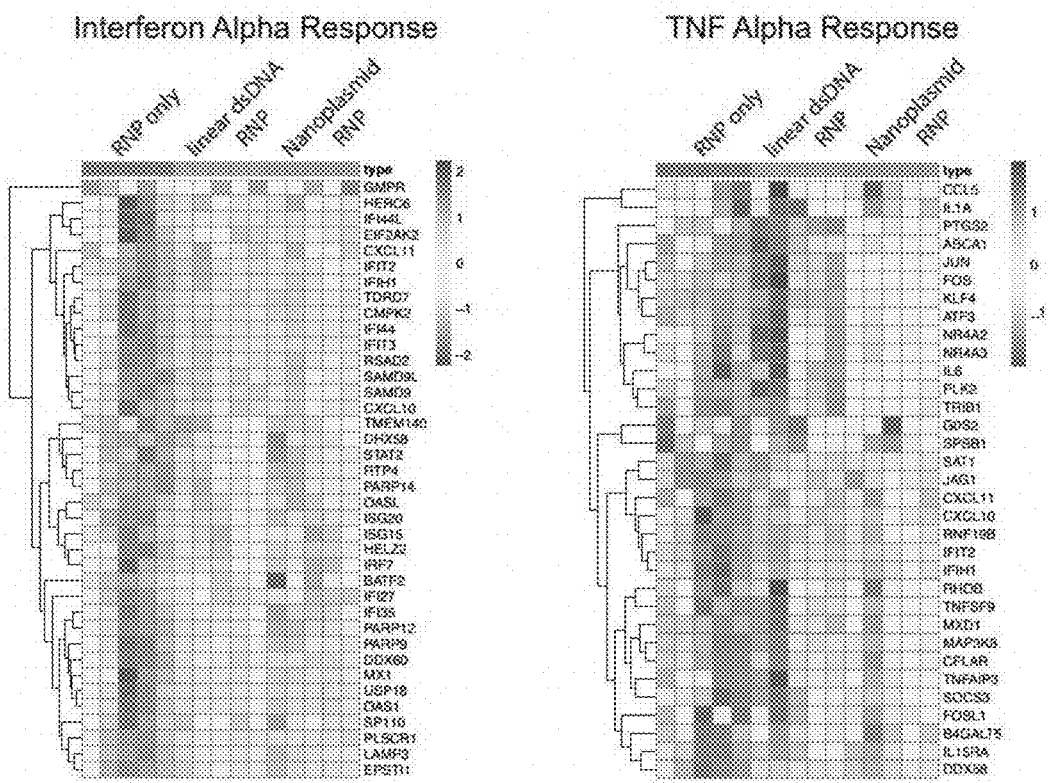
Figure 148G:
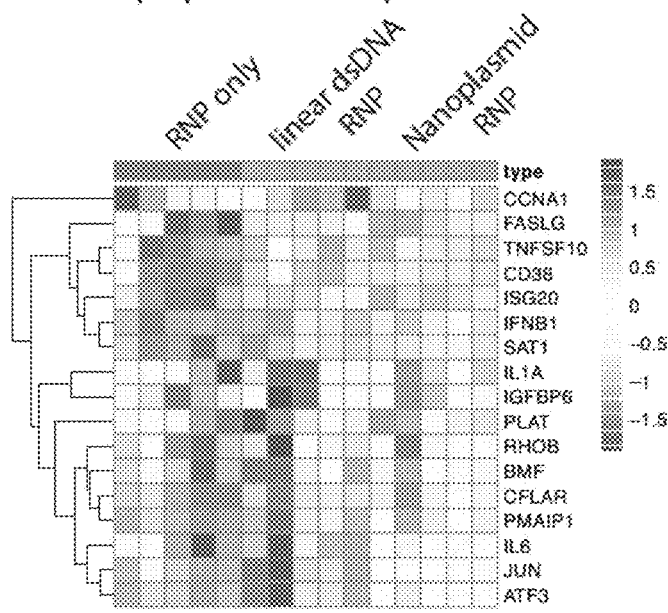
Figure 148H:
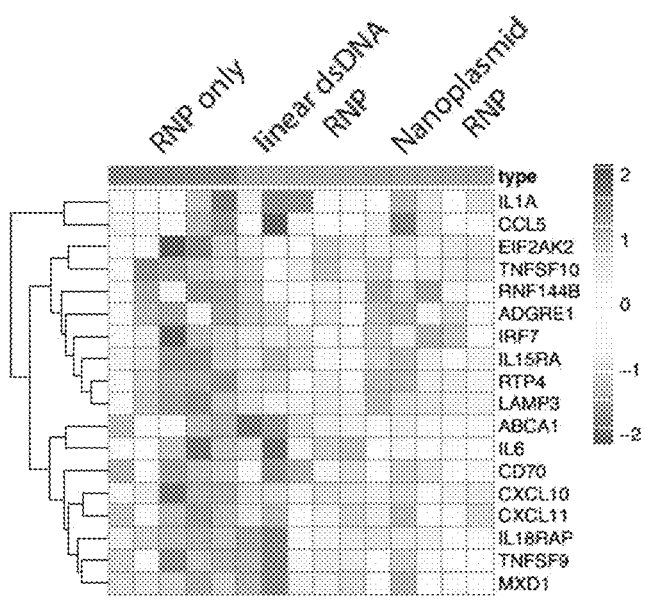

Our initial studies suggested that nanoplasmids had favorable qualities for gene targeting in T cells. However, higher amounts of donor DNA, regardless of format, impaired T cell viability. Therefore, we sought to better characterize the stress response induced in T cells following exposure to nanoplasmids. We compared cytokine production after overnight culture of CD8 T cells that had been transfection with sgTRAC Cas9-RNP and nanoplasmid or Cas9-RNP only to unedited T cells. Nanoplasmid transfection (but not Cas9-RNP alone) induced IFN-a, IFN-g, TNF-$\alpha$ and IL-2 levels (FIG. 148A). We also performed RNA sequencing comparing T cells transfected with Cas9-RNP plus nanoplasmid or Cas9-RNP only. Interferon-a and -beta as well as TNF-$\alpha$ and inflammatory response signatures were up-regulated in nanoplasmid transfected cells (FIG. 148B) in agreement with our cytokine data. Importantly, linear DNA and nanoplasmid induced qualitatively and quantitatively similar responses (FIG. 148C-H). In conclusion, we found that plasmid DNA donor templates enabled highly efficient CRISPR/Cas9-mediated knock-in in CD8+ T cells, circumventing a need for linear dsDNA production and purification. While nanoplasmid vectors yielded generally more consistent results with higher knock-in rates, conventional plasmid backbones, such as pUC57, can be used successfully with careful titration.

Figure 141A:
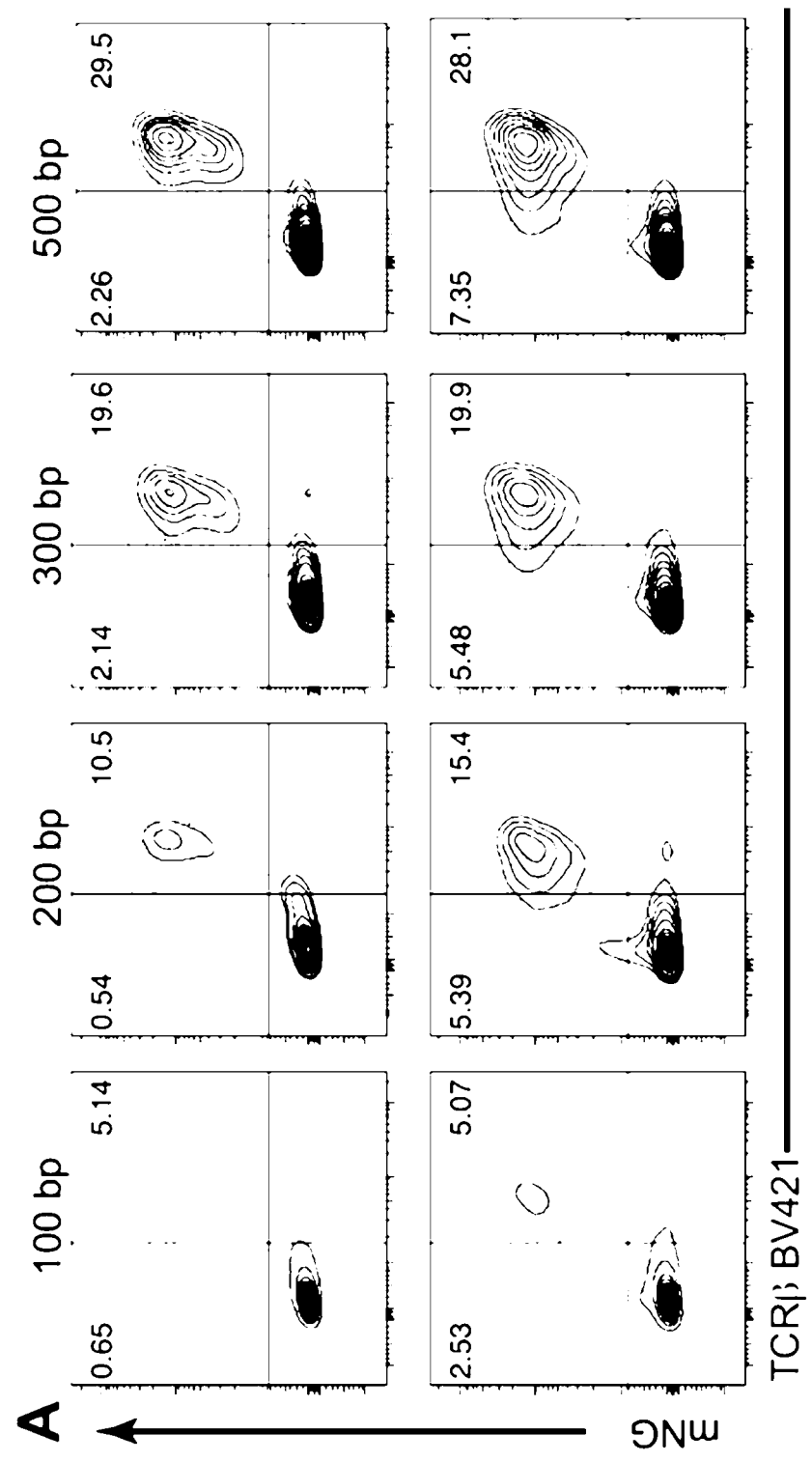
Figure 141B:
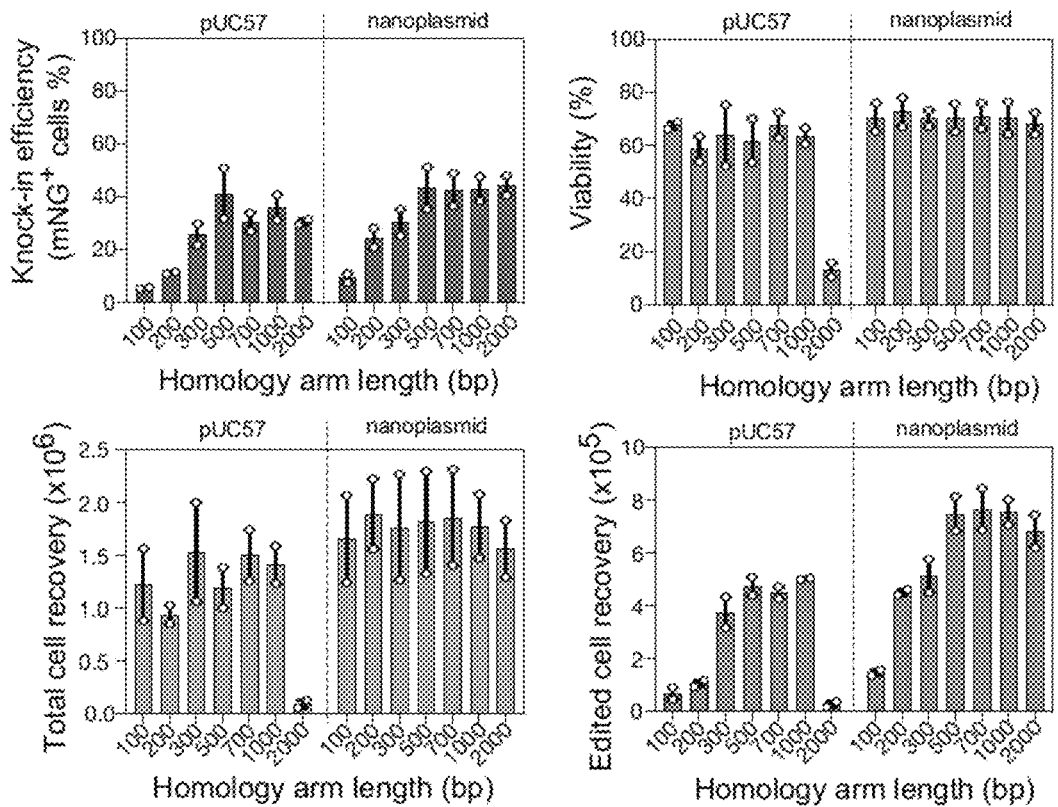

Optimization of CRISPR/Cas9-Mediated Gene Knock-In with Plasmid-Based Donor DNA in CD4 and CD8 T Cells After confirming the beneficial properties of plasmid-based gene editing, we sought to optimize this process further and extend our protocol to enable CD4+ T cell modification. Accordingly, we used CD8+ T cells to compare pUC57 and nanoplasmid donor templates with a fixed transgene comprising a bicistronic mNG reporter and 1G4 TCR alpha chain, along with TRAC homology arms of different lengths ranging from 0.1 to 2 kb. Transgene knock-in efficiency increased between 0.1 to 0.5 kb homology arm length, irrespective of the backbone used, with subtle improvement in knock-in efficiency observed with nanoplamids containing homology extended to 2 kb (FIG. 141A, B). Importantly, cell viability and cell recovery were comparable with both backbones except for the 2 kb homology arm pUC57 construct, which severely impaired cell viability (FIG. 141A, B). We conclude that a homology arm length of 0.5 kb represented the optimum regarding knock-in efficiency and cell recovery, but longer arms can be used with nanoplasmid without compromising cell viability (FIG. 141A, B).

Figure 141C:
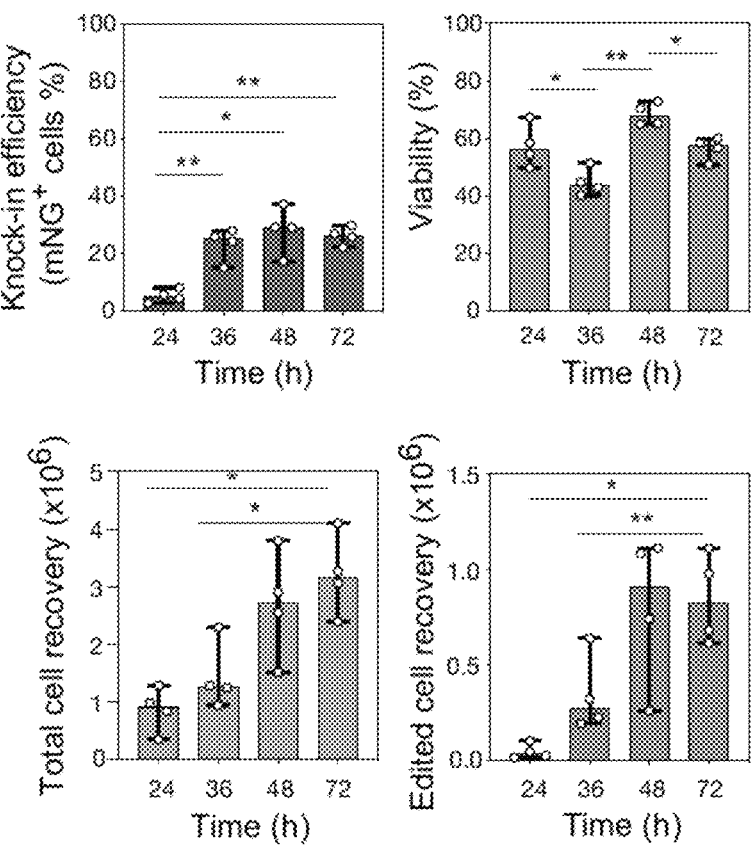
Figure 141D:
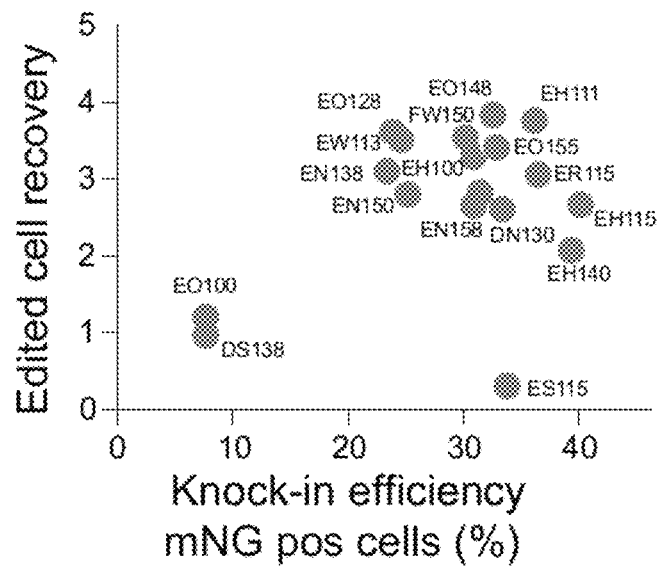

The timing of Cas9-RNP/nanoplasmid delivery following T cell activation is another parameter for optimization. We found that transfection at 24h post T-cell activation resulted in a drastically reduced knock-in efficiency compared to later transfection time points (FIG. 141C). A Cas9-RNP/nanoplasmid delivery at 48-72h resulted in maximal cell recovery (FIG. 141C). Lastly, we tested several nucleofection pulse codes with Cas9-RNP and nanoplasmid template and found that EH115 resulted in the highest target gene editing efficiency. Other pulse codes, such as EH111, further increased cell recovery with only a minimal reduction in knock-in efficiency (FIG. 141D). The desired application should drive the final selection of the nucleofection condition, depending on whether efficiency or cell recovery is a higher priority. For subsequent studies we used EH115.

Figure 141E:
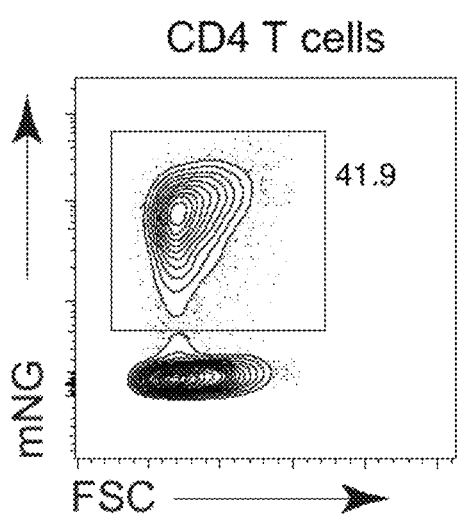
Figure 141F:
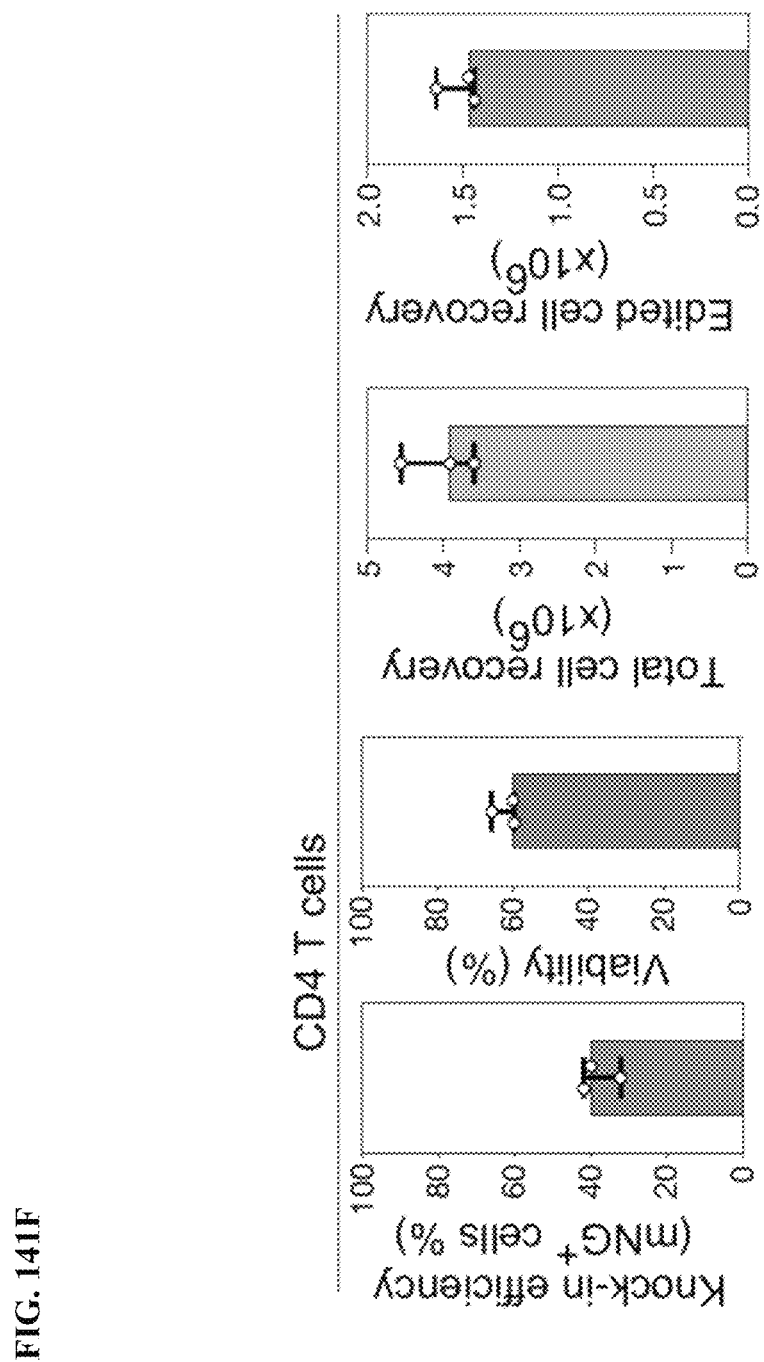

Using the above conditions as a baseline, we isolated and cultured human CD4+ T cells in PRIME XV media supplemented with recombinant IL-7 and IL-15. We also added IL-2 and activated with TransAct for 48h. We then nucleofected as before with TRAC-mNG nanoplasmid donor template and sgTRAC Cas9-RNP, and assessed knock-in rate, cell viability and recovery by flow cytometry. We observed a knock-in rate of 32.2-41.9 across three independent human T cell donors, with viability and recovery rates that were in line with our data from CD8 T cells (FIG. 141E, F). We concluded that our approach was equally applicable to human CD4 and CD8 T cells.

Efficient Non-Viral T Cell Receptor Editing Using Plasmid DNA Donors

Figure 142A:
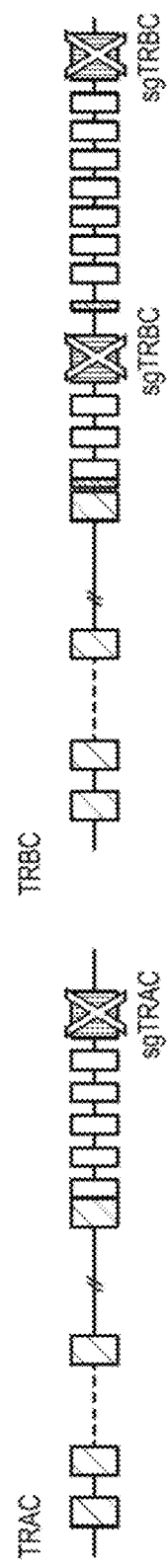
Figure 142B:
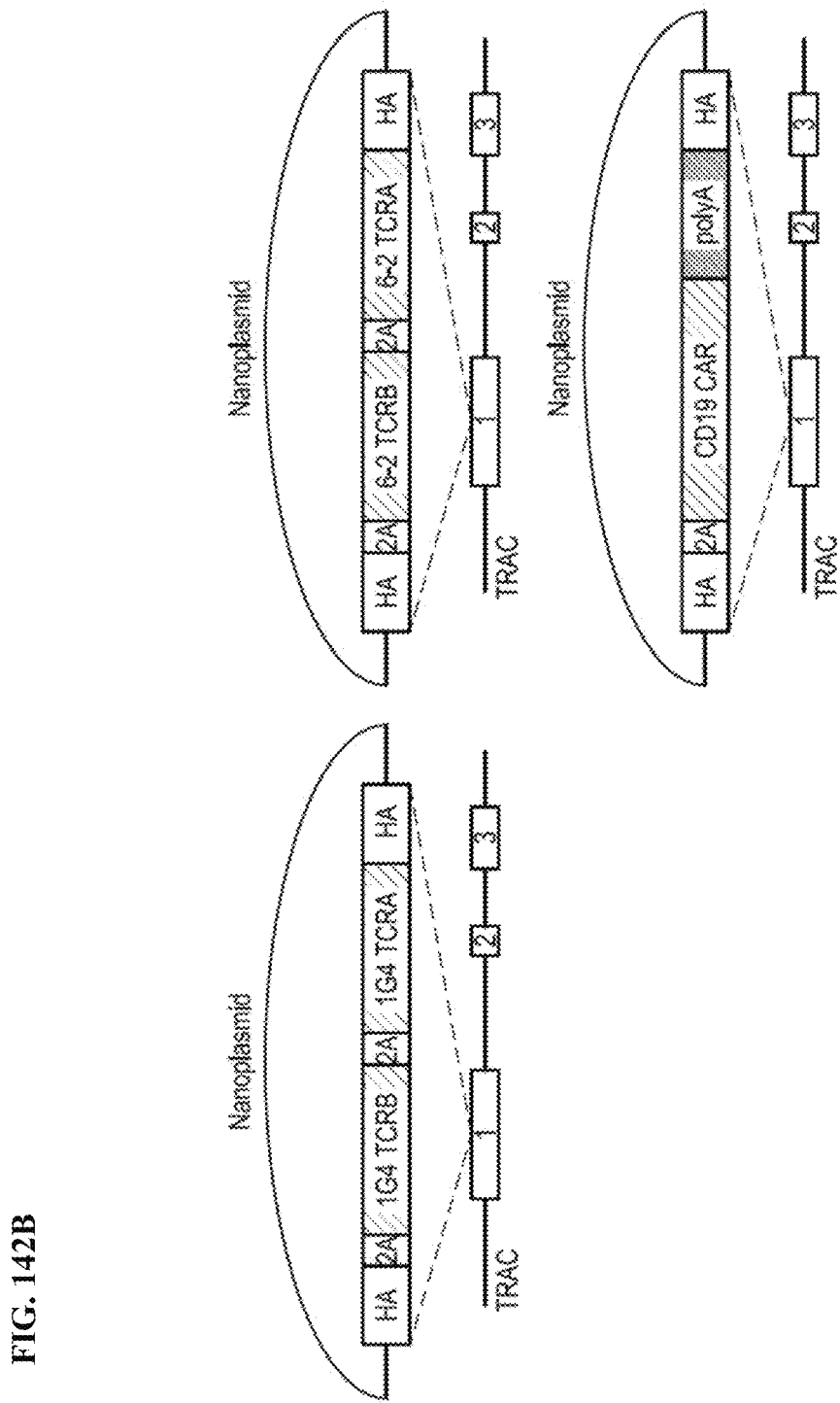

We next applied our protocol to TCR editing in T cells. The introduction of a transgenic TCR with desired antigen specificity also requires the knock-out of the endogenous TCR in order to prevent mispairing with its alpha and beta chains. Using our targeting strategy, insertion of transgenic TCRs containing both an alpha and beta chain within the TRAC locus on human chromosome 14 will disrupt the endogenous TCR alpha gene. However, the existing TCR beta chain on human chromosome 7 needs to be knocked-out separately. We therefore designed a single sgTRBC sequence that simultaneously targets T cell receptor β-chain constant domains 1 and 2 (TRBC1 and TRBC2) (FIG. 142A), leading to complete loss of TCR expression as detected by flow cytometry (FIG. 149A). We next designed nanoplasmid donor templates encoding TCRs with known specificity, the NY-ESO1 specific 1G4 and the CMV A2/pp65495-503-specific TCR6-2 (Schober et al., 2019) as well as a human CD19 CAR (Bloemberg et al., 2020), all targeting the TRAC locus (FIG. 142B).

Figure 142C:
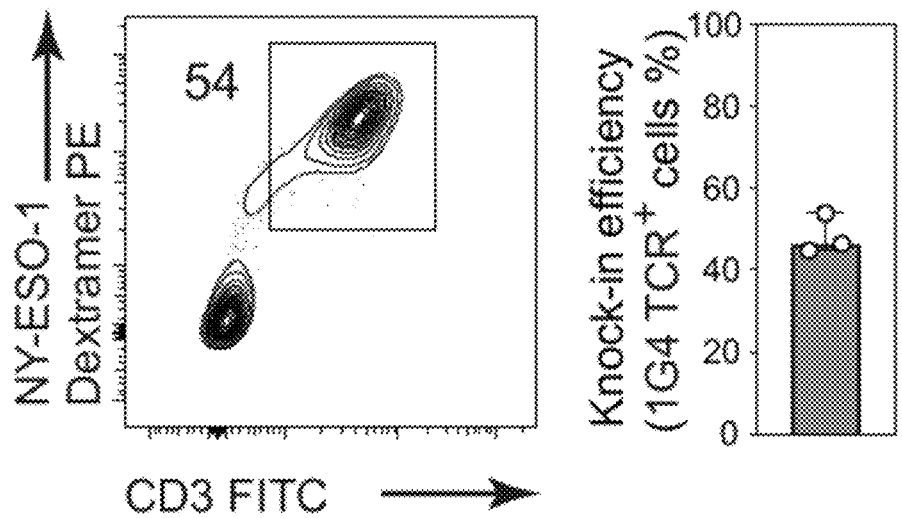
Figure 142D:
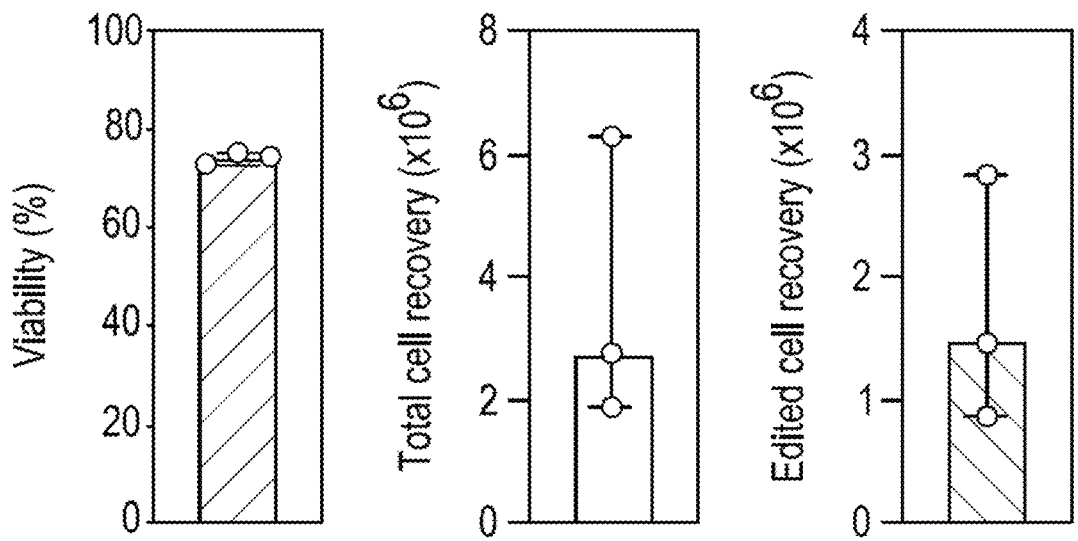
Figure 142E:
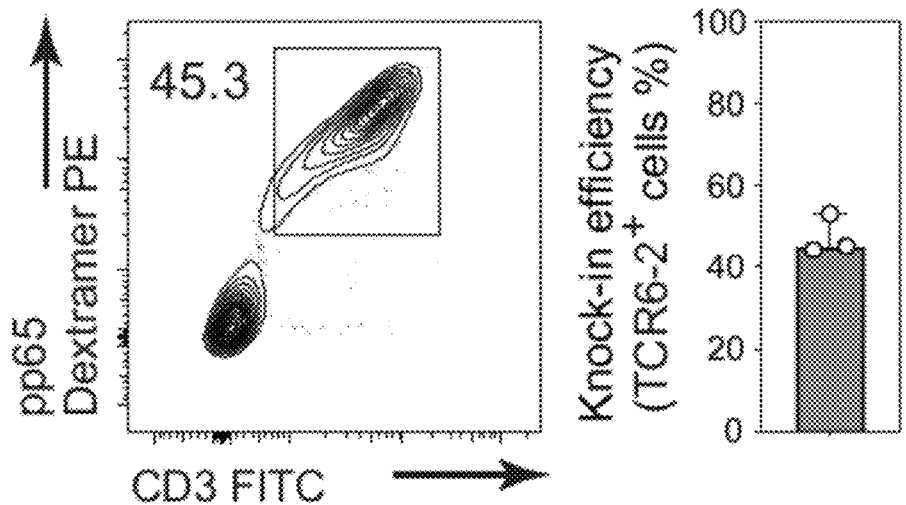
Figure 142F:
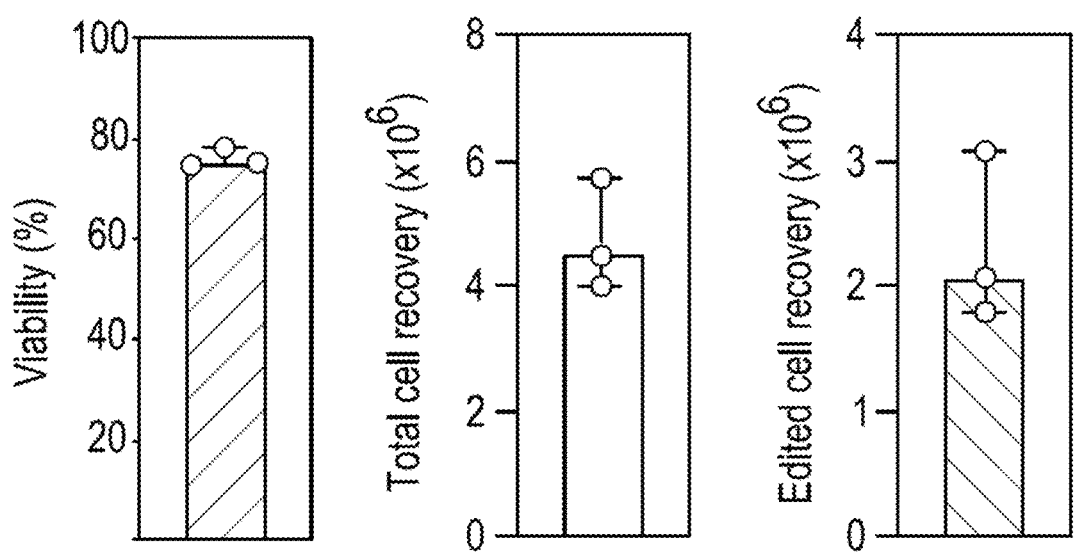
Figure 142G:
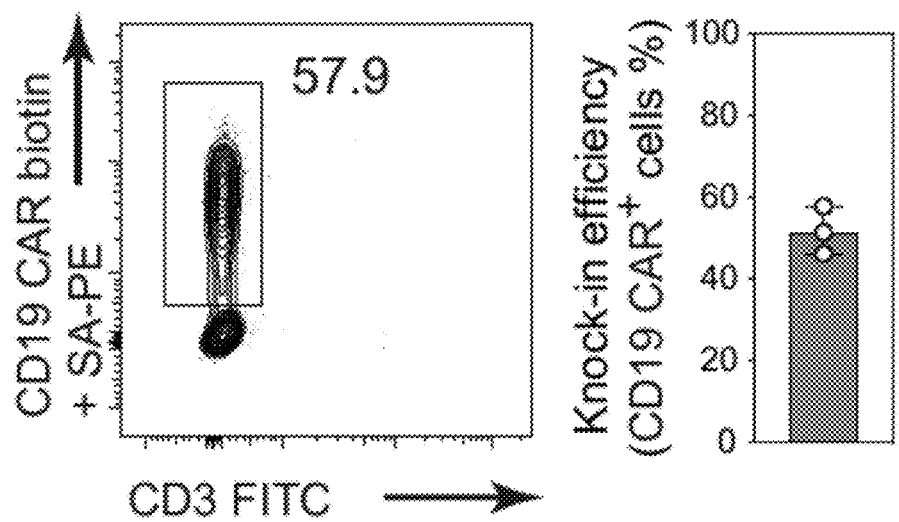
Figure 142H:
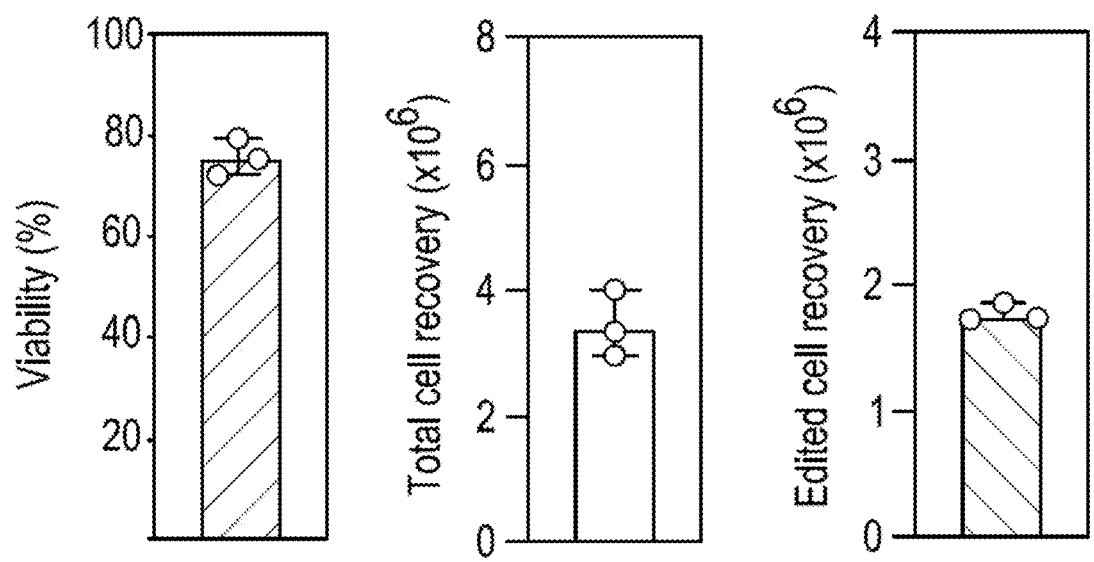
Figure 142I:
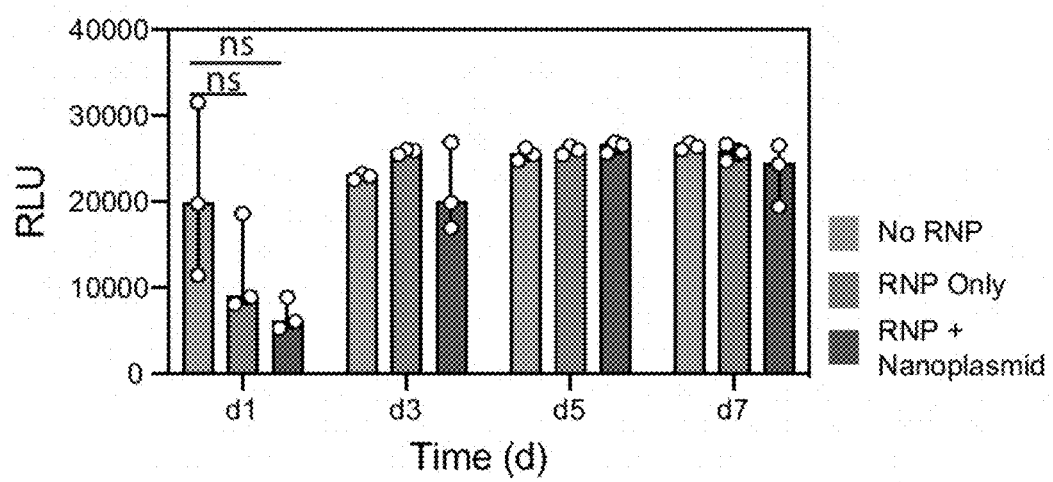
Figure 142J:
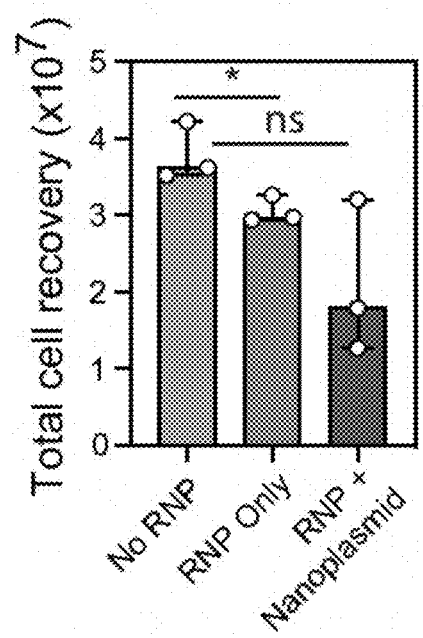

We activated and cultured $CD8^+$ T cells for 48h as before, and co-transfected with sgTRAC and sgTRBC-containing Cas9-RNPs, together with 2 μg of TCR or CAR-encoding nanoplasmids and assessed TCR expression five days later by flow cytometry. We detected 1G4 TCR expression on the surface of 44.9-54% of T cells with minimal impact on cell viability (FIG. 142C, D). Starting with $2 \times 10^6$ CD8 T cells, we recovered between $0.88-2.88 \times 10^6$ 1G4 TCR positive cells five days post electroporation (FIG. 142D). T cells negative for 1G4 expression did not express endogenous TCR complexes on their surface, demonstrating the highly efficient gene knockout (FIG. 142C). Transfections with nanoplasmids encoding the pp65 TCR and CD20 CAR constructs yielded similar results, with 44.4-53.3% and 46.3-57.9% knock-in rates (FIG. 142E, G), respectively and cell recovery of $1.7-3.1 \times 10^6$ edited cells (FIG. 142F, H). Again, the endogenous T cell receptor was knocked out in virtually all T cells (FIG. 142E, G).

Figure 149H:
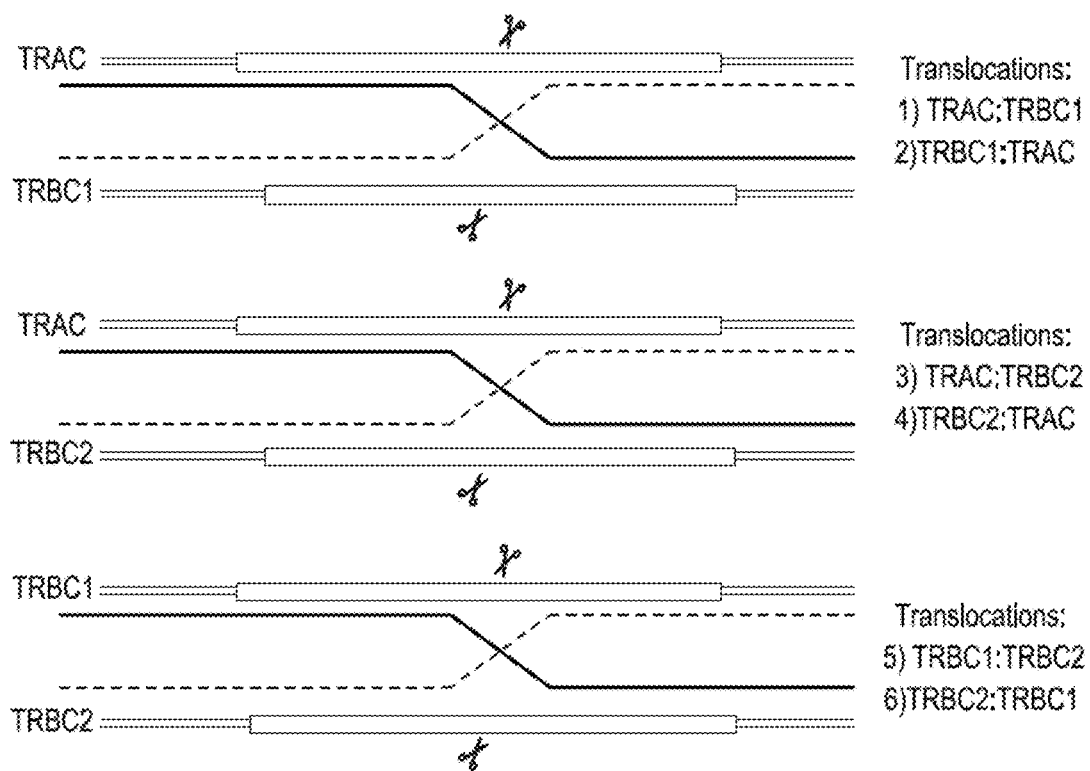
Figure 149I:
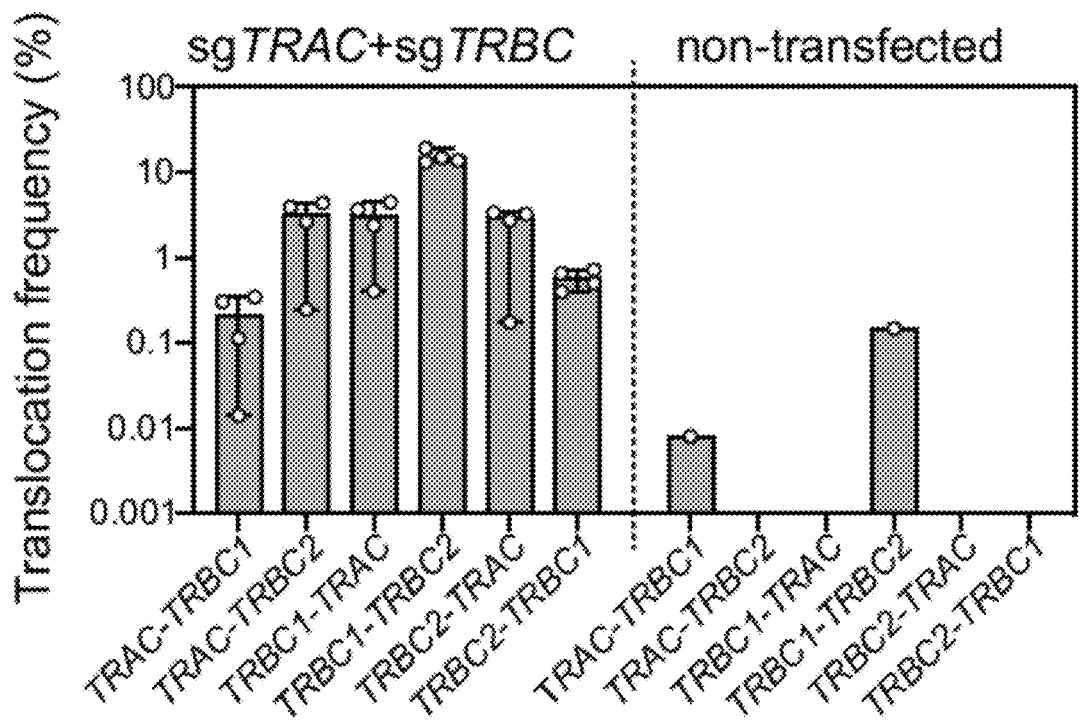
Figure 149J:
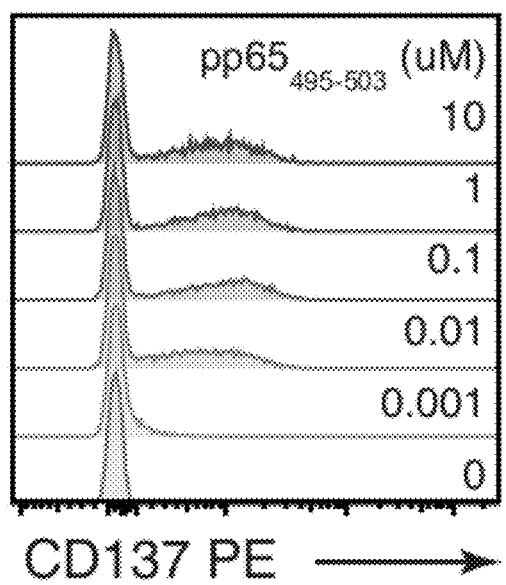
Figure 149K:
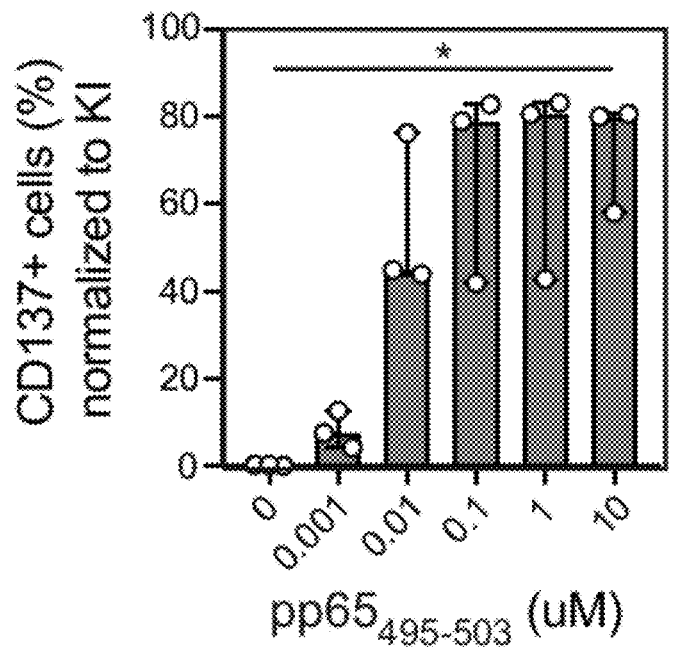
Figure 149L:
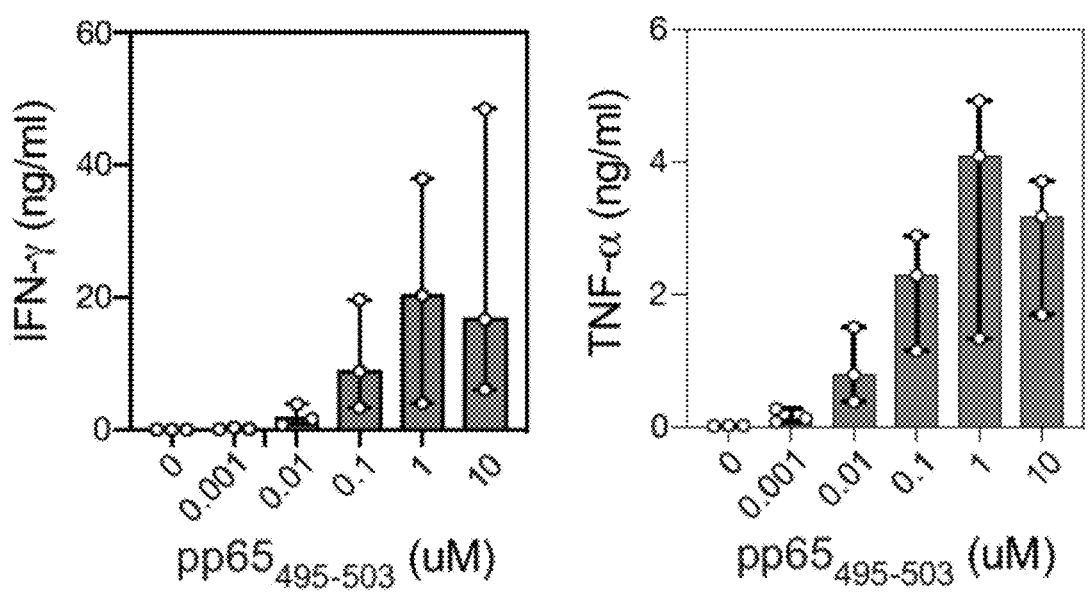
Figure 149M:
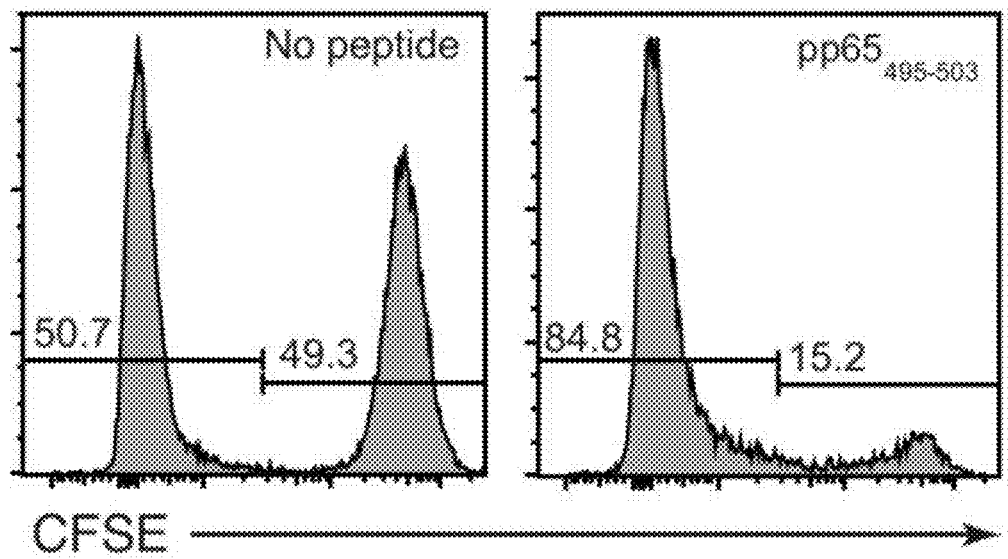
Figure 149N:
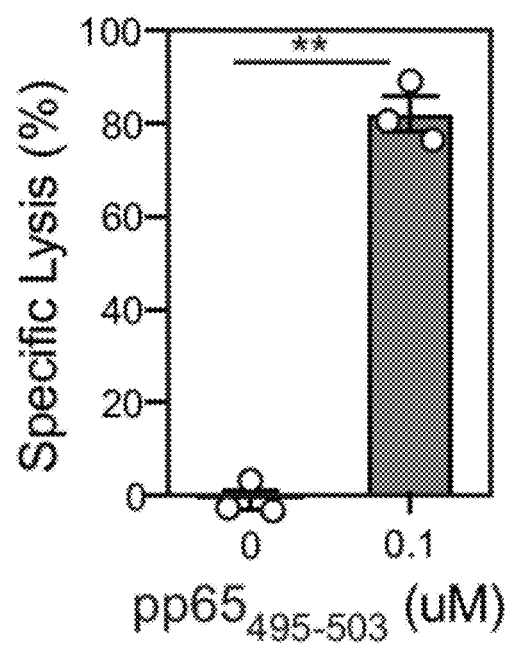

When we performed TCR editing in isolated CD4 T cells, using the same targeting strategy and TCR or CAR donor templates, we observed knock-out and knock-in rates comparable our results with CD8 T cells (FIGS. 149B-G). When attempting simultaneous multiplexed gene editing, such as the TRAC and TRBC knock-in/knock-out approach used here, the occurrence of chromosomal translocations between the cut sites has to be considered. We designed a ddPCR assay to quantify all possible translocation events involving the TRAC, TRBC1 and TRBC2 loci (FIG. 149H). While translocations between the TRAC and TRBC1 or TRBC2 loci occurred with frequencies of 0.01-4.4% depending on the orientation of the translocation and the donor, recombination of the neighboring TRBC1 and TRBC2 loci (corresponding to the deletion of 9.3 kb) occurred with a frequency of 13.1-19% (FIG. 149I). These numbers were in line with or slightly higher than previously reported data (Stadtmauer et al., 2020), likely reflecting the higher editing efficiency of our approach.

We next wanted to determine how the gene editing process, either knock-out (Cas9-RNP only condition) or combined knock-out and knock-in (Cas9-RNP+nanoplasmid) affected the overall expansion of T cells in culture over time. To this end we used the G-Rex culture system that allows for high cell densities and simple media exchanges without the need for splitting or replating over the course of one week. To minimally disturb the cultures, we measured lactate levels, a proxy for cell metabolism and culture performance, on days one, three five and seven post electroporation in addition to final cell recovery. Our data demonstrated that, as expected, cell growth and metabolic activity was impaired immediately following nucleofection; both the RNP only and the RNP with nanoplasmid conditions show reduced cell numbers compared to non-edited cells (FIG. 142E). However, cells completely recovered by day three and grew similarly to control cells throughout the remaining time in culture (FIG. 142E). Cell recovery on day seven was comparable between control cells and knock-out only condition, and about half compared to control cells for the knock-out/knock-in condition (FIG. 142F). Taken together, our approach enables highly efficient TCR editing, with near complete removal of endogenous TCR from all T cells and introduction of the transgenic TCR in up to 60% of the cells with minimal impact on viability and growth kinetics of the cells.

TCR-Engineered T Cells Recognize and Kill Antigen-Expressing Target Cells

Having demonstrated efficient TCR knock-in, we next wanted to assess whether our TCR-engineered CD8 T cells were functional and able to respond to antigen-expressing target cells. To this end, we harvested T cells engineered to express the NY-ESO1-reactive 1G4 TCR or CMVA2/pp65495-503 TCR6-2 on day eight and co-cultured them over-night with a HLA-A02:01 positive B cell line pulsed with increasing concentrations of NY-ESO1157-165 or pp65495-503 peptide and measured up-regulation of the T cell activation marker CD137 (4-1BB). No T cell activation was observed in the absence of exogenously added peptide, suggesting that the removal of endogenous TCRs effectively prevented alloreactivities (FIG. 143A-D). We observed a peptide concentration-dependent up-regulation of CD137 expression for both TCRs (FIG. 143A-D). The EC50 concentration was 0.001 μM for the 1G4 TCR (FIG. 143B), and about 0.01 μM for TCR6-2 (FIG. 143D).

To demonstrate antigen-specific target cell killing, we labeled B cells with CFSE and pulsed them with 0.1 μM peptide. We then co-cultured TCR-engineered T cells over-night with a 1:1 ratio of CFSE-labeled antigen positive and non-labeled antigen-negative B cells, and determined specific lysis of antigen-pulsed B cells by measuring the ratio of CFSE positive to CFSE-negative cells. For both NY-ESO1 and pp65 antigens, we observed-80% target cell-specific lysis at a 1:1 effector to target cell ratio (FIG. 143E-H), demonstrating highly potent cytotoxic potential of our TCR edited cells.

To demonstrate activity against target cells with endogenous antigen expression, we fluorescently labelled A-375 cells, which express the NY-ESO1 antigen, and co-cultured them at a 1:1 ratio with TCR knock-out or 1G4 TCR-expressing T cells. Target cell lysis/apoptosis was captured via real-time microscopy and measured using a caspase cleavage assay. Over the course of eighteen hours, we detected robust target cell lysis in co-cultures with 1G4 TCR expressing T cells but not in control cultures with TCR-negative T cells (FIG. 143I, J). Taken together, CD8 T cells that had undergone TCR-editing using our non-viral plasmid-based approach were activated by their cognate antigen in a concentration-dependent manner and exhibited potent cytolytic activity at a low effector to target cell ratio.

Figure 150C:
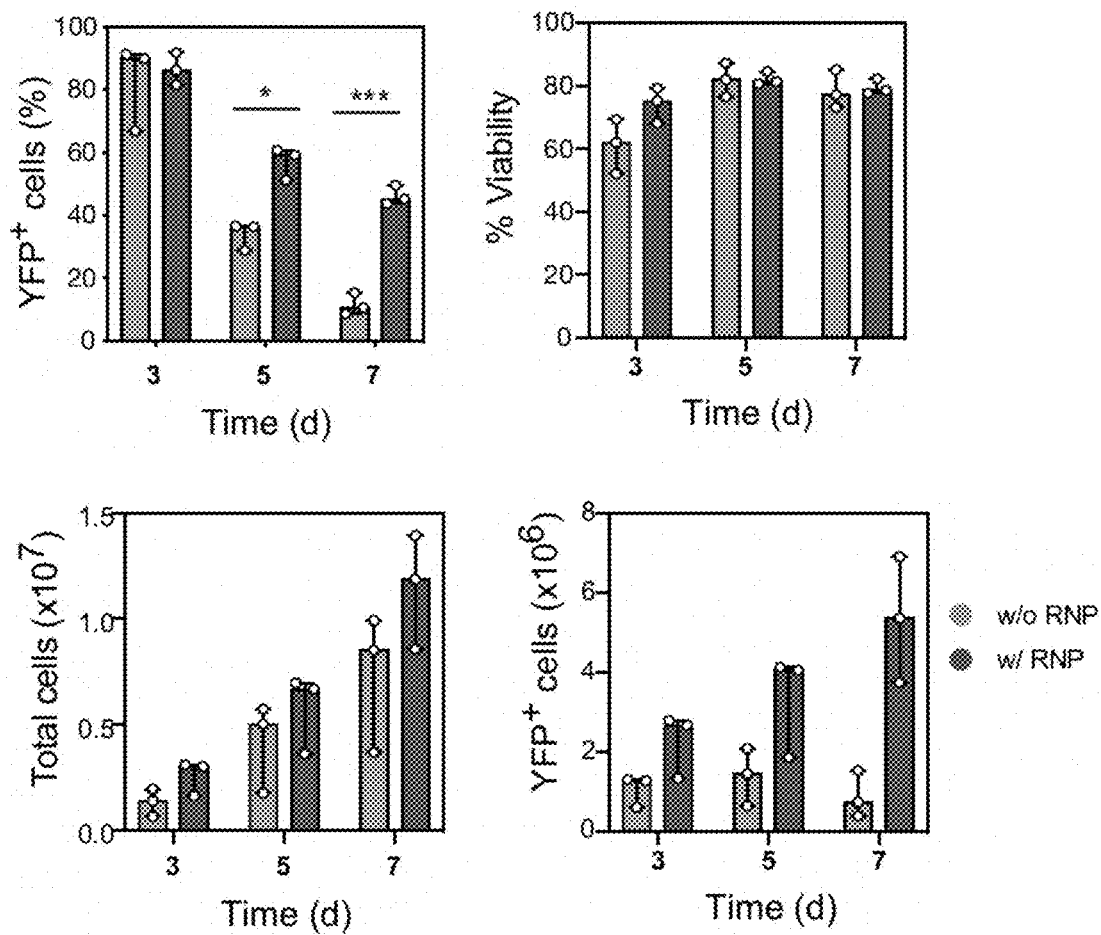
Figure 150D:
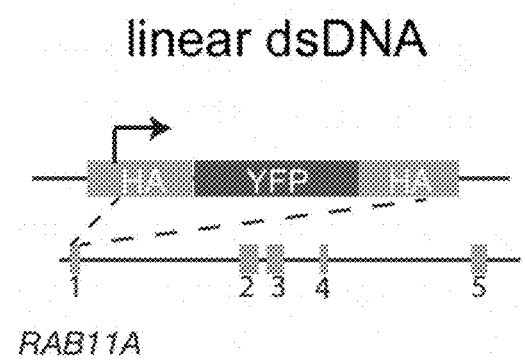
Figure 150E:
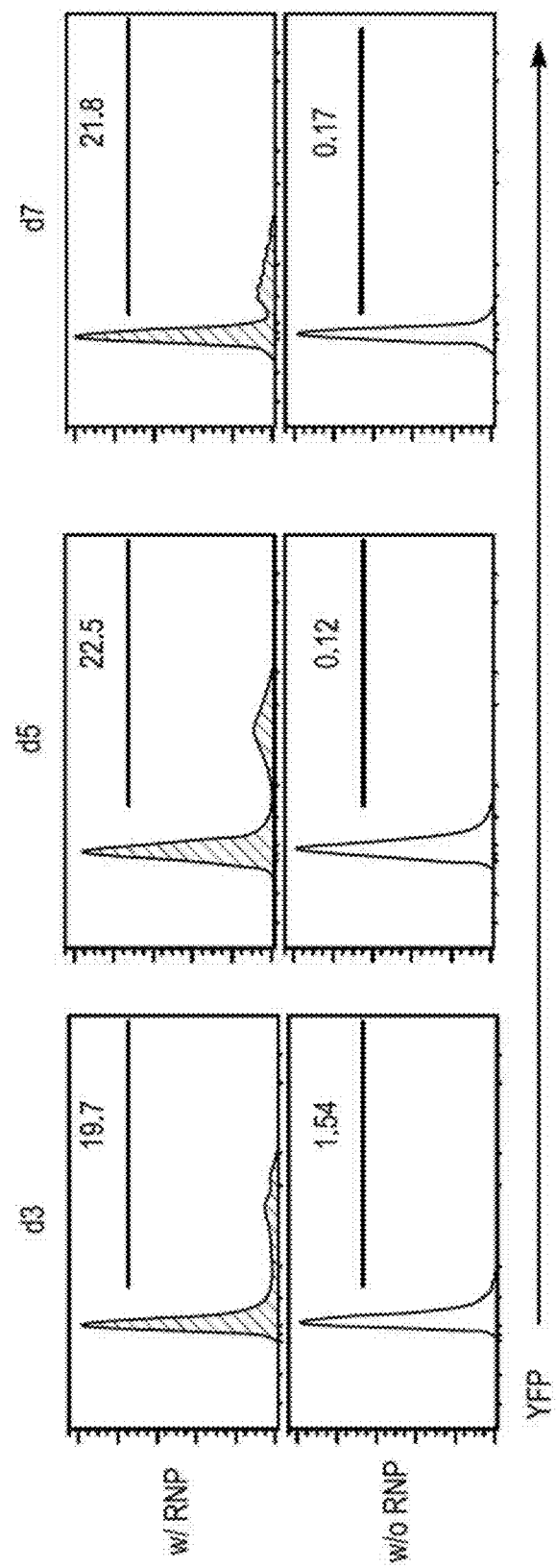
Figure 150F:
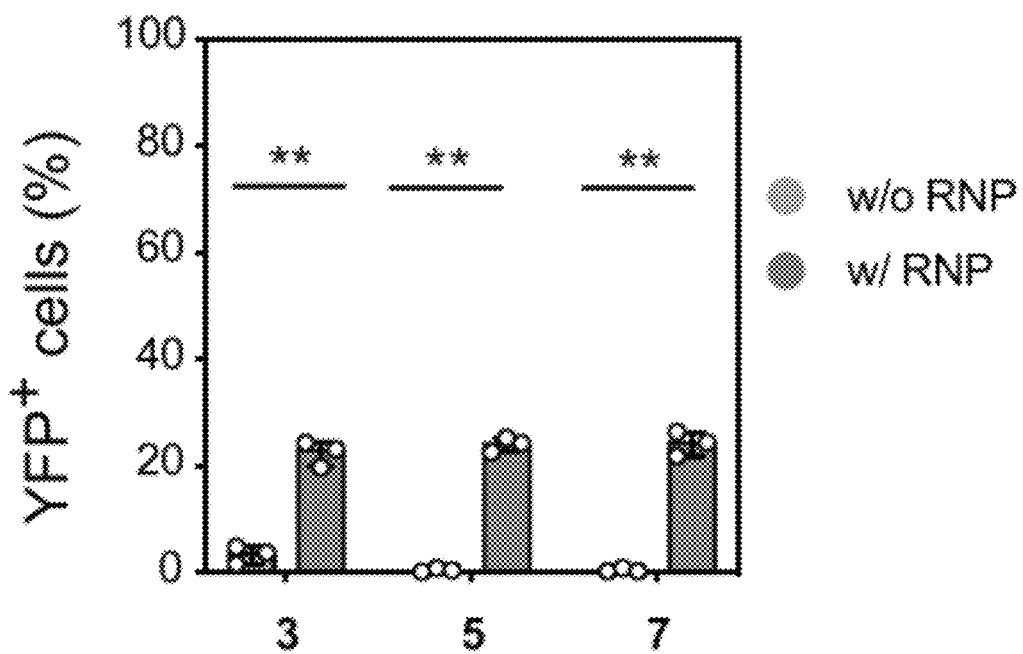
Figure 150G:
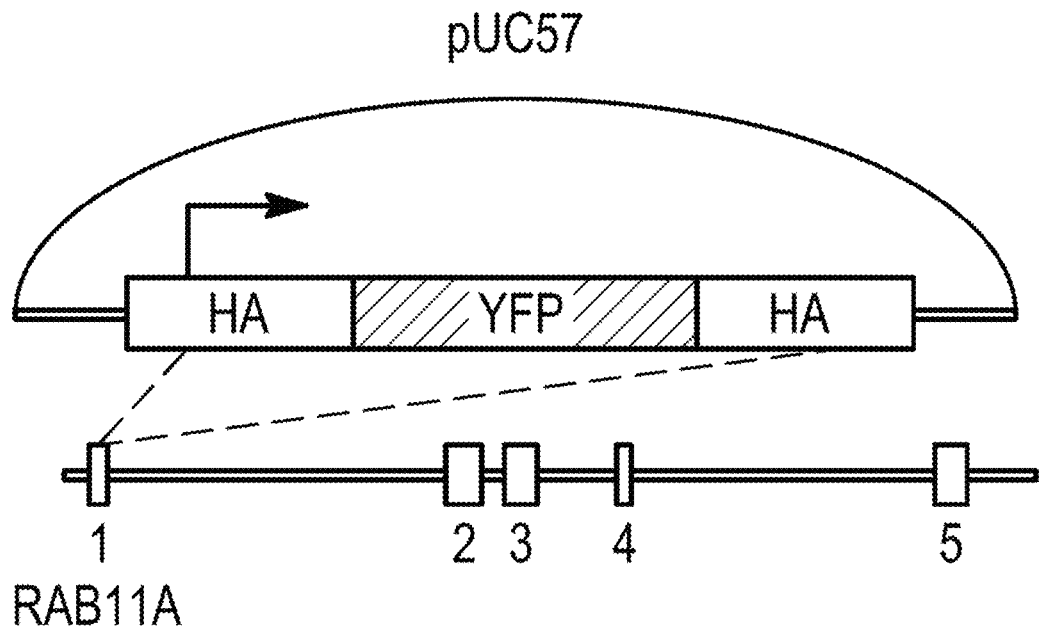
Figure 150H:
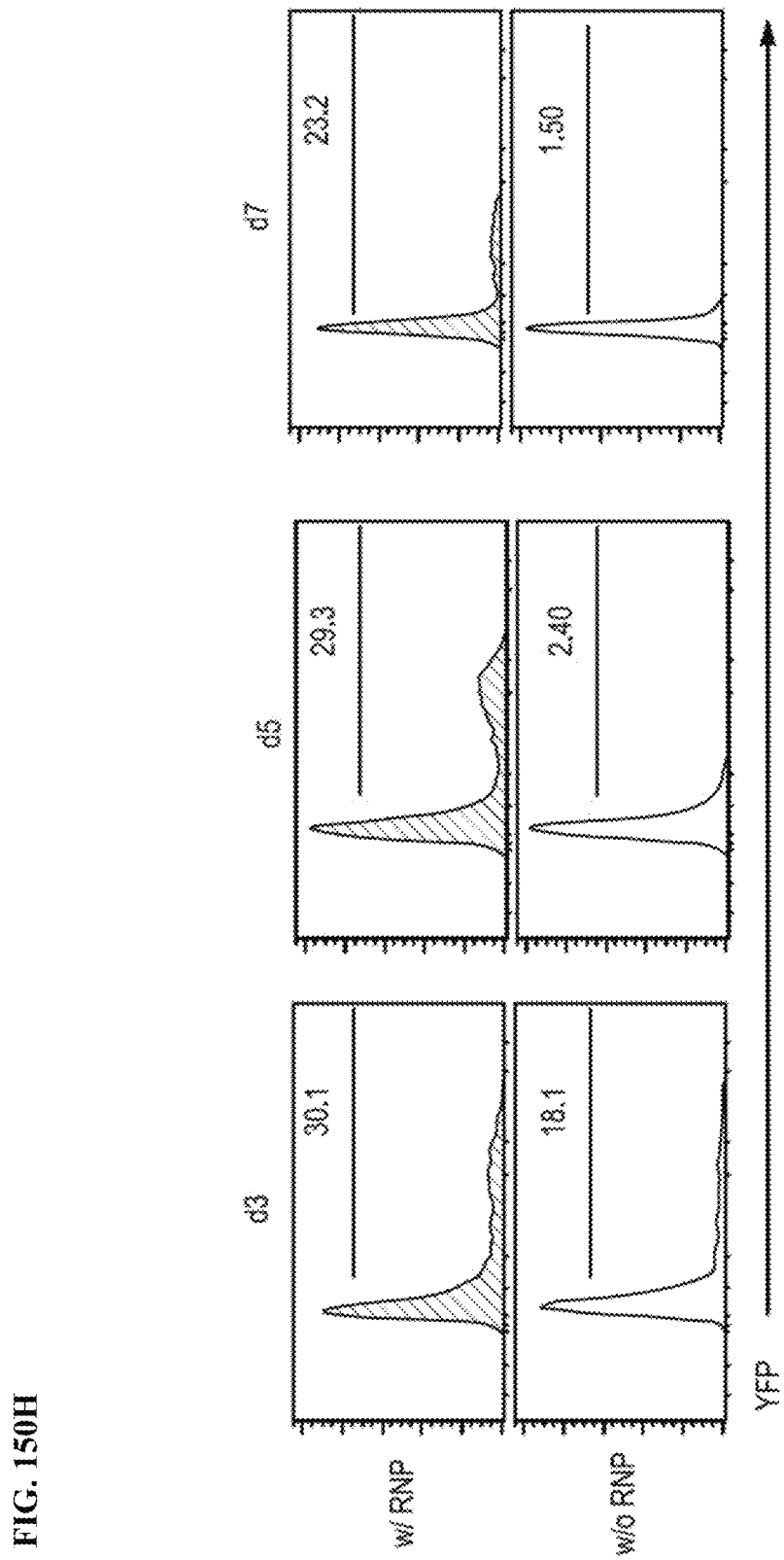
Figure 150I:
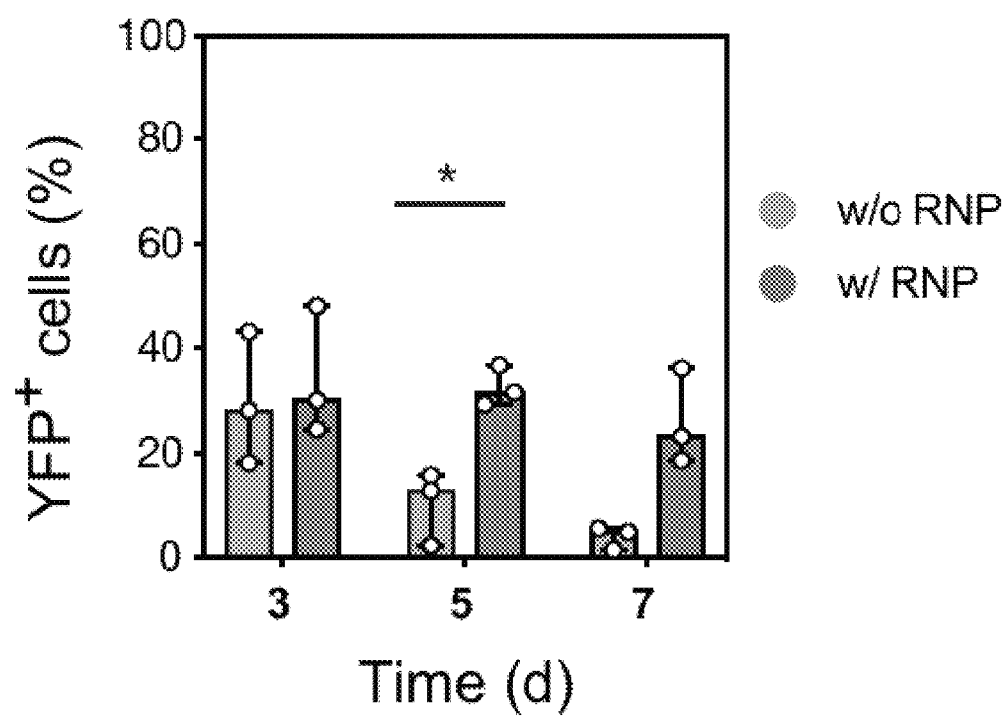

Promoter-Containing Nanoplasmids Enable Targeted Gene Knock-In and Prolonged Transient Gene Expression To assess whether our optimized non-viral CRISPR knock-in approach enabled efficient integration beyond the TRAC locus, we first targeted the RAB11A locus using a homology donor construct encoding a YFP-RAB11A fusion gene (Roth et al., 2018). Importantly, this construct contains the RAB11A promoter, suggesting that YFP expression in transfected T cells could result from the integrated transgene or, at least early after transfection, from the non-integrated donor plasmid. To identify an appropriate time point for accurately evaluation of knock-in efficiency (expression of integrated transgene), we transfected T cells with YFP-RAB11A encoding nanoplasmid, pUC57 or linear dsDNA (FIG. 150A, D, G) without Cas9-RNP (e.g. expression from non-integrated template only) or together with RAB11A-targeting sgRNA/Cas9-RNP (e.g. expression from non-integrated and integrated template). Three days after nucleofection, we observed 66.9-91.3% YFP-expressing $CD8^+$ T cells with nanoplasmid donor template alone and 81.5-91.8% with nanoplasmid and sgRAB11A Cas9-RNP (FIG. 150B, C), demonstrating that expression originated largely from non-integrated nanoplasmid. This transient YFP expression decreased over time to 8.6-15.4% by day seven post-transfection, whereas YFP expression in cells transfected with nanoplasmid plus sgRAB11A Cas9-RNP stabilized at 43.7-49.6% (FIG. 150B, C). Expression from unincorporated YFP-RAB11A nanoplasmid ceased by day nine post-nucleofection, revealing a stable 33.8-42.9% knock-in efficiency under the conditions tested (FIG. 143B, C). Interestingly, this prolonged expression from non-integrated promoter-containing donor templates was a unique feature of the nanoplasmid backbone, as electroporation of the construct encoded by linear dsDNA (FIG. 150D-F) or a pUC57 plasmid (FIG. 150G-I) resulted in no or substantially shorter transient YFP expression, respectively. Stable expression was observed in 18.6-36.2% of cells transfected with sgRAB11A-Cas9/RNP and a pUC57-based template (FIG. 150H, I). These studies demonstrated that when using promoter-containing nanoplasmid donor templates, knock-in efficiency as measured by transgene expression could only be accurately assessed at least seven days post electroporation. At the same time, these findings suggested a unique utility of nanoplasmids for broad applications in transient open-reading frame or reporter gene expression in T cells.

Figure 144A:
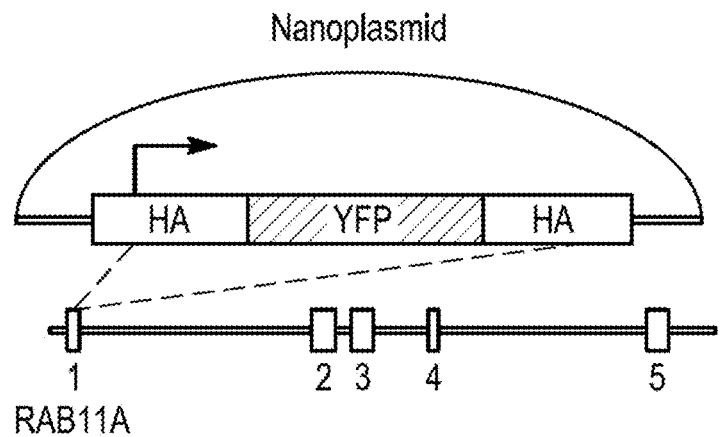
Figure 144B:
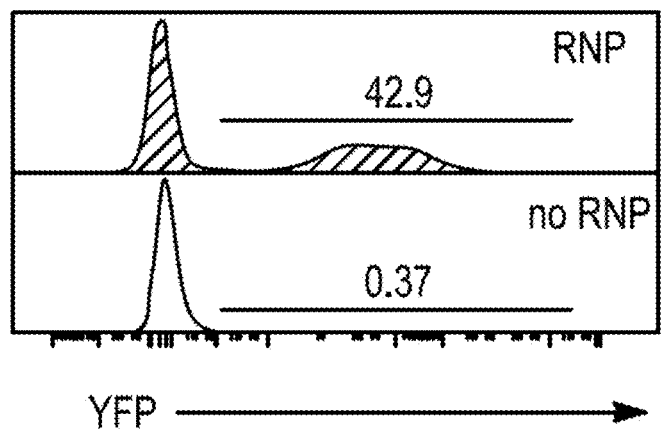
Figure 144C:
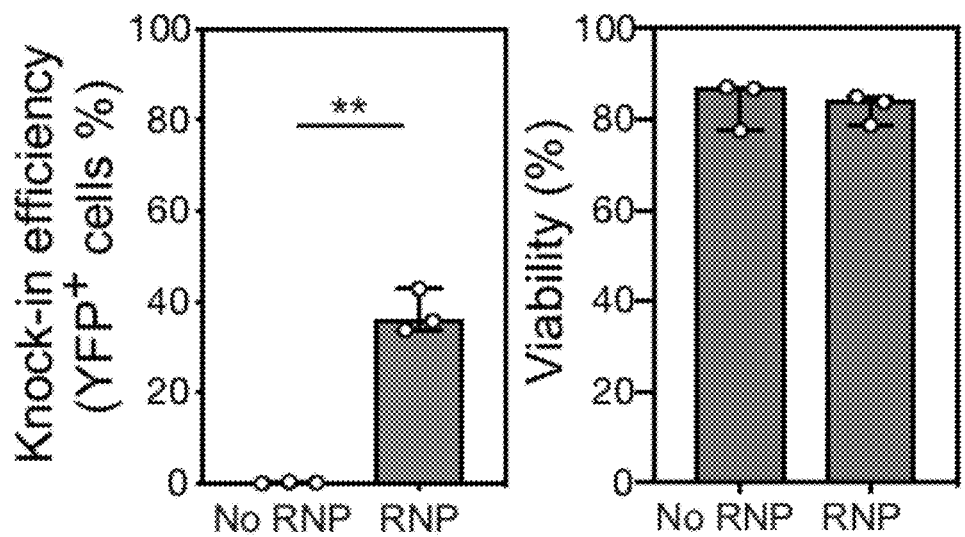
Figure 144D:
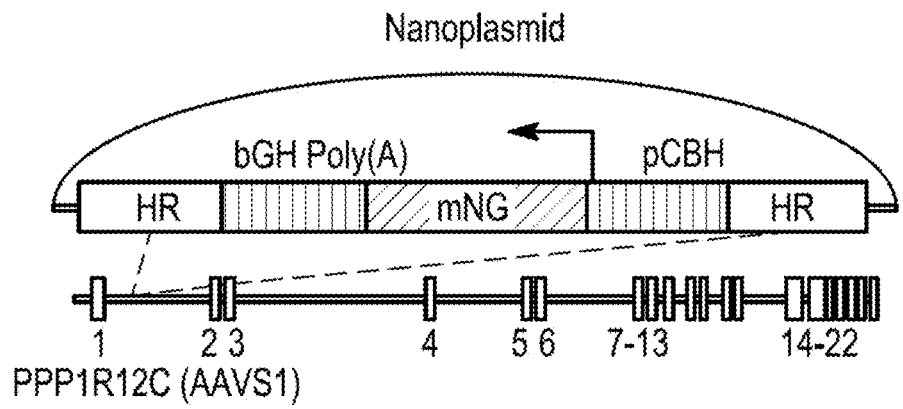
Figure 144E:
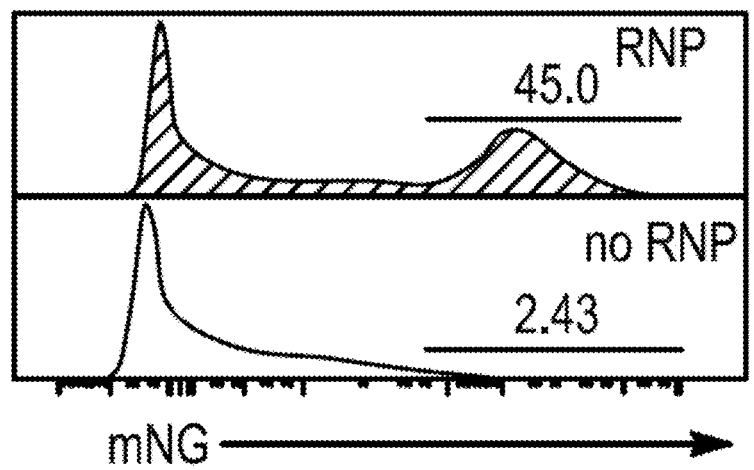
Figure 144F:
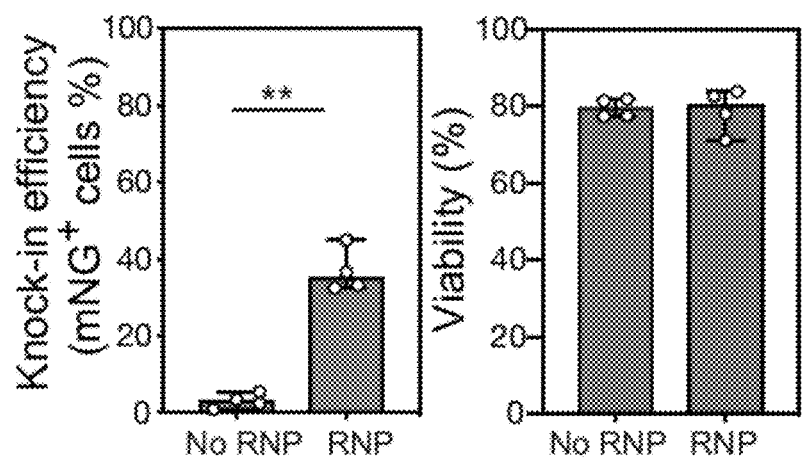

Given these results, we decided to evaluate knock-in rates for the promoter-containing YFP-RAB11A construct in comparison to a transient transfection of the nanoplasmid donor DNA nine days post transfection (FIG. 144A-C). Transient expression had ceased at this time and 33.8-42.9% knock-in rate was detected by flow cytometry (FIG. 144A-C). To extend this evaluation, we targeted the AAVS1 safe harbor locus, in intron 1 of the PPP1R12C (protein phosphatase 1 regulatory subunit 12C) gene, which is not expected to induce adverse physiological effects upon disruption and allows robust expression of exogenously inserted genes (Smith et al., 2008; Hockemeyer et al., 2009; Chu et al., 2015). We designed an AAVS1 homology donor construct (FIG. 144D) expressing mNG under the control of the chicken/beta actin hybrid intron (CBH) promoter (Gray et al., 2011). On day nine post transfection, we observed 32.5-45% knock-in efficiency across four donors tested (FIG. 144E, F). Taken together, our approach enabled targeting of transgenes to safe harbor loci with high efficiency.

T Cells Engineering with Endogenous Reporters of Gene Expression

Figure 144G:
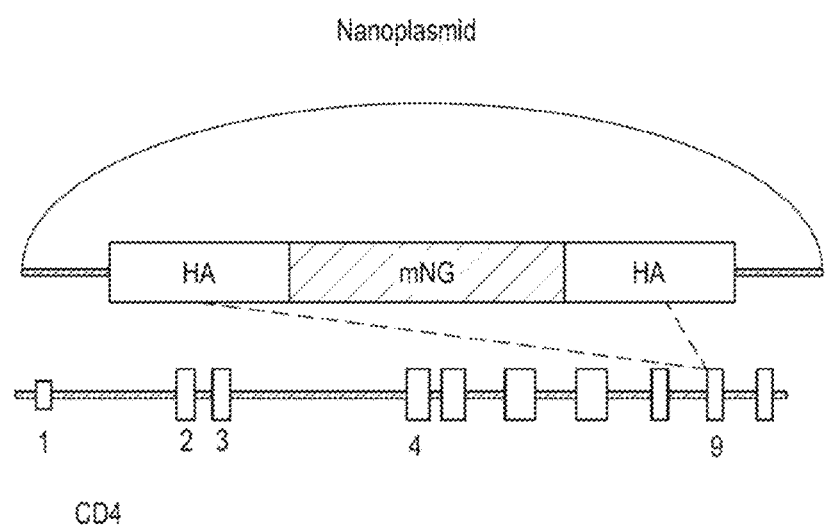
Figure 144H:
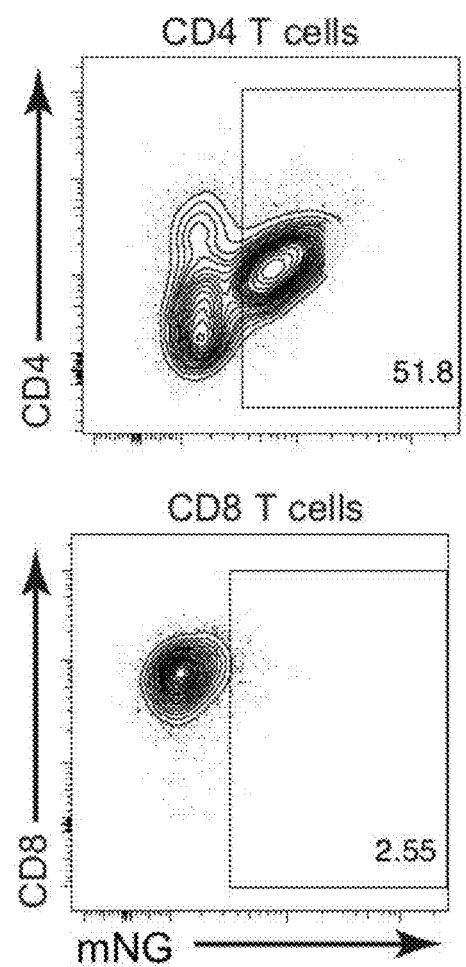
Figure 144I:
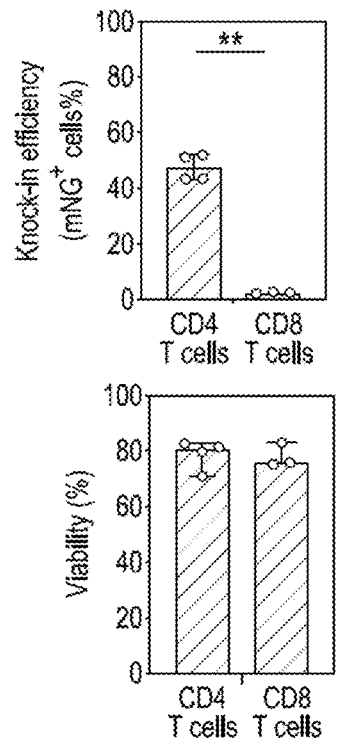
Figure 144J:
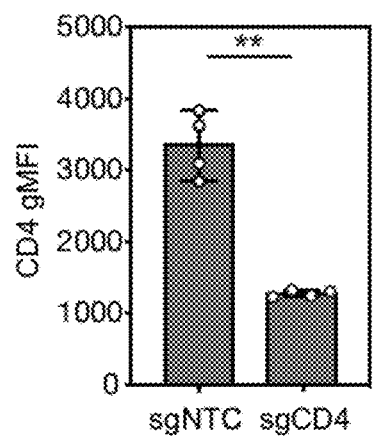

We next targeted the CD4 locus, which is active in $CD4^+$ T cells but inactive in $CD8^+$ T cells, with a nanoplasmid donor template designed to create a bicistronic transcript where the existing CD4 gene is fused in frame at the C terminus with a P2A peptide and mNG (FIG. 144G). When we transfected CD4 T cells with sgCD4 Cas9-RNP and nanoplasmid template, we observed 43-51.8% of the cells concomitantly expressing mNG and CD4, whereas no mNG expression was observed in $CD8^+$ T cells (FIG. 144H, I). CD4 expression levels in CD4 T cells that had successfully integrated the mNG gene were lower (on average about half) than in control CD4 T cells transfected with a non-targeting control guide RNA (FIG. 144J), suggesting that in most cells only one CD4 allele was successfully recombined, whereas the second allele was modified by NHEJ, likely resulting a loss-of-function mutation.

Figure 144K:
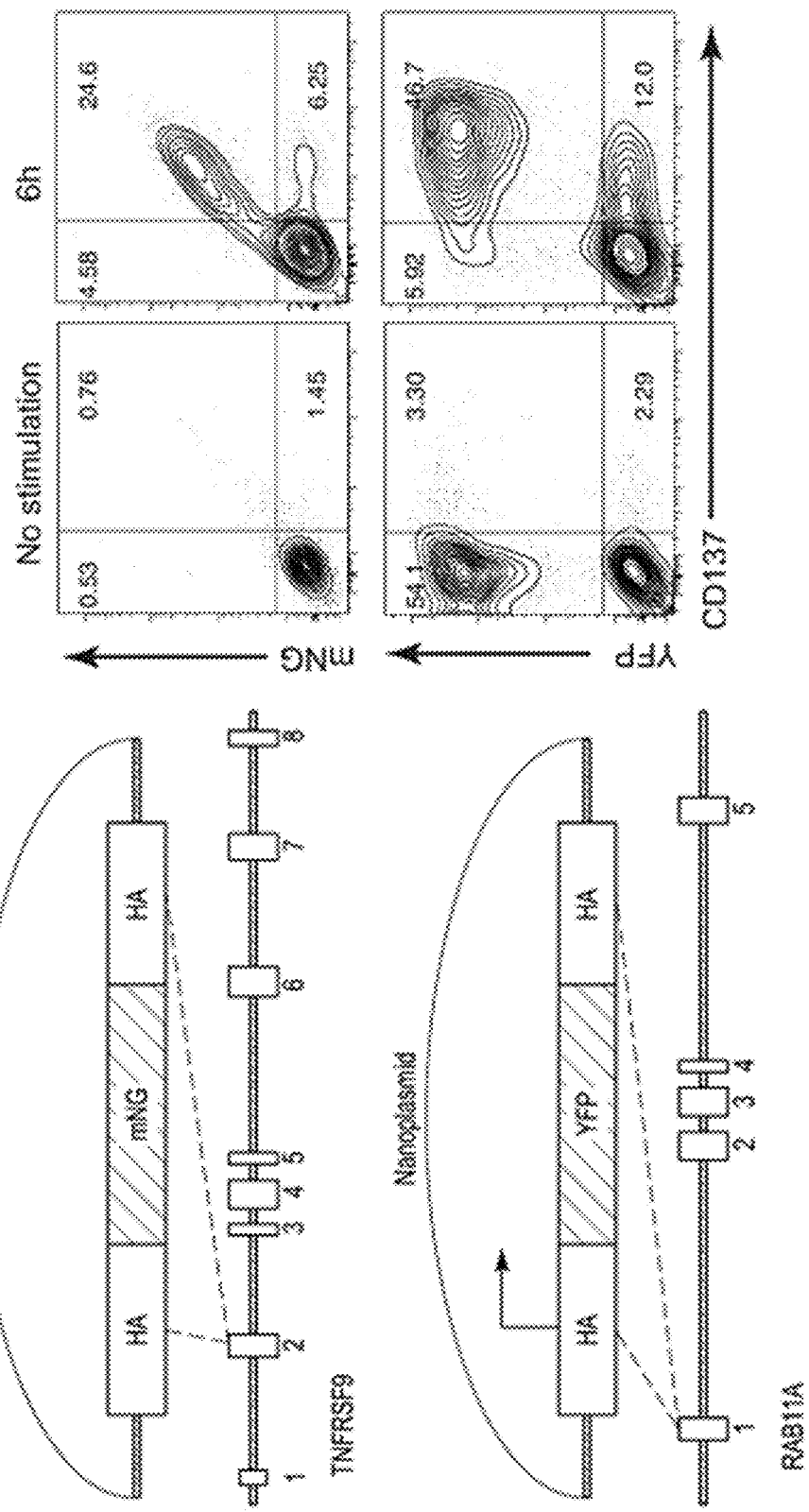
Figure 144L:
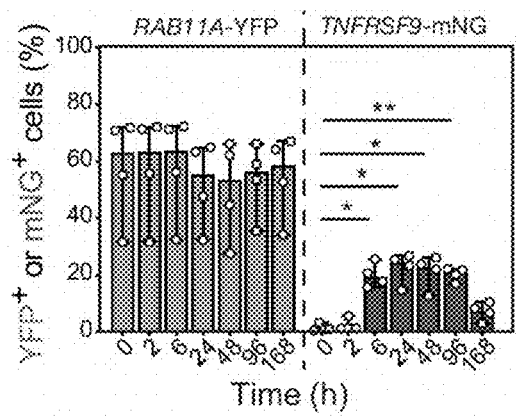
Figure 144M:
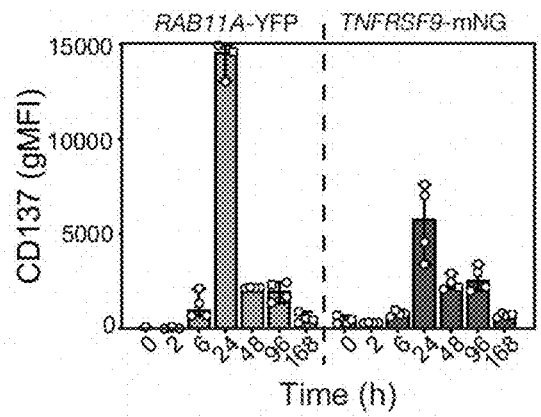

We next attempted to generate a reporter for T cell activation in primary CD8 T cells by targeting the TNFRSF9 gene, which encodes CD137 (Ward-Kavanagh et al., 2016), and is transiently up-regulated following TCR activation. We designed a nanoplasmid donor with a CD137 reporter construct that targeted the first coding exon (exon 2) of the TNFRSF9 gene and inserted mNG followed by P2A in frame with the N-terminus of CD137, thus generating a CD137 reporter gene (FIG. 144K). As a control, we included a constitutively expressed RAB11A-YFP construct. After nucleofection, we cultured $CD8^+$ T cells for ten days in order for any CD137 expression stemming from the initial T cell activation to subside before re-activating with TransAct. We then followed mNG expression by flow cytometry over the course of seven days. RAB11A-YFP transfected cells constitutively expressed YFP, irrespective of TCR activation, and up-regulated CD137 expression by 6h following reactivation (FIG. 144K, L). In contrast, CD8 T cells transfected with TNFRSF9-mNG construct did not express mNG or CD137 without reactivation or 2h post reactivation, but up-regulated and co-expressed both as early as 6h after activation (FIG. 144K, L). mNG expression faithfully recapitulated CD137 expression for seven days (168h) after TCR activation (FIG. 144L), reaching a maximum at 24 h and declining between days four and seven post activation. Similar to our observation with the CD4 reporter, we found that the expression level of CD137 itself was reduced by about half in cells that expressed the mNG reporter (FIG. 144M), again suggesting that only one allele had incorporated the reporter, whereas the second TNFRSF9 allele had been disrupted. Our data demonstrated that knock-in fusion constructs reliably reported transcriptional activity in primary human T cells. However, absolute target gene expression levels may differ between transgenic and wt cells, owing to incomplete (non-homozygous) gene editing. Improved construct designs, targeting strategies, or transgenic cell selection methods may help to minimize these effects.

Efficient Multiplexed Gene Knock-In in Human T Cells

Figure 145A:
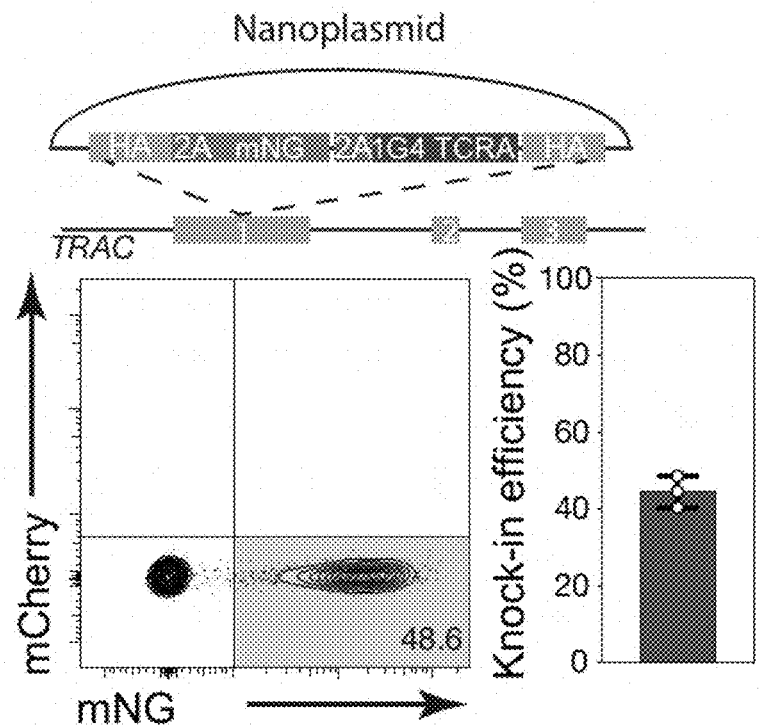
Figure 145B:
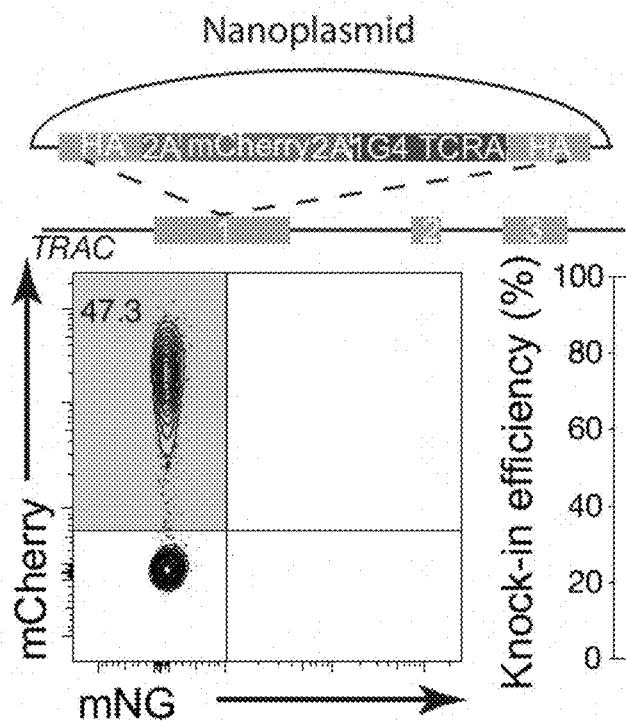
Figure 145C:
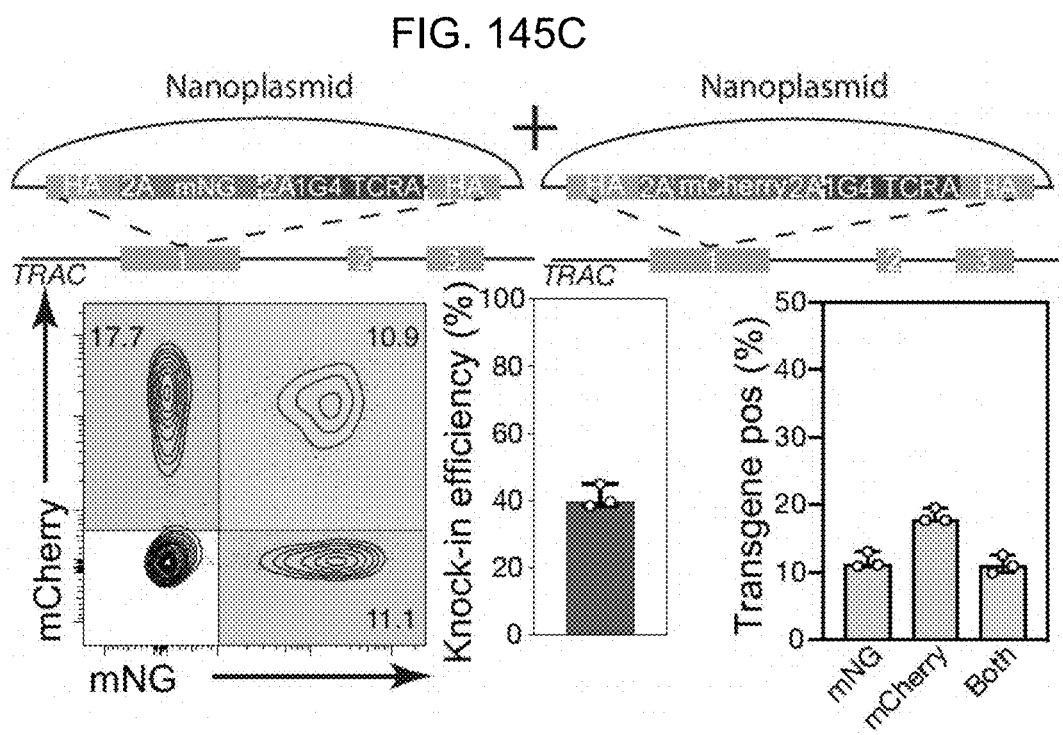
Figure 151A:
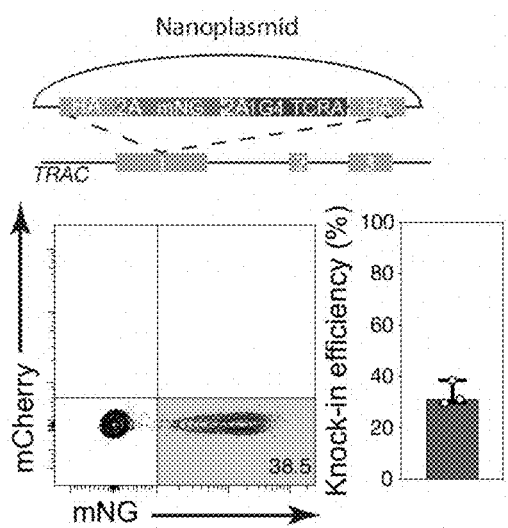
Figure 151B:
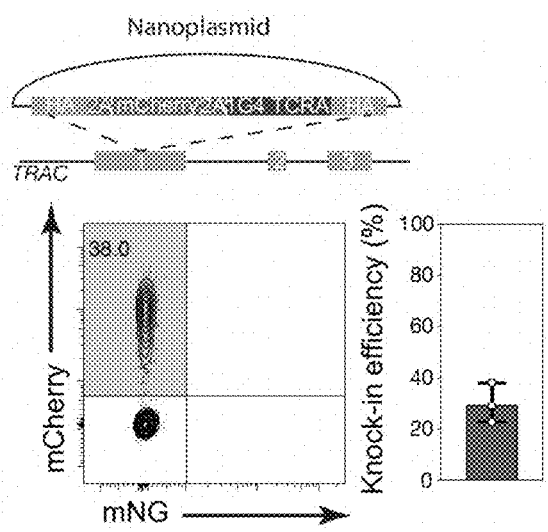
Figure 151C:
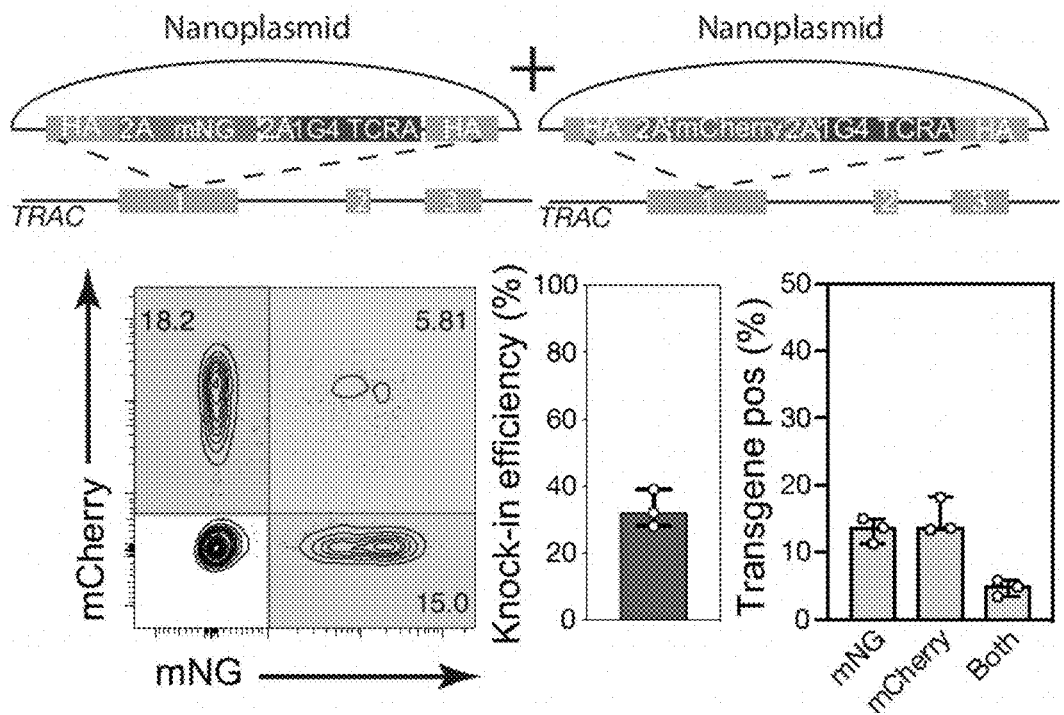
Figure 151B:
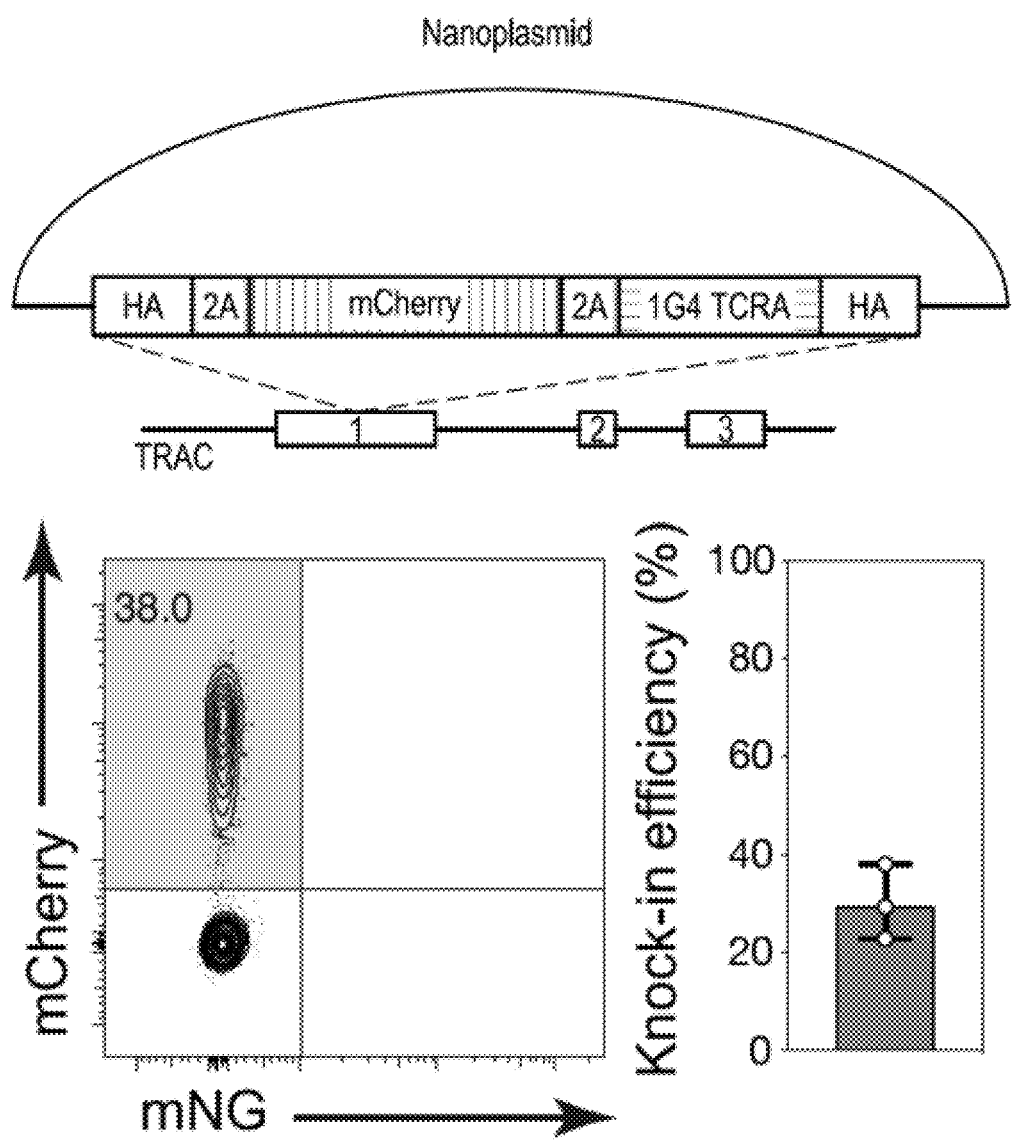
Figure 151D:
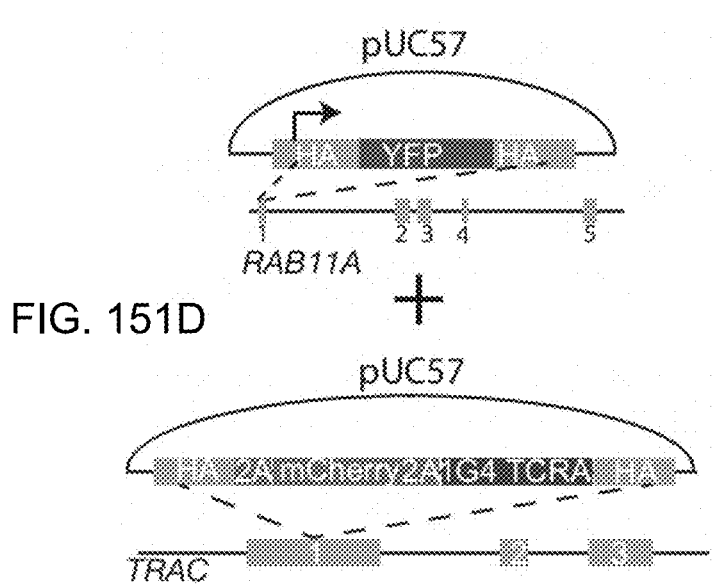
Figure 151E:
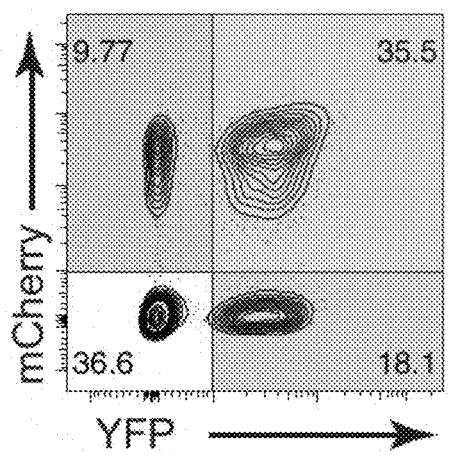
Figure 151F:
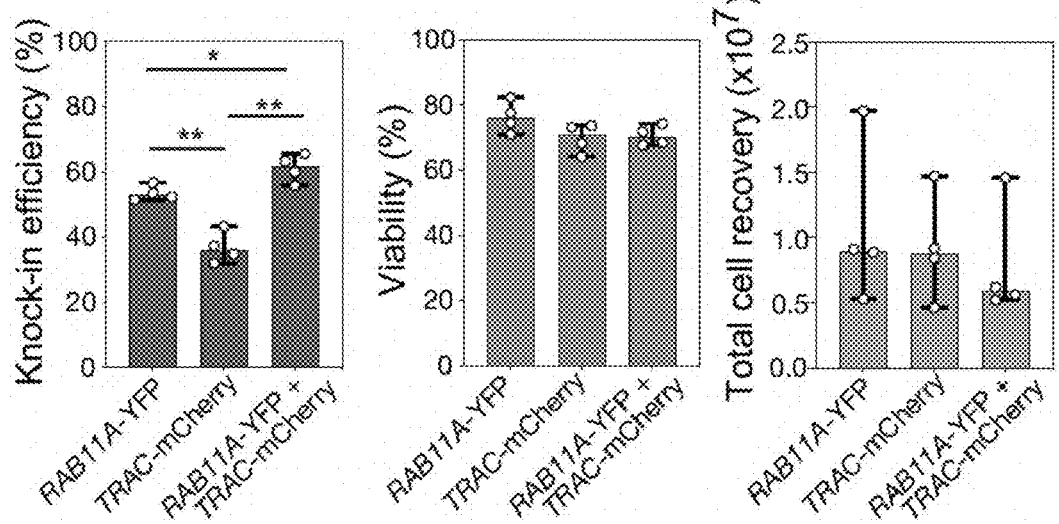
Figure 151G:
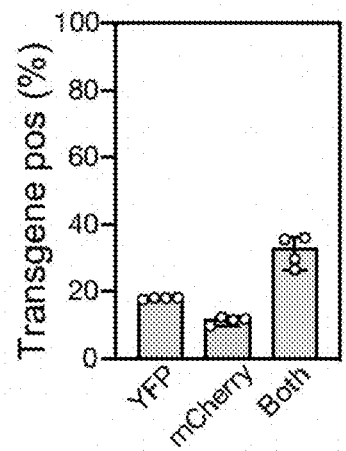

Given the reduced target gene expression observed with our knock-in reporters, we wanted to further assess the potential for biallelic transgene integration with our approach. In order to do so, we nucleofected CD8 T cells with TRAC-targeting nanoplasmid templates (identical homology arms) carrying mNG or mCherry reporter genes individually (FIG. 145A, B) or combined in equal quantities (FIG. 145C). The mNG and mCherry constructs alone resulted in 40.4-48.6% and 43.9-47.3% knock-in efficiency, respectively (FIG. 145A, B). When both donor templates were co-transfected, the overall knock-in rate remained at 38.5-45% (FIG. 145C). Of all T cells in culture, 10.9-13% expressed mNG only, 17.7-19.5% expressed mCherry only, and 9.9-12.5% expressed both reporters and had therefore undergone biallelic transgene integration (FIG. 145C). Of note, this experimental strategy will underestimate the true rate of biallelic integration, given that the single-positive cell population detected by flow cytometry may bear either one or two copies of the same donor template. However, at least 25% of the cells that successfully integrated the donor template did so on both alleles. Overall knock-in rates were slightly lower when using equivalent pUC57 plasmid templates (22.9-39%) and only 3.5-5.8% of all cells had a detectable biallelic integration (FIG. 151A-C).

Engineering of complex genetic circuits or multiplex reporter assays may require more than one gene edit at different loci for full effectiveness. Therefore, we assessed our protocol for integration of two homology donor templates at distinct genomic loci. We first tested a combination of a nanoplasmid donor containing the YFP-RAB11A transgene with a construct encoding mCherry-P2A as an in-frame fusion with the TRAC constant region (FIG. 145D). We transfected CD8 T cells with either construct alone or the combination of both together with the respective sgRAB11a and sgTRAC Cas9-RNPs and assessed reporter expression by flow cytometry ten days later. When transfected with YFP-RAB11A or TRAC-mCherry alone, 25.6-37.3% and 43-56.6% of the cells expressed the respective reporters (FIG. 145E, F). Of the cells transfected with both constructs, a total of 61.1-69.4% showed expression of either or both reporters (FIG. 145F). While 7.3-12% of all cells expressed only YFP and 19.4-30.6% expressed only mCherry, 23.2-35% of all cells, which corresponded to about 50% of transfected cells, co-expressed both transgenes (FIG. 145G). Although we had doubled the total amount of nanoplasmid (4 μg) for these experiments, we observed only a minor impact on cell viability and recovery (FIG. 145F), consistent with our initial nanoplasmid titration study. pUC57-based donor templates targeting the same loci yielded comparable dual knock-in rates (FIG. 151D-G). We obtained similar results when simultaneously targeting the AAVS1 and TRAC loci (FIG. 145H-K). Taken together, these data demonstrated that successful multi-gene knock-in occurred without reduction in the overall targeting efficiency and without interference between the two constructs.

Efficient Non-Viral CRISPR Gene Editing with Large Payloads

Figures 146F, 146G:
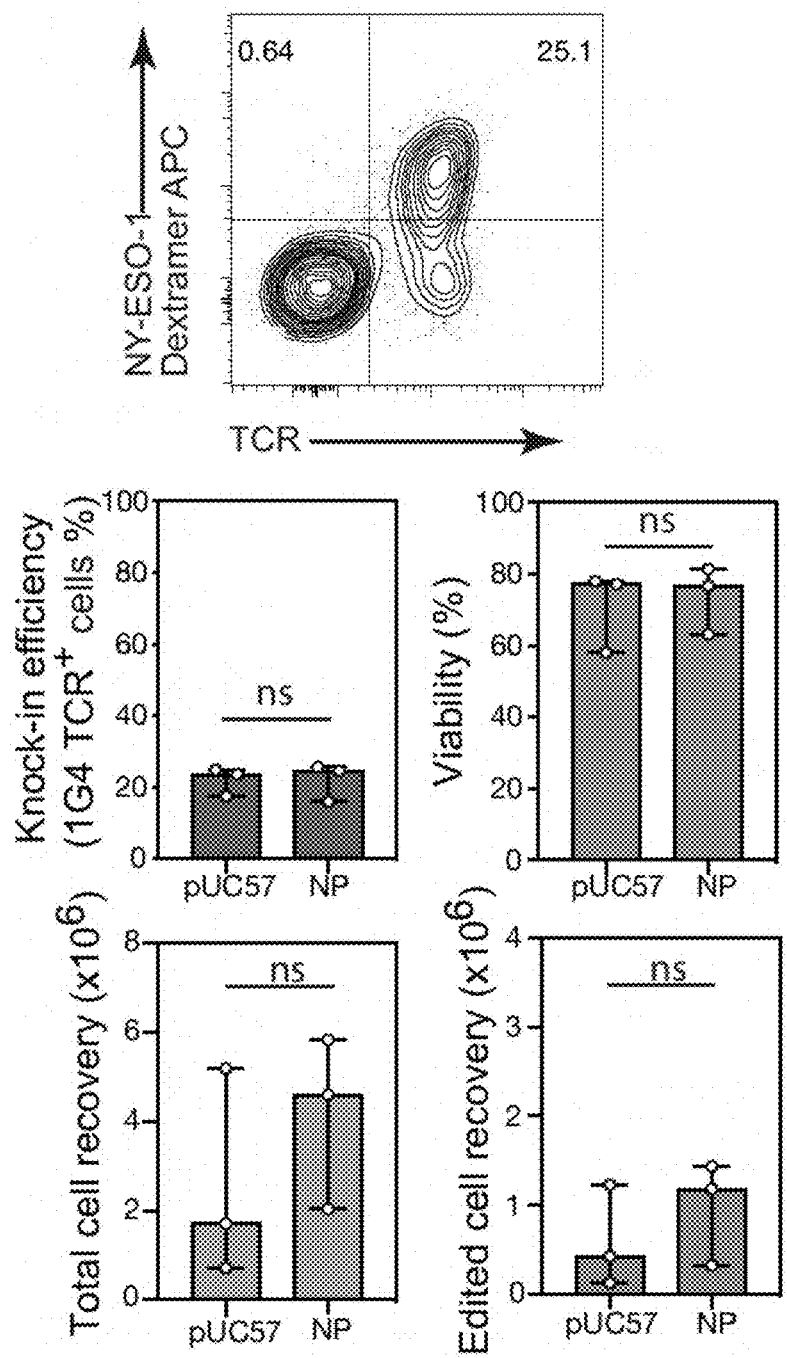
Figure 147A:
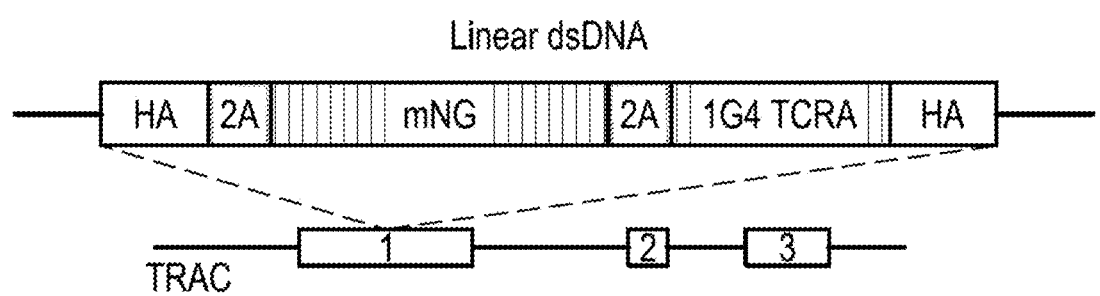
Figure 147B:
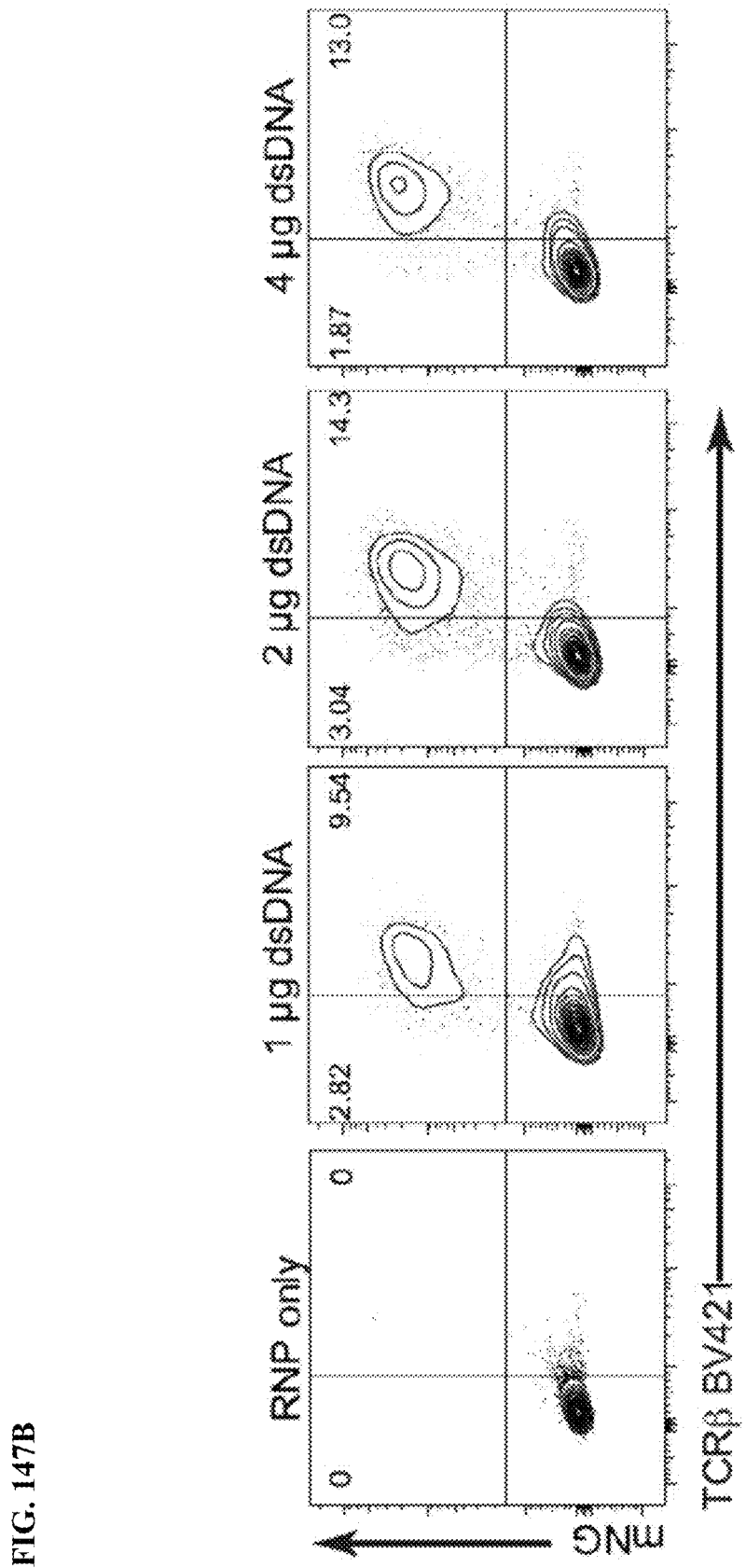
Figure 147C:
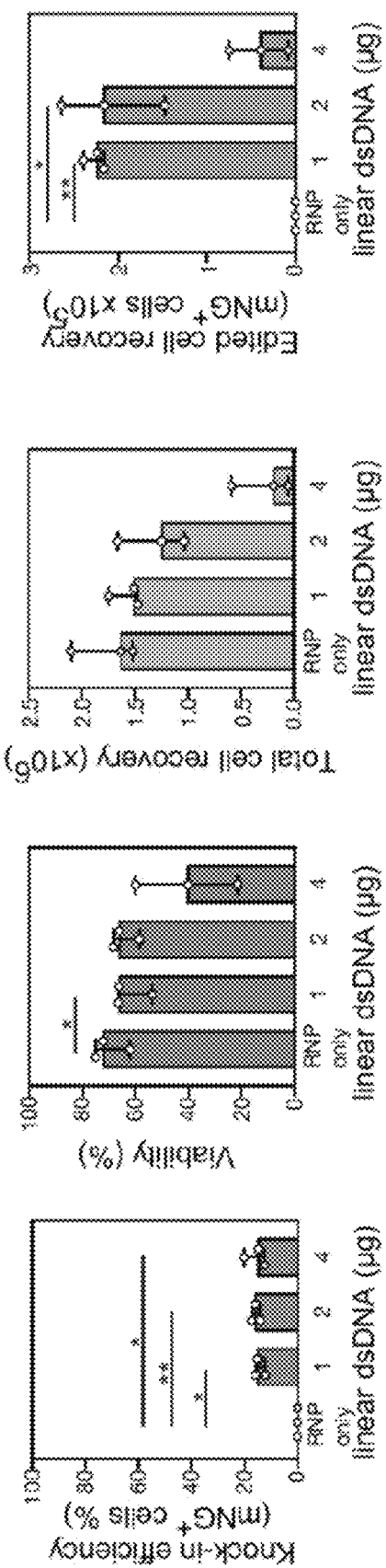
Figure 147D:
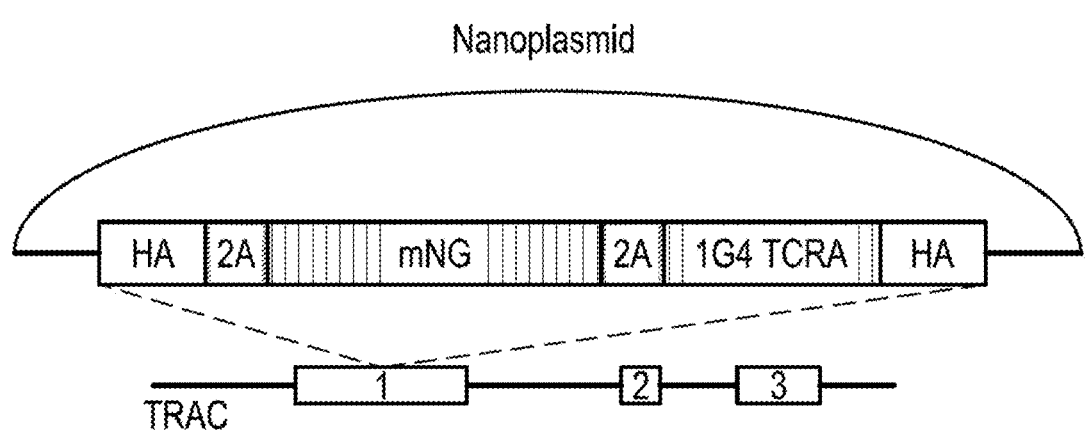
Figure 147E:
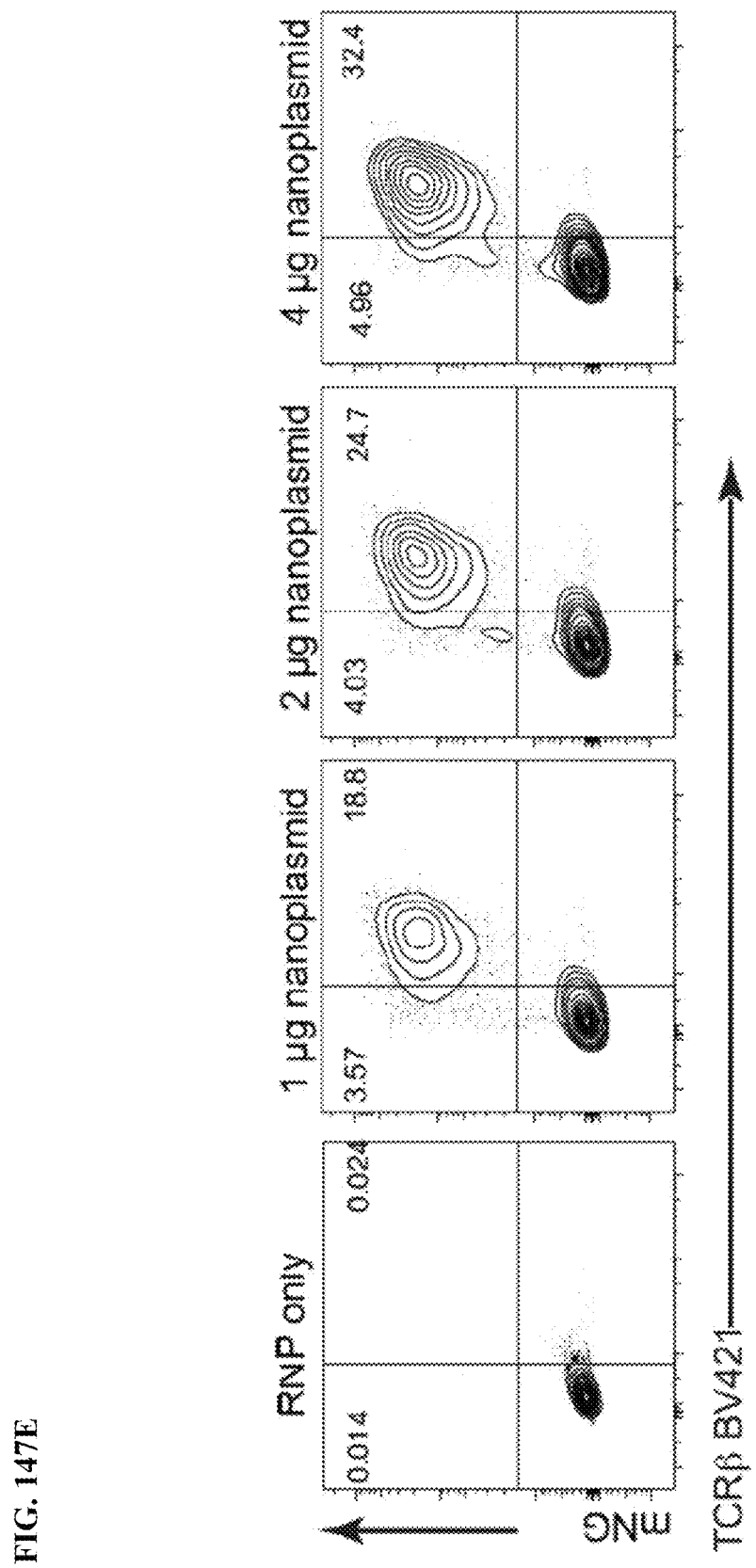
Figure 147F:
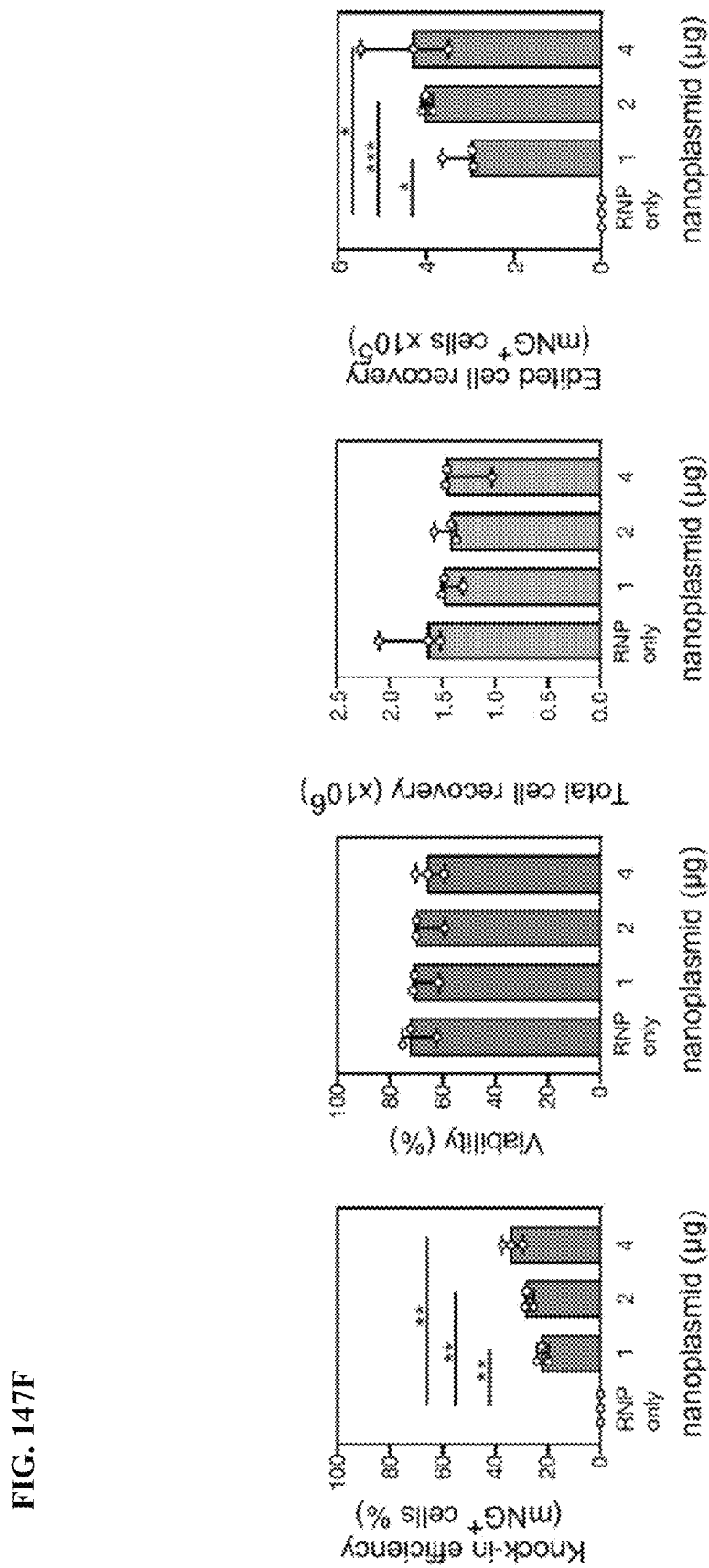
Figure 147G:
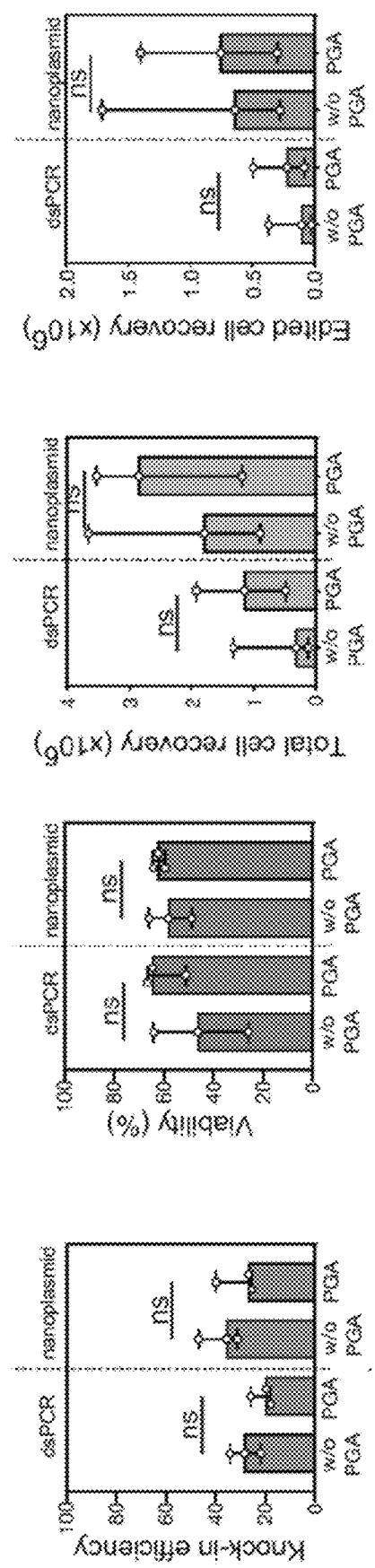
Figure 147H:
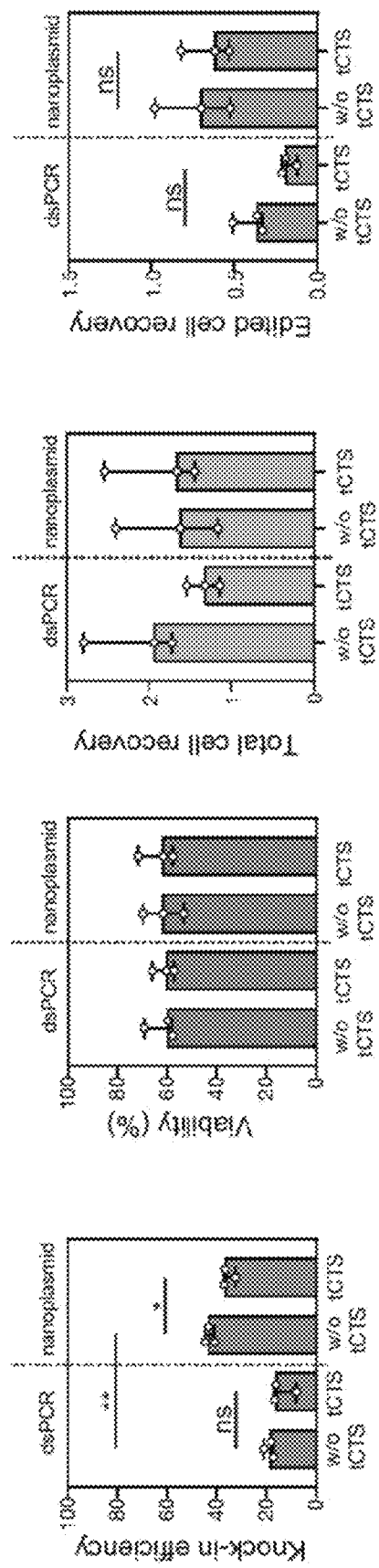

Finally, we sought to investigate whether transgenic payloads of greater size, including those that exceed the limitation of AAV-based homology donors, could be integrated using our optimized targeting strategy. Our NY-ESO1 TCR knock-in construct is 1.5 kb in size. Using the 1G4 template as the framework, we designed a series of constructs of increasing cargo sizes with 0.5 kb homology arms targeting the TRAC locus: the intracellular domain of human Notch1-P2A as an in-frame fusion with mNG-P2A and the 1G4 TCR alpha chain at 3.8 kb (TRAC_NotchICD_mNG); the intracellular domain of Notch1-P2A as an in-frame fusion with the full-length 1G4 TCR at 4 kb (TRAC_NotchICD_1G4), and the gene encoding THEMIS, which plays a regulatory role in both positive and negative T cell selection during late thymocyte development (Fu et al., 2013), as a P2A-in-frame fusion with the full length 1G4 TCR at 5.45 kb (TRAC_Themis_1G4, FIG. 146A). We transfected CD8 T cells with sgTRAC/Cas9-RNP and nanoplasmid or pUC57-based donor templates. For the 3.8 kb TRAC_NotchICD_mNG construct, we obtained 38.9-40.6% and 44.1-49.9% knock-in frequencies with the pUC57 and nanoplasmid templates, respectively (FIG. 146B, C). Transfection of the 4 kb TRAC_NotchICD_1G4 construct resulted in 27.1-30.5% (pUC57) and 28.6-32.8% (nanoplasmid) knock-in rates (FIG. 146D, E). The 5.45 KB TRAC_Themis_1G4 donor yielded 17.5-24.9% (pUC57) and 16-25.7% (nanoplasmid) transgene expressing T cell (FIG. 146F, G). A trend towards higher cell recovery with nanoplasmid DNA donors was observed for two of the three constructs, but did not reach statistical significance (FIG. 146C, E, G). Generally, knock-in efficiencies and cell recovery were comparable for the pUC57 and nanoplasmid formats for these longer donor templates, which is likely due to the plasmid backbone accounting for a lower percentage of the overall DNA amount delivered to the T cells. The data demonstrate that we could increase the payload size more than three-fold to over 5 kb and still achieve more than 20% knock-in rates with our non-viral plasmid-based CRISPR gene editing approach.

Precision gene editing in T cells has the potential to quickly advance our understanding of basic T cell biology and to be transformative for next generation engineered T cell therapies. Emerging approaches that make use of DNA nuclease technologies have enabled mutant gene correction, the introduction of entire genes or gene fusions into a desired location, or the manipulation of regulatory elements; none of which is possible with existing retro- or lentivirus-based methodology (citation Marson review). Several groups have developed protocols to introduce CARs or TCRs into the TRAC locus using AAV vectors together with Cas9 or Cas12a. Often demonstrating ≥50% transgene integration through combined Cas9-RNP electroporation and virus infection, AAV-based gene modification facilitates the generation of T cell populations that can recognize and kill desired target cell types without compromised functionality. These clear benefits of this approach notwithstanding, the use of AAV-based homology donors requires cumbersome and expensive virus production methods (Bak et al., 2018), which currently limits its broader application in the research community. Although sufficient for CAR or TCR editing, the cargo size limit of AAV is 4.8 kb (Salganik et al., 2015).

These limitations have spurred interest in developing entirely non-viral precision gene editing methods for increased versatility and ease of use, faster turn-around times and reduced cost compared to viral gene delivery methods. The first breakthrough in this regard was the demonstration that linear dsDNA donor temples, previously thought too toxic for T cells, could be used successfully to introduce longer DNA segments, including TCRs (citation). However, the achieved knock-in efficiencies when using linear dsDNA donors were modest for TCR editing, relative to AAV-based methods. Although the efficiency of gene editing with linear dsDNA can be improved, as we demonstrated here, the need for production and purification of linear dsDNA in the large quantities required for editing even a relatively small number of T cells limits the versatility and scalability of the approach.

Here, we report a fully non-viral gene editing protocol that takes advantage of readily available plasmid-based donor templates that are co-delivered with high-fidelity Cas-RNPs into T cell populations via electroporation. Through this approach, we achieved knock-in efficiencies at multiple loci (alone or in combination) on par with AAV-based methods, and preserved coincident high knock-out efficiency under multiplex editing conditions, thus realizing the full potential of non-viral editing technology regarding versatility, turn-around time and cost savings. Plasmid donors can be designed and synthesized quickly and inexpensively with high purity. They offer the ability for sequence verification and are amenable to large-scale, Good Manufacturing Practice (GMP)-grade qualification for use in cellular therapies. Importantly, we demonstrate the successful delivery of genetic cargo greater than 5 kb without a steep drop-off in knock-in efficiency compared to smaller transgenes, suggesting that the delivery of even larger constructs is possible. Further, under optimal parameters, the introduction of plasmid DNA had no impact on cell viability and, more importantly, the recovery of edited cells was similar to loss-of-function perturbations using Cas9-RNP alone. We believe that our method will serve as a foundation for unleashing the full potential of precision gene editing in primary human T cells for basic research and clinical applications alike.

Antibodies. All antibodies used for flow cytometric analyses are listed in Table 16.

TABLE 16

| Reagent | Manufacturer | Catalog Number |
| --- | --- | --- |
| Brilliant Violet 421 ™ anti-human TCR α/β Antibody | BioLegend ® | 306722 |
| Propidium Iodide Staining Solution | BD Biosciences | 556463 |
| Fixable Viability Dye eFluor ™ 780 | ThermoFisher Scientific | 65-0865-14 |
| CountBright ™ Absolute Counting Beads, for flow cytometry | Invitrogen ™ | C36950 |
| FcR Blocking Reagent, human | Miltenyi Biotec | 130-059-901 |
| HLA-A*0201/SLLMWITQV/PE or APC Dextramer (NYESO-1) | Immudex | WB3247-PE or APC |
| HLA-A*0201/NLVPMVATV/PE Dextramer (pp65) | Immudex | WB2132-PE |
| CD19 CAR Detection Reagent, human, Biotin | Miltenyi Biotec | 130-115-965 |
| Streptavidin PE | Biolegend | 405204 |
| BV605 CD137 | Biolegend | 309822 |
| FITC Mouse anti-Human CD3 | ThermoFisher Scientific | 11-0037-42 |
| BUV395 Mouse Anti-Human CD8 | BD Biosciences | 563795 |

Guide RNAs. Where applicable, *S. pyogenes* Cas9-based targeting sequences (20 mers) were identified using a custom sgRNA design tool. Guide RNAs were selected based on their predicted target specificity utilizing the Cutting Frequency Determination (CFD) specificity score as an off-target specificity prediction algorithm (Doench et al., 2016), as well as two on-target cutting efficiency scores, the Azimuth algorithm, a version of the popular Rule Set 2 on-target cutting efficiency prediction algorithm (Doench et al., 2016) and the DeepCas9 algorithm (Wang et al., 2019). It is critical to select several guide RNAs around the desired targeting site and to test them empirically. Guide RNAs targeting the TRAC and TRBC loci were previously described (Roth et al., 2018). All sgRNA sequences are listed in Table 17 All guide RNAs were ordered as Alt-R® CRISPR-Cas9 sgRNAs from Integrated DNA Technologies (IDT).

TABLE 17

| sgRNA | Sequence |
| --- | --- |
| sgTRAC | AGAGTCTCTCAGCTGGTACA |
| sgTRBC | GGAGAATGACGAGTGGACCC |
| sgRAB11A | GGTAGTCGTACTCGTCGTCG |
| sgCD4 | GGCAGGTCTTCTTCTCACTG |
| SgTNFRSF9 | GTTGAGGACCAGCAACAGAG |
| sgAAVS1 | GGGACCACCTTATATTCCCA |

HDR donor template design. Donor templates were designed in SnapGene (GSL Biotech, LLC). To design long homology-directed repair templates, the Cas9 cut site of an experimentally validated guide RNA in the vicinity of the desired knock-in site is identified within the genome (3 nucleotides, nts, upstream of the protospacer adjacent motif, PAM), and ~0.5 kb regions 5'- and 3' of the site are designated as left and right homology arms, respectively. Any native sequence between the actual guide RNA cut site and the desired knock-in site was included as part of the donor construct between the homology arms to avoid any off-set and to ensure perfect binding of the homology arms to the genomic sequence up to the cut site. In order to avoid nucleotide sequence duplications, this region should be codon-optimized. The sequence of any cargo is then included in the construct in frame with the target locus, if so desired. If not required for other reasons, codon optimization should be avoided as it can reduce knock-in efficiency or impact transgene expression relative to an endogenous equivalent. Guide RNA binding sites within the donor template need to mutated as extensively as possible (preferably mutation of the PAM, followed by maximum mutations within the spacer binding site). If utilizing an existing gene transcript to express an exogenous protein, the cut site should be located within the coding sequence of the target gene. A GSG-2A site is placed downstream of the left homology arm in frame with the target gene, followed by the open reading frame of the exogenous gene. Multiple GSG-2A-Gene cassettes can then be added after the first. Stop codons are excluded from all genes where ribosomal readthrough to the next cassette is desired. At the end of the last gene in the series, but before the right homology arm, a stop codon may be inserted, or another GSG-2A site, or a stop codon plus a polyadenylation sequence. Alternatively, the exogenous coding sequence may continue into the right homology arm, to create an in-frame fusion with the target locus. When designing templates targeting a non-coding region of the genome, left and right homology arms are selected as described above. Between the homology arms are placed an enhancer, promoter, and Kozak sequence, followed by the gene(s) of interest separated by GSG-2A sequences, as necessary. The last gene in the series terminates in a stop codon and poly-adenylation sequence. Construct organization is shown, where LHA is the left homology arm (500 bp unless otherwise indicated), GSG is a Glycine-Serine-Glycine linker, T2A and P2A are ribosomal cleavage sequences, furin is an Arginine-Alanine-Lysine-Arginine endoprotease cleavage site, bGHpA is the polyadenylation site from the bovine growth hormone gene, pCBH is a transcriptional regulatory element consisting of the CMV enhancer and chicken beta-actin promoter, and RHA is right homology arm (500 bp unless otherwise indicated). tCTS sites are truncated Cas9 targeting sequences with PAM sites that bear 4 bp mismatches at the 5' end. Templates with tCTS sites bear one at the 5' and 3' end, both oriented inwards and flanked by a 16 bp edge sequence (Nguyen et al., 2019). Donor template sequences are given in Table 18.

HDR template production. Refer to summary Table 18 of sequences. Nanoplasmid and pUC57 HDR templates were provided as primary cell transfection grade material and supplied at a concentration of 1 mg/mL resuspended in water by Nature Technology. Inc. TRAC_1G4_500HA and TRAC_mNG_500HA linear dsDNA donor DNAs were made via PCR (Roth et al., 2018). PCR product was generated using Q5 High-Fidelity Polymerase (NEB, Ipswich, MA) with 0.25 µM forward (5'-AACATACCAT-AAACCTCCCATTCTG-3', SEQ ID NO: 57) and reverse primers (5'-TTGGAGAGACTGAGGCTGGGCCACG-3', SEQ ID NO: 58), and 10 ng/ml of plasmid DNA template per reaction. The cycling parameters were 98 C for 15 sec, 60 C for 15 sec and 72 C for 1 min, for a total of 30 cycles. The products from 96×100 µL reactions were pooled and equilibrated in Qiagen buffer (Qiagen, Germantown, MD), and then purified through a HiSpeed Plasmid Maxi Kit (Qiagen, Germantown, MD). The final product was eluted in nuclease-free water and DNA concentration adjusted to 1 mg/mL. Isolation and culture of primary human T cells. Primary human CD8+ and CD4+ T cells were isolated by positive selection from buffy coats using the STRAIGHT-FROM® Buffy Coat CD8 MicroBead Kit, or CD4 Micro-Bead Kit, respectively, according to the manufacturer's instructions (Miltenyi Biotec). Residual red blood cells were lysed prior to culture. Cells were plated at an initial concentration of one million cells per ml of activation media. Unless otherwise noted, activation media consisted of PRIME-XV® T Cell CDM media (Irvine Scientific), supplemented with IL-7 (Miltenyi Biotec) at 25 ng/ml and IL-15 (Miltenyi Biotec) at 50 ng/ml for CD8+ T cells, and IL-7 (25 ng/ml), IL-15 (50 ng/ml) and IL-2 (Biolegend, 400 U/ml) for CD4+ T cells. T Cell TransAct™ (Miltenyi Biotec) was added to the cultures at a 1:100 dilution. In some experiments, the activation media consisted of X-VIVO™ 15 Serum-free Hematopoietic Cell Medium (Lonza Bioscience), supplemented with 5% heat-inactivated fetal bovine serum, IL-2 at 200 U/ml, IL-7 at 5 ng/mL, IL-15 at 5 ng/mL, 50 µM 2-mercaptoethanol, and 10 UM N-acetyl-L-cysteine, to which Human T-Activator CD3/CD28 Dynabeads (Gibco) were added at a 1:1 bead to cell ratio. T cell media was prepared using the following ingredients: RPMI 1640 medium (Gibco, cat. no. 11875093), 10% FBS (HyClone, cat. no. SH30071.03), 2 mML-alanyl-L-glutamine (GlutaMAX; Gibco), 1 mM sodium pyruvate (Gibco), 0.1 mM non-essential amino acids (Gibco), 55 µM 2-mercaptoethanol (Gibco), 100 U/ml penicillin (PenStrep), 100 µg/mL streptomycin (PenStrep; Gibco), and 10 mM HEPES (Gibco). Media was sterilized through a 0.22-µm filter. Unless indicated otherwise, T cells were cultured for 36 to 48 hours before electroporation. Over the course of the culture after electroporation, the culture volume was expanded to maintain cells at approximately 1 million per ml throughout.

RNP assembly. RNPs were produced by combining target-specific sgRNAs (IDT) and recombinant Cas9 (SpyFi, Aldevron). Briefly, lyophilized sgRNAs were reconstituted in Nuclease-free Duplex Buffer (IDT) to a concentration of 200 M. For every 60 pmols of Cas9 used, 180 pmols of sgRNA was added to obtain a 3:1 sgRNA: Cas9 ratio (in experiments recapitulating published conditions (Roth et al., 2018), a 2:1 sgRNA:Cas9 ratio was used). The sgRNA:Cas9 mixture was incubated at room temperature for 15 minutes to allow RNP formation. For combined TCR knock-in/TRBC knock-out experiments, 30 pmols each of TRAC and TRBC RNPs were assembled separately and then mixed together using equal volumes. A total of 60 pmols of combined TRAC and TRBC RNPs were used for a single nucleofection reaction. For knock-in experiments targeting other loci, 60 pmols of total Cas9/RNP were used per nucleofection reaction.

Nucleofection. Following 36 to 48 hours of activation, T cells were pelleted, washed with phosphate buffered saline (PBS), and gently resuspended in P3 buffer with supplement (Lonza Bioscience) at 2 million cells per 20 l. Cells activated with Human T-Activator CD3/CD28 Dynabeads (Gibco) were magnetically separated from the beads prior to the PBS wash step. The following components of a single nucleofection reaction were added to a PCR tube and mixed gently: pre-formed RNPs (60 pmols total), HDR template (up to 8 g), and T cells resuspended in P3 buffer. In some cases, poly-L-glutamic acid (Sigma Aldrich, 150 g) was also added to the mixture. This mixture was then transferred to one well of a 16-well 4D-Nucleofector cuvette (Lonza Bioscience), and pulsed with code EH115. Following electroporation, the 4D-Nucleofector cuvette was placed in a 37 C tissue culture incubator for 15 minutes to allow for cell recovery. After recovery, the cells were transferred to a 24-well tissue culture plate containing 2 ml of pre-warmed PRIME-XV media supplemented with 25 ng/ml IL-7 and 50 ng/ml IL-15 (CD8+ T cells) or 25 ng/ml IL-7, 50 ng/ml IL-15, and 400 U/mL IL-2 (CD4+ T cells). In some experiments, following electroporation cells were cultured in X-VIVO™ 15 Serum-free Hematopoietic Cell Medium (Lonza Bioscience), supplemented with 5% heat-inactivated fetal bovine serum, 50 µM 2-mercaptoethanol, 10 µM N-acetyl-L-cysteine, and IL-2 at 500 U/mL.

Flow cytometry. Transfected cells at different timepoints were analyzed by flow cytometry to measure the knock-in efficacy. All reagents were used according to manufacturer's recommendations. Briefly, cells were pelleted, washed with phosphate buffered saline, and gently resuspended and incubated for 10 mins at room temperature in pre-diluted Fixable Viability Dye eFluor™ 780 or Propidium Iodide. After incubation, cells were washed twice in the FACS buffer and were subject to surface staining with fluorochrome-conjugated CD3 and/or anti-TCRa/b, along with anti-CD4 (for CD4+ T cells) or anti-CD8 (for CD8+ T cells). In some experiments, cells were also stained with either IG4 or pp65 TCR dextramer (PE or APC) for 10 mins at room temperature protected from light before surface antibodies were added. Following the addition of other surface antibodies, cells were incubated at 4 C in the dark for an additional 15 minutes. For CD19 CAR staining, cells were first stained with biotin anti-human CD19 CAR detection reagent (Miltenyi Biotec) followed by Streptavidin PE. For staining cells with anti-CD137 PE, a FASER (Fluorescence Amplification by Sequential Employment of Reagents) Kit-PE (Miltenyi Biotec) was used to amplify the fluorescence intensity. Stained cells were washed twice in the FACS buffer before proceeding to FACS acquisition. To calculate the absolute number of cells in some samples, CountBright Absolute Count Beads (Thermo Fisher Scientific) were added to the samples prior to FACS acquisition. Samples were acquired using a FACSymphony or an LSR Fortessa equipped with FACSDiva software (all from BD Biosciences). Compensation was performed using single-stained controls prepared with Ultra-comp ebeads (Thermo Fisher Scientific). Flow-cytometry standard (FCS) 3.0 files were imported and analyzed using FlowJo software version 3.0 (FlowJo). A conventional gating strategy was used to remove aggregates and dead cells were excluded based on viability dye staining.

SIMOA Assay. IFN-α analysis in pre- and post-electroporation culture supernatants were analyzed using the Simoa IFN-α Advantage Kit (HD-1/HD-X Item 100860) according to the manufacturer's protocol. Briefly, 200 µL of IFN-α calibrators and experimental samples were added to wells in a 96-well plate. Kit provided bead reagent, detector reagent, SBG (streptavidin beta galactosidase) reagent, and sample diluent were added to the reagent bay in the Quanterix HD-X, and the RGP (Resorufin-D-galactopyranoside) was added to the sample bay. Following IFN-α assay set-up in the Simoa software, the plate containing calibrator and experimental samples was loaded into the sample bay and analyzed on the Quanterix HD-X.

T cell activation. T cell activation cultures comprised CRISPR-engineered T cells, an HLA-A*02:01+ target cell line, and a non-target HLA-A*02:01-negative target cell line that served as a reference population for the calculation of target cell lysis. Both cell lines were obtained from the Fred Hutch International Histocompatibility Working Group. The target and reference cell lines were labeled with CFSE and Cell Trace Violet (CTV) (Invitrogen) respectively to distinguish populations during flow cytometric analysis. For peptide pulsing, CFSE-labeled HLA-A*02:01+ target cells were incubated with varying concentrations of the appropriate target peptide at 37 C for 2 hours. Following the incubation period, cells were washed twice with PBS and then resuspended in 10% FBS RPMI T cell media. Peptide-loaded CFSE-labeled target cells were cultured with CTV-labeled reference population at 1:1 ratio, and CRISPR-engineered T cells were added at a 1:1 ratio of T cells to CFSE-labeled target cells. No peptide added conditions were included as controls. Approximately 24 hours later, T cell activation was analyzed as follows: (1) Cells were collected and analyzed by flow cytometry to determine CD137 (Biolegend, Clone 4B4-1) upregulation and target cell lysis and (2) supernatants were collected for analysis of effector molecule production by Luminex. For analysis of target cell lysis, Count-Bright Absolute Count Beads (Thermo Fisher Scientific) were added to flow cytometric analysis samples to quantitate the numbers of CFSE-labeled target cells and CTV-labeled non-target cells during FACS acquisition. Specific target cell lysis was calculated using the following equation:

percent specific lysis=[1−(No peptide control ratio/ Experimental ratio)]×100

Ratios were calculated by dividing the numbers of the CTV-labeled reference population by the numbers of CFSE-labeled HLA-A*02:01+ target cells.

In vitro killing assay. The A375 (malignant human melanoma) cell line that express NYESO antigen were labeled with 1 µM of Incucyte® Cytolight Rapid Dyes (Cat 4706) and plated in 96 well plate with the seeding density of 50000 cells. Two hours after seeding a caspase-3/7 green apoptosis reagent (2272582, Invitrogen) and IG4 KI or KO controls (50000 cells per well) were added to A375 cells. Cell killing was measured by evaluating the number of A375 cells present in each well expressing caspase-3/7 reagent. The co-culture was monitored for growth and apoptosis using the IncuCyte imaging system for 18 hrs. Following co-culturing, CD137 expression on CD8+ T cells was measured by Flow Cytometry (BioLegend, Clone 4B4-1).

T cell expansion cultures/Lactate measurement. Activated CD8+ T cells were electroporated at 48 hours with only the sgTRAC and sgTRBC RNPs (knock-out) or with sgTRAC RNP, sgTRBC RNP, and the TCR-encoding nanoplasmid (knock-in). As a control for no electroporation (no RNP), CD8+ T cells only were added to the Lonza electroporation cuvette but not subjected to an electroporation pulse code. The No RNP, knock-out, and knock-in T cells were cultured in a 24-well G-Rex plate (Wilson-Wolf) following electroporation in PRIME-XV media supplemented with 25 ng/ml IL-7 (Miltenyi) and 50 ng/mL IL-15 (Miltenyi). Supernatants were collected from the No RNP, knock-out, and knock-in conditions on the day one post-electroporation, and every 2-3 days thereafter for 7 days.

Extracellular lactate levels were analyzed as a surrogate for cell proliferation (Grist et al., 2018) using the Lactate-Glo Assay (Promega) according to the manufacturer's protocol. Briefly, following thaw, the Luciferin Detection Solution was brought to room temperature while all other kit components were maintained on ice. Lactate dehydrogenase was reconstituted using water, and then placed on ice. Immediately prior to use, the Lactate Detection Reagent was prepared by mixing the Luciferin Detection Solution, Reductase, Reductase Substrate, Lactate Dehydrogenase, and NAD at ratios specified by the manufacturer. Cell culture supernatants were diluted in PBS, and 50 µL of samples or the lactate control was added to a 96-well plate followed by 50 µL of the Lactate Detection Reagent. The plate was shaken for 30-60 seconds and incubated for 60 minutes at room temperature. Luminescence was recorded using a plate-reading luminometer.

Translocation assay. A set of ddPCR-based assays are developed to detect potential chromosomal translocations during simultaneous CRISPR mediated editing of the three target sites (TRAC, TRBC1 and TRBC2) in engineered T cells (Bio-Rad's QX200 ddPCR platform). These 6 translocations are designated as: TRAC-TRBC1, TRAC-TRBC2, TRBC1-TRAC, TRBC1-TRBC2, TRBC2-TRAC, TRBC2-TRBC1. A reference assay to detect the RPP30 gene of interest is used to measure the ratio of target sequence (copies/µL) over the RPP30 sequence as the measure of chromosomal translocation at each DNA target site. Primer and probe sequences are:

```
TRAC-Forward:
                                  (SEQ ID NO: 59)
TGGGGCAAAGAGGGAAATGAG, TRAC-Reverse:
                                  (SEQ ID NO: 60)
AGAACCTGGCCATTCCTGAAG, TRAC-Probe:
                                  (SEQ ID NO: 61)
CATGTGCAAACGCCTTCAACAACAG, TRBC1-Forward:
                                  (SEQ ID NO: 62)
CTGGGATGGTGACCCCAAAA, TRBC1-Reverse:
                                  (SEQ ID NO: 63)
GGCCACATAGAAAGGGGACC, TRBC1-Probe:
                                  (SEQ ID NO: 64)
ACCATGAAGGAGAATTGGGCACCT, TRBC2-Forward:
                                  (SEQ ID NO: 65)
GGGGGATGGACAGACAATGG, TRBC2-Reverse:
                                  (SEQ ID NO: 66)
GCTGACCCTGTGAACCTTGA, TRBC2-Probe:
                                  (SEQ ID NO: 67)
ATCCAGGTAGCGGACAAGACTAGAT, RPP30-Forward:
                                  (SEQ ID NO: 68)
TCAGCCATATTGTCCCCTAAACT, RPP30-Reverse:
                                  (SEQ ID NO: 69)
TGGTCTGTCCATGGCATCTT, RPP30-Probe:
                                  (SEQ ID NO: 70)
CTGTATGGACACAGTGCCTA
```

Whole genomic DNA isolated from T cells were tested using the 7 ddPCR assays and translocations were reported as % Ratio relative to the reference assay.

RNASeq analysis. Human CD8+ T cells were isolated from five donors and activated as indicated above followed by electroporation with 60 pmols TRAC RNP, without or with 3 µg of TRAC-684 mNeonGreen-500HA template in either PCR or nanoplasmid format. Twenty hours post-electroporation RNA was isolated from the cells using an RNeasy Mini kit (Qiagen) according to the manufacturer's instructions with an on-column deoxyribonuclease (DNase) I digestion. Differential expression analysis of the transcriptome data was performed using the R package DESeq2 (Anders and Huber, 2010) (ref 1, see below). Heatmaps were generated by transforming RNA-seq reads count into normalized expression using variance stabilizing transformation (VST). GSEA analysis was performed using R Bioconductor package enrichplot (Yu G (2021). enrichplot: Visualization of Functional Enrichment Result. R package version 1.14.1, yulab-smu.top/biomedical-knowledge-mining-book/) and MSigDB (Subramanian et al., 2005; Liberzon et al., 2015). MSigDB Hallmark 2020 gene sets were used for GSEA analysis.

Activation of CD4+ T cells with CD19 CAR construct. Fifty thousand CD4+ T cells with a CD19-specific CAR or a pp65-specific 6-2 TCR (control irrelevant TCR) were plated at a 1:1 E:T ratio with CD19 expressing Granta-519 B cells and incubated for 24 hrs. Culture supernatants were analyzed for IFN-gamma and TNF-alpha production by Luminex.

Statistical analysis. GraphPad Prism software was used for plotting graphs and statistical analysis. Unpaired t test or one-way ANOVA was used to determine statistical significance.

Example 36. Test Construct Design Containing Full-Length TCR-Alpha ("Schober Construct"), and TRBC1/TRBC2 Knock-In Constructs Experimental Conditions Plating was done by adding Prime-XV with IL-7 (25 ng/ml), IL-15 (50 ng/mL), and TransAct 1:100 (No Pen/Strep), Electroporation at 48 hours post-activation in P3 buffer, EW113, using Haley Lonza 4D, Post-electroporation rest for 15 min @ 37 C, then add 75 µL plain Prime and transfer.

Templates: TRAC3_WT1C13_pUC57 (control); Schober_TRAC3_WT1C13_pUC57 (test); TRAC3_mNeon-NP (control); TRBCg22_TRBC1_mNeon_NoAlpha-NP; TRBCg22_TRBC2_mNeon_NoAlpha-NP.

RNP=For Schober test, use 30 pmols each TRACsg3 and TRBCsg22 at 3:1 sgRNA: Cas9 ratio. For TRBC test, use 60 pmols TRBCsg22 with 3:1 sgRNA: Cas9 ratio.

Order of addition: 1—RNP preincubated for 15 min, 2—Template (3 µg), 3—Cells (2 million per cuvette).

Staining conditions (days 5 and 7): Live/Dead APC-Cy7 (1:1000 per stain), Fc Blocker (5 µl/stain), TCR-BV421 (5 µl/stain), pMHC Immudex dextramer for WT1C13 samples only Example 37. Pilot Test of Non-Viral TCR Knock-In Using Jurkat and Primary Human CD4+ Cells An experiment was performed to determine conditions for a non-viral TCR knock-in using Jurkat and primary human CD4+ cells. The conditions are as follows: Jurkat NF-kB-Luc media: RPMI 1640+10% HI FBS+2 mM L-Glut+10 mM HEPES+1 mM NaPyr+10 µg/ml Blasticidin+100 µg/ml Zeocin, with or without 10 ng/ml rhIL-2. CD4 media: Prime-XV, with or without 10 ng/ml rhIL-2. Activation used TransAct @ 1:100. Electroporation at 44 hours post-activation in P3 buffer, EW113, used Haley Lonza 4D. RNP=60 pmols of TRAC3 RNPs in all samples with 3:1 sgRNA: Cas9 ratio. Order of addition: 1—Non-targeting or TRAC3 RNP (preincubated 15 min at RT) 2—2 µg of TRAC3-mNeon nanoplasmid template or water 3—Cells (1.5 million per cuvette). Post-electroporation: Incubated for 15 min at 37 C, Add 75 µl plain prewarmed media without supplements and transferred to 48-well plate. Staining conditions were (days 5 and 7): TCRa/b-BV421, 5 µl/stain, PI (1:200 per stain)

Culture conditions. FIGS. 160 and 161 show the resulting flow cytometer scatter plots for Jurkat and donor CD4 cells. The following conditions are shown: unactivated Jurkat (no IL-2); Unactivated Jurkat (no IL-2); Unactivated Jurkat (with IL-2); Unactivated CD4, donor #1 (no IL-2); aCD3/28-activated CD4, donor #1 (with IL-2); Unactivated CD4, donor #1 (with IL-2); Unactivated CD4, donor #2 (no IL-2); aCD3/28-activated CD4, donor #2 (with IL-2); Unactivated CD4, donor #2 (with IL-2).

Electroporation conditions. The electroporation conditions were as follows: RNP with non-targeting crRNA: tracrRNA; RNP with TRACsg3 (knockout only); and TRACsg3 RNP with TRAC3-mNeon template (knock-in).

Jurkat data: Around 40% of Jurkats appear to be TCR negative with the staining antibody we used. Knock-out worked well regardless of activation condition. A very small amount (0.5%) of "knock-in" expression occurred, regardless of activation condition. It might be worth sorting and trying to expand this population.

Follow-up can include checking the TRAC locus sequence in Jurkats for mutations that could inhibit HDR, checking the length/splicing/sequence of transcripts that arise from the locus, and testing additional gRNAs in case the TRAC3 site is not accessible in these cells. In addition, Jurkats are known to be resistant to plasmid uptake. It has also been difficult to produce knock-in in these cells using oligos.

Primary CD4+ Data:

Unactivated cells did not survive until day 5, and did not show evidence of knock-in. Activated cells showed good TCR knock-out by day 5. By day 5, roughly 20% knock-in was seen in both donors. By day 7, this increased to 40%. In CD8 cells were generally see slight (~5%) increases between days 5 and 7.

SEQUENCES

Sequences Used in eJH52_WT1C_13_TRAC3 Construct:

WT1C13 alpha chain amino acid sequence: (the underlined portion comes from the endogenous sequence), SEQ ID NO: 53:

MTRVSLLWAVVVSTCLESGMAQTVTQSQPEMSVQE

AETVTLSCTYDTSENNYYLFWYKQPPSRQMILVIR

QEAYKQQNATENRFSVNFQKAAKSFSLKISDSQLG

DTAMYFCAFMGYYGGSQGNLIFGKGTKLSVKPNIQ

NPDPAVYQLRDSKSSDKSVCLFTDFDSQTNVSQSK

DSDVYITDKTVLDM<u>RSMDFKSNSAVAWSNKSDFAC</u>

<u>ANAFNNSIIPEDTFFPSPESSCDVKLVEKSFETDT</u>

<u>NLNFQNLSVIGFRILLLKVAGFNLLMTLRLWSS</u>*

WT1C13 beta chain amino acid sequence (no stop codon) SEQ ID NO: 54:

MDSWTFCCVSLCILVAKHTDAGVIQSPRHEVTEMG

QEVTLRCKPISGHNSLFWYRQTMMRGLELLIYFNN

NVPIDDSGMPEDRFSAKMPNASFSTLKIQPSEPRD

SAVYFCASSSLQYEQYFGPGTRLTVTEDLKNVFPP

EVAVFEPSEAEISHTQKATLVCLATGFYPDHVELS

WWVNGKEVHSGVSTDPQPLKEQPALNDSRYCLSSR

LRVSATFWQNPRNHFRCQVQFYGLSENDEWTQDRA

KPVTQIVSAEAWGRADCGFTSESYQQGVLSATILY

EILLGKATLYAVLVSALVLMAMVKRKDSRG

WT1C13 alpha chain nucleotide sequence: (text not underlined is codon-optimized; the underlined portion is the endogenous sequence), SEQ ID NO: 55:

ATGACCCGGGTGAGCCTGCTGTGGGCCGTGGTGGT

GAGCACCTGCCTGGAGAGCGGCATGGCCCAGACCG

TGACCCAGTCTCAGCCCGAGATGAGCGTGCAGGAG

GCCGAGACCGTGACCCTGAGCTGTACCTACGACAC

CAGCGAGAACAACTACTACCTGTTCTGGTACAAGC

AGCCCCCCAGCCGGCAGATGATCCTGGTGATCCGG

CAGGAGGCCTACAAGCAGCAGAACGCCACCGAGAA

CAGATTCTCTGTGAACTTCCAGAAGGCCGCCAAGA

GCTTCAGCCTGAAGATCAGCGACTCCCAGCTGGGC

GATACCGCCATGTATTTCTGCGCCTTCATGGGCTA

CTACGGCGGCAGCCAGGGCAATCTGATCTTTGGCA

AGGGCACAAAGCTGAGCGTGAAGCCCAACATCCAG

AACCCCGACCCTGCCGTGTACCAGCTGAGGGACTC

CAAGTCTAGCGATAAGAGCGTGTGCCTGTTCACCG

ACTTTGATTCCCAGACAAACGTGAGCCAGAGCAAG

GACTCTGACGTGTACATCACCGACAAGACAGTGCT

GGAT<u>ATGAGGTCTATGGACTTCAAGAGCAACAGTG</u>

<u>CTGTGGCCTGGAGCAACAAATCTGACTTTGCATGT</u>

<u>GCAAACGCCTTCAACAACAGCATTATTCCAGAAGA</u>

<u>CACCTTCTTCCCCAGCCCAGAAAGTTCCTGTGATG</u>

<u>TCAAGCTGGTCGAGAAAAGCTTTGAAACAGATACG</u>

<u>AACCTAAACTTTCAAAACCTGTCAGTGATTGGGTT</u>

<u>CCGAATCCTCCTCCTGAAAGTGGCCGGGTTTAATC</u>

<u>TGCTCATGACGCTGCGGCTGTGGTCCAGCTGA</u>

WT1C13 beta chain nucleotide sequence (all codon optimized, no stop codon) SEQ ID NO: 56:

ATGGACAGCTGGACCTTCTGCTGCGTGAGCCTGTG

CATCCTGGTGGCCAAGCACACAGACGCAGGCGTGA

TCCAGAGCCCAAGGCACGAGGTGACAGAGATGGGC

CAGGAGGTGACCCTGAGGTGTAAGCCCATCAGCGG

CCACAACTCCCTGTTCTGGTATAGGCAGACCATGA

TGCGGGGACTGGAGCTGCTGATCTACTTCAACAAC

AACGTGCCCATCGATGACAGCGGCATGCCCGAGGA

CAGATTCAGCGCCAAGATGCCCAACGCCAGCTTCA

GCACCCTGAAGATCCAGCCCAGCGAGCCCAGAGAC

TCCGCCGTGTATTTCTGCGCCAGCAGCAGCCTGCA

GTATGAGCAGTACTTCGGCCCAGGCACACGCCTGA

CCGTGACAGAGGATCTGAAGAACGTGTTCCCCCCT

GAGGTGGCCGTGTTTGAGCCTTCTGAGGCCGAGAT

CAGCCACACCCAGAAGGCCACCCTGGTGTGCCTGG

CAACCGGCTTCTACCCAGACCACGTGGAGCTGAGC

TGGTGGGTGAACGGCAAGGAGGTGCACAGCGGCGT

GTCCACAGACCCACAGCCCCTGAAGGAGCAGCCCG

CCCTGAATGATTCTAGATATTGCCTGTCTAGCCGG

CTGAGAGTGAGCGCCACCTTTTGGCAGAACCCTAG

GAATCACTTCCGCTGTCAGGTGCAGTTTTACGGCC

TGAGCGAGAATGACGAGTGGACCCAGGATAGGGCC

AAGCCTGTGACACAGATCGTGTCCGCCGAGGCATG

GGGAAGGGCAGATTGCGGCTTCACAAGCGAGTCCT

ACCAGCAGGGCGTGCTGTCCGCCACCATCCTGTAT

GAGATCCTGCTGGGCAAGGCCACACTGTACGCCGT

GCTGGTGAGCGCCCTGGTGCTGATGGCCATGGTGA

AGAGGAAGGACTCCAGGGGC

TRAC_mNeonGreen_500HA forward primer (SEQ ID NO: 105):

AACATACCATAAACCTCCCATTCTG

TRAC_mNeonGreen_500HA reverse primer (SEQ ID NO: 106):

TTGGAGAGACTGAGGCTGGGCCACG

TRAC_tCTS_mNeonGreen_500HA forward primer (SEQ ID NO: 107):

TGGCGGGACTAGTGGCCACATCTCT

TRAC_tCTS_mNeonGreen_500HA reverse primer (SEQ ID NO: 108):

TGGCGGGACTAGTGGCCACATCTCT

REFERENCES

1. Marson et al., "A Cas9 nanoparticle system with truncated Cas9 target sequences on DNA repair templates enhances genome targeting in diverse human immune cell types," doi: 10.1101/591719
2. Miller, B. C., et al. Subsets of exhausted CD8+ T cells differentially mediate tumor control and respond to checkpoint blockade. Nat Immunol 20, 326-336 (2019). doi: 10.1038/s41590-019-0312-6
3. Sade-Feldman, M. et al. Defining T Cell States Associated with Response to Checkpoint Immunotherapy in Melanoma. Cell, Volume 175, Issue 4, 1 Nov. 2018, Pages 998-1013. doi: 10.1016/j.cell.2018.10.038
4. Siddiqui, I., et al. Immunity, Volume 50, Issue 1, 15 Jan. 2019, Pages 195-211. doi: 10.1016/j.immuni.2018.12.021
5. Anders, S., and W. Huber. 2010. Differential expression analysis for sequence count data. Genome Biol. 11: R106. doi: 10.1186/gb-2010-11-10-r106.
6. Bak, R. O., et al. 2018. CRISPR/Cas9 genome editing in human hematopoietic stem cells. Nat Protoc. 13:358-376. doi: 10.1038/nprot.2017.143.
7. Bloemberg, D., et al. 2020. A High-Throughput Method for Characterizing Novel Chimeric Antigen Receptors in Jurkat Cells. Mol Ther—Methods Clin Dev. 16:238-254. doi: 10.1016/j.omtm.2020.01.012.
8. Choi, B. D., et al. 2019. CRISPR-Cas9 disruption of PD-1 enhances activity of universal EGFRvIII CAR T cells in a preclinical model of human glioblastoma. J Immunother Cancer. 7:304. doi: 10.1186/s40425-019-0806-7.
9. Chu, V., T. et al. 2015. Increasing the efficiency of homology-directed repair for CRISPR-Cas9-induced precise gene editing in mammalian cells. 33. doi: 10.1038/nbt.3198.
10. Dai, X., et al. 2019. One-step generation of modular CAR-T cells with AAV-Cpf1. Nat Methods. 16:247-254. doi: 10.1038/s41592-019-0329-7.
11. Dash, P., et al. 2011. Paired analysis of TCRa and TCRB chains at the single-cell level in mice. J Clin Invest. 121:288-295. doi: 10.1172/jci44752.
12. Davidsson, M., et al. 2020. A comparison of AAV-vector production methods for gene therapy and preclinical assessment. Sci Rep-uk. 10:21532. doi: 10.1038/s41598-020-78521-w.
13. Doench, J. G., et al. 2016. Optimized sgRNA design to maximize activity and minimize off-target effects of CRISPR-Cas9. 34. doi: 10.1038/nbt.3437.
14. Eyquem, J., et al. 2017. Targeting a CAR to the TRAC locus with CRISPR/Cas9 enhances tumour rejection. Nature. 543:113-117. doi: 10.1038/nature21405.
15. Fu, G., et al. 2013. Themis sets the signal threshold for positive and negative selection in T-cell development. Nature. 504:441-445. doi: 10.1038/nature12718.
16. Gray, et al. 2011. Optimizing Promoters for Recombinant Adeno-Associated Virus-Mediated Gene Expression in the Peripheral and Central Nervous System Using Self-Complementary Vectors. Hum Gene Ther. 22:1143-1153. doi: 10.1089/hum.2010.245.
17. Grist, J. T., et al. 2018. Extracellular Lactate: A Novel Measure of T Cell Proliferation. J Immunol Author Choice. 200:1220-1226. doi: 10.4049/jimmunol.1700886.
18. Hacein-Bey-Abina, S., A. Garrigue, G. P. Wang, J. Soulier, A. Lim, E. Morillon, E. Clappier, L. Caccavelli, E. Delabesse, K. Beldjord, V. Asnafi, E. MacIntyre, L. D. Cortivo, I. Radford, N. Brousse, F. Sigaux, D. Moshous, J. Hauer, A. Borkhardt, B. H. Belohradsky, U. Wintergerst, M. C. Velez, L. Leiva, R. Sorensen, N. Wulffraat, S. Blanche, F. D. Bushman, A. Fischer, and M. Cavazzana-Calvo. 2008. Insertional oncogenesis in 4 patients after retrovirus-mediated gene therapy of SCID-X1. J Clin Invest. 118:3132-3142. doi: 10.1172/jci35700.
19. Hacein-Bey-Abina, S., C. V. Kalle, M. Schmidt, M. P. McCormack, N. Wulffraat, P. Leboulch, A. Lim, C. S. Osborne, R. Pawliuk, E. Morillon, R. Sorensen, A. Forster, P. Fraser, J. I. Cohen, G. de S. Basile, I. Alexander, U. Wintergerst, T. Frebourg, A. Aurias, D. Stoppa-Lyonnet, S. Romana, I. Radford-Weiss, F. Gross, F. Valensi, E. Delabesse, E. Macintyre, F. Sigaux, J. Soulier, L. E. Leiva, M. Wissler, C. Prinz, T. H. Rabbitts, F. L. Deist, A. Fischer, and M. Cavazzana-Calvo. 2003. LMO2-Associated Clonal T Cell Proliferation in Two Patients after Gene Therapy for SCID-X1. Science. 302:415 419. doi: 10.1126/science.1088547.
20. Halbert, C. L., J. M. Allen, and J. S. Chamberlain. 2018. AAV6 Vector Production and Purification for Muscle Gene Therapy. Methods Mol Biology Clifton N J. 1687: 257-266. doi: 10.1007/978-1-4939-7374-3_18.
21. Hardee, C., L. Arévalo-Soliz, B. Hornstein, and L. Zechiedrich. 2017. Advances in Non-Viral DNA Vectors for Gene Therapy. Genes-basel. 8:65. doi: 10.3390/genes8020065.
22. Hendel, A., R. O. Bak, J. T. Clark, A. B. Kennedy, D. E. Ryan, S. Roy, I. Steinfeld, B. D. Lunstad, R. J. Kaiser, A. B. Wilkens, R. Bacchetta, A. Tsalenko, D. Dellinger, L. Bruhn, and M. H. Porteus. 2015. Chemically modified guide RNAs enhance CRISPR-Cas genome editing in human primary cells. 33. doi: 10.1038/nbt.3290.
23. Hockemeyer, D., F. Soldner, C. Beard, Q. Gao, M. Mitalipova, R. C. DeKelver, G. E. Katibah, R. Amora, E. A. Boydston, B. Zeitler, X. Meng, J. C. Miller, L. Zhang, E. J. Rebar, P. D. Gregory, F. D. Urnov, and R. Jaenisch. 2009. Efficient targeting of expressed and silent genes in human ESCs and iPSCs using zinc-finger nucleases. Nat Biotechnol. 27:851-857. doi: 10.1038/nbt.1562.
24. Hudecek, M., and Z. Ivics. 2018. Non-viral therapeutic cell engineering with the Sleeping Beauty transposon system. Curr Opin Genet Dev. 52:100-108. doi: 10.1016/j.gde.2018.06.003.
25. Kebriaei, P., H. Singh, M. H. Huls, M. J. Figliola, R. Bassett, S. Olivares, B. Jena, M. J. Dawson, P. R. Kumaresan, S. Su, S. Maiti, J. Dai, B. Moriarity, M.-A. A. Forget, V. Senyukov, A. Orozco, T. Liu, J. McCarty, R. N. Jackson, J. S. Moyes, G. Rondon, M. Qazilbash, S. Ciurea, A. Alousi, Y. Nieto, K. Rezvani, D. Marin, U. Popat, C. Hosing, E. J. Shpall, H. Kantarjian, M. Keating, W. Wierda, K. A. Do, D. A. Largaespada, D. A. Lee, P. B. Hackett, R. E. Champlin, and L. J. Cooper. 2016. Phase I trials using Sleeping Beauty to generate CD19-specific CAR T cells. *The Journal of clinical investigation.* 126: 3363-76. doi: 10.1172/JCI86721.
26. Li, H., Y. Yang, W. Hong, M. Huang, M. Wu, and X. Zhao. 2020. Applications of genome editing technology in the targeted therapy of human diseases: mechanisms, advances and prospects. *Signal Transduct Target Ther.* 5:1. doi: 10.1038/s41392-019-0089-y.
27. Li, Y., R. Moysey, P. E. Molloy, A.-L. Vuidepot, T. Mahon, E. Baston, S. Dunn, N. Liddy, J. Jacob, B. K. Jakobsen, and J. M. Boulter. 2005. Directed evolution of human T-cell receptors with picomolar affinities by phage display. *Nat Biotechnol.* 23:349-354. doi: 10.1038/nbt1070.
28. Liberzon, A., C. Birger, H. Thorvaldsdóttir, M. Ghandi, J. P. Mesirov, and P. Tamayo. 2015. The Molecular Signatures Database Hallmark Gene Set Collection. *Cell Syst.* 1:417-425. doi: 10.1016/j.cels.2015.12.004.
29. Loo, J. C. M. van der, and J. F. Wright. 2016. Progress and challenges in viral vector manufacturing. *Hum Mol Genet.* 25: R42-R52. doi: 10.1093/hmg/ddv451.
30. Luke, J., A. E. Carnes, C. P. Hodgson, and J. A. Williams. 2009. Improved antibiotic-free DNA vaccine vectors utilizing a novel RNA based plasmid selection system. *Vaccine.* 27:6454-6459. doi: 10.1016/j.vaccine.2009.06.017.
31. Mandal, P. K., L. M. Ferreira, R. Collins, T. B. Meissner, C. L. Boutwell, M. Friesen, V. Vrbanac, B. S. Garrison, A. Stortchevoi, A. Bryder, K. Musunuru, H. Brand, A. M. Tager, T. M. Allen, M. E. Talkowski, D. J. Rossi, and C. A. Cowan. 2014. Efficient ablation of genes in human hematopoietic stem and effector cells using CRISPR/Cas9. 15. doi: 10.1016/j.stem.2014.10.004.
32. Mansilla-Soto, J., J. Eyquem, S. Haubner, M. Hamieh, J. Feucht, N. Paillon, A. E. Zucchetti, Z. Li, M. Sjöstrand, P. L. Lindenbergh, M. Saetersmoen, A. Dobrin, M. Maurin, A. Iyer, A. G. Angus, M. M. Miele, Z. Zhao, T. Giavridis, S. J. C. van der Stegen, F. Tamzalit, I. Rivière, M. Huse, R. C. Hendrickson, C. Hivroz, and M. Sadelain. 2022. HLA-independent T cell receptors for targeting tumors with low antigen density. *Nat Med.* 1-8. doi: 10.1038/s41591-021-01621-1.
33. Modlich, U., S. Navarro, D. Zychlinski, T. Maetzig, S. Knoess, M. H. Brugman, A. Schambach, S. Charrier, A. Galy, A. J. Thrasher, J. Bueren, and C. Baum. 2009. Insertional Transformation of Hematopoietic Cells by Self-inactivating Lentiviral and Gammaretroviral Vectors. *Mol Ther.* 17:1919-1928. doi: 10.1038/mt.2009.179.
34. Monjezi, R., C. Miskey, T. Gogishvili, M. Schleef, M. Schmeer, H. Einsele, Z. Ivics, and M. Hudecek. 2017. Enhanced CAR T-cell engineering using non-viral Sleeping Beauty transposition from minicircle vectors. *Leukemia.* 31:186-194. doi: 10.1038/leu.2016.180.
35. Nguyen, D. N., T. L. Roth, P. J. Li, P. A. Chen, R. Apathy, M. R. Mamedov, L. T. Vo, V. R. Tobin, D. Goodman, E. Shifrut, J. A. Bluestone, J. M. Puck, F. C. Szoka, and A. Marson. 2019. Polymer-stabilized Cas9 nanoparticles and modified repair templates increase genome editing efficiency. *Nat Biotechnol.* 38:44-49. doi: 10.1038/s41587-019-0325-6.
36. Oh, S. A., A. Seki, and S. Rutz. 2019. Ribonucleoprotein Transfection for CRISPR/Cas9-Mediated Gene Knockout in Primary T Cells. *Curr Protoc Immunol.* 124: e69. doi: 10.1002/cpim.69.
37. Redmond, D., A. Poran, and O. Elemento. 2016. Single-cell TCRseq: paired recovery of entire T-cell alpha and beta chain transcripts in T-cell receptors from single-cell RNAseq. *Genome Med.* 8:80. doi: 10.1186/s13073-016-0335-7.
38. Roth, T. L., C. Puig-Saus, R. Yu, E. Shifrut, J. Carnevale, P. J. Li, J. Hiatt, J. Saco, P. Krystofinski, H. Li, V. Tobin, D. N. Nguyen, M. R. Lee, A. L. Putnam, A. L. Ferris, J. W. Chen, J.-N. Schickel, L. Pellerin, D. Carmody, G. Alkorta-Aranburu, D. del Gaudio, H. Matsumoto, M. Morell, Y. Mao, M. Cho, R. M. Quadros, C. B. Gurumurthy, B. Smith, M. Haugwitz, S. H. Hughes, J. S. Weissman, K. Schumann, J. H. Esensten, A. P. May, A. Ashworth, G. M. Kupfer, S. A. W. Greeley, R. Bacchetta, E. Meffre, M. G. Roncarolo, N. Romberg, K. C. Herold, A. Ribas, M. D. Leonetti, and A. Marson. 2018. Reprogramming human T cell function and specificity with non-viral genome targeting. *Nature.* 559:405-409. doi: 10.1038/s41586-018-0326-5.
39. Salganik, M., M. L. Hirsch, and R. J. Samulski. 2015. Mobile DNA III. *Microbiol Spectr.* 3:829-851. doi: 10.1128/microbiolspec.mdna3-0052-2014.
40. Sather, B. D., G. S. R. Ibarra, K. Sommer, G. Curinga, M. Hale, I. F. Khan, S. Singh, Y. Song, K. Gwiazda, J. Sahni, J. Jarjour, A. Astrakhan, T. A. Wagner, A. M. Scharenberg, and D. J. Rawlings. 2015. Efficient modification of CCR5 in primary human hematopoietic cells using a megaTAL nuclease and AAV donor template. *Sci Transl Med.* 7: 307ra156-307ra156. doi: 10.1126/scitranslmed.aac5530.
41. Schober, K., T. R. Müller, F. Gökmen, S. Grassmann, M. Effenberger, M. Poltorak, C. Stemberger, K. Schumann, T. L. Roth, A. Marson, and D. H. Busch. 2019. Orthotopic replacement of T-cell receptor α- and β-chains with preservation of near-physiological T-cell function. *Nature Biomedical Engineering.* 1-11. doi: 10.1038/s41551-019-0409-0.
42. Schuldt, N. J., and B. A. Binstadt. 2019. Dual TCR T Cells: Identity Crisis or Multitaskers? *J Immunol.* 202: 637-644. doi: 10.4049/jimmunol.1800904.
43. Schumann, K., S. Lin, E. Boyer, D. R. Simeonov, M. Subramaniam, R. E. Gate, G. E. Haliburton, C. J. Ye, J. A. Bluestone, J. A. Doudna, and A. Marson. 2015. Generation of knock-in primary human T cells using Cas9 ribonucleoproteins. 112. doi: 10.1073/pnas.1512503112.
44. Seki, A., and S. Rutz. 2018. Optimized RNP transfection for highly efficient CRISPR/Cas9-mediated gene knockout in primary T cells. *The Journal of experimental medicine.* 215:985-997. doi: 10.1084/jem.20171626.
45. Shaner, N. C., G. G. Lambert, A. Chammas, Y. Ni, P. J. Cranfill, M. A. Baird, B. R. Sell, J. R. Allen, R. N. Day, M. Israelsson, M. W. Davidson, and J. Wang. 2013. A bright monomeric green fluorescent protein derived from *Branchiostoma lanceolatum. Nat Methods.* 10:407-409. doi: 10.1038/nmeth.2413.
46. Simeonov, D. R., and A. Marson. 2019. CRISPR-Based Tools in Immunity. *Annual review of immunology.* 37:1-27. doi: 10.1146/annurev-immunol-042718-041522.
47. Singh, N., J. Shi, C. H. June, and M. Ruella. 2017. Genome-Editing Technologies in Adoptive T Cell Immunotherapy for Cancer. *Curr Hematol Malig R.* 12:522-529. doi: 10.1007/s11899-017-0417-7.
48. Smith, J. R., S. Maguire, L. A. Davis, M. Alexander, F. Yang, S. Chandran, C. ffrench-Constant, and R. A. Pedersen. 2008. Robust, Persistent Transgene Expression in Human Embryonic Stem Cells Is Achieved with AAVS1-Targeted Integration. *Stem Cells.* 26:496-504. doi: 10.1634/stemcells.2007-0039.

49. Stadtmauer, E. A., J. A. Fraietta, M. M. Davis, A. D. Cohen, K. L. Weber, E. Lancaster, P. A. Mangan, I. Kulikovskaya, M. Gupta, F. Chen, L. Tian, V. E. Gonzalez, J. Xu, I. Jung, J. J. Melenhorst, G. Plesa, J. Shea, T. Matlawski, A. Cervini, A. L. Gaymon, S. Desjardins, A. Lamontagne, J. Salas-Mckee, A. Fesnak, D. L. Siegel, B. L. Levine, J. K. Jadlowsky, R. M. Young, A. Chew, W.-T. Hwang, E. O. Hexner, B. M. Carreno, C. L. Nobles, F. D. Bushman, K. R. Parker, Y. Qi, A. T. Satpathy, H. Y. Chang, Y. Zhao, S. F. Lacey, and C. H. June. 2020. CRISPR-engineered T cells in patients with refractory cancer. *Sci New York NY.* 367: caba7365. doi: 10.1126/science.aba7365.
50. Su, S., B. Hu, J. Shao, B. Shen, J. Du, Y. Du, J. Zhou, L. Yu, L. Zhang, F. Chen, H. Sha, L. Cheng, F. Meng, Z. Zou, X. Huang, and B. Liu. 2016. CRISPR-Cas9 mediated efficient PD-1 disruption on human primary T cells from cancer patients. 6. doi: 10.1038/srep20070.
51. Subramanian, A., P. Tamayo, V. K. Mootha, S. Mukherjee, B. L. Ebert, M. A. Gillette, A. Paulovich, S. L. Pomeroy, T. R. Golub, E. S. Lander, and J. P. Mesirov. 2005. Gene set enrichment analysis: A knowledge-based approach for interpreting genome-wide expression profiles. *Proc National Acad Sci.* 102:15545-15550. doi: 10.1073/pnas.0506580102.
52. Vakulskas, C. A., D. P. Dever, G. R. Rettig, R. Turk, A. M. Jacobi, M. A. Collingwood, N. M. Bode, M. S. McNeill, S. Yan, J. Camarena, C. M. Lee, S. Park, V. Wiebking, R. O. Bak, N. Gomez-Ospina, M. Pavel-Dinu, W. Sun, G. Bao, M. H. Porteus, and M. A. Behlke. 2018. A high-fidelity Cas9 mutant delivered as a ribonucleoprotein complex enables efficient gene editing in human hematopoietic stem and progenitor cells. *Nature Medicine.* 24:1216-1224. doi: 10.1038/s41591-018-0137-0.
53. Wang, D., C. Zhang, B. Wang, B. Li, Q. Wang, D. Liu, H. Wang, Y. Zhou, L. Shi, F. Lan, and Y. Wang. 2019. Optimized CRISPR guide RNA design for two high-fidelity Cas9 variants by deep learning. *Nat Commun.* 10:4284. doi: 10.1038/s41467-019-12281-8.
54. Wang, J., J. J. DeClercq, S. B. Hayward, P. W.-L. Li, D. A. Shivak, P. D. Gregory, G. Lee, and M. C. Holmes. 2016. Highly efficient homology-driven genome editing in human T cells by combining zinc-finger nuclease mRNA and AAV6 donor delivery. *Nucleic Acids Res.* 44: e30-e30. doi: 10.1093/nar/gkv1121.
55. Wang, X., and I. Rivière. 2016. Clinical manufacturing of CAR T cells: foundation of a promising therapy. *Mol Ther Oncolytics.* 3:16015. doi: 10.1038/mto.2016.15.
56. Ward-Kavanagh, L. K., W. W. Lin, J. R. Šedý, and C. F. Ware. 2016. The TNF Receptor Superfamily in Co-activating and Co-inhibitory Responses. *Immunity.* 44:1005-1019. doi: 10.1016/j.immuni.2016.04.019.
57. Williams, J. A., J. Luke, L. Johnson, and C. Hodgson. 2006. pDNAVACCultra vector family: high throughput intracellular targeting DNA vaccine plasmids. *Vaccine.* 24:4671-4676. doi: 10.1016/j.vaccine.2005.08.033.
58. Zhang, C., J. Liu, J. F. Zhong, and X. Zhang. 2017. Engineering CAR-T cells. *Biomarker research.* 5:22. doi: 10.1186/s40364-017-0102-y.
59. Zhang, L., J. A. Zuris, R. Viswanathan, J. N. Edelstein, R. Turk, B. Thommandru, H. T. Rube, S. E. Glenn, M. A. Collingwood, N. M. Bode, S. F. Beaudoin, S. Lele, S. N. Scott, K. M. Wasko, S. Sexton, C. M. Borges, M. S. Schubert, G. L. Kurgan, M. S. McNeill, C. A. Fernandez, V. E. Myer, R. A. Morgan, M. A. Behlke, and C. A. Vakulskas. 2021. AsCas12a ultra nuclease facilitates the rapid generation of therapeutic cell medicines. *Nat Commun.* 12:3908. doi: 10.1038/s41467-021-24017-8.

Each of the references cited herein is incorporated by reference in its entirety for everything taught therein.

TABLE 18

| Homology-directed repair template | Construct organization | Vector format | Vector backbone size (bp) | 5' homology arm length (bp) | 3' homology arm length (bp) | Total insert size | Total construct size (bp) | Locus targeted | Contains promoter | What does it express? |
|---|---|---|---|---|---|---|---|---|---|---|
| TRAC_1G4_500HA (SEQ ID NO: 72) | LHA-GSG-T2A-TCRb-Furin-GSG-P2A-TCRa-RHA | dsDNA | N/A | 500 | 500 | 2503 | 2503 | TRAC locus, N-terminus | No | NY-ESO-1 TCR alpha and beta chains |
| TRAC_1G4_500HA (SEQ ID NO: 73) | LHA-GSG-T2A-TCRb-Furin-GSG-P2A-TCRa-RHA | pUC57 | 2710 | 500 | 500 | 2503 | 5601 | TRAC locus, N-terminus | No | NY-ESO-1 TCR alpha and beta chains |
| TRAC_1G4_500HA (SEQ ID NO:74) | LHA-GSG-T2A-TCRb-Furin-GSG-P2A-TCRa-RHA | Nano-plasmid | 427 | 500 | 500 | 2503 | 2930 | TRAC locus, N-terminus | No | NY-ESO-1 TCR alpha and beta chains |
| TRAC_mNeonGreen_500HA (SEQ ID NO: 75) | LHA-GSG-T2A-mNeonGreen-GSG-P2A-TCRa-RHA | dsDNA | N/A | 500 | 500 | 2503 | 2503 | TRAC locus, N-terminus | No | mNeonGreen and the NY-ESO-1 TCR alpha chain |
| TRAC_mNeonGreen_500HA (SEQ ID NO: 76) | LHA-GSG-T2A-mNeonGreen-GSG-P2A-TCRa-RHA | pUC57 | 2710 | 500 | 500 | 2263 | 4973 | TRAC locus, N-terminus | No | mNeonGreen and the NY-ESO-1 TCR alpha chain |

TABLE 18-continued

| Homology-directed repair template | Construct organization | Vector format | Vector backbone size (bp) | 5' homology arm length (bp) | 3' homology arm length (bp) | Total insert size | Total construct size (bp) | Locus targeted | Contains promoter | What does it express? |
|---|---|---|---|---|---|---|---|---|---|---|
| TRAC_mNeonGreen_500HA (SEQ ID NO: 77) | LHA-GSG-T2A-mNeonGreen-GSG-P2A-TCRa-RHA | Nano-plasmid | 427 | 500 | 500 | 2263 | 2690 | TRAC locus, N-terminus | No | mNeonGreen and the NY-ESO-1 TCR alpha chain |
| TRAC_mNeonGreen_100HA (SEQ ID NO: 78) | LHA-GSG-T2A-mNeonGreen-GSG-P2A-TCRa-RHA | pUC57 | 2710 | 100 | 100 | 1463 | 4173 | TRAC locus, N-terminus | No | mNeonGreen and the NY-ESO-1 TCR alpha chain |
| TRAC_mNeonGreen_100HA (SEQ ID NO: 79) | LHA-GSG-T2A-mNeonGreen-GSG-P2A-TCRa-RHA | Nano-plasmid | 427 | 100 | 100 | 1463 | 1890 | TRAC locus, N-terminus | No | mNeonGreen and the NY-ESO-1 TCR alpha chain |
| TRAC_mNeonGreen_200HA (SEQ ID NO: 80) | LHA-GSG-T2A-mNeonGreen-GSG-P2A-TCRa-RHA | pUC57 | 2710 | 200 | 200 | 1663 | 4373 | TRAC locus, N-terminus | No | mNeonGreen and the NY-ESO-1 TCR alpha chain |
| TRAC_mNeonGreen_200HA (SEQ ID NO: 81) | LHA-GSG-T2A-mNeonGreen-GSG-P2A-TCRa-RHA | Nano-plasmid | 427 | 200 | 200 | 1663 | 2090 | TRAC locus, N-terminus | No | mNeonGreen and the NY-ESO-1 TCR alpha chain |
| TRAC_mNeonGreen_300HA (SEQ ID NO: 82) | LHA-GSG-T2A-mNeonGreen-GSG-P2A-TCRa-RHA | pUC57 | 2710 | 300 | 300 | 1863 | 4573 | TRAC locus, N-terminus | No | mNeonGreen and the NY-ESO-1 TCR alpha chain |
| TRAC_mNeonGreen_300HA (SEQ ID NO: 83) | LHA-GSG-T2A-mNeonGreen-GSG-P2A-TCRa-RHA | Nano-plasmid | 427 | 300 | 300 | 1863 | 2290 | TRAC locus, N-terminus | No | mNeonGreen and the NY-ESO-1 TCR alpha chain |
| TRAC_mNeonGreen_700HA (SEQ ID NO: 84) | LHA-GSG-T2A-mNeonGreen-GSG-P2A-TCRa-RHA | pUC57 | 2710 | 700 | 700 | 2663 | 5373 | TRAC locus, N-terminus | No | mNeonGreen and the NY-ESO-1 TCR alpha chain |
| TRAC_mNeonGreen_700HA (SEQ ID NO: 85) | LHA-GSG-T2A-mNeonGreen-GSG-P2A-TCRa-RHA | Nano-plasmid | 427 | 700 | 700 | 2663 | 3090 | TRAC locus, N-terminus | No | mNeonGreen and the NY-ESO-1 TCR alpha chain |
| TRAC_mNeonGreen_1000HA (SEQ ID NO: 86) | LHA-GSG-T2A-mNeonGreen-GSG-P2A-TCRa-RHA | pUC57 | 2710 | 1000 | 1000 | 3263 | 5973 | TRAC locus, N-terminus | No | mNeonGreen and the NY-ESO-1 TCR alpha chain |
| TRAC_mNeonGreen_1000HA (SEQ ID NO: 87) | LHA-GSG-T2A-mNeonGreen-GSG-P2A-TCRa-RHA | Nano-plasmid | 427 | 1000 | 1000 | 3263 | 3690 | TRAC locus, N-terminus | No | mNeonGreen and the NY-ESO-1 TCR alpha chain |
| TRAC_mNeonGreen_2000HA (SEQ ID NO: 88) | LHA-GSG-T2A-mNeonGreen-GSG-P2A-TCRa-RHA | pUC57 | 2710 | 2000 | 2000 | 5263 | 7973 | TRAC locus, N-terminus | No | mNeonGreen and the NY-ESO-1 TCR alpha chain |
| TRAC_mNeonGreen_2000HA (SEQ ID NO: 89) | LHA-GSG-T2A-mNeonGreen-GSG-P2A-TCRa-RHA | Nano-plasmid | 427 | 2000 | 2000 | 5263 | 5690 | TRAC locus, N-terminus | No | mNeonGreen and the NY-ESO-1 TCR alpha chain |
| TRAC_pp65_500HA (SEQ ID NO: 90) | LHA-GSG-T2A-TCRb-Furin-GSG-P2A-TCRa-RHA | Nano-plasmid | 427 | 500 | 500 | 2491 | 2918 | TRAC locus, N-terminus | No | pp65 TCR alpha and beta chains |

TABLE 18-continued

| Homology-directed repair template | Construct organization | Vector format | Vector backbone size (bp) | 5' homology arm length (bp) | 3' homology arm length (bp) | Total insert size | Total construct size (bp) | Locus targeted | Contains promoter | What does it express? |
|---|---|---|---|---|---|---|---|---|---|---|
| TRAC_Nflag_CD19_CAR_500HA (SEQ ID NO: 91) | LHA-GSG-T2A-CAR-bGHpA-RHA | Nano-plasmid | 427 | 500 | 500 | 2789 | 3216 | TRAC locus, N-terminus | No | Human CD19-specific CAR |
| RAB11A_YFP (SEQ ID NO: 92) | LHA-YFP-RHA | pUC57 | 2710 | 306 | 315 | 1350 | 4060 | RAB11A locus, N-terminus | Yes | YFP under the control of the endogenous RAB11A promoter |
| RAB11A_YFP (SEQ ID NO: 93) | LHA-YFP-RHA | Nano-plasmid | 427 | 306 | 315 | 1350 | 1777 | RAB11A locus, N-terminus | Yes | YFP under the control of the endogenous RAB11A promoter |
| AAVS1_CBH_mNeonGreen_500HA (SEQ ID NO: 94) | LHA-pCBH-mNeonGreen-bGHpA-RHA | pUC57 | 2710 | 500 | 500 | 2754 | 5464 | PPP1R12C, first intron | Yes | mNeonGreen under the control of the CMV enhancer and chicken beta-actin promoter |
| AAVS1_CBH_mNeonGreen_500HA (SEQ ID NO: 95) | LHA-pCBH-mNeonGreen-bGHpA-RHA | Nano-plasmid | 427 | 500 | 500 | 2754 | 3181 | PPP1R12C, first intron | Yes | mNeonGreen under the control of the CMV enhancer and chicken beta-actin promoter |
| CD4_2A_mNeonGreen_500HA (SEQ ID NO: 96) | LHA-CD4(C-term)-Furin-GSG-T2A-mNeonGreen-RHA | Nano-plasmid | 427 | 500 | 500 | 1841 | 2268 | CD4, exon 9 | No | mNeonGreen |
| TNFRSF9_mNeonGreen_500HA (SEQ ID NO: 97) | LHA-GSG-T2A-mNeonGreen-Furin-GSG-P2A-TNFRSF9(N-term)-RHA | Nano-plasmid | 427 | 500 | 500 | 1882 | 2309 | TNFRSF9, exon 2 | No | mNeonGreen |
| TRAC_mCherry_500HA (SEQ ID NO: 98) | LHA-GSG-T2A-mCherry-GSG-P2A-TCRa-RHA | pUC57 | 2710 | 500 | 500 | 2263 | 4973 | TRAC locus, N-terminus | No | mCherry and the NY-ESO-1 TCR alpha chain |
| TRAC_mCherry_500HA (SEQ ID NO: 99) | LHA-GSG-T2A-mCherry-GSG-P2A-TCRa-RHA | Nano-plasmid | 427 | 500 | 500 | 2263 | 2690 | TRAC locus, N-terminus | No | mCherry and the NY-ESO-1 TCR alpha chain |
| TRAC_NotchICD_mNeonGreen_500HA (SEQ ID NO: 100) | LHA-GSG-T2A-NICD-Flag-Furin-GSG-T2A-mNeonGreen-GSG-P2A-TCRa-RHA | Nano-plasmid | 427 | 500 | 500 | 4774 | 5201 | TRAC locus, N-terminus | No | Notch-ICD, mNeonGreen, and the NY-ESO-1 TCR alpha chain |
| TRAC_NotchICD_1G4_500HA (SEQ ID NO: 101) | LHA-GSG-T2A-NICD-Flag-Furin-GSG-T2A-TCRb-Furin-GSG-P2A-TCRa-RHA | Nano-plasmid | 427 | 500 | 500 | 5014 | 5441 | TRAC locus, N-terminus | No | Notch-ICD and the NY-ESO-1 TCR alpha and beta chains |
| TRAC_Themis_1G4_500HA (SEQ ID NO: 102) | LHA-GSG-T2A-Flag-Themis-Furin-GSG-T2A-TCRb-Furin-GSG-P2A-TCRa-RHA | Nano-plasmid | 427 | 500 | 500 | 6448 | 6875 | TRAC locus, N-terminus | No | Themis and the NY-ESO-1 TCR alpha and beta chains |

TABLE 18-continued

| Homology-directed repair template | Construct organization | Vector format | Vector backbone size (bp) | 5' homology arm length (bp) | 3' homology arm length (bp) | Total insert size | Total construct size (bp) | Locus targeted | Contains promoter | What does it express? |
|---|---|---|---|---|---|---|---|---|---|---|
| TRAC_tCTS_mNeonGreen_500HA (SEQ ID NO: 103) | tCTS-LHA-GSG-T2A-mNeonGreen-GSG-P2A-TCRa-RHA-tCTS | dsDNA | N/A | 500 | 500 | 2341 | 2341 | TRAC locus, N-terminus | No | mNeonGreen and the NY-ESO-1 TCR alpha chain |
| TRAC_tCTS_mNeonGreen_500HA (SEQ ID NO: 104) | tCTS-LHA-GSG-T2A-mNeonGreen-GSG-P2A-TCRa-RHA-tCTS | Nano-plasmid | 427 | 500 | 500 | 2341 | 2768 | TRAC locus, N-terminus | No | mNeonGreen and the NY-ESO-1 TCR alpha chain |

What is claimed is:

1. A method for making a population of engineered T cells, the method comprising:
   a) contacting a population of T cells with a first ribonucleoprotein particle (RNP) and a donor DNA, wherein the first RNP comprises a first guide RNA that targets an endogenous TCR locus, and wherein the donor DNA comprises a nucleic acid sequence comprising a gene encoding a polypeptide comprising an exogenous TCR-beta and an exogenous TCR-alpha or portion thereof, under conditions to allow the RNP and the donor DNA to enter the T cells;
   b) incubating the population of T cells for a period of time; and
   c) culturing the population of T cells in a medium for a period of time to allow the gene to be inserted into the endogenous TCR locus, thereby forming a population of engineered T cells
   wherein the amount of donor DNA is about 0.0004 pmol/μL to about 0.4 pmol/μL,
   wherein the donor DNA is on a nanoplasmid,
   and wherein the efficiency of the gene insertion is at least 27%.

2. The method of claim 1, wherein the endogenous TCR locus is a TCR-alpha locus, and the T cell is contacted with a second RNP comprising a second guide RNA that targets an endogenous TCR-beta locus.

3. The method of claim 2, wherein the second RNP comprises a second gene editing protein, and the ratio of the second guide RNA to the second gene editing protein is between 1:1 and 100:1.

4. The method of claim 2, wherein the second guide RNA targets exon 1 of TRBC1, TRBC2, TRBC3 (SEQ ID NO: 25), TRBC4, TRBC5, TRBC6, TRBC7, TRBC8, TRBC9, TRBC10, TRBC11, TRBC12, TRBC13, TRBC14, TRBC15, TRBC16, TRBC17, TRBC18, TRBC19, TRBC20, TRBC21, TRBC22, TRBC23, TRBC24, TRBC25, or TRBC26.

5. The method of claim 4, wherein the second guide RNA comprises the nucleic acid sequence of SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO: 31, SEQ ID NO:32, SEQ ID NO:33, SEQ ID NO:34, SEQ ID NO:35, SEQ ID NOW: 36, SEQ ID NO:37, SEQ ID NO:38, SEQ ID NO:39, SEQ ID NO:40, SEQ ID NO:41, SEQ ID NO: 42, SEQ ID NO:43, SEQ ID NO:44, SEQ ID NO:45, SEQ ID NO:46, SEQ ID NO:47, or SEQ ID NO:48.

6. The method of claim 1, wherein the first RNP comprises a first gene editing protein, and the ratio of the first guide RNA to the first gene editing protein is between 1:1 and 100:1.

7. The method of claim 1, wherein the population of engineered T cells does not express an endogenous TCR-beta protein.

8. The method of claim 1, wherein the first guide RNA targets exon 1, 2, or 3 of TRAC1, TRAC2, TRAC3, TRAC4, TRAC5, TRAC6, TRAC7, TRAC8, TRAC9, TRAC10, TRAC11, TRAC12, TRAC13, TRAC14, TRAC15, or TRAC16.

9. The method of claim 8, wherein the first guide RNA comprises the nucleic acid sequence of SEQ ID NO:8, SEQ ID NO:9, SEQ ID NO: 10, SEQ ID NO: 11, SEQ ID NO: 12, SEQ ID NO:13, SEQ ID NO:14, SEQ ID NO: 15, SEQ ID NO:16, SEQ ID NO:17, SEQ ID NO:18, SEQ ID NO: 19, SEQ ID NO:20, SEQ ID NOW: 21, or SEQ ID NO: 22.

10. The method of claim 1, wherein the conditions to allow the RNP and the donor DNA to enter the T cells comprise electroporation.

11. The method of claim 1, wherein the medium comprises cytokines.

12. The method of claim 11, wherein the cytokines comprise IL-2, IL-7, and/or IL-15.

13. The method of claim 1, wherein step a) is performed in the presence of a negatively charged polymer.

14. The method of claim 1, wherein the amount of RNP is about 0.2 pmol/μL to about 8 pmol/μL.

15. The method of claim 1, wherein at least about 5% of the population of T cells are recovered as engineered T cells.

16. The method of claim 1, wherein at least about 25% of the population of T cells are viable after step c).

17. The method of claim 1, further comprising contacting the T cells with a second RNP comprising a guide RNA that targets an endogenous TCR-beta locus, and wherein at least about 5% of the population of T cells are recovered as engineered T cells, wherein the engineered T cells express less than about 20% endogenous TCR-beta.

18. A population of engineered T cells made by the method of claim 1.

19. A composition comprising a population of isolated T cells, wherein at least 5% of the cells in the population are engineered T cells, each engineered T cell comprising a nucleic acid sequence encoding a polypeptide comprising an exogenous TCR-beta and/or an exogenous TCR-alpha or portion thereof, wherein the nucleic acid sequence is inserted into a TCR locus of the engineered T cell, and wherein the engineered T cells do not express an endogenous TCR beta.

20. A population of engineered T cell comprising a nucleic acid sequence encoding a polypeptide comprising an exogenous TCR-beta and/or an exogenous TCR-alpha or portion thereof, wherein the nucleic acid sequence is inserted into a TCR-alpha or TCR-beta locus of the population of engineered T cells.

21. The population of engineered T cells of claim 20, wherein expression of the endogenous TCR-beta gene is disrupted in greater than about 80% of the engineered T cells.

22. A pharmaceutical composition comprising a population of the engineered T cells of claim 20 and a pharmaceutically acceptable excipient.

23. A method of treating cancer comprising administering the population of engineered T cells of claim 20 to a patient having a cancer.

24. A method for treating a subject having cancer, the method comprising:
   a) providing a population of T cells;
   b) engineering at least a subset of the population of T cells to express an exogenous T cell receptor (TCR) and to knock out an endogenous TCR-beta, thereby forming a population of engineered T cells, wherein the exogenous TCR binds to an antigen expressed by the cancer, wherein the exogenous TCR is on a nanoplasmid, and wherein at least 27% of the population of engineered T cells express the exogenous TCR;
   c) expanding the population of engineered T cells; and
   d) administering the expanded population of engineered T cells to the subject.

25. A method for treating a subject having cancer, the method comprising:
   a) providing a first population of T cells isolated from the subject;
   b) engineering at least a subset of the first population of T cells to express a first exogenous T cell receptor (TCR) and to knock out an endogenous TCR-beta, thereby forming a first population of engineered T cells, wherein the exogenous TCR binds to a first antigen expressed by the cancer, wherein the first exogenous TCR is on a first nanoplasmid, and wherein at least 27% of the first population of engineered T cells express the first exogenous TCR;
   c) expanding the first population of engineered T cells;
   d) administering the expanded first population of engineered T cells to the subject;
   e) providing a second population of T cells isolated from the subject;
   f) engineering at least a subset of the second population of T cells to express a second exogenous TCR and to knock out the endogenous TCR-beta, thereby forming a second population of engineered T cells, wherein the exogenous TCR binds to a second antigen expressed by the cancer, wherein the second exogenous TCR is on a second nanoplasmid, and wherein at least 27% of the second population of engineered T cells express the second exogenous TCR;
   g) expanding the second population of engineered T cells; and
   h) administering the expanded second population of engineered T cells to the subject.

26. A method for making a population of engineered T cells, the method comprising:
   a) contacting a population of T cells with a first ribonucleoprotein particle (RNP) and a donor DNA, wherein the first RNP comprises a first guide RNA that targets an endogenous TCR locus, and wherein the donor DNA comprises a nucleic acid sequence comprising a gene encoding a polypeptide comprising an exogenous TCR-beta and an exogenous TCR-alpha or portion thereof, under conditions to allow the RNP and the donor DNA to enter the population of T cells;
   b) incubating the population of T cells for a period of time; and
   c) culturing the population of T cells in a medium for a period of time to allow the donor DNA to be inserted into the endogenous TCR-alpha locus, thereby forming a population of engineered T cells
   wherein the amount of donor DNA is about 0.0004 pmol/µL to about 0.4 pmol/µL,
   wherein the donor DNA is on a nanoplasmid,
   wherein at least 27% of the population of engineered T cells express the endogenous gene,
   and wherein the viability of the population of engineered T cells is at least 60%.

* * * * *